US012642002B2

(12) United States Patent
Kim et al.

(10) Patent No.: US 12,642,002 B2

(45) Date of Patent: May 26, 2026

(54) ORGANIC ELECTROLUMINESCENT COMPOUND, A PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Chi-Sik Kim, Gyeonggi-do (KR); Kyoung-Jin Park, Gyeonggi-do (KR); Soo-Yong Lee, Gyeonggi-do (KR); Hyun-Woo Kang, Gyeonggi-do (KR); So-Mi Park, Gyeonggi-do (KR); Mi-Ja Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 685 days.

(21) Appl. No.: 17/978,872

(22) Filed: Nov. 1, 2022

(65) Prior Publication Data

US 2023/0157165 A1 May 18, 2023

(30) Foreign Application Priority Data

Nov. 2, 2021 (KR) ........................ 10-2021-0149092
Sep. 27, 2022 (KR) ........................ 10-2022-0122588

(51) Int. Cl.

| | |
|---|---|
| ***H10K 85/60*** | (2023.01) |
| ***C07D 487/04*** | (2006.01) |
| ***C09K 11/06*** | (2006.01) |
| ***H10K 50/11*** | (2023.01) |
| ***H10K 101/00*** | (2023.01) |

(52) U.S. Cl.

CPC ....... *H10K 85/6572* (2023.02); *C07D 487/04* (2013.01); *C09K 11/06* (2013.01); *H10K 85/654* (2023.02); *C09K 2211/1018* (2013.01); *H10K 50/11* (2023.02); *H10K 2101/90* (2023.02)

(58) Field of Classification Search

CPC .. H10K 85/6572; H10K 85/654; H10K 50/11; H10K 2101/90; C07D 487/04; C07D 209/86; C07D 405/14; C07D 409/14; C09K 11/06; C09K 2211/1018; C09K 2211/1007; C09K 2211/1011; C09K 2211/1029; C09K 2211/1044; C09K 2211/1059; C09K 2211/1088; C09K 2211/1092

See application file for complete search history.

(56) References Cited

U.S. PATENT DOCUMENTS

| | | | | |
|---|---|---|---|---|
| 2010/0187977 | A1 | 7/2010 | Kai et al. | |
| 2012/0104940 | A1 | 5/2012 | Shin et al. | |
| 2012/0305903 | A1 | 12/2012 | Kai et al. | |
| 2013/0248849 | A1 | 9/2013 | Feldman et al. | |
| 2015/0236262 | A1 | 8/2015 | Cho et al. | |
| 2022/0006022 | A1 | 1/2022 | Suh et al. | |
| 2022/0181561 | A1 † | 6/2022 | Fleetham | |
| 2022/0259187 | A1 | 8/2022 | Lee et al. | |
| 2022/0399517 | A1 * | 12/2022 | Fleetham | C07D 405/14 |
| 2023/0080974 | A1 | 3/2023 | Parham et al. | |

FOREIGN PATENT DOCUMENTS

| | | | |
|---|---|---|---|
| CN | 112174944 | A | 1/2021 |
| CN | 113502156 | A † | 10/2021 |
| EP | 4318622 | A1 | 2/2024 |
| JP | H083547 | A | 1/1996 |
| KR | 20140015299 | A † | 2/2014 |
| KR | 20210018127 | A † | 2/2021 |
| KR | 20220122557 | A | 9/2022 |
| KR | 20220151566 | A | 11/2022 |
| KR | 20230022391 | A | 2/2023 |

OTHER PUBLICATIONS

3rd Party Observation for Korean application No. 10-2022-0122588; Application Date: Sep. 27, 2022.

Request for the Submission of an Opinion from Korea Intellectual Property Office, Application No. 10-2022-0122588, Filing Date: Sep. 27, 2022.

* cited by examiner
† cited by third party

*Primary Examiner* — Andrew J. Oyer

(74) *Attorney, Agent, or Firm* — G. Creston Campbell

(57) ABSTRACT

The present disclosure relates to an organic electroluminescent compound represented by formula 2', a plurality of host materials comprising at least one first host compound represented by formula 1 and at least one second host compound represented by formula 2, and an organic electroluminescent device comprising the same. By comprising the organic electroluminescent compound or a specific combination of compounds according to the present disclosure as a host material, it is possible to produce an organic electroluminescent device having significantly improved lifetime properties.

11 Claims, No Drawings

ORGANIC ELECTROLUMINESCENT COMPOUND, A PLURALITY OF HOST MATERIALS AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. In many applications such as TVs and lightings, the lifetime of OLEDs is insufficient and higher efficiency of OLEDs is still required. Typically, the higher the luminance of an OLED, the shorter the lifetime that the OLED has. Thus, an OLED which has high luminous efficiency and/or long lifetime is required for long time uses and high resolution of displays.

In order to enhance luminous efficiency, driving voltage and/or lifetime, various materials or concepts for an organic layer of an OLED have been proposed. However, they were not satisfactory in practical use.

Korean Patent Publication No. 10-2054806 discloses an OLED in which a compound having an indolocarbazole as a core is used as a host. However, the aforementioned reference does not specifically disclose an OLED using a specific compound or a specific combination of a plurality of host materials comprising the same claimed in the present disclosure. In addition, there is still a need to develop host materials for improving OLED performance.

DISCLOSURE OF INVENTION

Technical Problem

The objective of the present disclosure is to provide an organic electroluminescent compound having a new structure suitable for applying it to an organic electroluminescent device. Another objective of the present disclosure is to provide a plurality of host materials capable of providing an organic electroluminescent device having high luminous efficiency and/or long lifetime properties. Still another objective of the present disclosure is to provide an organic electroluminescent device having high luminous efficiency and/or improved lifetime properties by comprising the compound according to the present disclosure as a single host material or a specific combination of compounds according to the present disclosure as a plurality of host materials.

Solution to Problem

As a result of intensive studies to solve the technical problems, the present inventors found that the above objective can be achieved by a compound represented by the following formula 2'. In addition, the present inventors have found that the above objective can be achieved by a plurality of host materials comprising at least one first host material represented by the following formula 1 and at least one second host material represented by the following formula 2.

(2')

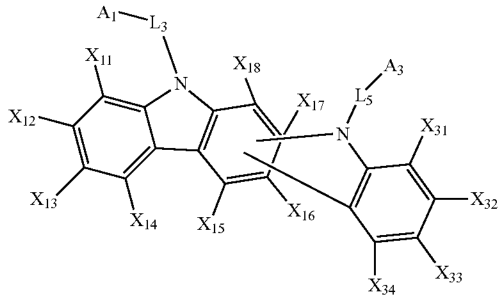

In formula 2', $A_1$ and $A_3$, each independently, represent a substituted or unsubstituted (C6-C30)aryl, a substituted or unsubstituted dibenzofuranyl, a substituted or unsubstituted dibenzothiophenyl, or a substituted or unsubstituted carbazolyl;

$L_3$ and $L_5$, each independently, represent a single bond, or a substituted or unsubstituted (C6-C30)arylene; and $X_{11}$ to $X_{18}$, and $X_{31}$ to $X_{34}$, each independently, represent hydrogen, deuterium, a substituted or unsubstituted (C6-C30)aryl, or a substituted or unsubstituted (3- to 30-membered)heteroaryl, and two or more adjacent $X_{11}$ to $X_{13}$ are linked to each other to form a ring(s);

with the proviso that at least one of $X_{11}$, $X_{15}$ to $X_{18}$, and $X_{31}$ represents deuterium.

(1)

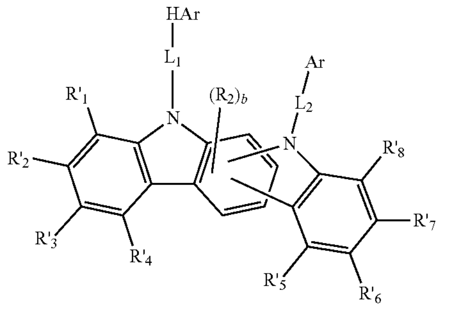

In formula 1, $L_1$ and $L_2$, each independently, represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

HAr represents a substituted or unsubstituted (3- to 30-membered)heteroaryl;

Ar represents a substituted or unsubstituted (C6-C30)aryl, or a substituted or unsubstituted (3- to 30-membered) heteroaryl;

$R'_1$ to $R'_8$, and $R_2$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $—NR_{13}R_{14}$, or $—SiR_{15}R_{16}R_{17}$; or may be linked to an adjacent substituent(s) to form a ring(s);

$R_{13}$ to $R_{17}$, each independently, represent a substituted or unsubstituted (C1-C30)alkyl, a substituted or unsubstituted (C6-C30)aryl, or a substituted or unsubstituted (3- to 30-membered)heteroaryl;

with the proviso that at least one of $R'_1$ to $R'_8$, and $R_2$ represents deuterium; and b represents an integer of 1 or 2, where if b is an integer of 2, each of $R_2$ may be the same or different from each other;

(2)

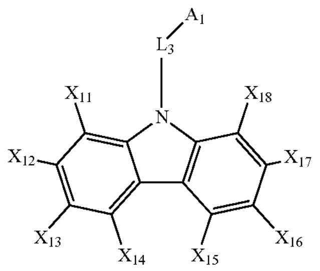

in formula 2, $A_1$ represents a substituted or unsubstituted (C6-C30)aryl, a substituted or unsubstituted dibenzofuranyl, a substituted or unsubstituted dibenzothiophenyl, or a substituted or unsubstituted carbazolyl;

$L_3$ represents a single bond, or a substituted or unsubstituted (C6-C30)arylene; and $X_{11}$ to $X_{18}$, each independently, represent hydrogen, deuterium, a substituted or unsubstituted (C6-C30)aryl, or a substituted or unsubstituted (3- to 30-membered) heteroaryl, and two or more adjacent $X_{11}$ to $X_{18}$ may be linked to each other to form a ring(s);

with the proviso that when two or more adjacent $X_{11}$ to $X_{18}$ are linked to each other to form a ring(s), at least one of $X_{11}$ to $X_{18}$ represents deuterium or is substituted with deuterium;

and when two or more adjacent $X_{11}$ to $X_{18}$ are not linked to each other to form a ring(s), $X_{11}$ to $X_{18}$ are not deuterium and are not substituted with deuterium.

Advantageous Effects of Invention

The organic electroluminescent compound according to the present disclosure exhibits performances suitable for using it in an organic electroluminescent device. In addition, an organic electroluminescent device having significantly improved lifetime properties compared to conventional organic electroluminescent devices can be provided by comprising the compound according to the present disclosure as a single host material, or as a plurality of host materials.

MODE FOR THE INVENTION

Hereinafter, the present disclosure will be described in detail. However, the following description is intended to explain the present disclosure and is not meant in any way to restrict the scope of the present disclosure.

The present disclosure relates to a plurality of host materials comprising a first host material comprising at least one compound represented by formula 1 and a second host material comprising at least one compound represented by formula 2, and an organic electroluminescent device comprising the host materials.

The term “organic electroluminescent compound” in the present disclosure means a compound that may be used in an organic electroluminescent device, and may be comprised in any material layer constituting an organic electroluminescent device, as necessary.

The term “an organic electroluminescent material” in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term “a plurality of organic electroluminescent materials” in the present disclosure means an organic electroluminescent material comprising a combination of at least two compounds, which may be comprised in any organic layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials of the present disclosure may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. The at least two compounds may be comprised in the same layer or different layers, and may be mixture-evaporated or co-evaporated, or may be individually evaporated.

The term “a plurality of host materials” in the present disclosure means an organic electroluminescent material comprising a combination of at least two host materials. It may mean both a material before being comprised in an organic electroluminescent device (for example, before vapor deposition) and a material after being comprised in an organic electroluminescent device (for example, after vapor deposition). The plurality of host materials of the present disclosure may be comprised in any light-emitting layer constituting an organic electroluminescent device, and at least two compounds comprised in the plurality of host materials may be comprised together in one light-emitting layer, or each may be comprised in different light-emitting layers. When the at least two host materials are comprised in one layer, for example, they may be mixture-evaporated to form a layer, or separately co-evaporated at the same time to form a layer.

Herein, the term “(C1-C30)alkyl” is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. The term “(C3-C30)cycloalkyl” is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(C6-C30)aryl(ene)" is meant to be a monocyclic or fused ring radical derived from an aromatic hydrocarbon having 6 to 30 ring backbone carbon atoms, and may be partially saturated. The number of ring backbone carbon atoms is preferably 6 to 20, and more preferably 6 to 15. The above aryl may comprise a Spiro structure. The above aryl may include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cummenyl, spiro[fluorene-fluorene]yl, spiro[fluorene-benzofluorene]yl, azulenyl, tetramethyl-dihydrophenanthrenyl etc. Specifically, the above aryl may include o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenyl, 4"-tert-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. The term "(3- to 30-membered) heteroaryl(ene)" is meant to be an aryl(ene) having 3 to 30 ring backbone atoms, and including at least one heteroatom selected from the group consisting of B, N, O, S, Si, P, Se, and Ge, in which the number of ring backbone atoms is preferably 3 to 30, and more preferably 5 to 20. The number of heteroatoms is preferably 1 to 4. The above heteroaryl (ene) may be a monocyclic ring, or a fused ring condensed with at least one benzene ring; may be partially saturated. In addition, the above heteroaryl or heteroarylene may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethyl benzopyrimidinyl, indolocarbazolyl, indenocarbazolyl, etc. More specifically, the above heteroaryl may include 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]benzofuranyl, 10-naphtho-[2,1-b]benzofuranyl, 1-naphtho-[1,2-b]-benzothiophenyl, 2-naphtho-[1,2-b]-benzothiophenyl, 3-naphtho-[1,2-b]benzothiophenyl, 4-naphtho-[1,2-b]-benzothiophenyl, 5-naphtho-[1,2-b]benzothiophenyl, 6-naphtho-[1,2-b] benzothiophenyl, 7-naphtho-[1,2-b]-benzothiophenyl, 8-naphtho-[1,2-b]benzothiophenyl, 9-naphtho-[1,2-b]-benzothiophenyl, 10-naphtho-[1,2-b]benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]benzothiophenyl, 1-naphtho-[2,1-b]-benzothiophenyl, 2-naphtho-[2,1-b]-benzothiophenyl, 3-naphtho-[2,1-b]benzothiophenyl, 4-naphtho-[2,1-b]-benzothiophenyl, 5-naphtho-[2,1-b]benzothiophenyl, 6-naphtho-[2,1-b]benzothiophenyl, 7-naphtho-[2,1-b]-benzothiophenyl, 8-naphtho-[2,1-b]benzothiophenyl, 9-naphtho-[2,1-b]-benzothiophenyl, 10-naphtho-[2,1-b]benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. The term "a fused ring group of a (C3-C30) aliphatic ring(s) and a (C6-C30) aromatic ring(s)" is meant to be a functional group in which at least one aliphatic ring having 3 to 30, preferably 3 to 25, and more preferably 3 to 18 ring backbone carbon atoms and at least one aromatic ring having 6 to 30, preferably 6 to 25, and more preferably 6 to 18 ring backbone carbon atoms are fused. For example, the fused ring group may include a fused ring group of at least one benzene and at least one cyclohexane, a fused ring group of at least one naphthalene and at least one cyclopentane, etc. Herein, the carbon atom(s) of the fused ring group of a (C3-C30) aliphatic ring(s) and a (C6-C30) aromatic ring(s) may be replaced with at least one heteroatom selected from B, N, O, S, Si, and P, preferably at least one heteroatom selected from N, O, and S. Furthermore, "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

In the present disclosure, "a ring formed by a linkage of adjacent substituents" means that at least two adjacent substituents are linked or fused to each other to form a substituted or unsubstituted, mono- or polycyclic, (3- to 30-membered) alicyclic or aromatic ring, or the combination thereof, preferably a substituted or unsubstituted, mono- or polycyclic, (5- to 25-membered) alicyclic or aromatic ring, or the combination thereof. In addition, the formed ring may contain at least one heteroatom selected from B, N, O, S, Si, and P, preferably at least one heteroatom selected from N, O, and S. According to one embodiment of the present disclosure, the number of ring backbone atoms is 5 to 20, and according to another embodiment of the present disclosure, the number of ring backbone atoms is 5 to 15. For example, the fused ring may be a substituted or unsubstituted dibenzothiophene ring, a substituted or unsubstituted dibenzofuran ring, a substituted or unsubstituted nanphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring, etc.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl(ene), the substituted aryl(ene), the substituted heteroaryl(ene), the substituted cycloalkyl(ene), the substituted cycloalkenyl, the substituted heterocycloalkyl, the substituted dibenzofuranyl, the substituted dibenzothiophenyl, and the substituted carbazolyl in the formulas of the present disclosure, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium, a cyano(s), a (C1-C30)alkyl(s), and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl, and may be further substituted with deuterium. For example, the substituent(s) of the substituents may be deuterium; or may be at least one selected from a methyl; a phenyl unsubstituted or substituted with at least one of a cyano(s), a carbazolyl(s), a dibenzofuranyl(s), and a dibenzothiophenyl(s); a biphenyl; a naphthyl; a terphenyl; a carbazolyl unsubstituted or substituted with a phenyl(s); a dibenzofuranyl; a dibenzothiophenyl; and a cyano, which may be further substituted with deuterium.

Hereinafter, an organic electroluminescent compound according to one embodiment will be described in more detail.

The organic electroluminescent compound according to one embodiment is represented by the following formula 2'.

(2')

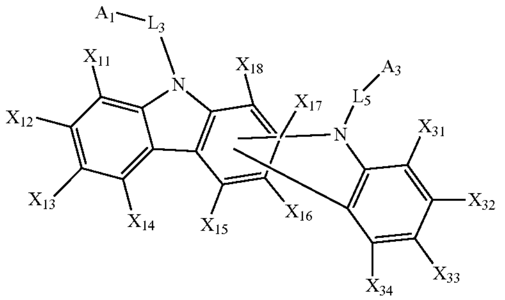

In formula 2', $A_1$ and $A_3$, each independently, represent a substituted or unsubstituted (C6-C30)aryl, a substituted or unsubstituted dibenzofuranyl, a substituted or unsubstituted dibenzothiophenyl, or a substituted or unsubstituted carbazolyl;

$L_3$ and $L_5$, each independently, represent a single bond, or a substituted or unsubstituted (C6-C30)arylene; and $X_{11}$ to $X_{18}$, and $X_{31}$ to $X_{34}$, each independently, represent hydrogen, deuterium, a substituted or unsubstituted (C6-C30)aryl, or a substituted or unsubstituted (3- to 30-membered)heteroaryl, and adjacent two or more of $X_{11}$ to $X_{18}$ are linked to each other to form a ring(s);

with the proviso that at least one of $X_{11}$, $X_{15}$ to $X_{18}$, and $X_{31}$ represents deuterium.

In one embodiment, $A_1$ and $A_3$, each independently, represent a substituted or unsubstituted (C6-C30)aryl, preferably a substituted or unsubstituted (C6-C25)aryl, more preferably a substituted or unsubstituted (C6-C18)aryl; a substituted or unsubstituted dibenzofuranyl; a substituted or unsubstituted dibenzothiophenyl; or a substituted or unsubstituted carbazolyl. For example, $A_1$ and $A_3$, each independently, may be a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted dimethylfluorenyl, a substituted or unsubstituted dibenzofuranyl, a substituted or unsubstituted dibenzothiophenyl, or a substituted or unsubstituted carbazolyl, in which the substituent(s) may be at least one of deuterium, a phenyl, a naphthyl, a carbazolyl, a dibenzofuranyl, and dibenzothiophenyl.

In one embodiment, $L_3$ and $L_5$, each independently, represent a single bond, or a substituted or unsubstituted (C6-C30)arylene; preferably a single bond, or a substituted or unsubstituted (C6-C25)arylene; and more preferably a single bond, or a substituted or unsubstituted (C6-C18) arylene. For example, $L_3$ and $L_5$, each independently, may be a single bond, a phenylene unsubstituted or substituted with deuterium, or a biphenylene unsubstituted or substituted with deuterium.

In one embodiment, $X_{11}$ to $X_{18}$, and $X_{31}$ to $X_{34}$, each independently, represent hydrogen or deuterium, and two or more adjacent $X_{11}$, to $X_{18}$ are linked to each other to form a ring(s); and at least one of $X_{11}$, $X_{15}$ to $X_{18}$, and $X_{31}$ represents deuterium.

The compound represented by formula 2' according to one embodiment may be represented by any one of the following formulas 2'-1 to 2'-6.

(2'-1)

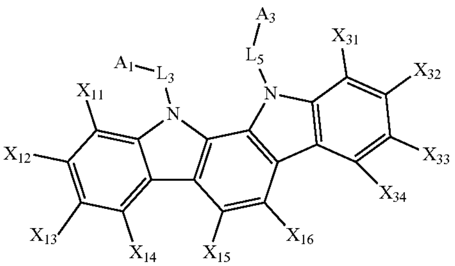

(2'-2)

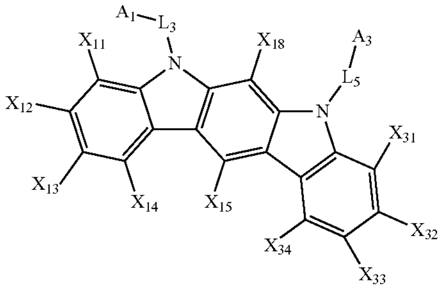

-continued
(2'-3)
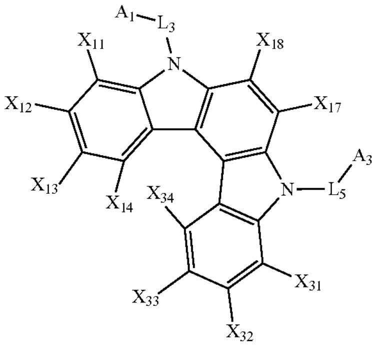
(2'-4)
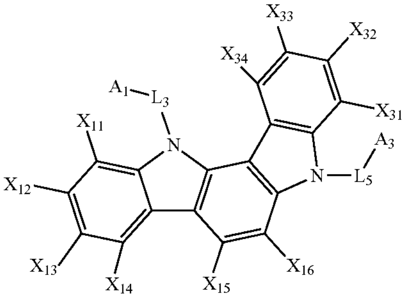
(2'-5)
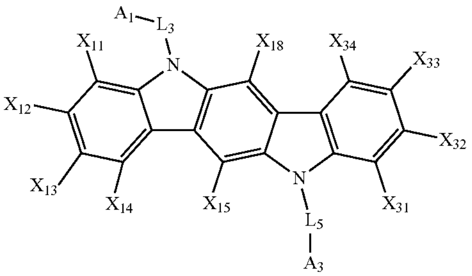
(2'-6)
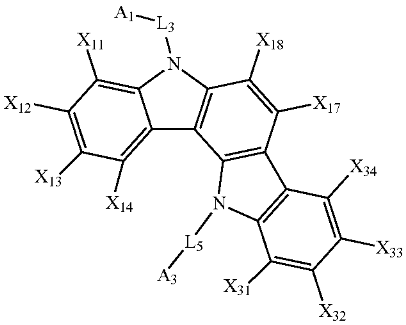
In formulas 2'-1 to 2'-6, $A_1$, $A_3$, $L_3$, $L_5$, $X_{11}$ to $X_{18}$, and $X_{31}$ to $X_{34}$ are as defined in formula 2'.
According to one embodiment, the organic electroluminescent compound represented by formula 2' may be exemplified as the following compounds, but is not limited thereto.
C-1
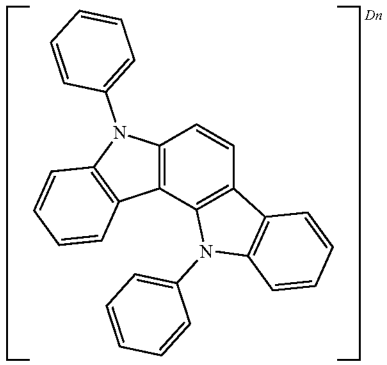
C-2
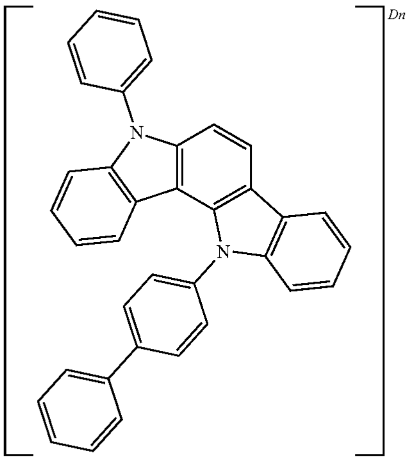
C-3
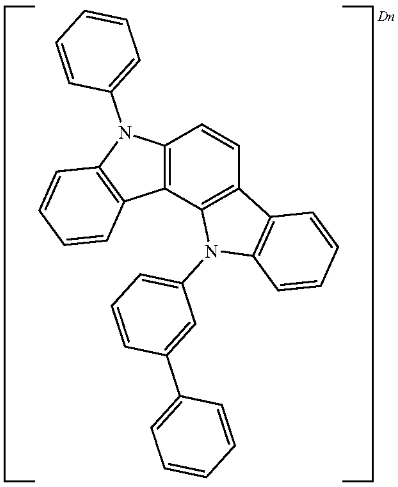

-continued
C-4
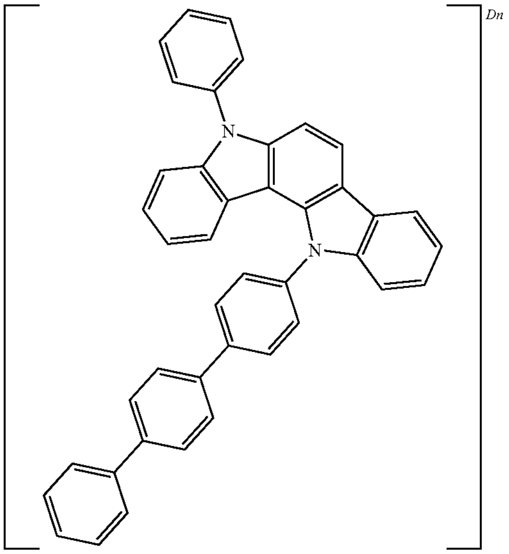
C-5
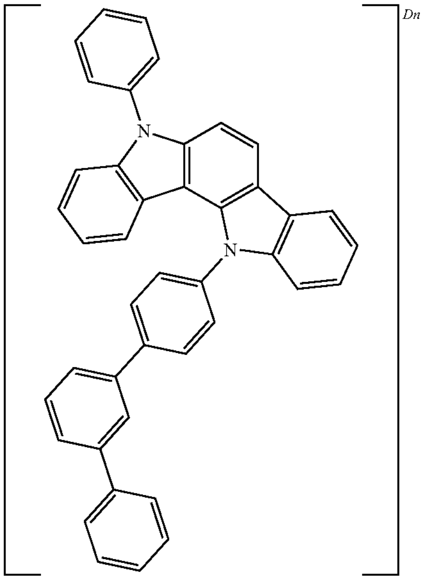
C-6
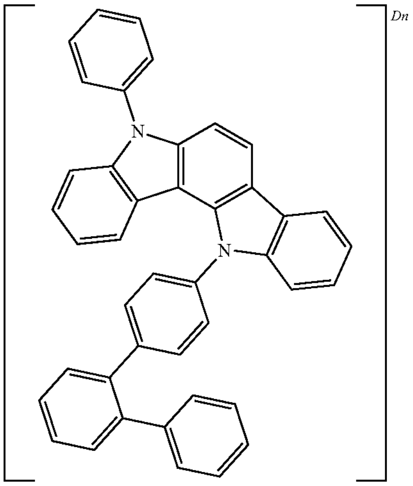
-continued
C-7
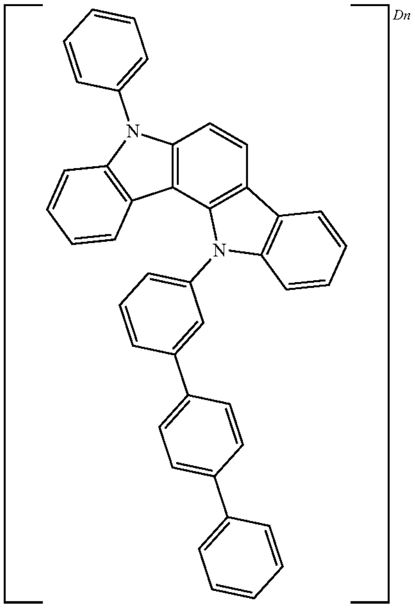
C-8
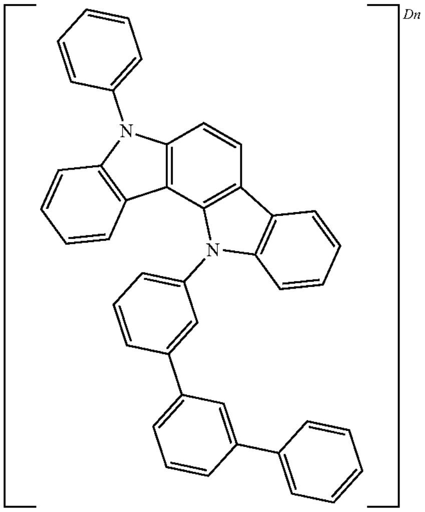
C-9
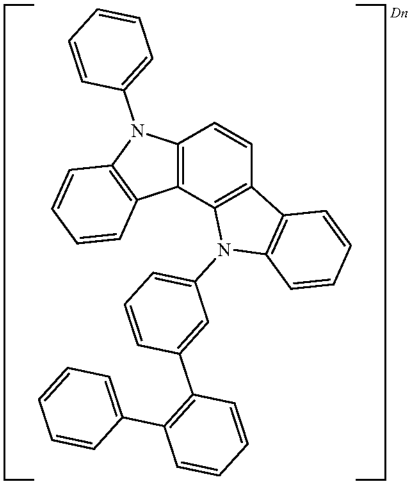

-continued
C-10
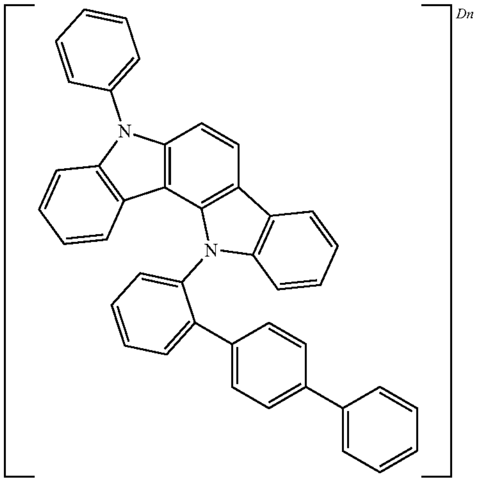
C-11
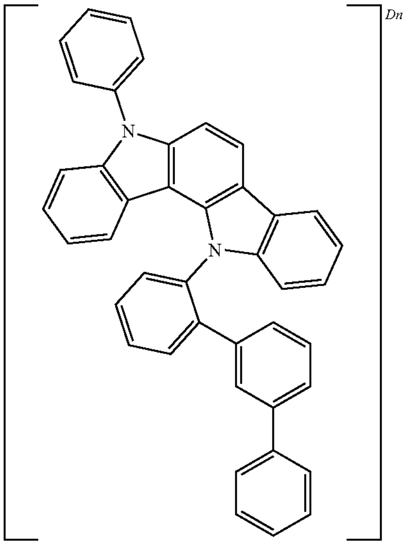
C-12
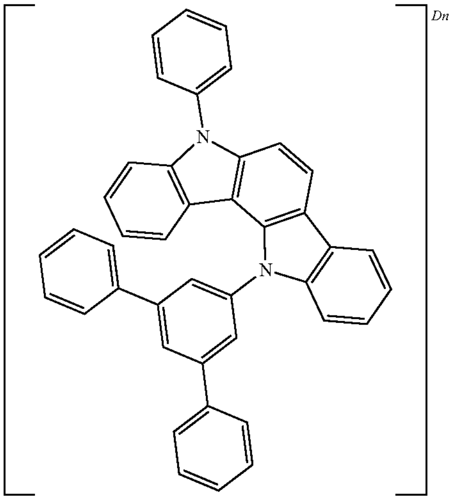
-continued
C-13
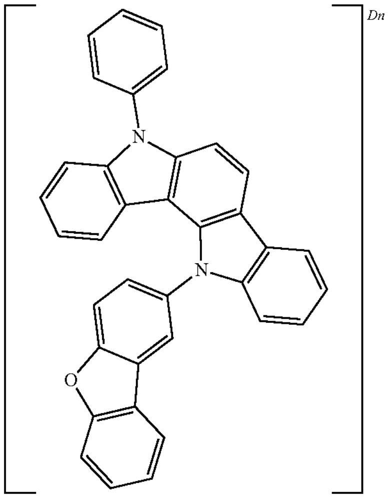
C-14
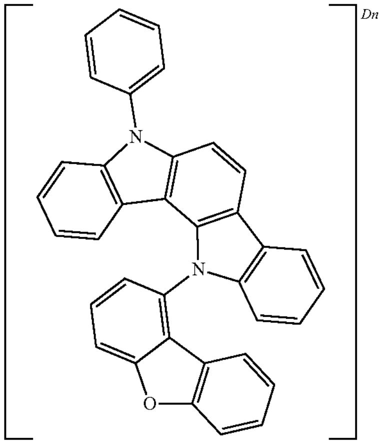
C-15
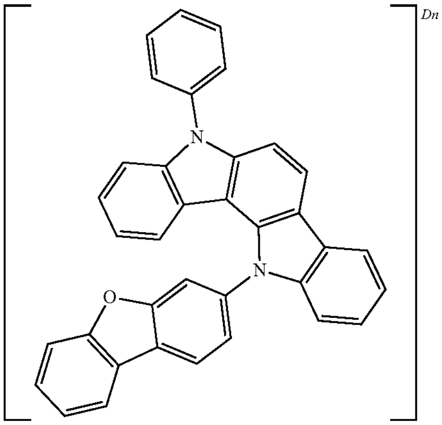

-continued
C-16
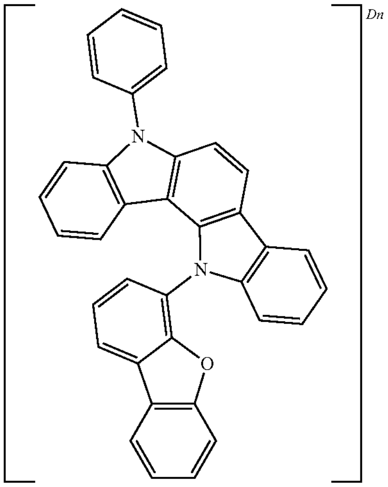
C-17
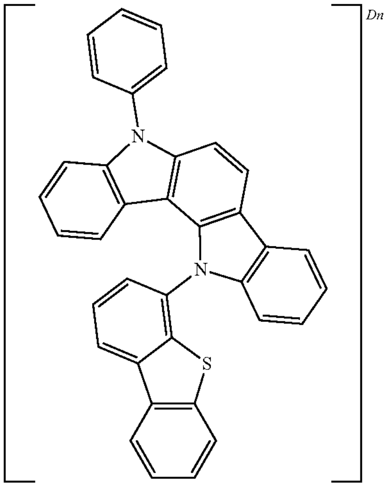
C-18
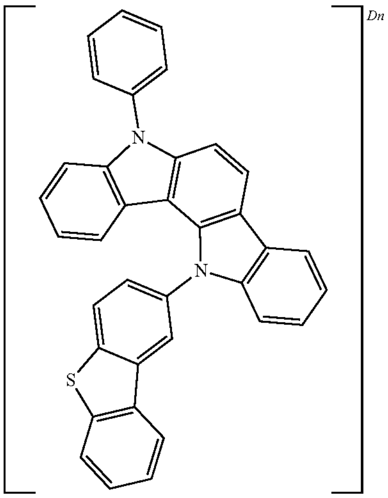
-continued
C-19
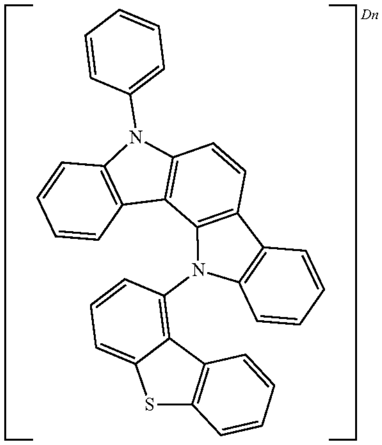
C-20
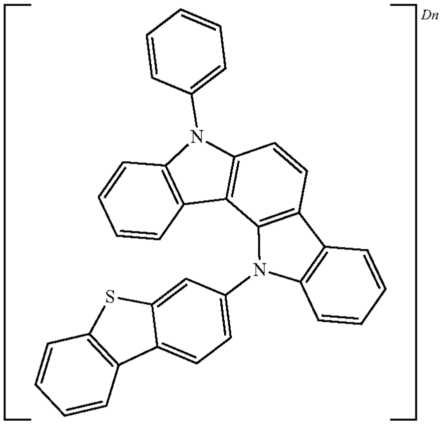
C-21
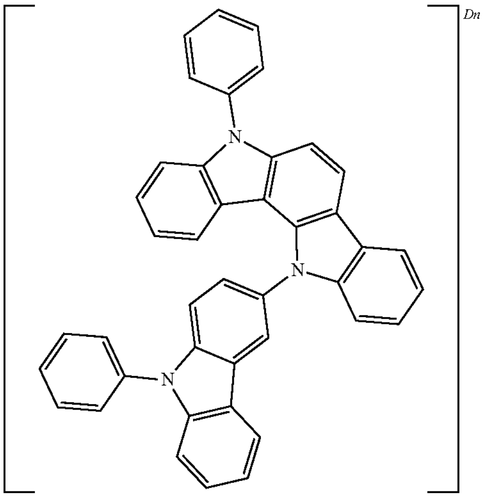

-continued
C-22
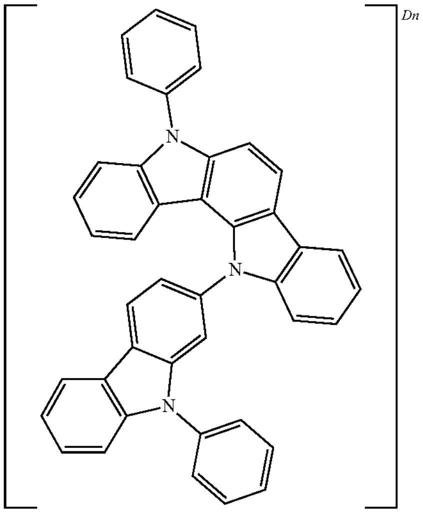
C-23
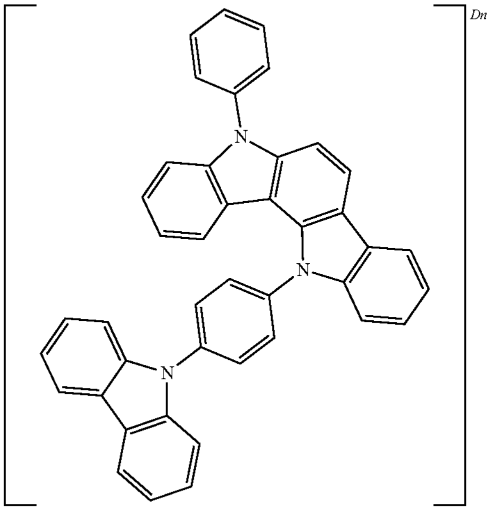
C-24
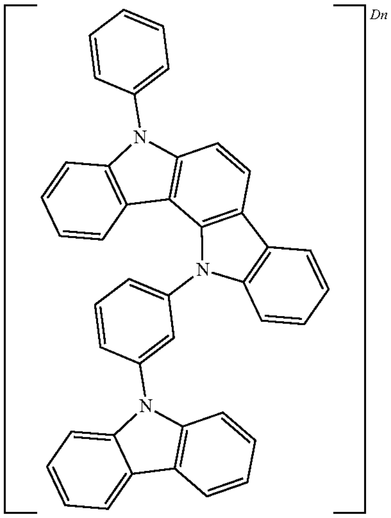
-continued
C-25
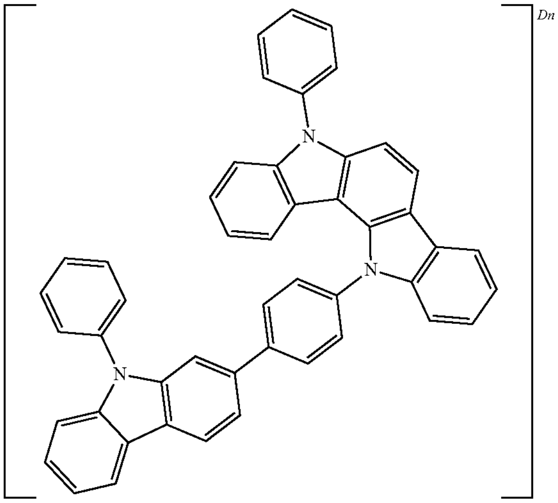
C-26
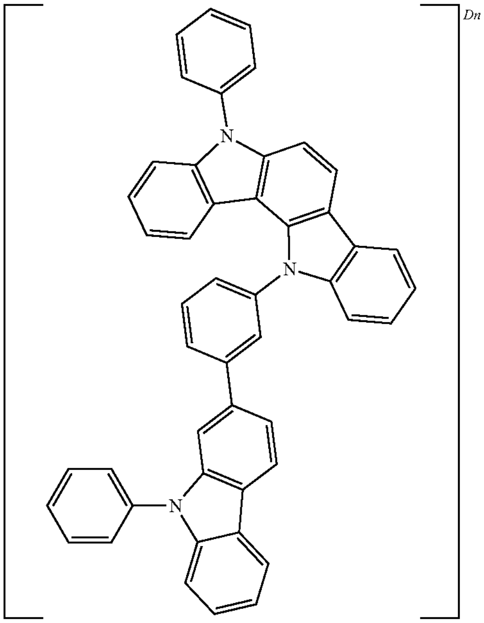

-continued
C-27
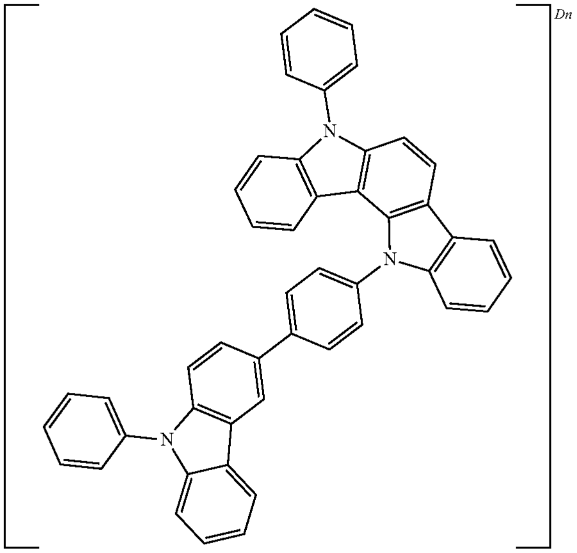
C-28
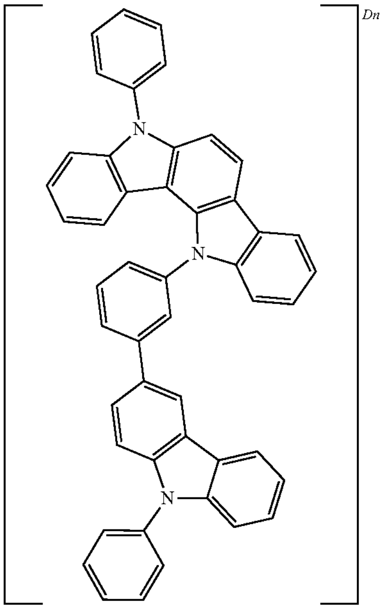
-continued
C-29
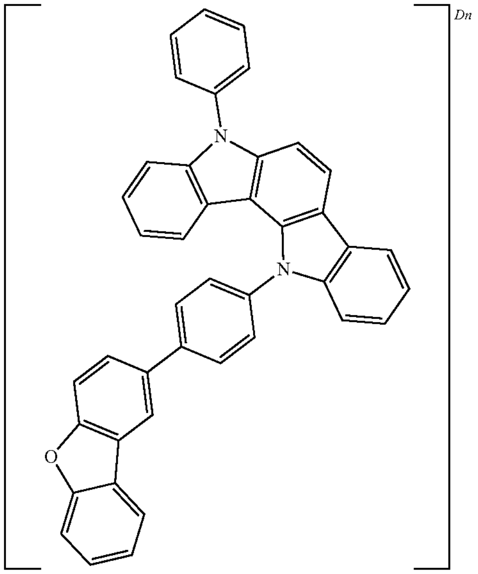
C-30
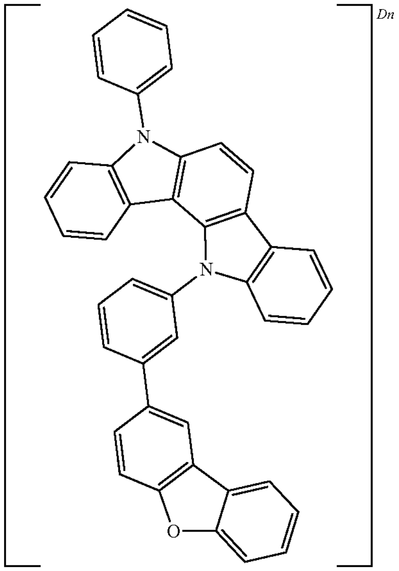

-continued
C-31
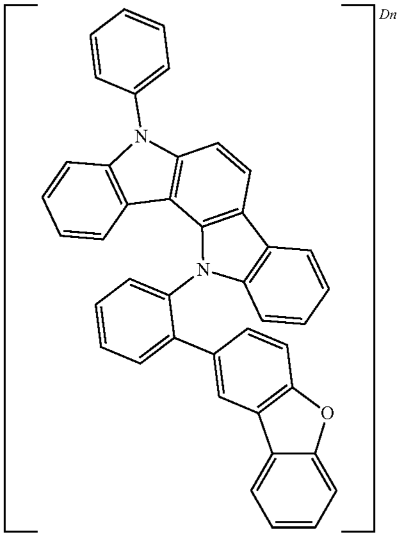
C-32
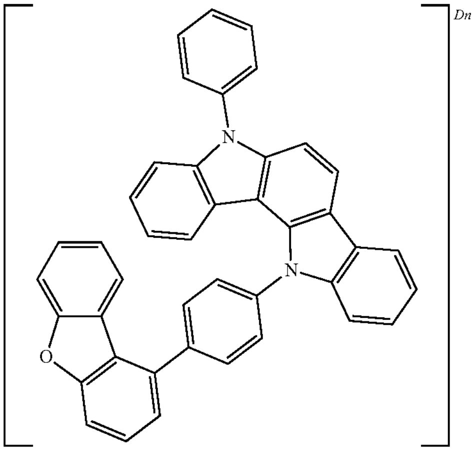
C-33
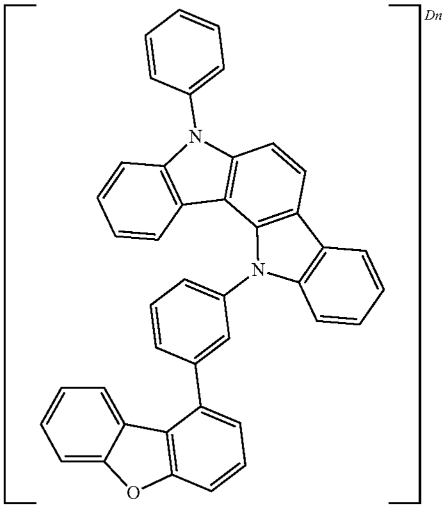
-continued
C-34
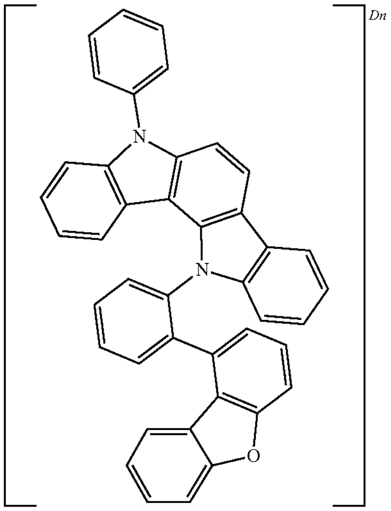
C-35
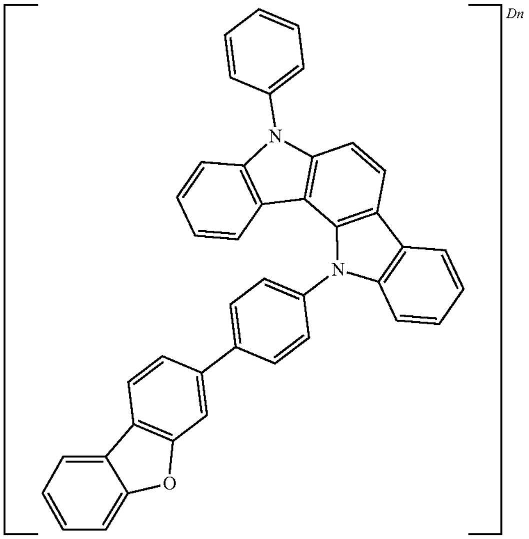

-continued
C-36
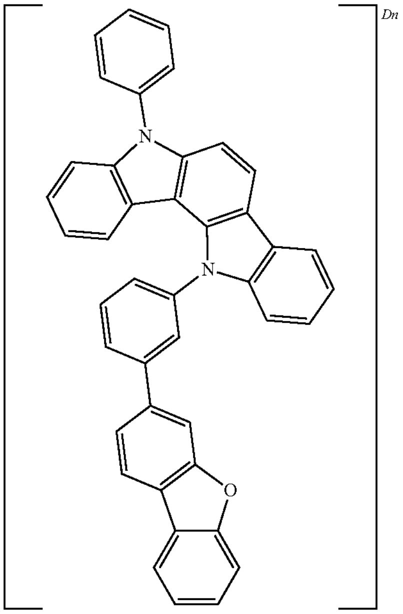
C-37
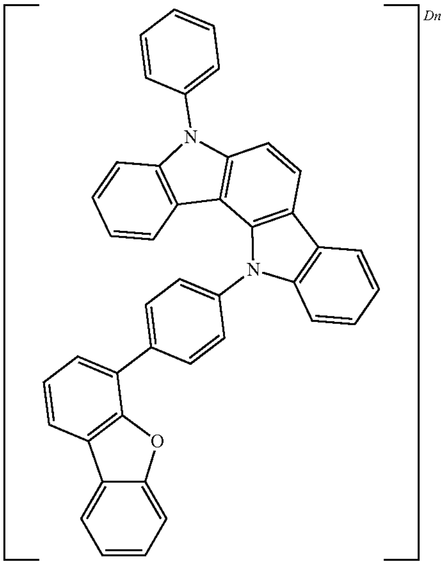
-continued
C-38
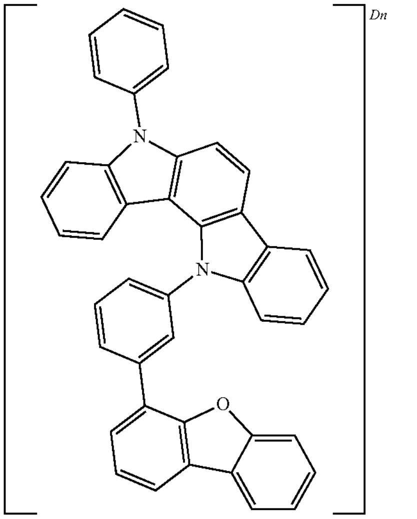
C-39
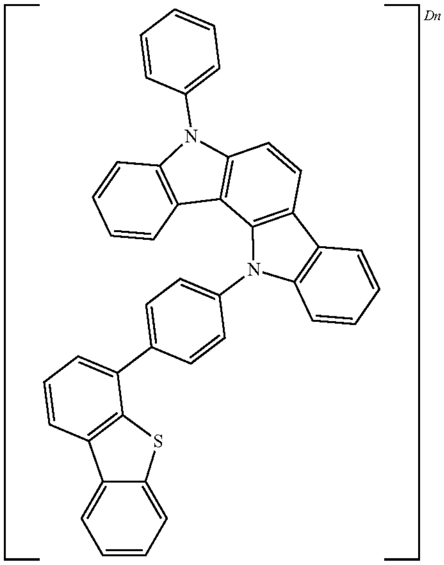
C-40
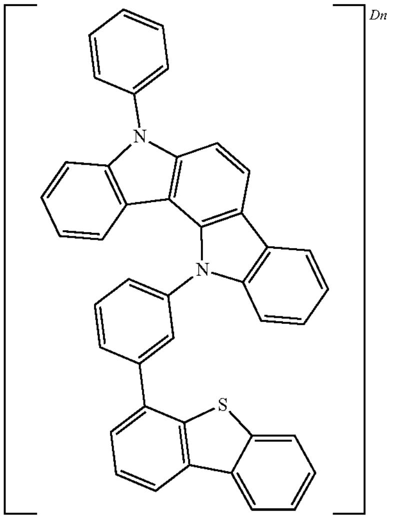

-continued
C-41
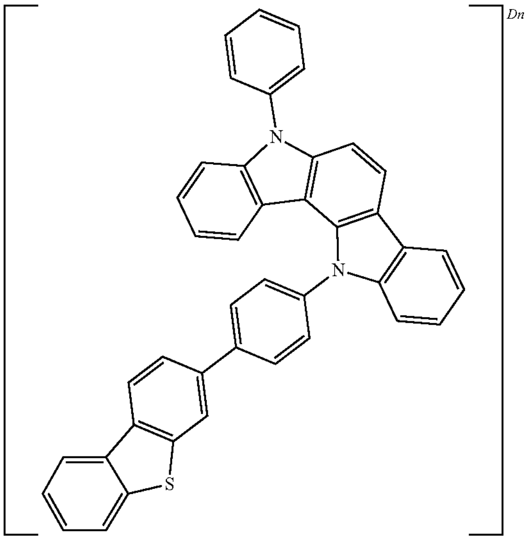
C-42
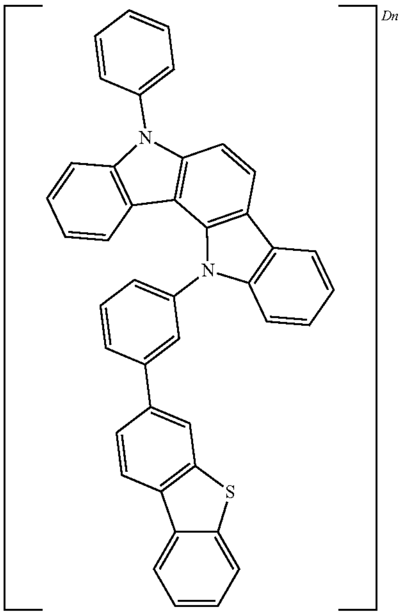
C-43
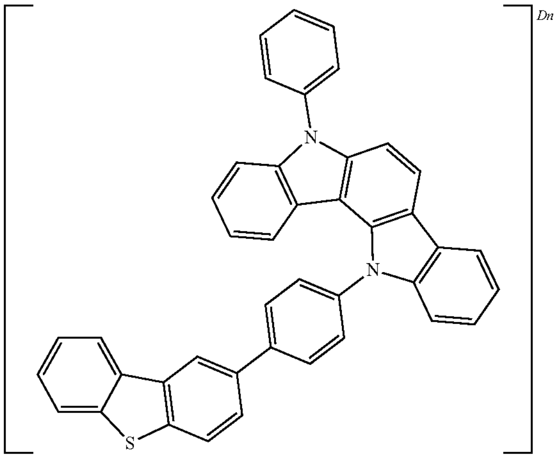
-continued
C-44
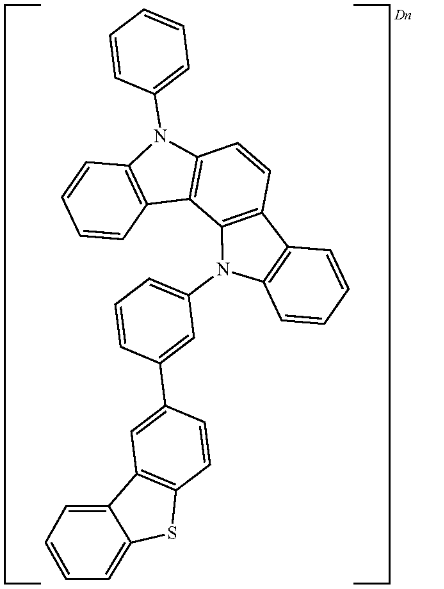
C-45
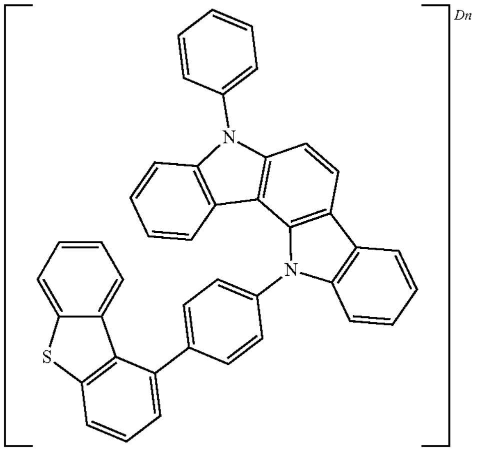
C-46
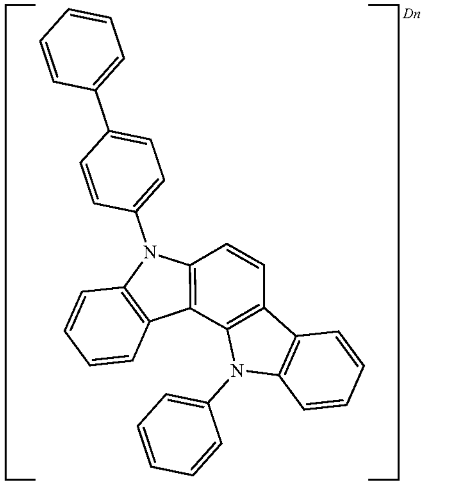

-continued
C-47
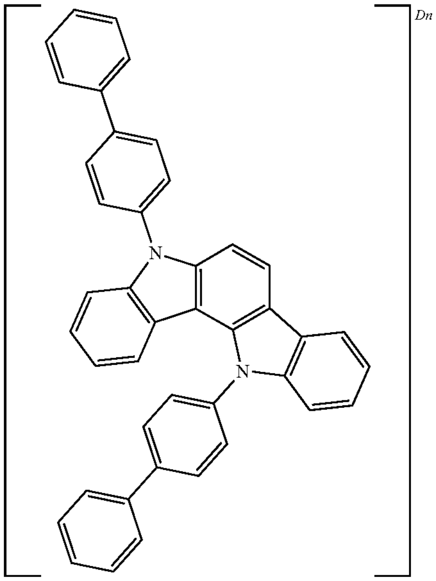
C-48
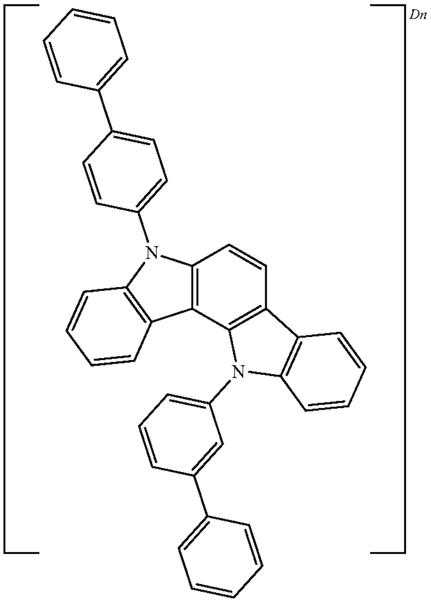
-continued
C-49
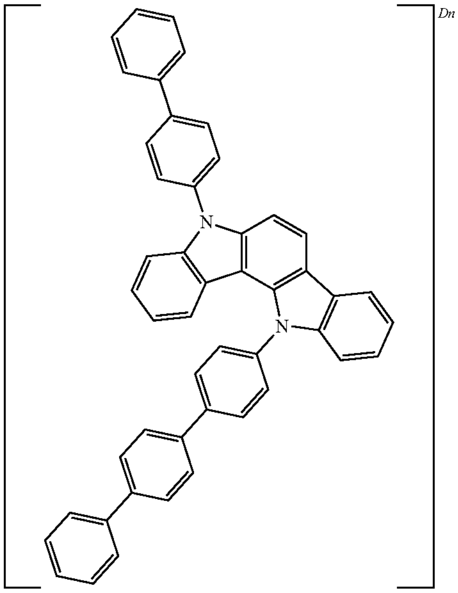
C-50
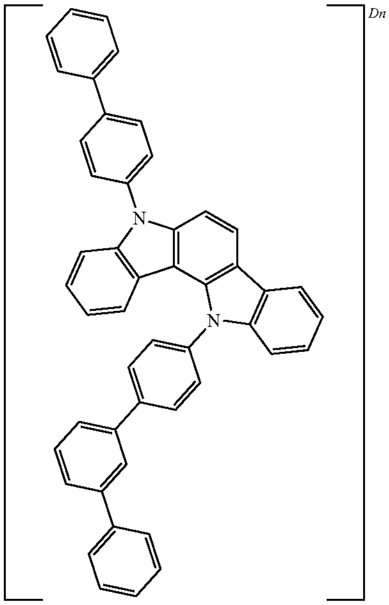

-continued
C-51
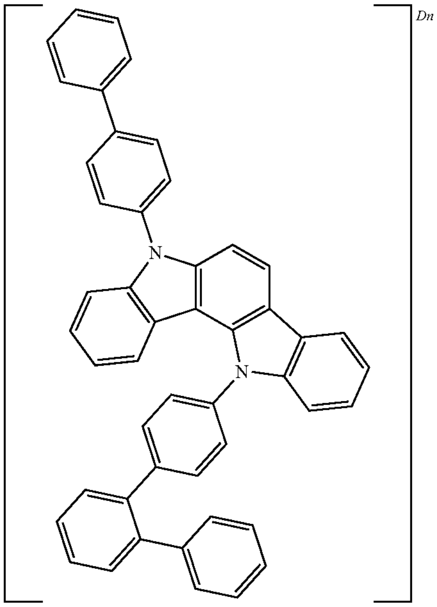
C-52
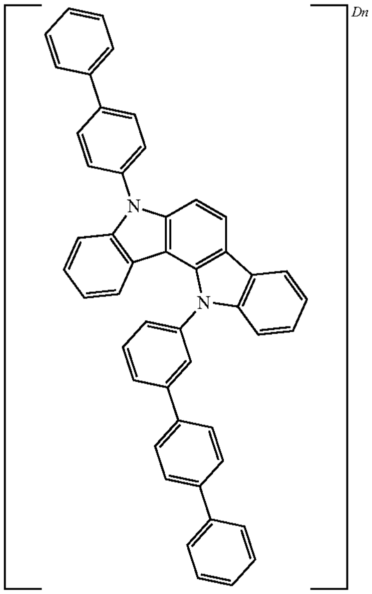
-continued
C-53
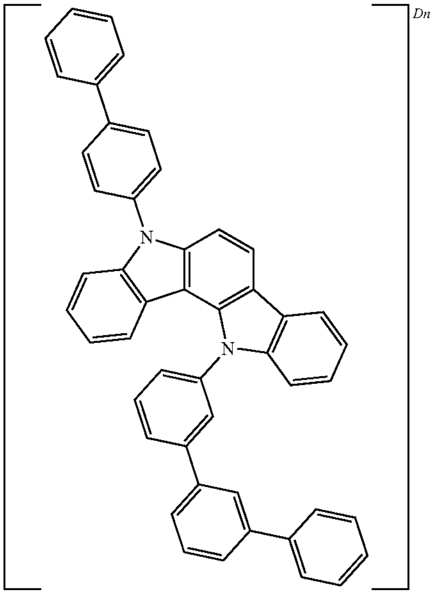
C-54
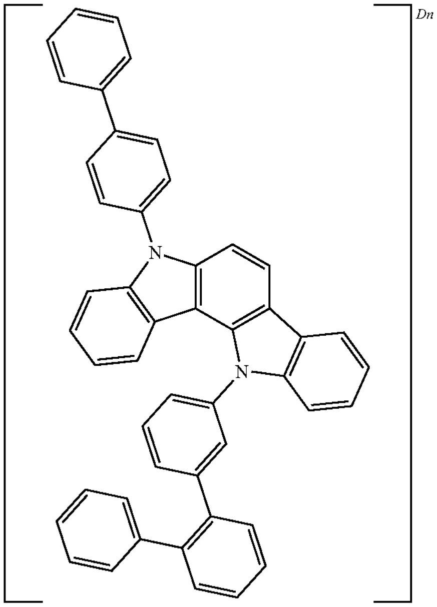

-continued
C-55
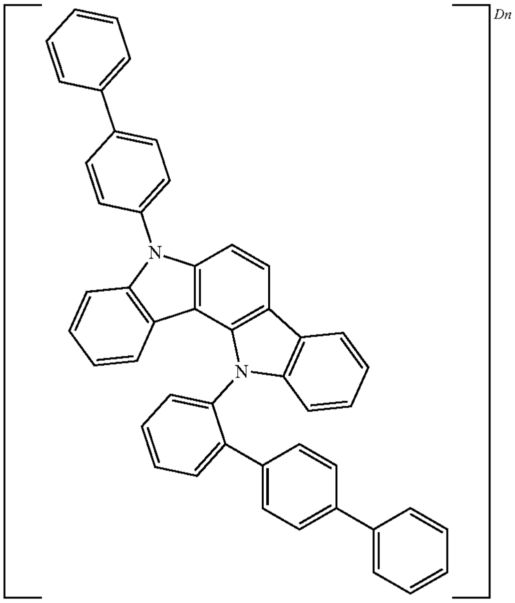
C-56
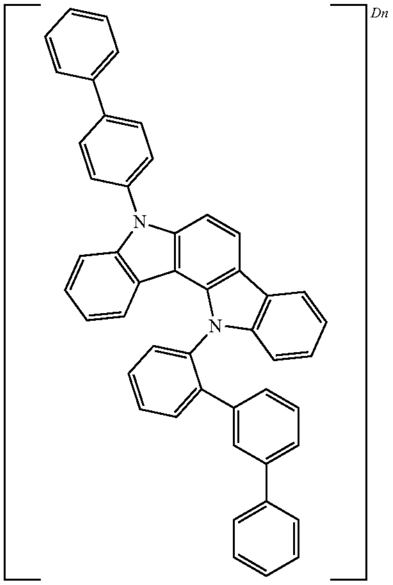
-continued
C-57
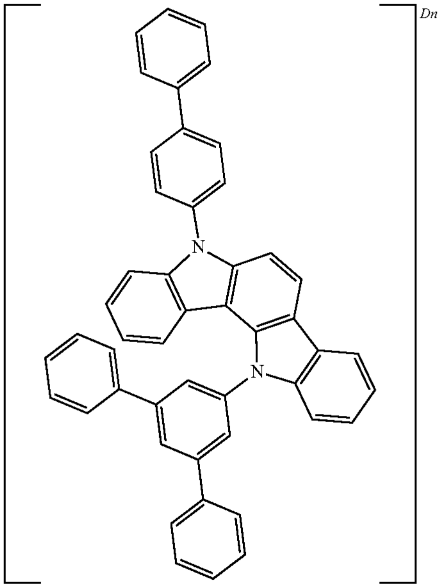
C-58
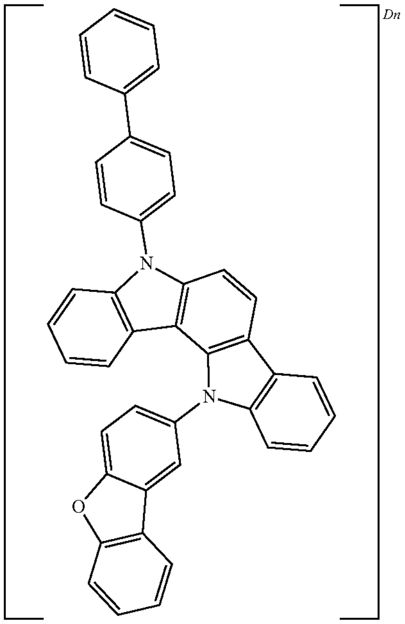

-continued
C-59
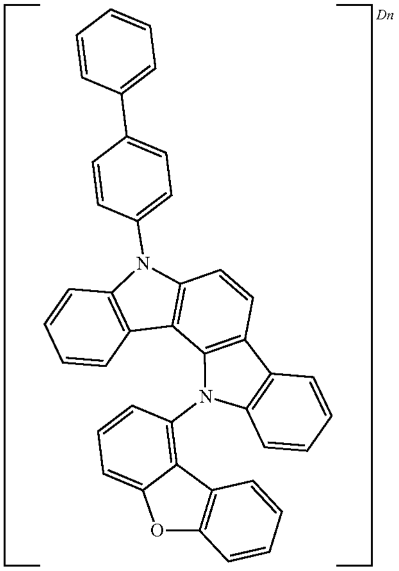
C-60
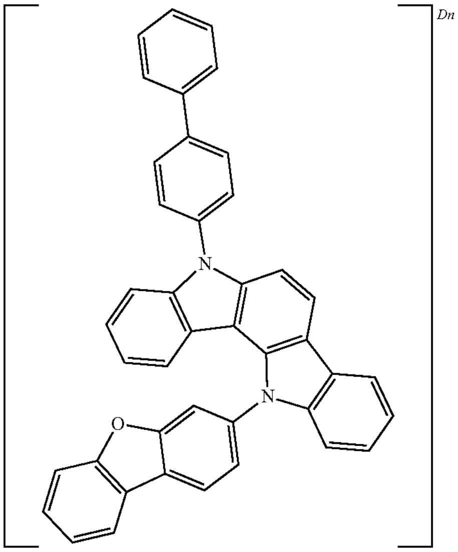
-continued
C-61
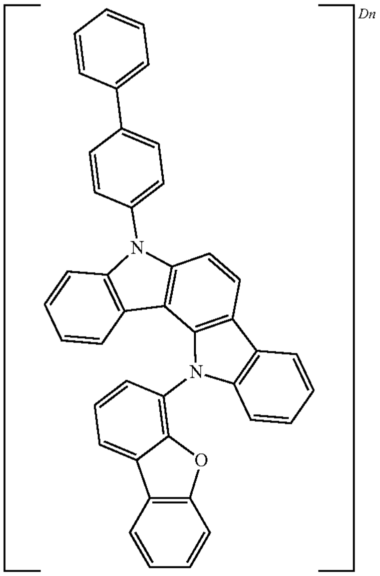
C-62
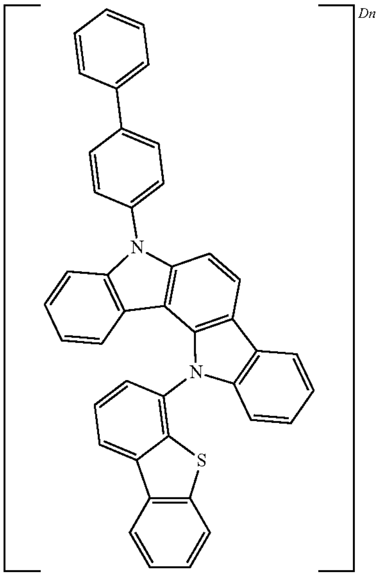

C-63
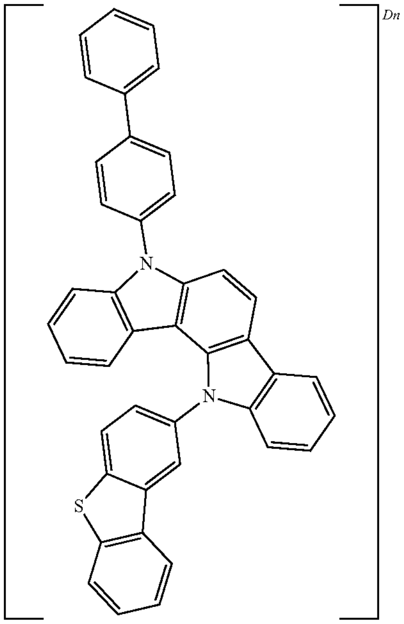
C-64
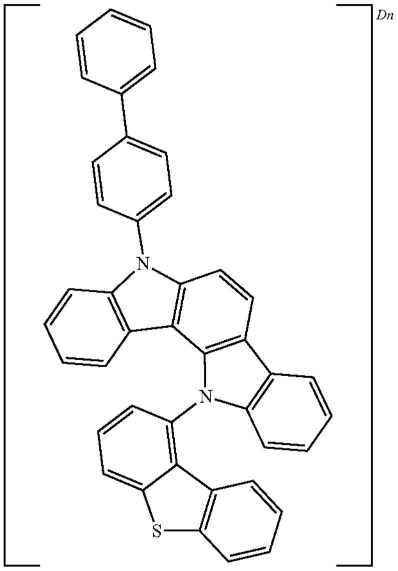
C-65
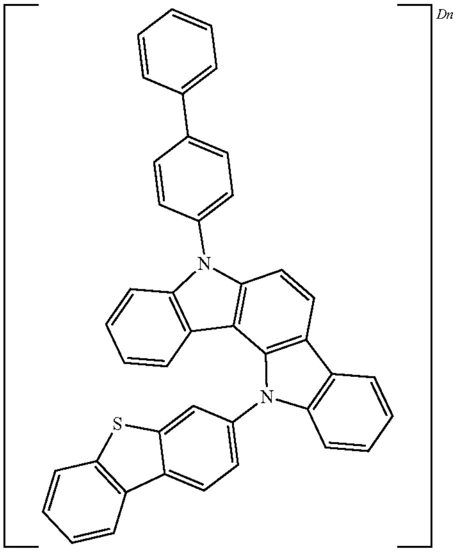
C-66
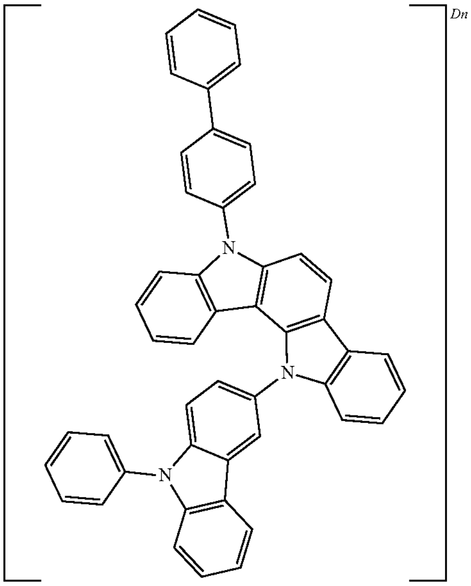

-continued
C-67
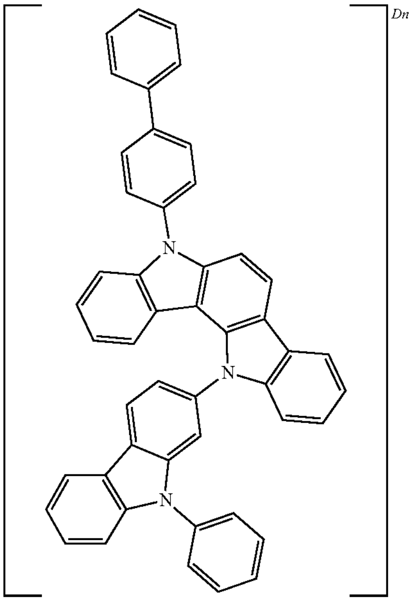
C-68
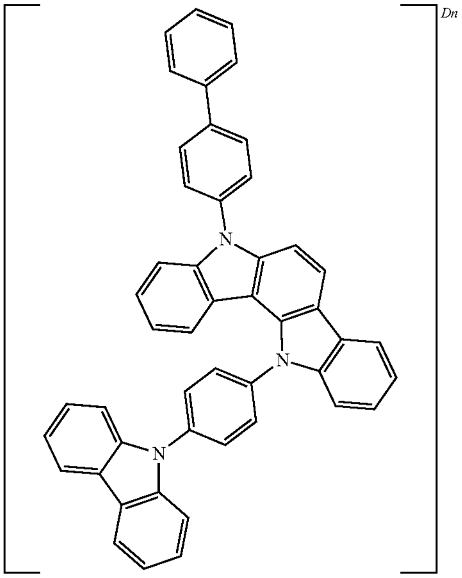
-continued
C-69
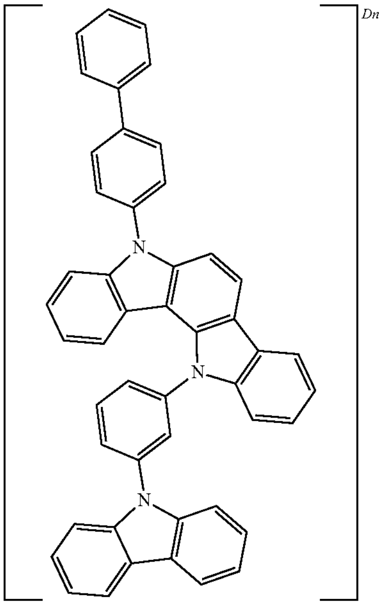
C-70
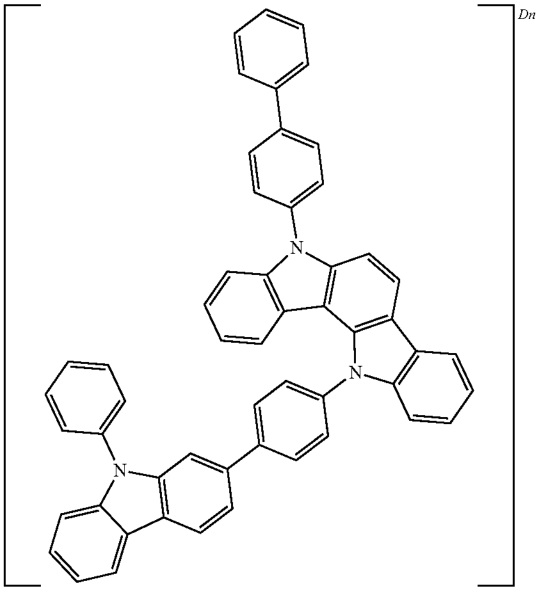

-continued
C-71
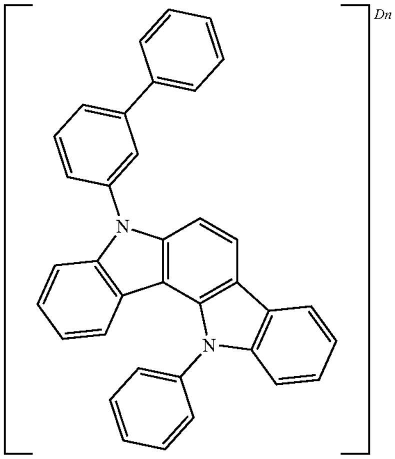
C-72
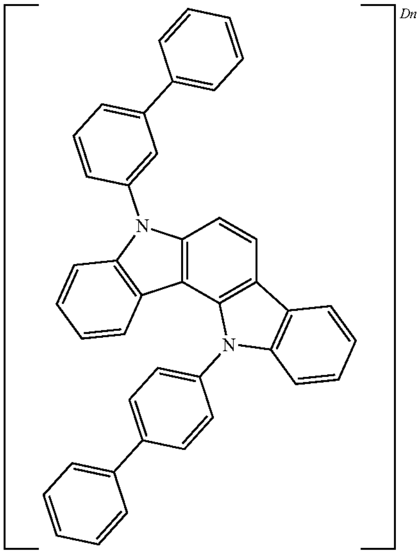
C-73
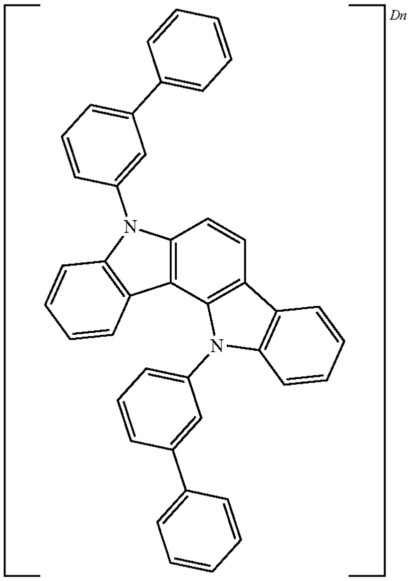
-continued
C-74
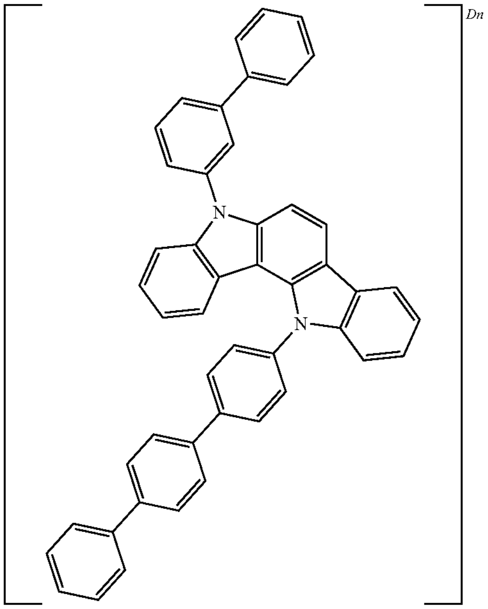
C-75
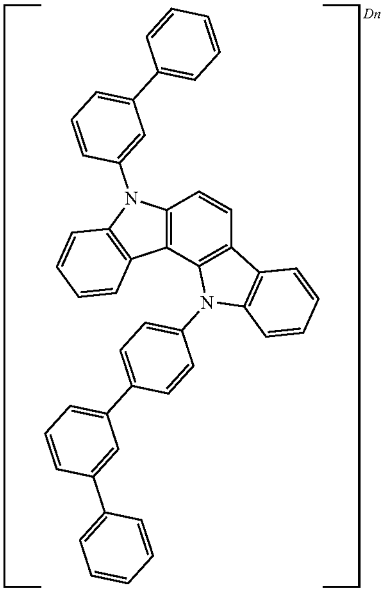

-continued
C-76
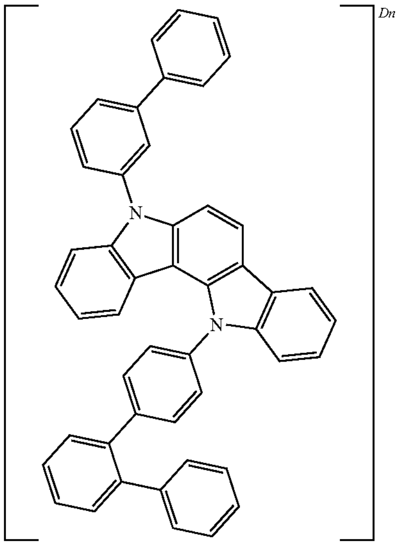
C-77
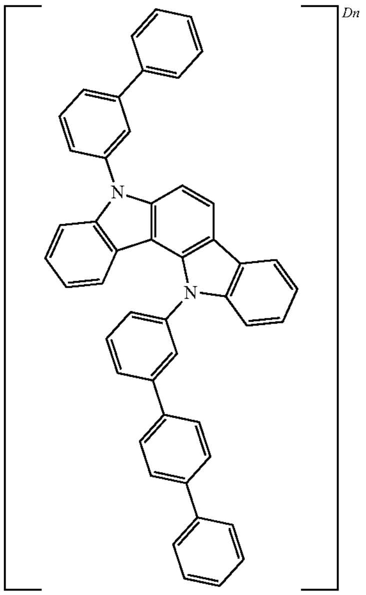
-continued
C-78
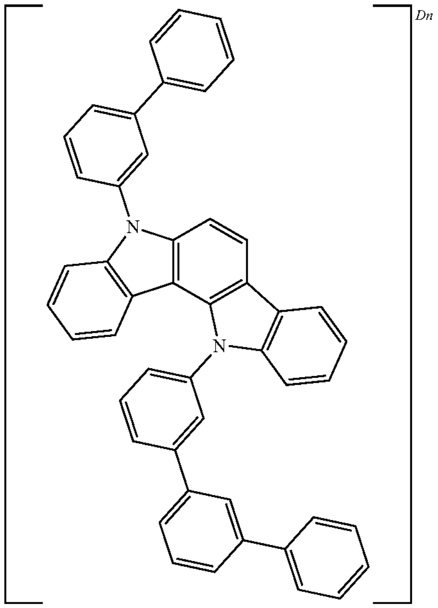
C-79
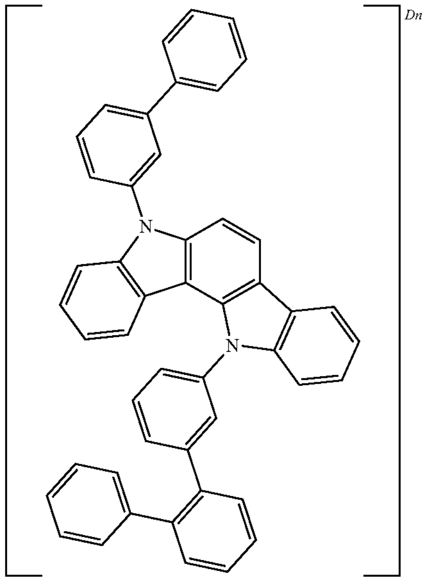

-continued
C-80
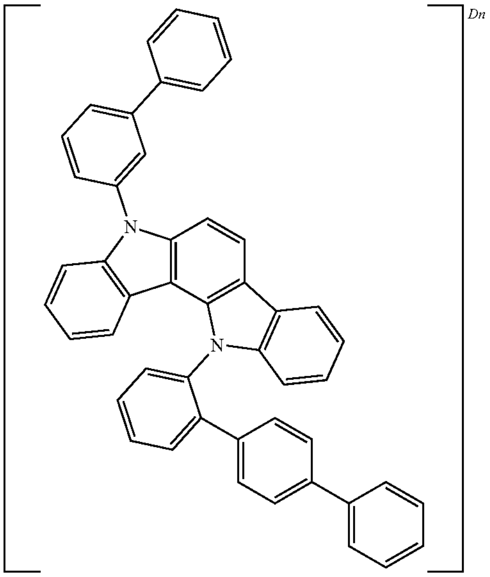
C-81
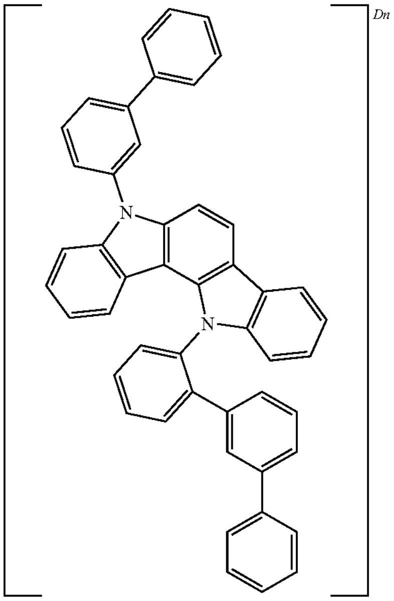
-continued
C-82
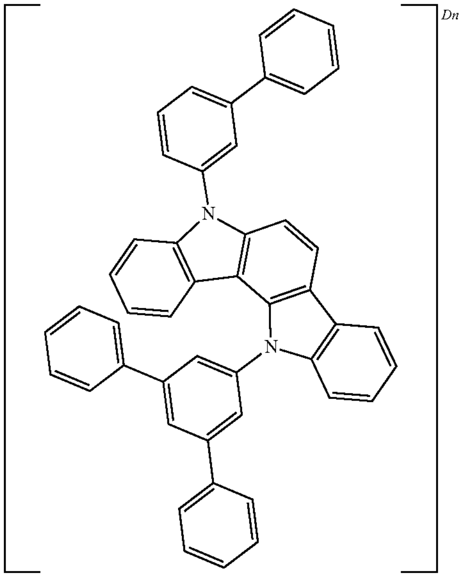
C-83
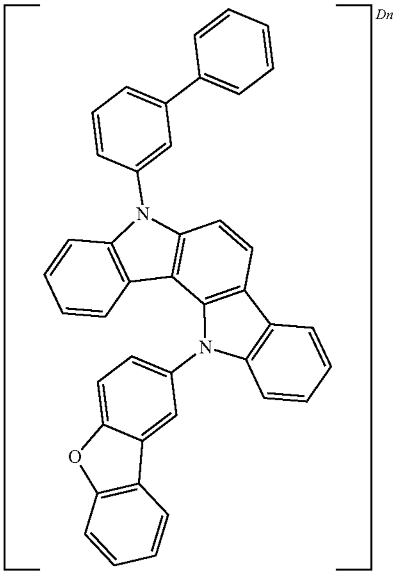

-continued
C-84
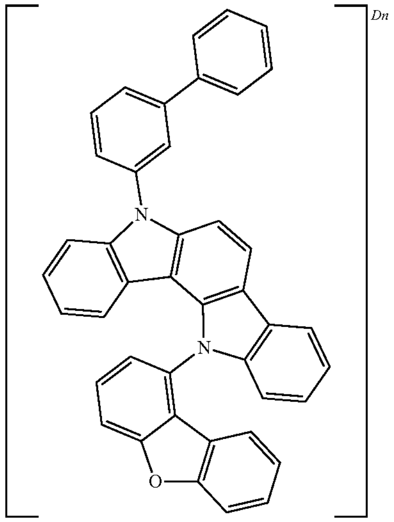
C-85
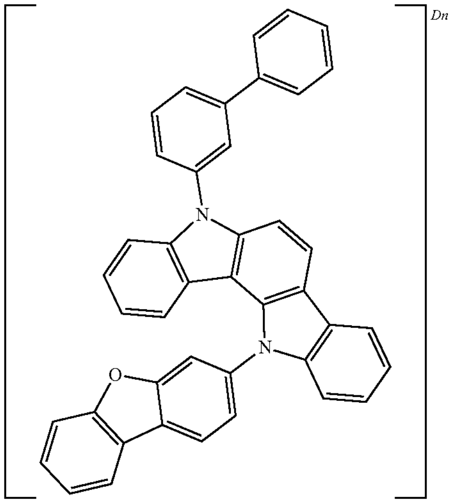
C-86
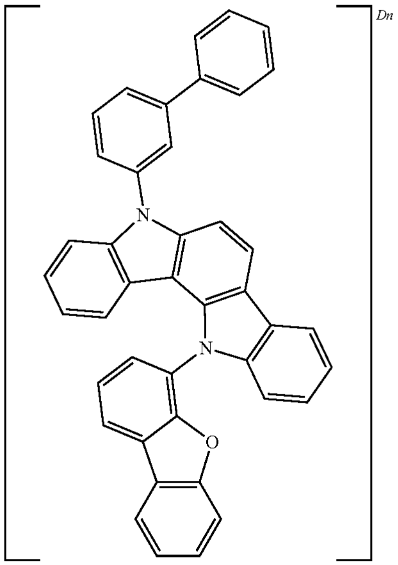
-continued
C-87
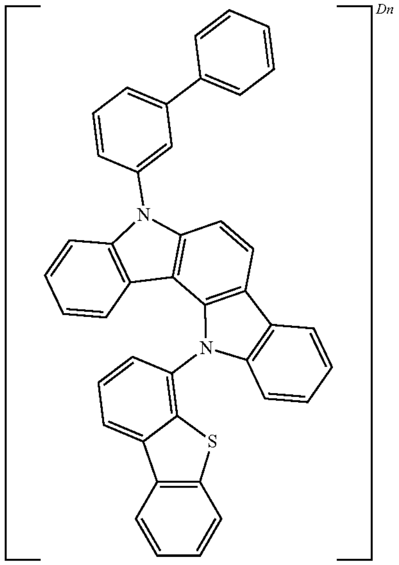
C-88
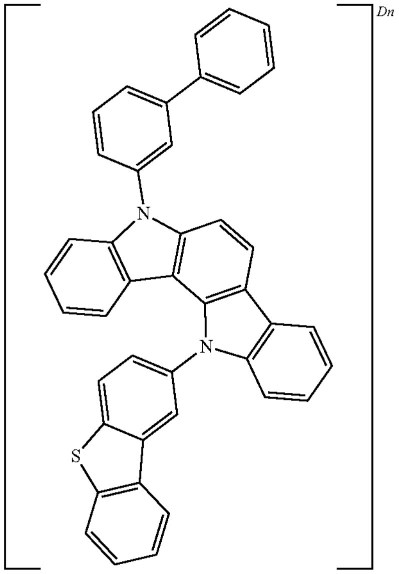
C-89
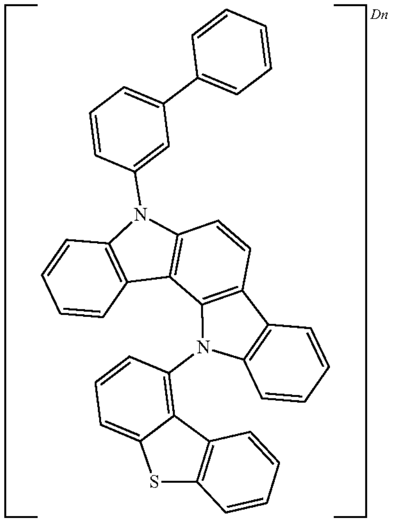

-continued
C-90
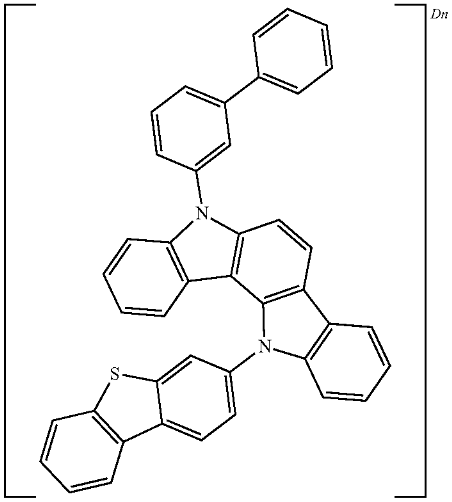
C-91
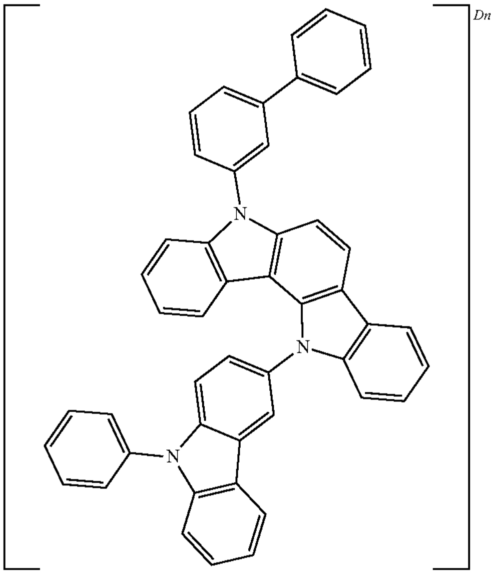
-continued
C-92
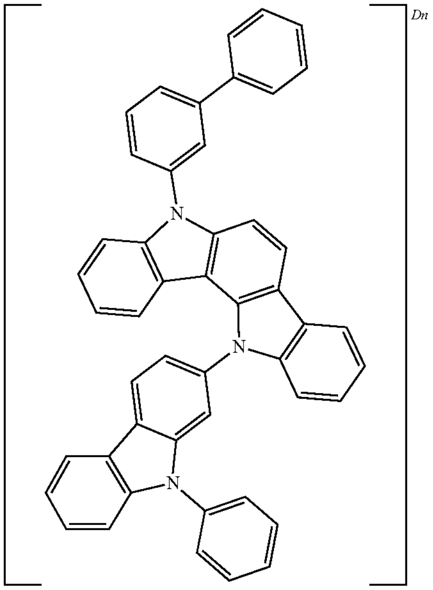
C-93
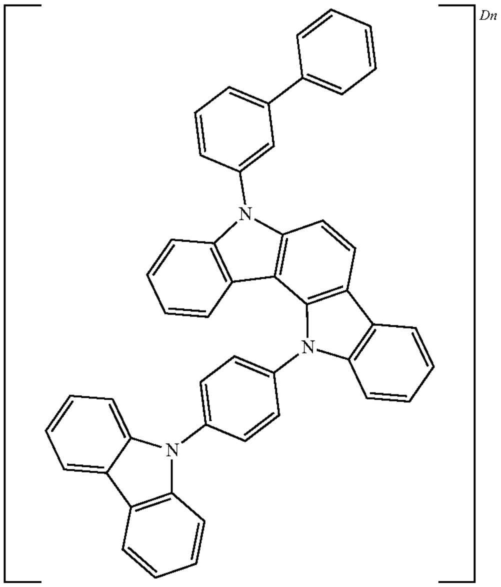

-continued
C-94
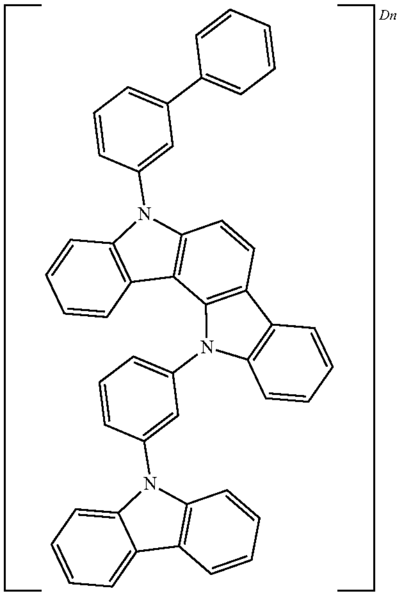
C-95
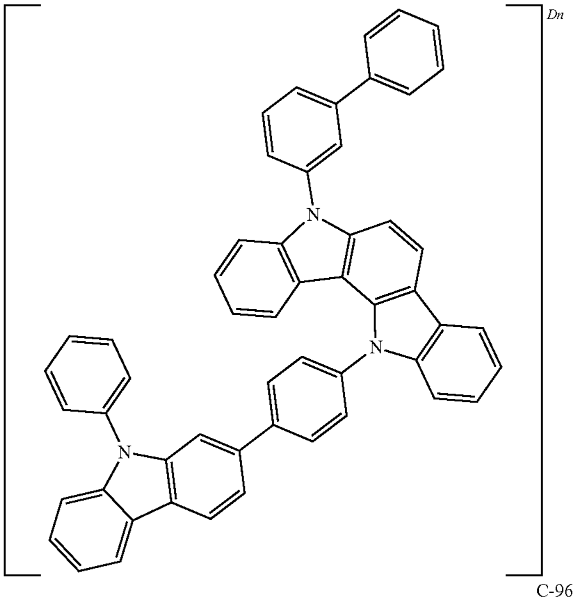
C-96
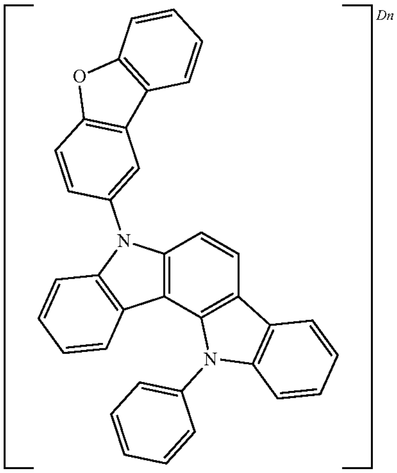
-continued
C-97
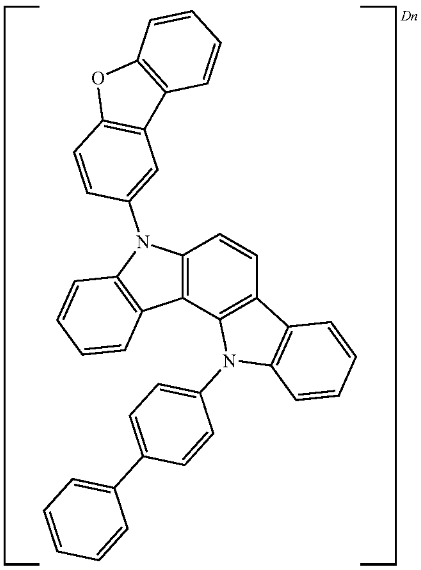
C-98
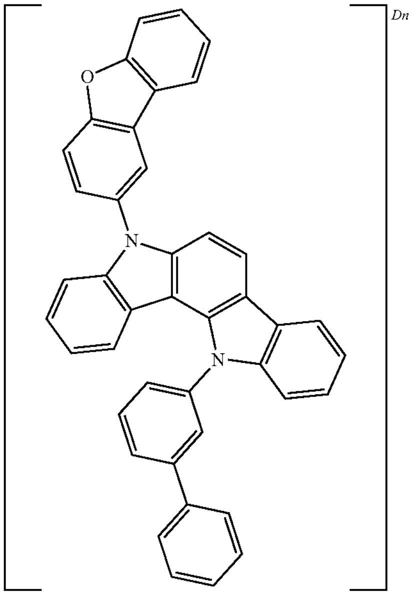

-continued
C-99
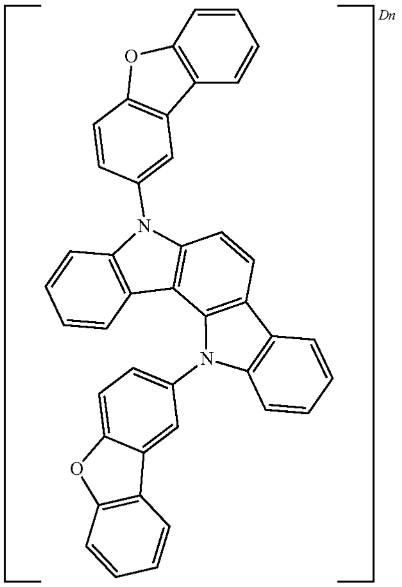
C-100
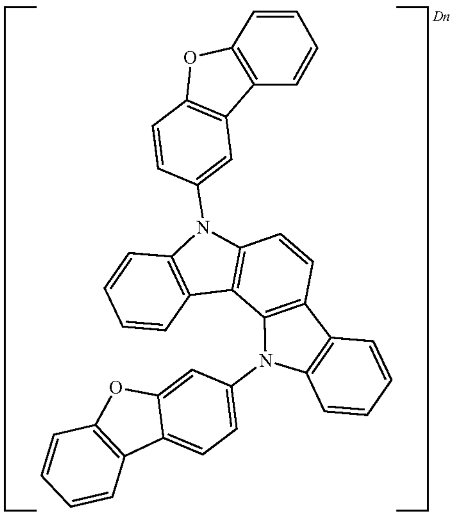
-continued
C-101
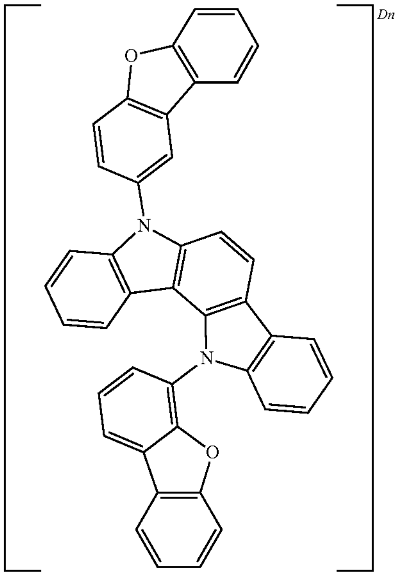
C-102
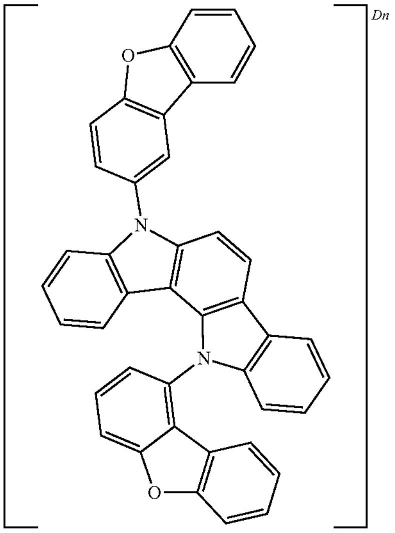

-continued
C-103
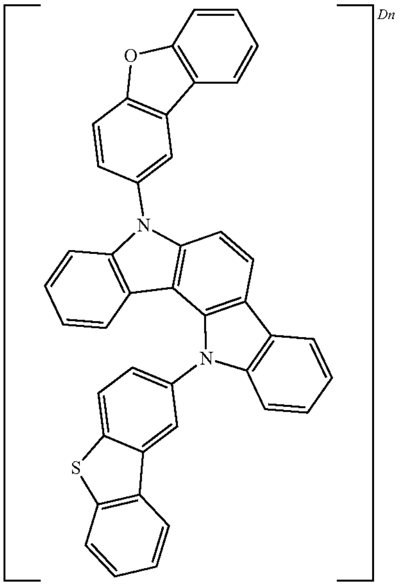
C-104
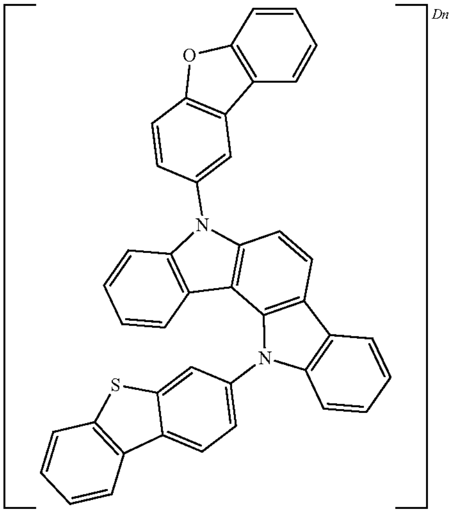
-continued
C-105
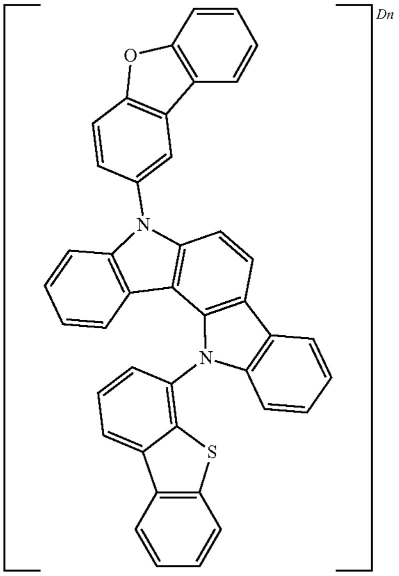
C-106
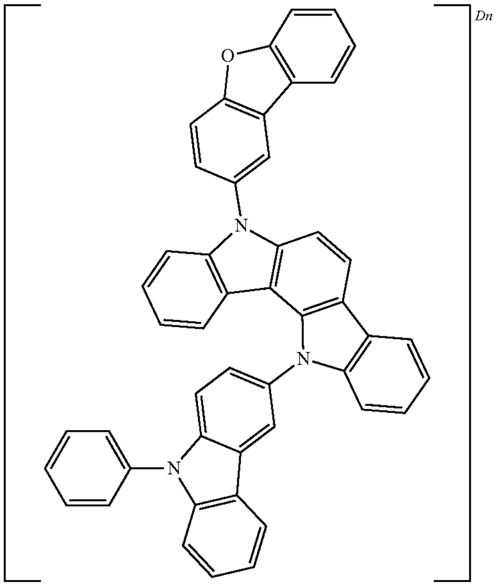

-continued
C-107
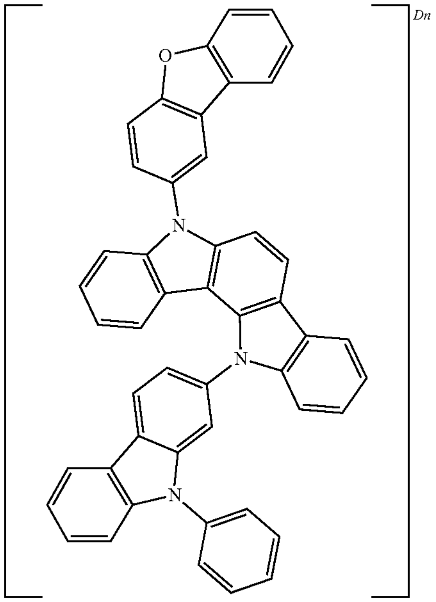
C-108
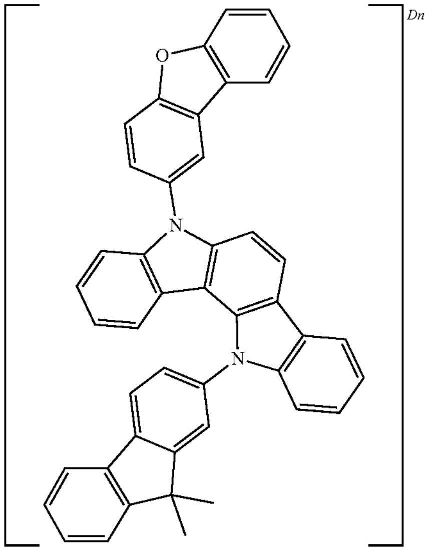
C-109
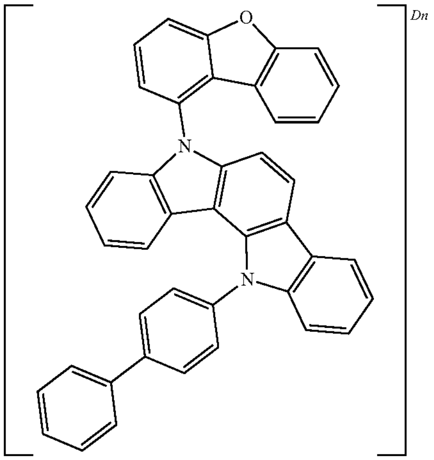
-continued
C-110
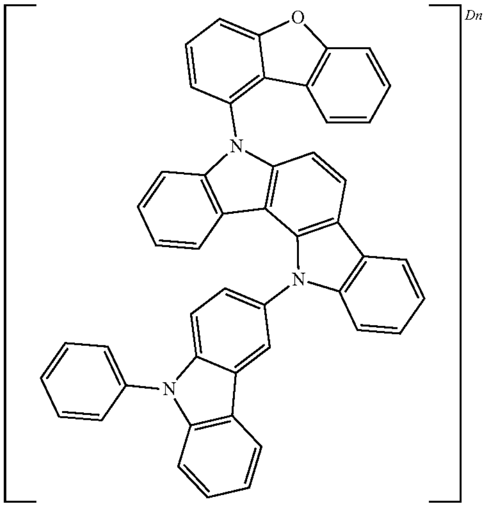
C-111
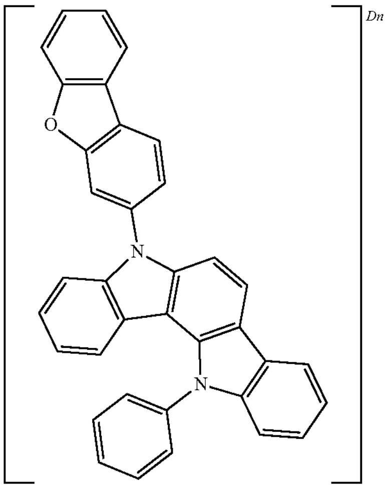
C-112
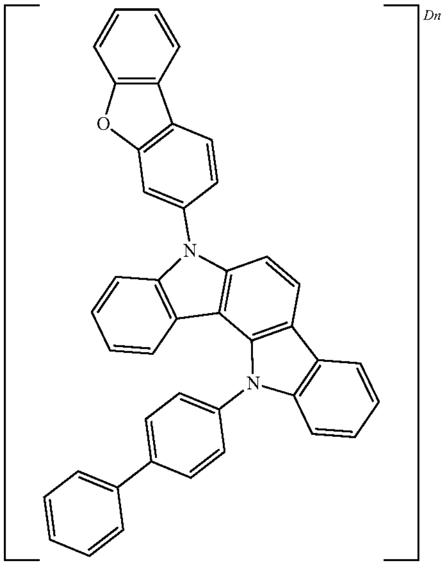

-continued
C-113
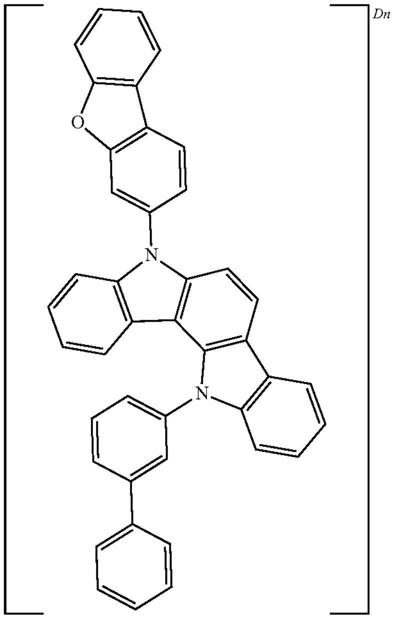
C-114
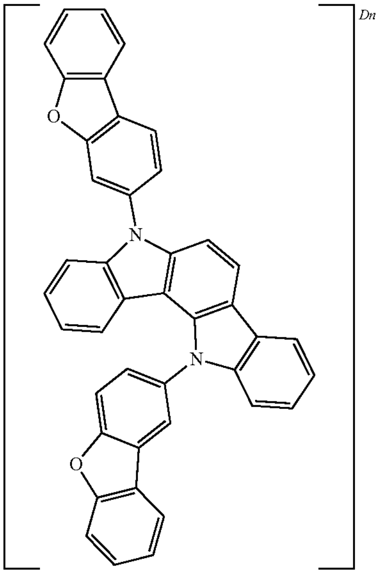
-continued
C-115
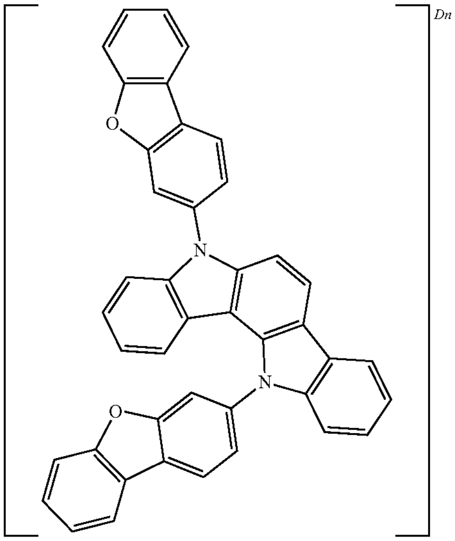
C-116
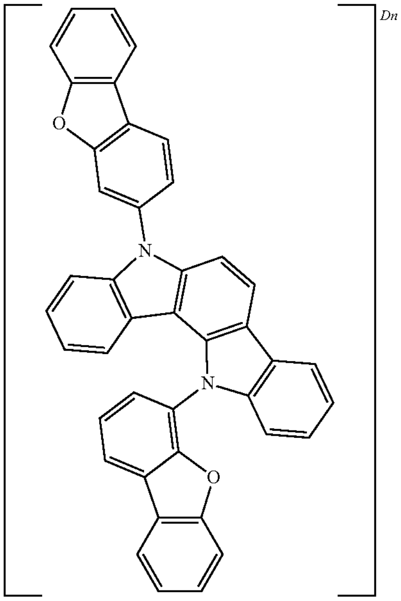

-continued
C-117
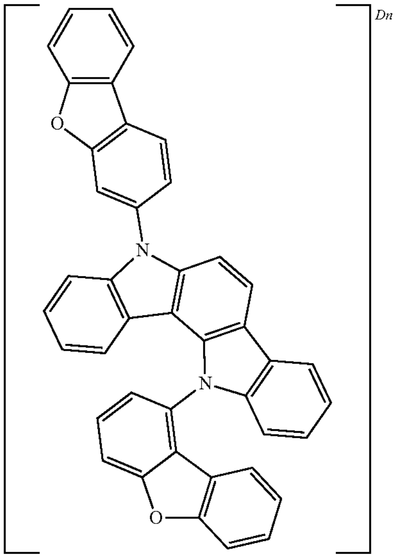
C-118
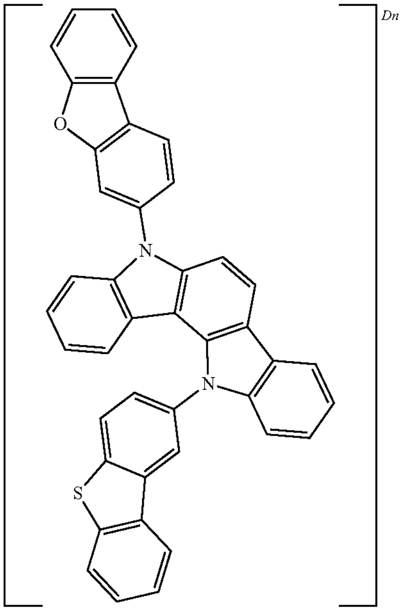
-continued
C-119
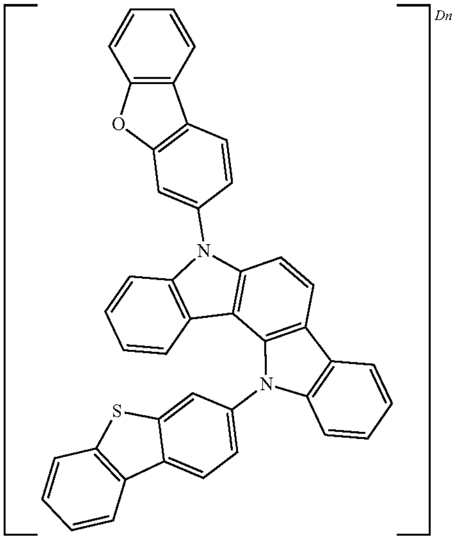
C-120
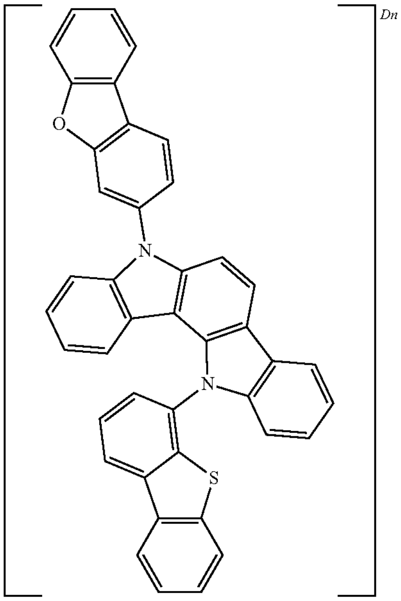
C-121
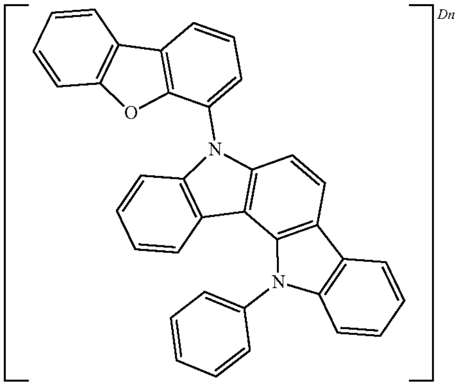

C-122
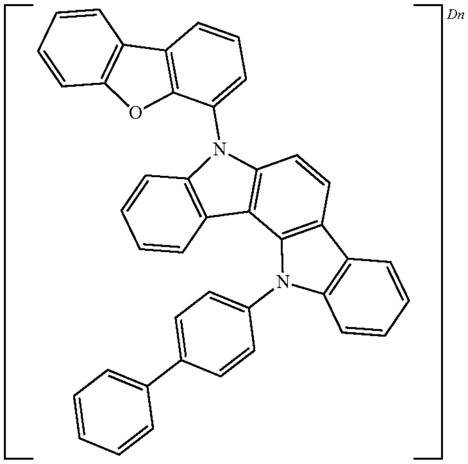
C-123
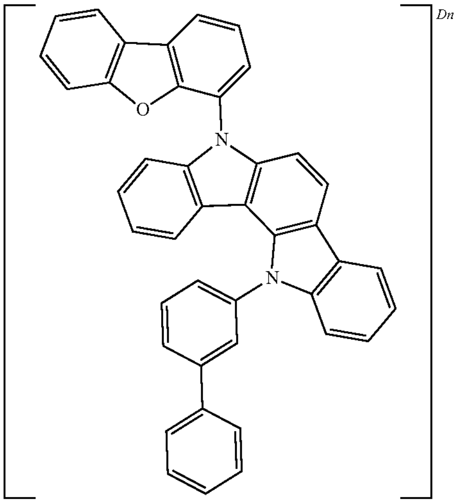
C-124
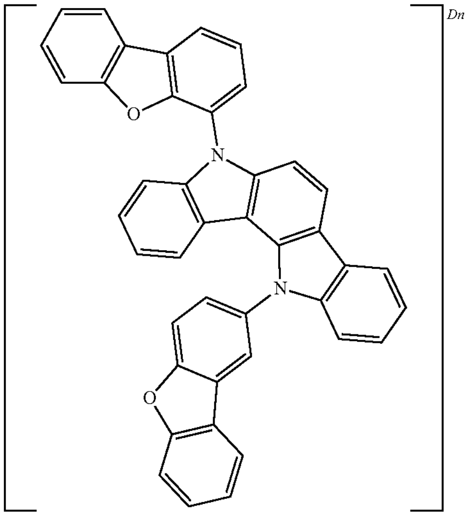
C-125
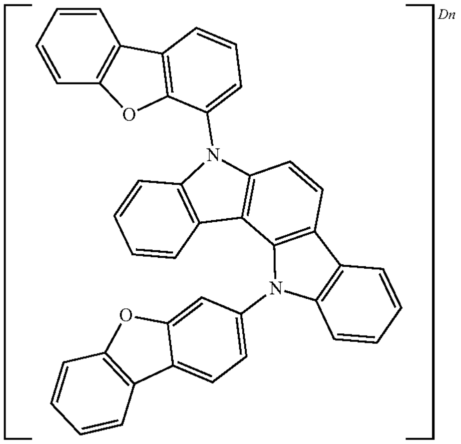
C-126
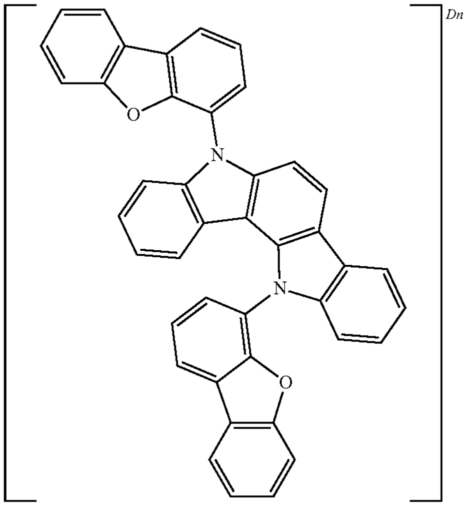
C-127
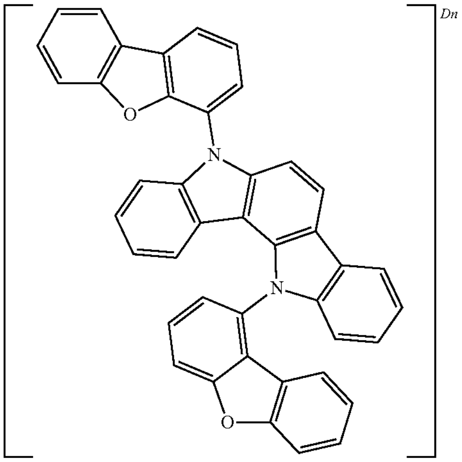

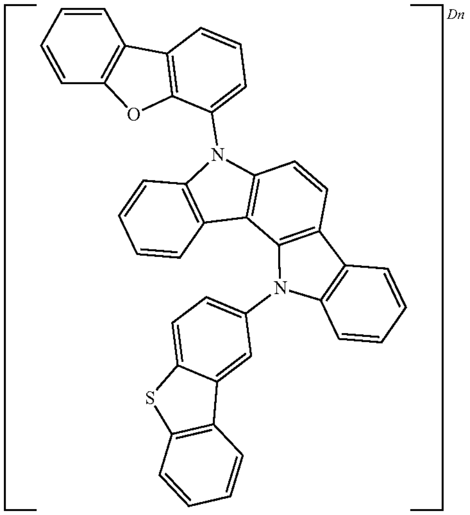
C-128
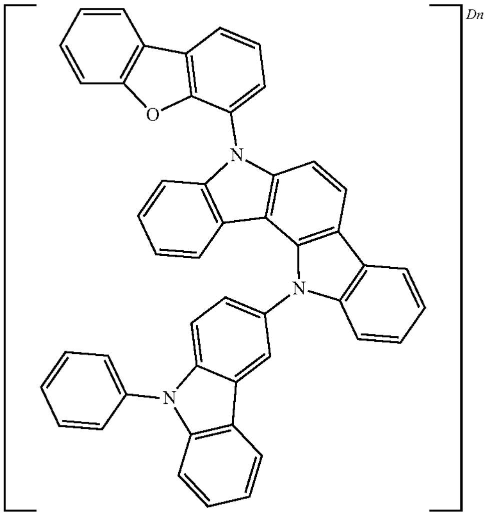
C-129
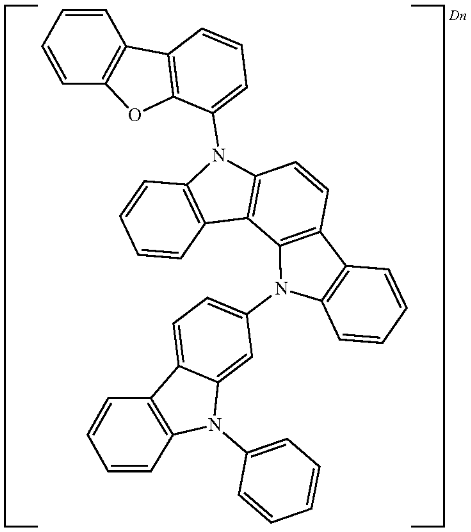
C-130
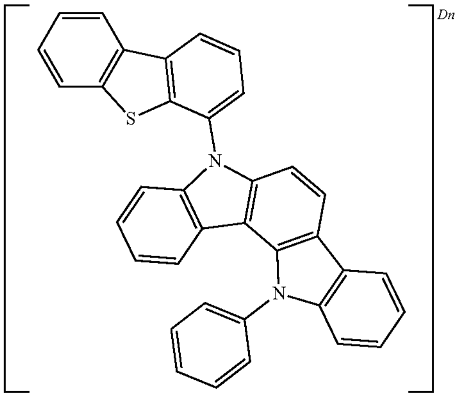
C-131
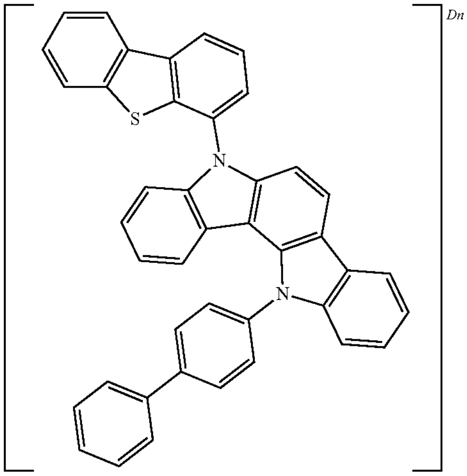
C-132
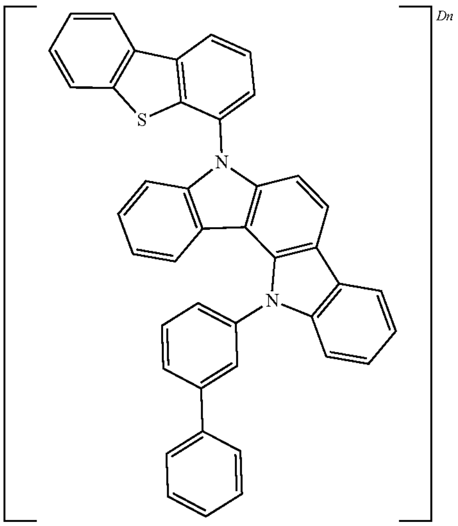
C-133

-continued
C-134
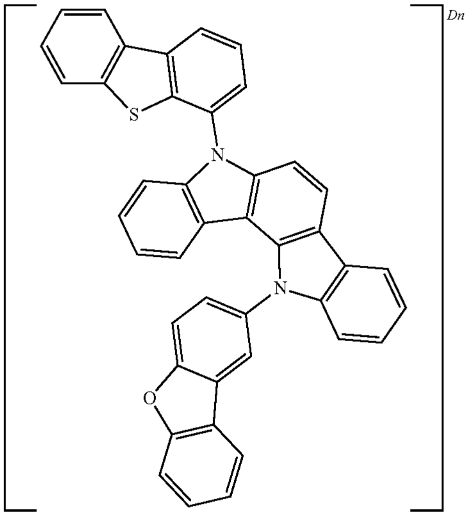
C-135
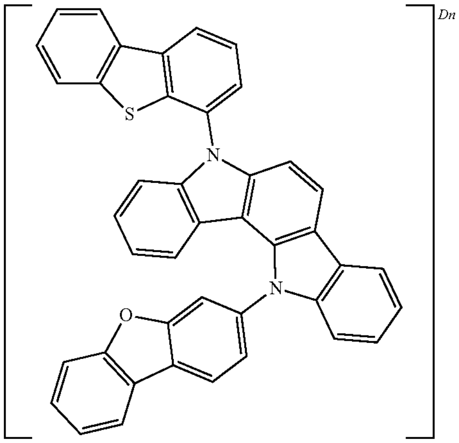
C-136
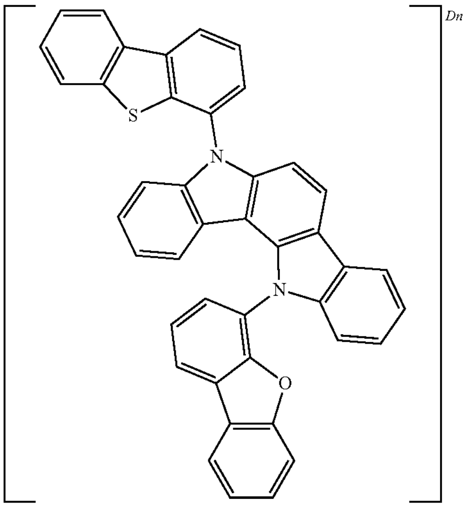
-continued
C-137
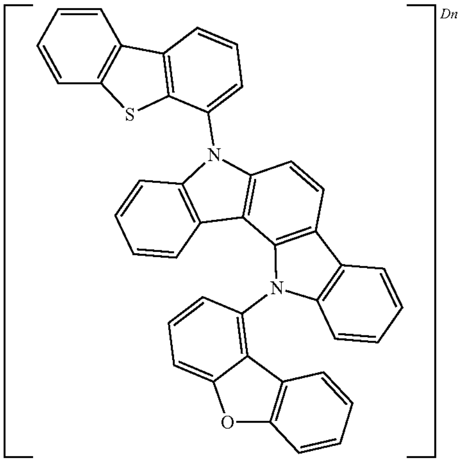
C-138
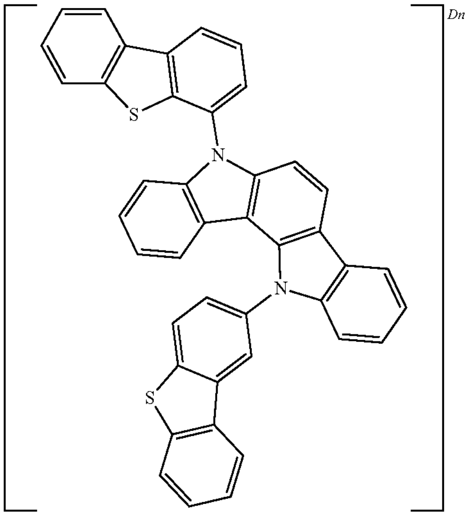
C-139
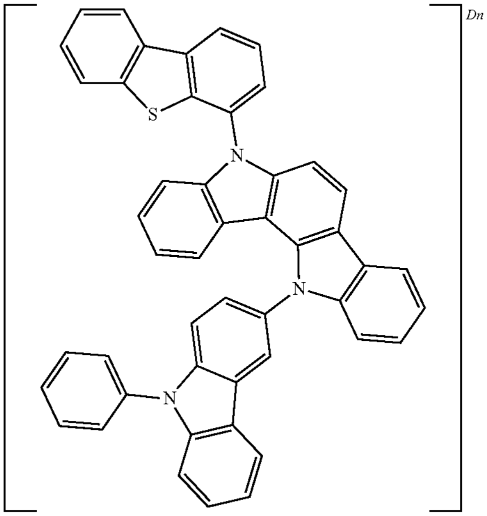

-continued
C-140
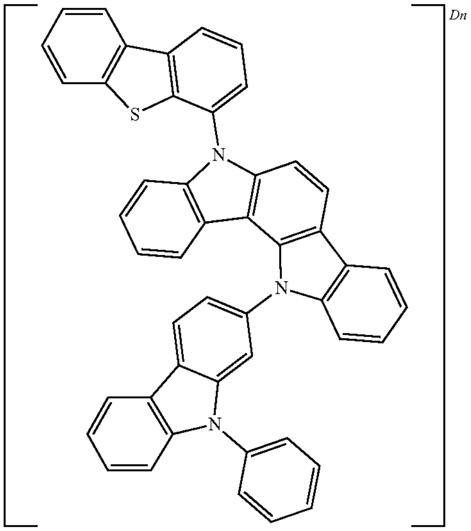
C-141
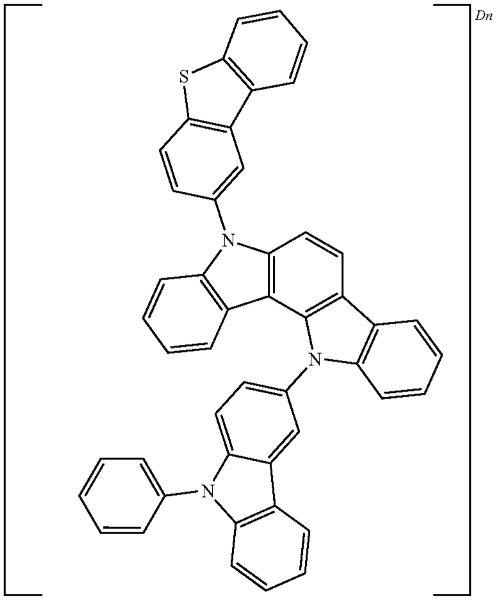
-continued
C-142
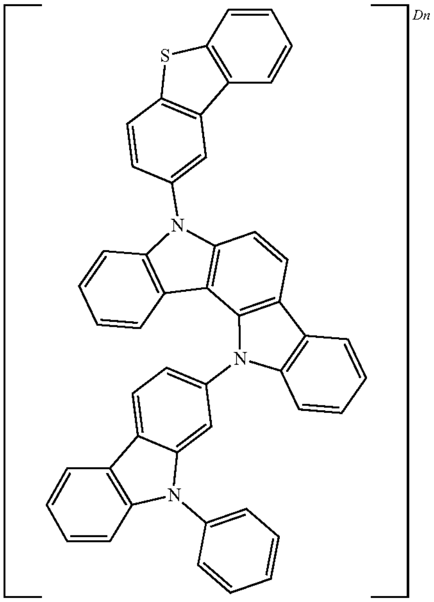
C-143
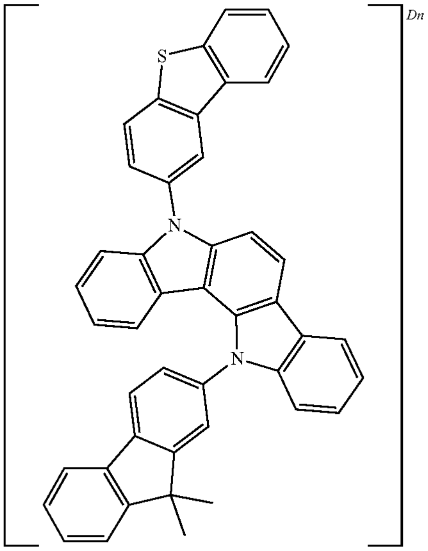
C-144
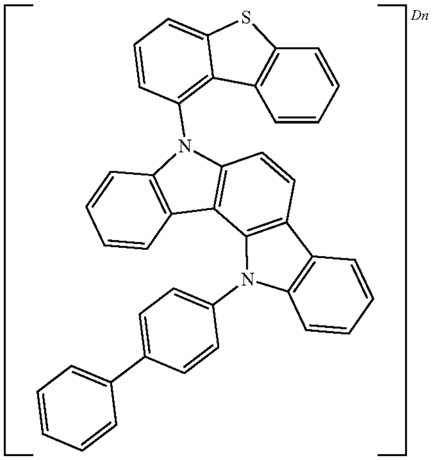

-continued
C-145
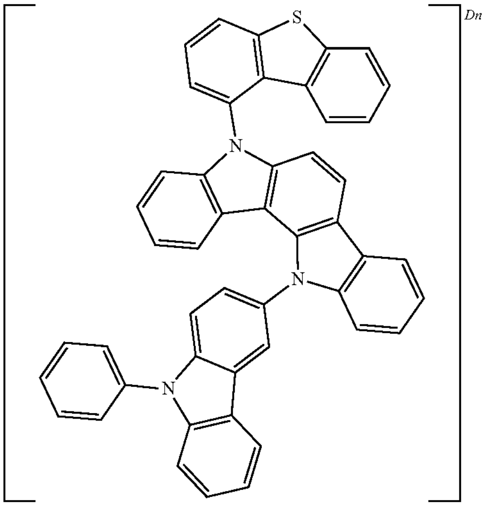
C-146
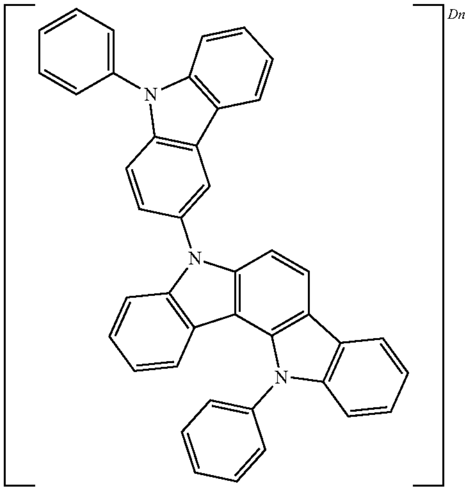
C-147
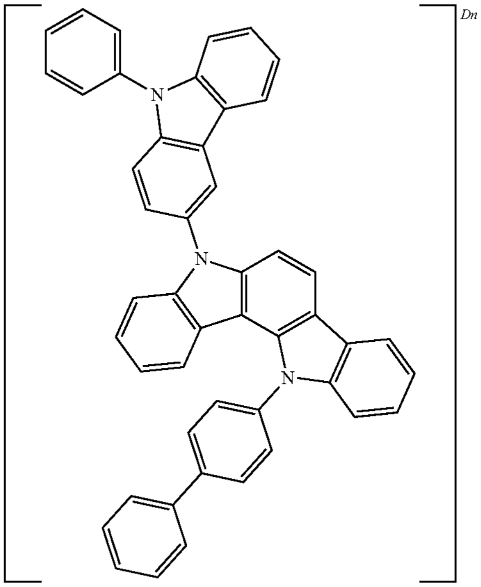
-continued
C-148
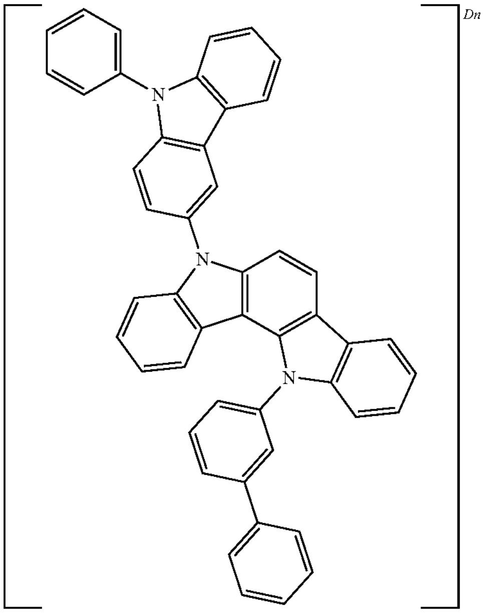
C-149
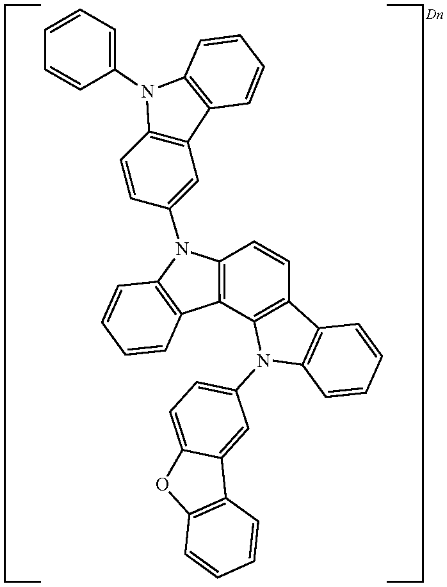

C-150
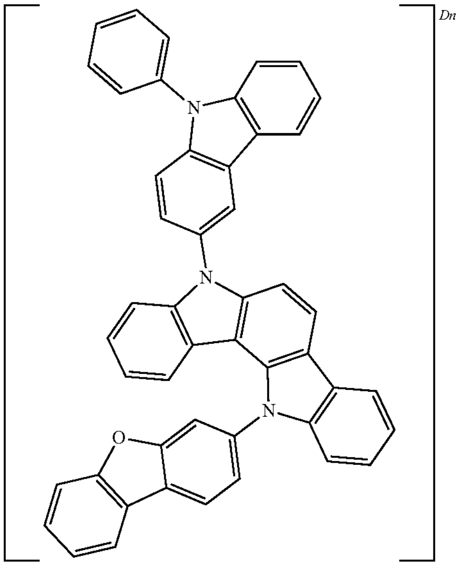
C-151
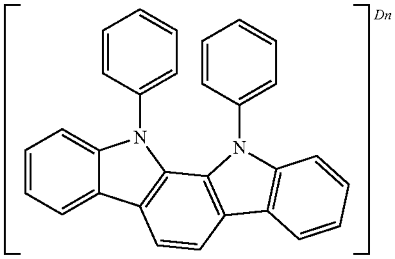
C-152
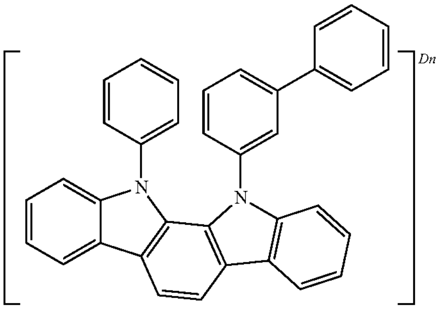
C-153
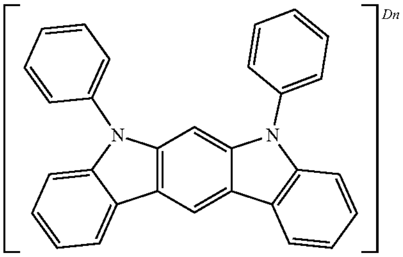
C-154
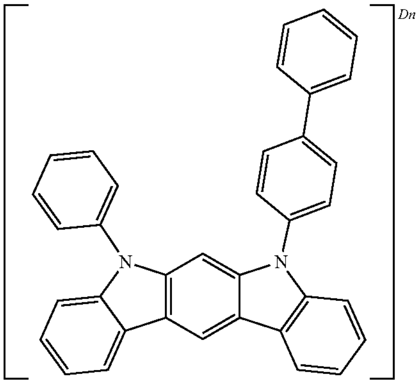
C-155
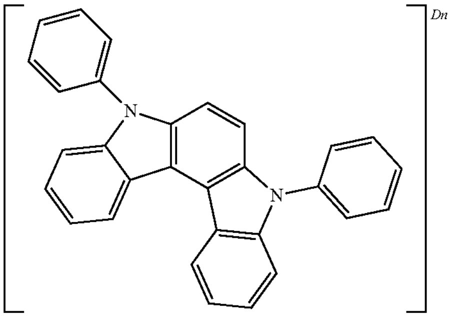
C-156
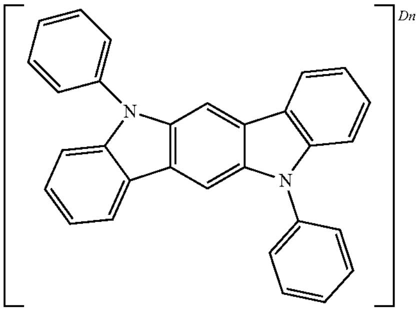
C-157
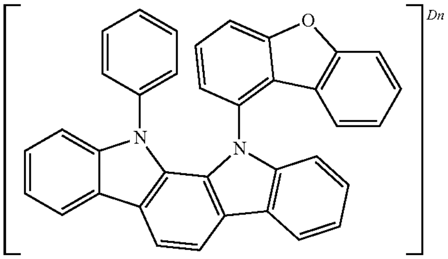

-continued

C-158

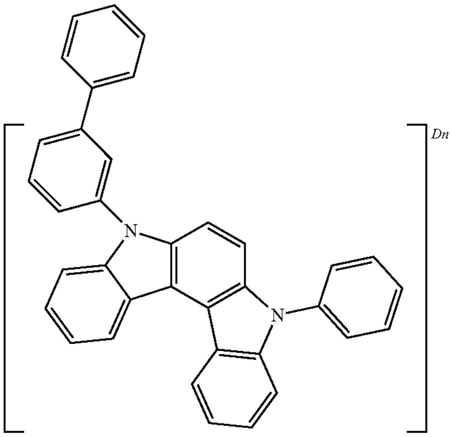

C-159

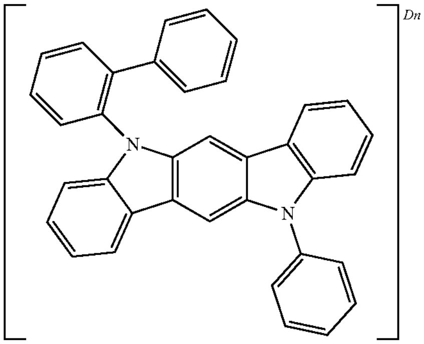

C-160

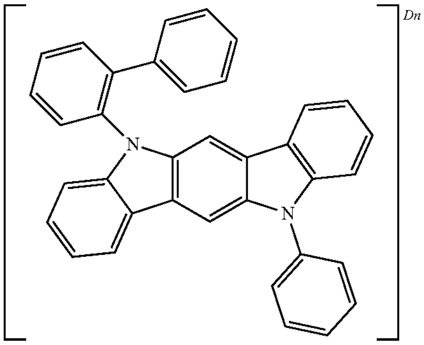

C-161

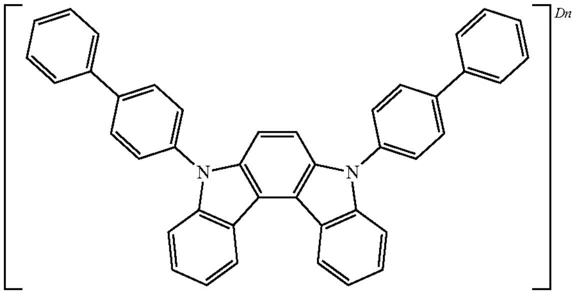

-continued

C-162

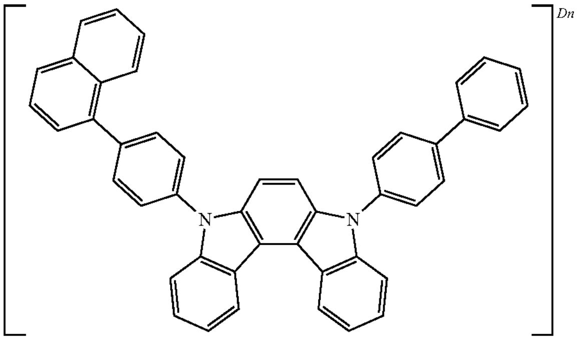

C-163

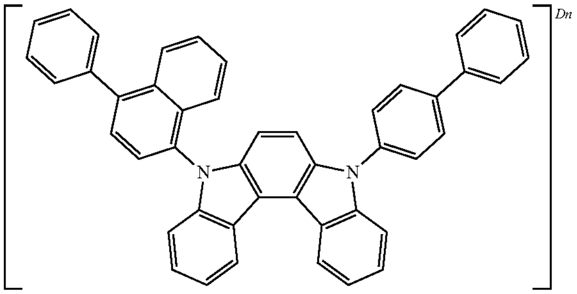

C-164

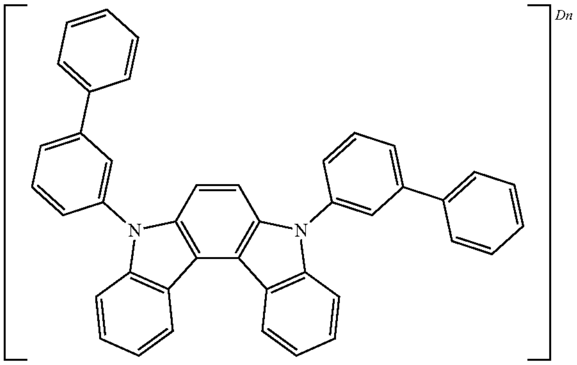

In said compounds, Dn represents that n number of hydrogens are replaced with deuterium; and n represents an integer of 1 to 50. According to one embodiment, n represents an integer of 3 or more, preferably an integer of 4 or more, more preferably an integer of 5 or more, even more preferably an integer of 6 or more. When being deuterated to the number of the lower limit or more, the bond dissociation energy related to deuteration may increase to enhance the stability of the compound. When such a compound is used in an organic electroluminescent device, the organic electroluminescent device may exhibit improved lifetime property.

The present disclosure provides an organic electroluminescent material comprising the organic electroluminescent compound represented by formula 2', and an organic electroluminescent device comprising the same.

The organic electroluminescent device according to the present disclosure has a first electrode, a second electrode, and at least one light-emitting layer between the first electrode and the second electrode, wherein the at least one light-emitting layer may comprise the compound represented by formula 2'.

The organic electroluminescent material may solely consist of the organic electroluminescent compound of the present disclosure, or may further comprise conventional materials included in the organic electroluminescent material.

Hereinafter, a plurality of host materials according to one embodiment will be described in more detail.

The plurality of host materials according to one embodiment are a plurality of host materials comprising at least one first host compound and at least one second host compound, wherein the first host material is the compound represented by formula 1, the second host material is the compound represented by formula 2, and the plurality of host materials may be comprised in a light-emitting layer of the organic electroluminescent device according to one embodiment.

The first host material, which is the host material according to one embodiment, is represented by the following formula 1.

(1)

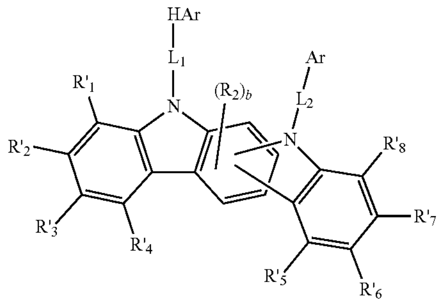

In formula 1,

- $L_1$ and $L_2$, each independently, represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;
- HAr represents a substituted or unsubstituted (3- to 30-membered)heteroaryl;
- Ar represents a substituted or unsubstituted (C6-C30)aryl, or a substituted or unsubstituted (3- to 30-membered) heteroaryl;
- $R'_1$, to $R'_8$, and $R_2$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_{13}R_{14}$, or $-SiR_{15}R_{16}R_{17}$; or may be linked to an adjacent substituent(s) to form a ring(s);
- $R_{13}$ to $R_{17}$, each independently, represent a substituted or unsubstituted (C1-C30)alkyl, a substituted or unsubstituted (C6-C30)aryl, or a substituted or unsubstituted (3- to 30-membered)heteroaryl;
- with the proviso that at least one of $R'_1$ to $R'_8$, and $R_2$ represents deuterium; and
- b represents an integer of 1 or 2, where if b is an integer of 2, each of $R_2$ may be the same or different from each other.

In one embodiment, $L_1$ represents a single bond, a substituted or unsubstituted (C6-C30)arylene, or a substituted or unsubstituted (5- to 30-membered)heteroarylene; preferably a single bond, a substituted or unsubstituted (C6-C25) arylene, or a substituted or unsubstituted (5- to 18-membered)heteroarylene; more preferably a single bond, a substituted or unsubstituted (C6-C18)arylene, or a substituted or unsubstituted (5- to 15-membered)heteroarylene. For example, $L_1$ may be a single bond, or may be a substituted or unsubstituted phenylene, a substituted or unsubstituted biphenylene, a substituted or unsubstituted pyridylene, a substituted or unsubstituted dibenzofuranylene, or a substituted or unsubstituted dibenzothiophenyl, which may be further substituted with deuterium.

In one embodiment, HAr represents a substituted or unsubstituted (5- to 30-membered)heteroaryl containing at least one nitrogen; preferably a substituted or unsubstituted (5- to 25-membered)heteroaryl containing at least two nitrogens; more preferably a substituted or unsubstituted (5- to 18-membered)heteroaryl containing at least three nitrogens. For example, HAr may be a substituted or unsubstituted triazinyl, in which the substituent(s) of the triazinyl may be, for example, at least one of a substituted or unsubstituted (C6-C30)aryl and a substituted or unsubstituted (5- to 30-membered)heteroaryl, for example, at least one of a phenyl unsubstituted or substituted with at least one of deuterium, a dibenzofuranyl(s), a dibenzothiophenyl(s), a carbazolyl(s), and a cyano(s); a p-biphenyl unsubstituted or substituted with deuterium; a m-biphenyl unsubstituted or substituted with deuterium; a p-terphenyl unsubstituted or substituted with deuterium; a m-terphenyl unsubstituted or substituted with deuterium; a dibenzofuranyl unsubstituted or substituted with deuterium; a dibenzothiophenyl unsubstituted or substituted with deuterium; and a carbazolyl unsubstituted or substituted with at least one of deuterium and a phenyl(s).

In one embodiment, $L_2$ represents a single bond, a substituted or unsubstituted (C6-C30)arylene, or a substituted or unsubstituted (5- to 30-membered)heteroarylene; preferably a single bond, or a substituted or unsubstituted (C6-C25) arylene; more preferably a single bond, or a substituted or unsubstituted (C6-C18)arylene. For example, $L_2$ may be a single bond, or a phenylene unsubstituted or substituted with deuterium.

In one embodiment, Ar represents a substituted or unsubstituted (C6-C30)aryl, or a substituted or unsubstituted (5- to 30-membered)heteroaryl; preferably a substituted or unsubstituted (C6-C25)aryl, or a substituted or unsubstituted (5- to 25-membered)heteroaryl; more preferably a substituted or unsubstituted (C6-C18)aryl, or a substituted or unsubstituted (5- to 18-membered)heteroaryl. For example, Ar may be a phenyl unsubstituted or substituted with at least one of deuterium and a cyano(s); a m-biphenyl unsubstituted or substituted with deuterium; a p-biphenyl unsubstituted or substituted with deuterium; a dibenzofuranyl unsubstituted or substituted with deuterium; or a dibenzothiophenyl unsubstituted or substituted with deuterium.

In one embodiment, $R'_1$ to $R'_8$, and $R_2$ represent hydrogen or deuterium, with the proviso that at least one of $R'_1$ to $R'_8$, and $R_2$ represents deuterium; preferably at least two of $R'_1$ to $R'_8$, and $R_2$ represent deuterium; more preferably at least four of $R'_1$ to R'8, and $R_2$ represent deuterium.

The compound represented by formula 1 according to one embodiment may be represented by any one of the following formulas 1-1 to 1-6.

-continued
(1-1)
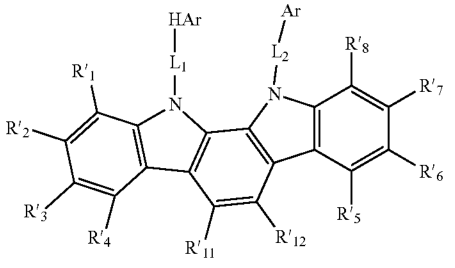
(1-2)
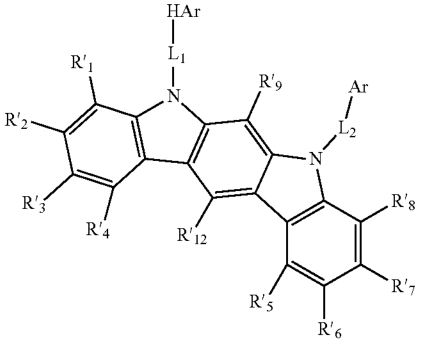
(1-3)
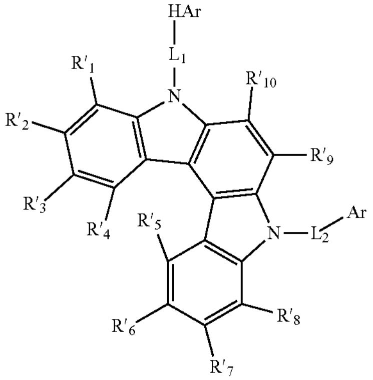
(1-4)
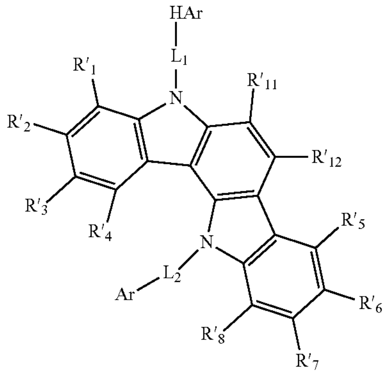
(1-5)
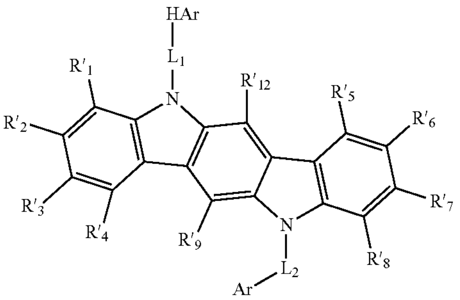
(1-6)
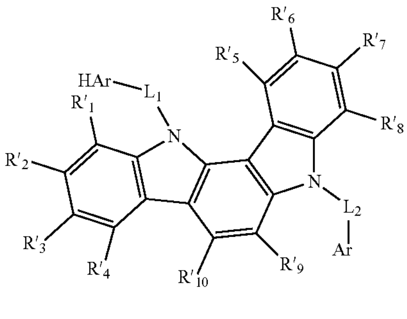
In formulas 1-1 to 1-6,
HAr, Ar, $L_1$, $L_2$, and $R'_1$ to $R'_8$ are as defined in formula 1,
$R'_9$ to $R'_{12}$ are as defined for $R'_1$ to $R_8$,
with the proviso that at least one of $R'_1$ to $R'_{12}$ is deuterium.
According to one embodiment, the first host compound represented by formula 1 may be exemplified as the following compounds, but is not limited thereto.

H1-1
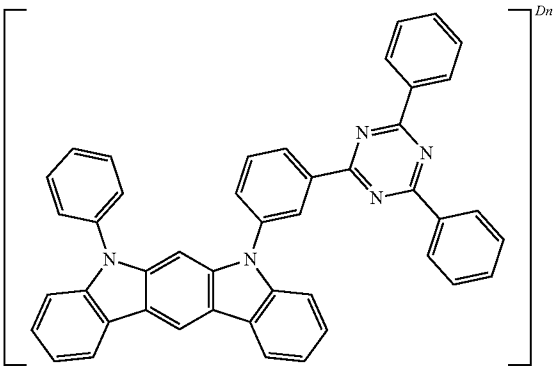
H1-2
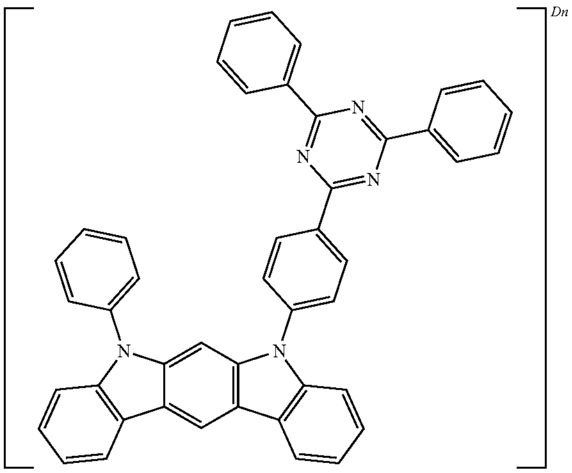
H1-3
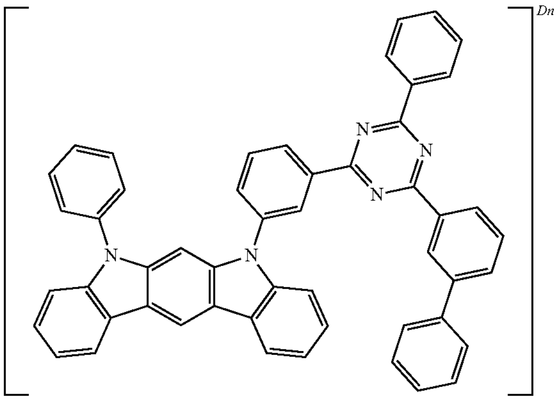

-continued
H1-4
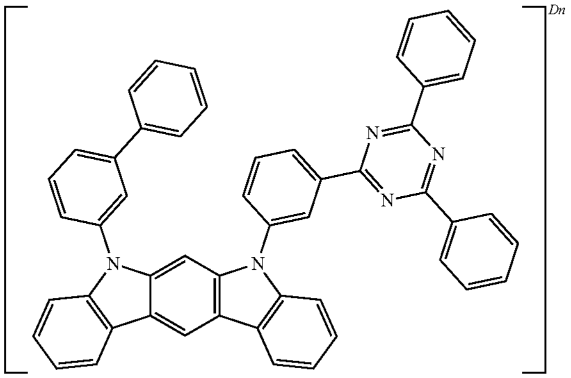
H1-5
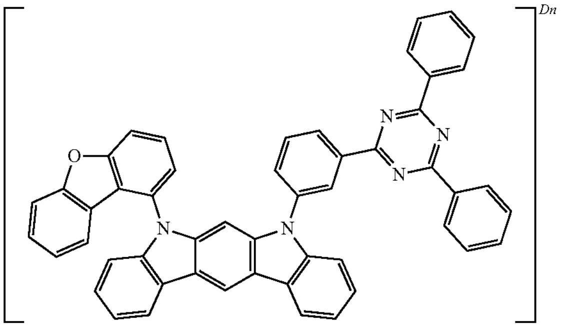
H1-6
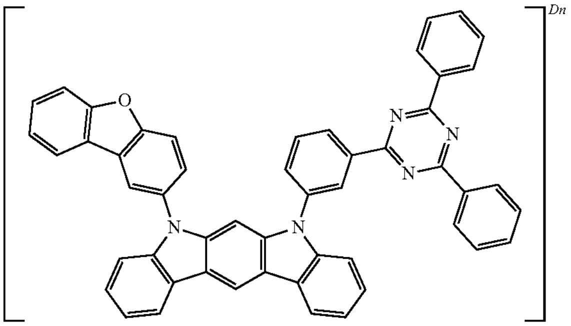
H1-7
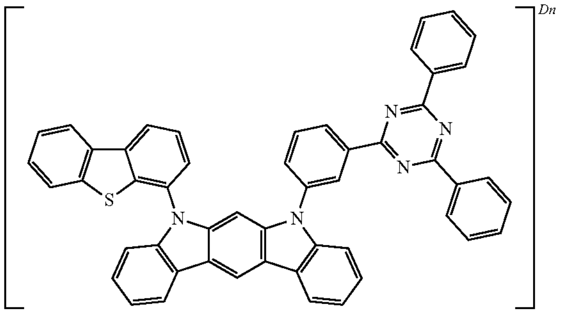

-continued
H1-8
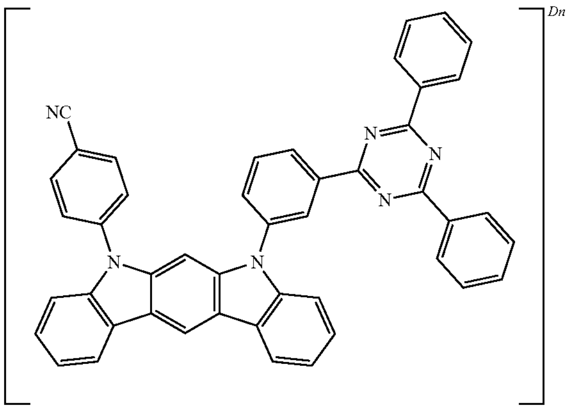
H1-9
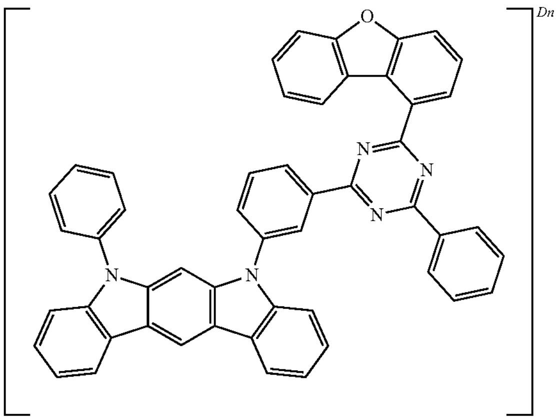
H1-10
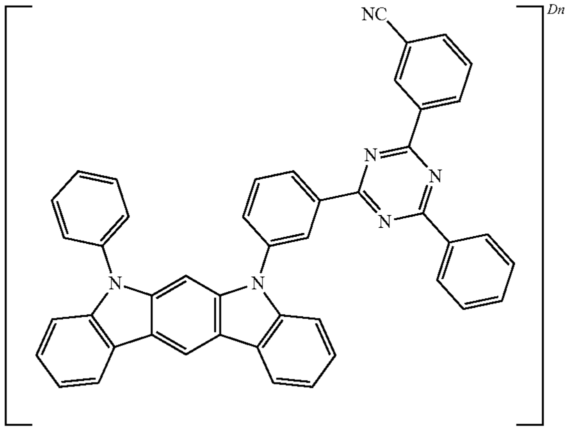

-continued
H1-11
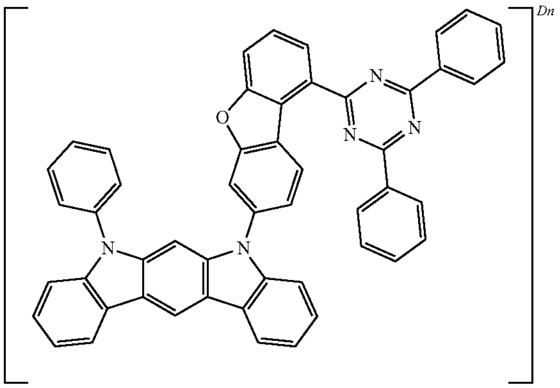
H1-12
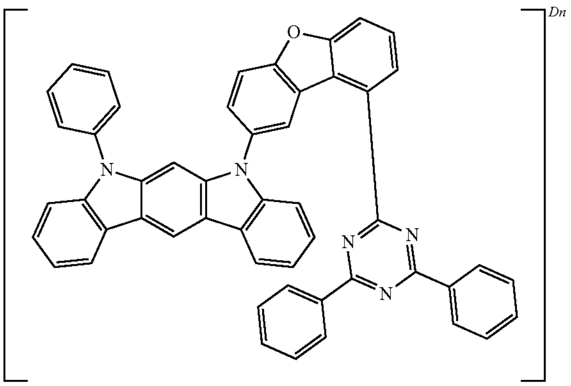
H1-13
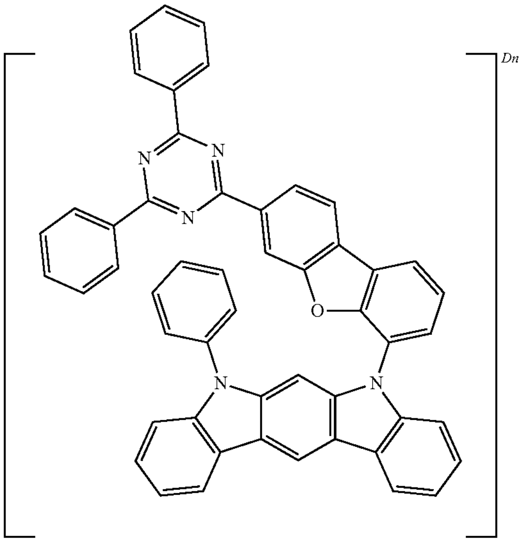

-continued
H1-14
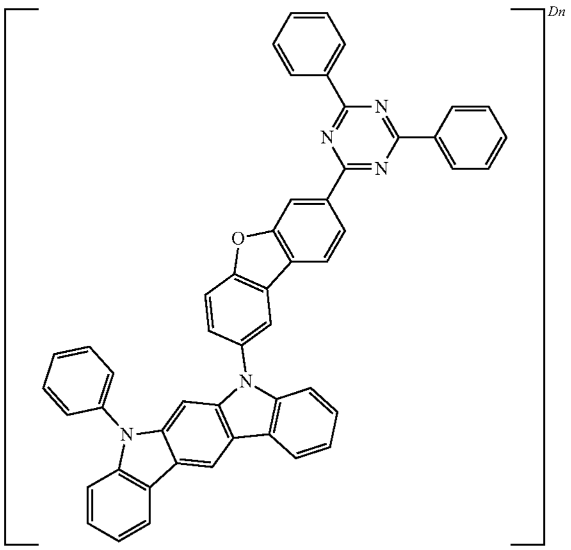
H1-15
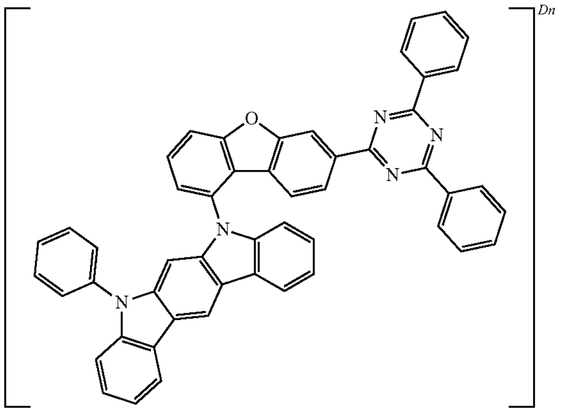
H1-16
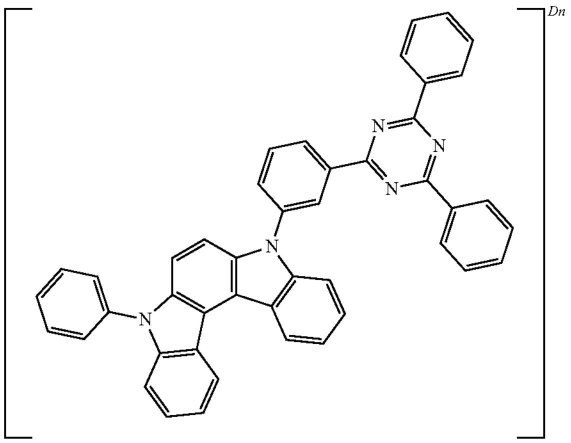

-continued
H1-17
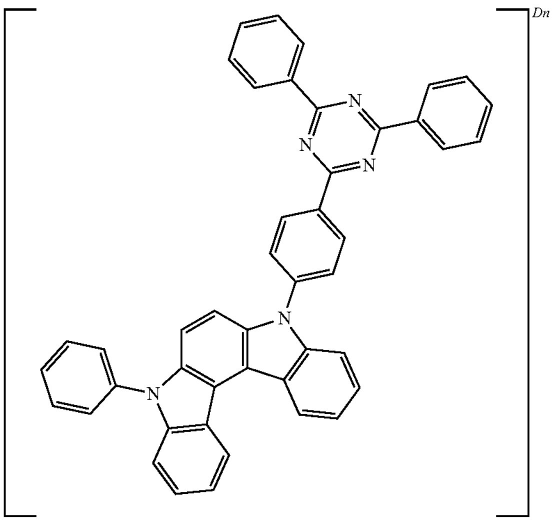
H1-18
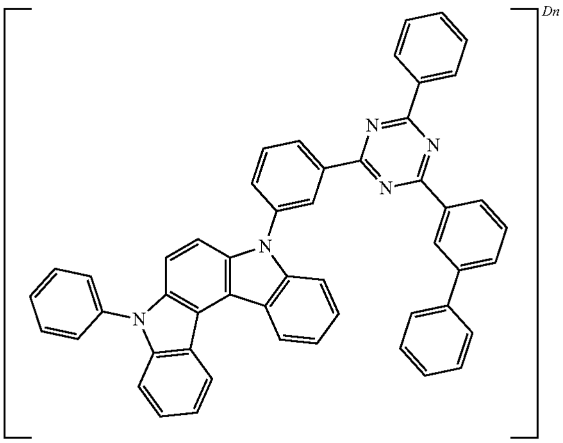
H1-19
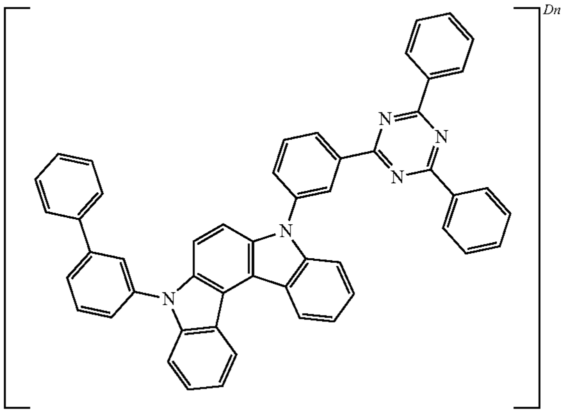

-continued
H1-20
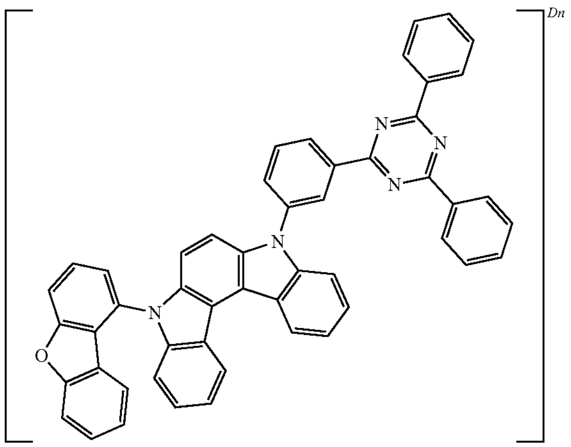
H1-21
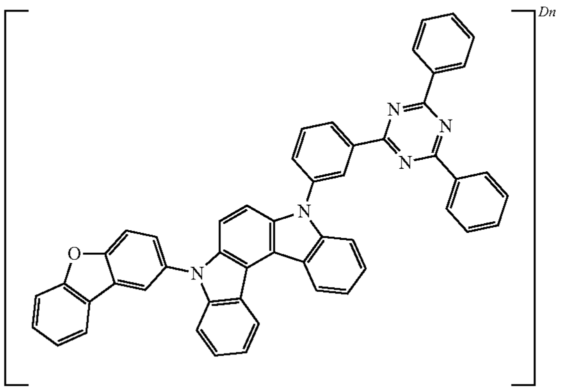
H1-22
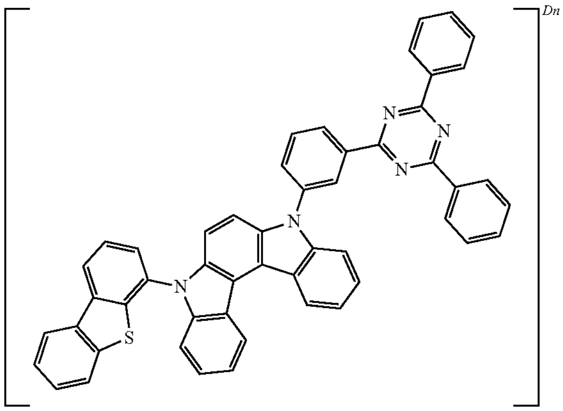

-continued
H1-23
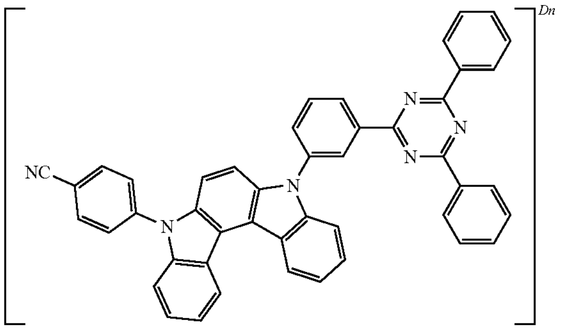
H1-24
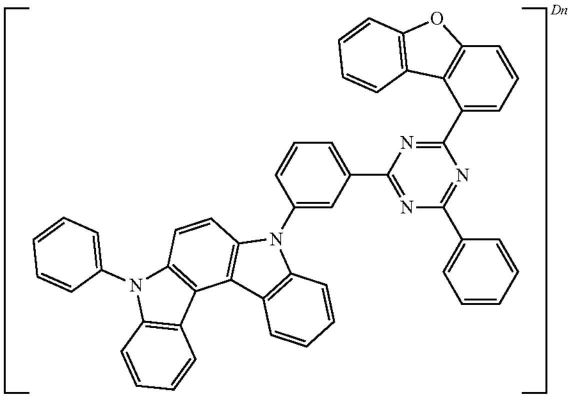
H1-25
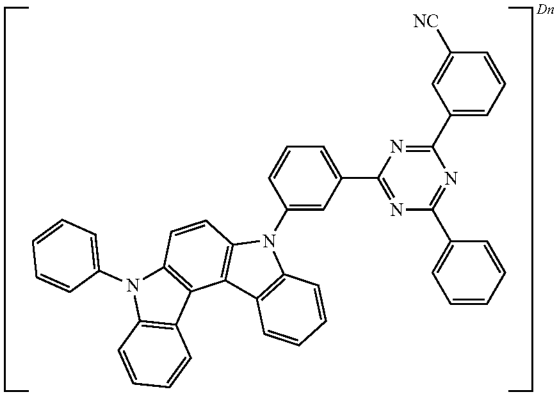

-continued
H1-26
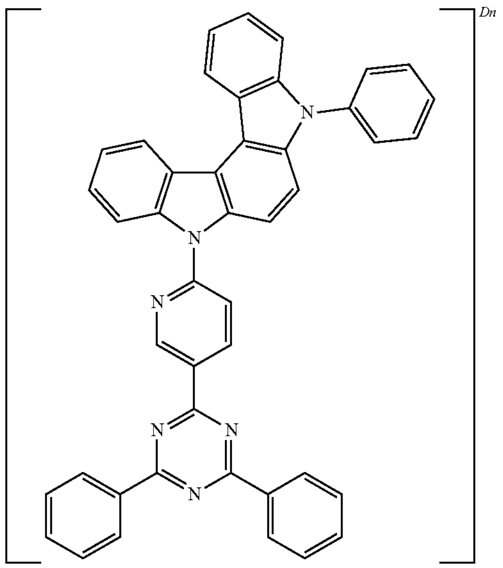
H1-27
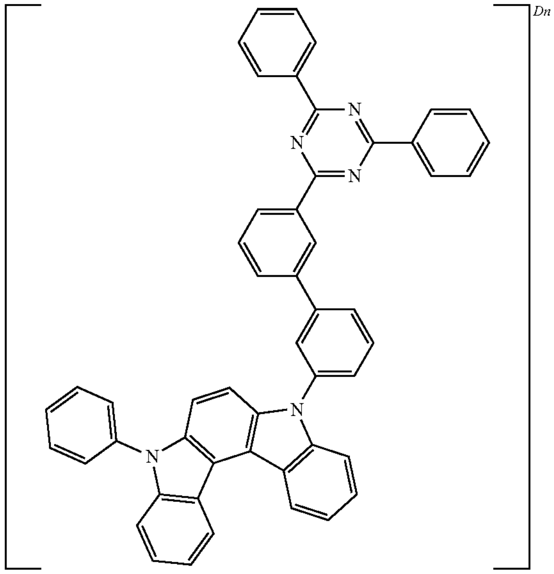

-continued
H1-28
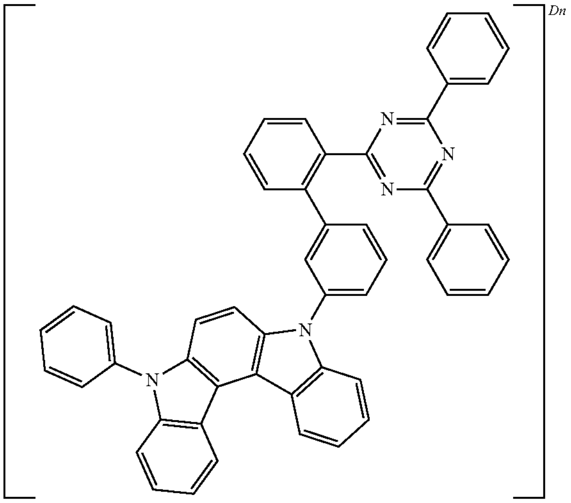
H1-29
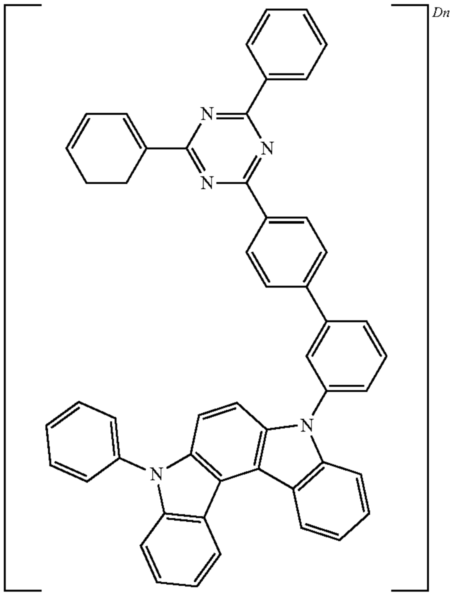

-continued
H1-30
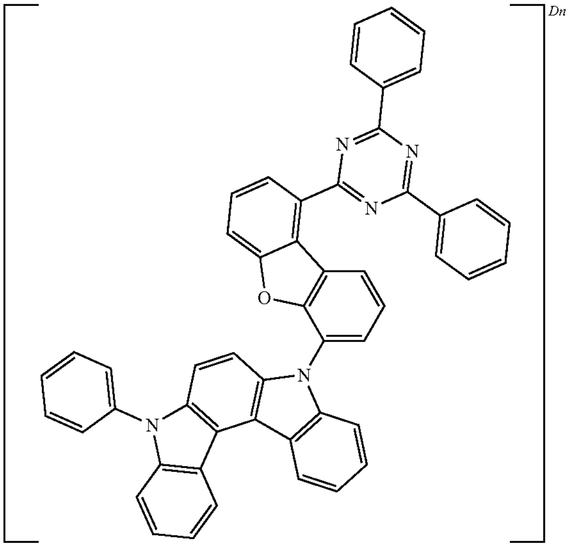
H1-31
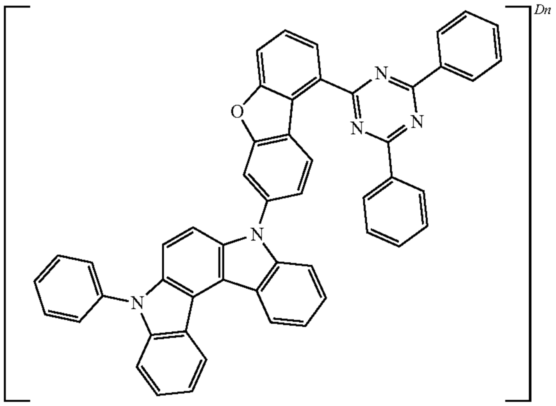
H1-32
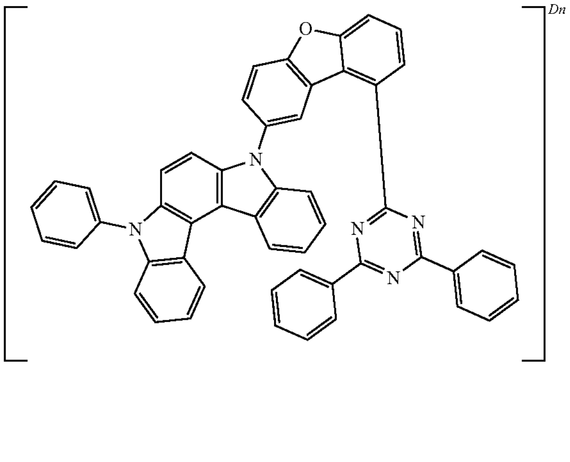

-continued
H1-33
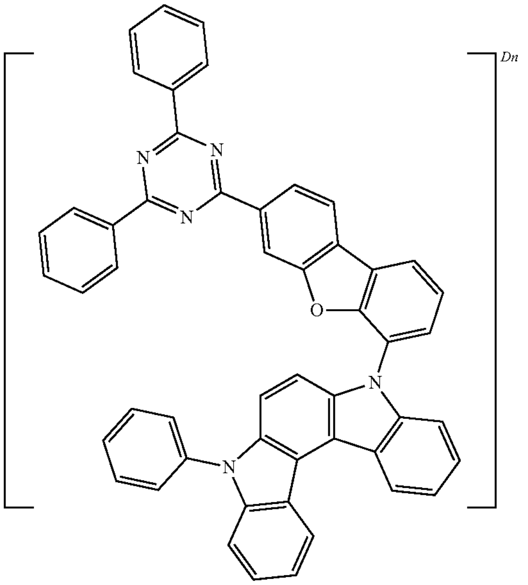
H1-34
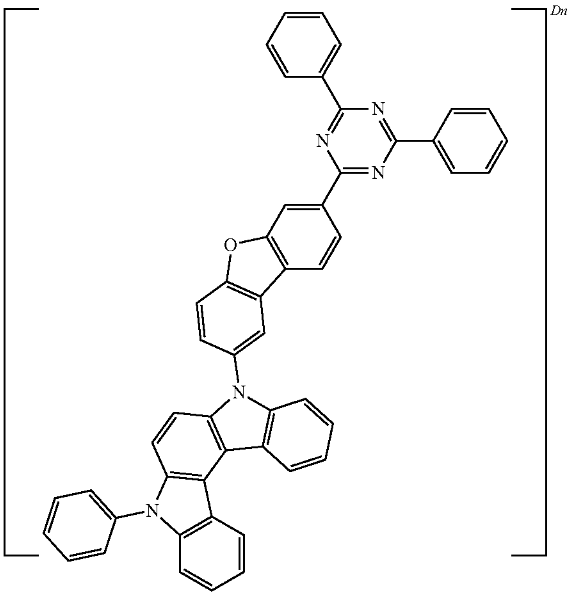

-continued
H1-35
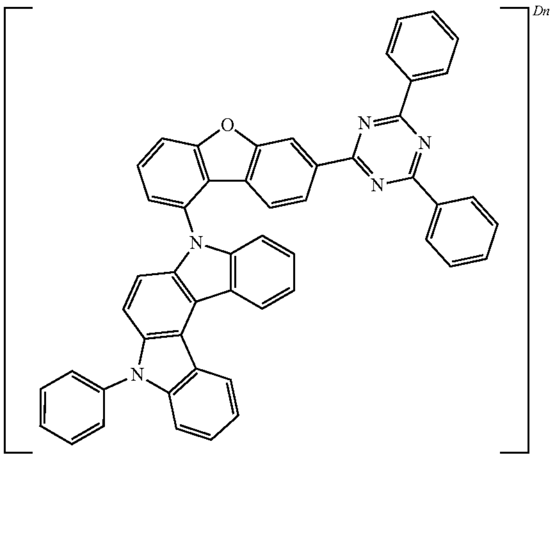
H1-36
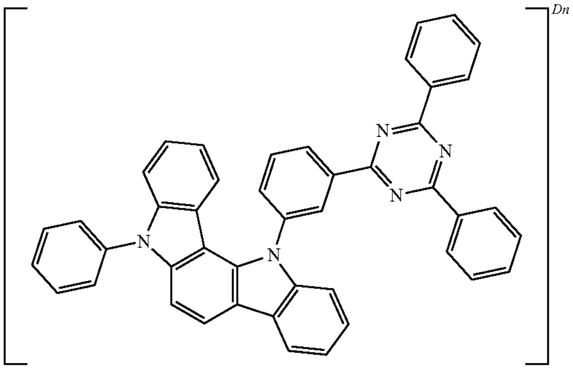
H1-37
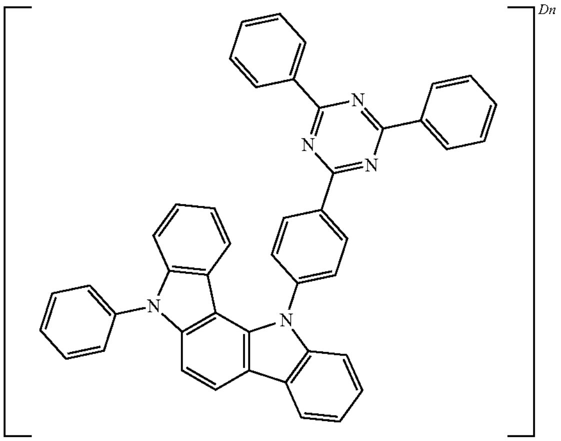

-continued
H1-38
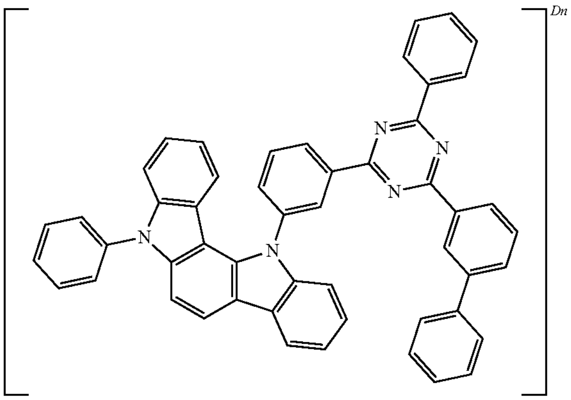
H1-39
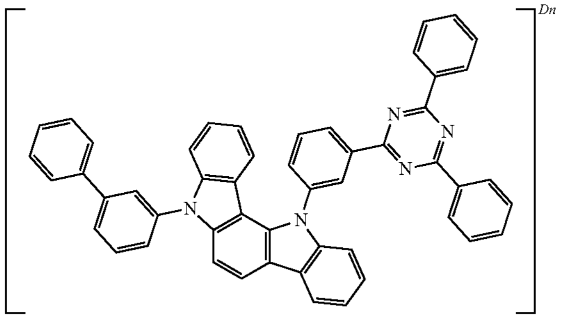
H1-40
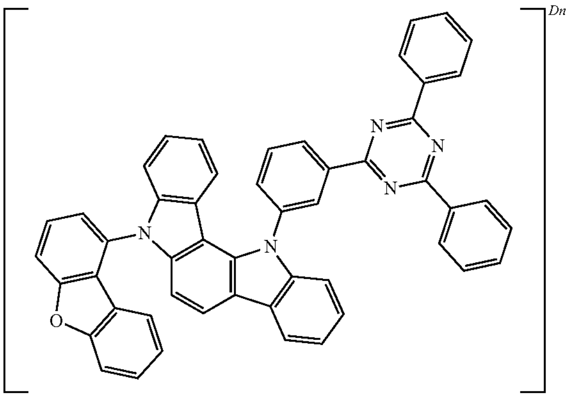
H1-41
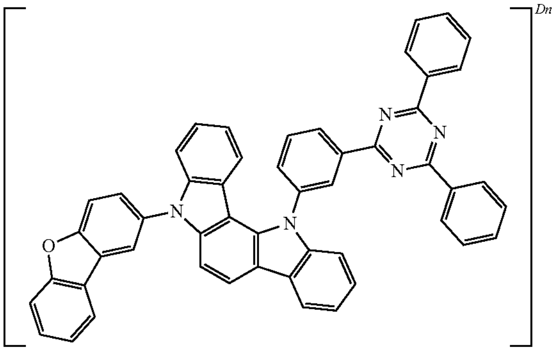

-continued
H1-42
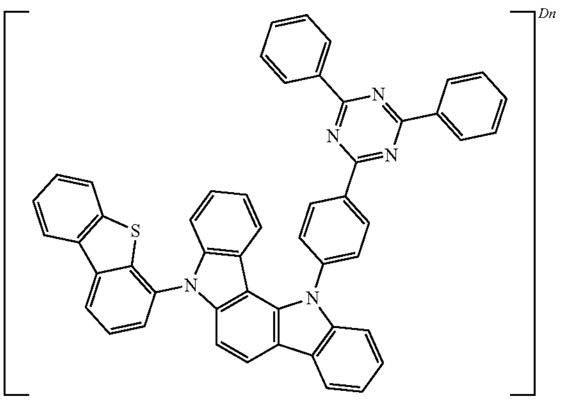
H1-43
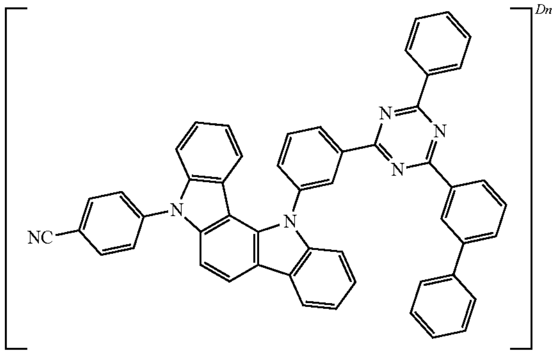
H1-44
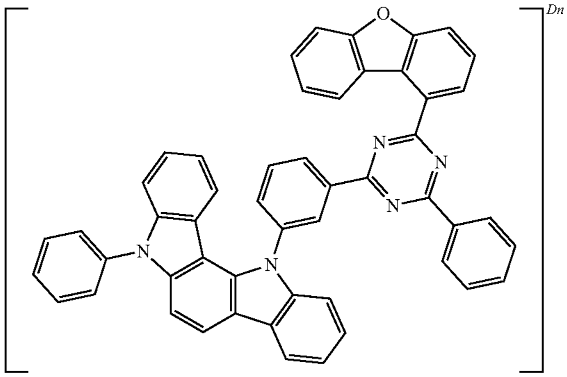
H1-45
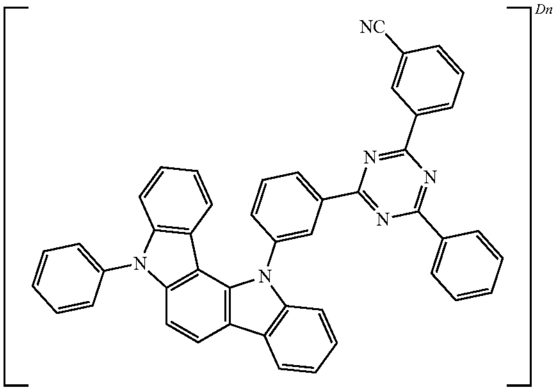

-continued
H1-46
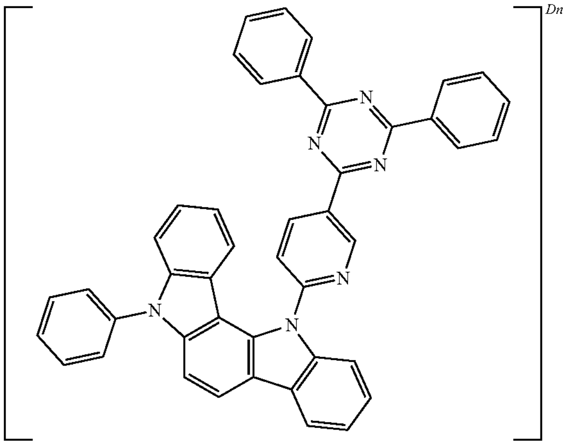
H1-47
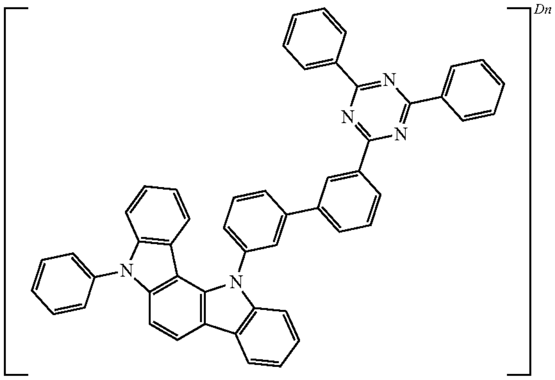
H1-48
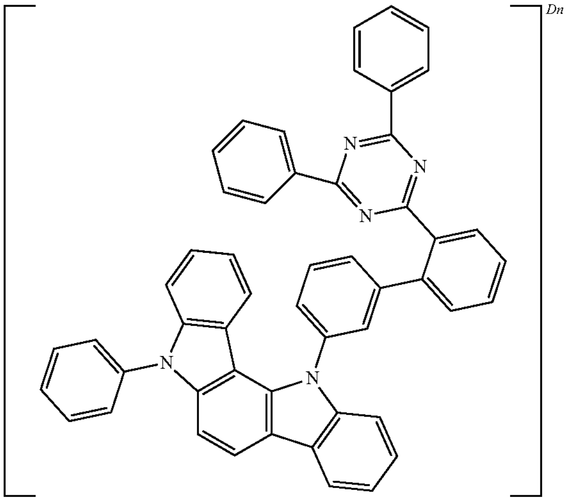

-continued
H1-49
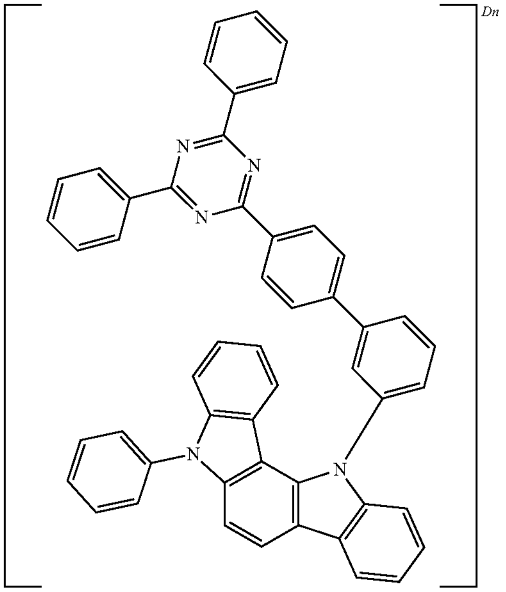
H1-50
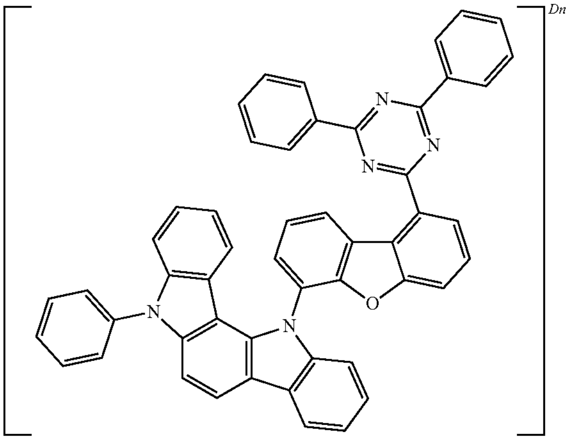
H1-51
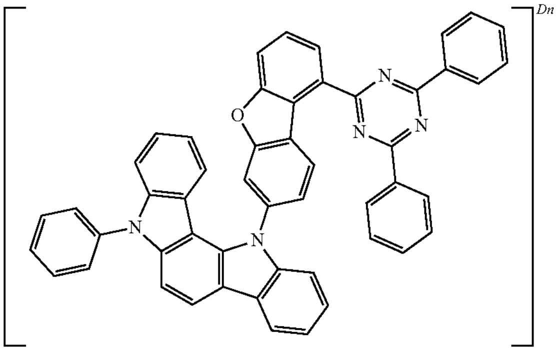

-continued
H1-52
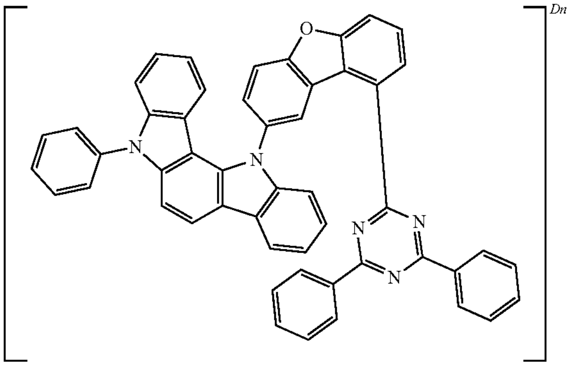
H1-53
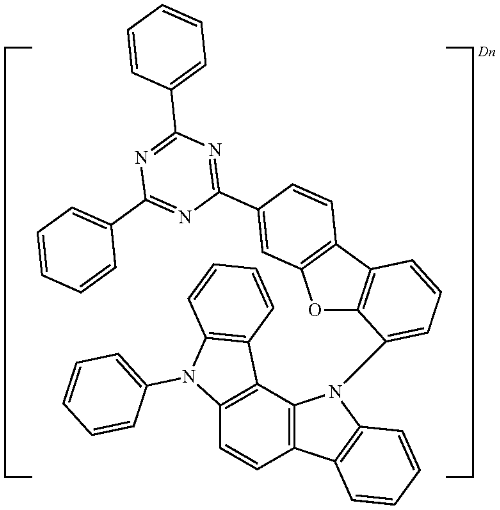
H1-54
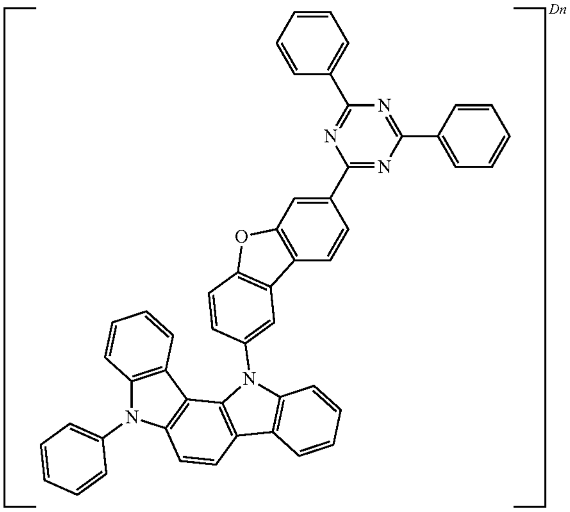

-continued
H1-55
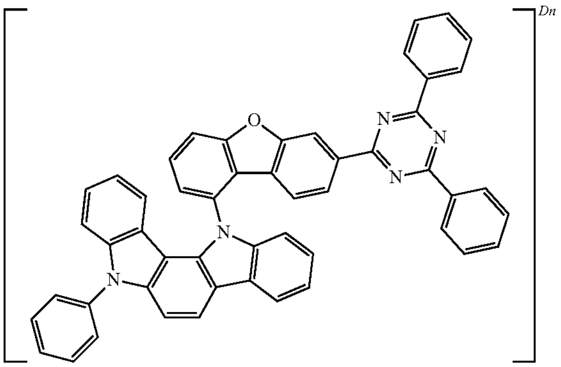
H1-56
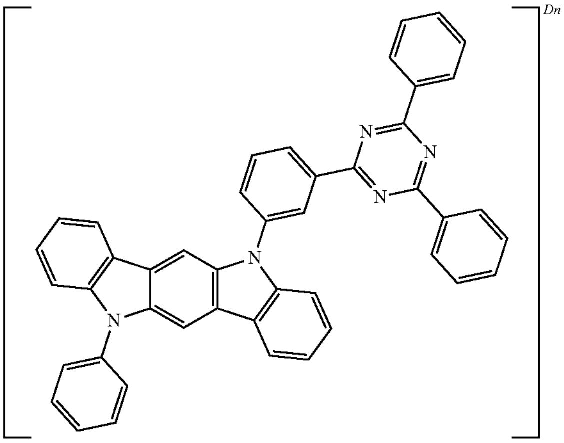
H1-57
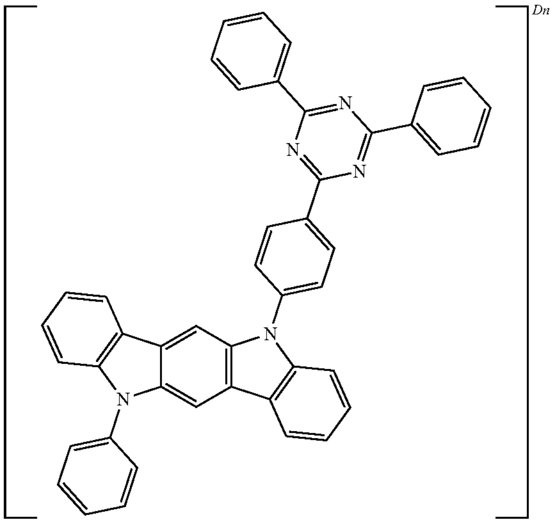

-continued
H1-58
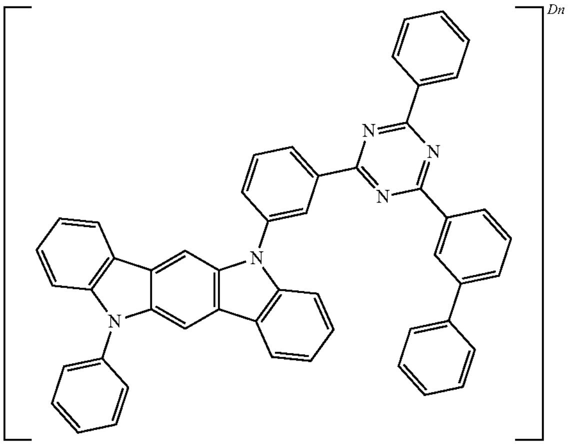
H1-59
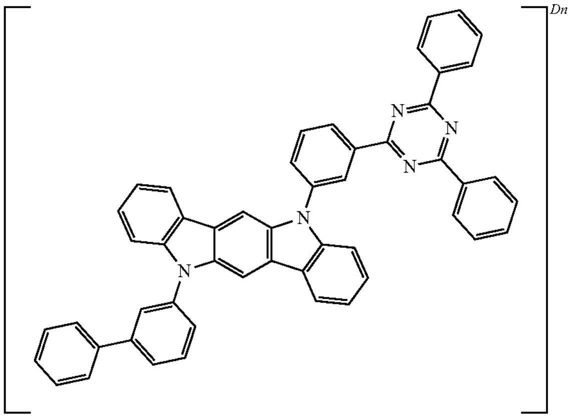
H1-60
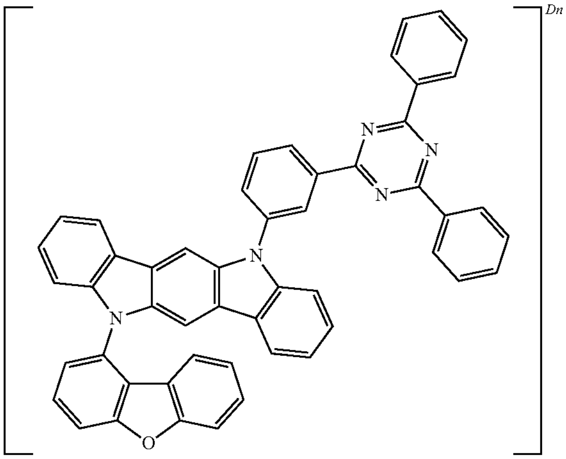

-continued
H1-61
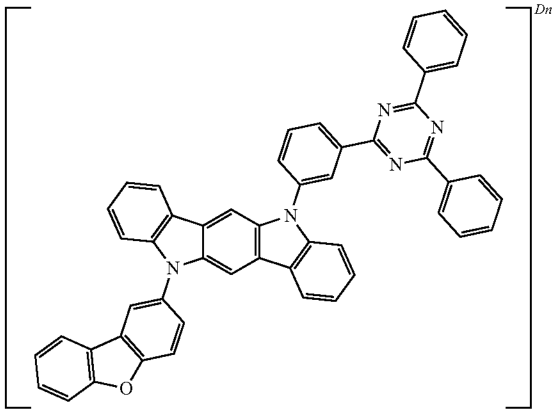
H1-62
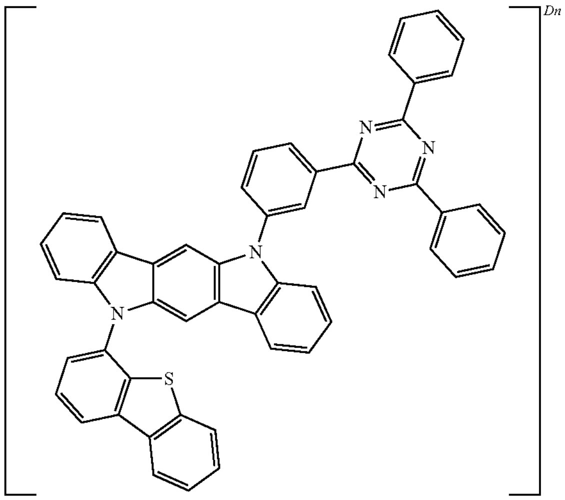
H1-63
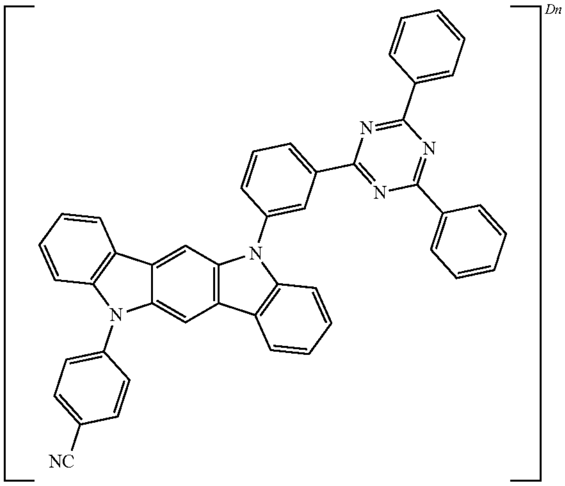

-continued
H1-64
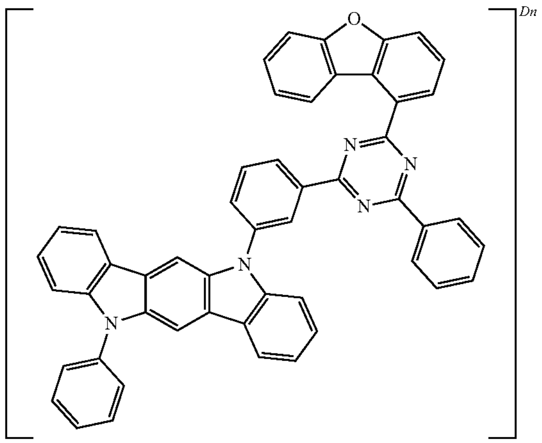
H1-65
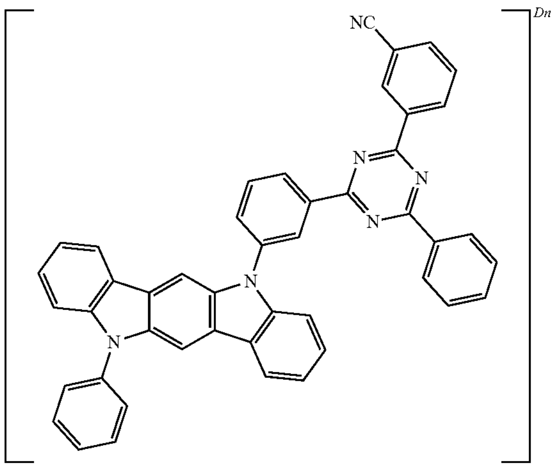
H1-66
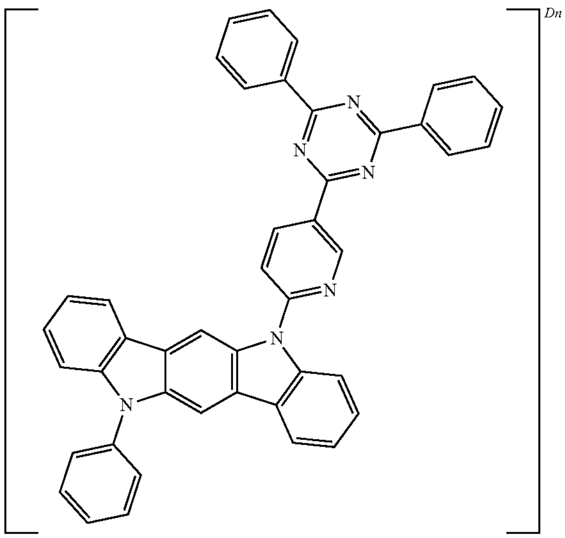

-continued
H1-67
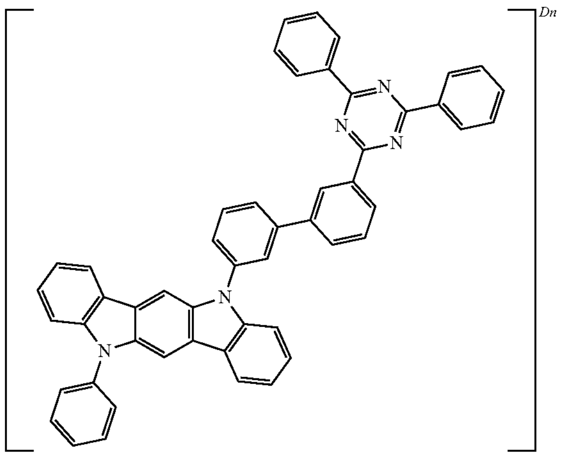
H1-68
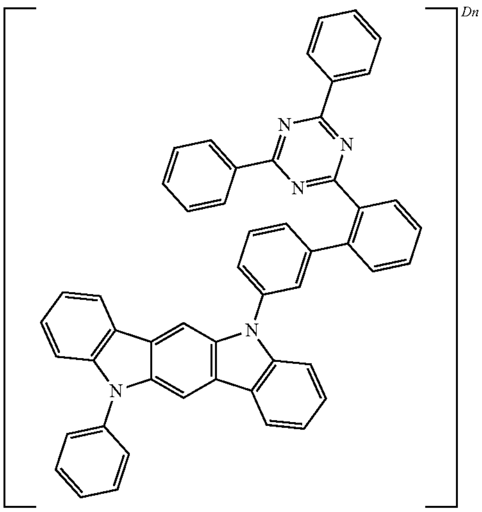
H1-69
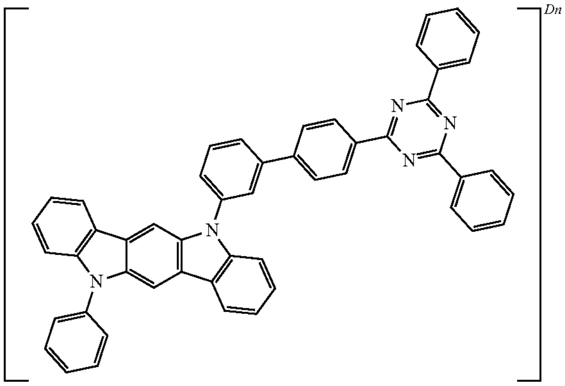

-continued
H1-70
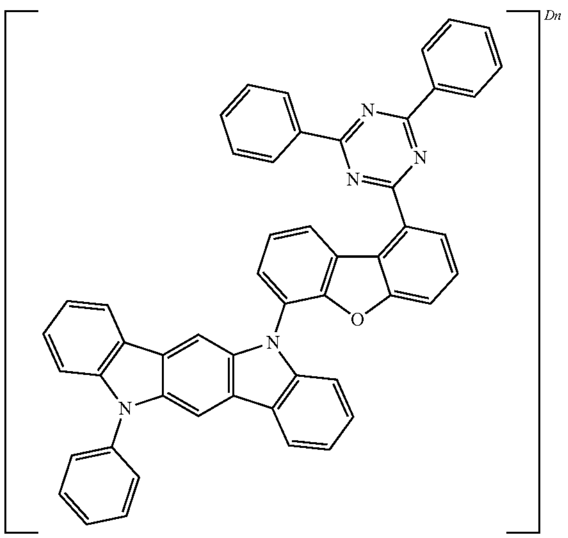
H1-71
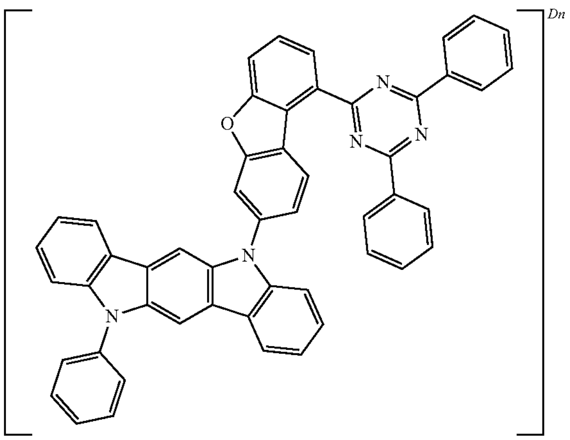
H1-72
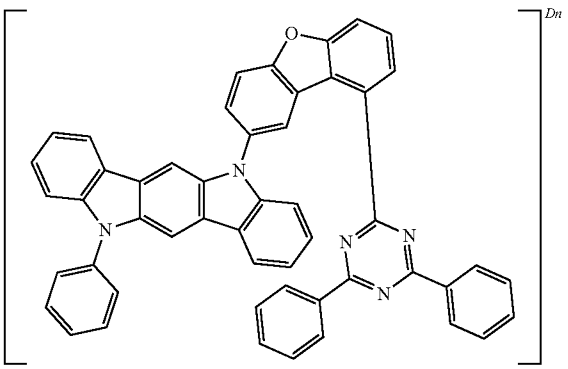

-continued
H1-73
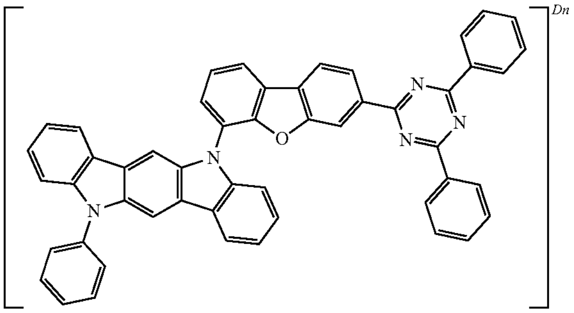
H1-74
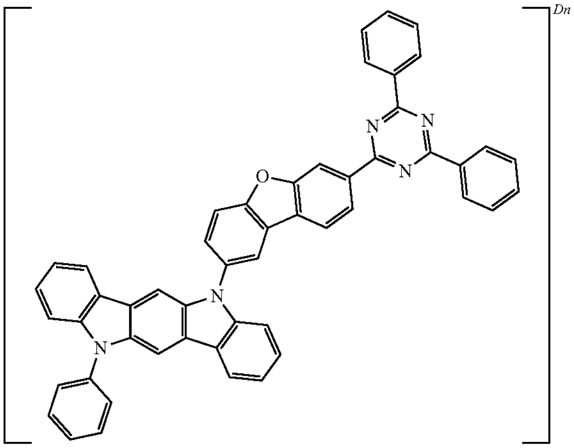
H1-75
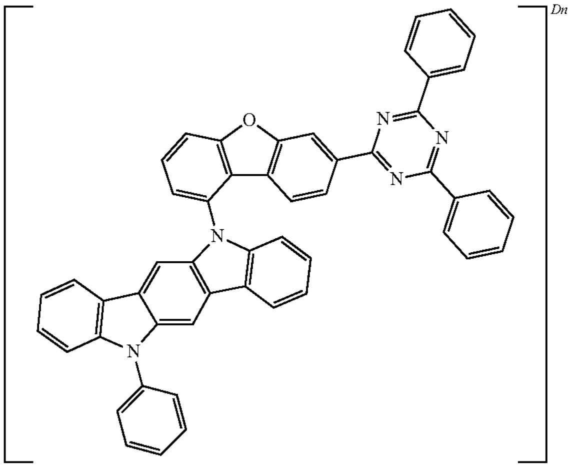

-continued
H1-76
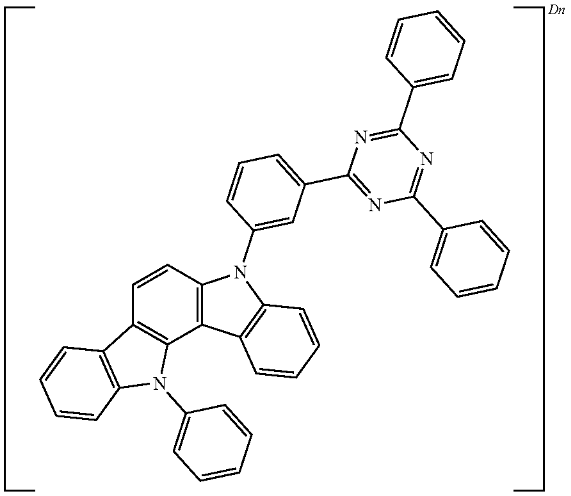
H1-77
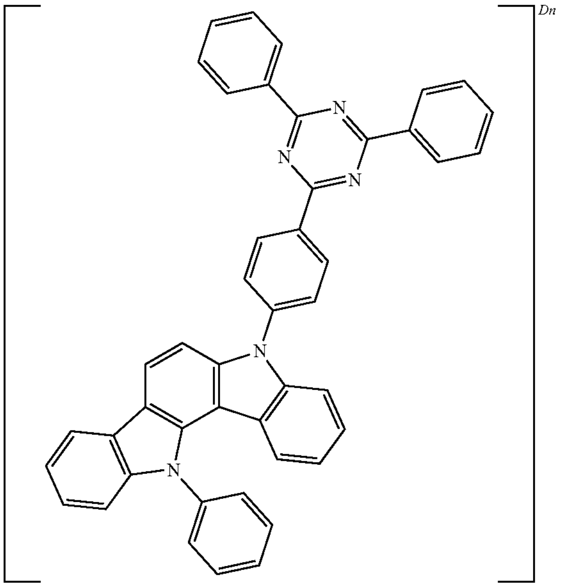
H1-78
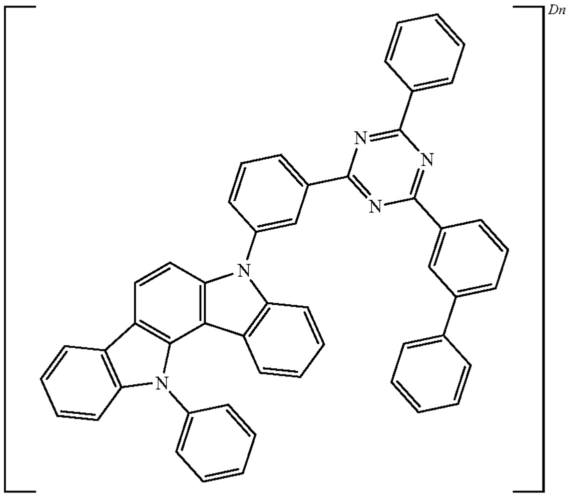

-continued
H1-79
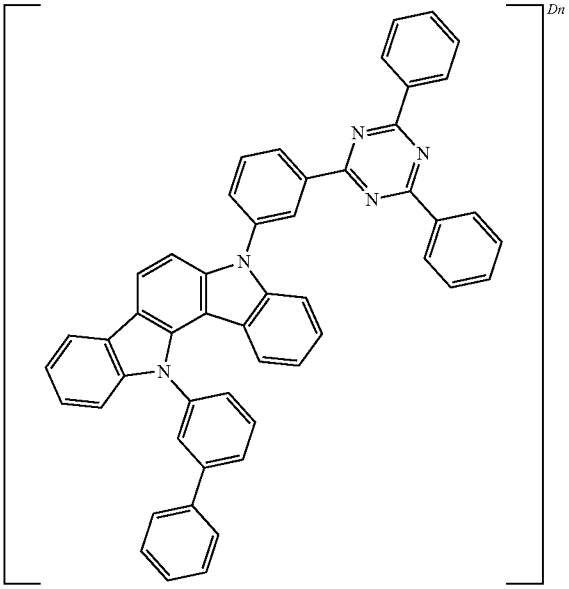
H1-80
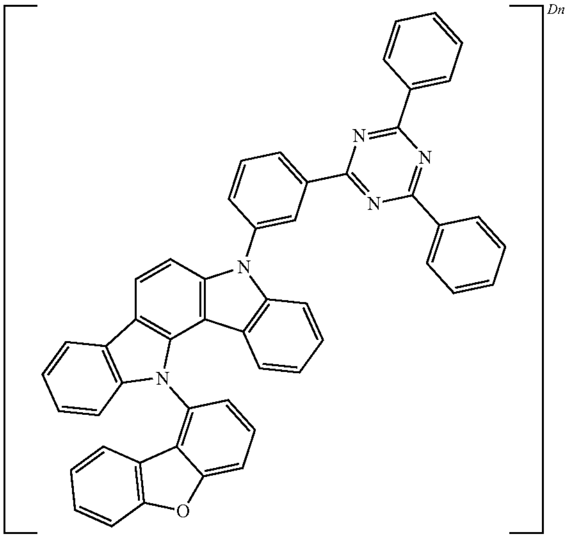

-continued
H1-81
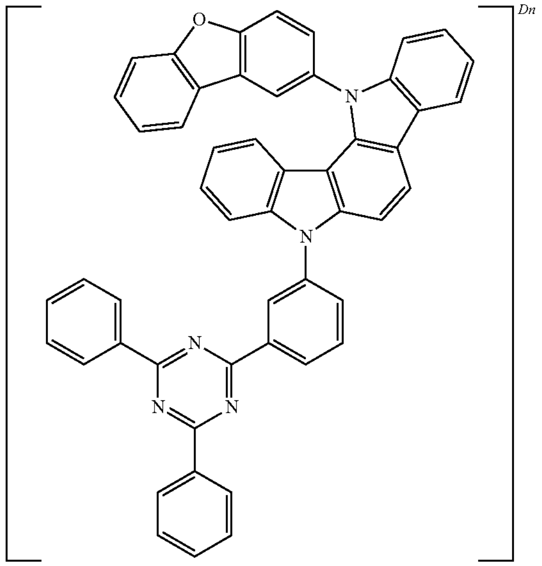
H1-82
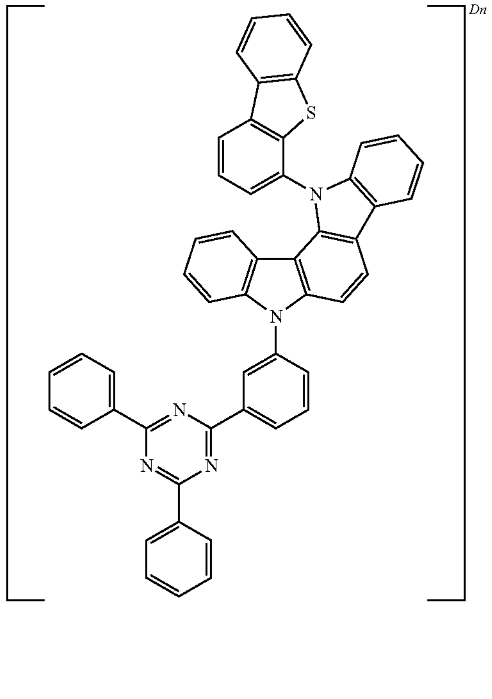

-continued
H1-83
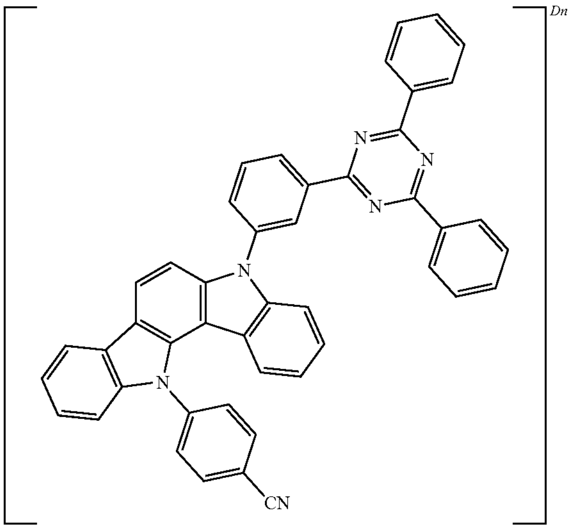
H1-84
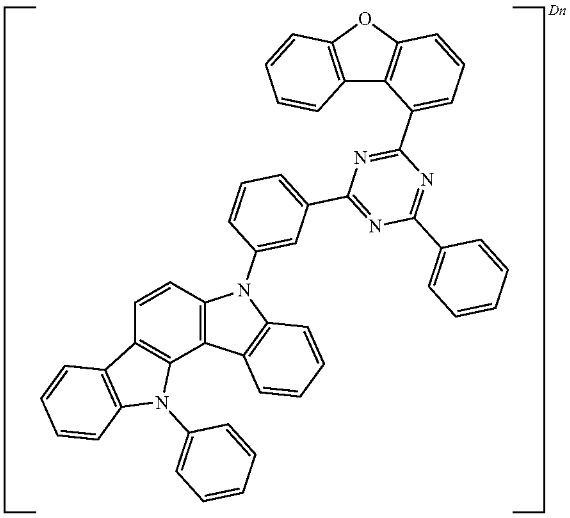
H1-85
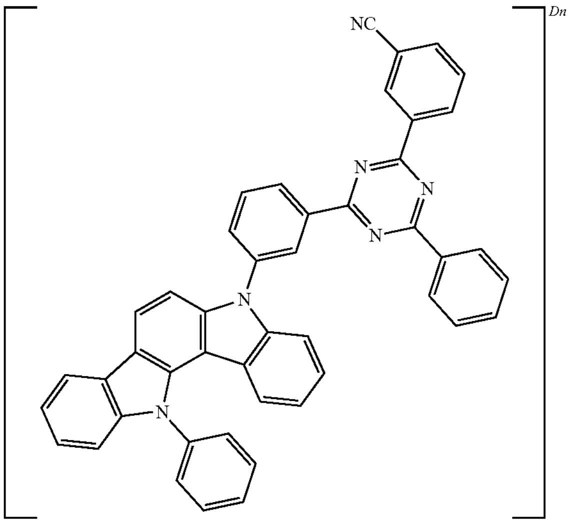

-continued
H1-86
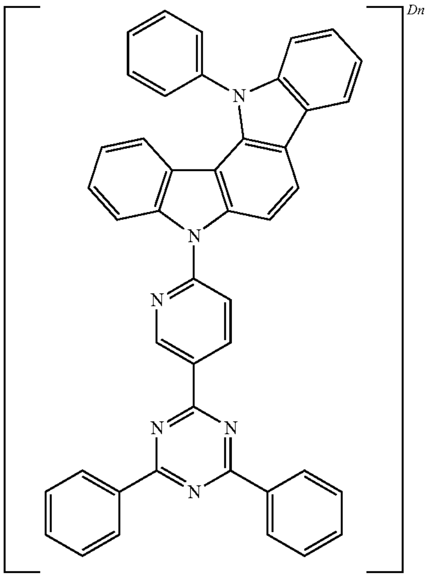
H1-87
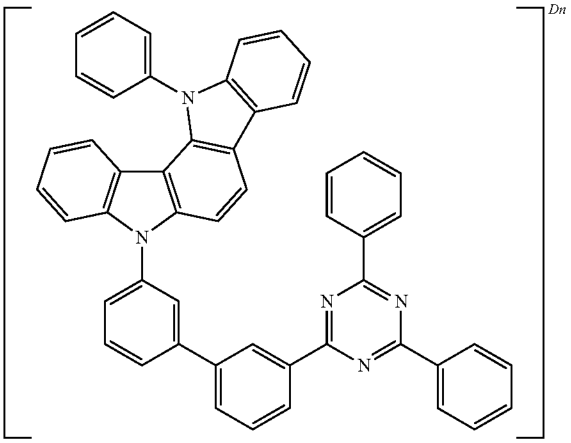
H1-88
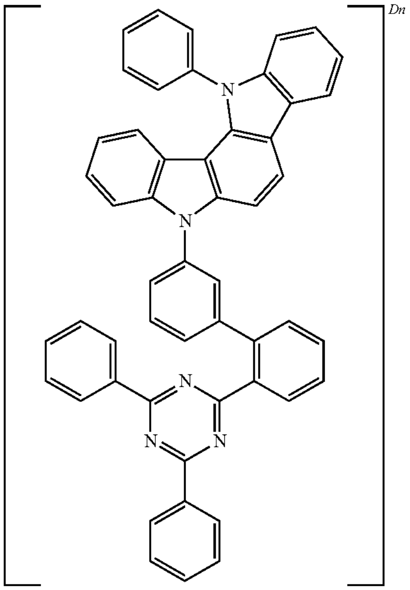

-continued
H1-89
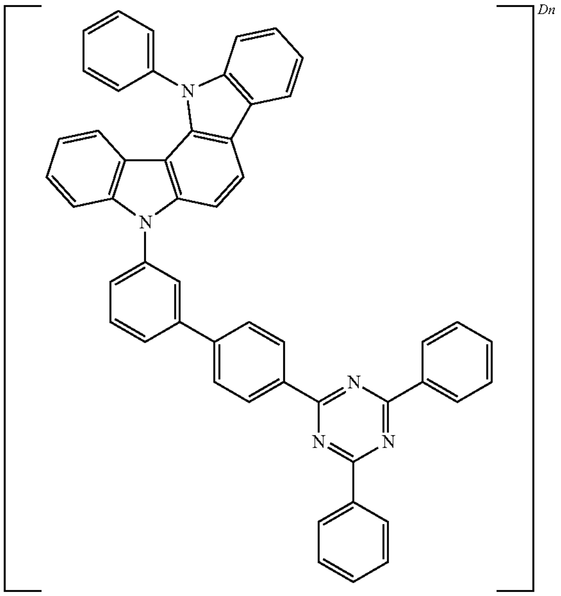
H1-90
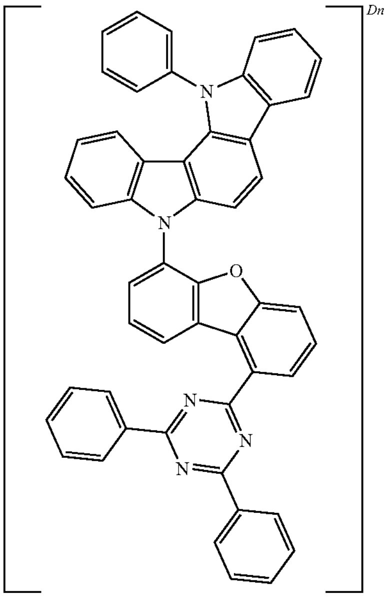

-continued
H1-91
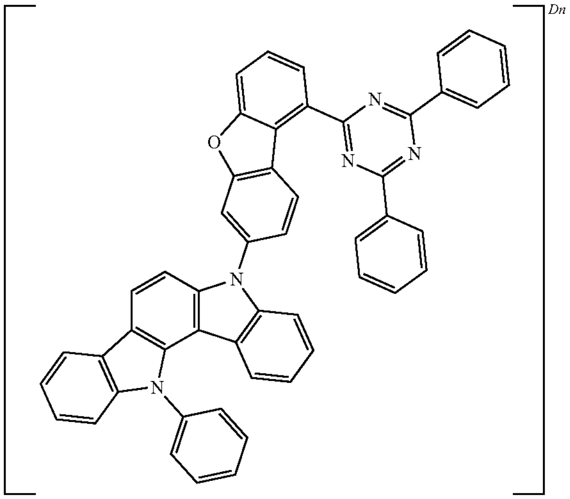
H1-92
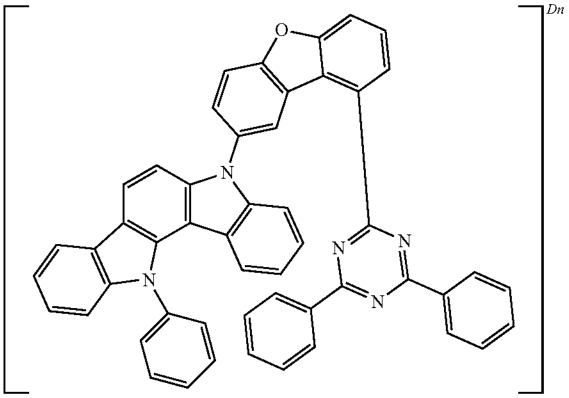
H1-93
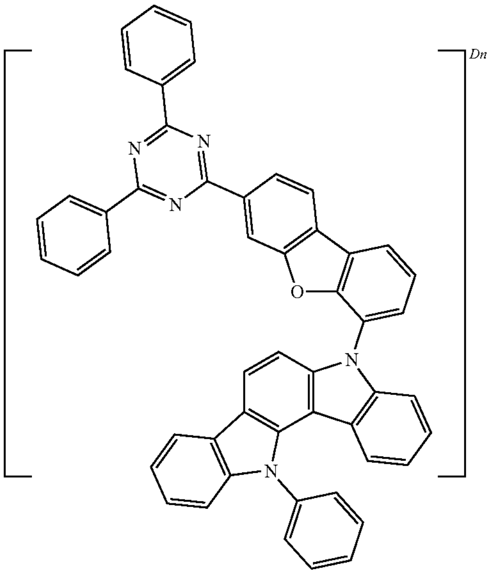

-continued
H1-94
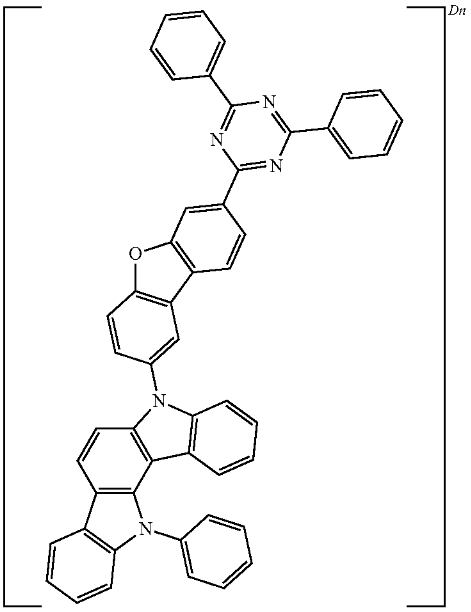
H1-95
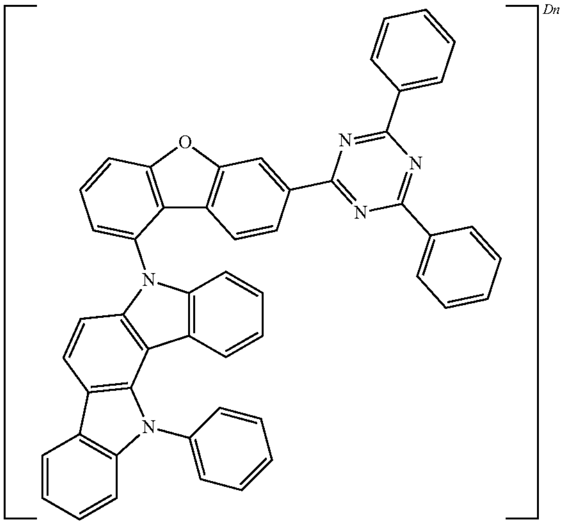
H1-96
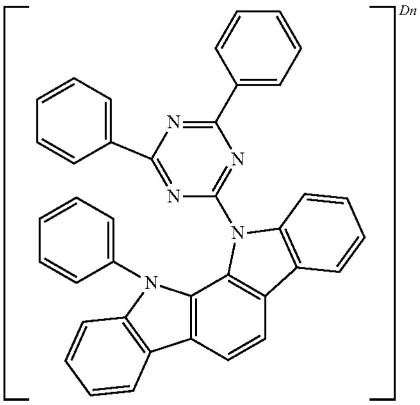

-continued
H1-97
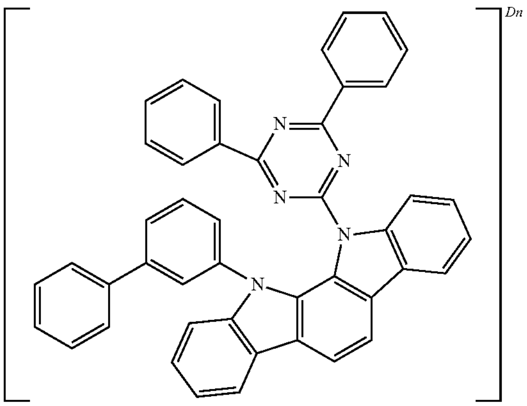
H1-98
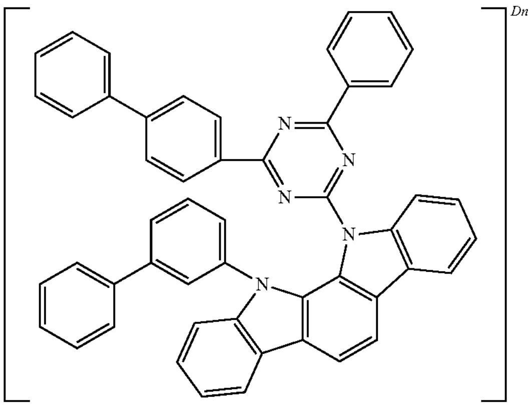
H1-99
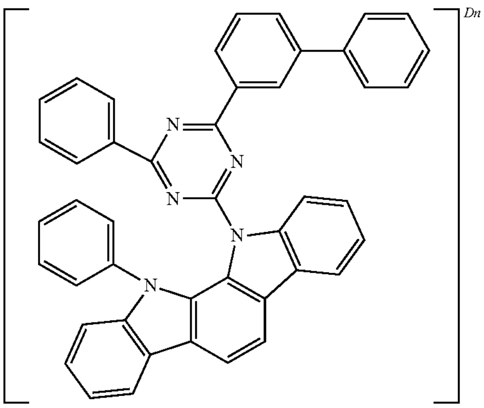

-continued
H1-100
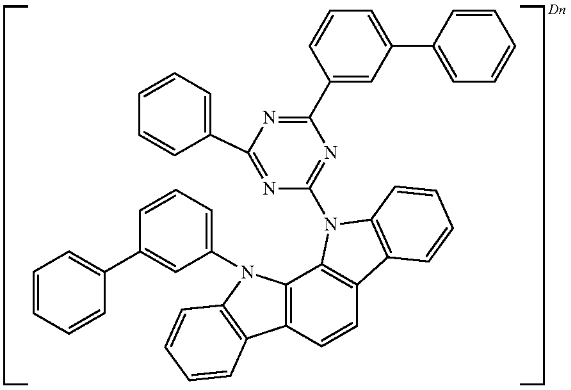
H1-101
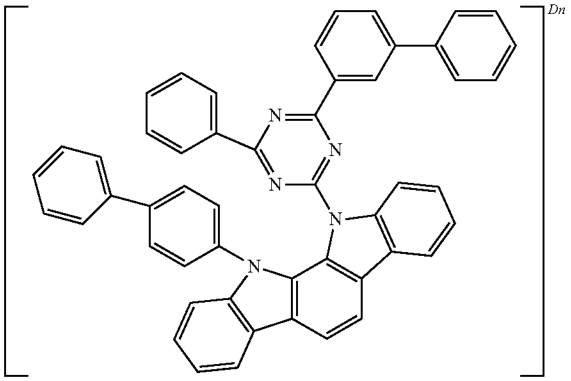
H1-102
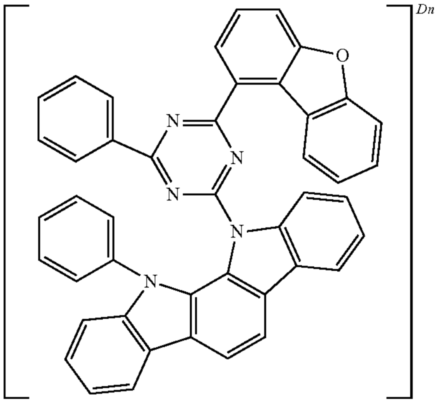

-continued
H1-103
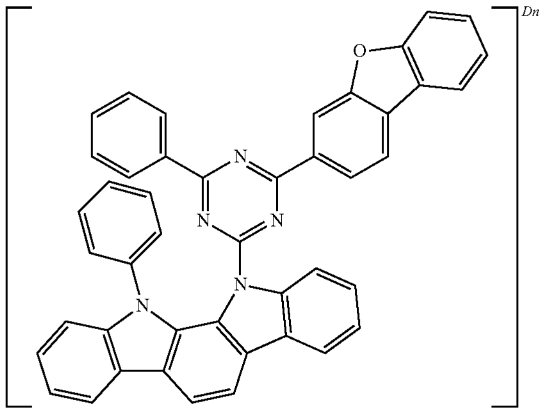
H1-104
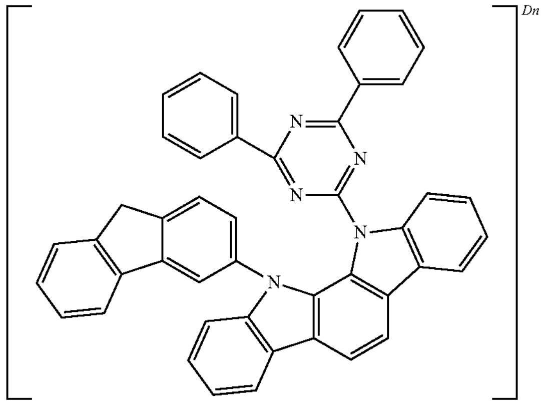
H1-105
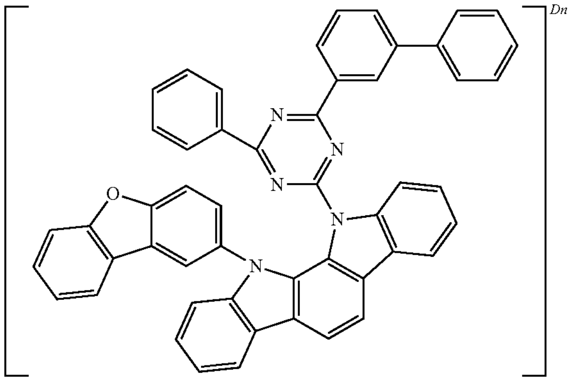

-continued
H1-106
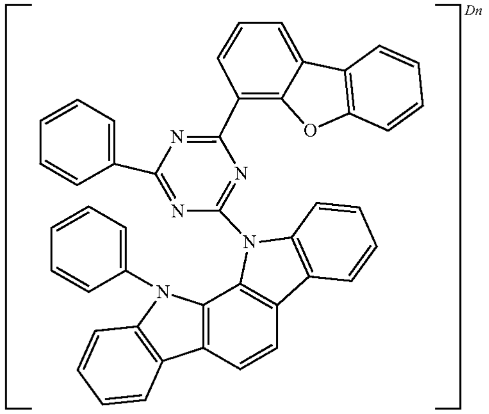
H1-109
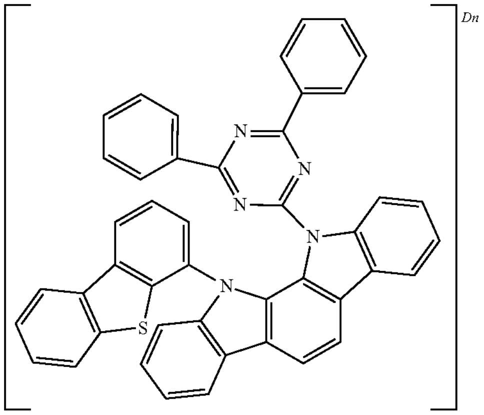
H1-107
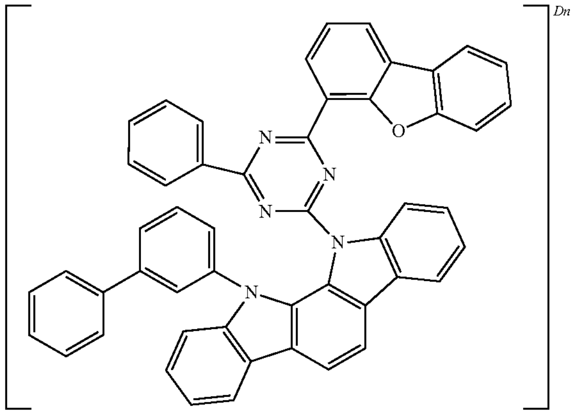
H1-110
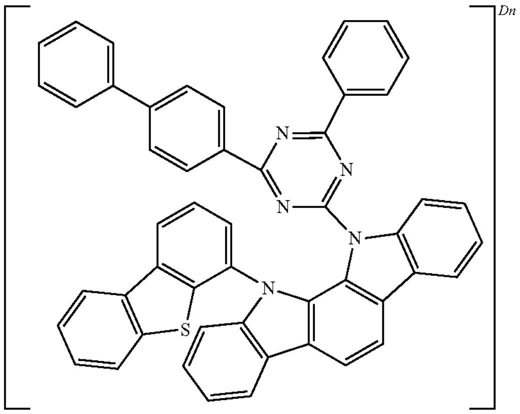
H1-108
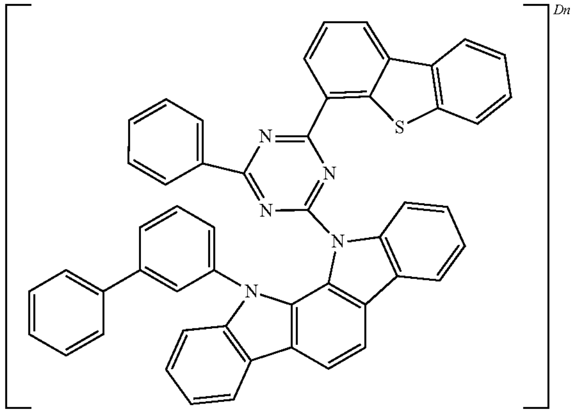
H1-111
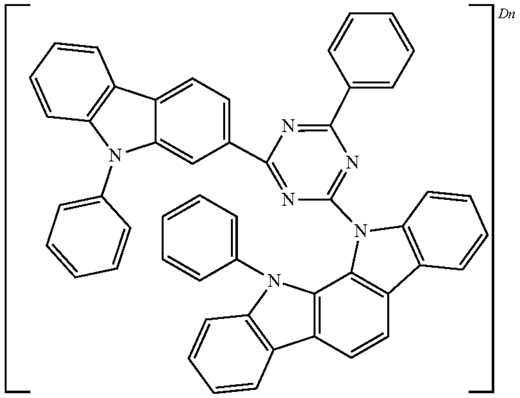

-continued
H1-112
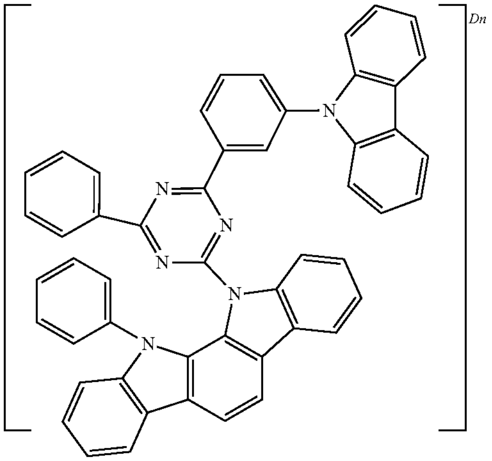
H1-113
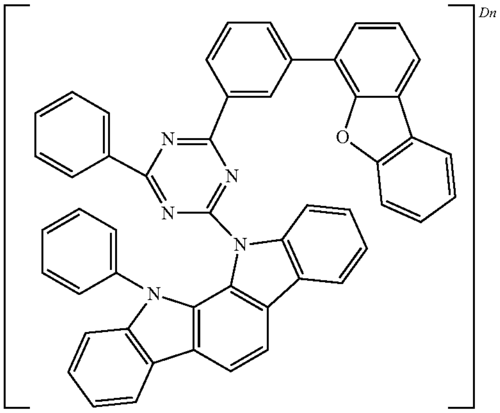
H1-114
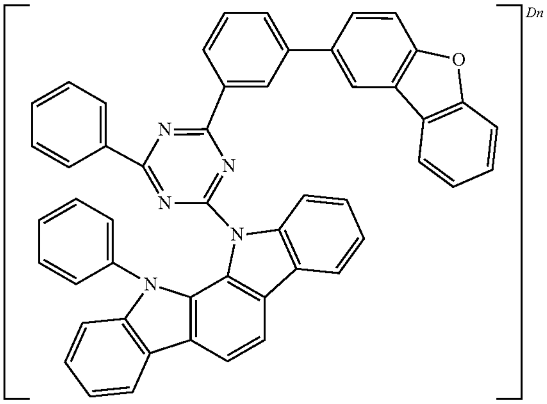
-continued
H1-115
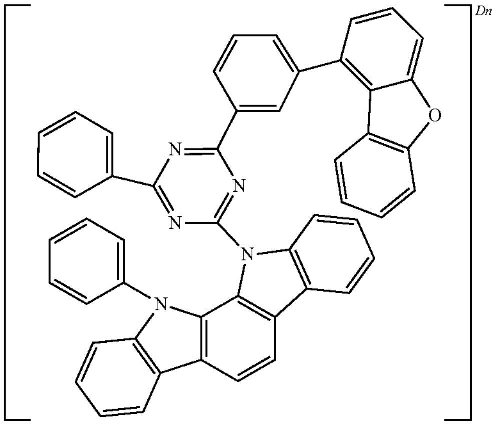
H1-116
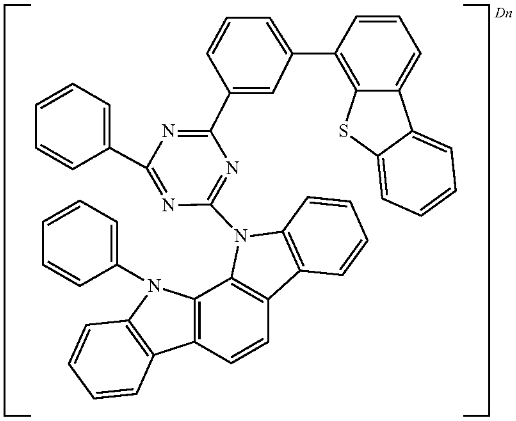
H1-117
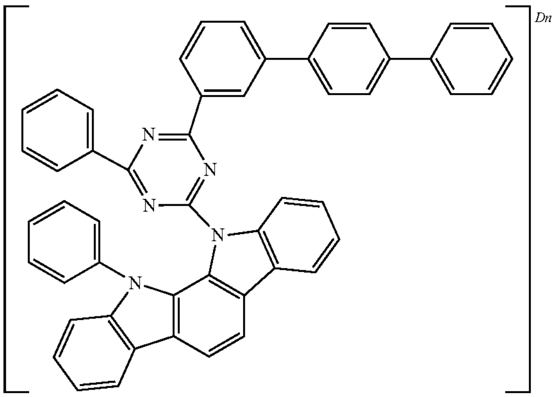

-continued
H1-118
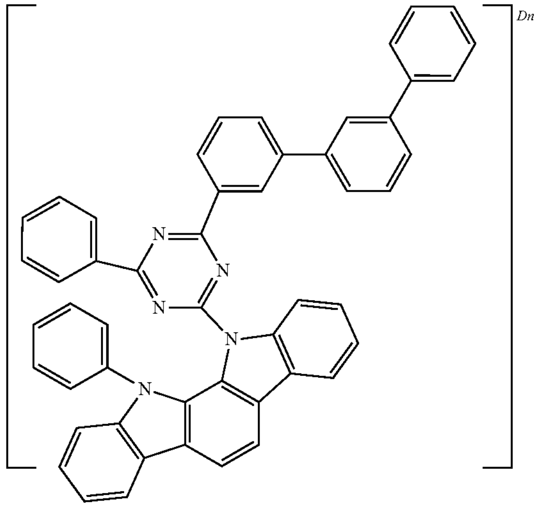
H1-119
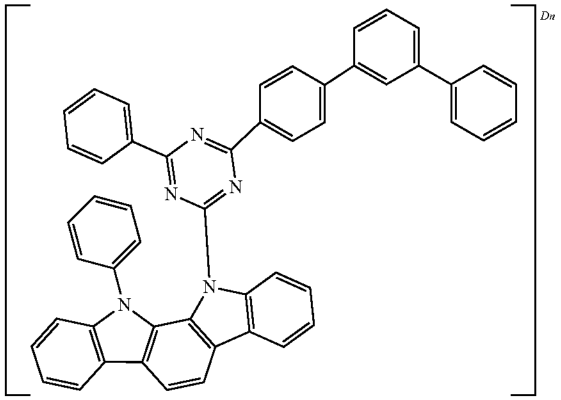
H1-120
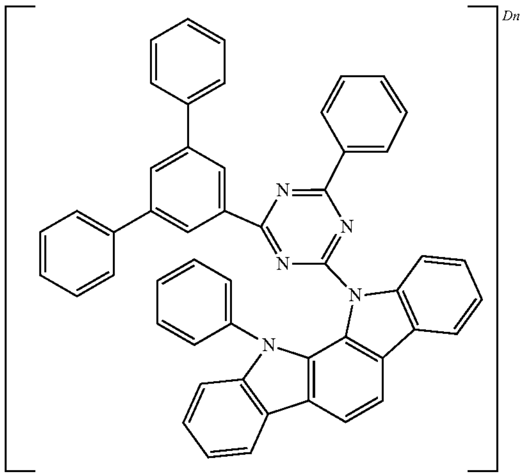
-continued
H1-121
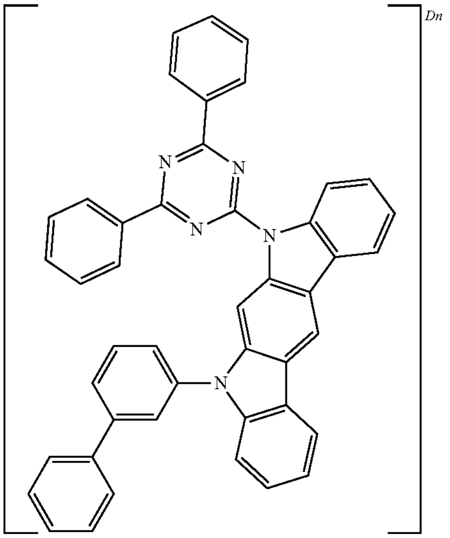
H1-122
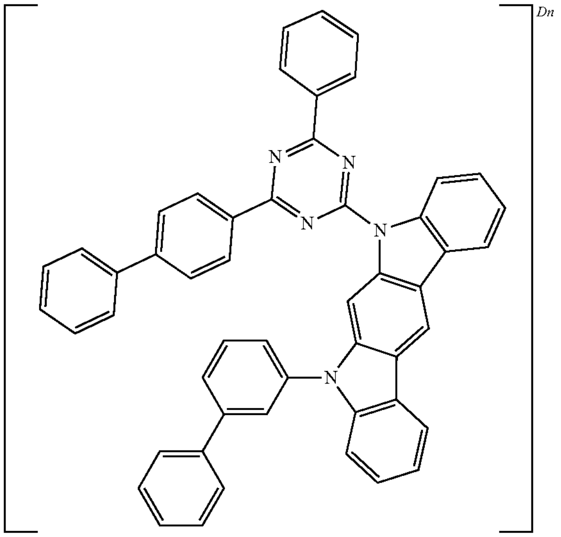

-continued
H1-123
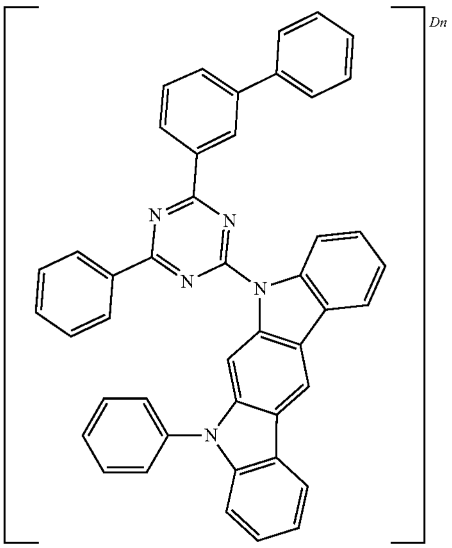
H1-124
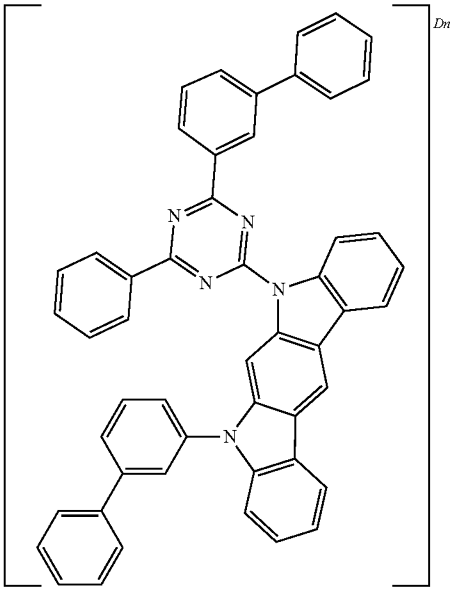
H1-125
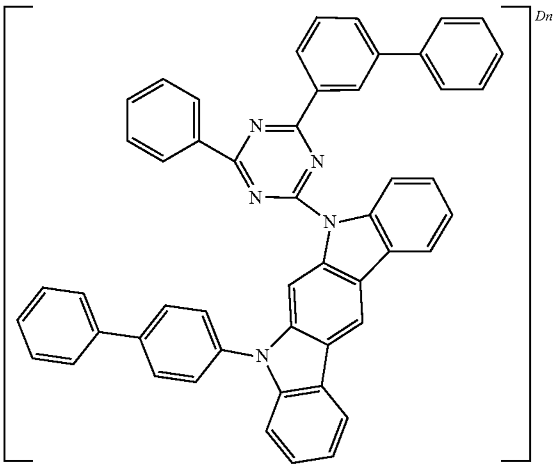
-continued
H1-126
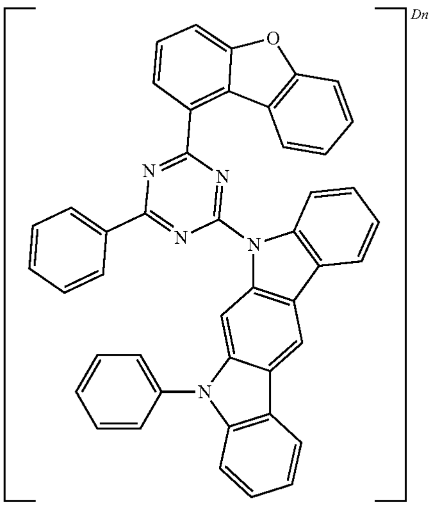
H1-127
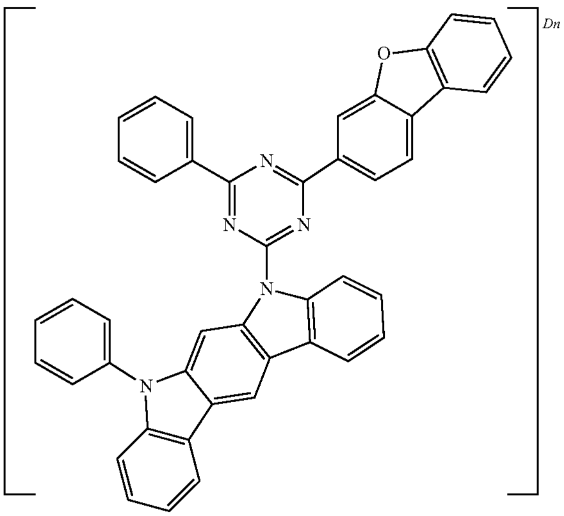
H1-128
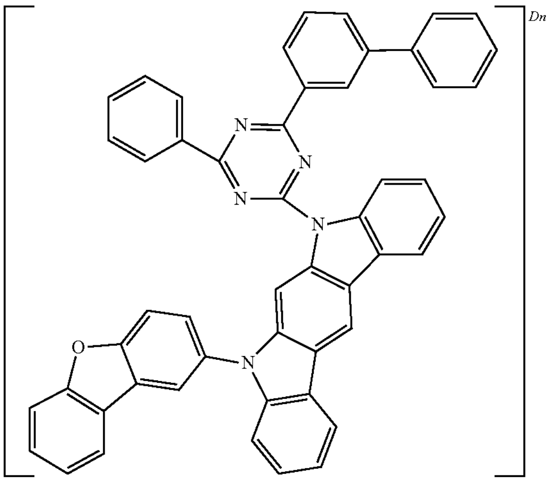

-continued
H1-129
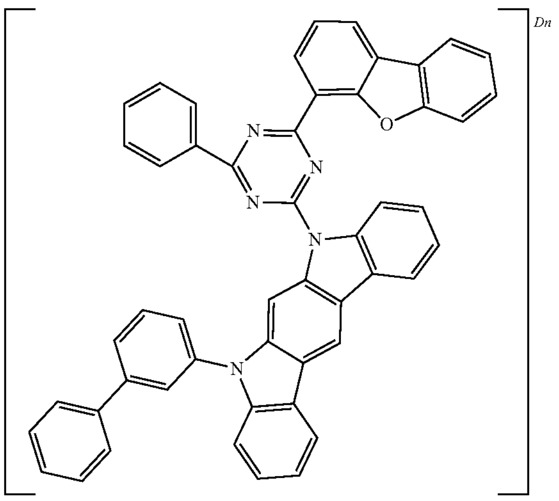
H1-130
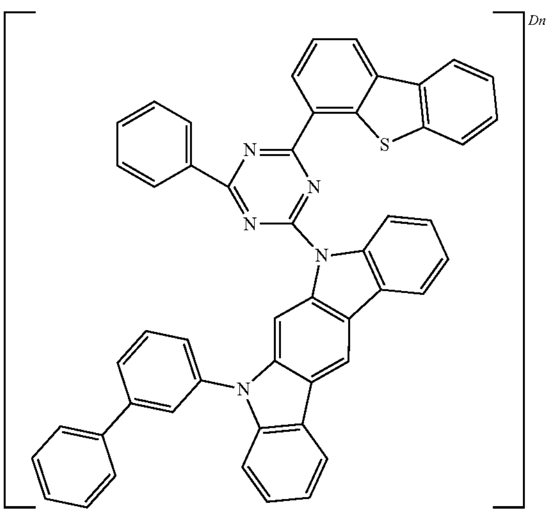
H1-131
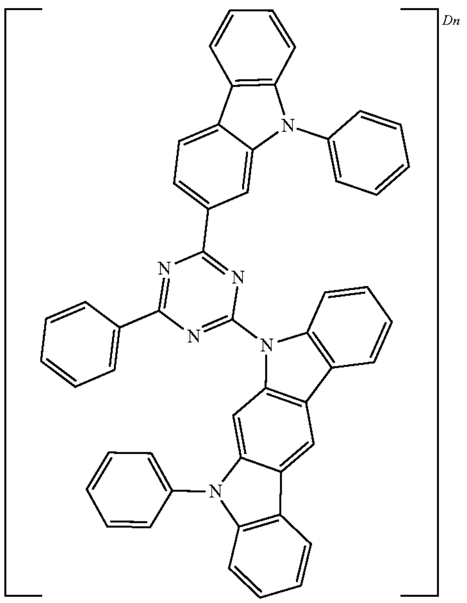
-continued
H1-132
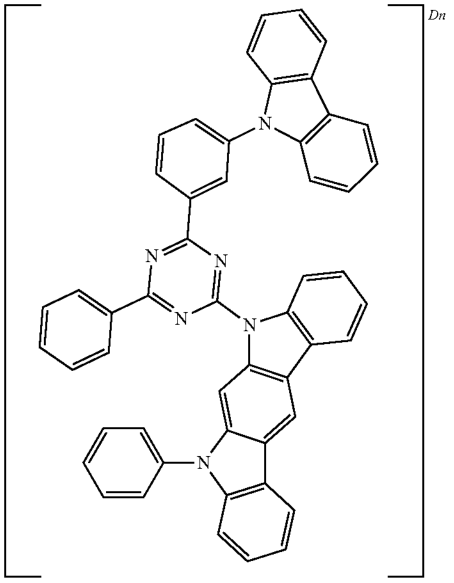
H1-133
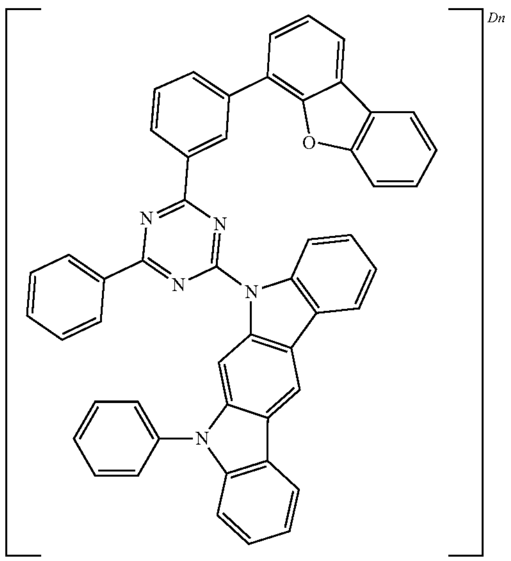

-continued
H1-134
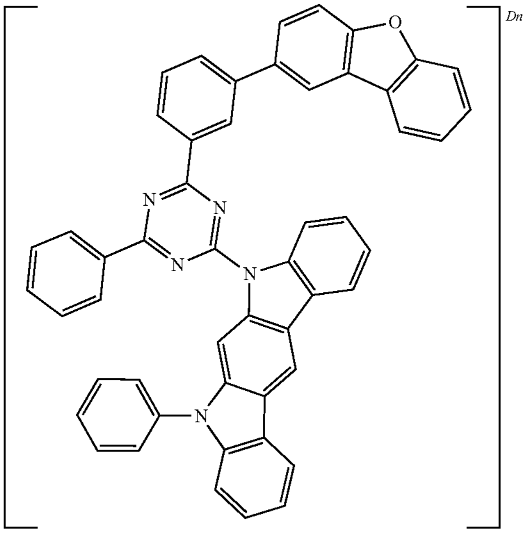
H1-135
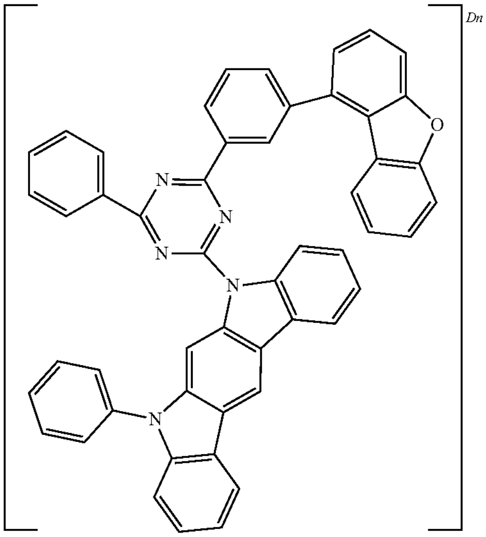
-continued
H1-136
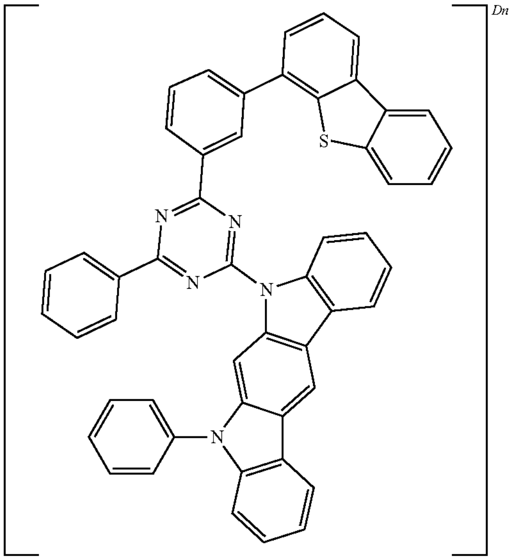
H1-137
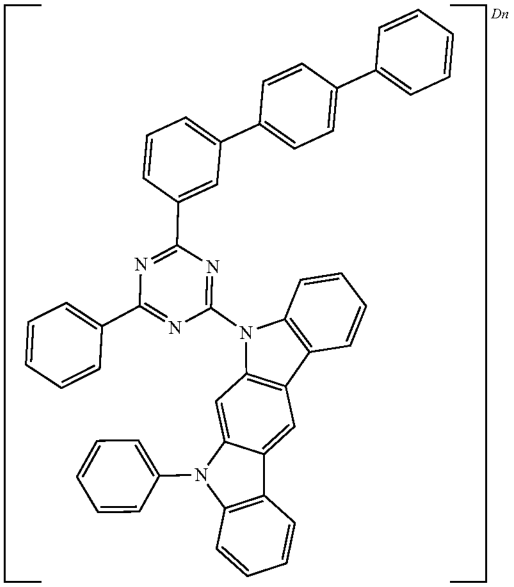

-continued
H1-138
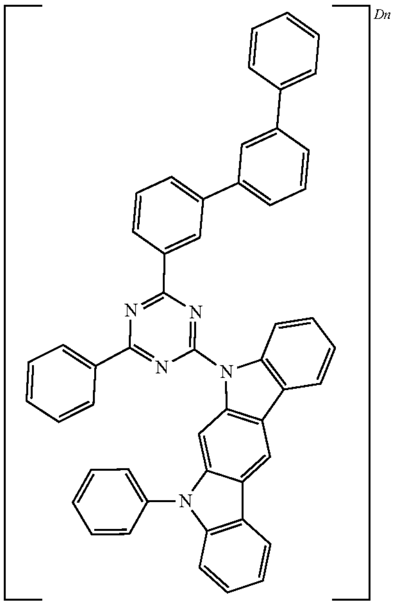
H1-139
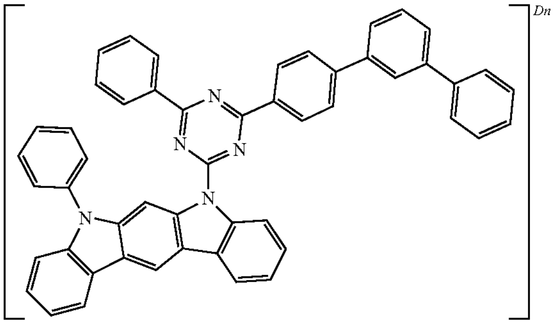
H1-140
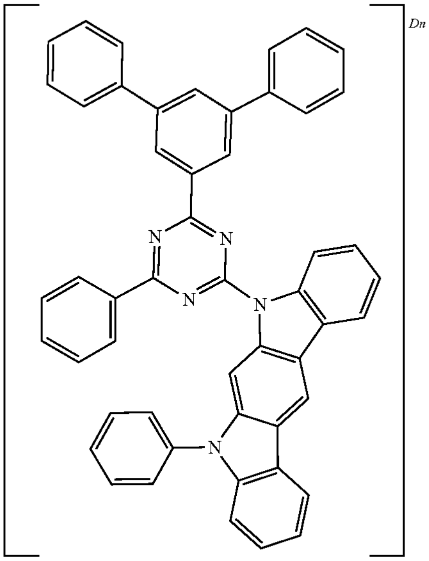
-continued
H1-141
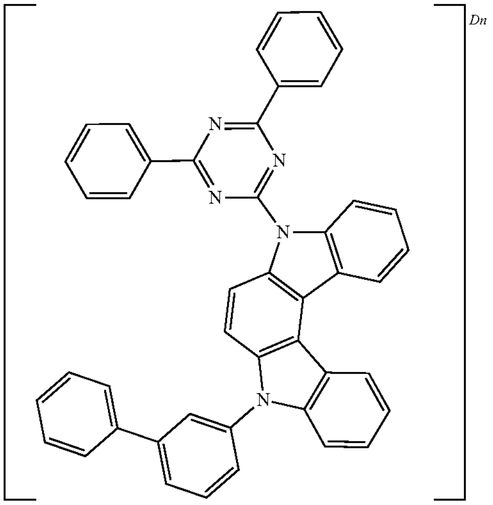
H1-142
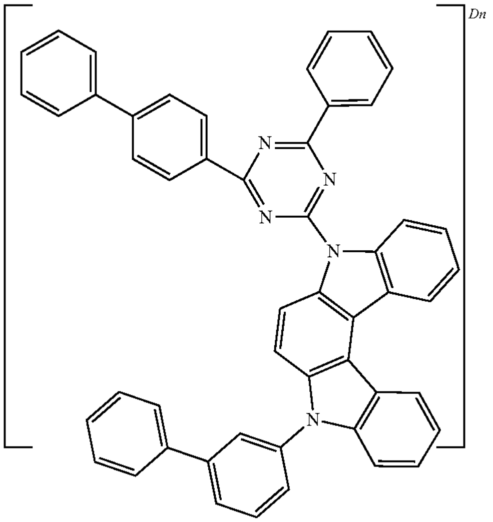
H1-143
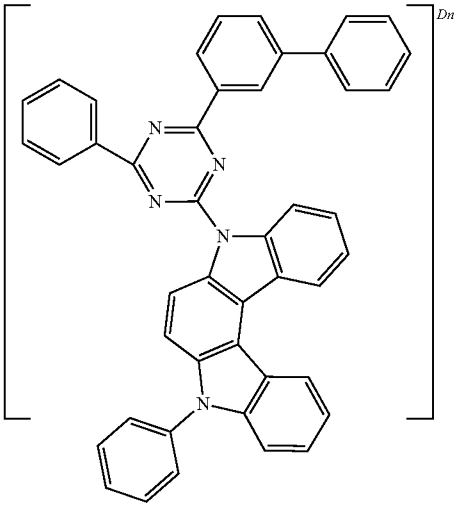

-continued
H1-144
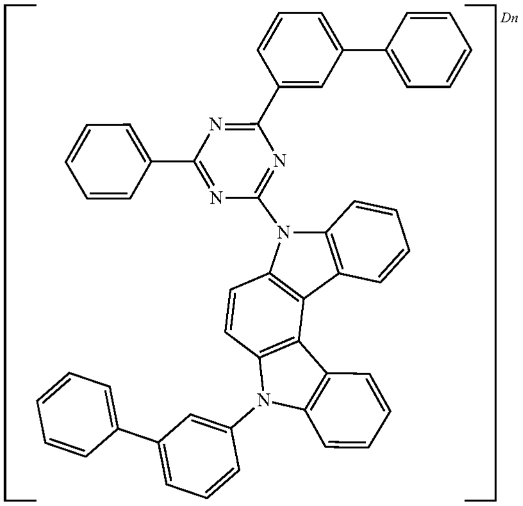
H1-145
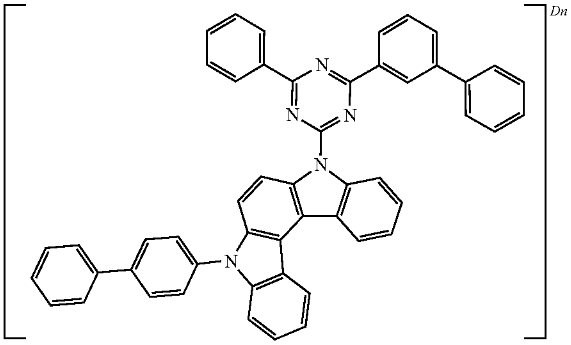
H1-146
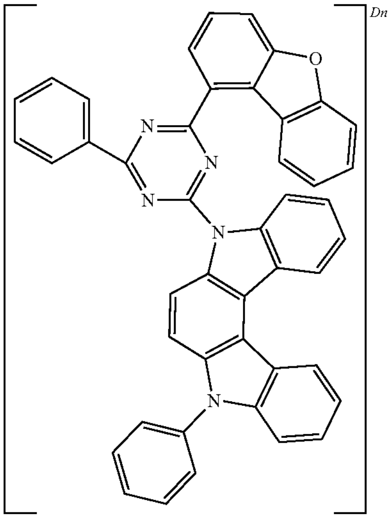
-continued
H1-147
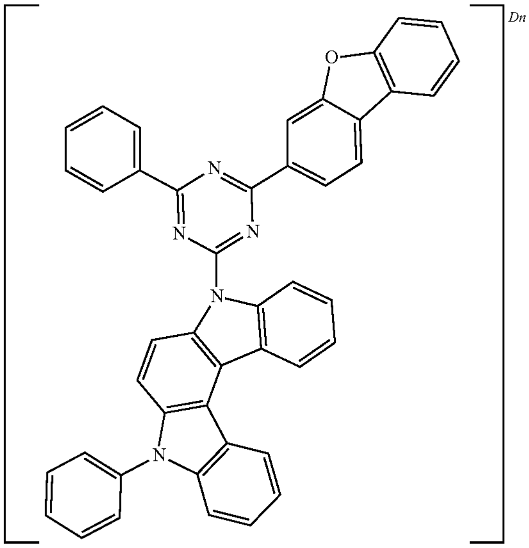
H1-148
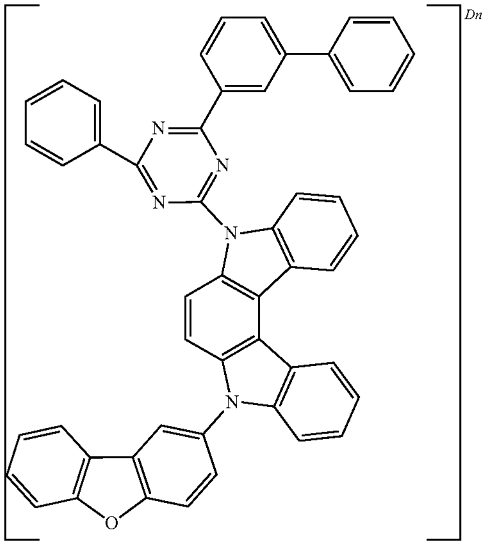

-continued
H1-149
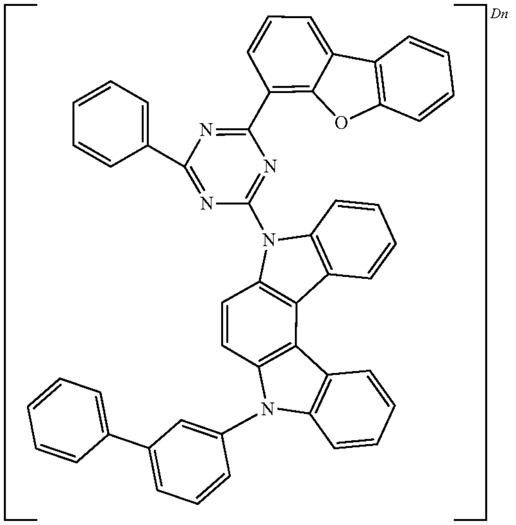
H1-150
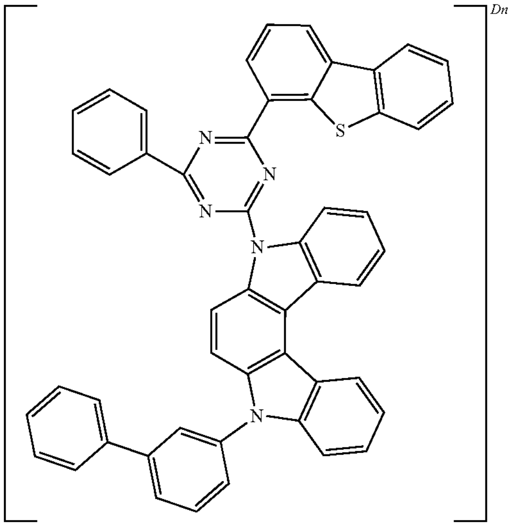
H1-151
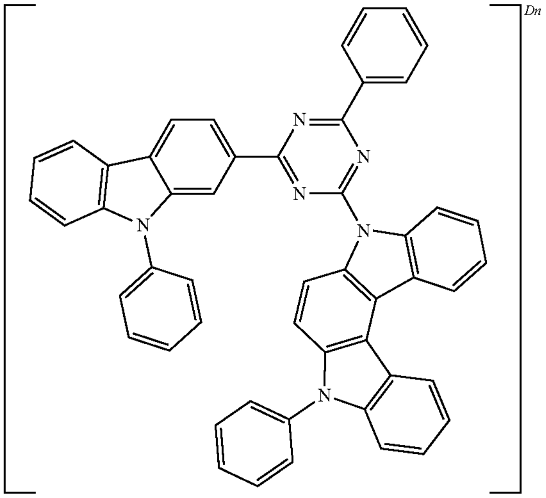
-continued
H1-152
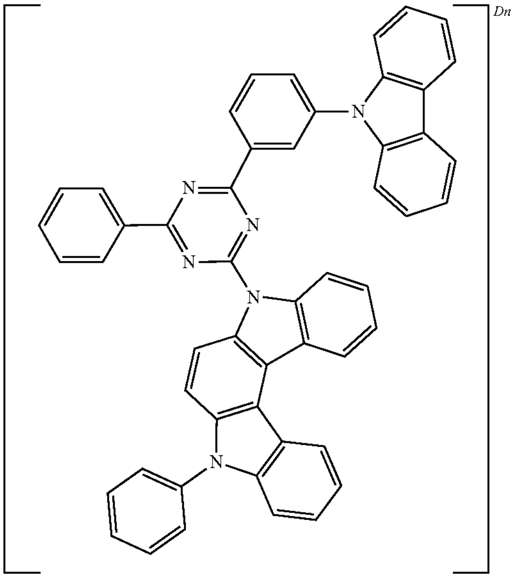
H1-153
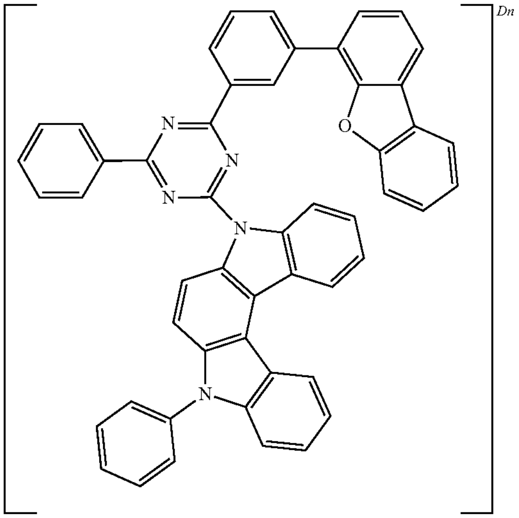

-continued
H1-154
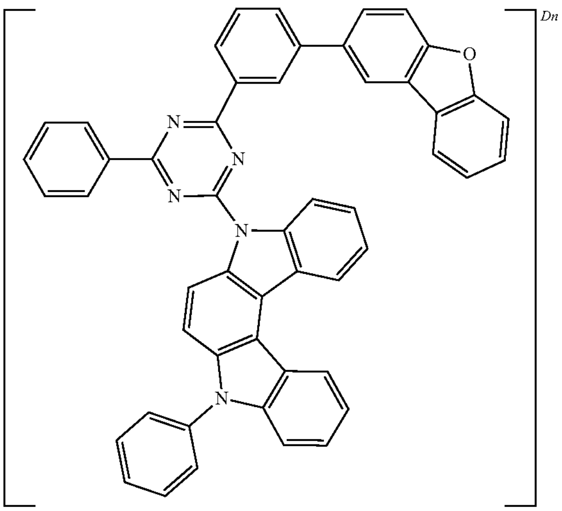
H1-155
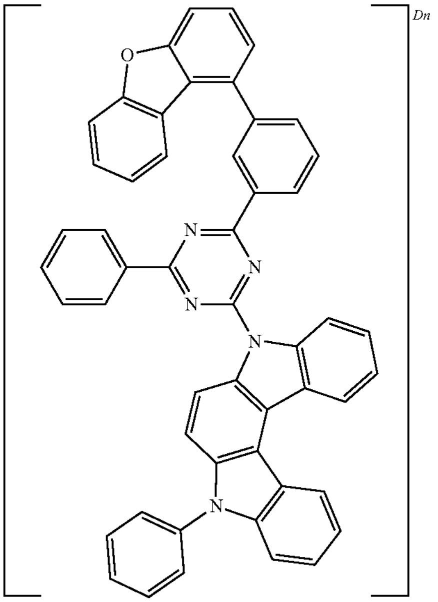
H1-156
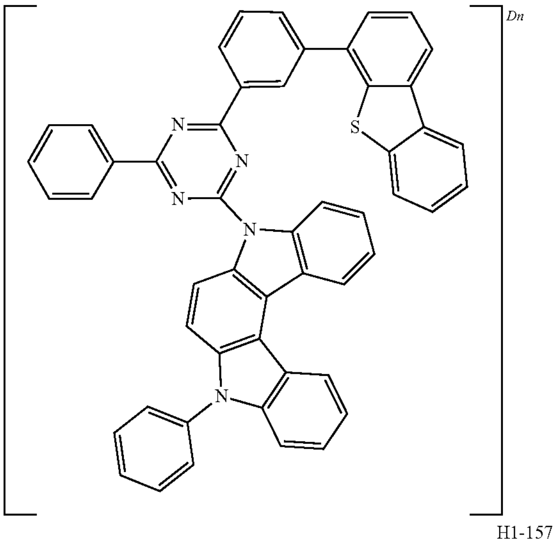
H1-157
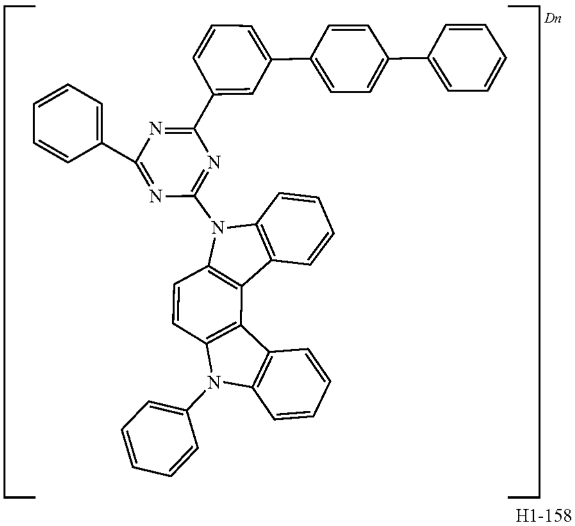
H1-158
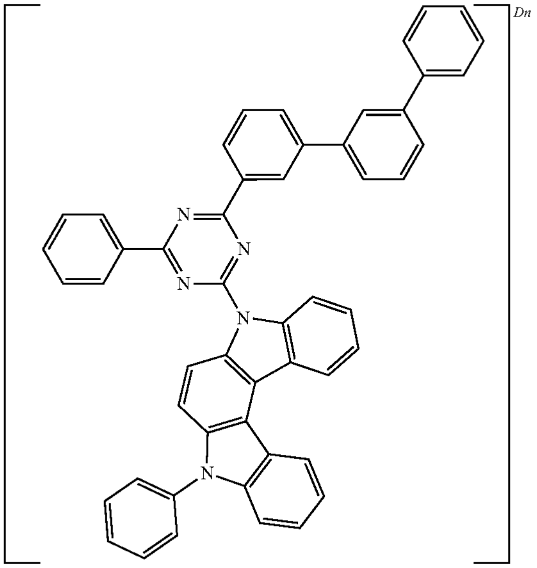

-continued
H1-159
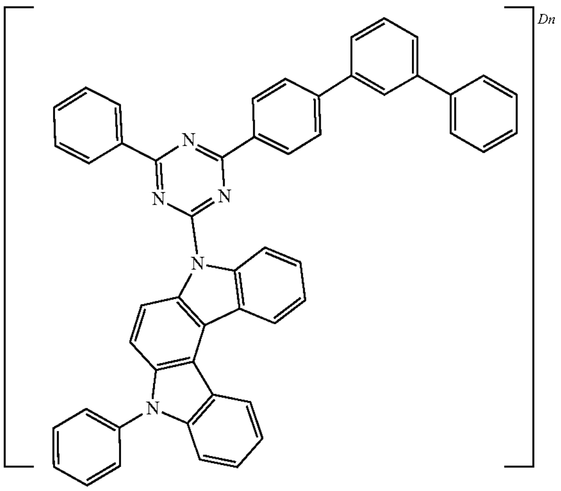
H1-160
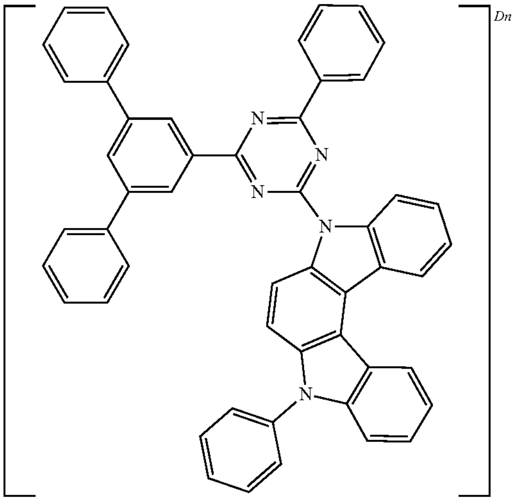
H1-161
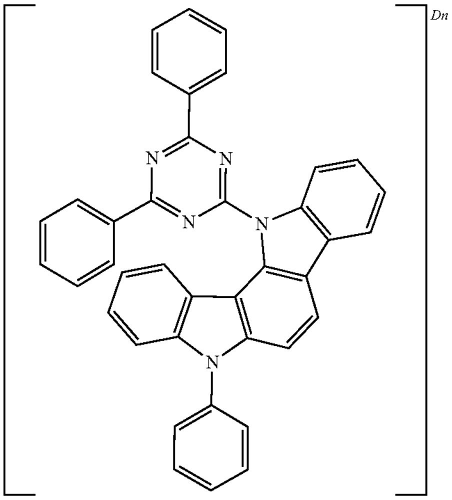
-continued
H1-162
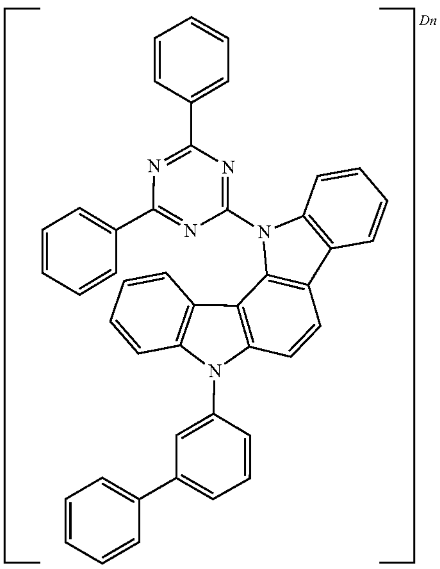
H1-163
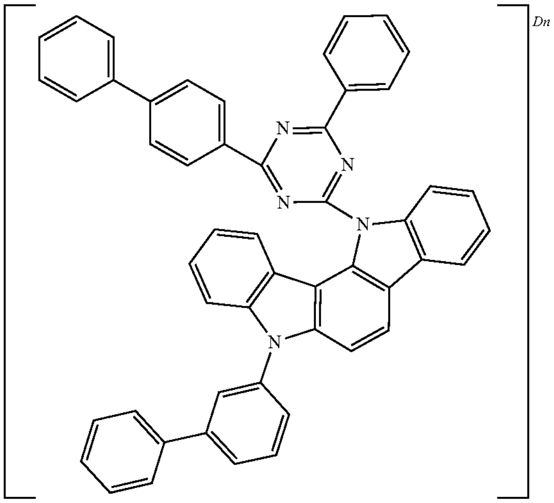

-continued
H1-164
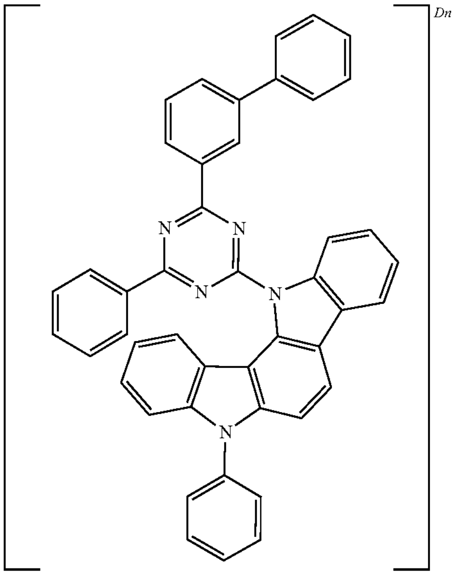
H1-165
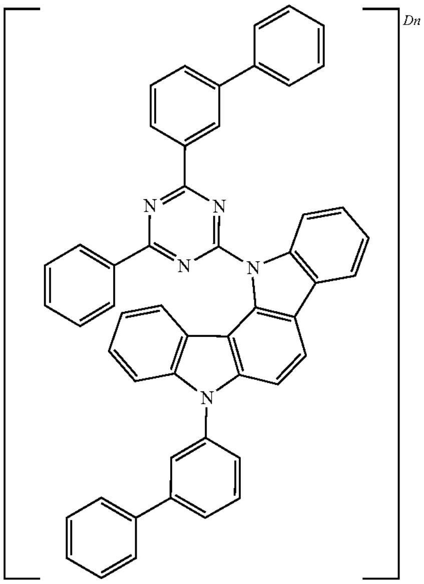
-continued
H1-166
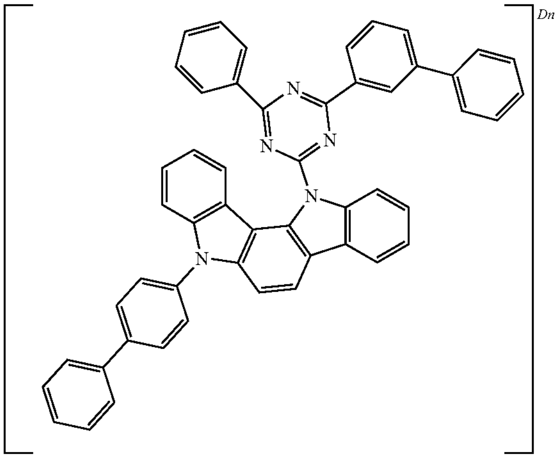
H1-167
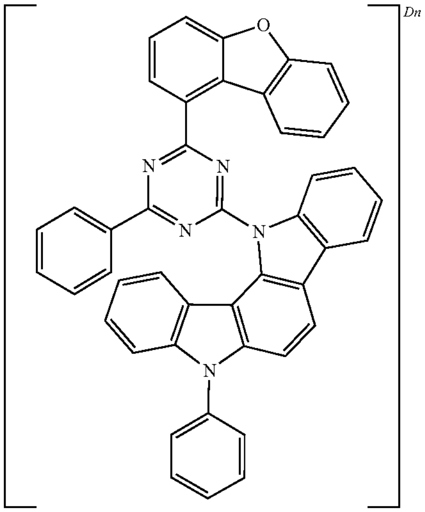
H1-168
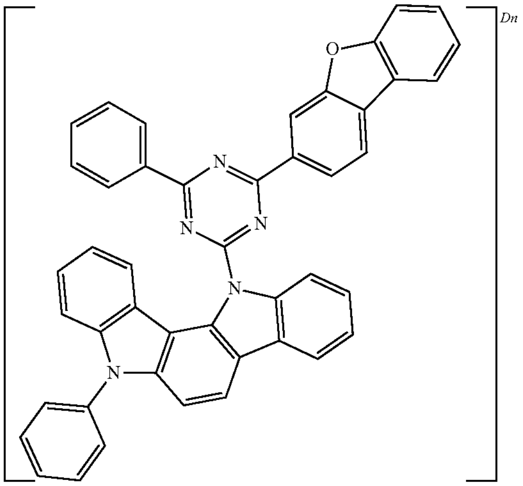

-continued
H1-169
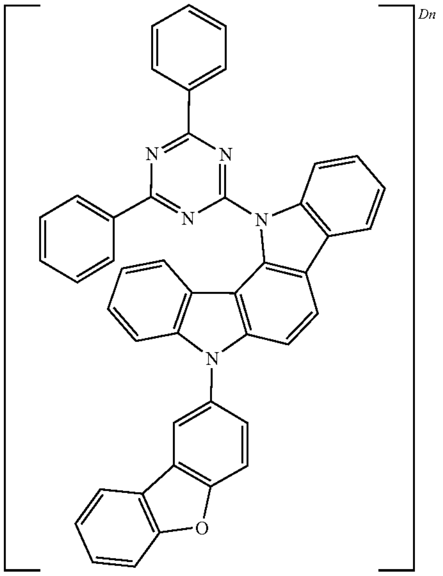
H1-170
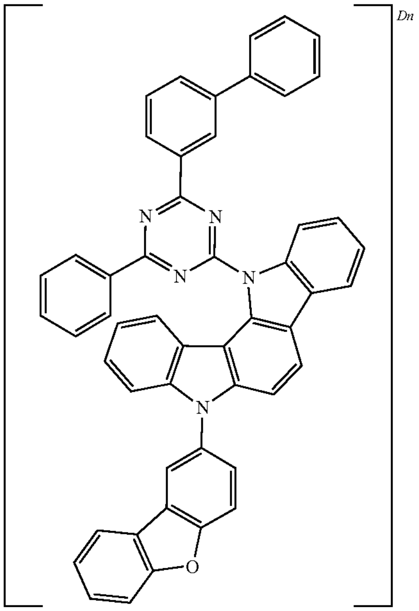
-continued
H1-171
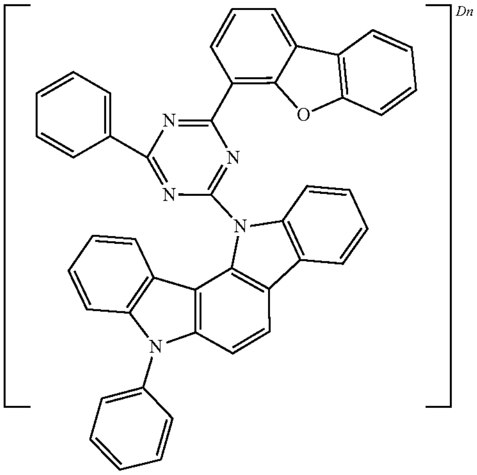
H1-172
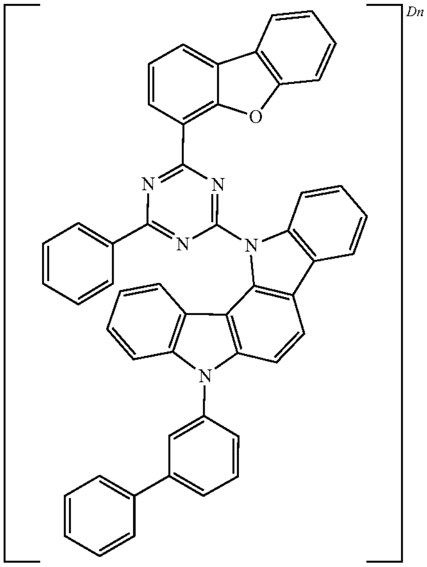
H1-173
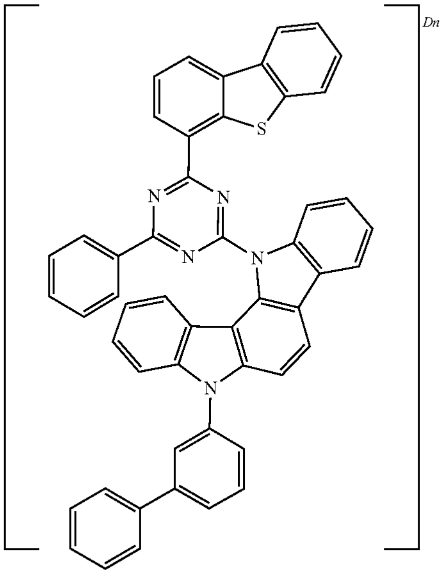

-continued
H1-174
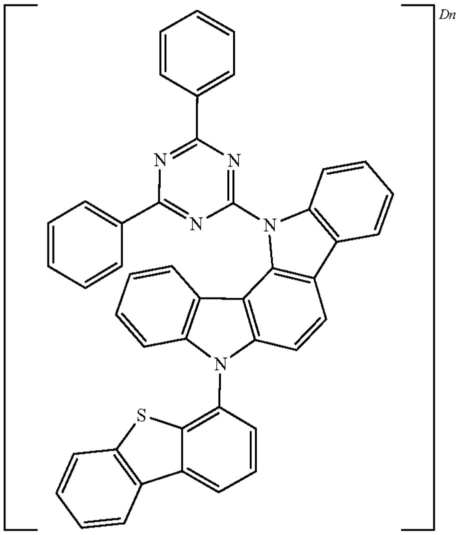
H1-175
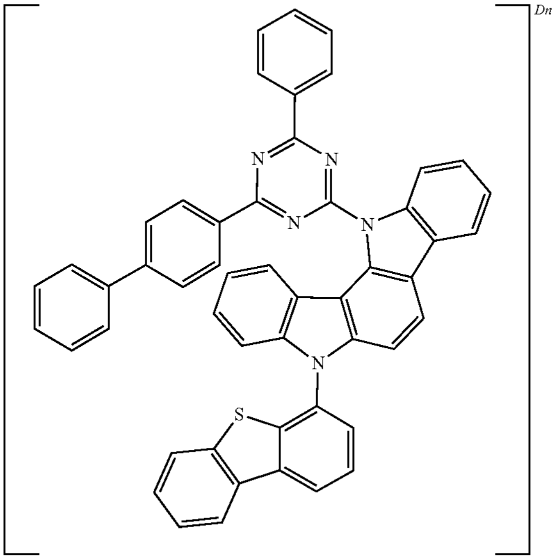
-continued
H1-176
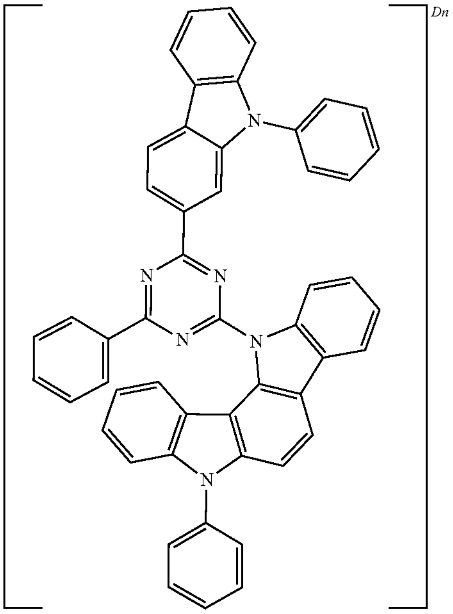
H1-177
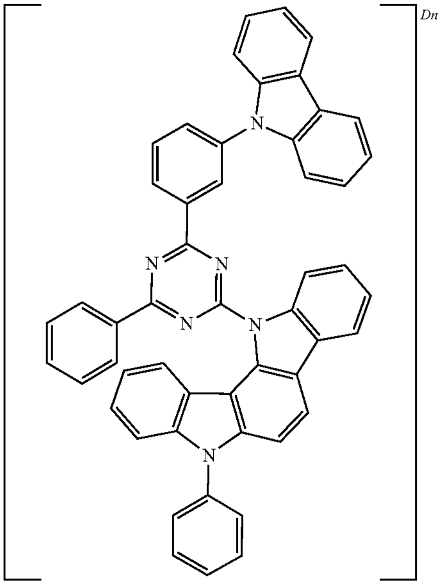

-continued
H1-178
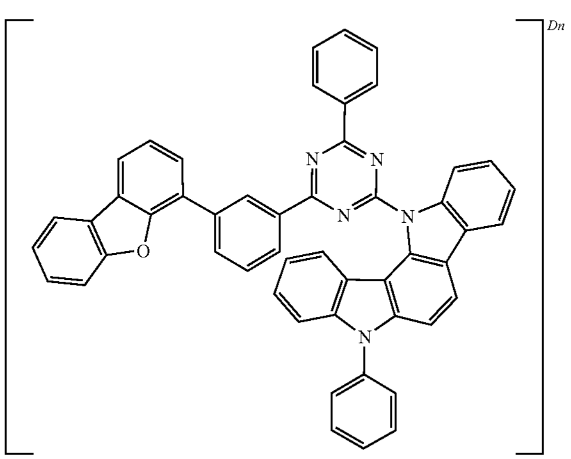
H1-179
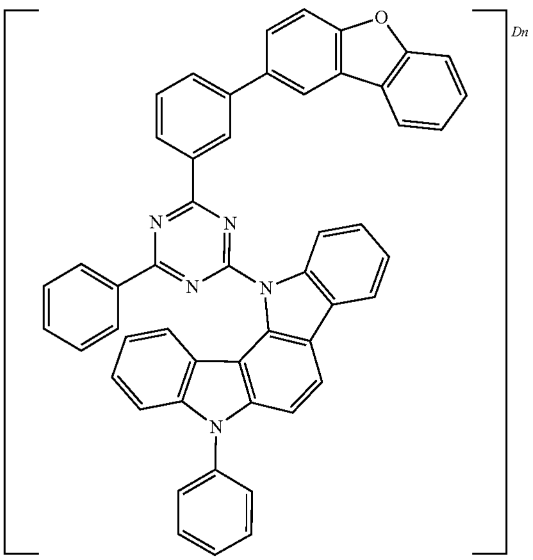
H1-180
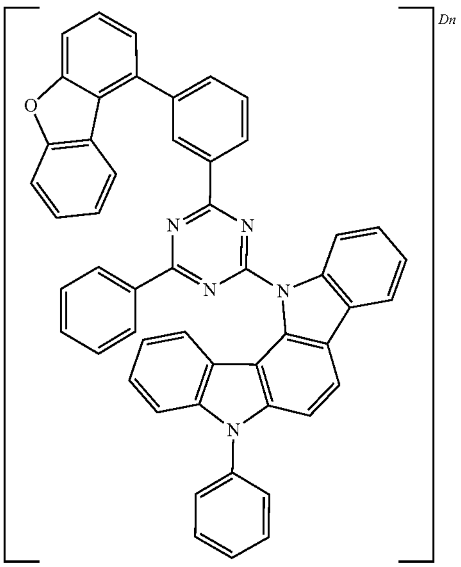
-continued
H1-181
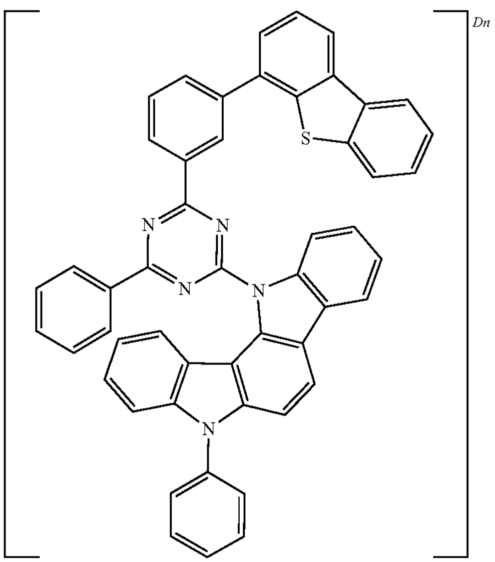
H1-182
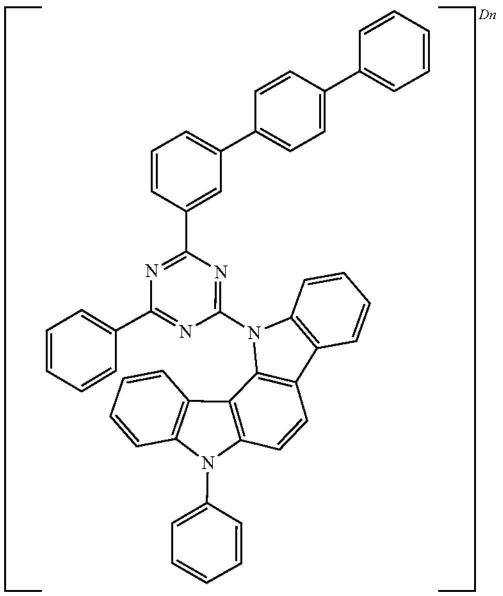

-continued
H1-183
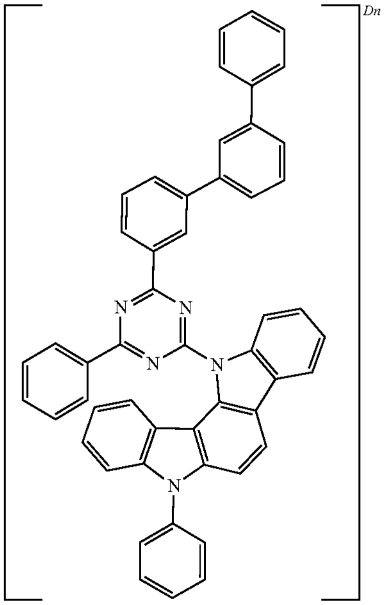
H1-184
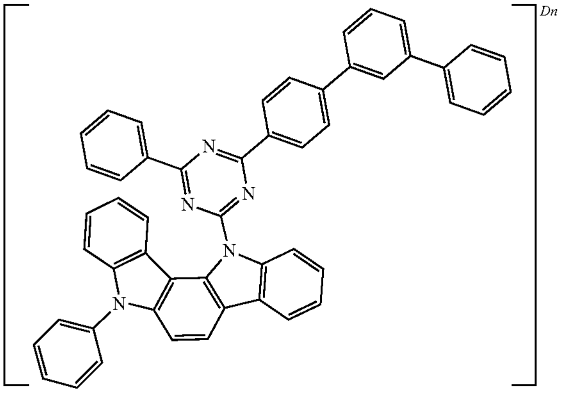
H1-185
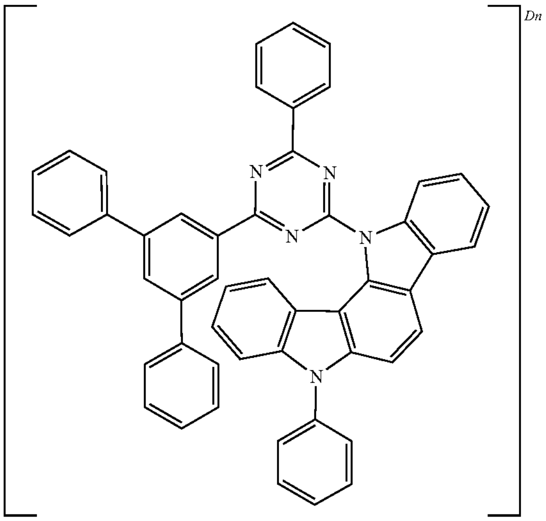
-continued
H1-186
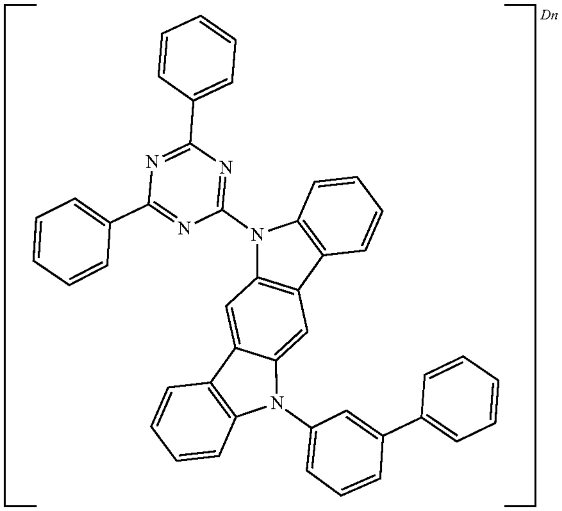
H1-187
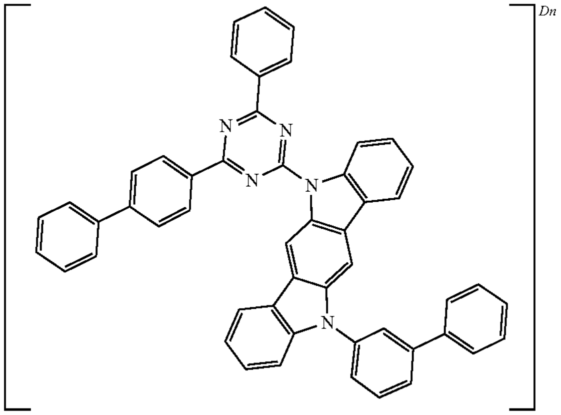
H1-188
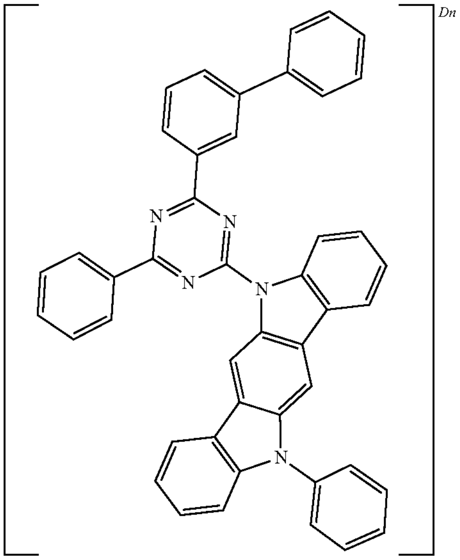

-continued
H1-189
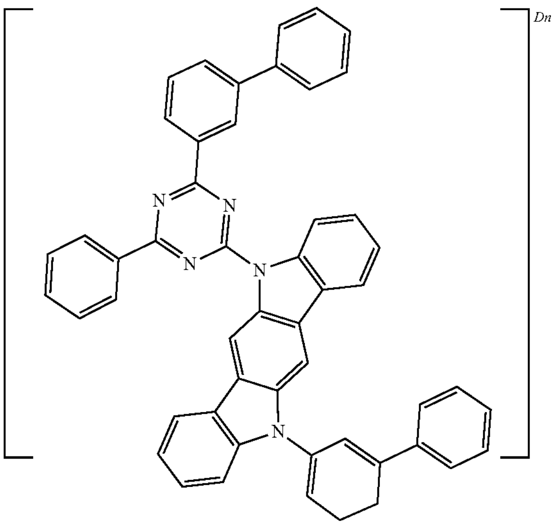
-continued
H1-191
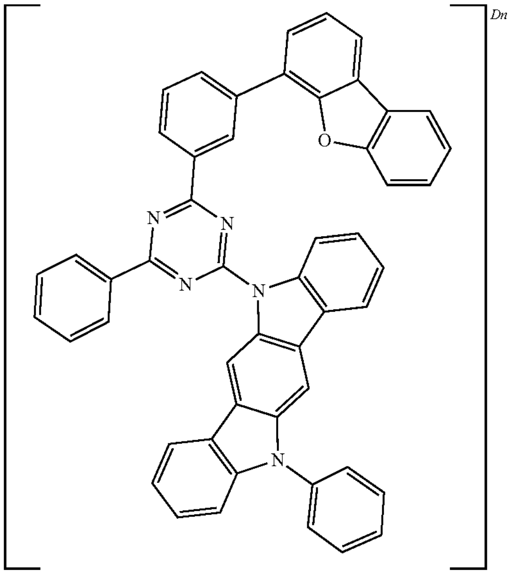
H1-190
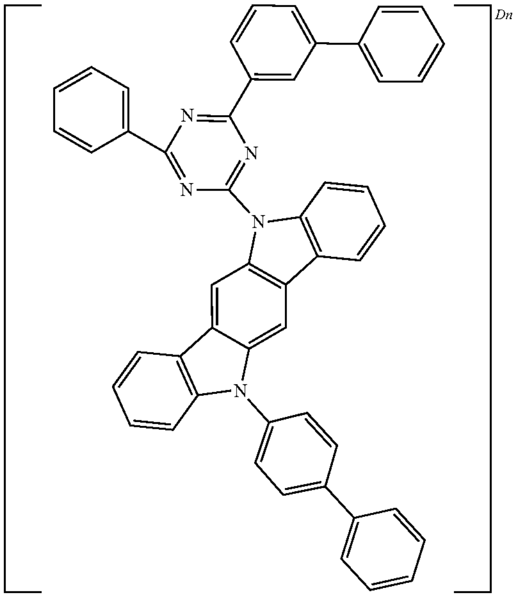
H1-192
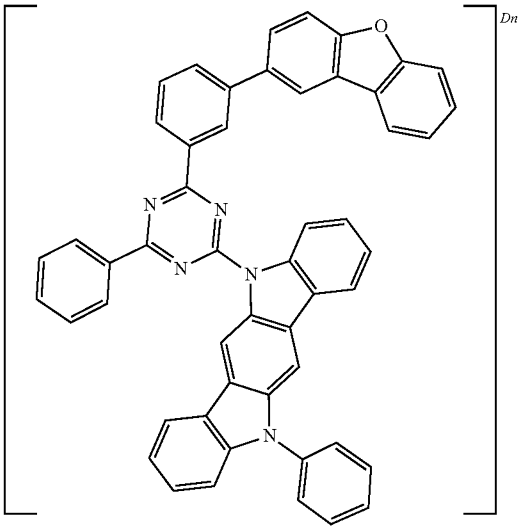

-continued
H1-193
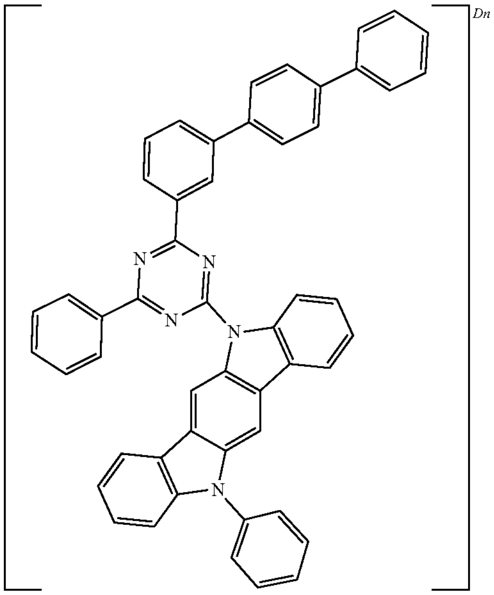
H1-194
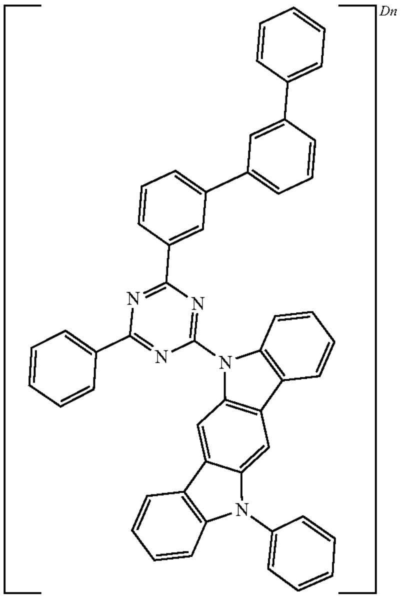
H1-195
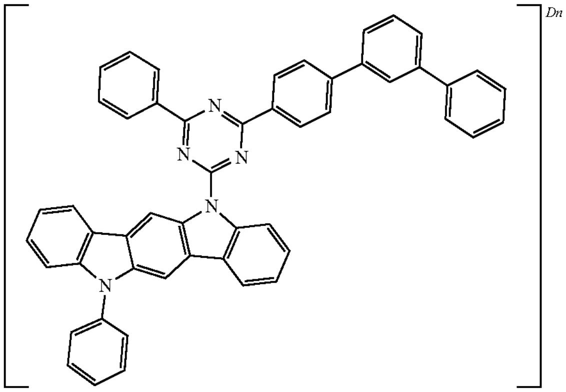
-continued
H1-196
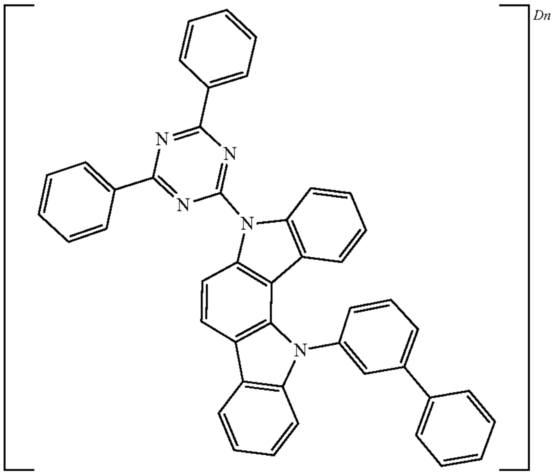
H1-197
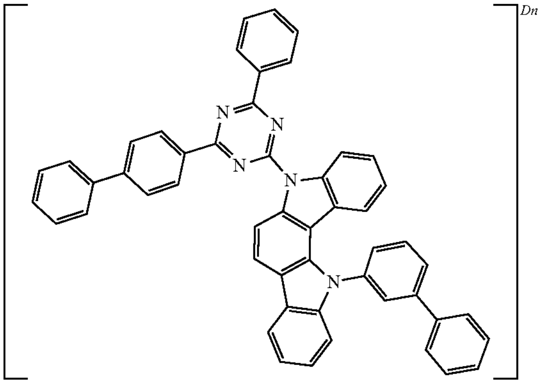
H1-198
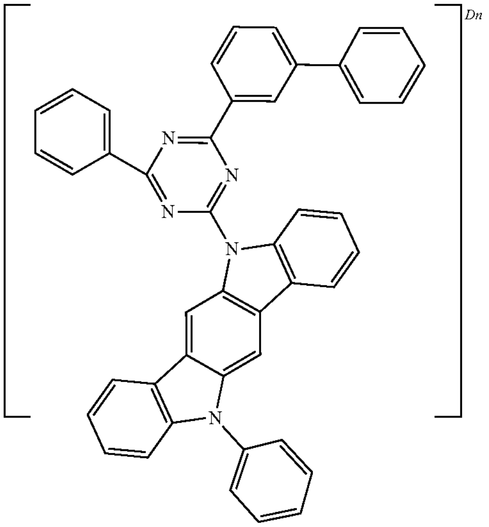

-continued
H1-199
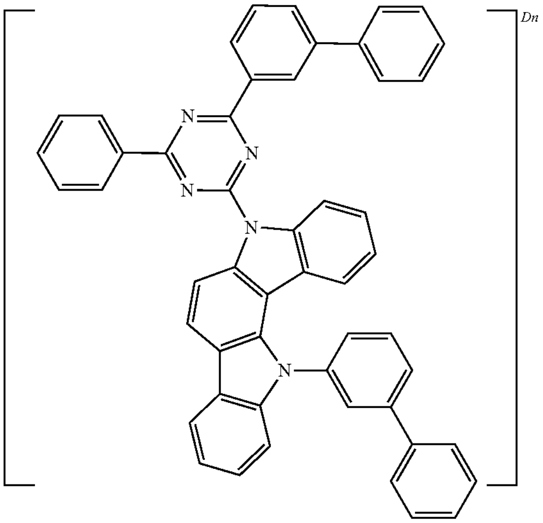
H1-200
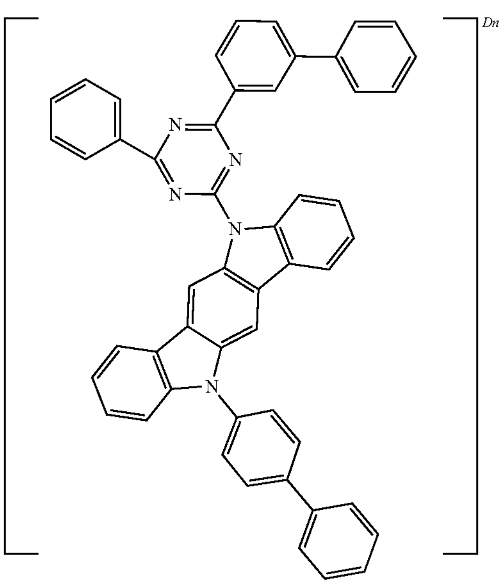
H1-201
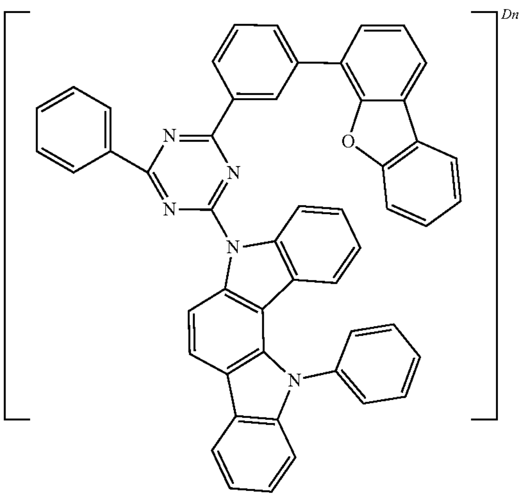
-continued
H1-202
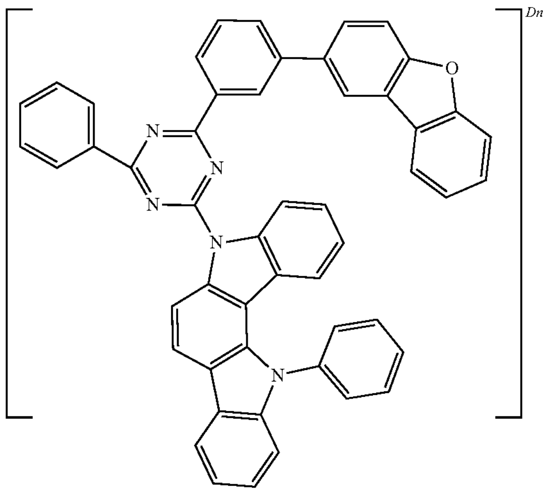
H1-203
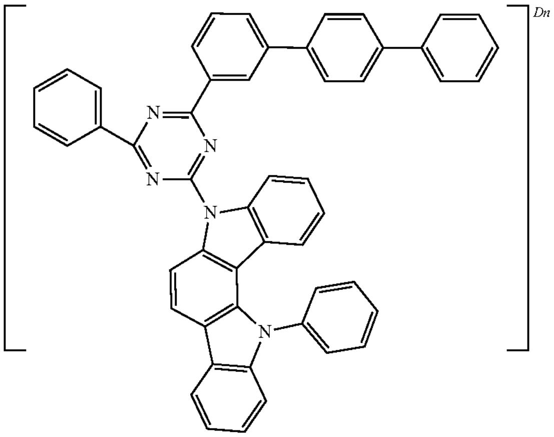
H1-204
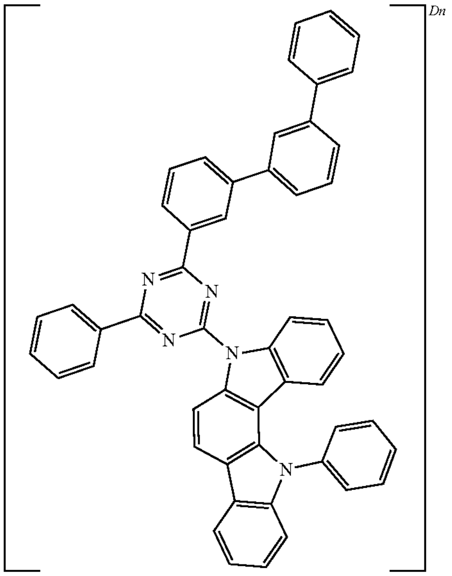

-continued
H1-205
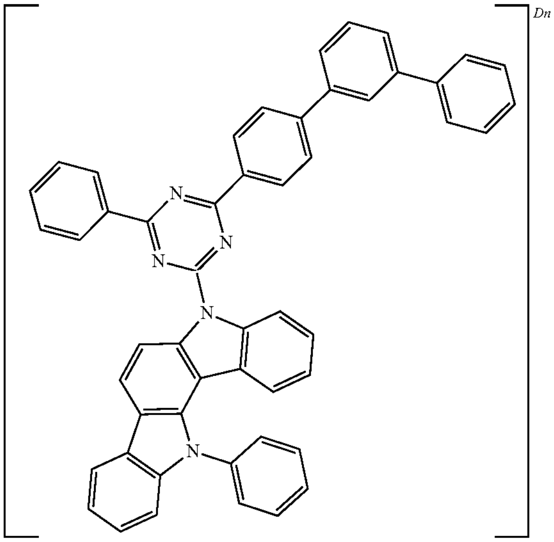
H1-206
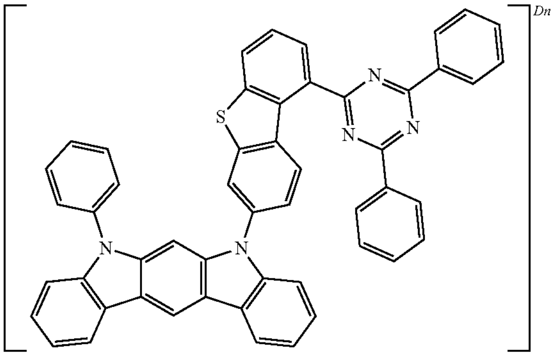
H1-207
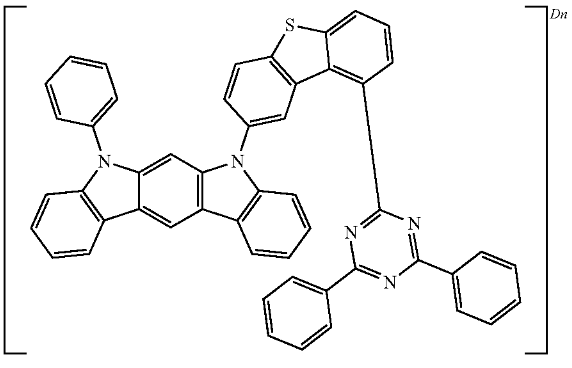
-continued
H1-208
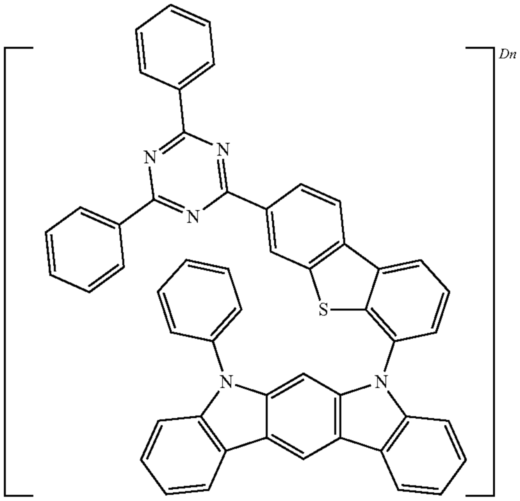
H1-209
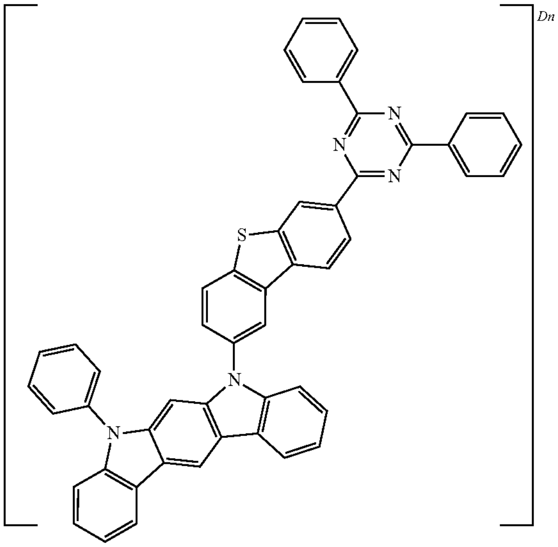
H1-210
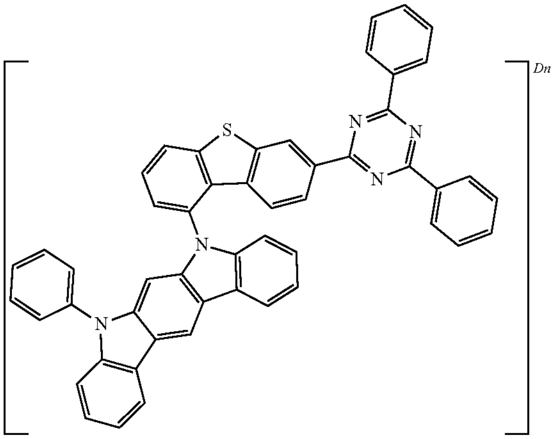
In said compounds, Dn represents that n number of hydrogens are replaced with deuterium; and n represents an integer of 1 to 50. According to one embodiment, n represents an integer of 3 or more, preferably an integer of 4 or more, more preferably an integer of 5 or more, even more preferably an integer of 6 or more. When being deuterated to the number of the lower limit or more, the bond dissociation energy related to deuteration may increase to enhance the stability of the compound. When such a compound is used in an organic electroluminescent device, the organic electroluminescent device may exhibit improved lifetime property.

The compound represented by formula 1 according to the present disclosure may be produced by synthetic methods known to one skilled in the art, in particular by referring to the synthetic methods disclosed in a number of patents. For example, the compound of formula 1 may be prepared in a similar manner by using deuterated precursor materials, or more generally may be prepared by treating the non-deuterated compound with a deuterated solvent or D6-benzene in the presence of an H/D exchange catalyst such as a Lewis acid, e.g., aluminum trichloride or ethyl aluminum chloride, in the methods disclosed in Korean Patent Application Laid-Open No. 2010-0108903, Korean Patent Publication No. 1313730, Korean Patent Application Laid-Open No. 2009-0086057, etc. In addition, the degree of deuteration can be controlled by changing the reaction conditions such as the reaction temperature, time, the equivalent of the acid, etc.

The second host material, which is another host material according to one embodiment, comprises the compound represented by the following formula 2.

(2)

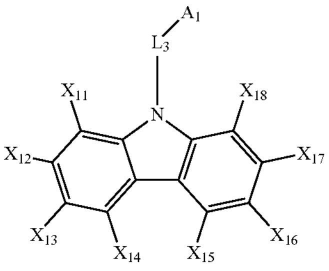

In formula 2, $A_1$ represents a substituted or unsubstituted (C6-C30)aryl, a substituted or unsubstituted dibenzofuranyl, a substituted or unsubstituted dibenzothiophenyl, or a substituted or unsubstituted carbazolyl;

$L_3$ represents a single bond, or a substituted or unsubstituted (C6-C30)arylene, or a substituted or unsubstituted (3- to 30-membered)heteroarylene; and $X_{11}$ to $X_{18}$, each independently, represent hydrogen, deuterium, a substituted or unsubstituted (C6-C30)aryl, or a substituted or unsubstituted (3- to 30-membered) heteroaryl, and two or more adjacent $X_{11}$ to $X_{18}$ may be linked to each other to form a ring(s);

with the proviso that when two or more adjacent $X_{11}$ to $X_{18}$ are linked to each other to form a ring(s), at least one of $X_{11}$ to $X_{18}$ represents deuterium or is substituted with deuterium;

and when two or more adjacent $X_{11}$ to $X_{18}$ are not linked to each other to form a ring(s), $X_{11}$ to $X_{18}$ are not deuterium and are not substituted with deuterium.

In one embodiment, two or more adjacent $X_{11}$ to $X_{18}$ may be linked to each other to form a substituted or unsubstituted indole ring, a substituted or unsubstituted indene ring, a substituted or unsubstituted benzofuran ring, a substituted or unsubstituted benzothiophene ring, etc.

The compound represented by formula 2 according to one embodiment may be represented by the following formula 2-1 or 2-2.

(2-1)

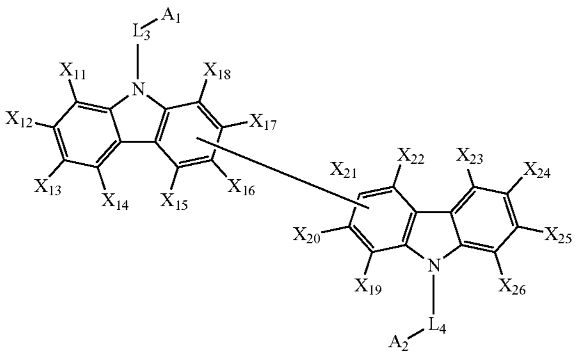

(2-2)

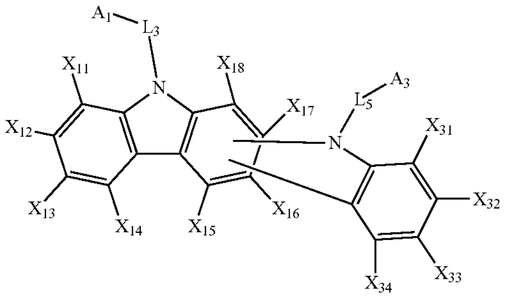

in formulas 2-1 and 2-2, $A_1$, $L_3$, and $X_{11}$ to $X_{18}$ are as defined in formula 2, $A_2$ and $A_3$ are as defined for $A_1$, $L_4$ and $L_5$ are as defined for $L_3$, $X_{31}$ to $X_{34}$ are as defined for $X_{11}$ to $X_{18}$, and $X_{19}$ to $X_{26}$, each independently, represent hydrogen, a substituted or unsubstituted (C6-C30)aryl, or a substituted or unsubstituted (3- to 30-membered)heteroaryl, with the proviso that in formula 2-2, at least one of $X_{11}$ to $X_{18}$, and $X_{31}$ to $X_{34}$ represents deuterium or is substituted with deuterium.

In one embodiment, $A_1$ to $A_3$, each independently, represent a substituted or unsubstituted (C6-C30)aryl, a substituted or unsubstituted dibenzofuranyl, a substituted or unsubstituted dibenzothiophenyl, or a substituted or unsubstituted carbazolyl; preferably a substituted or unsubstituted (C6-C25)aryl, a substituted or unsubstituted dibenzofuranyl, a substituted or unsubstituted dibenzothiophenyl, or a substituted or unsubstituted carbazolyl; more preferably a substituted or unsubstituted (C6-C18)aryl, a substituted or unsubstituted dibenzofuranyl, a substituted or unsubstituted dibenzothiophenyl, or a substituted or unsubstituted carbazolyl. For example, $A_1$ to $A_3$, each independently, may be a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted triphenylenyl, a substituted or unsubstituted dimethylfluorenyl, a substituted or unsubstituted dibenzofuranyl, a substituted or unsubstituted dibenzothiophenyl, or a substituted or unsubstituted carbazolyl, in which, for example, the substituent(s) of the substituents may be at least one of deuterium, a phenyl, a naphthyl, a triphenylenyl, a carbazolyl, a dibenzofuranyl, and dibenzothiophenyl.

In one embodiment, $L_3$ to $L_5$, each independently, represent a single bond, or a substituted or unsubstituted (C6-C30)arylene; preferably, each independently, a single bond, or a substituted or unsubstituted (C6-C25)arylene; and more preferably, each independently, a single bond, or a substituted or unsubstituted (C6-C18)arylene. For example, $L_3$ to $L_5$, each independently, may be a single bond, a phenylene unsubstituted or substituted with deuterium, a biphenylene unsubstituted or substituted with deuterium, or a naphthylene unsubstituted or substituted with deuterium.

In one embodiment, $X_{11}$ to $X_{26}$, and $X_{31}$ to $X_{34}$, each independently, represent hydrogen, deuterium, a substituted or unsubstituted (C6-C30)aryl, or a substituted or unsubstituted (5 to 30-membered)heteroaryl. Preferably, in formula 2-1, $X_{11}$ to $X_{26}$ may be hydrogen, and in formula 2-2, $X_{11}$ to $X_{18}$, and $X_{31}$ to $X_{34}$, each independently, may be hydrogen or deuterium, and at least one thereof may be deuterium or may be substituted with deuterium.

According to one embodiment of the present disclosure, when the compound represented by formula 2 contains deuterium, the deuterium replacement ratio is 40% or more, preferably 45% or more, more preferably 50% or more, of the total number of hydrogen. When the compound of formula 2 is deuterated in said deuterium replacement ratio, the bond dissociation energy related to deuteration may increase to enhance the stability of the compound. The organic electroluminescent device comprising said compound may exhibit improved lifetime property.

The compound represented by formula 2 according to one embodiment may be represented by any one of the following formulas 2-3 to 2-16.

(2-3)

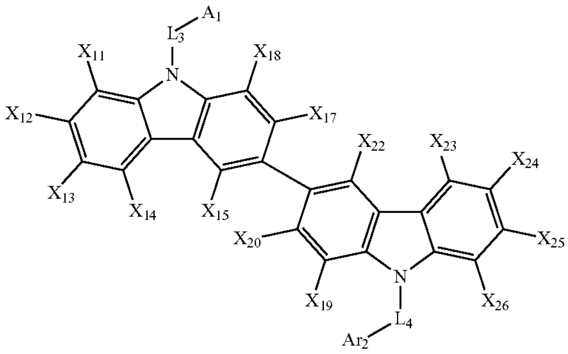

(2-4)

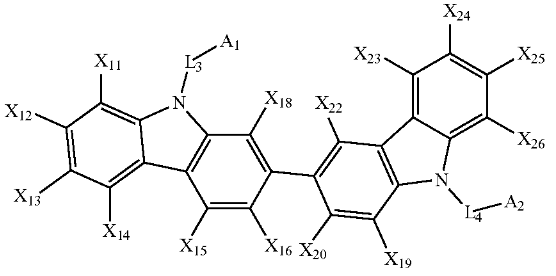

-continued (2-5)

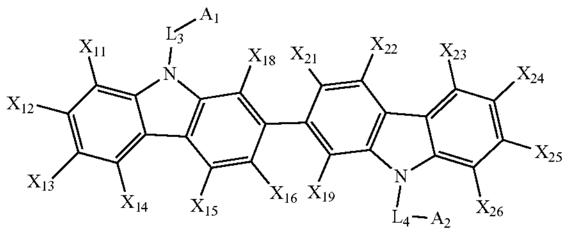

(2-6)

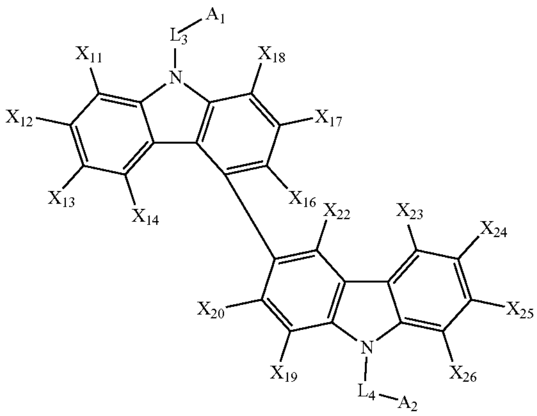

(2-7)

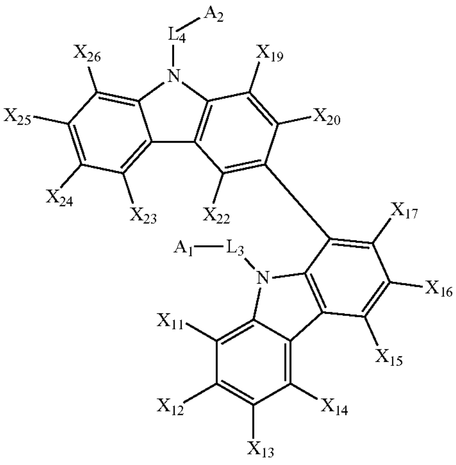

-continued
(2-8)
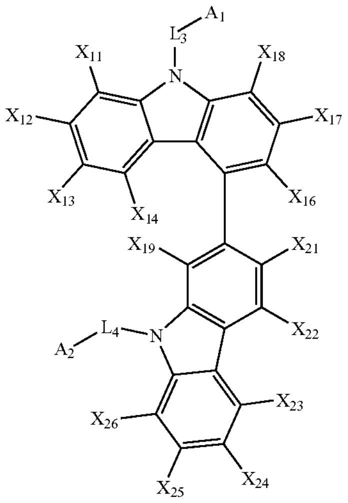
(2-9)
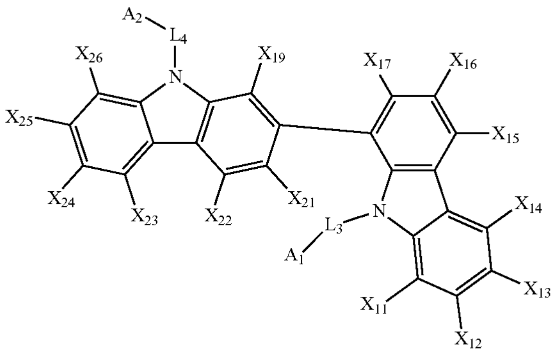
(2-10)
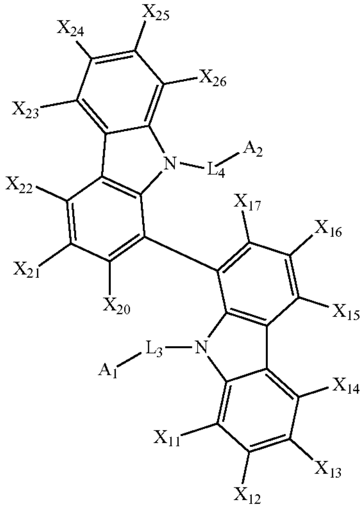
(2-11)
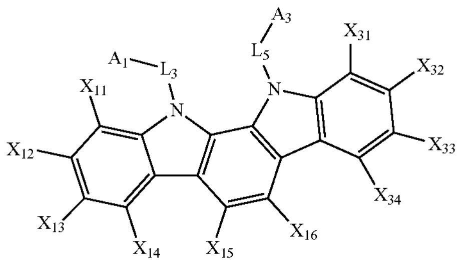
-continued
(2-12)
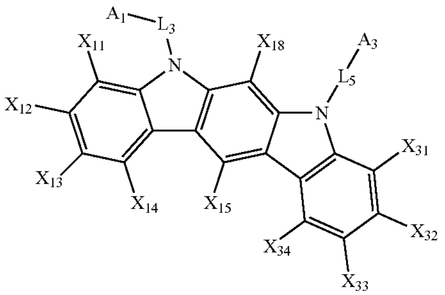
(2-13)
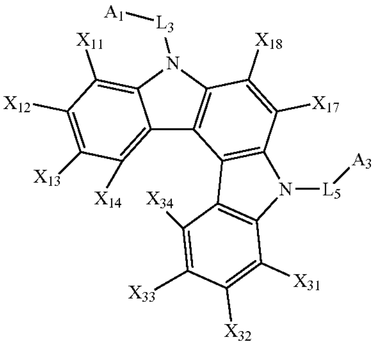
(2-14)
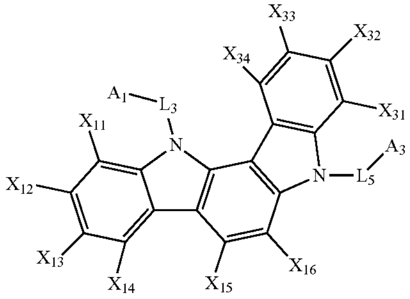
(2-15)
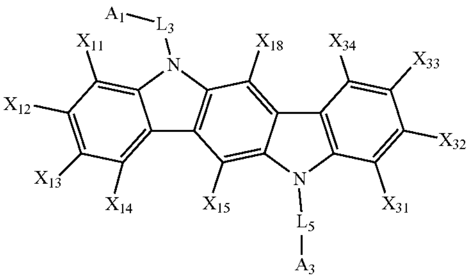
(2-16)
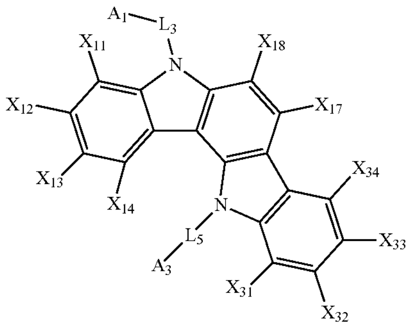
In formulas 2-3 to 2-16, $A_1$ to $A_3$, $L_3$ to $L_5$, $X_{11}$ to $X_{26}$, and $X_{31}$ to $X_{34}$ are as defined in formulas 2-1 and 2-2.

According to one embodiment, the second host compound comprising the compound represented by formula 2 may be exemplified as the following compounds, but is not limited thereto.
H2-1
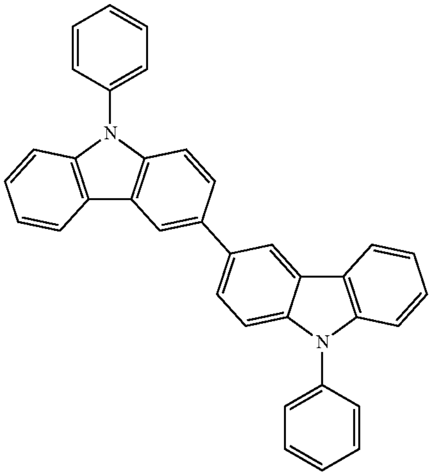
H2-2
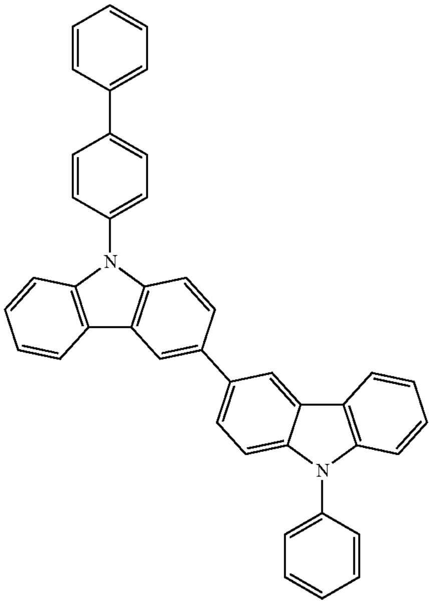
-continued
H2-3
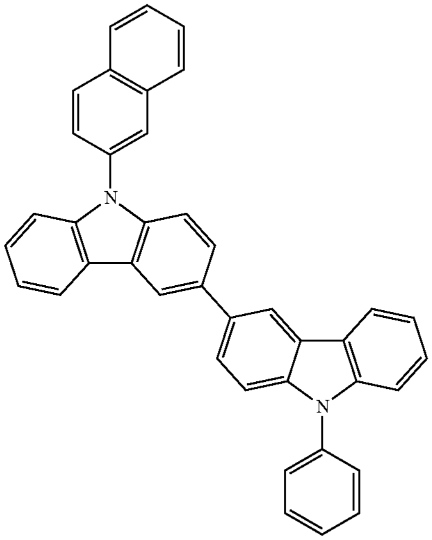
H2-4
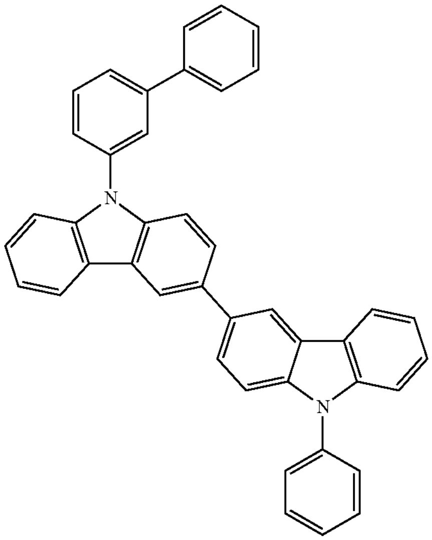
H2-5
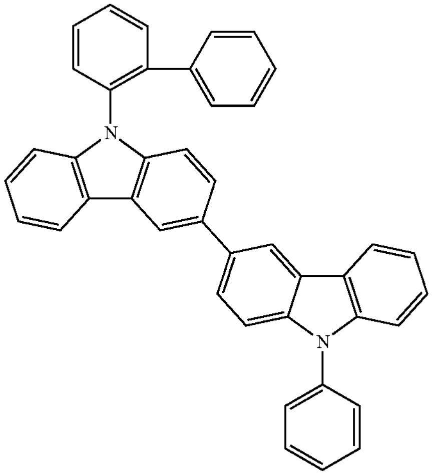

-continued
H2-6
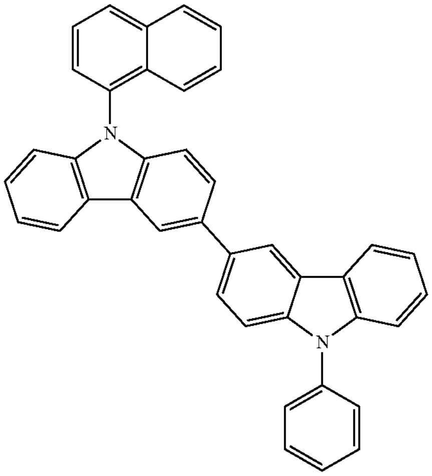
H2-7
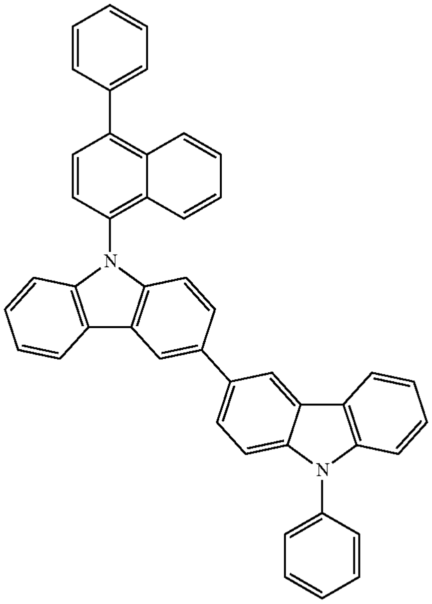
H2-8
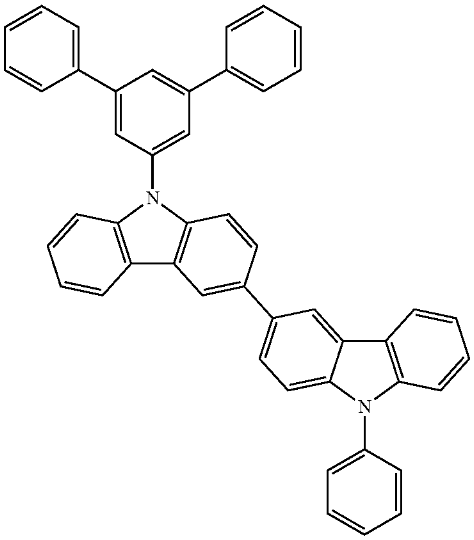
-continued
H2-9
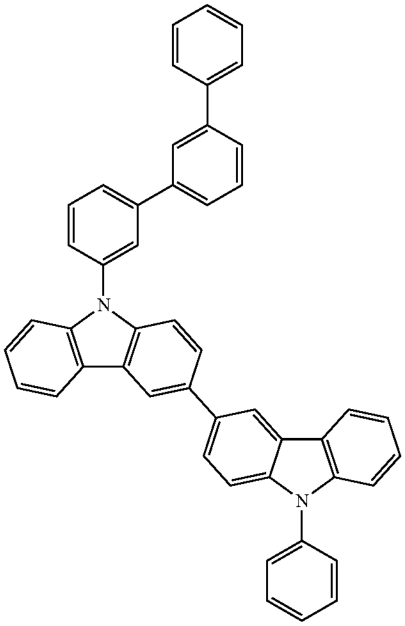
H2-10
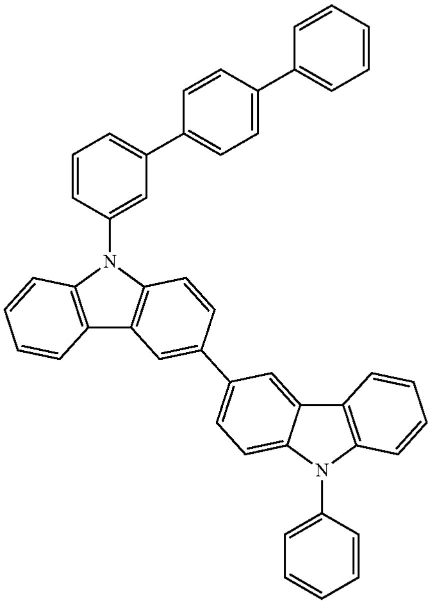

-continued
H2-11
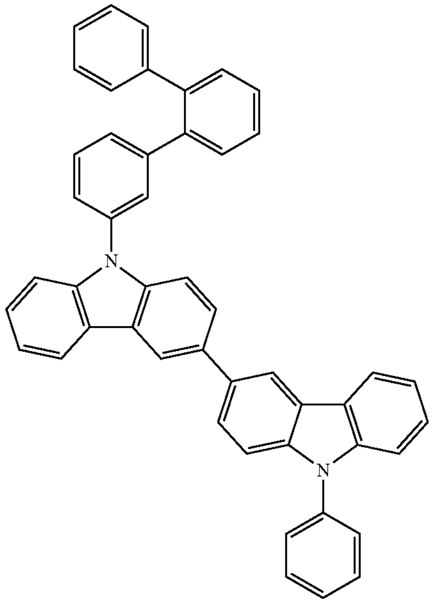
H2-12
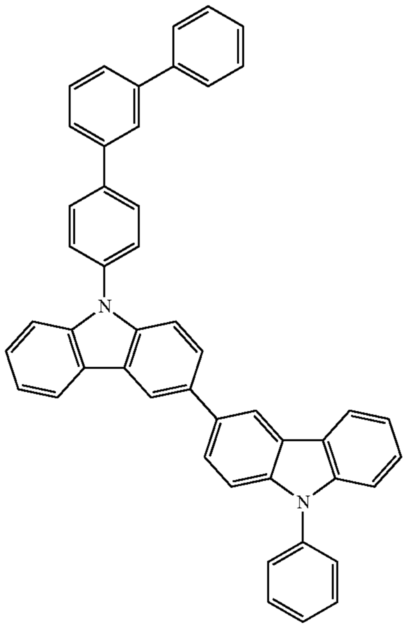
-continued
H2-13
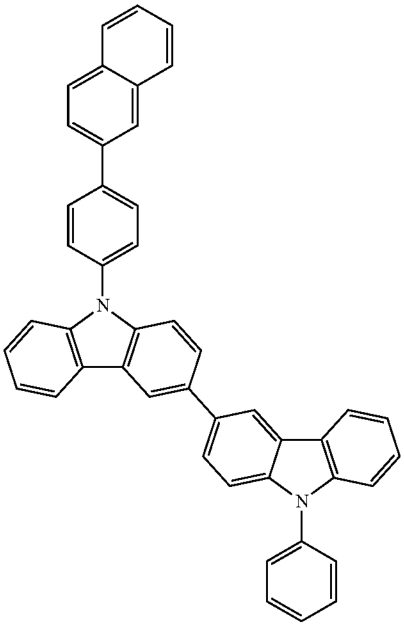
H2-14
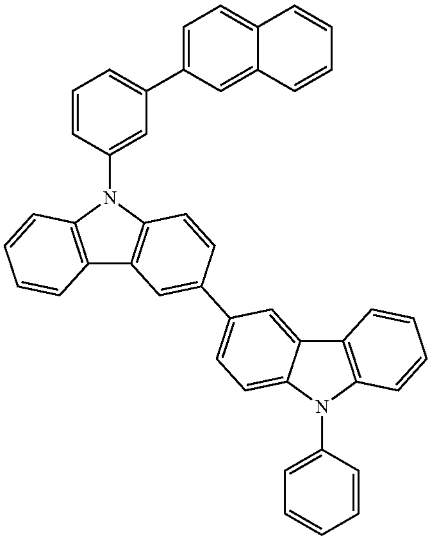
H2-15
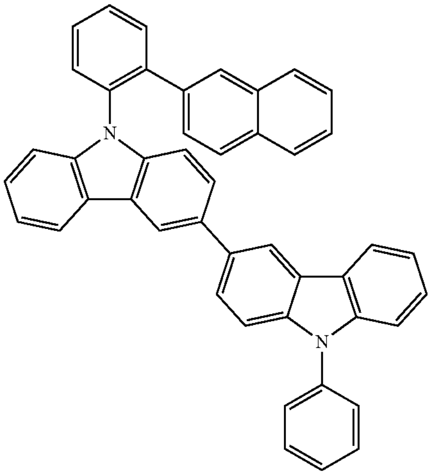

-continued
H2-16
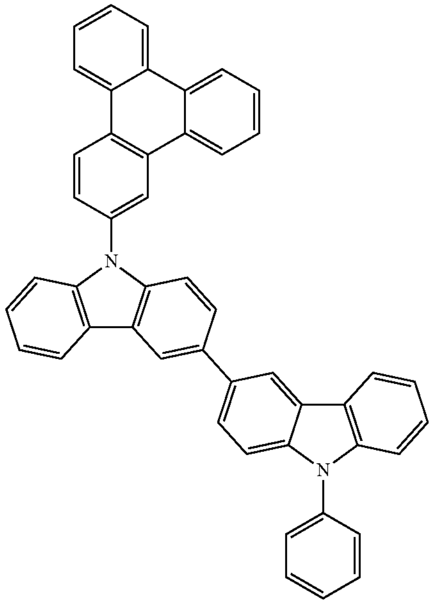
H2-17
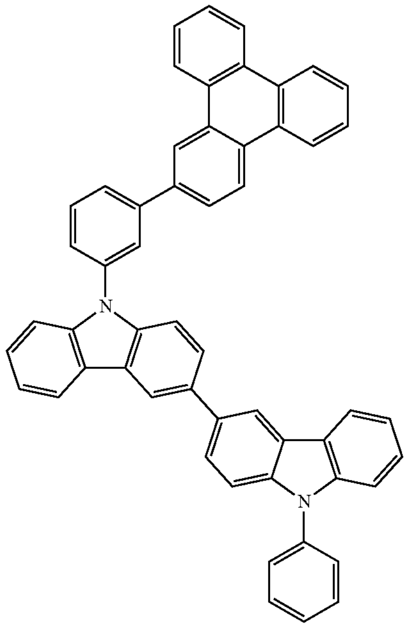
-continued
H2-18
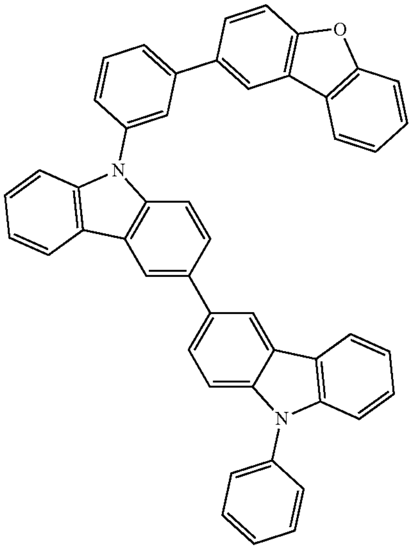
H2-19
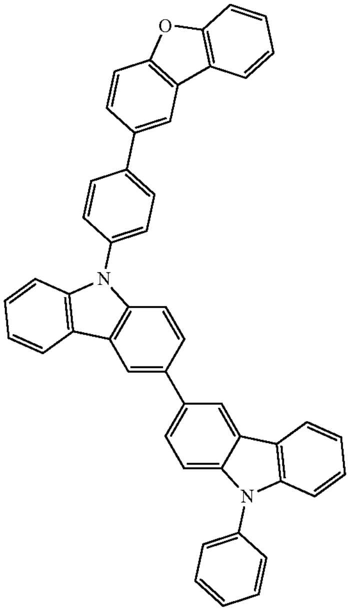

-continued
H2-20
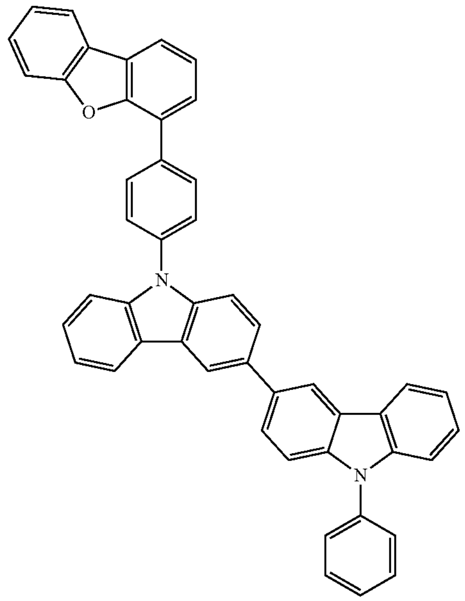
H2-21
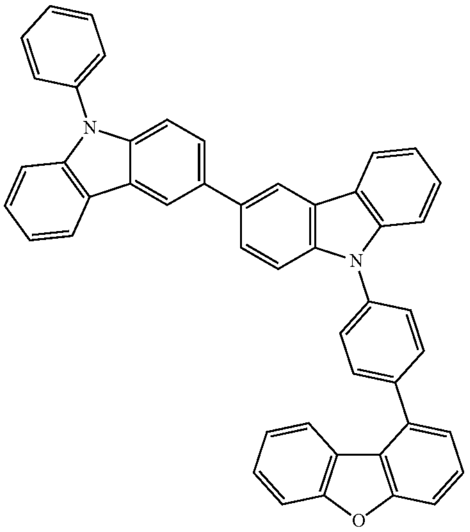
H2-22
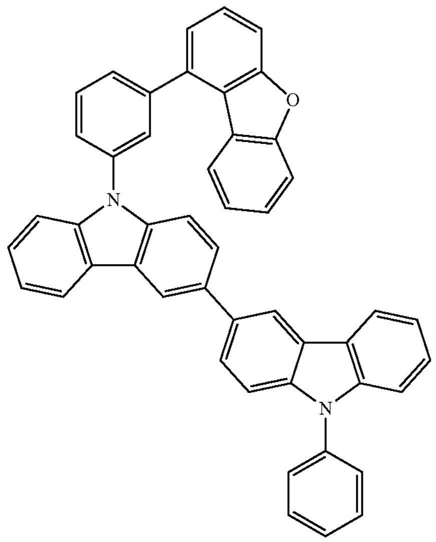
-continued
H2-23
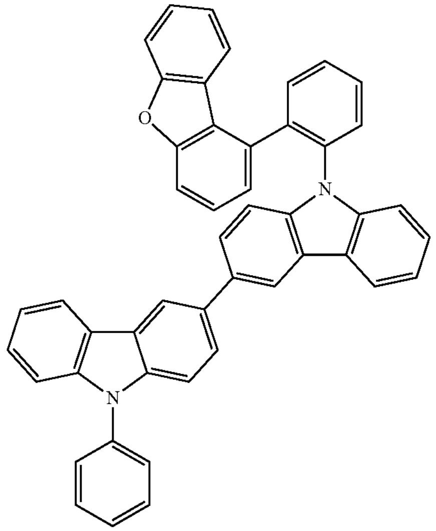
H2-24
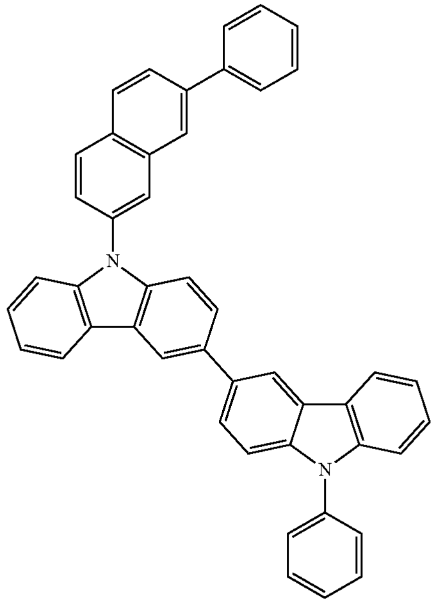

-continued
H2-25
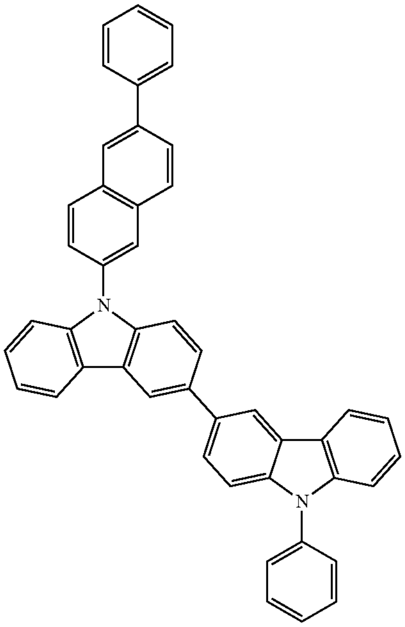
H2-26
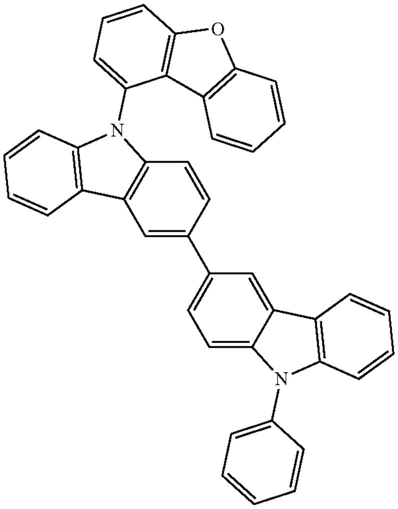
H2-27
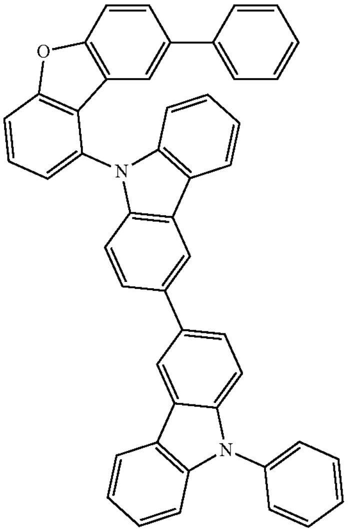
-continued
H2-28
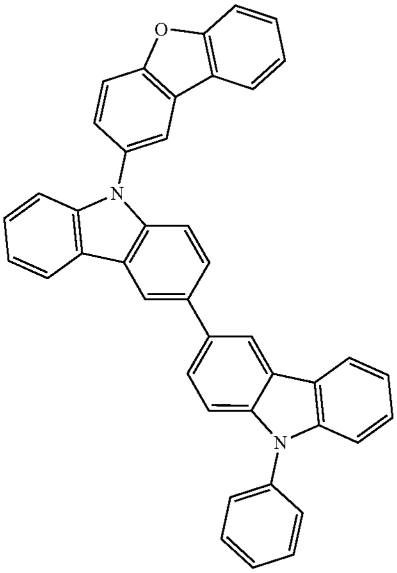
H2-29
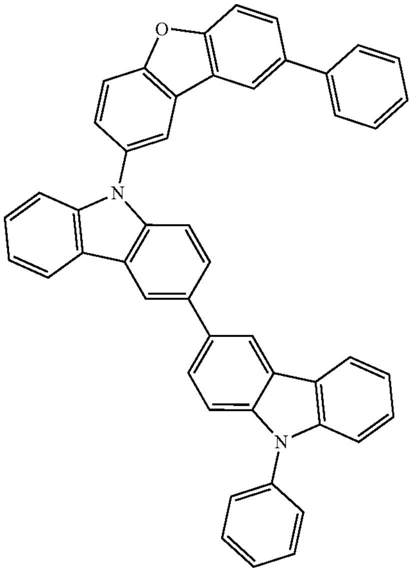

-continued
H2-30
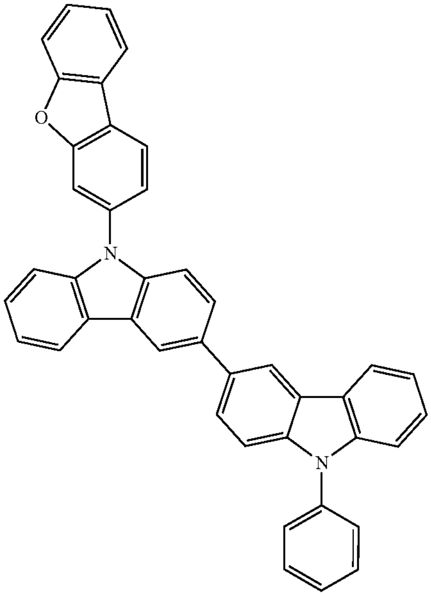
H2-31
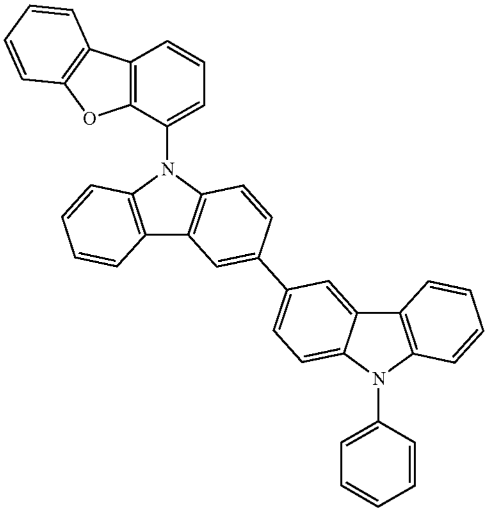
H2-32
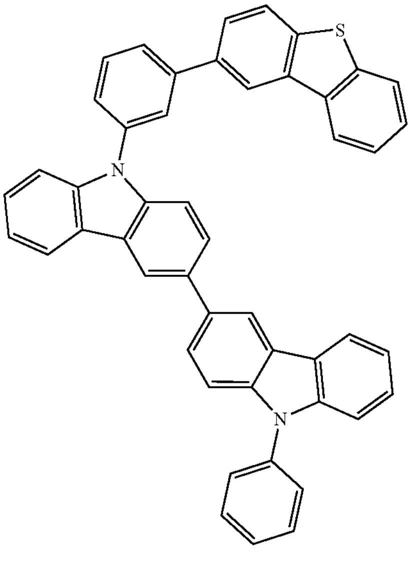
-continued
H2-33
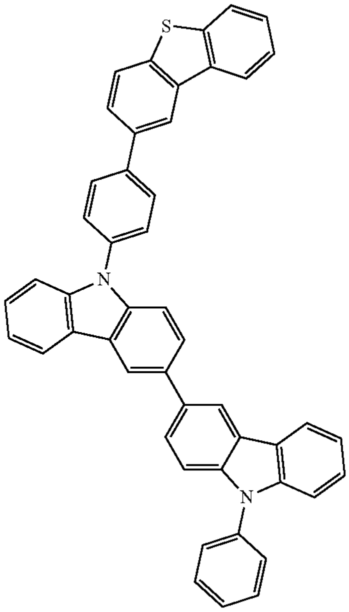
H2-34
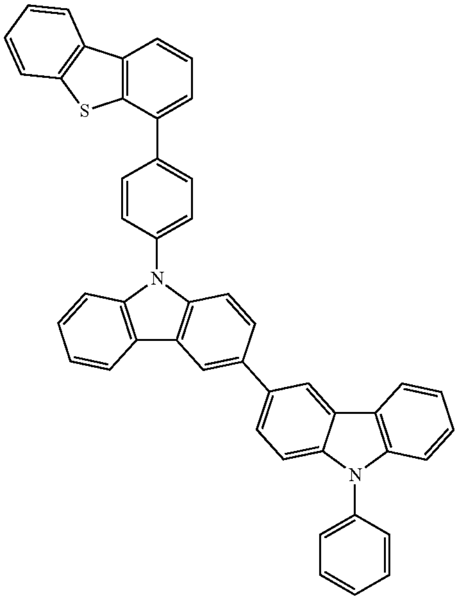

-continued
H2-35
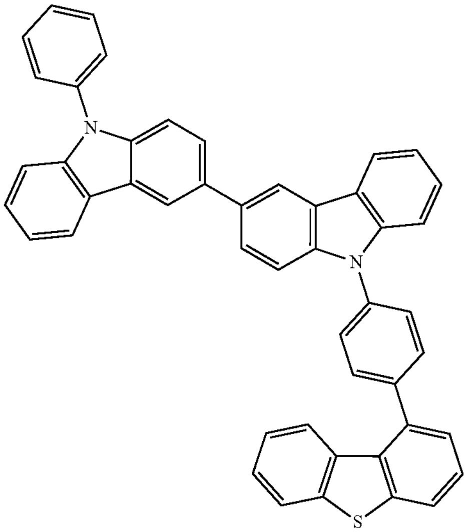
H2-36
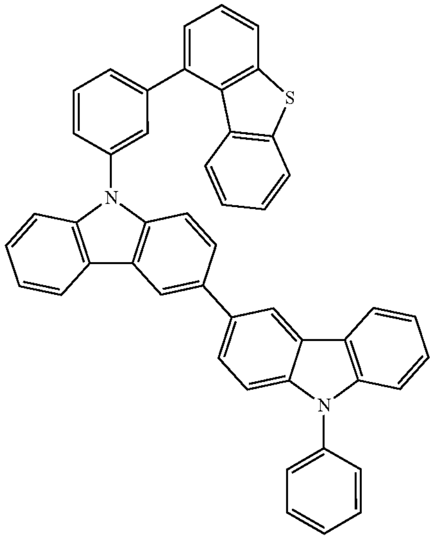
H2-37
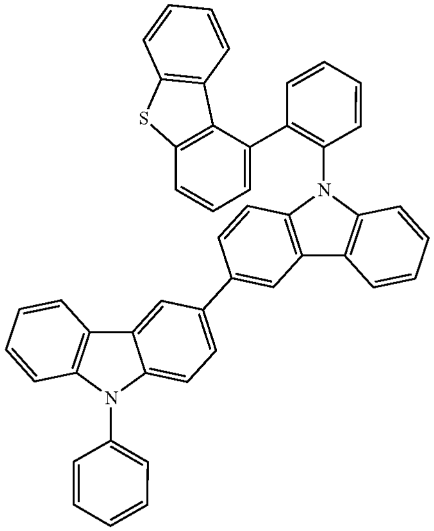
-continued
H2-38
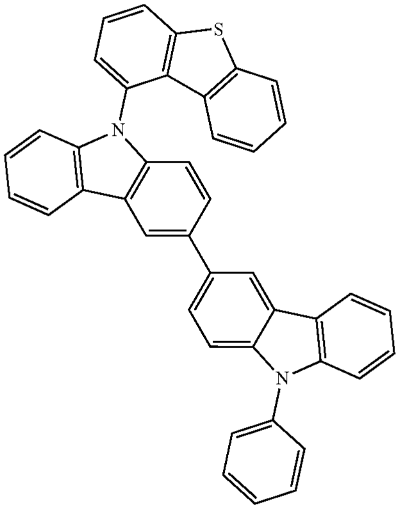
H2-39
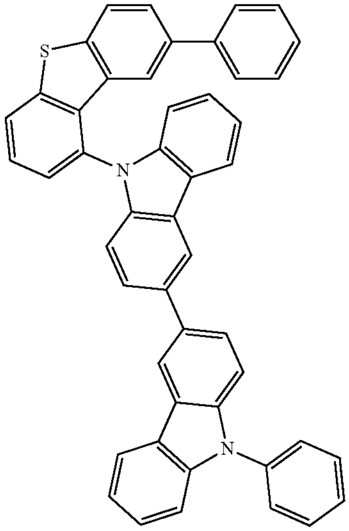
H2-40
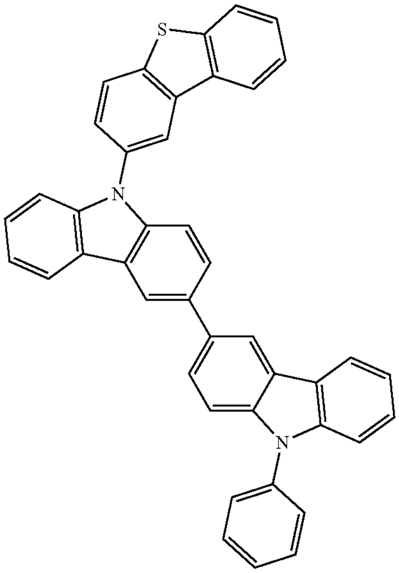

-continued
H2-41
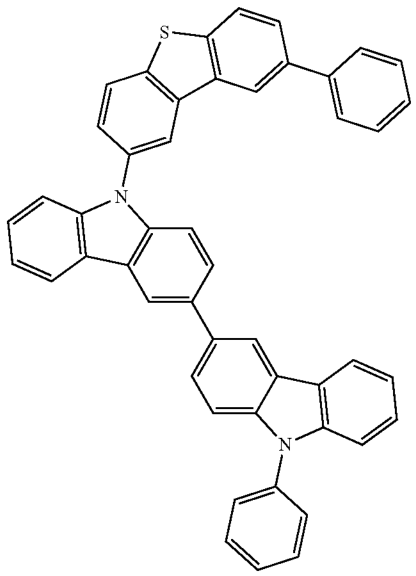
H2-42
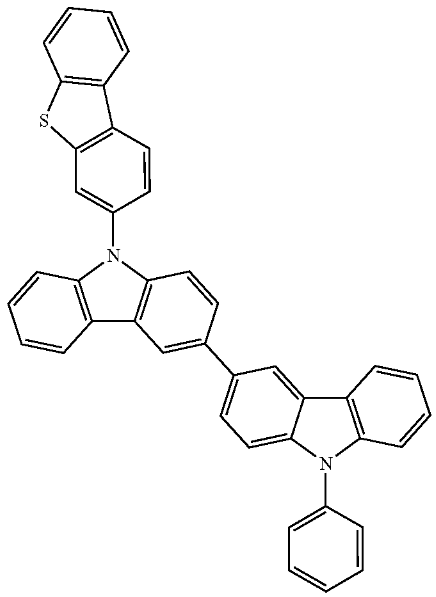
-continued
H2-43
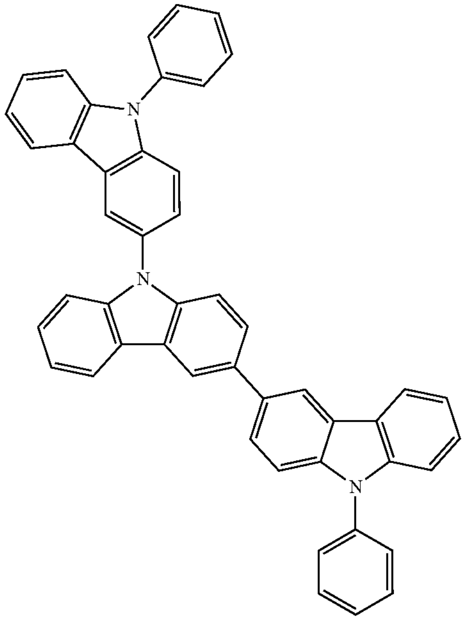
H2-44
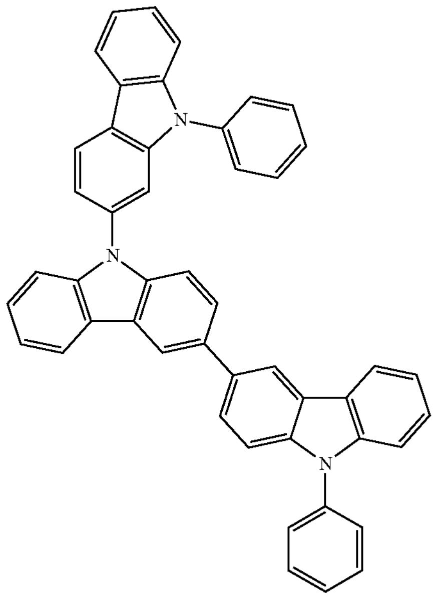

-continued
H2-45
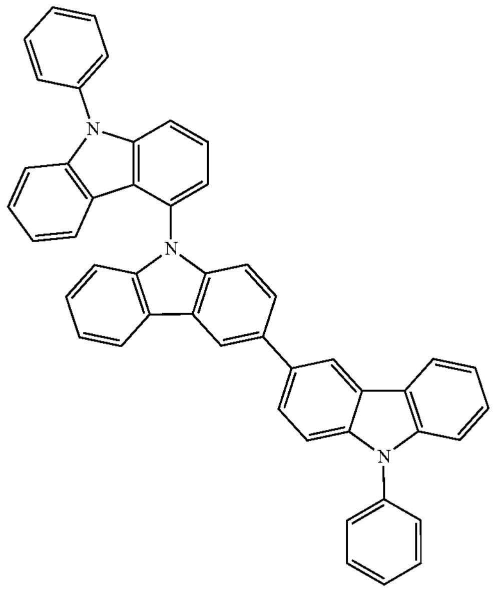
H2-46
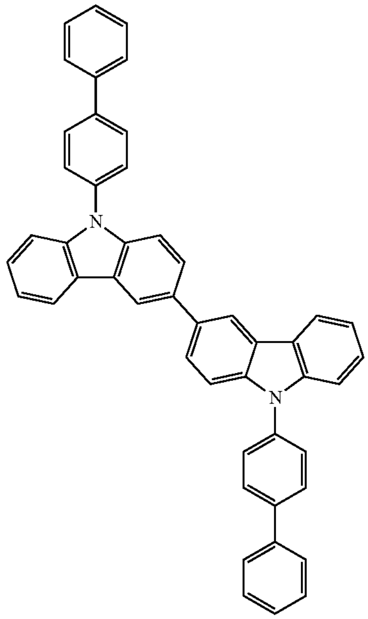
-continued
H2-47
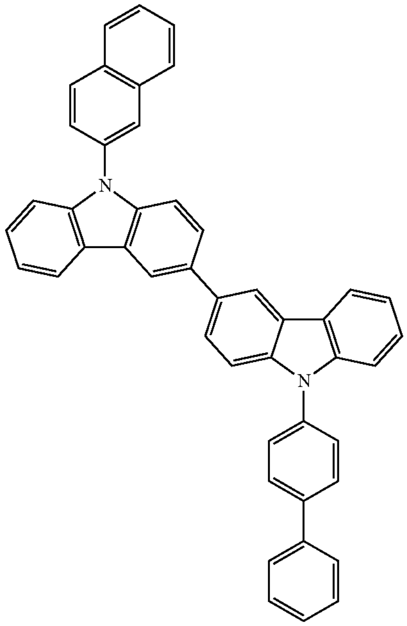
H2-48
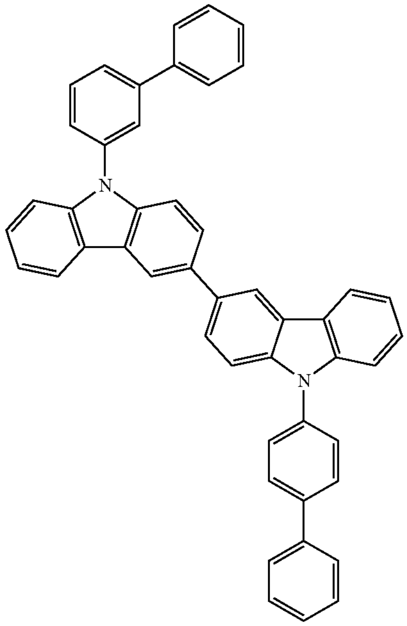

-continued
H2-49
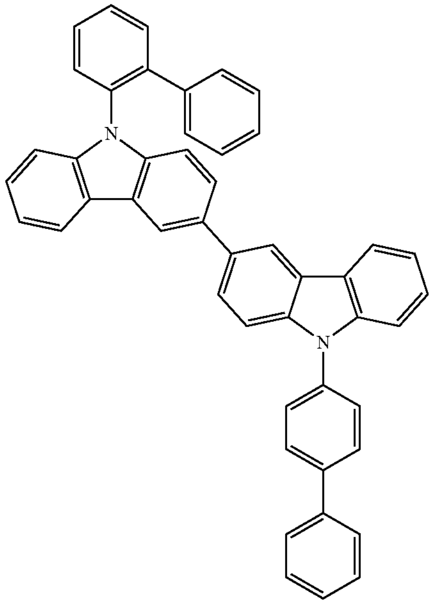
H2-50
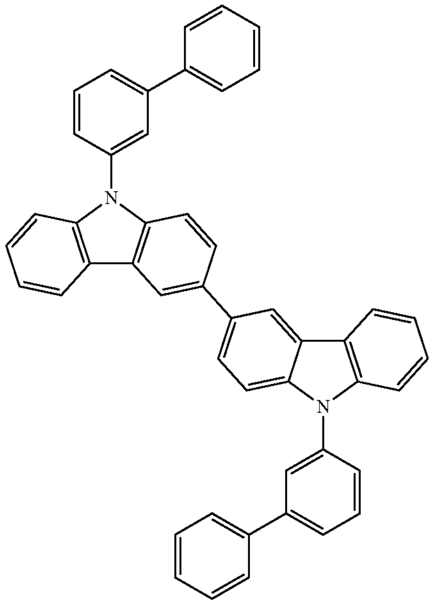
-continued
H2-51
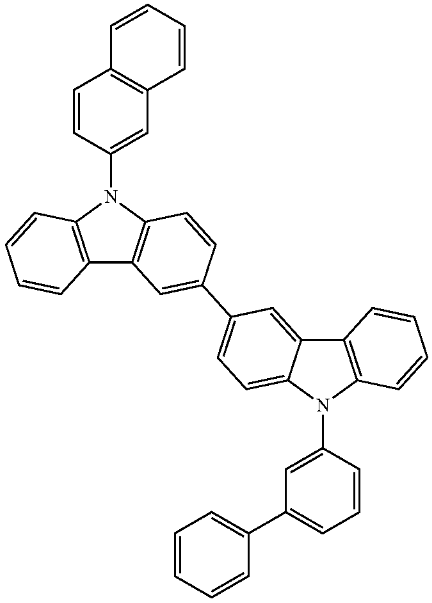
H2-52
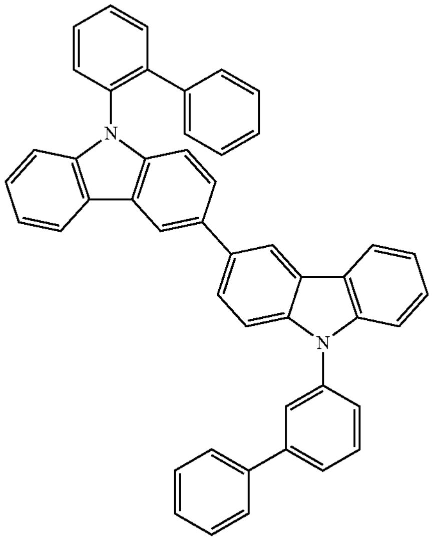

-continued
H2-53
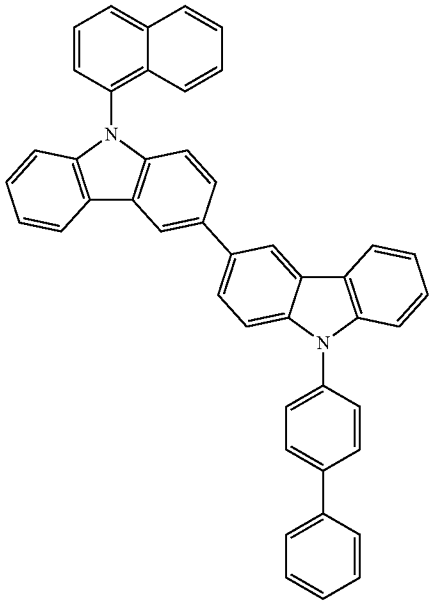
H2-54
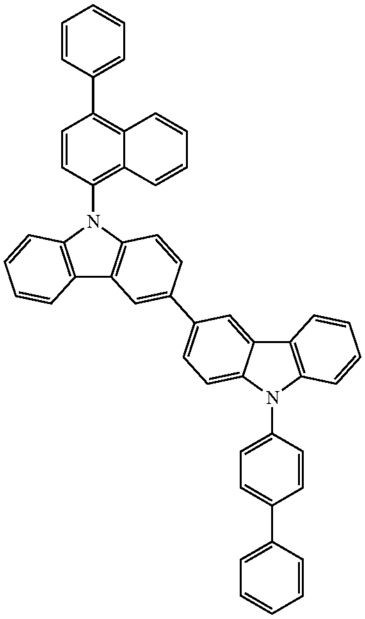
-continued
H2-55
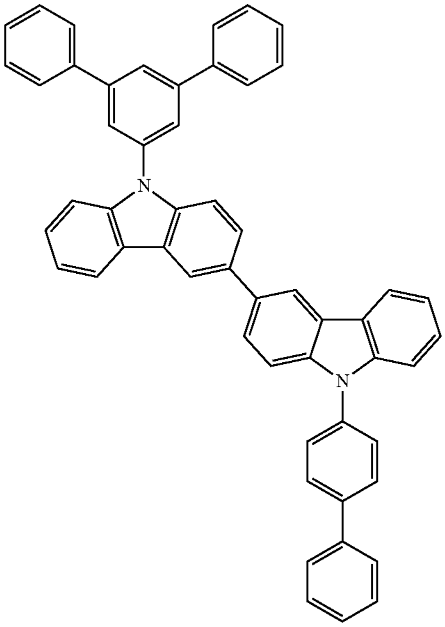
H2-56
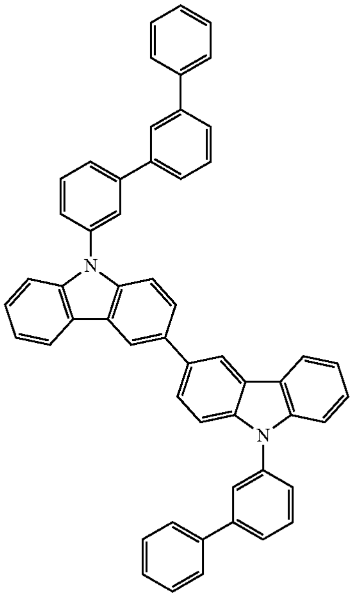

-continued
H2-57
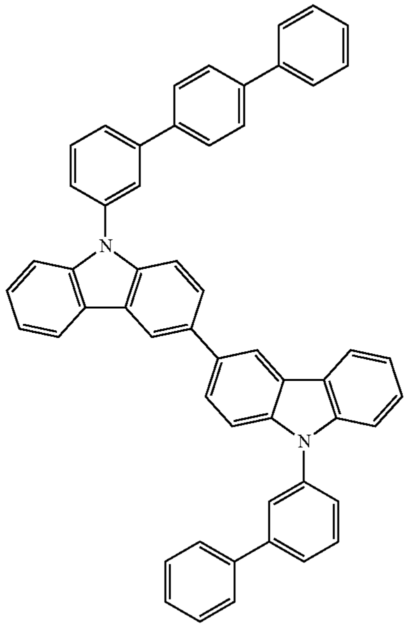
H2-58
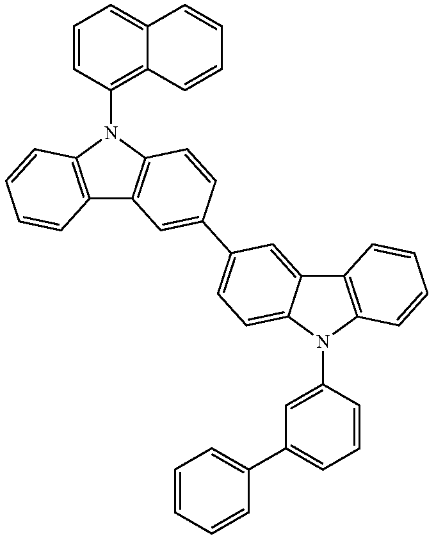
-continued
H2-59
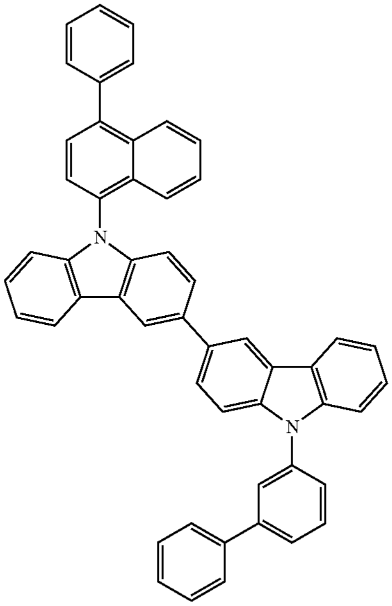
H2-60
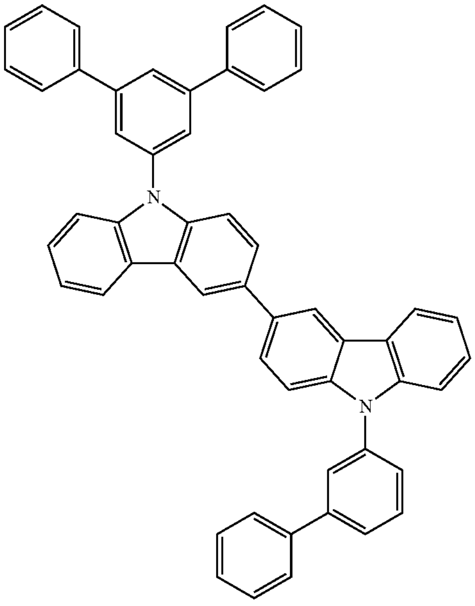

-continued
H2-61
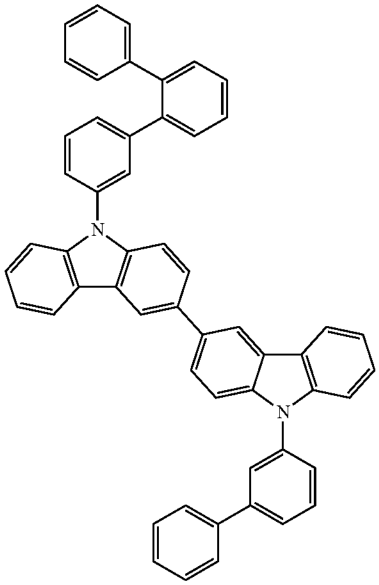
-continued
H2-63
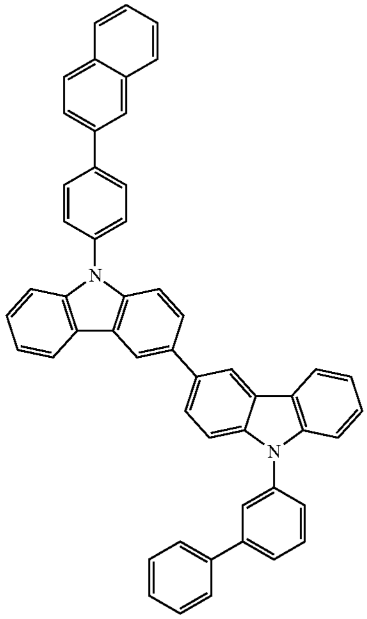
H2-62
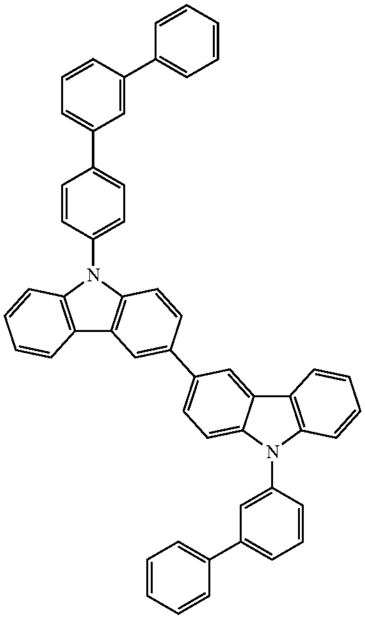
H2-64
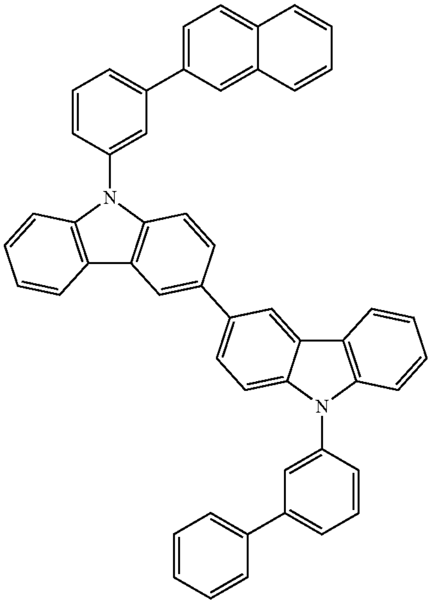

-continued
H2-65
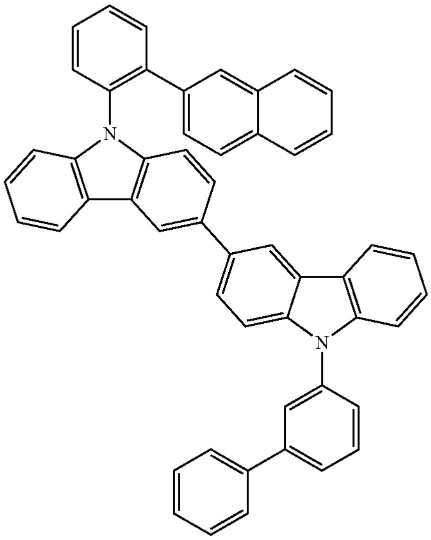
H2-66
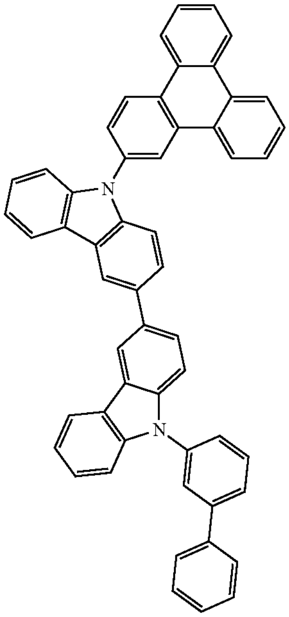
-continued
H2-67
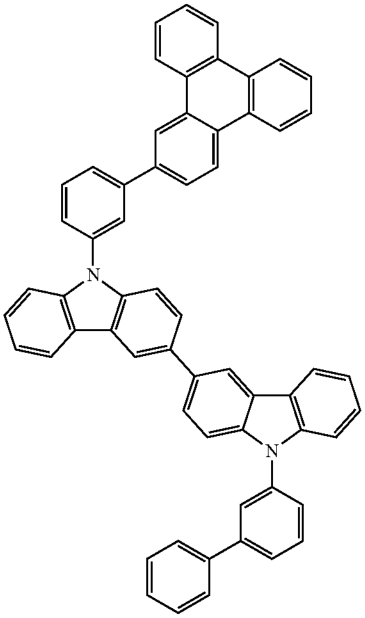
H2-68
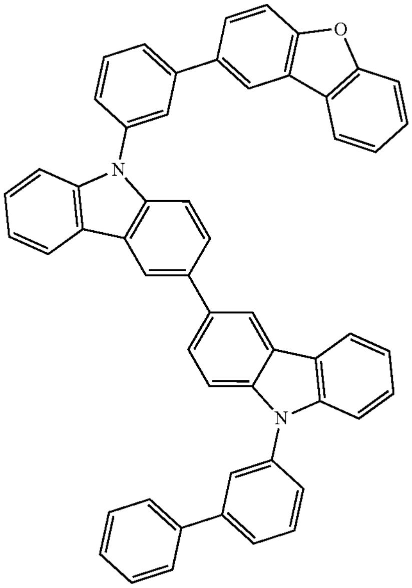

-continued
H2-69
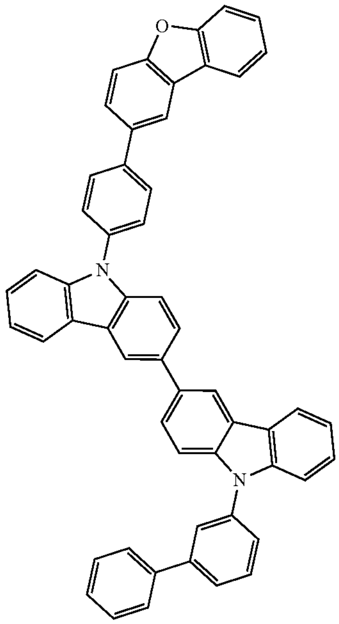
H2-70
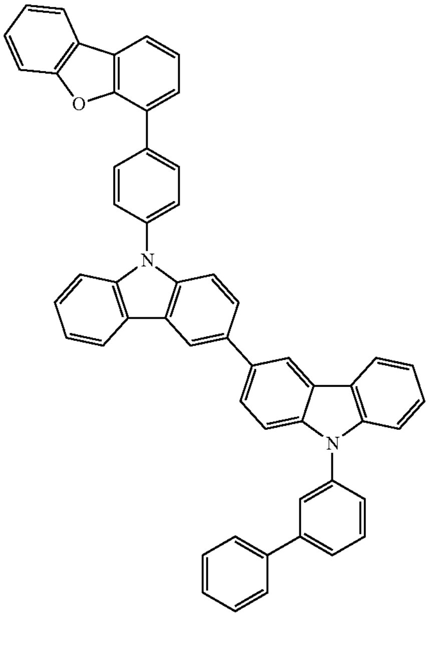
-continued
H2-71
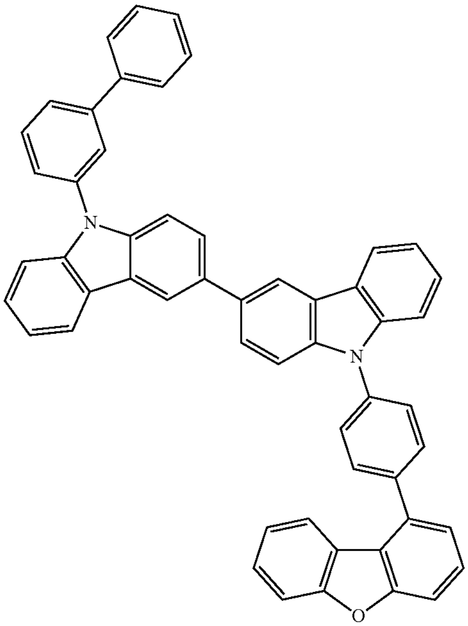
H2-72
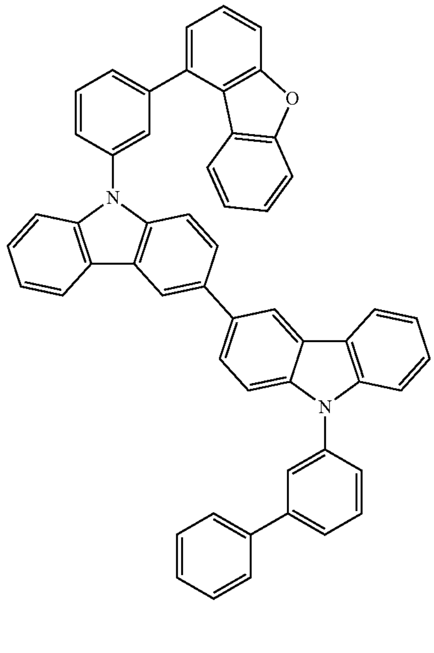

-continued
H2-73
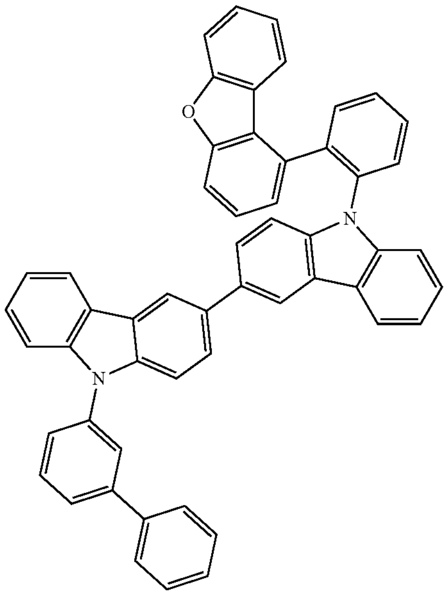
H2-74
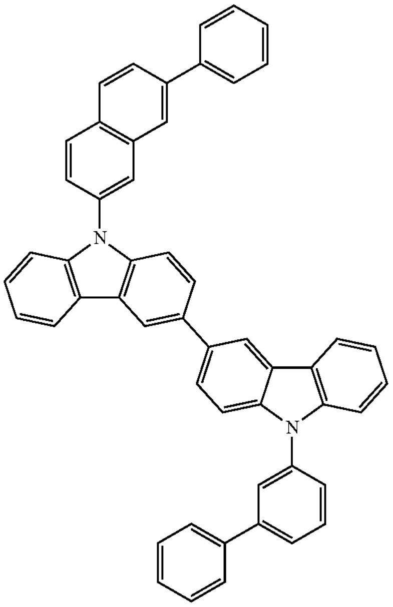
-continued
H2-75
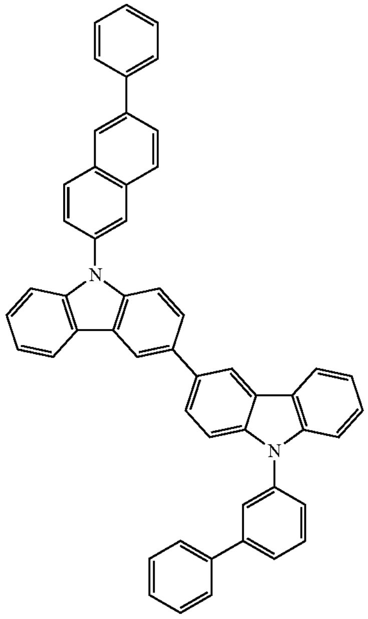
H2-76
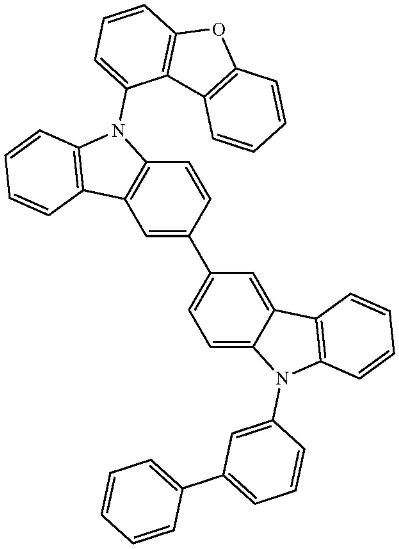

-continued
H2-77
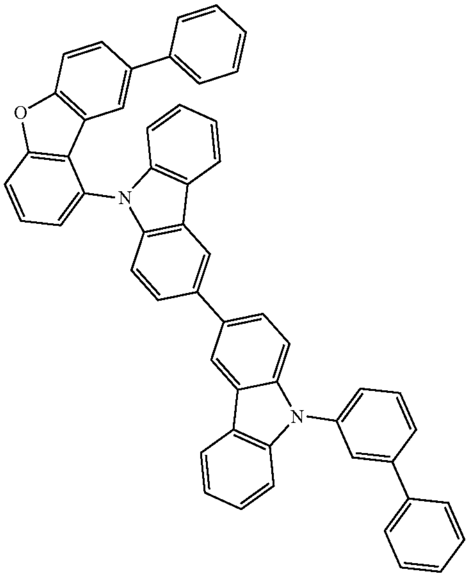
H2-78
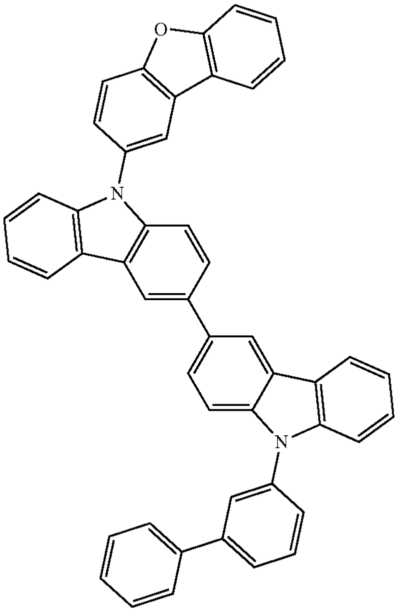
-continued
H2-79
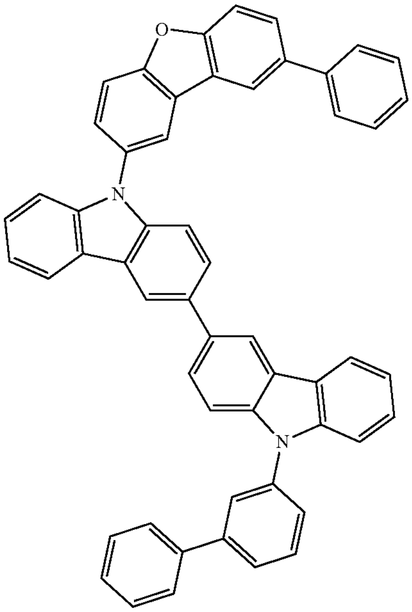
H2-80
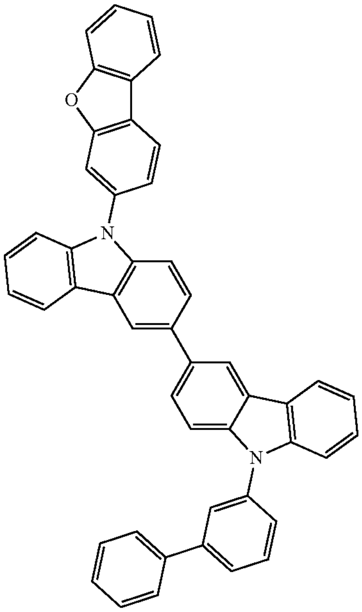

-continued
H2-81
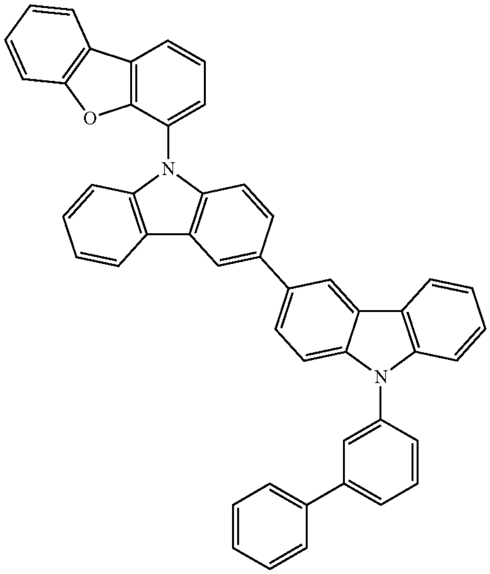
H2-82
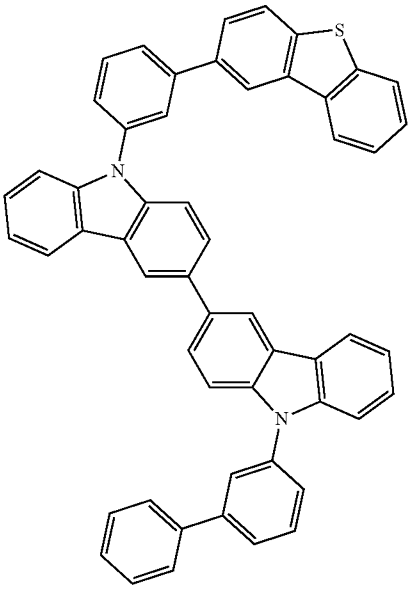
-continued
H2-83
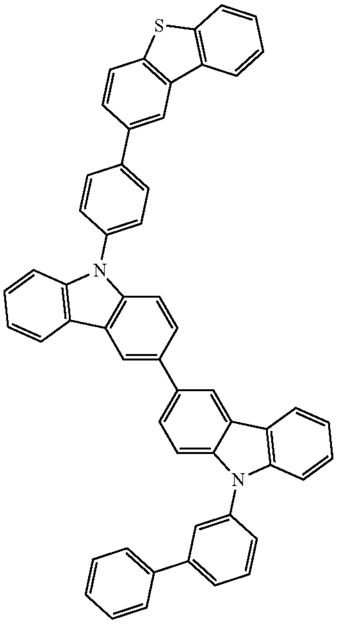
H2-84
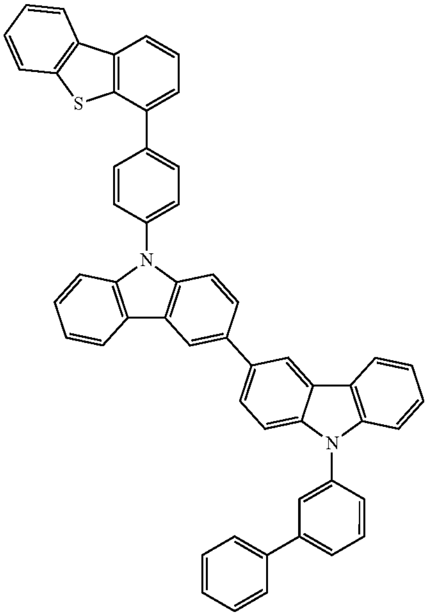

H2-85
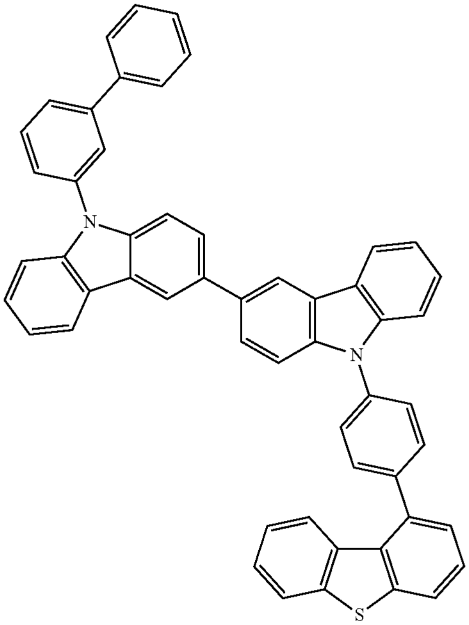
H2-86
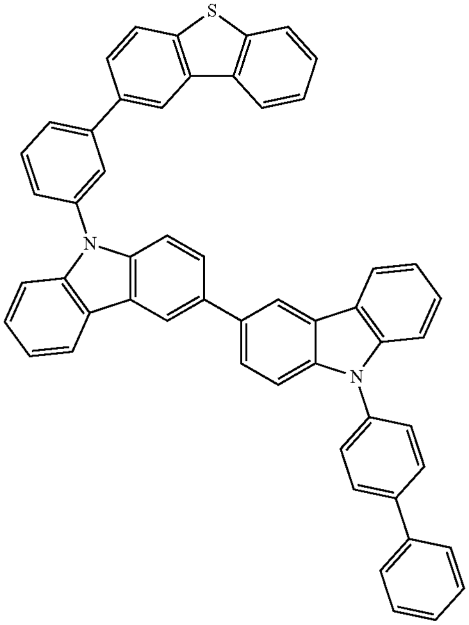
H2-87
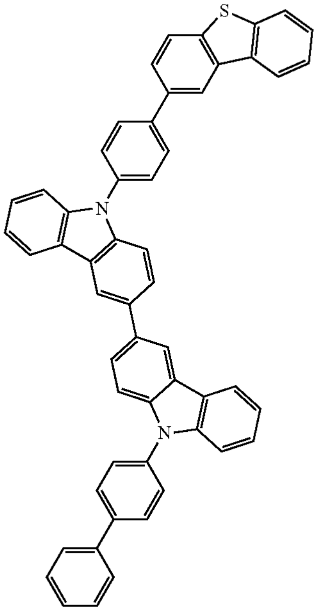
H2-88
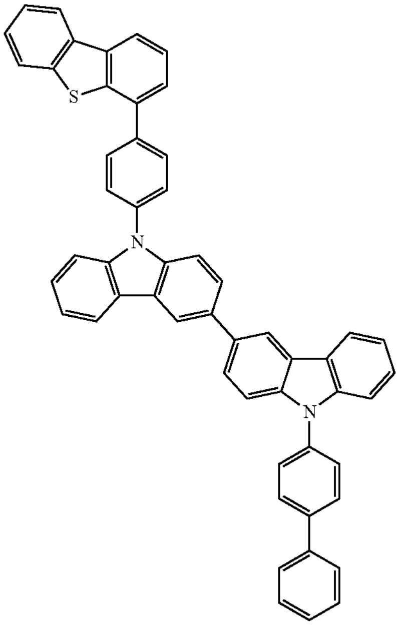

-continued
H2-89
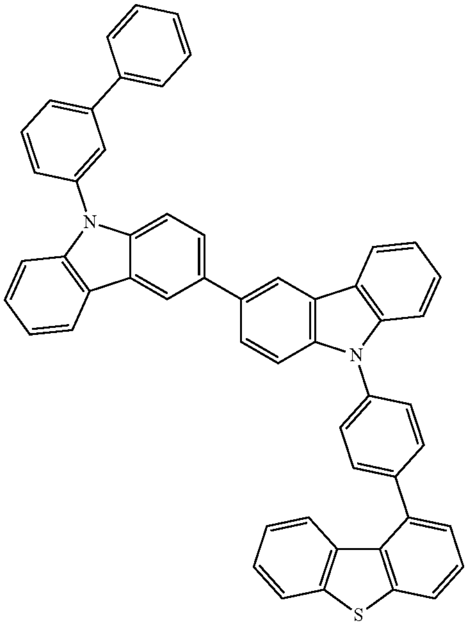
H2-90
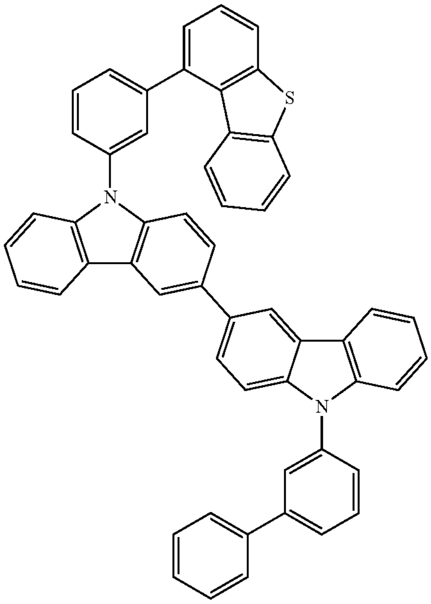
-continued
H2-91
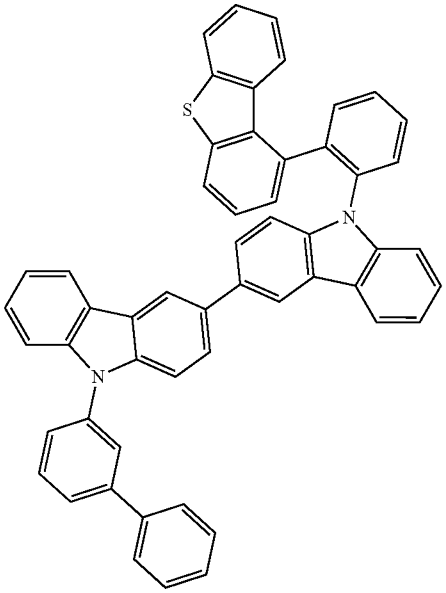
H2-92
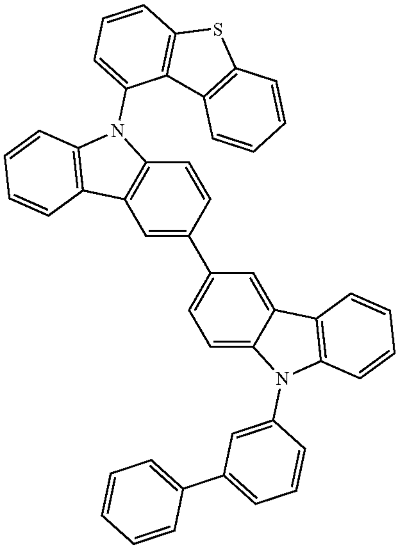

-continued
H2-93
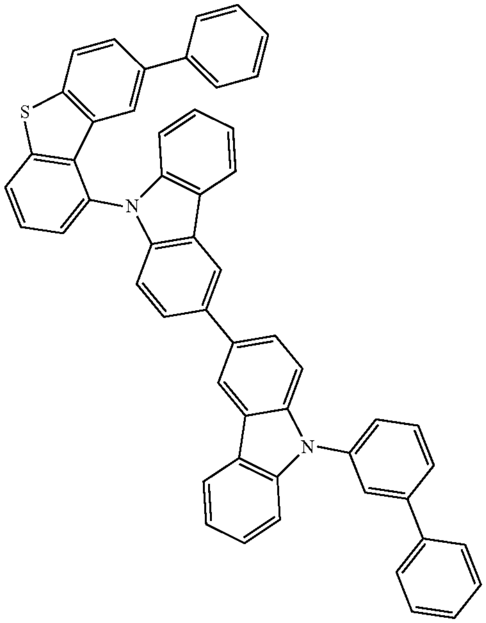
-continued
H2-95
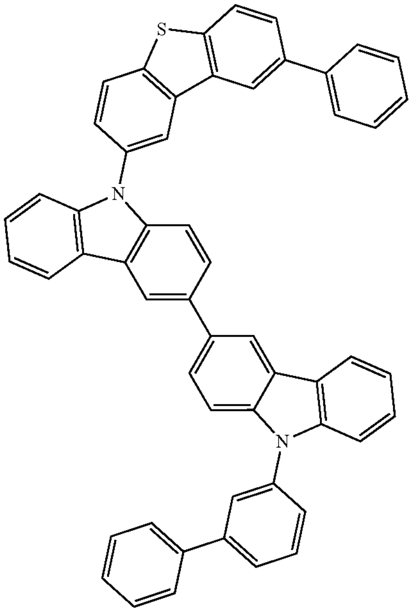
H2-94
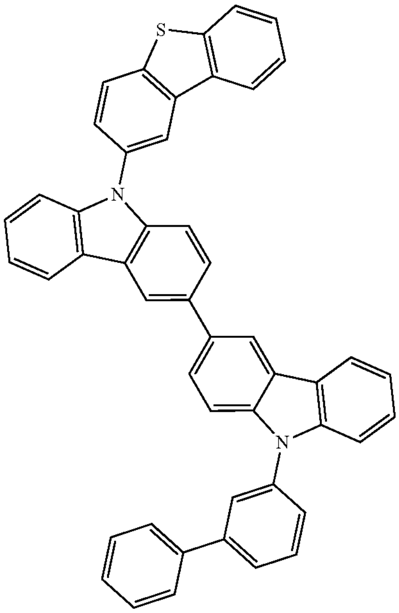
H2-96
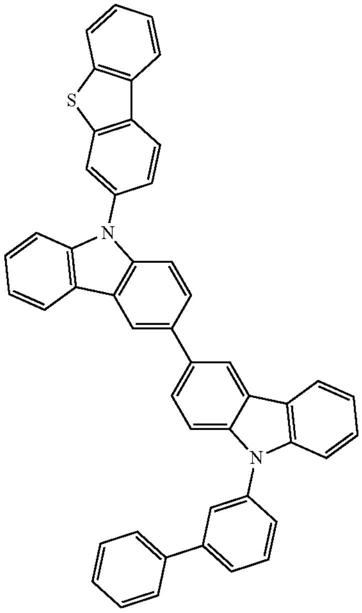

-continued
H2-97
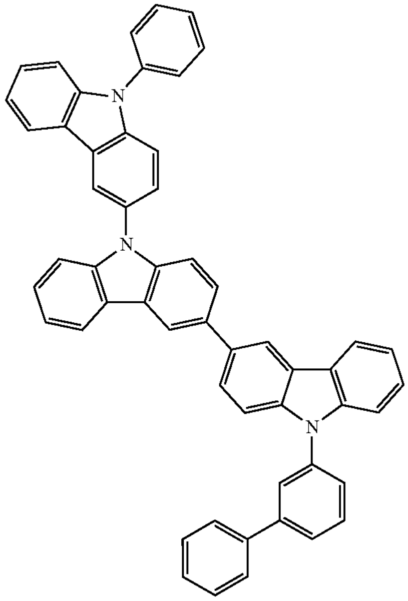
H2-98
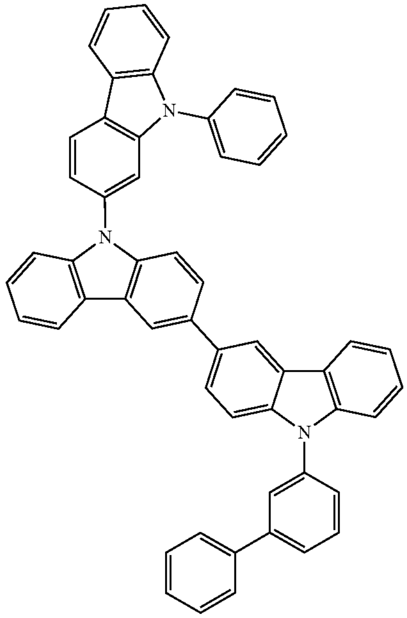
-continued
H2-99
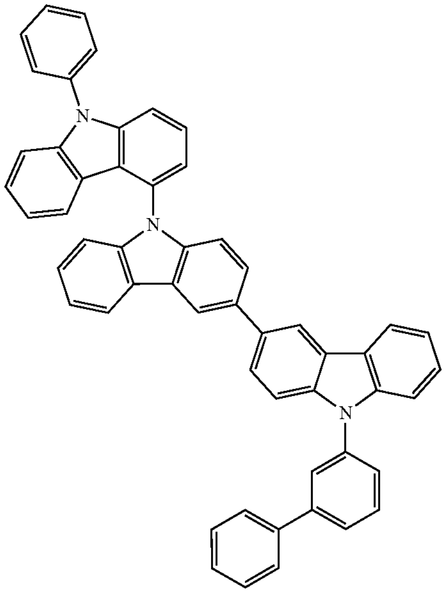
H2-100
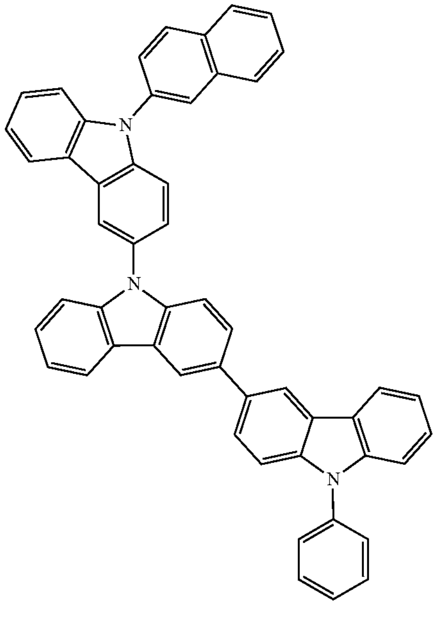

H2-101
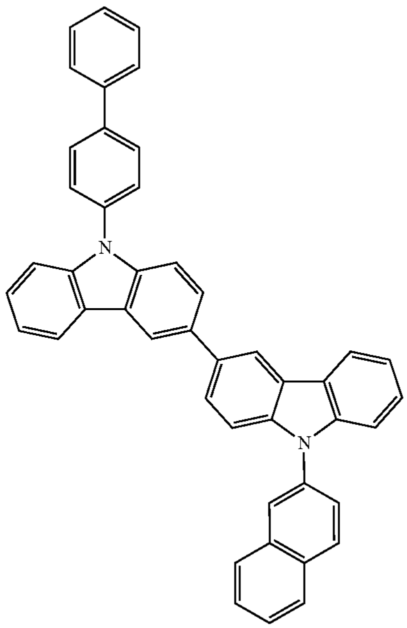
H2-102
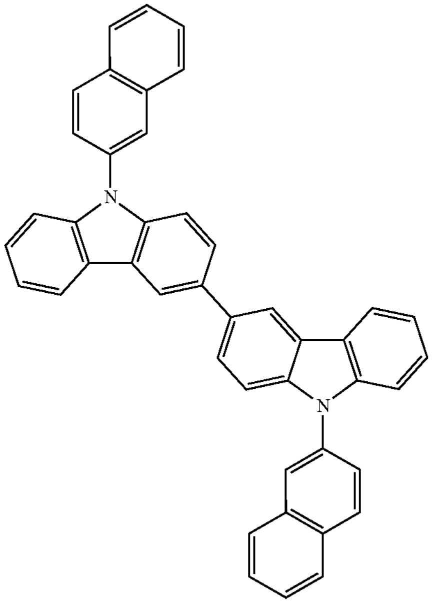
H2-103
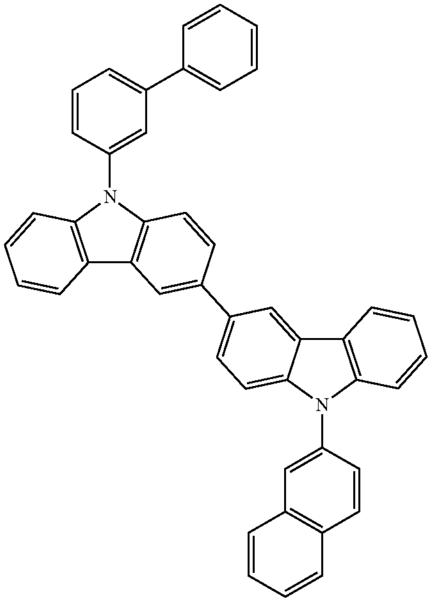
H2-104
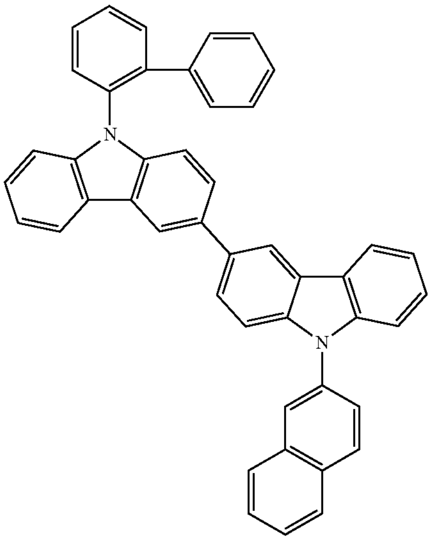

-continued
H2-105
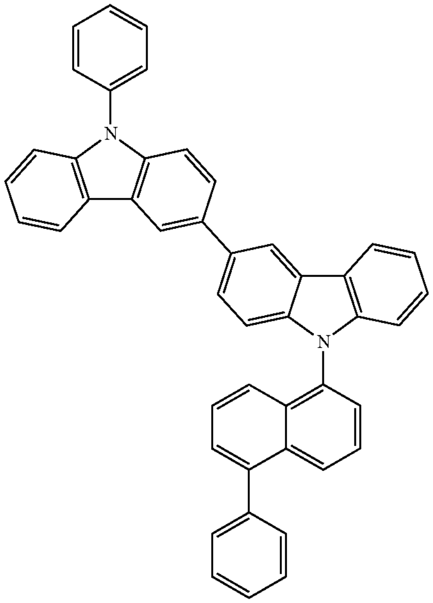
H2-106
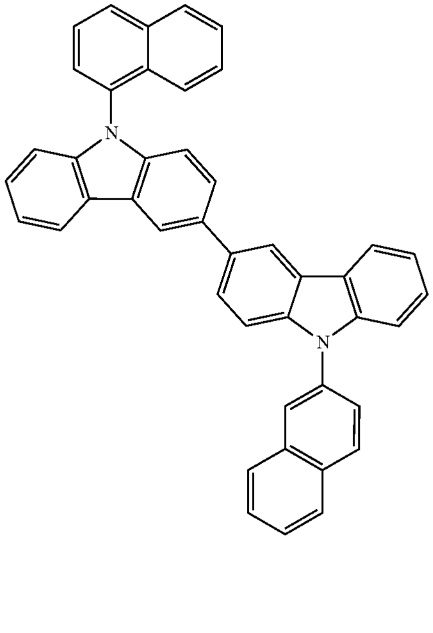
-continued
H2-107
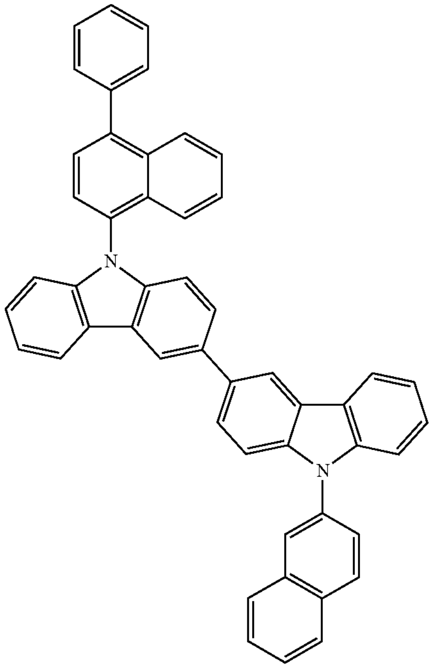
H2-108
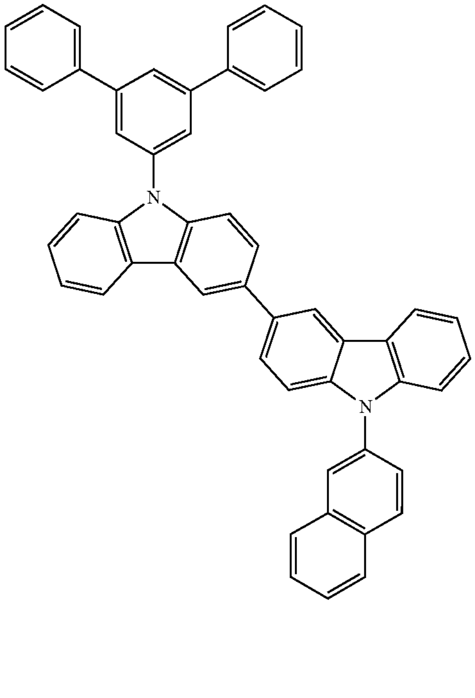

-continued
H2-109
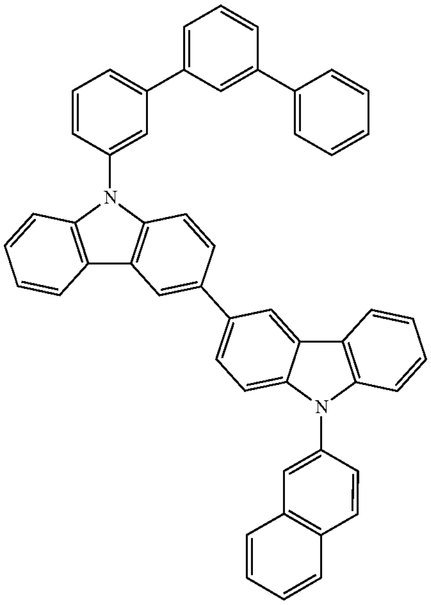
H2-110
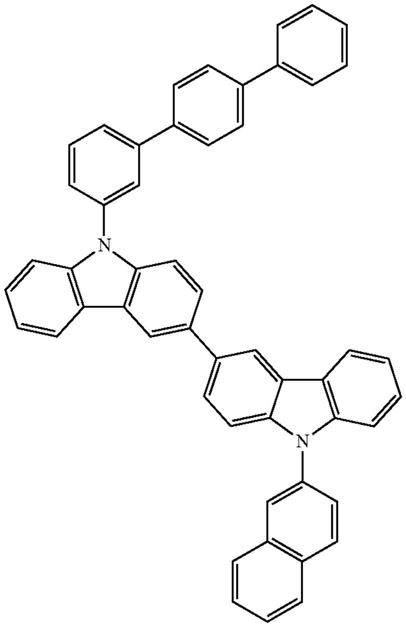
-continued
H2-111
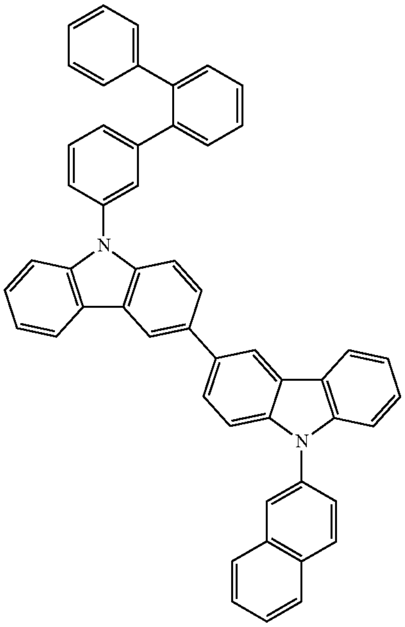
H2-112
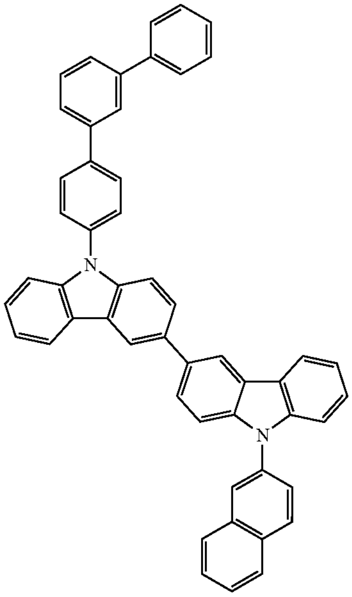

-continued
H2-113
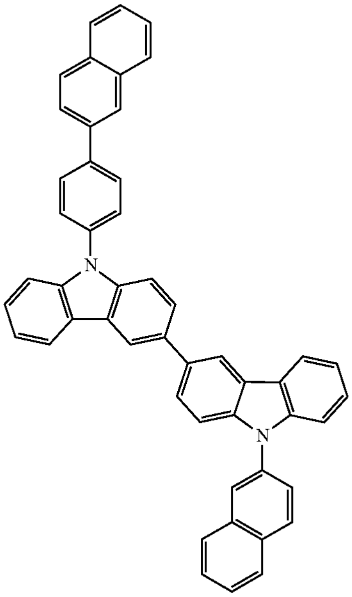
H2-114
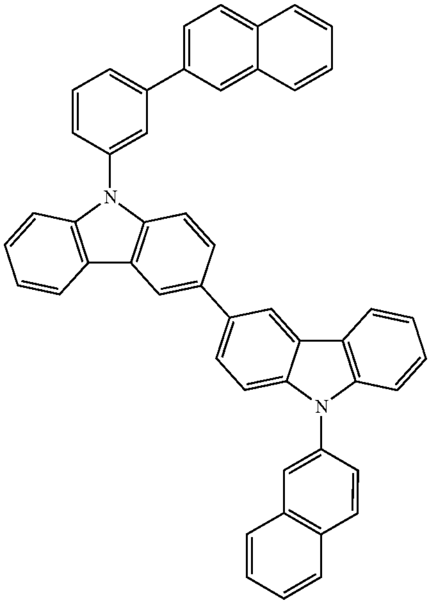
-continued
H2-115
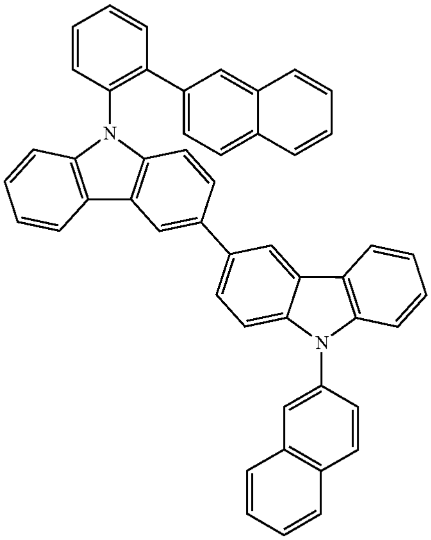
H2-116
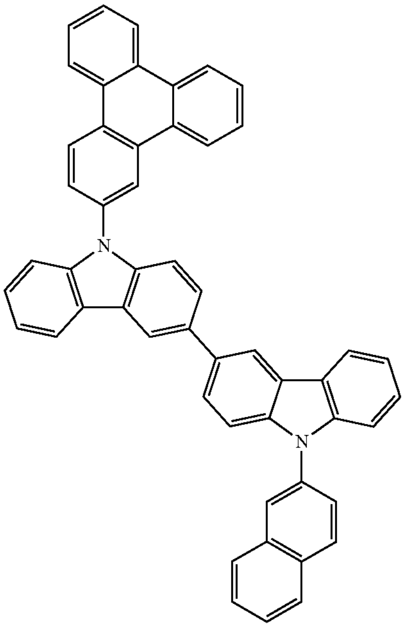

-continued
H2-117
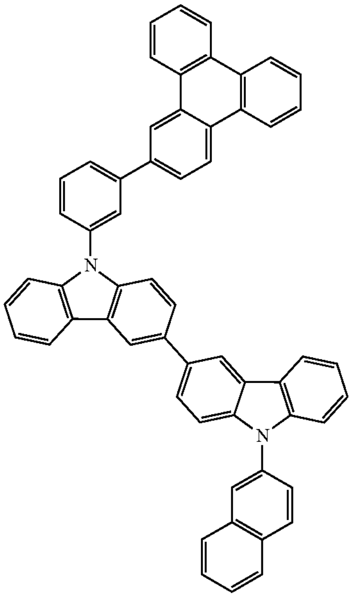
H2-118
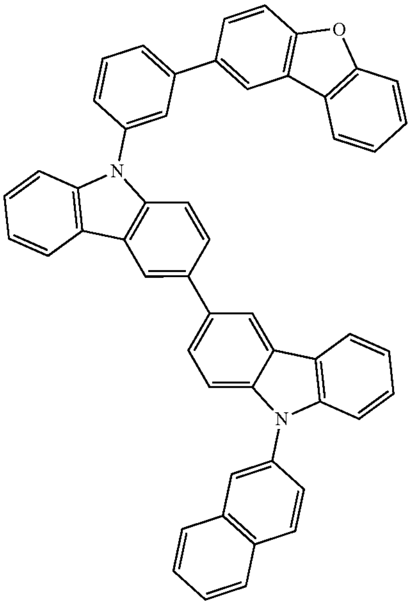
-continued
H2-119
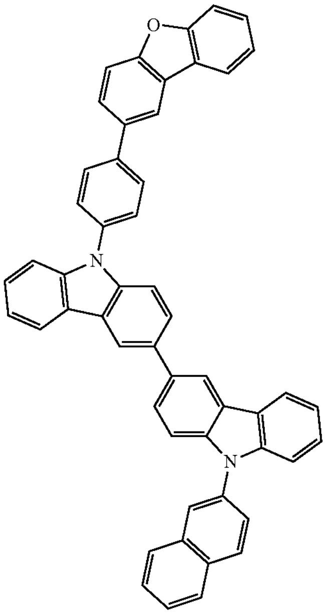
H2-120
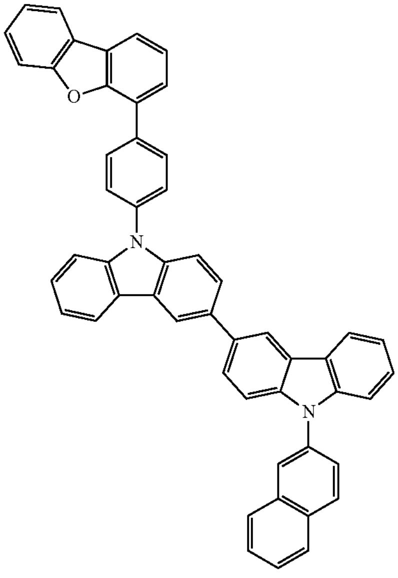

-continued
H2-121
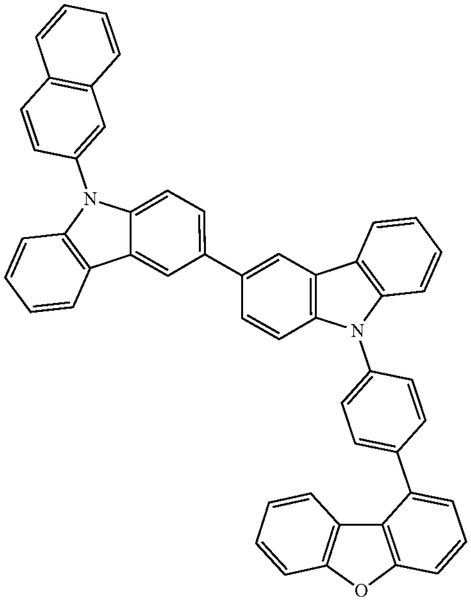
H2-123
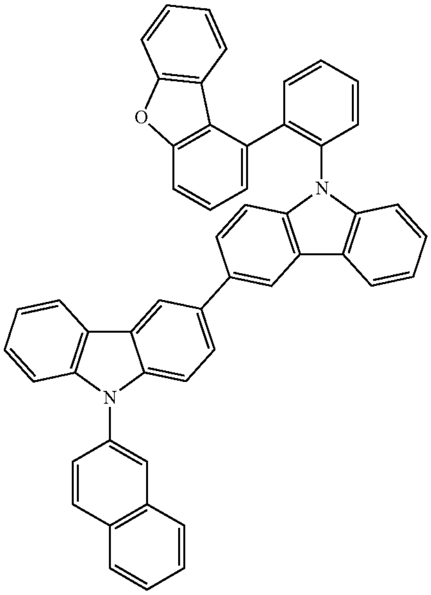
H2-122
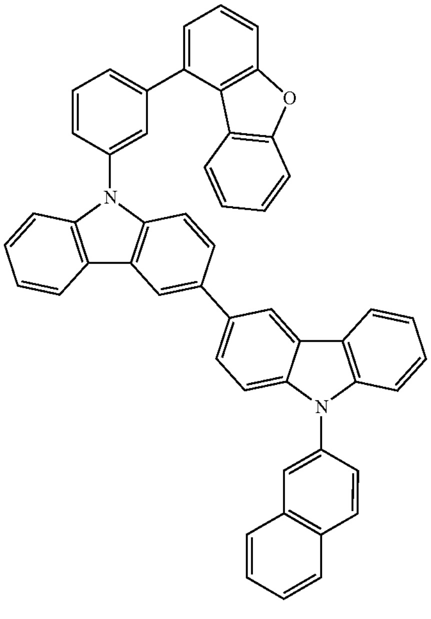
H2-124
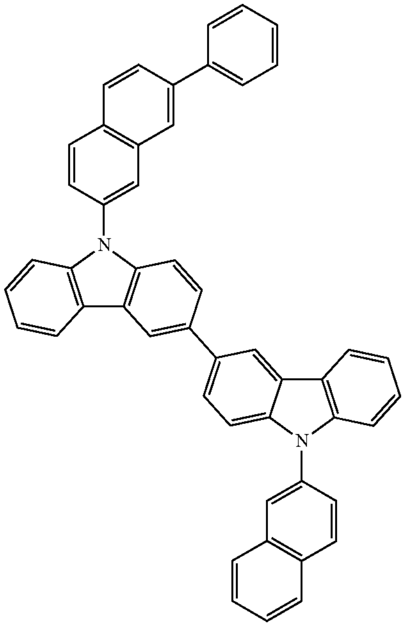

-continued
H2-125
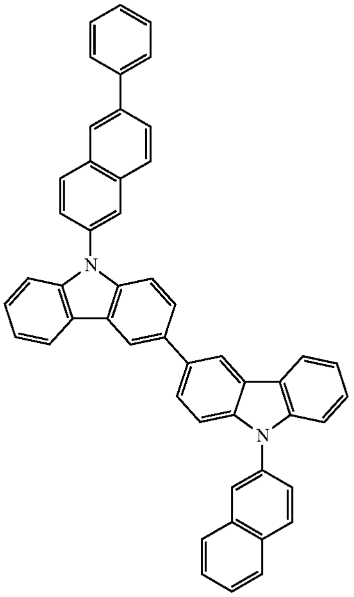
H2-126
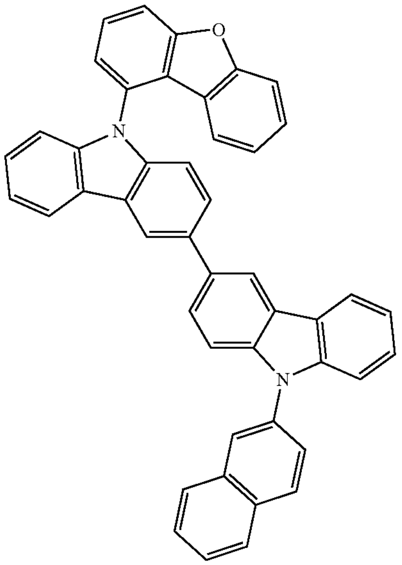
-continued
H2-127
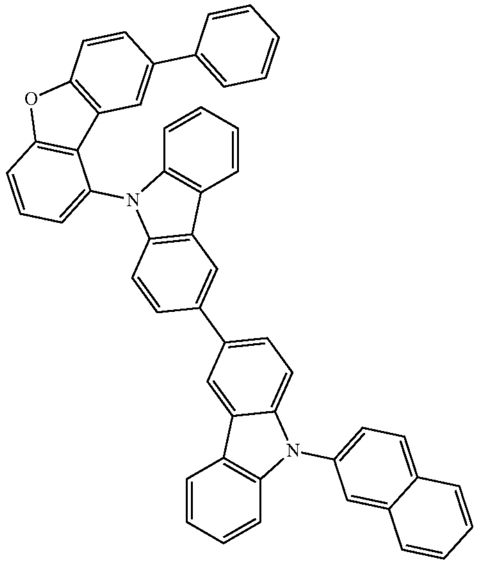
H2-128
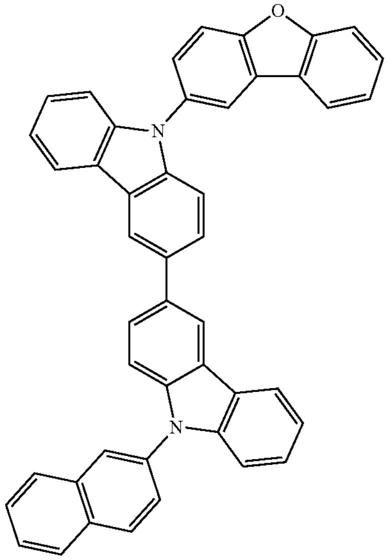

-continued
H2-129
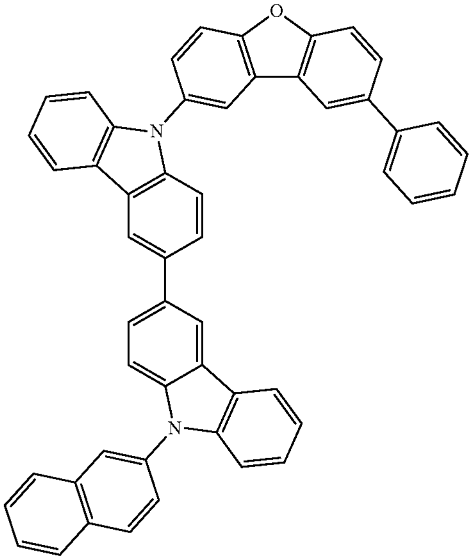
H2-130
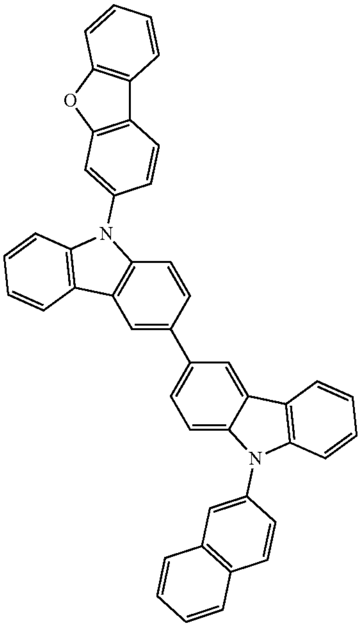
-continued
H2-131
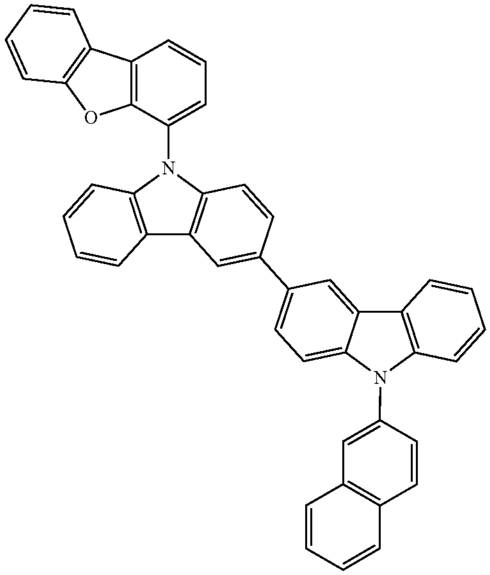
H2-132
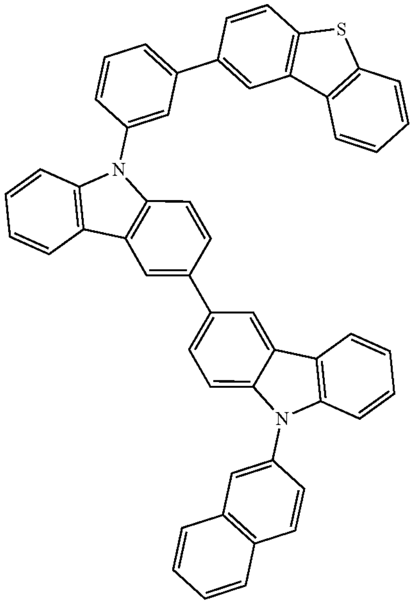

-continued
H2-133
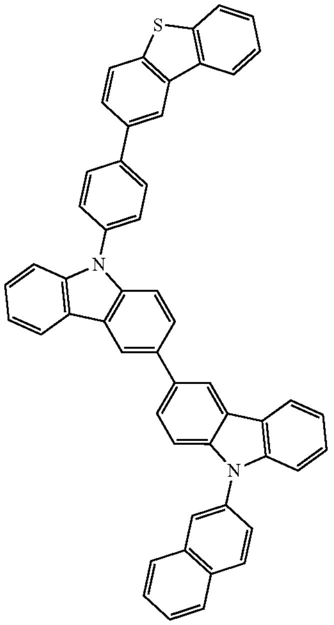
H2-134
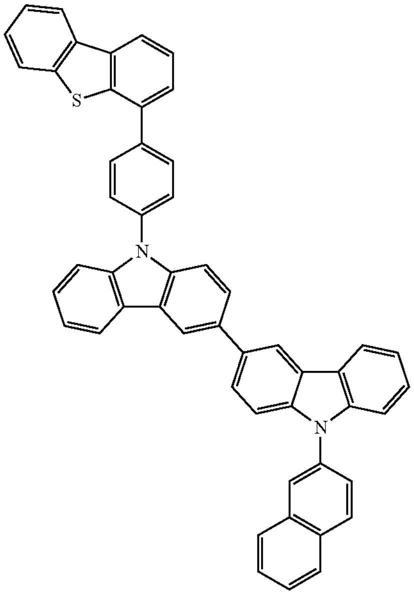
-continued
H2-135
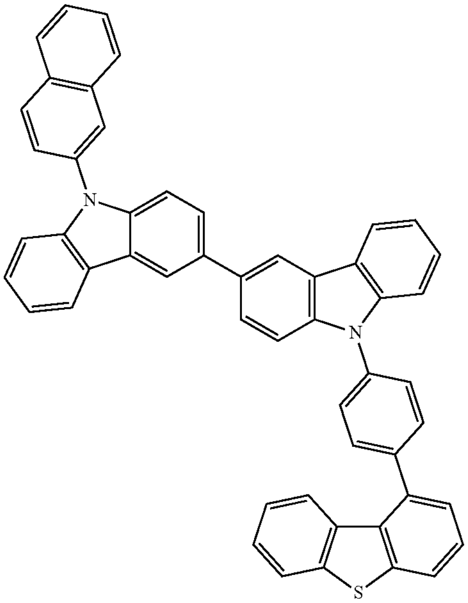
H2-136
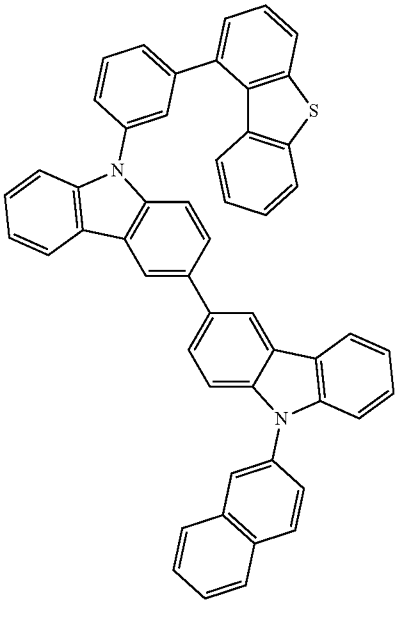

-continued
H2-137
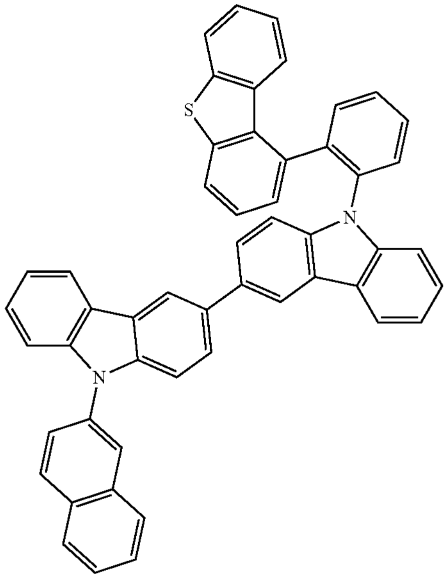
H2-138
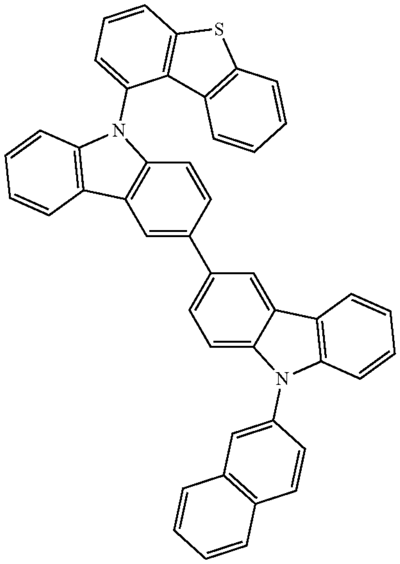
-continued
H2-139
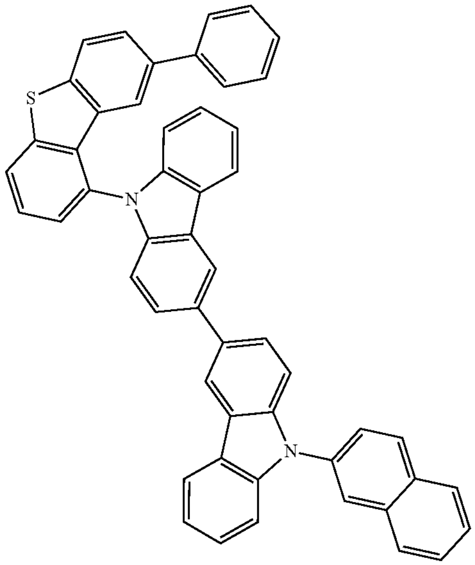
H2-140
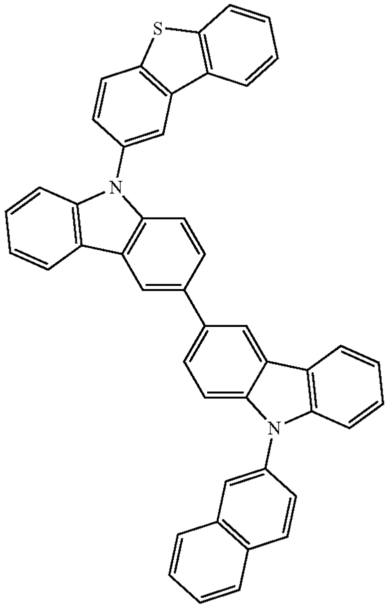

-continued
H2-141
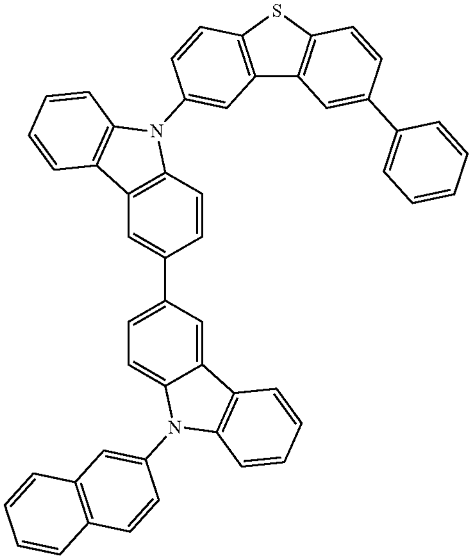
H2-142
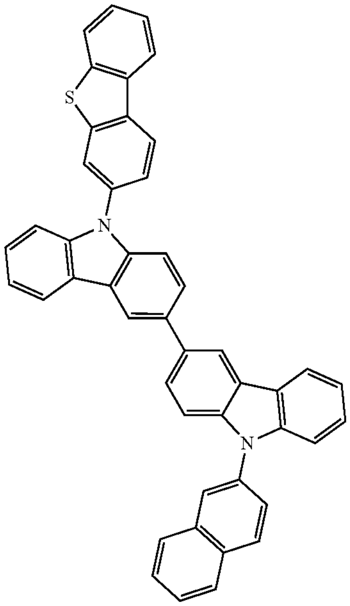
-continued
H2-143
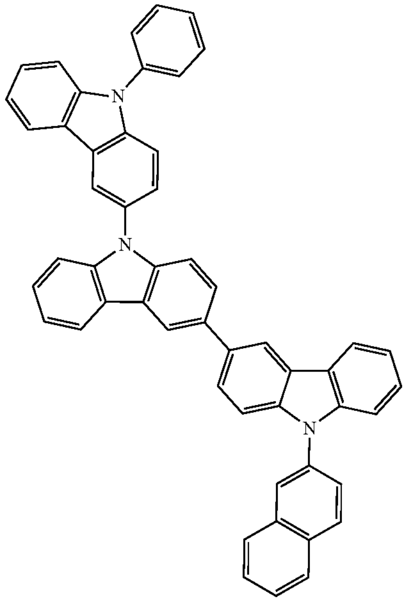
H2-144
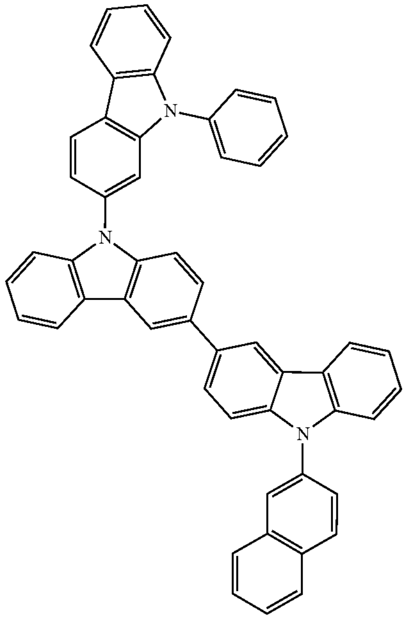

-continued
H2-145
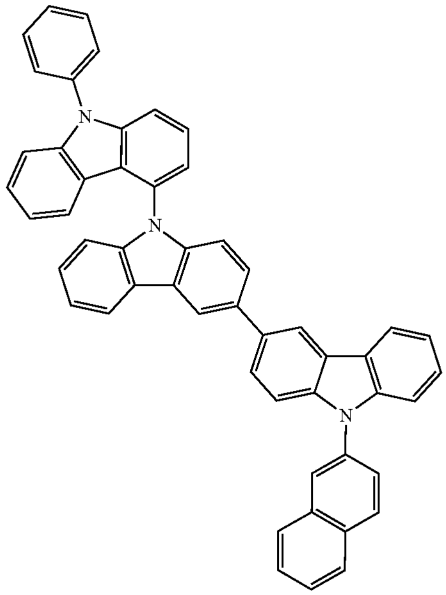
C-1
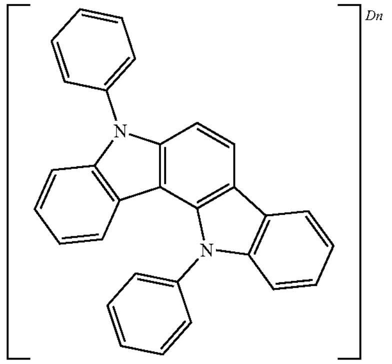
C-2
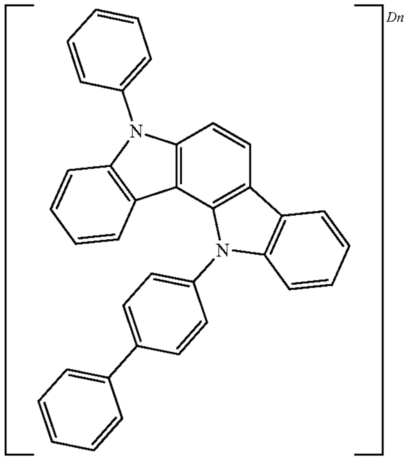
-continued
C-3
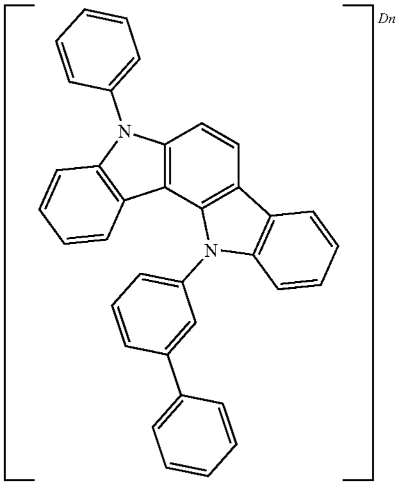
C-4
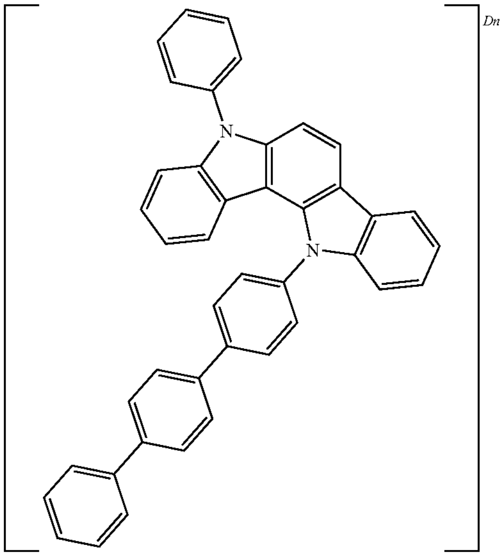
C-5
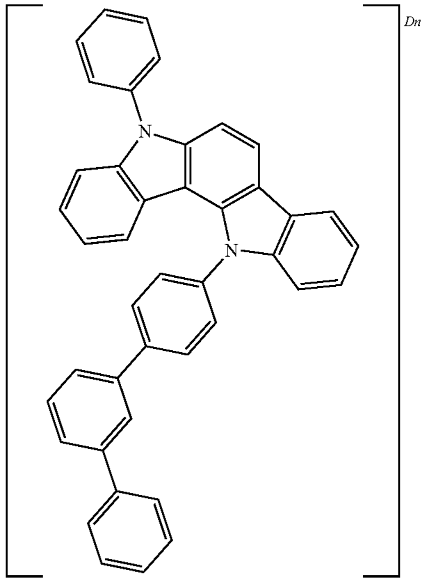

-continued
C-6
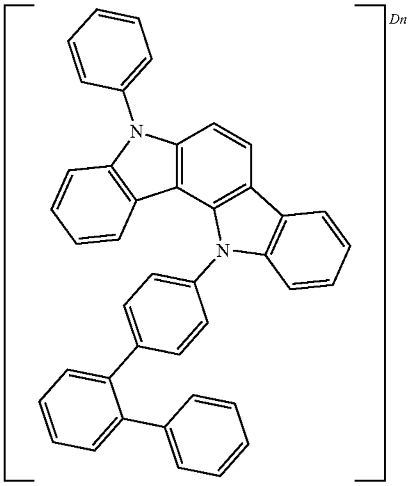
C-7
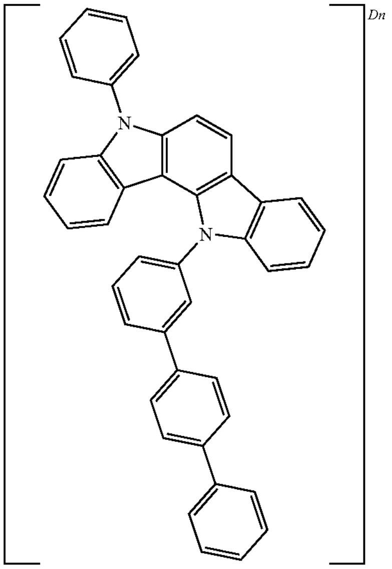
C-8
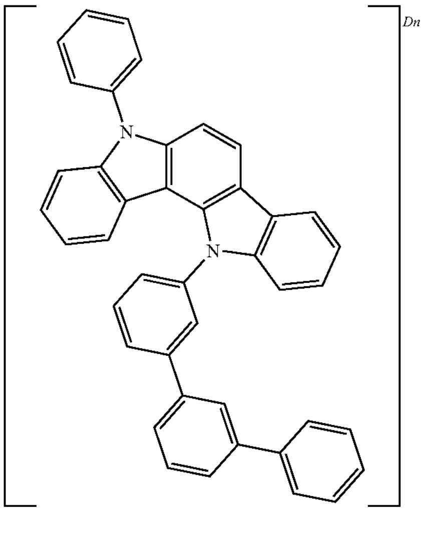
-continued
C-9
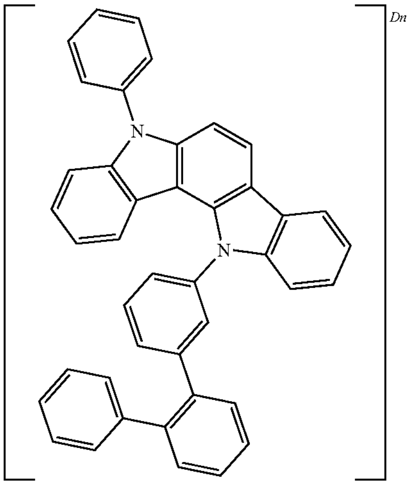
C-10
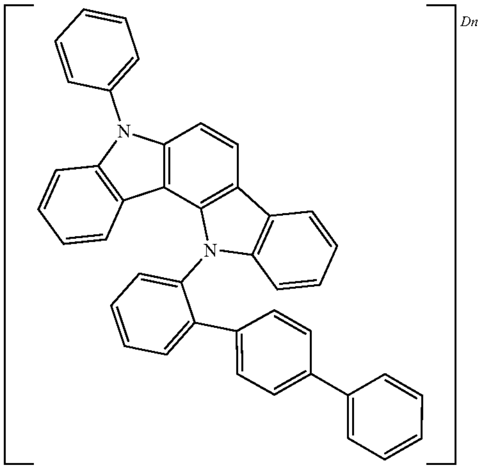
C-11
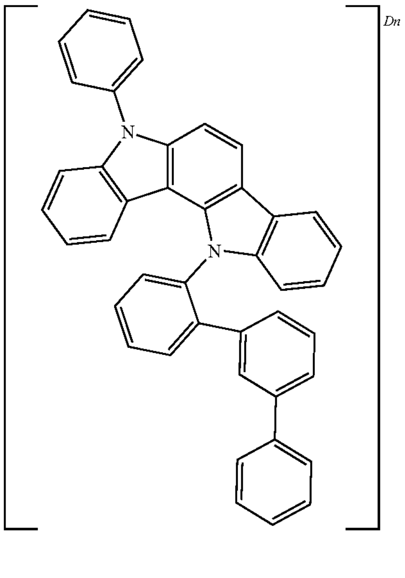

-continued
C-12
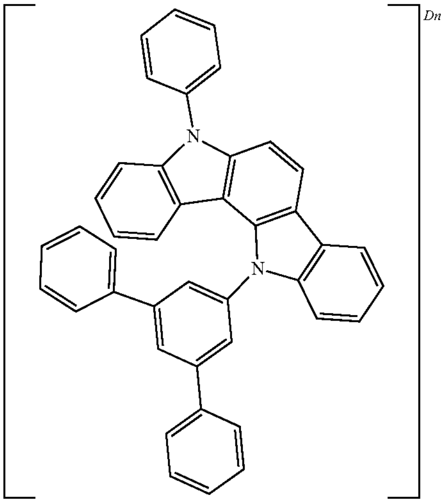
C-13
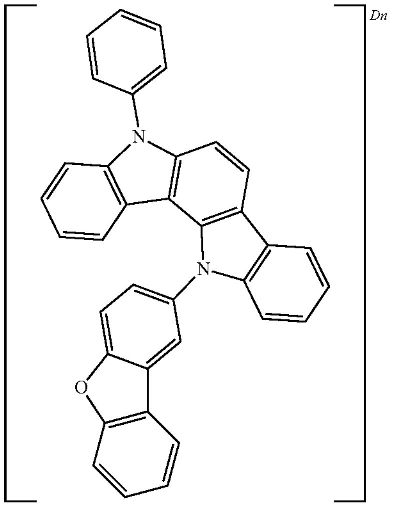
C-14
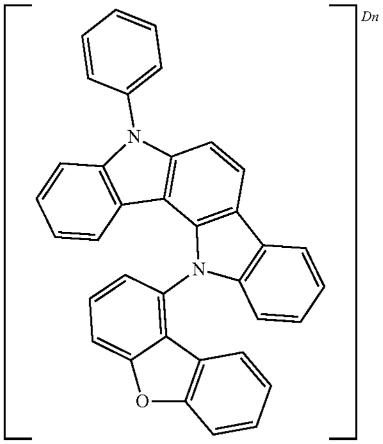
-continued
C-15
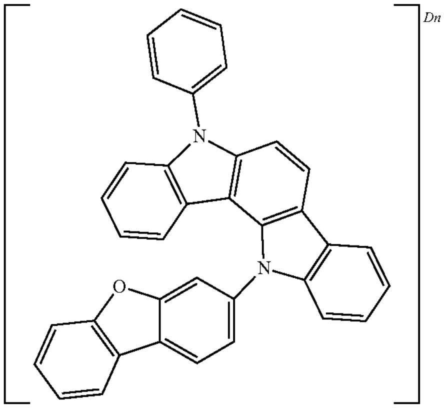
C-16
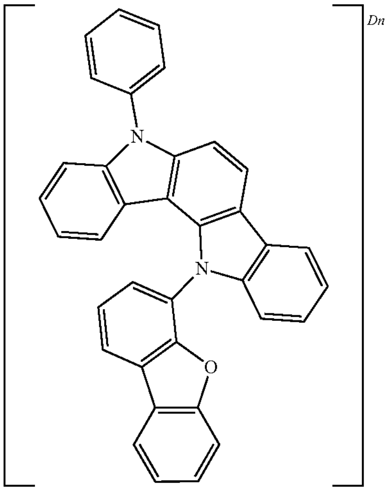
C-17
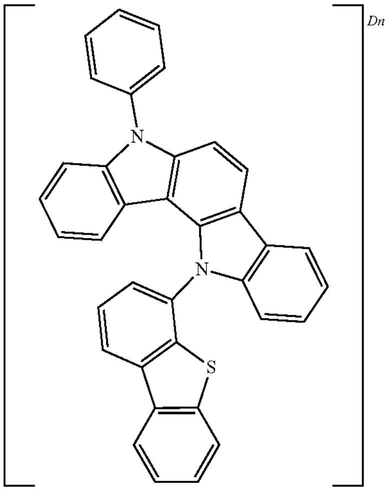

-continued
C-18
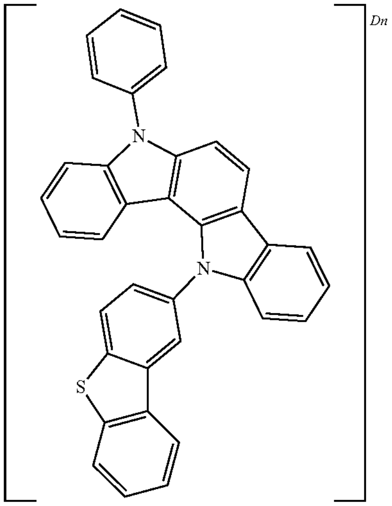
C-19
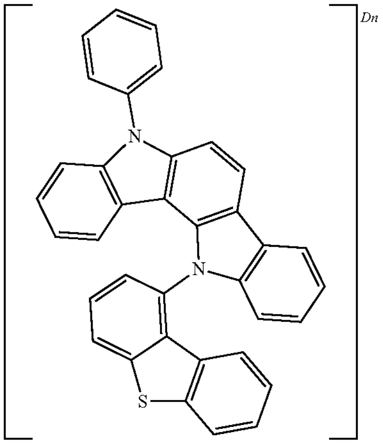
C-20
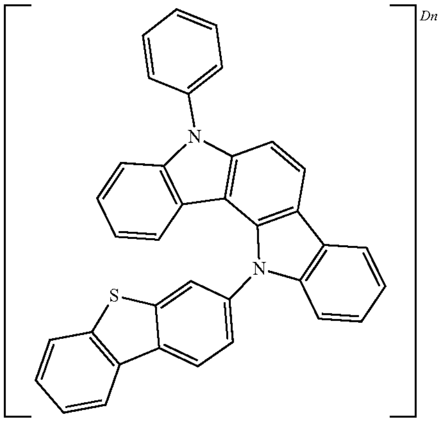
-continued
C-21
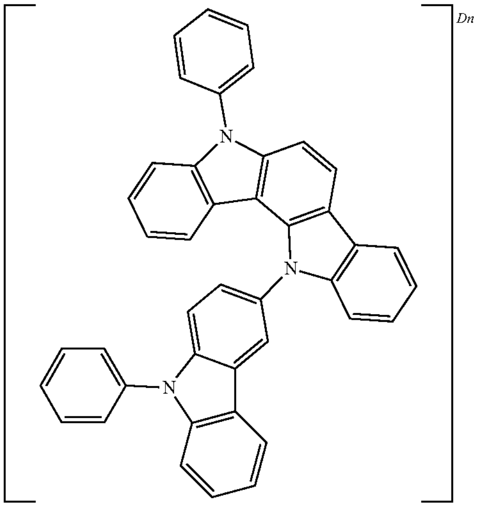
C-22
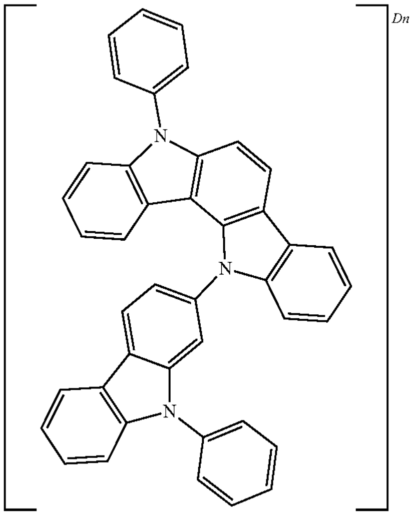
C-23
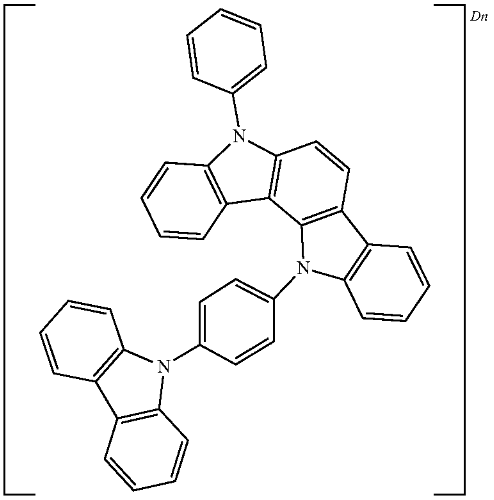

-continued
C-24
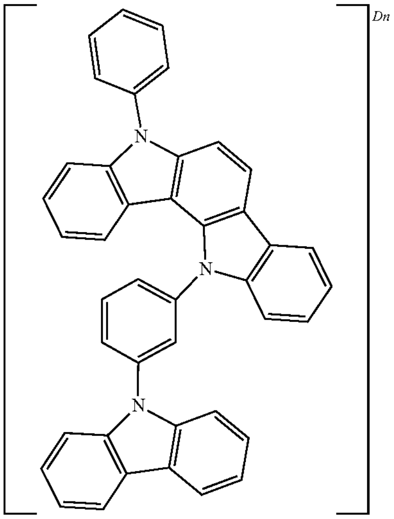
C-25
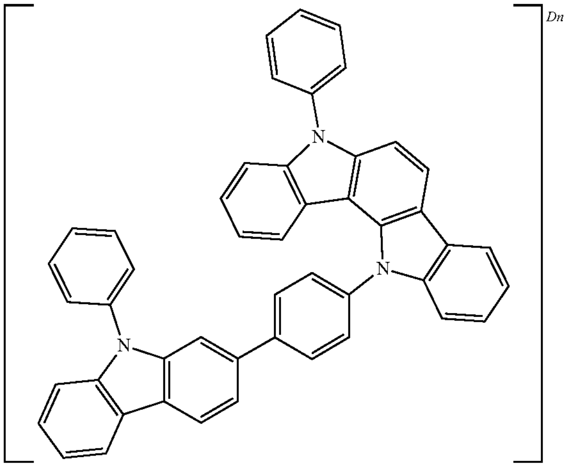
C-26
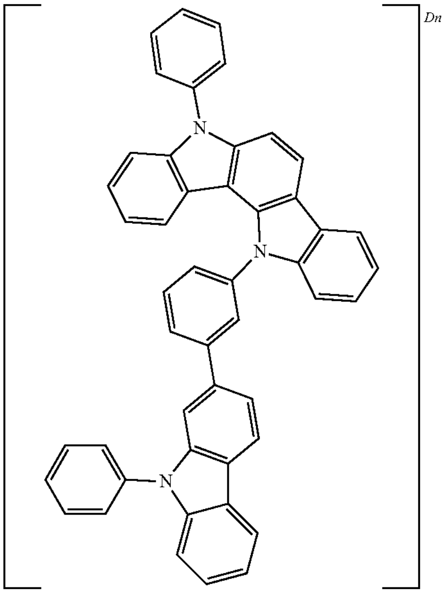
-continued
C-27
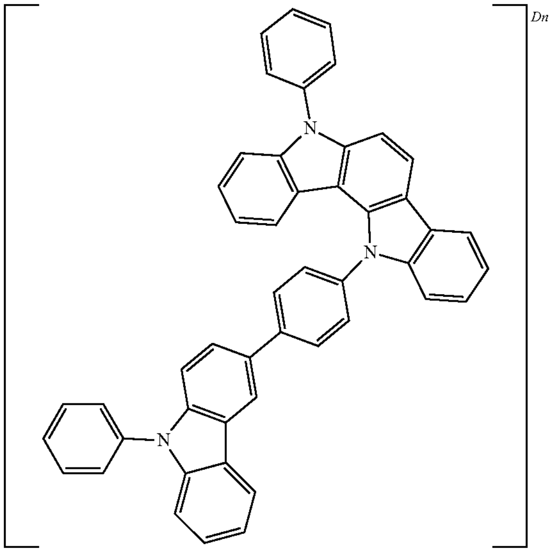
C-28
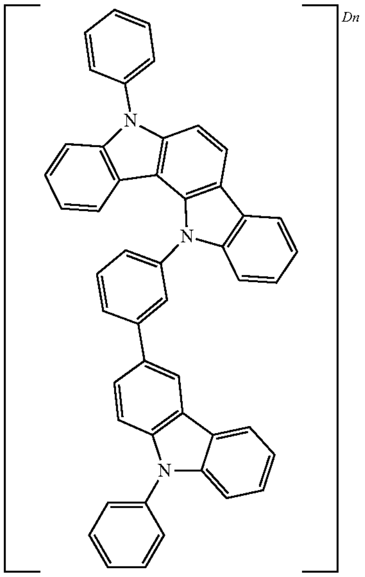

-continued
C-29
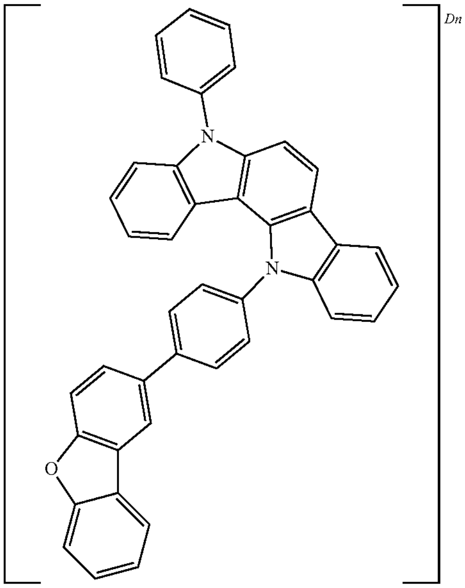
C-30
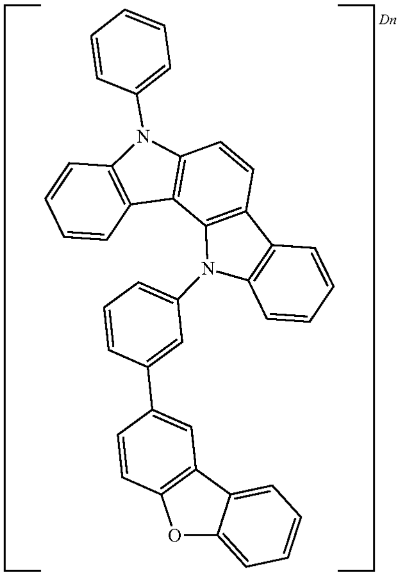
-continued
C-31
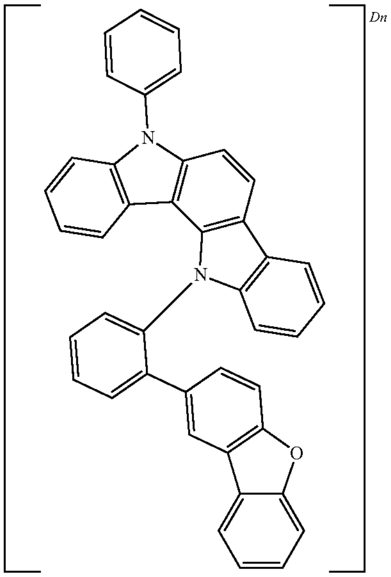
C-32
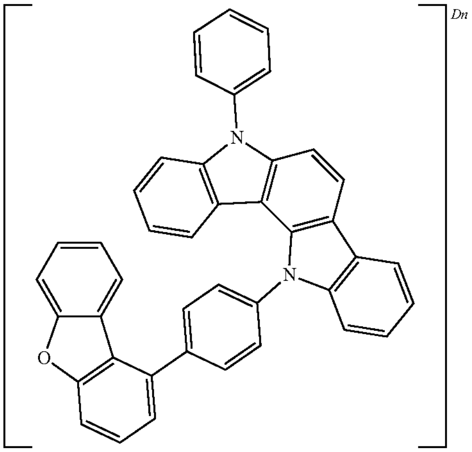
C-33
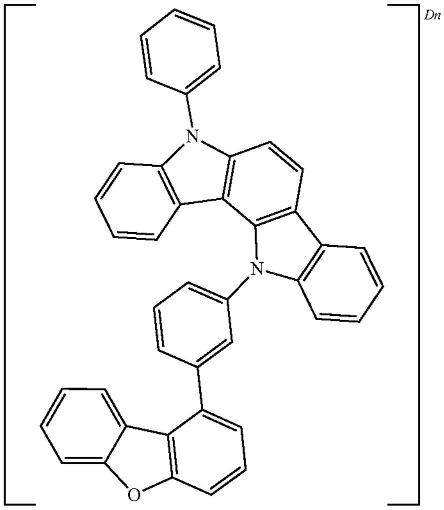

-continued
C-34
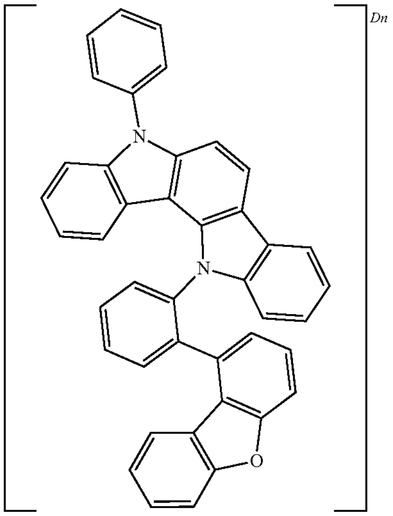
C-35
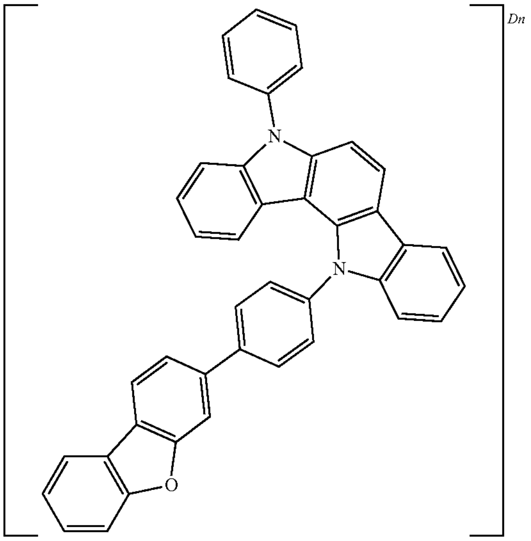
C-36
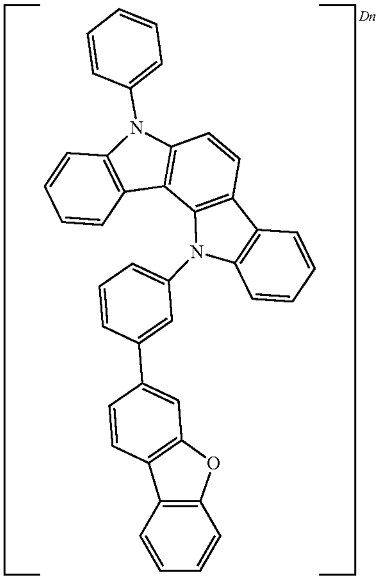
-continued
C-37
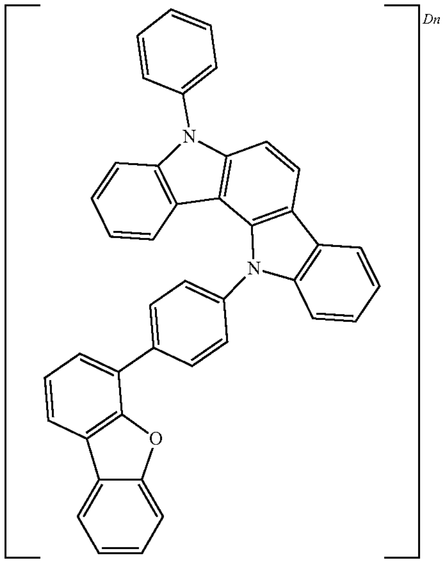
C-38
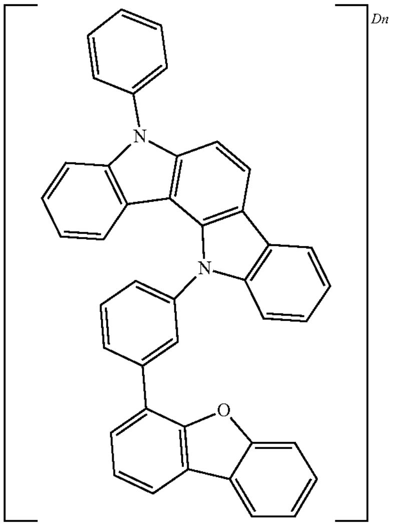
C-39
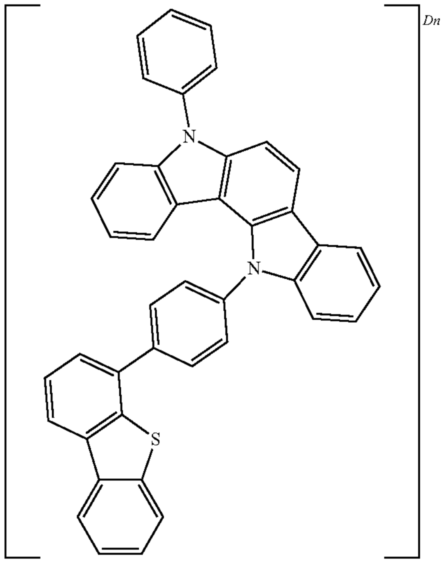

-continued
C-40
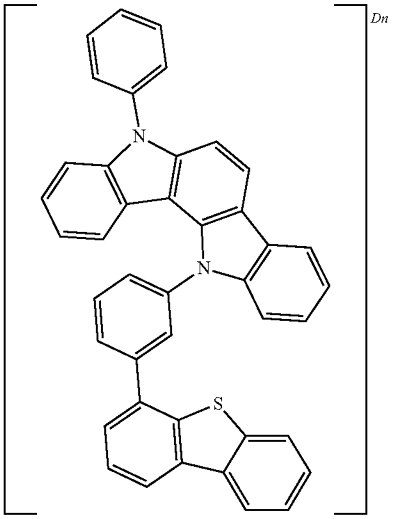
C-41
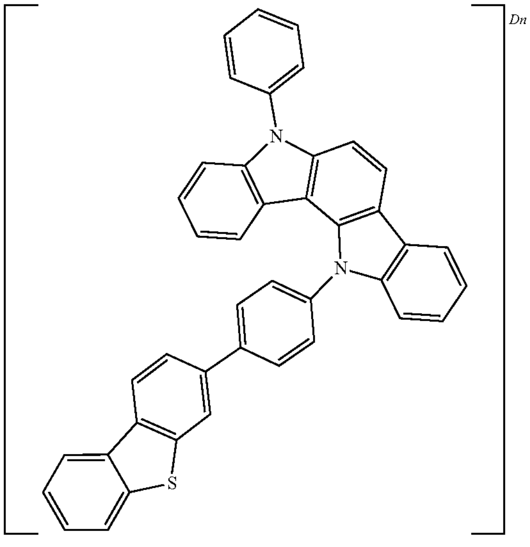
-continued
C-42
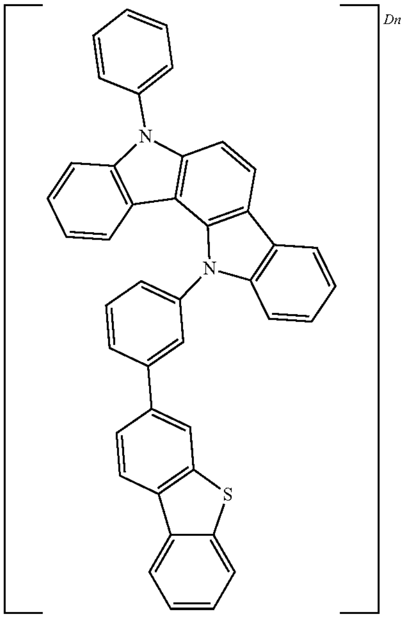
C-43
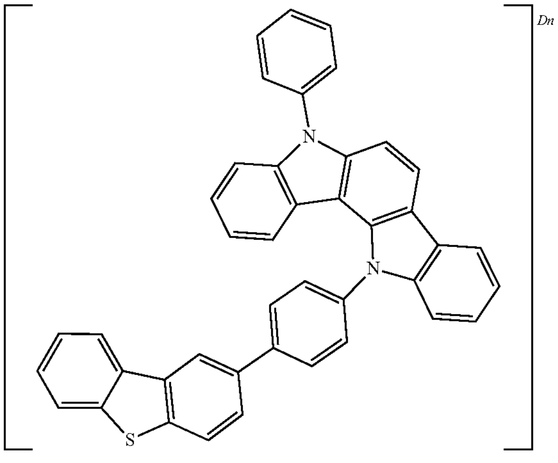

-continued
C-44
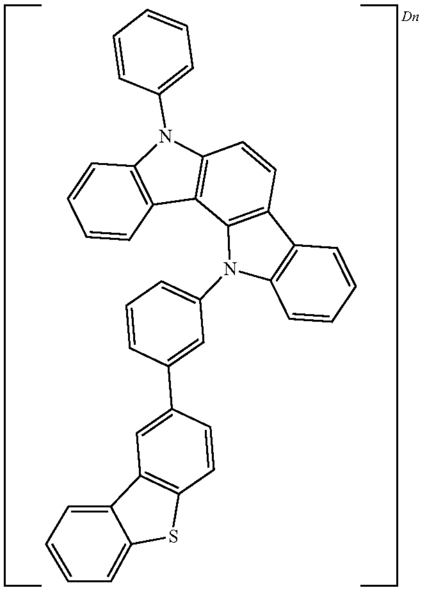
C-45
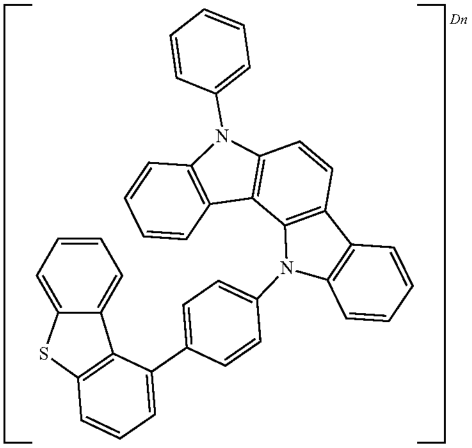
C-46
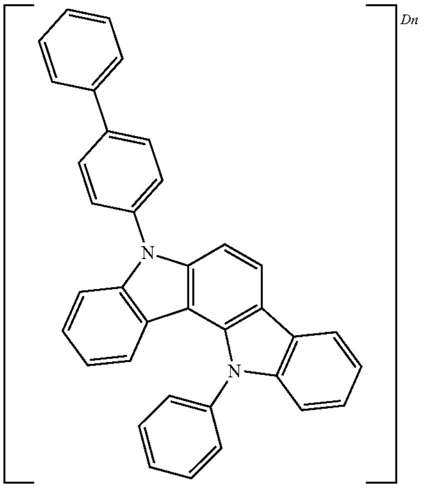
-continued
C-47
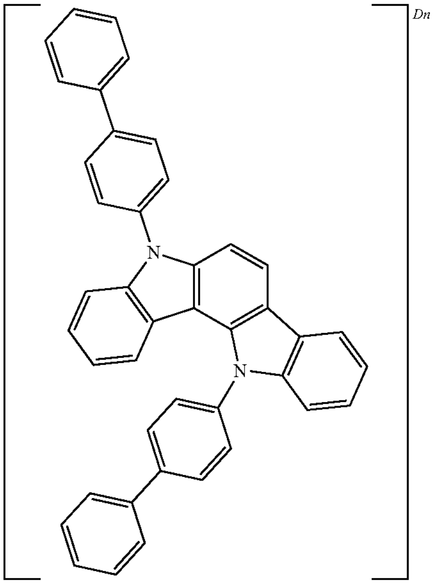
C-48
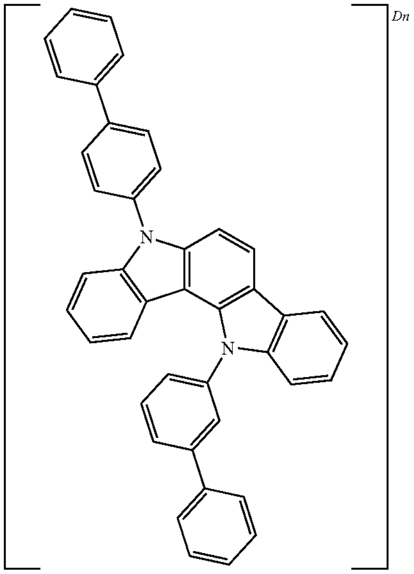

-continued
C-49
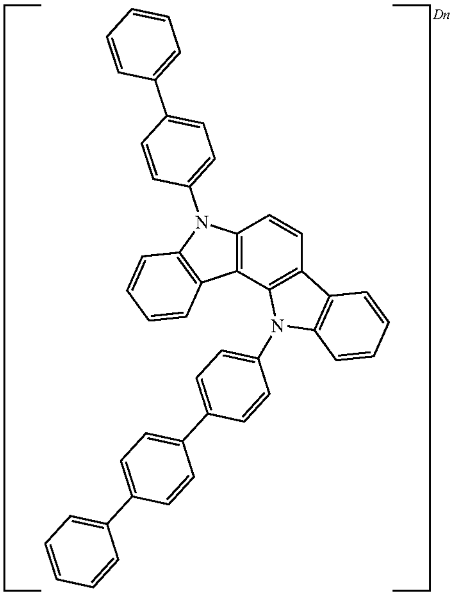
C-50
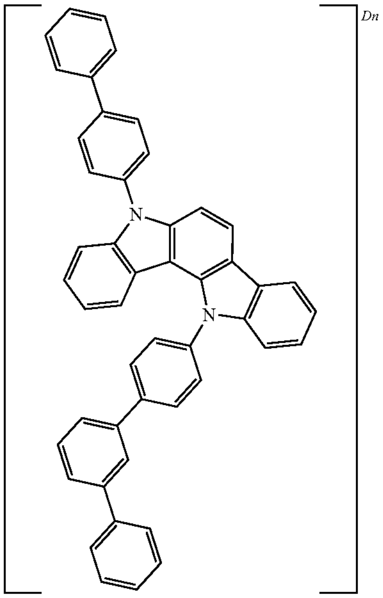
-continued
C-51
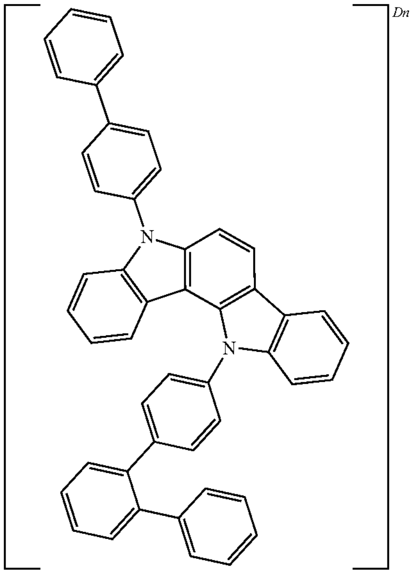
C-52
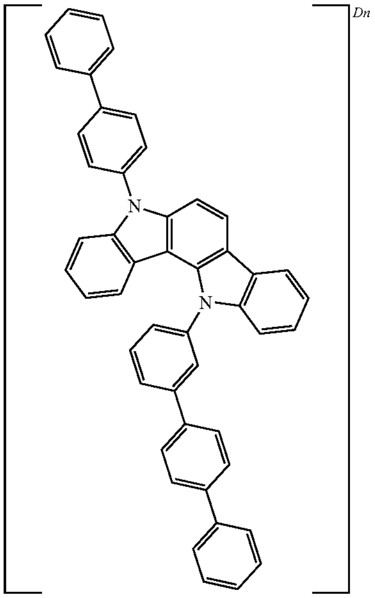

-continued
C-53
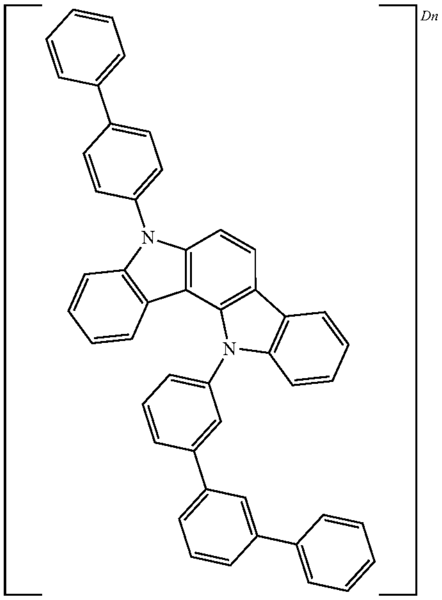
C-54
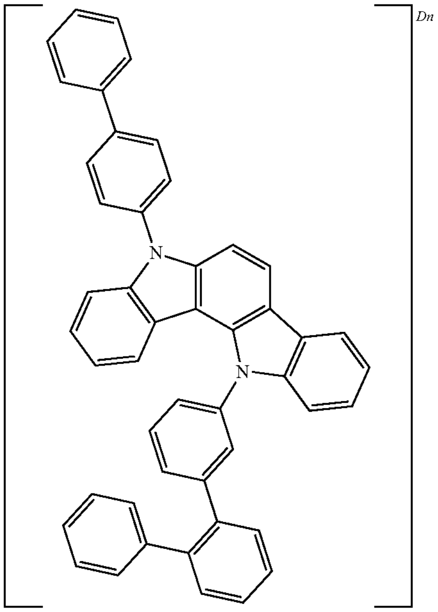
-continued
C-55
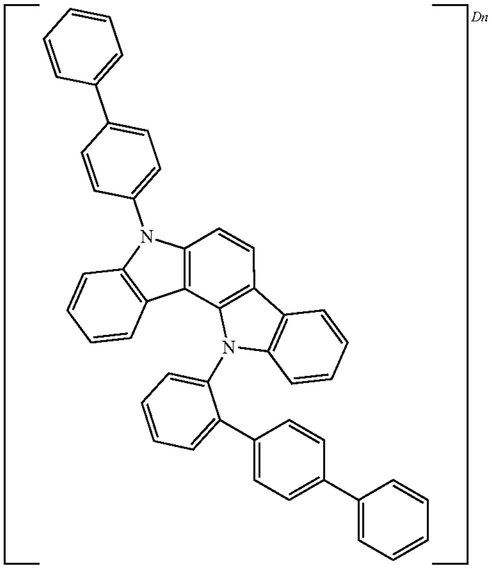
C-56
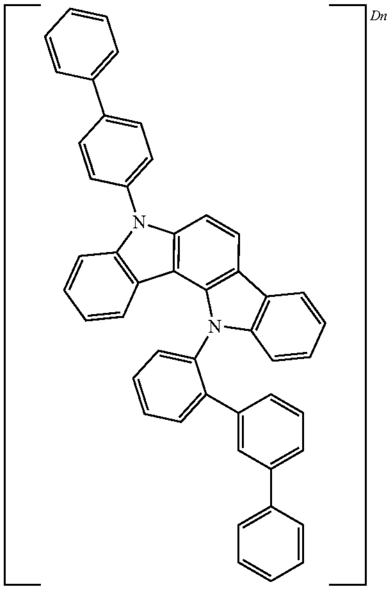

290
-continued
C-57
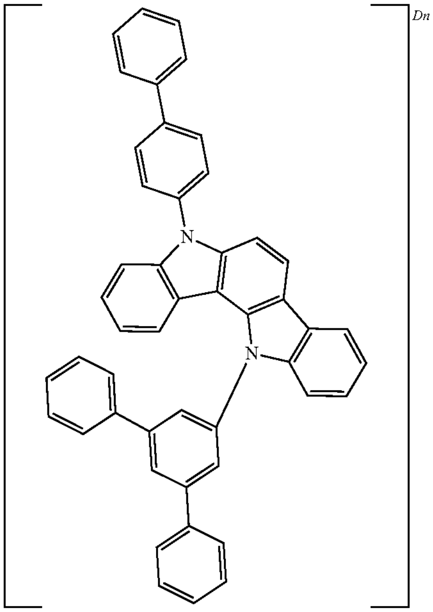
C-58
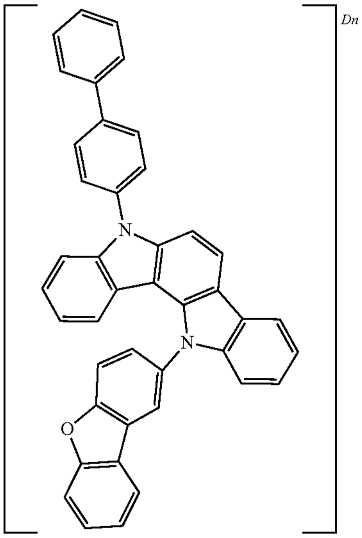
C-59
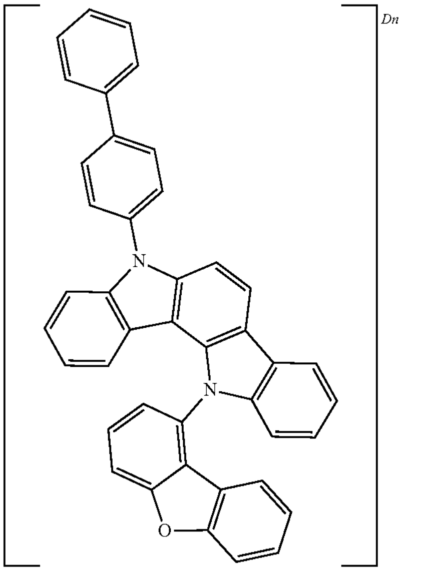
C-60
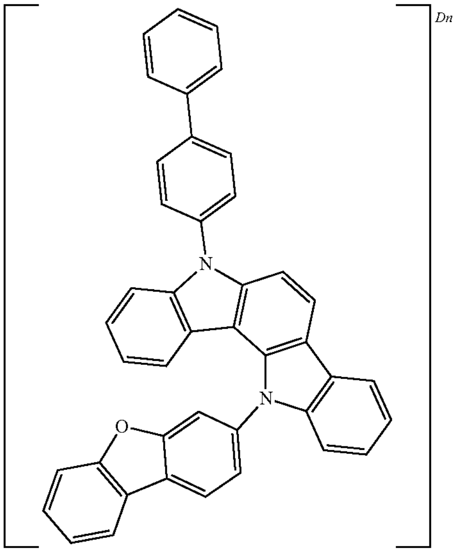

-continued
C-61
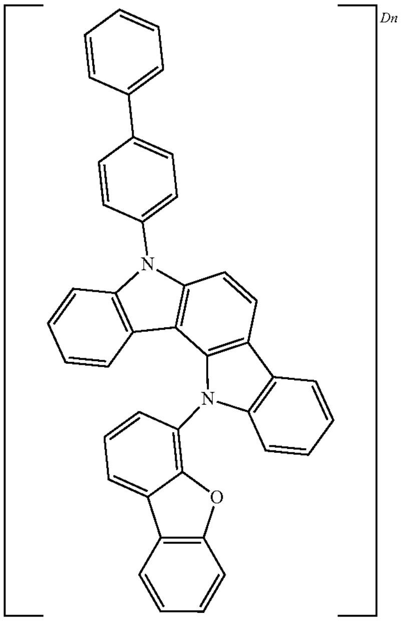
C-62
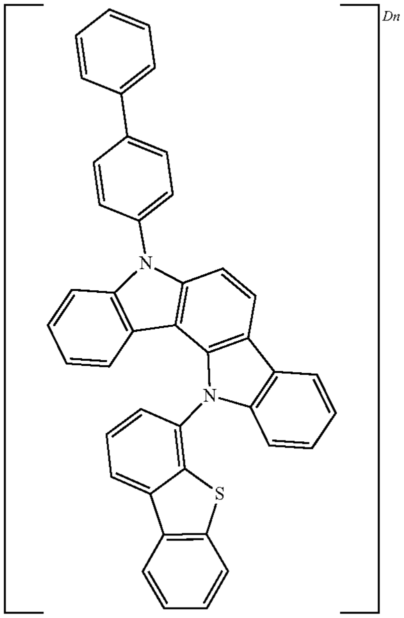
-continued
C-63
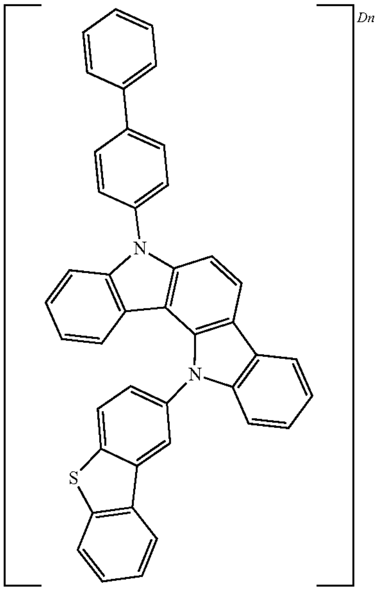
C-64
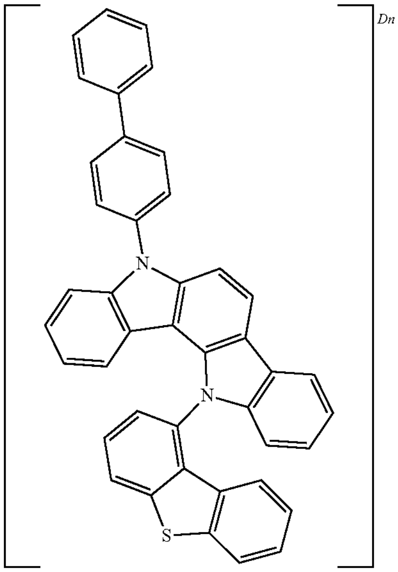

-continued
C-65
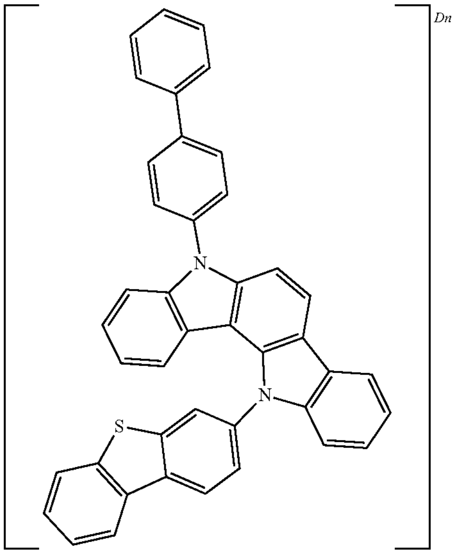
C-66
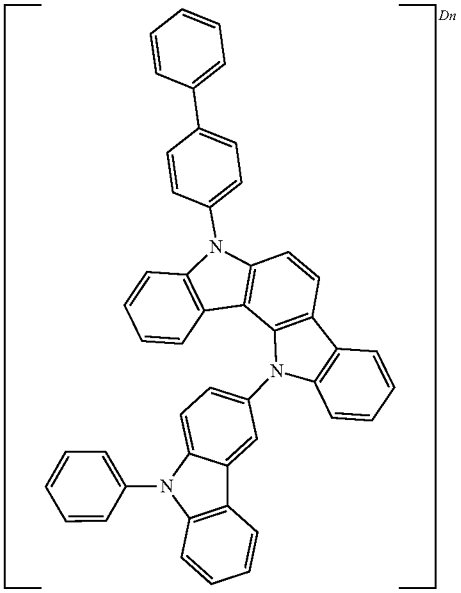
-continued
C-67
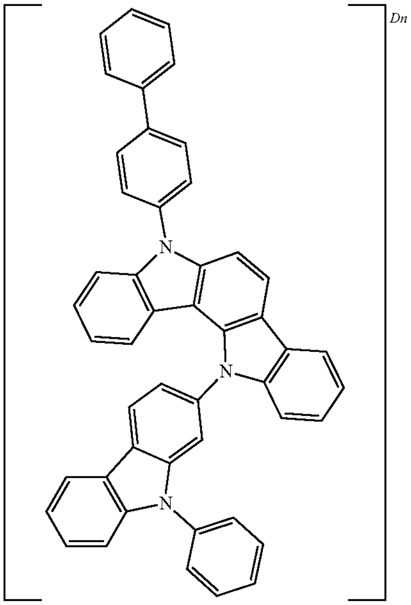
C-68
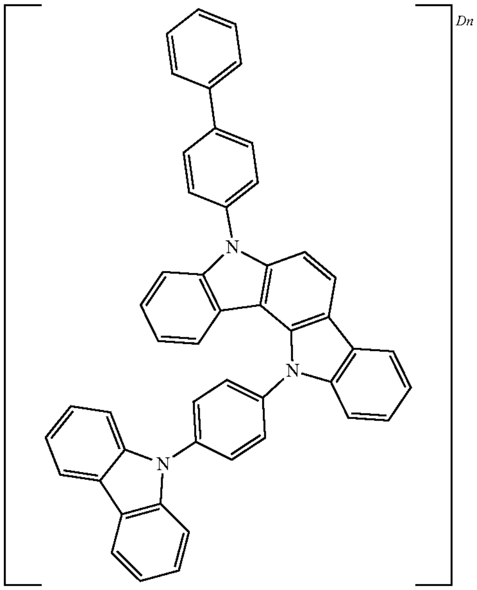

-continued
C-69
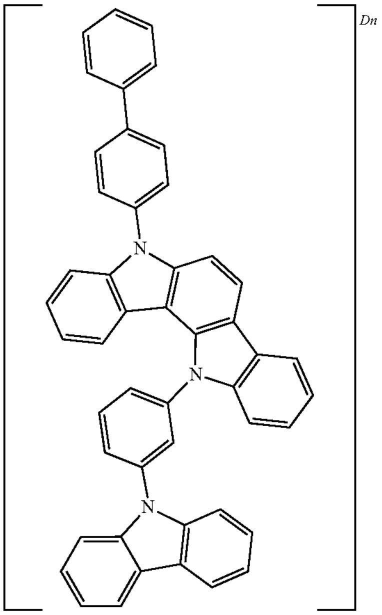
C-70
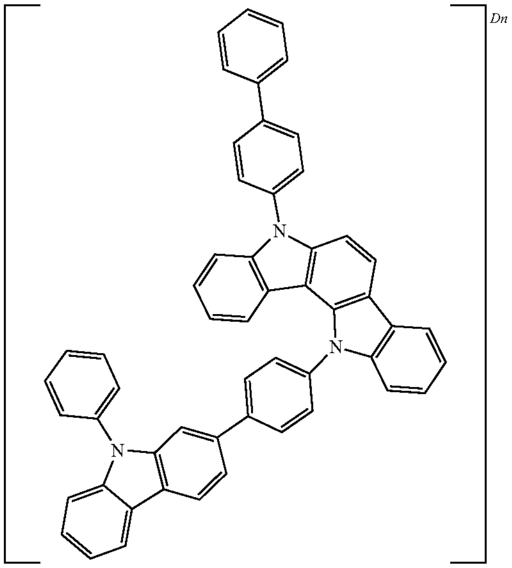
C-71
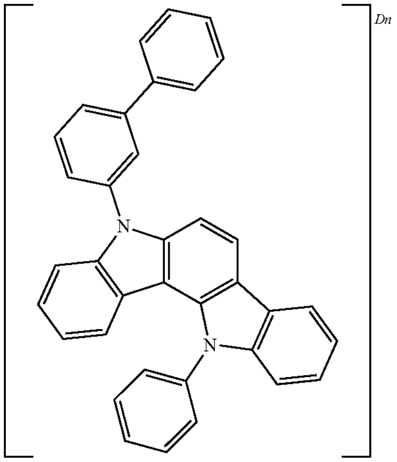
-continued
C-72
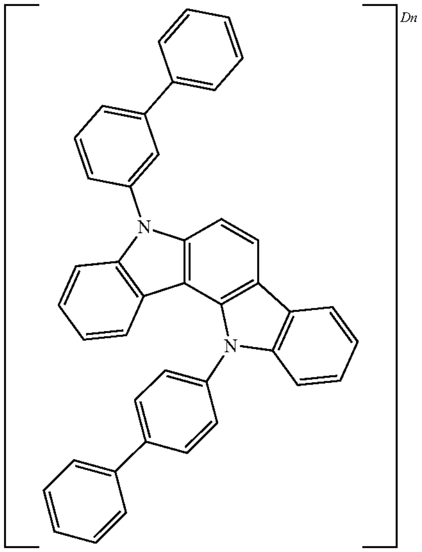
C-73
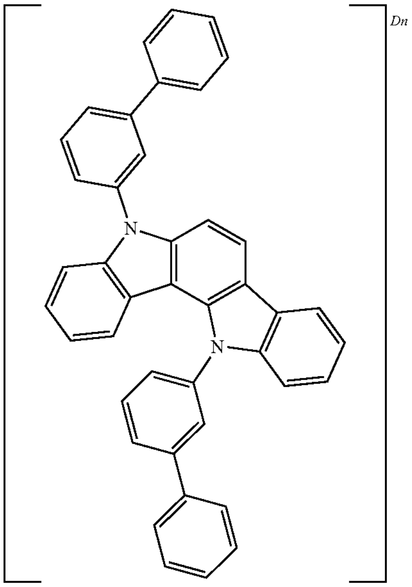

-continued
C-74
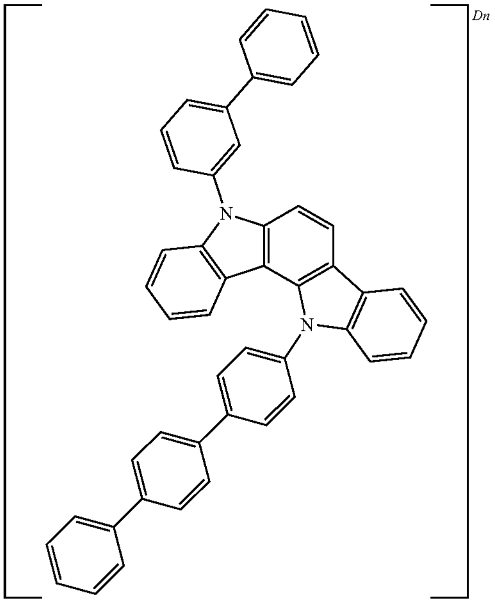
C-75
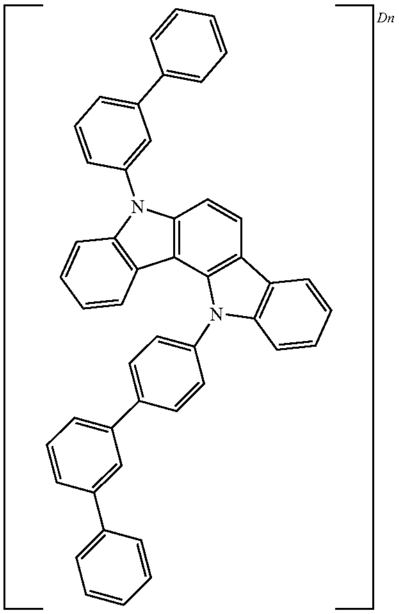
-continued
C-76
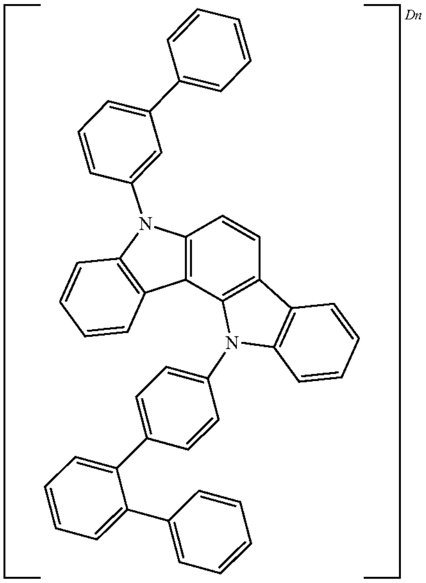
C-77
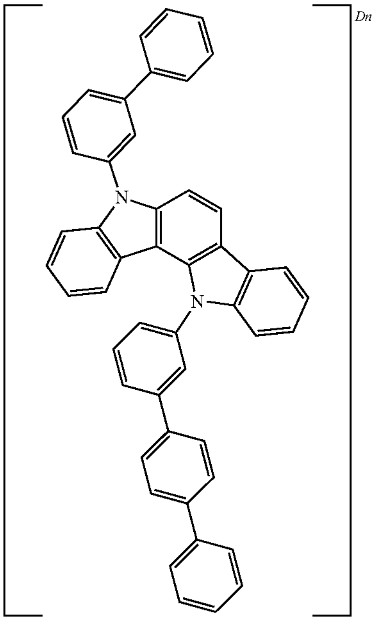

-continued
C-78
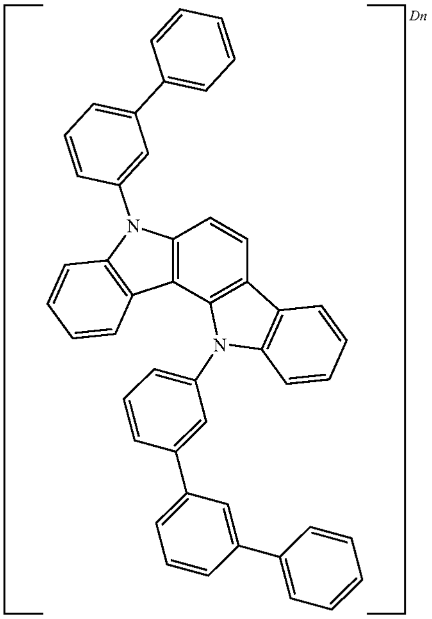
C-80
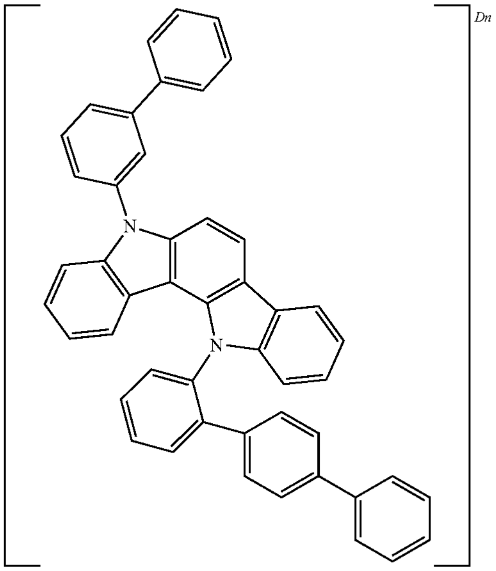
C-79
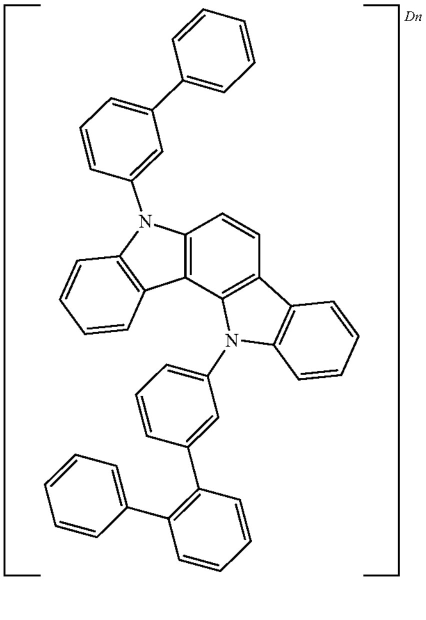
C-81
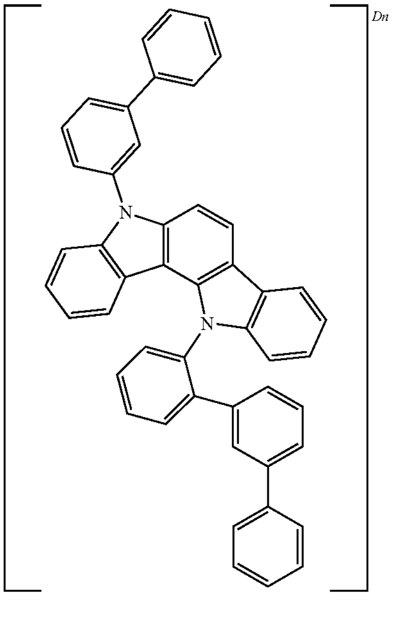

-continued
C-82
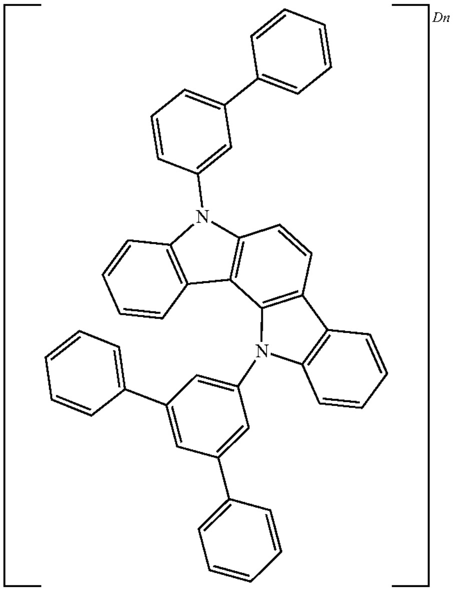
C-83
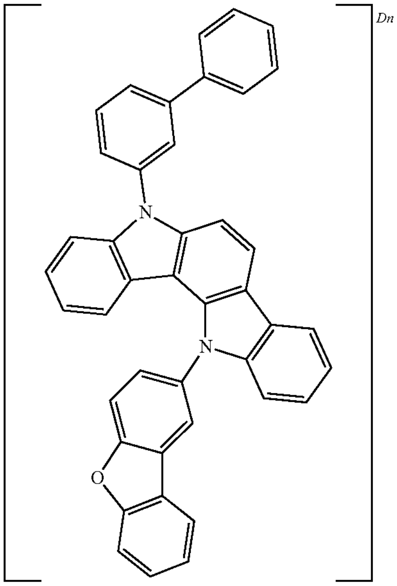
-continued
C-84
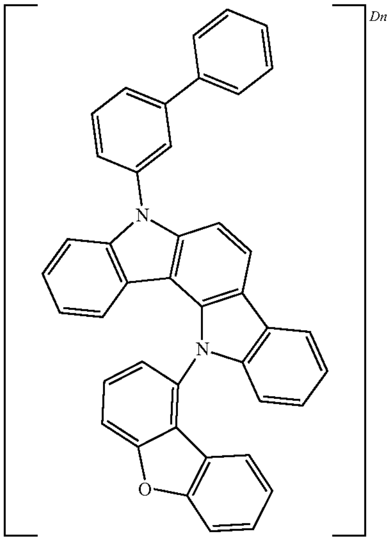
C-85
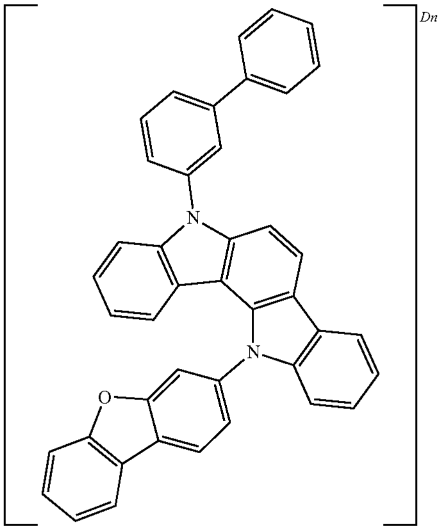
C-86
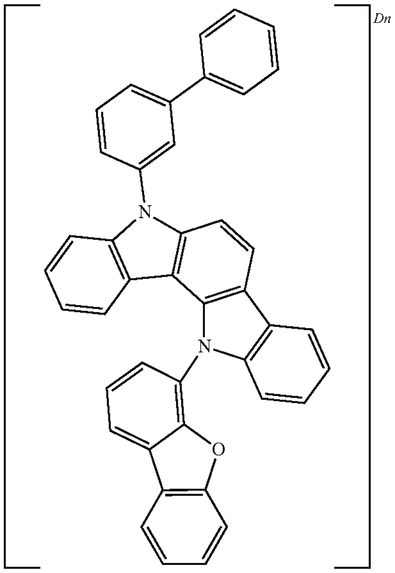

-continued
C-87
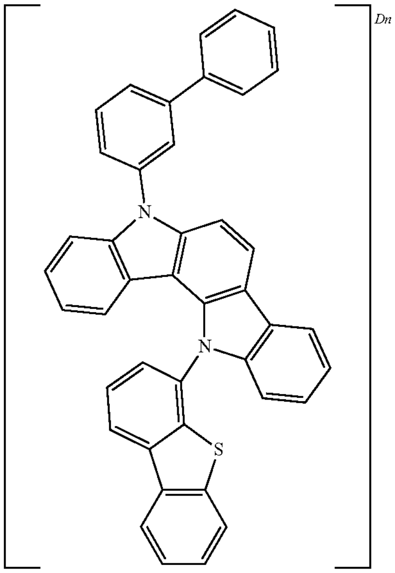
C-88
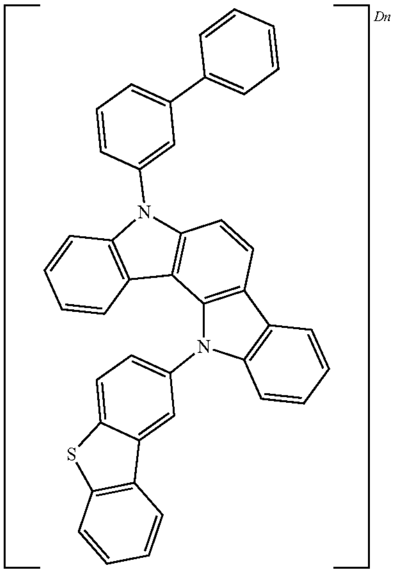
-continued
C-89
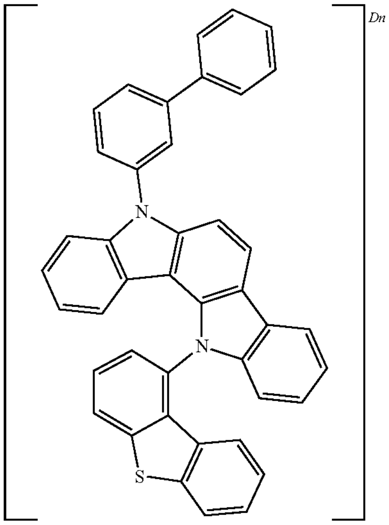
C-90
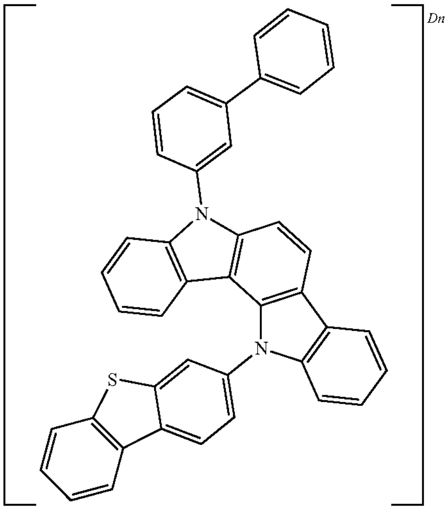
C-91
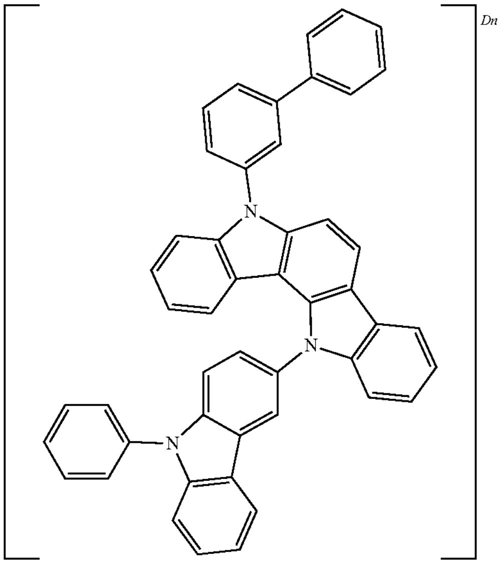

-continued
C-93
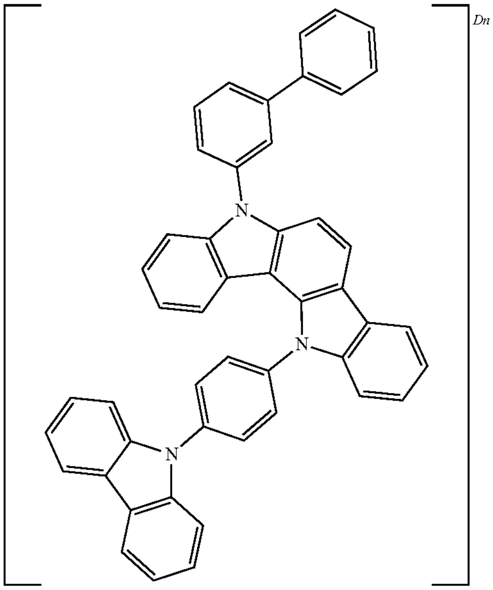
C-94
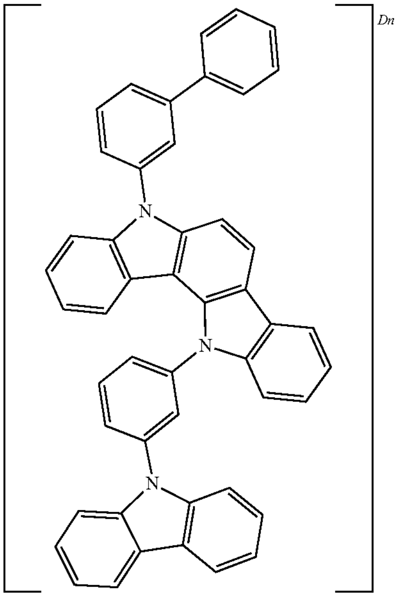
-continued
C-95
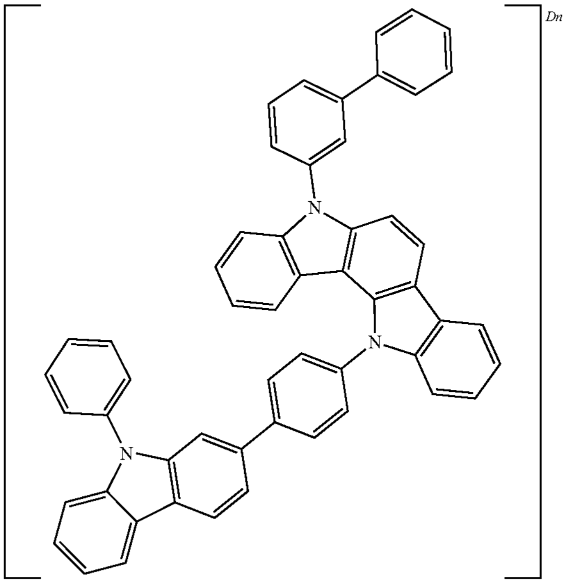
C-96
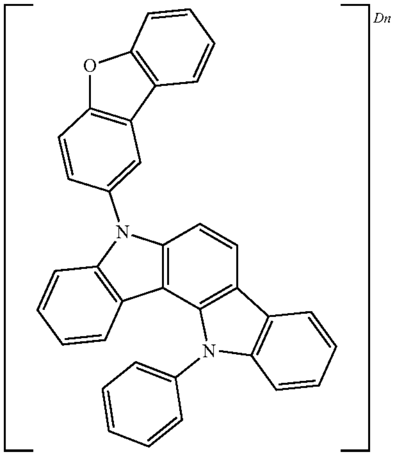
C97
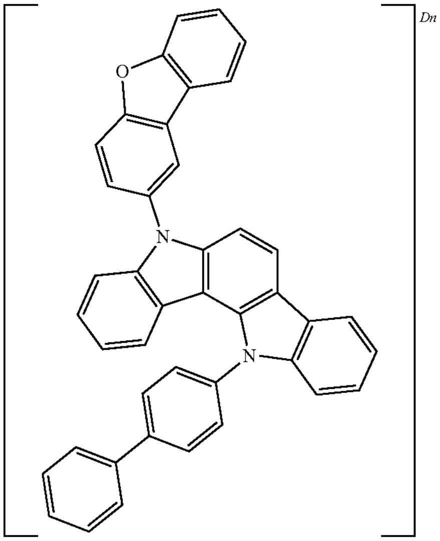

C-98
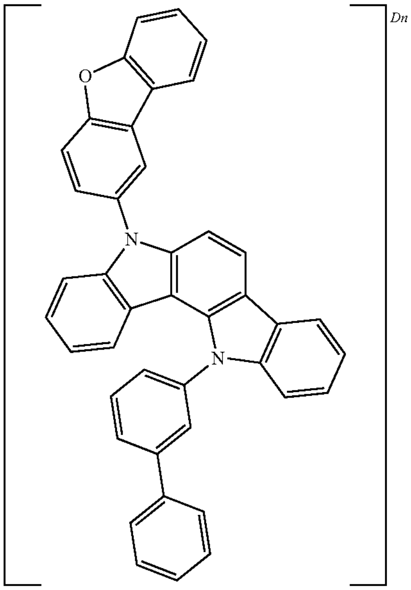
C-99
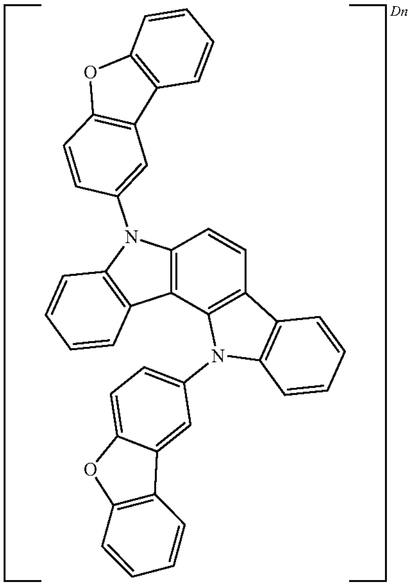
C-100
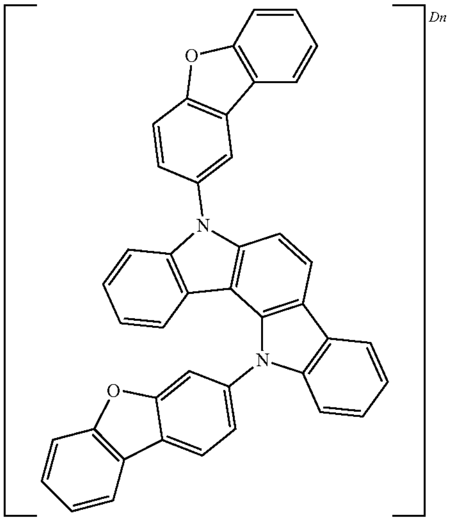
C-101
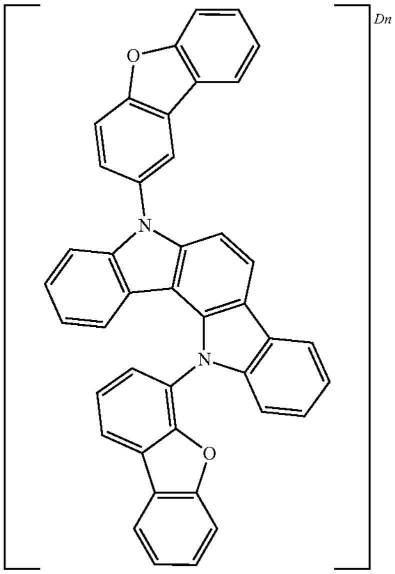
C-102
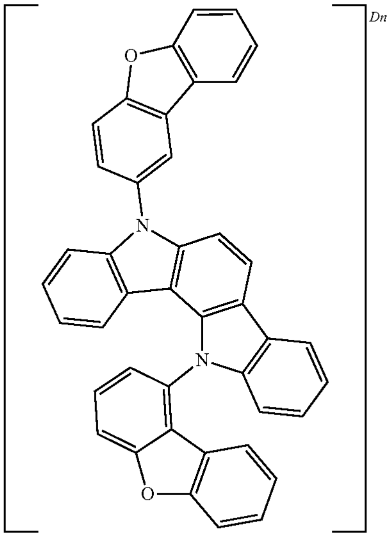

-continued
C-103
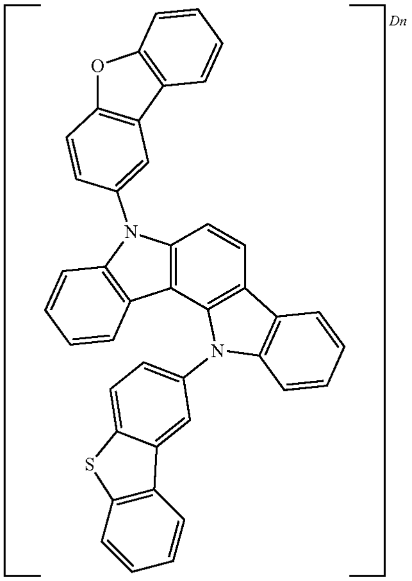
-continued
C-105
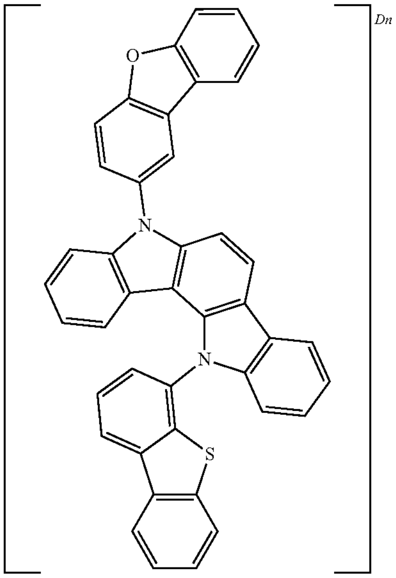
C-104
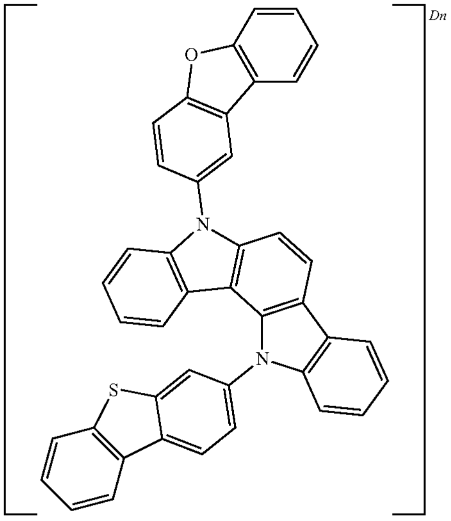
C-106
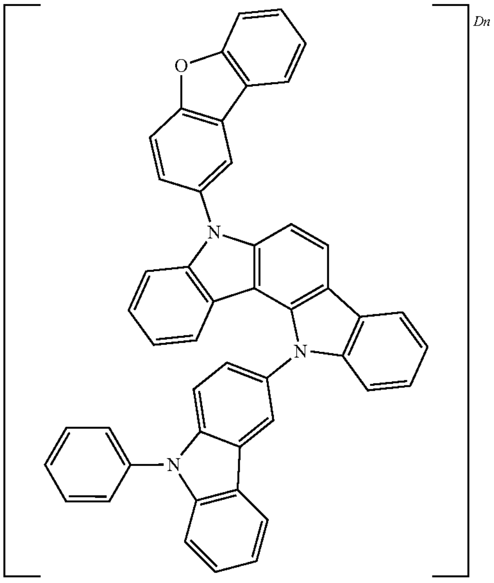

-continued
C-107
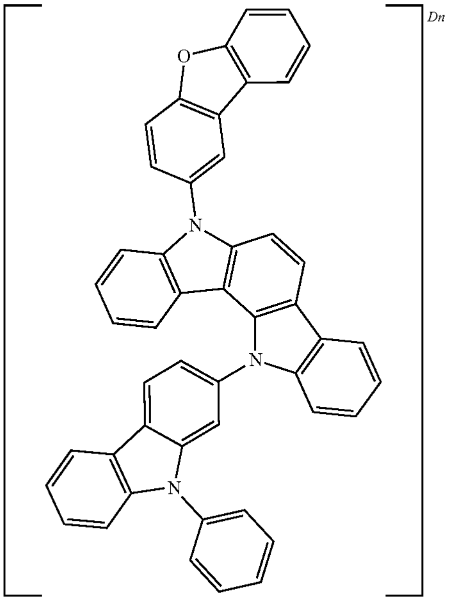
C-108
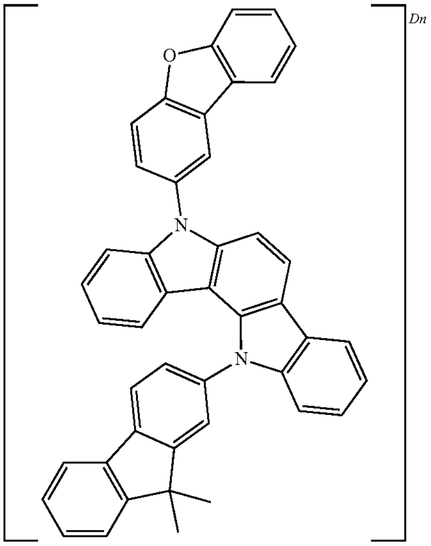
C-109
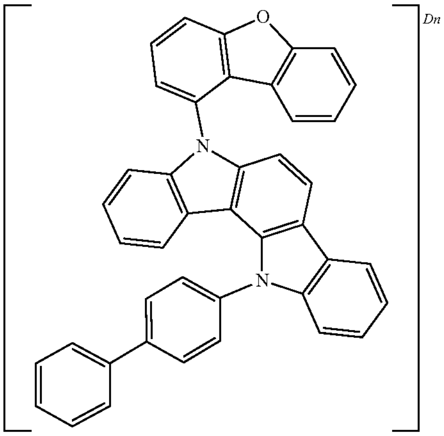
-continued
C-110
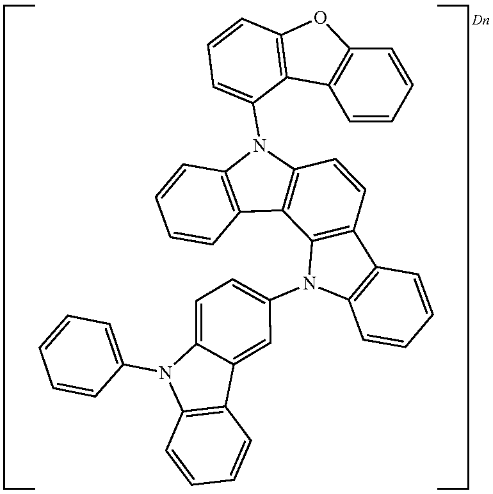
C-111
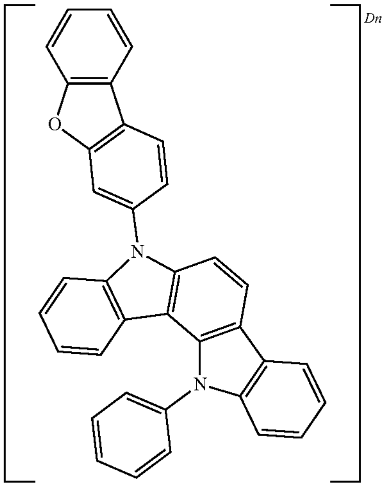
C-112
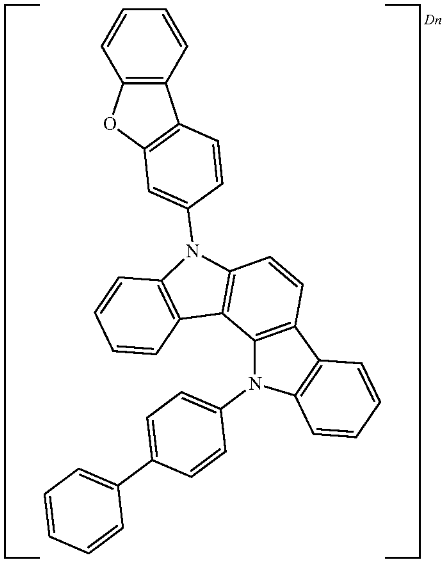

C-113
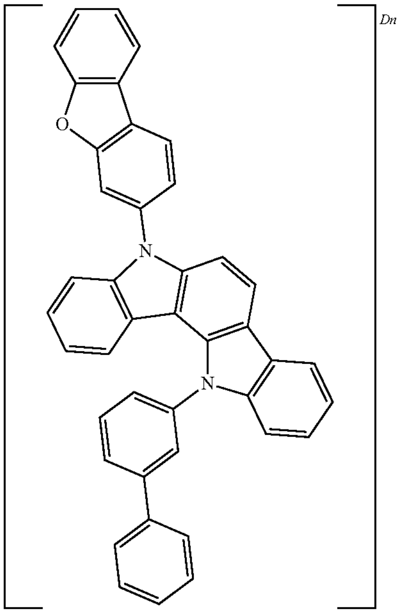
C-115
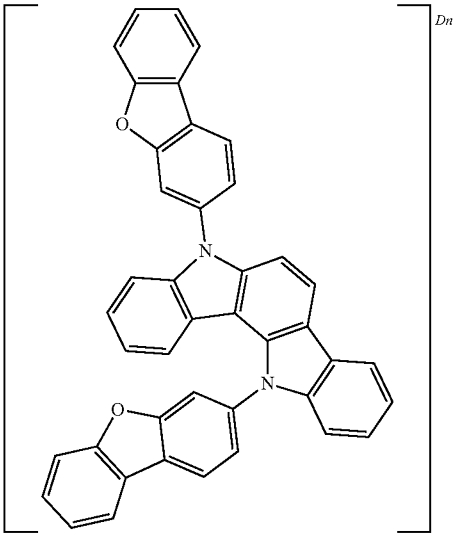
C-114
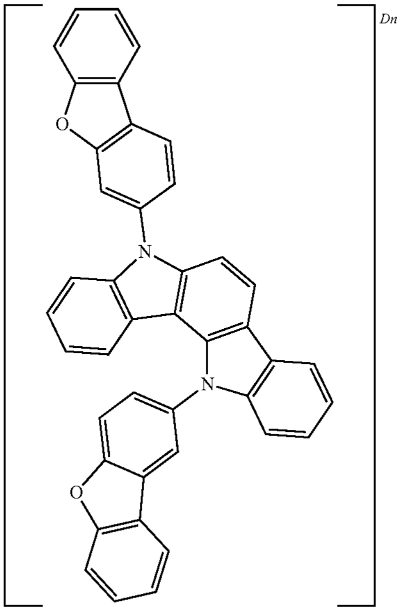
C-116
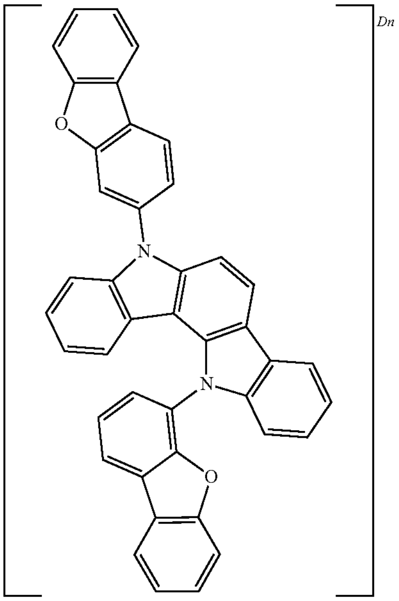

-continued
C-117
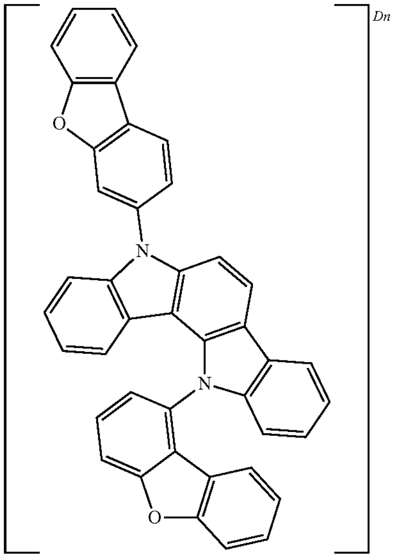
C-118
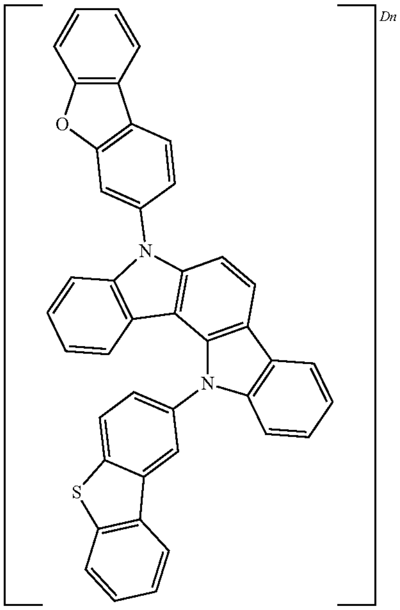
-continued
C-119
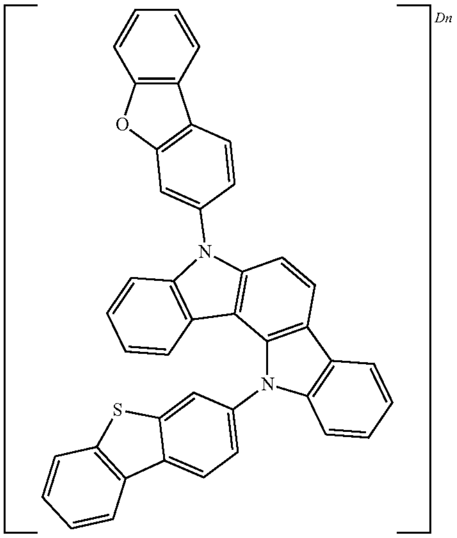
C-120
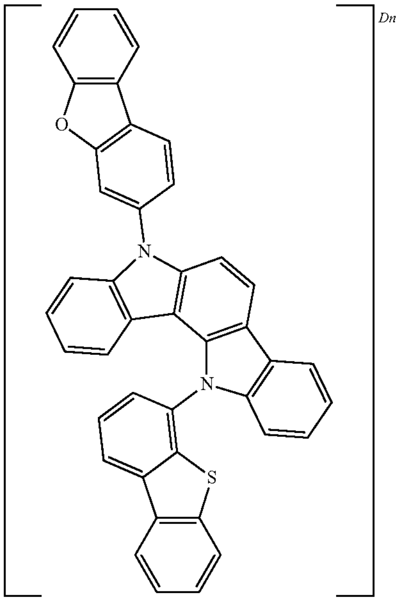
C-121
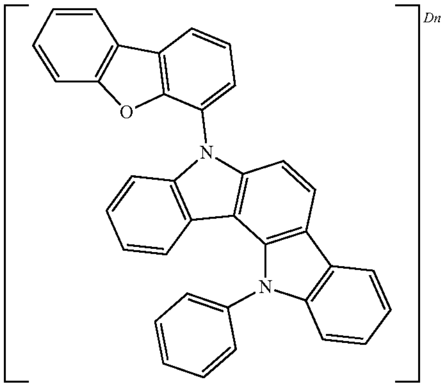

-continued
C-122
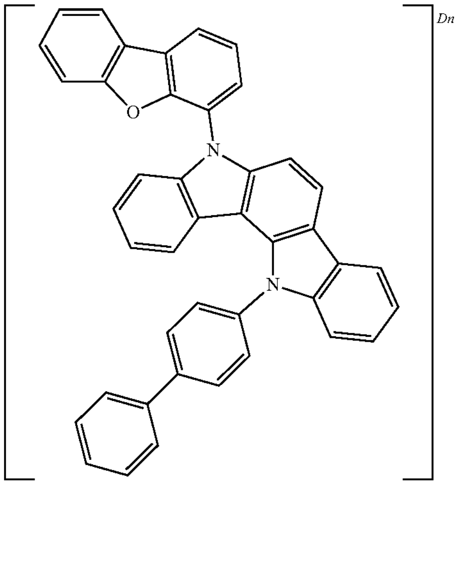
C-123
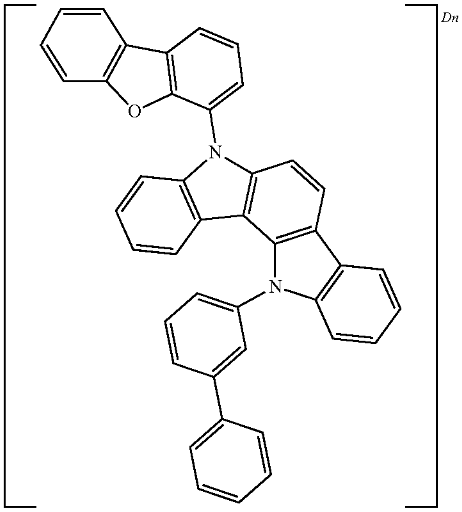
C-124
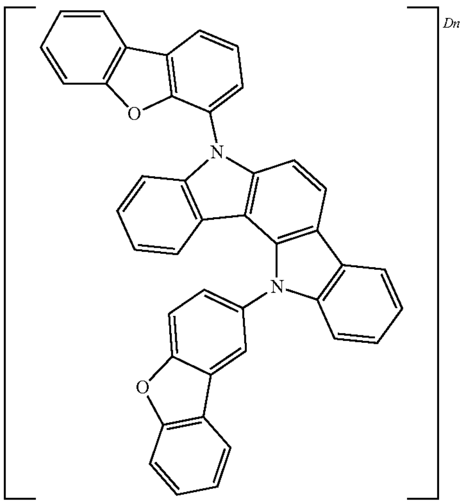
-continued
C-125
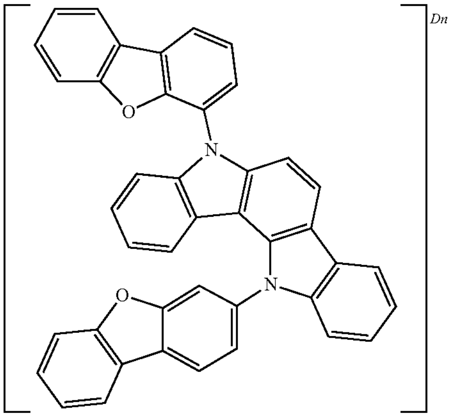
C-126
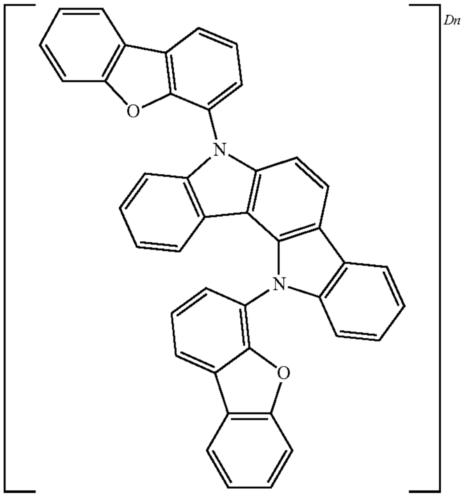
C-127
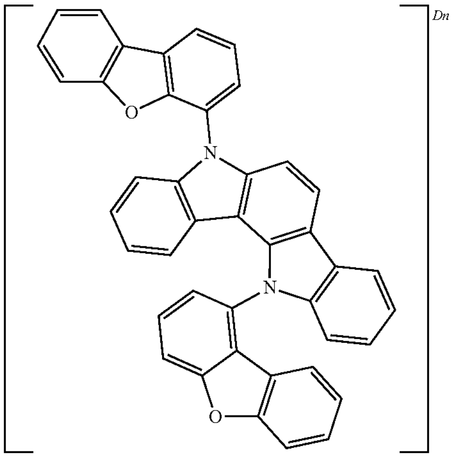

-continued
C-128
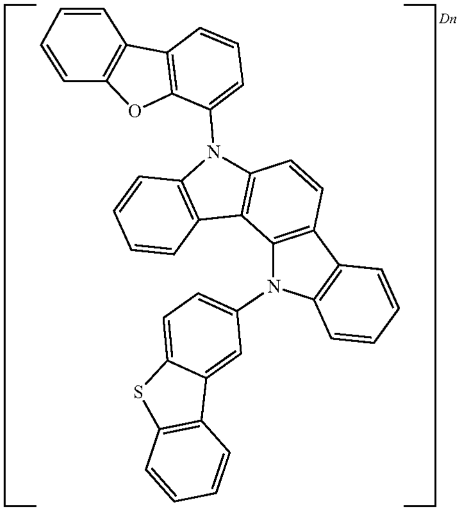
C-129
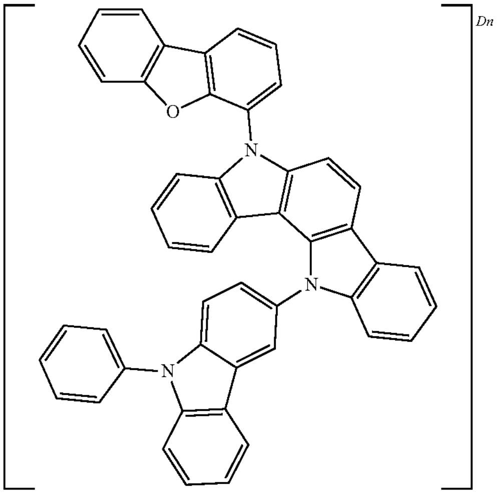
C-130
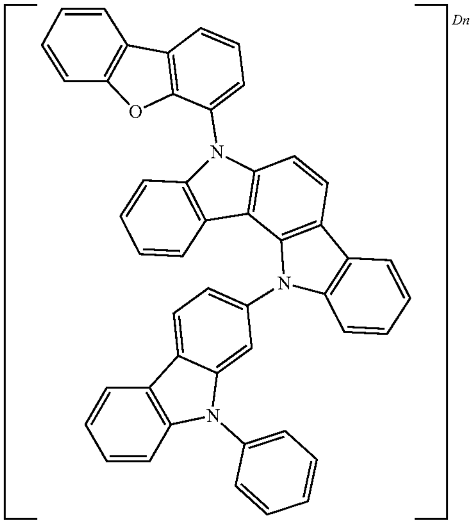
-continued
C-131
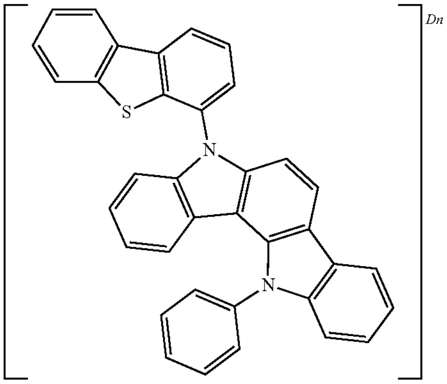
C-132
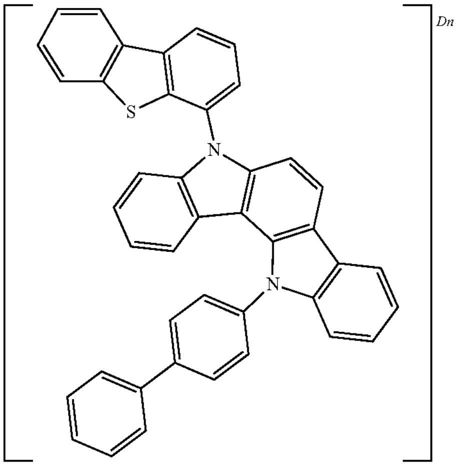
C-133
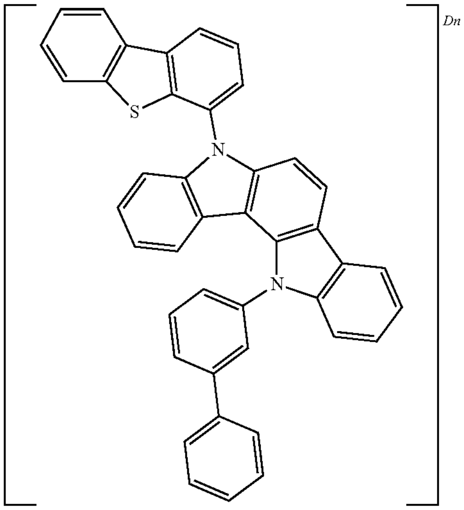

-continued
C-134
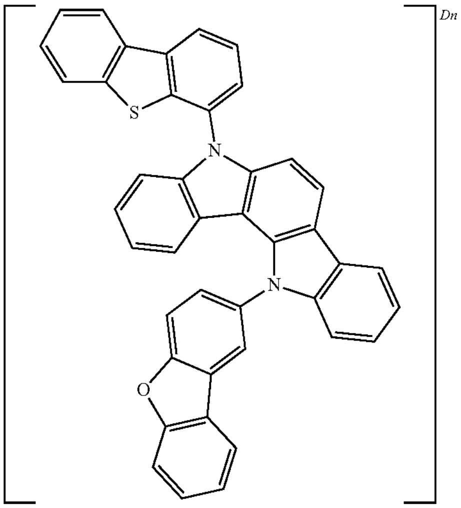
C-135
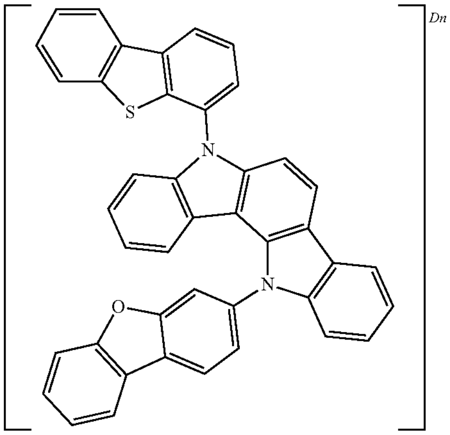
C-136
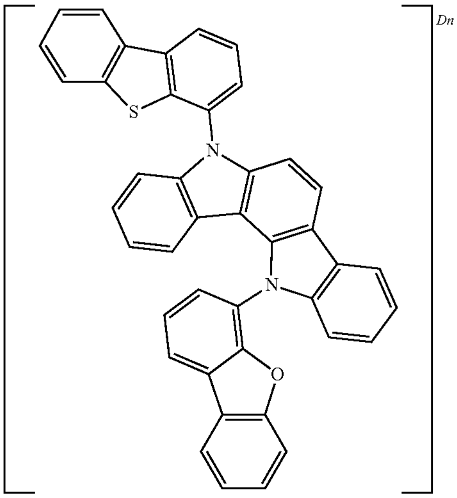
-continued
C-137
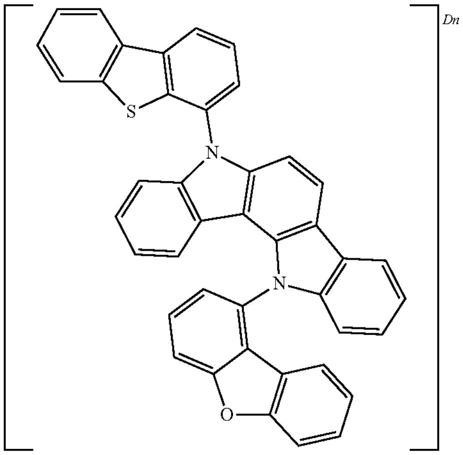
C-138
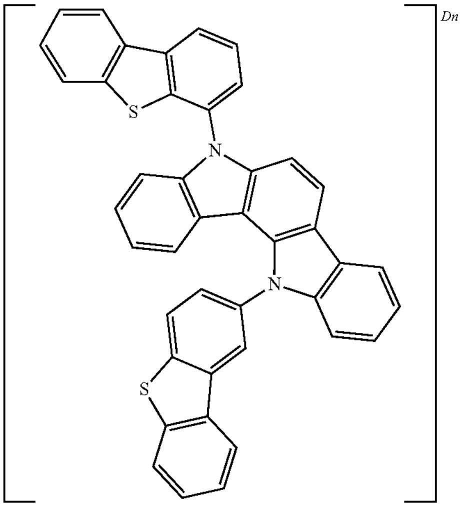
C-139
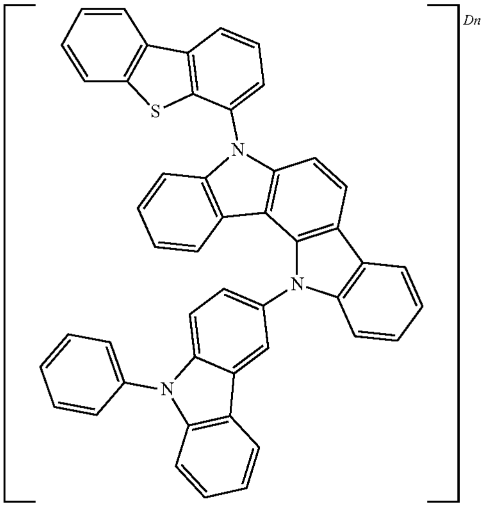

-continued
C-140
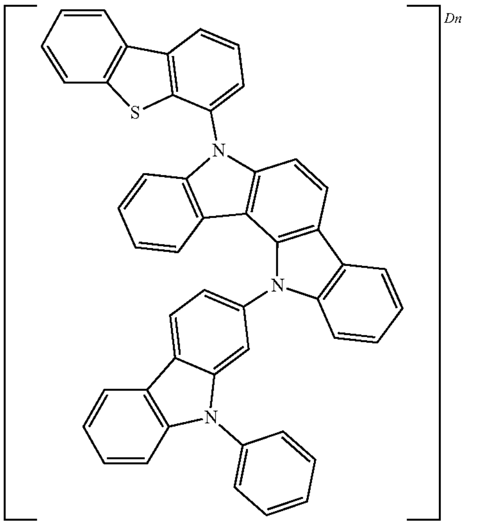
C-141
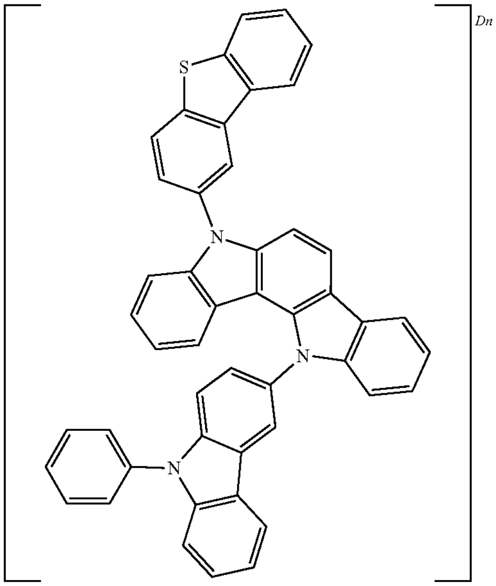
-continued
C-142
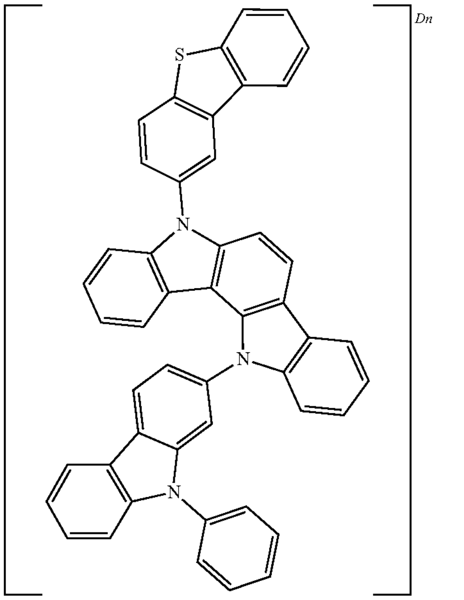
C-143
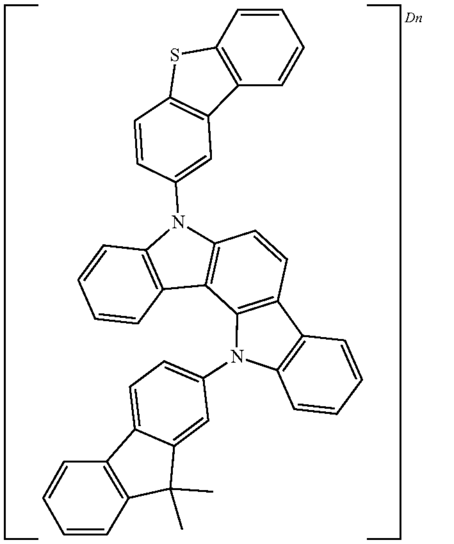
C-144
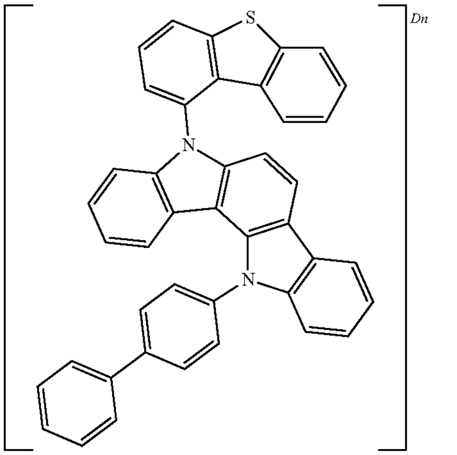

-continued
C-145
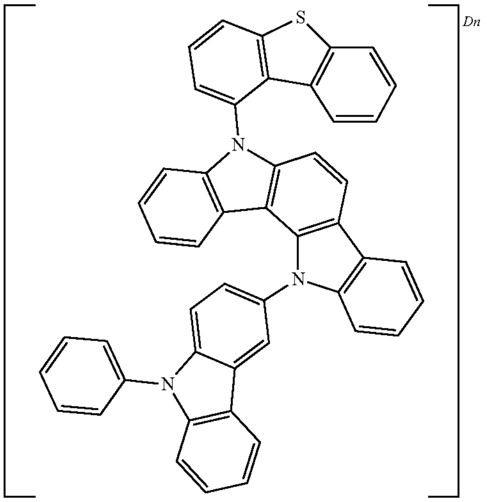
C-146
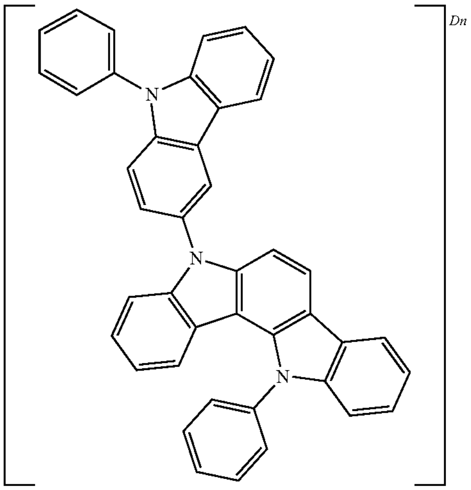
C-147
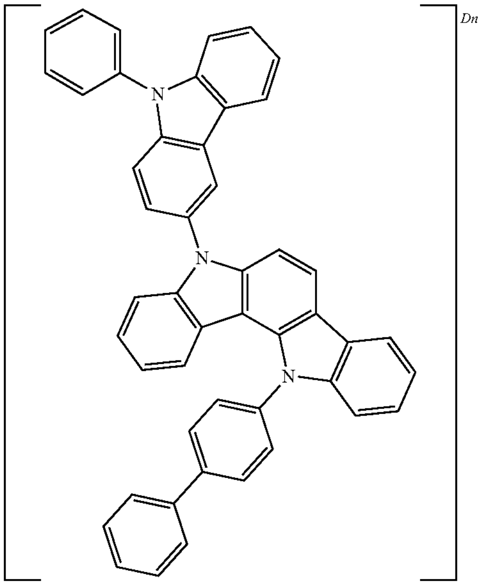
-continued
C-148
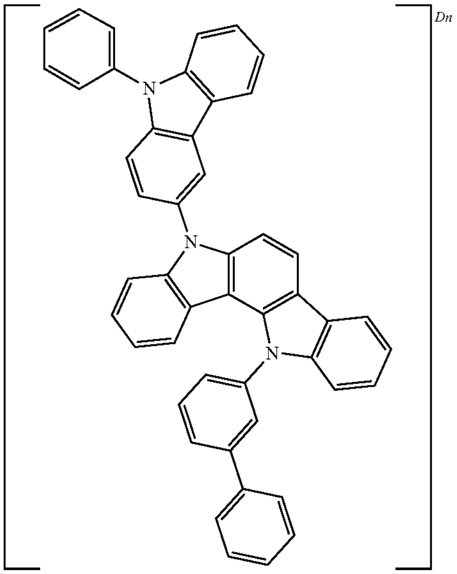
C-149
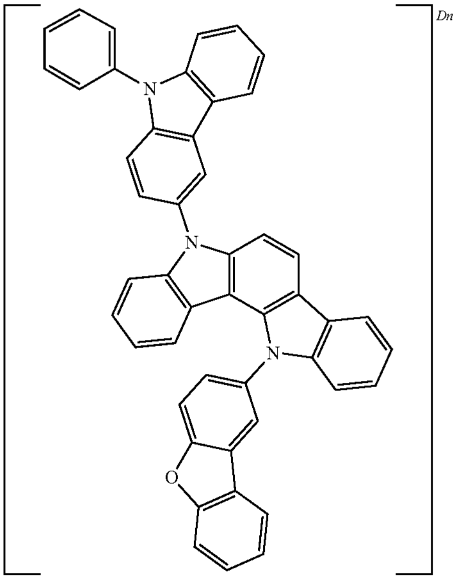

C-150
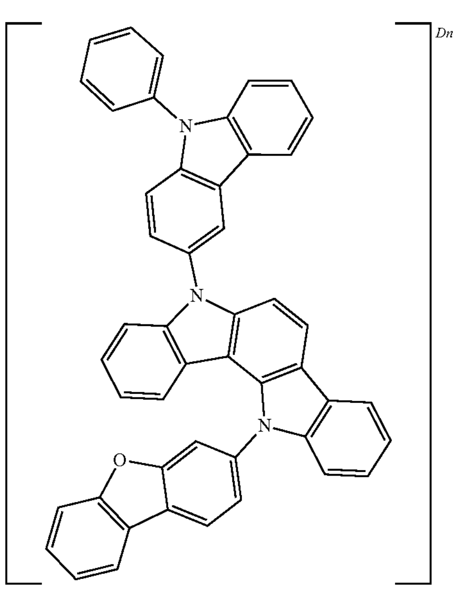
C-151
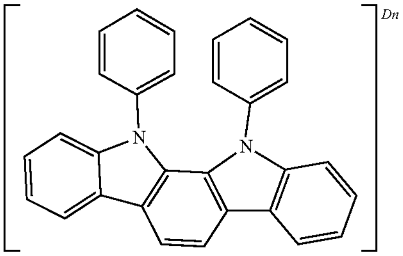
C-152
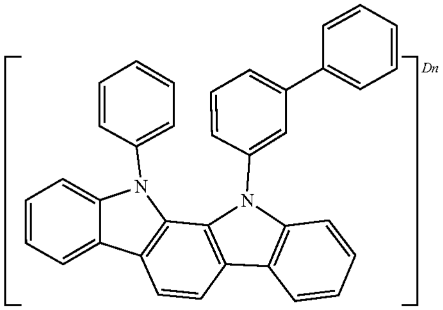
C-153
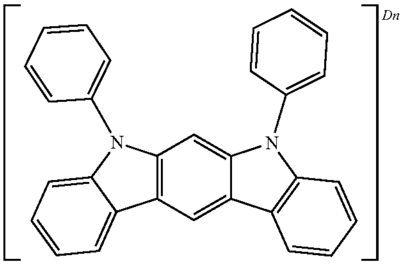
C-154
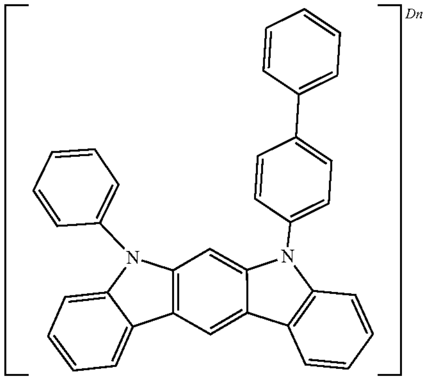
C-155
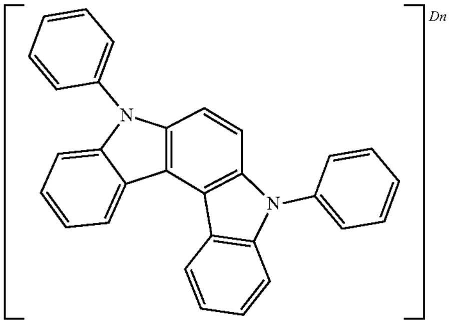
C-156
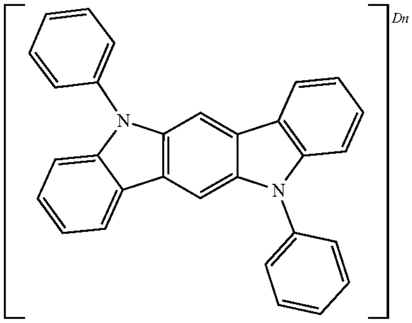
C-157
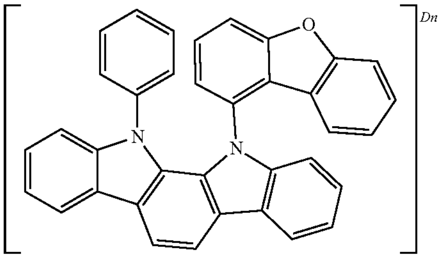

-continued

C-158

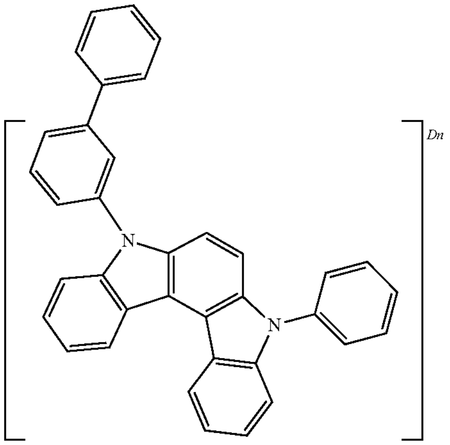

C-159

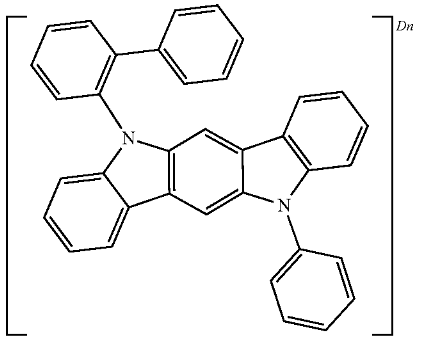

C-160

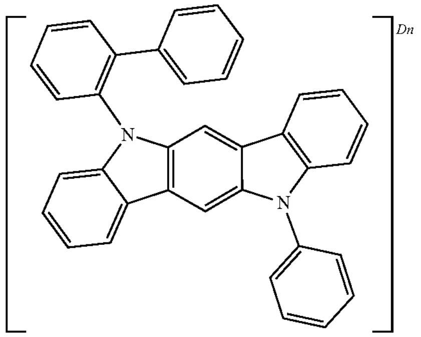

C-161

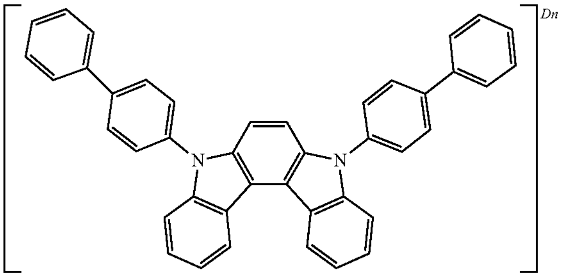

-continued

C-162

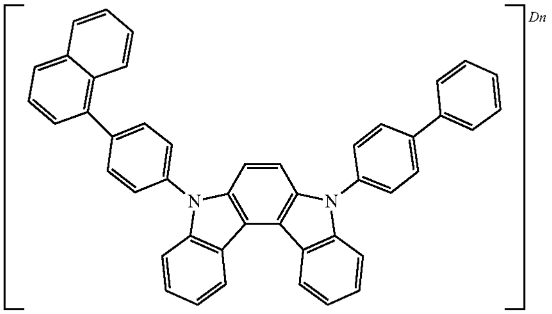

C-163

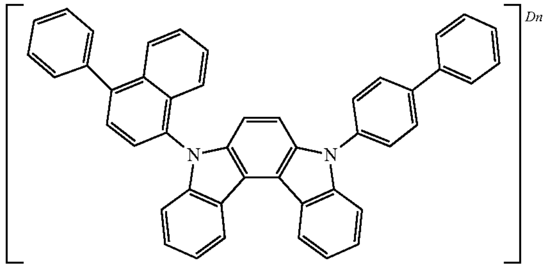

C-164

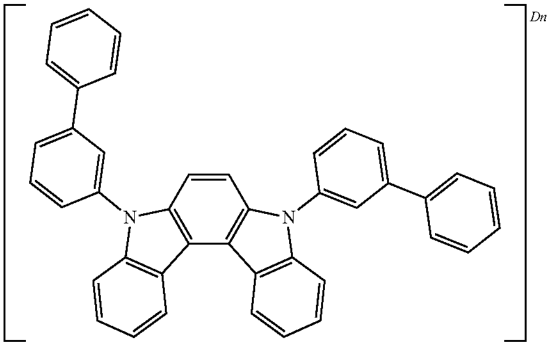

In said compounds, Dn represents that n number of hydrogens are replaced with deuterium; and n represents an integer of 1 to 50. According to one embodiment, n represents an integer of 3 or more, preferably an integer of 4 or more, more preferably an integer of 5 or more, even more preferably an integer of 6 or more. When being deuterated to the number of the lower limit or more, the bond dissociation energy related to deuteration may increase to enhance the stability of the compound. When such a compound is used in an organic electroluminescent device, the organic electroluminescent device may exhibit improved lifetime property.

The compound represented by formula 2-1 according to one embodiment may be produced by synthetic methods known to one skilled in the art, for example, by referring to Japanese Patent Application Laid-Open No. 1996-003547, but is not limited thereto.

The compound represented by formula 2-2 according to one embodiment may be produced by synthetic methods known to one skilled in the art, for example, by referring to the following reaction scheme 1, but is not limited thereto.

[Reaction Scheme 1]

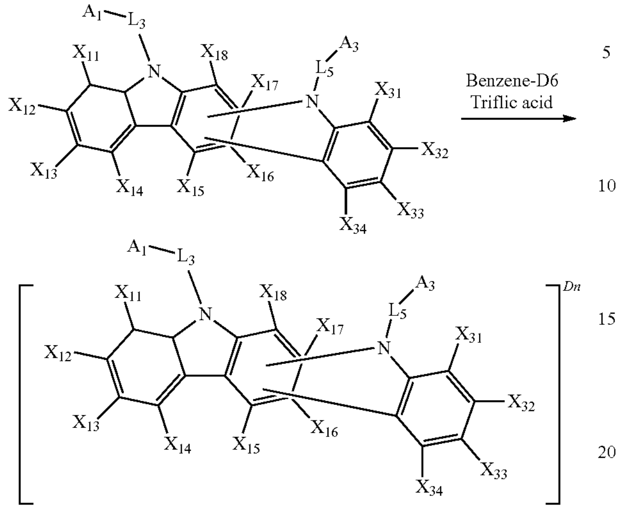

In reaction scheme 1, $A_1$, $A_3$, $L_3$, $L_5$, $X_{11}$, to $X_{18}$, and $X_{31}$ to $X_{34}$ are as defined in formula 2-2, and Dn represents that n number of hydrogens are replaced with deuterium.

Although illustrative synthesis examples of the compound represented by formula 2-2 are described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, and a Phosphine-mediated reductive cyclization reaction, etc., and the reactions above proceed even when substituents which are defined in formula 2-2 above, but are not specified in the specific synthesis examples, are bonded.

In addition, the deuterated compounds represented by formulas 1 and 2 may be prepared in a similar manner by using deuterated precursor materials, or more generally may be prepared by treating the non-deuterated compound with a deuterated solvent or D6-benzene in the presence of an H/D exchange catalyst such as a Lewis acid, e.g., aluminum trichloride or ethyl aluminum chloride. Further, the degree of deuteration can be controlled by changing the reaction conditions such as the reaction temperature. For example, the number of n in formulas 1 and 2 can be controlled by adjusting the reaction temperature and time, the equivalent of the acid, etc.

Hereinafter, an organic electroluminescent device to which the plurality of host materials as stated above are applied will be described.

An organic electroluminescent device according to one embodiment has a first electrode, a second electrode, and at least one organic layer between the first electrode and the second electrode, wherein the organic layer may comprise a light-emitting layer, and the light-emitting layer may comprise a plurality of host materials comprising at least one first host material represented by formula 1 and at least one second host material represented by formula 2.

According to one embodiment, the organic electroluminescent material of the present disclosure comprises at least one compound selected from compounds H1-1 to H1-210, which is the first host material, and at least one compound selected from compounds H2-1 to H2-145, and C-1 to C-164, which is the second host material, and the plurality of host materials may be comprised in the same organic layer, for example, in a light-emitting slyer, or may be respectively comprised in different light-emitting layers.

The organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer, besides the light-emitting layer. The organic layer may further comprise an amine-based compound and/or an azine-based compound besides the light-emitting material of the present disclosure. Specifically, the hole injection layer, the hole transport layer, the hole auxiliary layer, the light-emitting layer, the light-emitting auxiliary layer, or the electron blocking layer may comprise an amine-based compound, for example, an arylamine-based compound, a styrylarylamine-based compound, etc., as a hole injection material, a hole transport material, a hole auxiliary material, a light-emitting material, a light-emitting auxiliary material, or an electron blocking material. Further, the electron transport layer, the electron injection layer, the electron buffer layer, and the hole blocking material may comprise an azine-based compound as an electron transport material, an electron injection material, an electron buffer material, and a hole blocking material. Further, the organic layer may further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising the metal.

The plurality of host materials according to one embodiment may be used as a light-emitting material for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. In addition, the plurality of host materials according to one embodiment of the present disclosure may also be used in an organic electroluminescent device comprising a quantum dot (QD).

One of the first and second electrodes may be an anode, and the other may be a cathode. The first and second electrodes may be respectively formed with a transparent conductive material, or a transflective or reflective conductive material. The first and second electrodes may be a top emission type, a bottom emission type, or a both-sides emission type, depending on the materials forming the electrodes.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. In addition, the hole injection layer may be further doped with a p-dopant(s). The electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, wherein each of the multi-layers may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer is placed between the electron transport layer (or the electron injection layer) and the light-emitting layer, and prevents holes from reaching the cathode, thereby improving the recombination possibility of electrons and holes in the light-emitting layer. The hole blocking layer or the electron transport layer may also be multi-layers, wherein each of the multi-layers may use a plurality of compounds. In addition, the electron injection layer may be doped with an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

In the organic electroluminescent device of the present disclosure, preferably, at least one layer selected from the group consisting of a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x$($1 \leq X \leq 2$), $AlO_x$($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to produce an organic electroluminescent device having two or more light-emitting layers and emitting white light.

The organic electroluminescent device according to one embodiment may further comprise at least one dopant in the light-emitting layer.

The dopant comprised in the organic electroluminescent material of the present disclosure may be at least one phosphorescent or fluorescent dopant, and is preferably a phosphorescent dopant. The phosphorescent dopant material applied to the present disclosure is not particularly limited, but may be a complex compound of a metal atom selected from iridium (Ir), osmium (Os), copper (Cu) and platinum (Pt), and preferably ortho-metallated complex compounds of a metal atom selected from iridium (Ir), osmium (Os), copper (Cu), and platinum (Pt), and more preferably ortho-metallated iridium complex compounds.

The dopant comprised in the organic electroluminescent device of the present disclosure may comprise a compound represented by the following formula 101, but is not limited thereto.

(101)

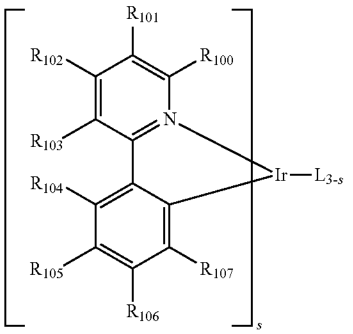

In formula 101,

L is selected from the following structures 1 to 3:

[Structure 1]

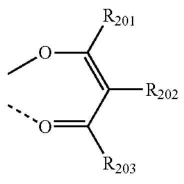

-continued

[Structure 2]

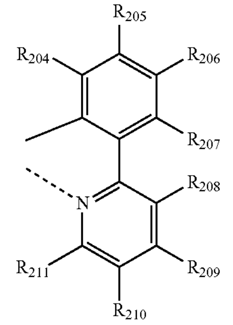

[Structure 3]

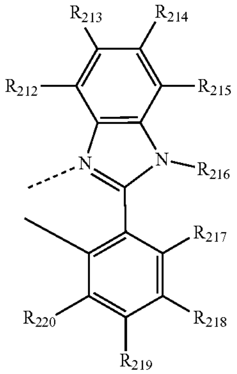

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent(s) to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent(s) to form a substituted or unsubstituted ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent(s) to form a substituted or unsubstituted ring(s); and s represents an integer of 1 to 3.

The specific examples of the dopant compound are as follows, but are not limited thereto.

D-1

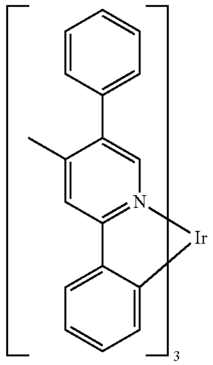

D-2

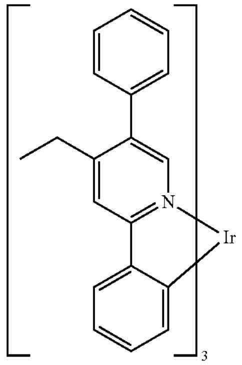

D-3

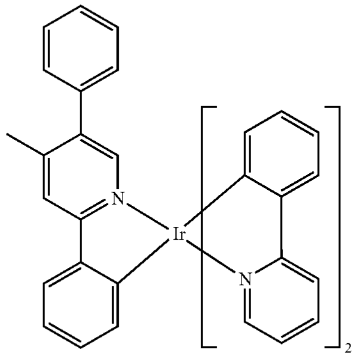

D-4

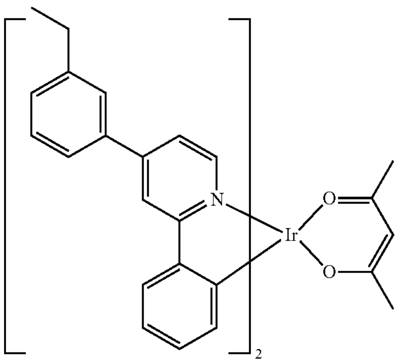

-continued
D-5
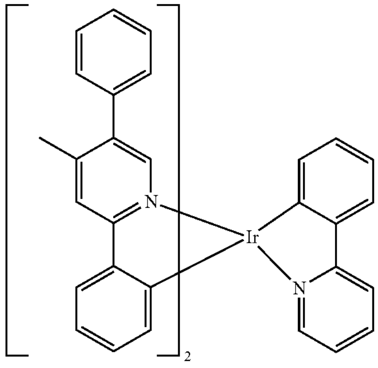
D-6
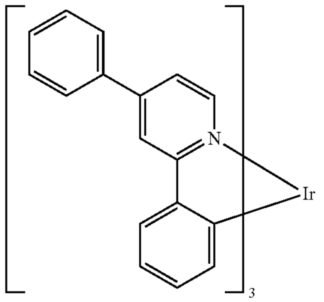
D-7
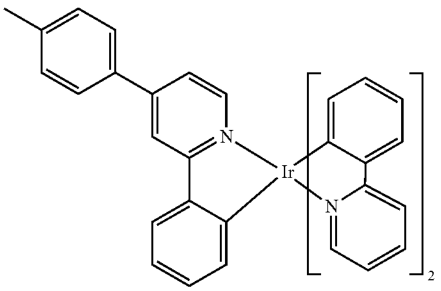
D-8
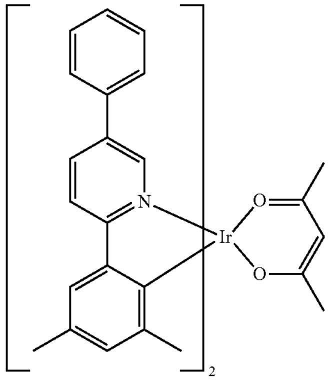
-continued
D-9
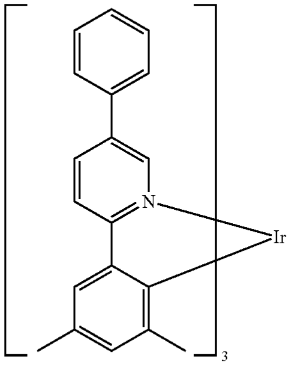
D-10
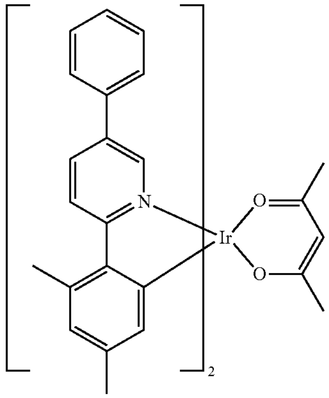
D-11
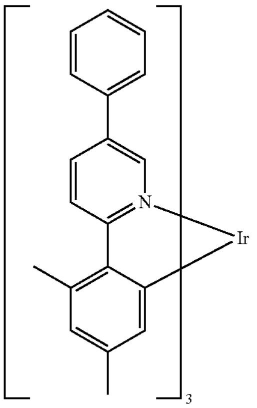
D-12
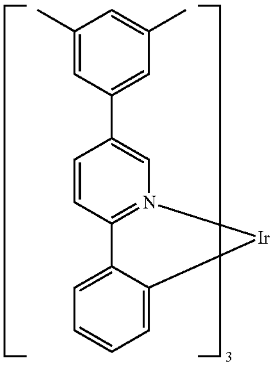

-continued
D-13
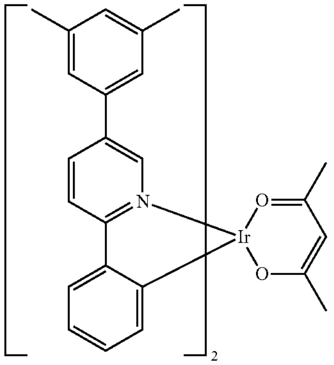
D-14
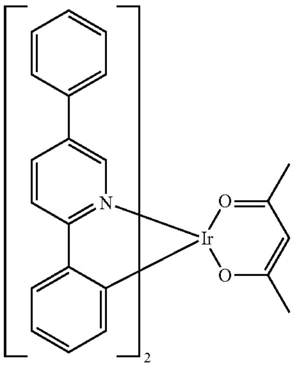
D-15
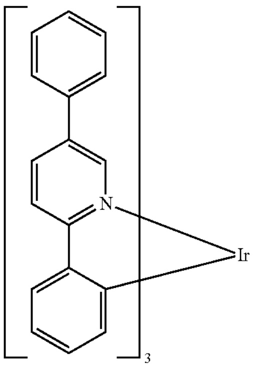
D-16
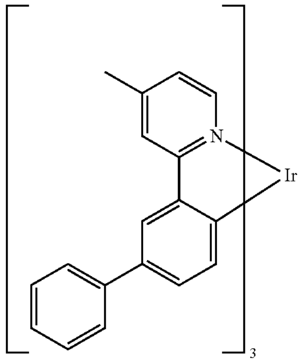
-continued
D-17
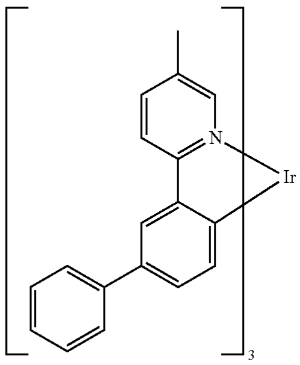
D-18
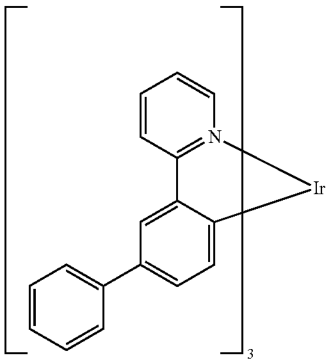
D-19
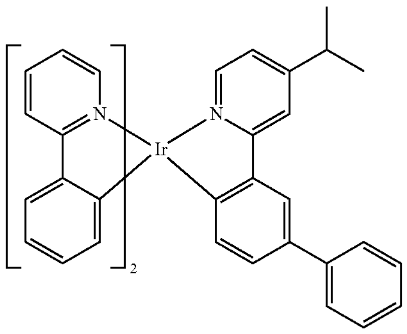
D-20
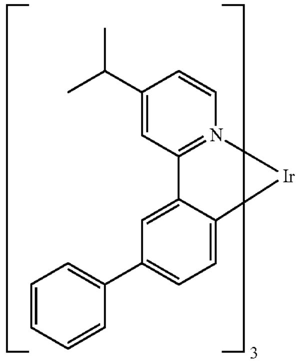

-continued
D-21
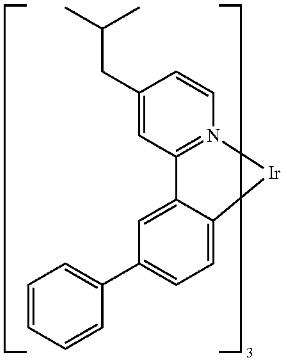
D-22
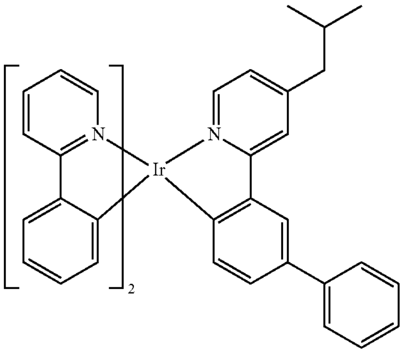
D-23
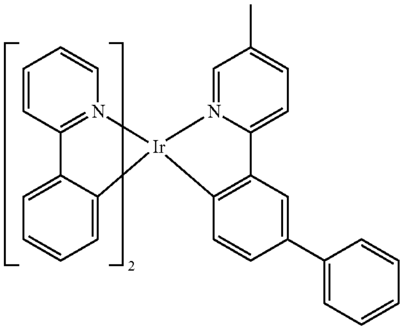
D-24
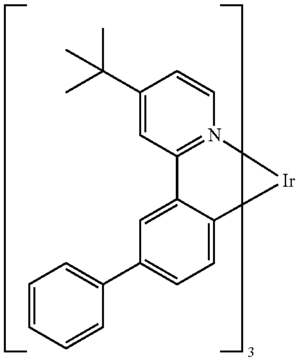
-continued
D-25
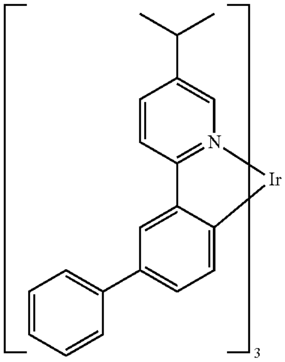
D-26
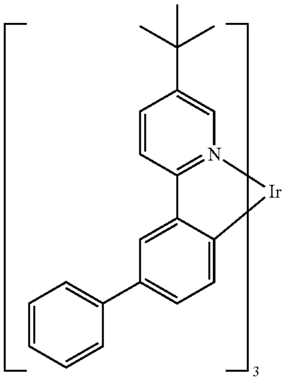
D-27
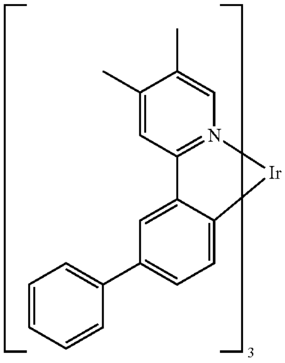
D-28
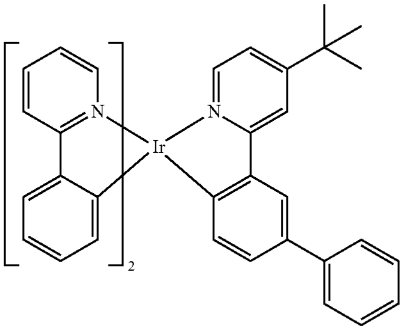

-continued
D-29
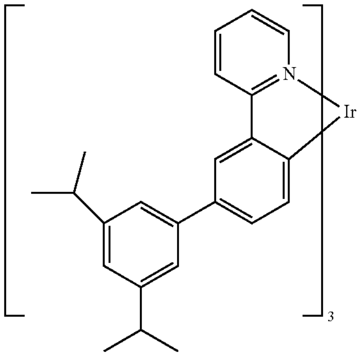
D-30
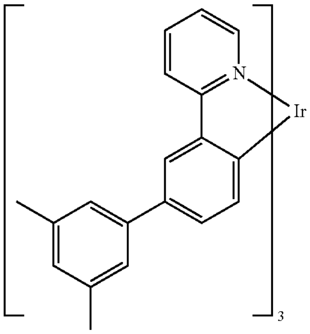
D-31
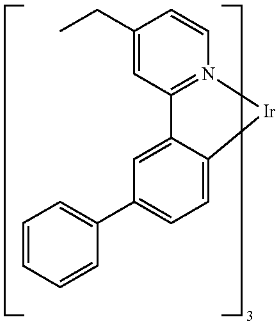
D-32
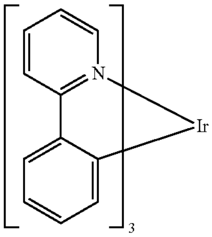
D-33
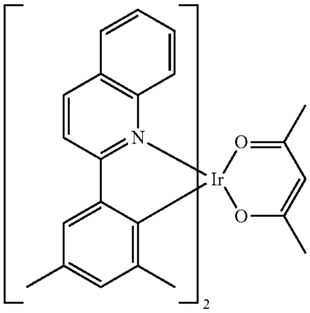
-continued
D-34
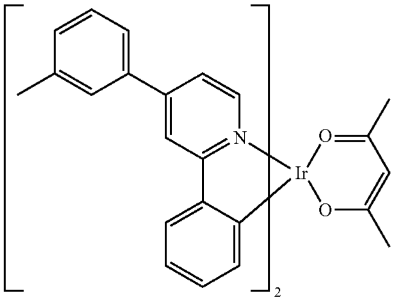
D-35
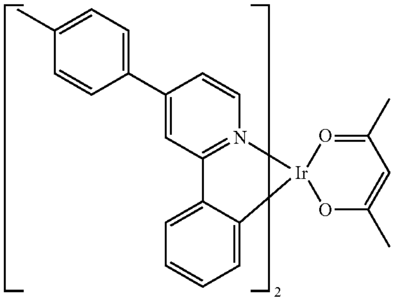
D-36
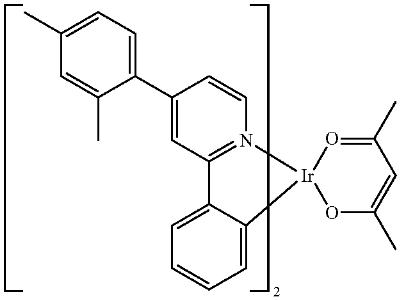
D-37
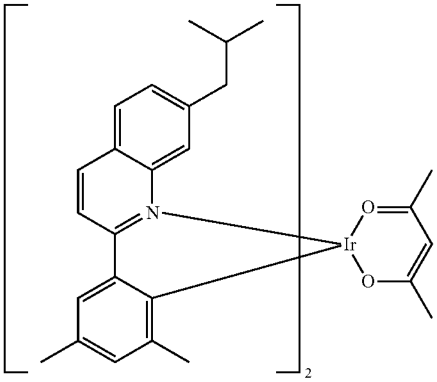
D-38
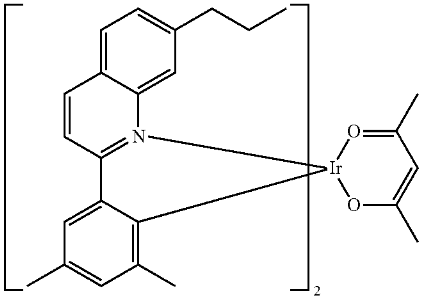

D-39
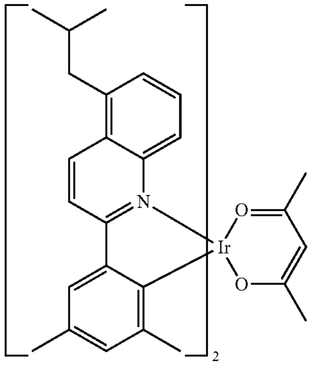
D-40
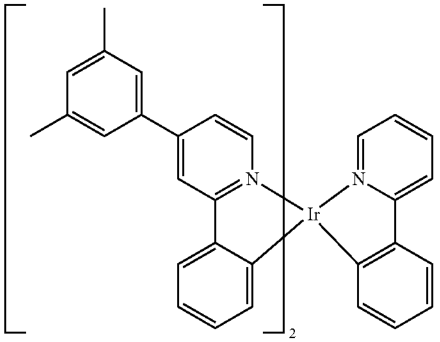
D-41
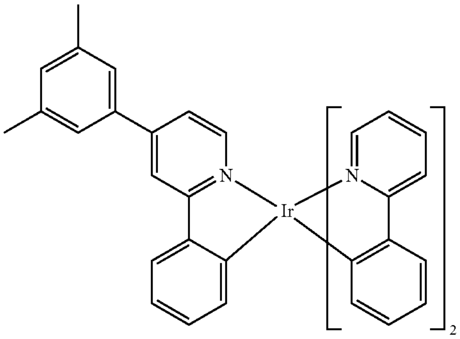
D-42
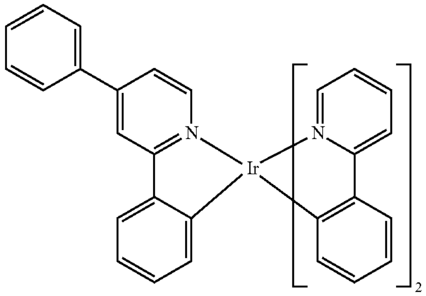
D-43
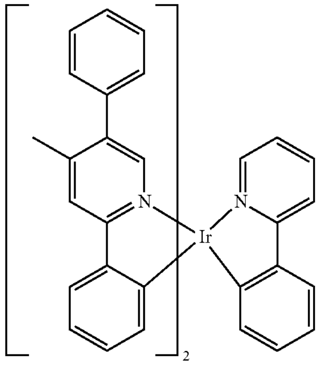
D-44
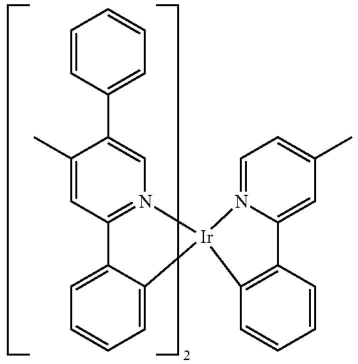
D-45
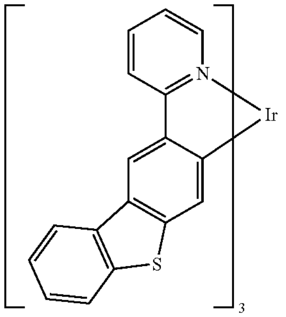
D-46
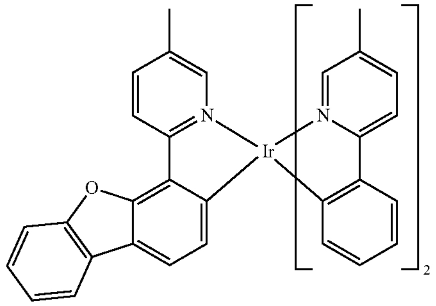

-continued
D-47
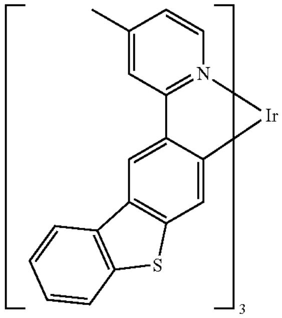
D-48
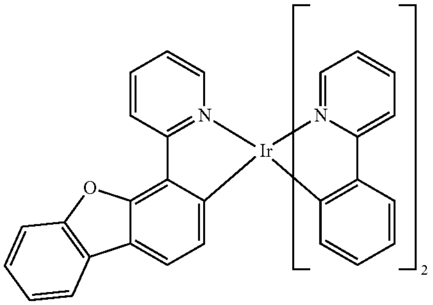
D-49
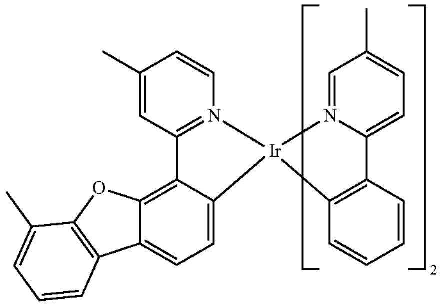
D-50
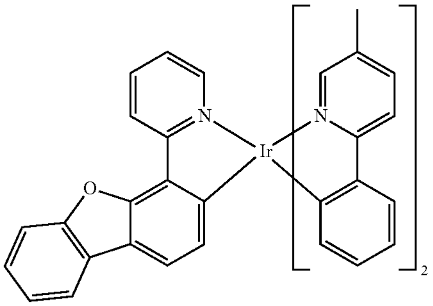
D-51
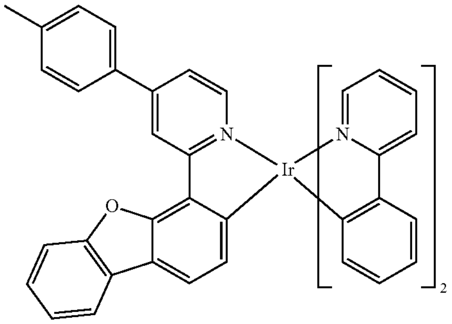
-continued
D-52
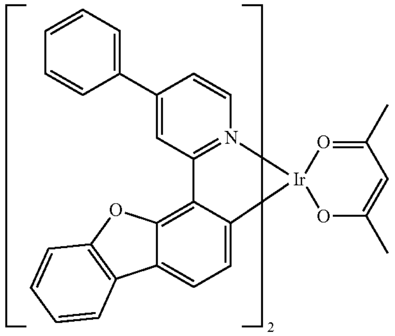
D-53
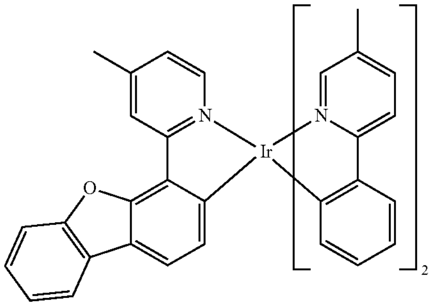
D-54
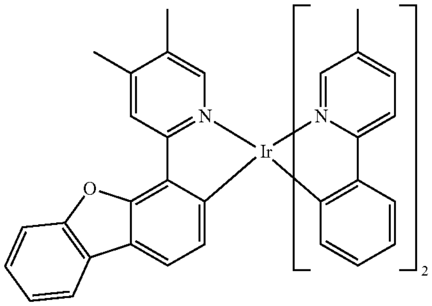
D-55
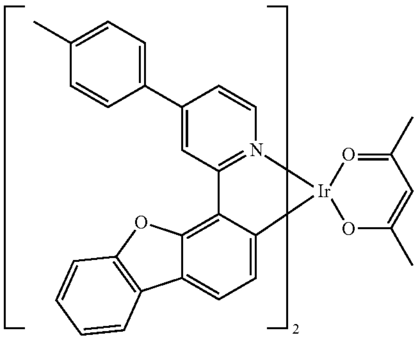
D-56
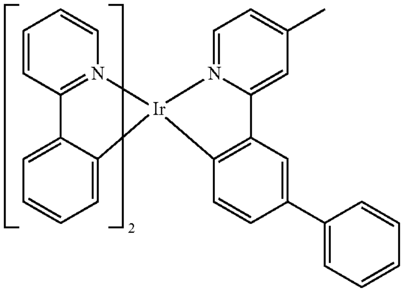

-continued
D-57
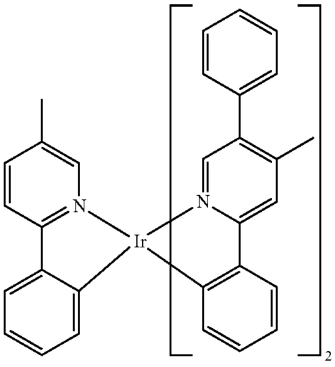
D-58
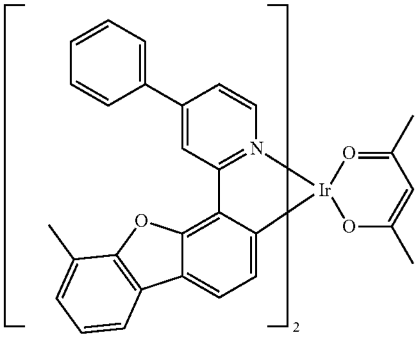
D-59
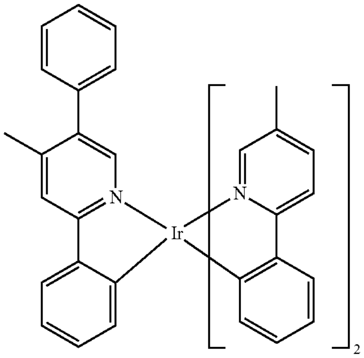
D-60
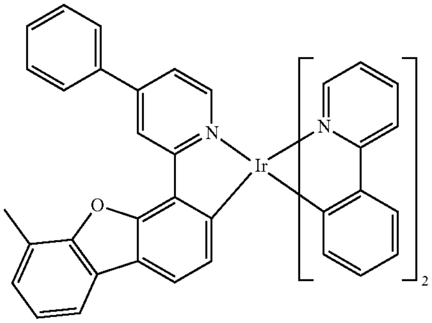
-continued
D-61
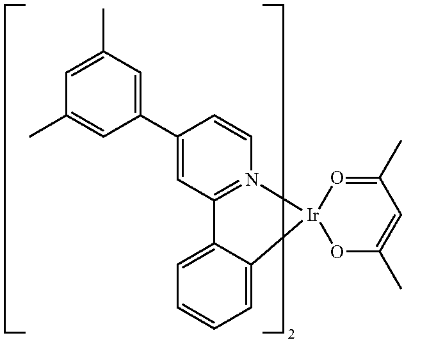
D-62
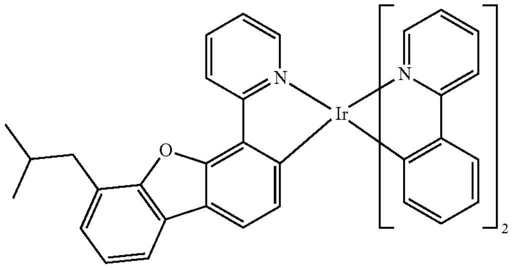
D-63
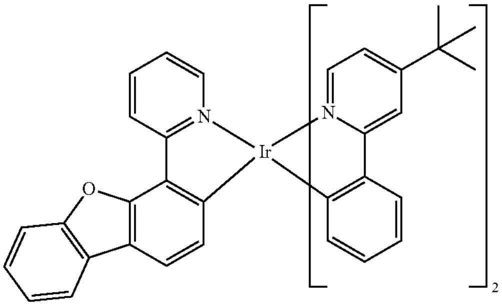
D-64
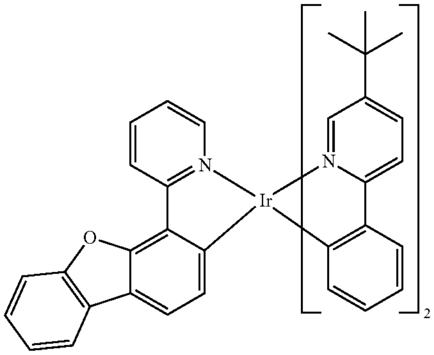

-continued
D-65
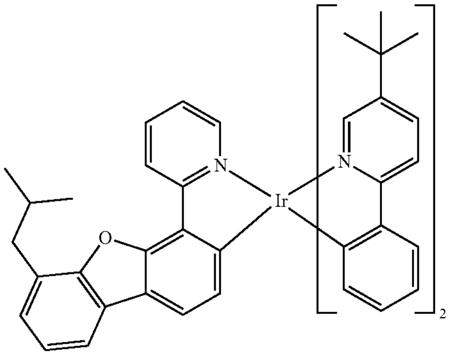
D-66
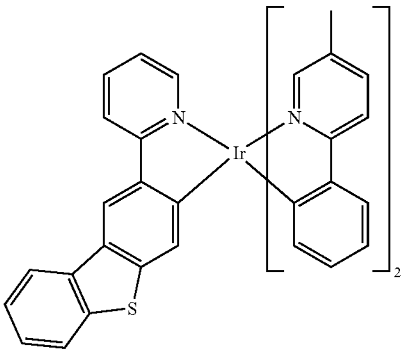
D-67
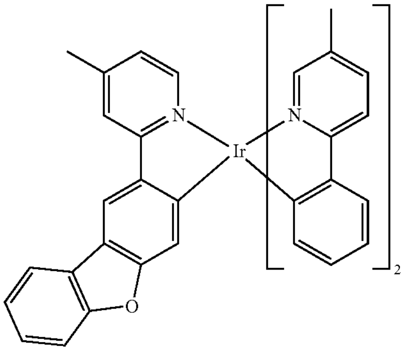
D-68
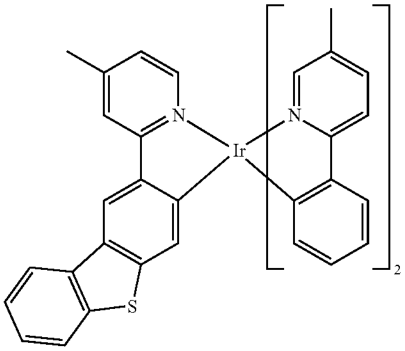
-continued
D-69
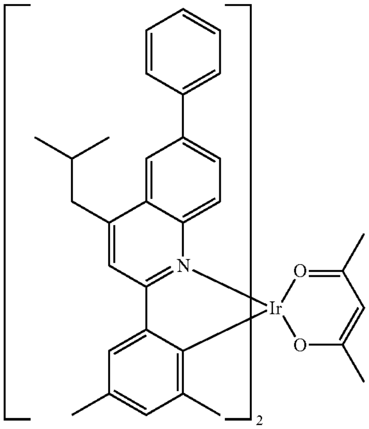
D-70
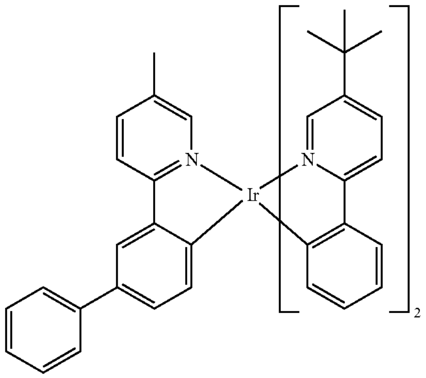
D-71
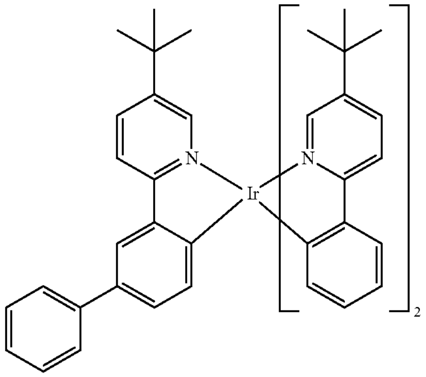
D-72
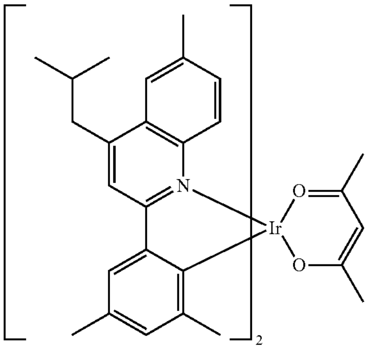

-continued
D-73
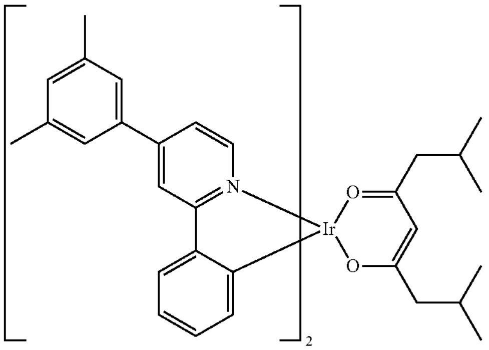
D-74
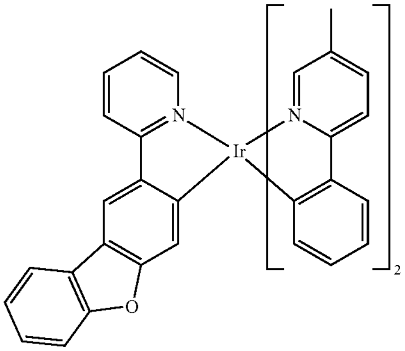
D-75
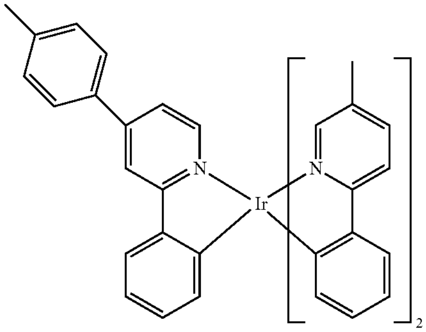
D-76
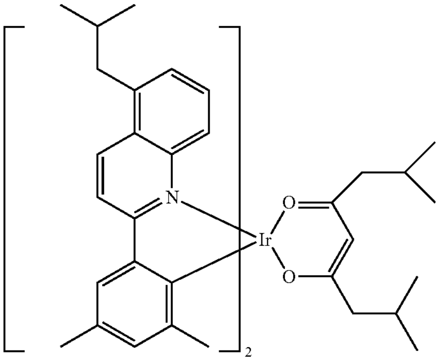
-continued
D-77
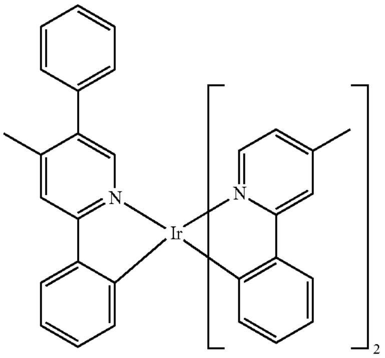
D-78
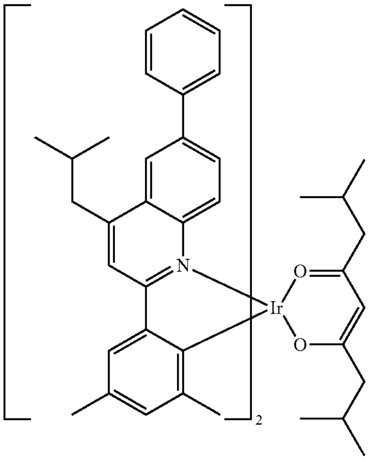
D-79
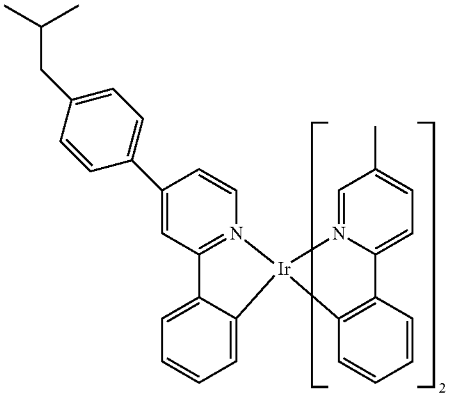
D-80
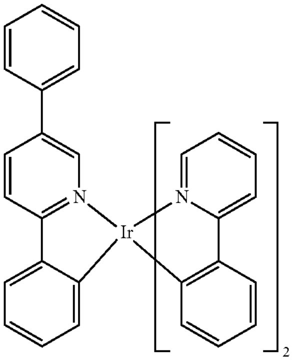

-continued
D-81
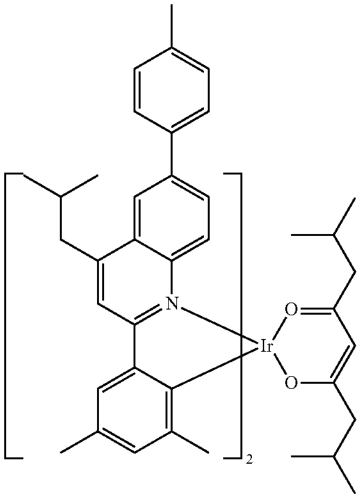
D-82
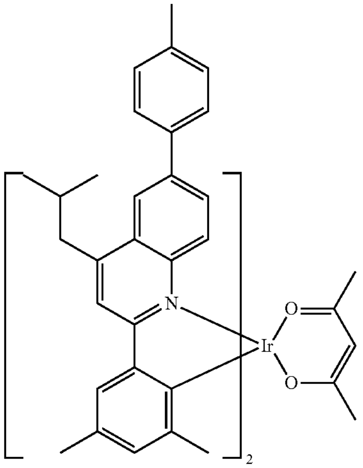
D-83
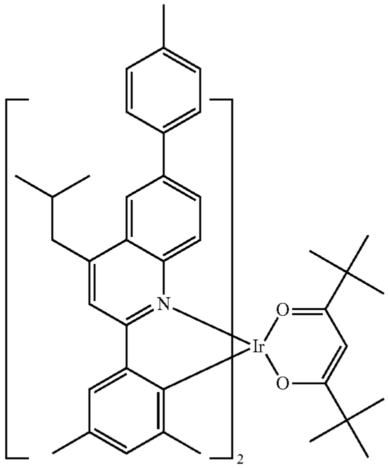
-continued
D-84
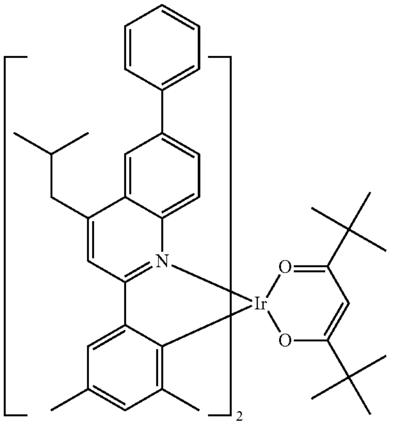
D-85
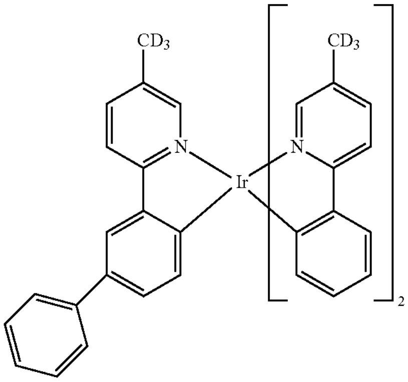
D-86
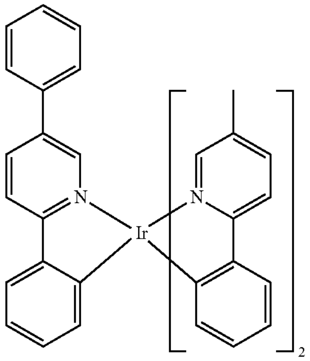
D-87
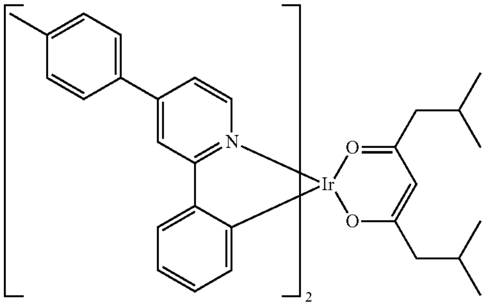

-continued
D-88
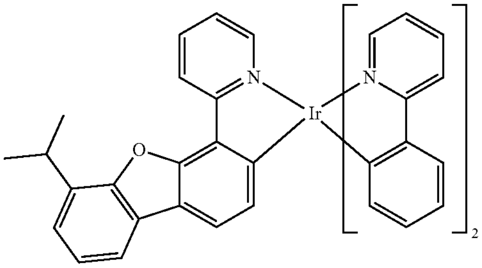
D-89
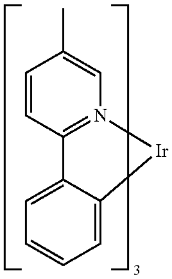
D-90
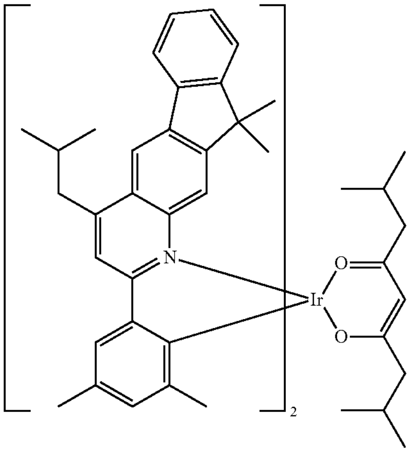
D-91
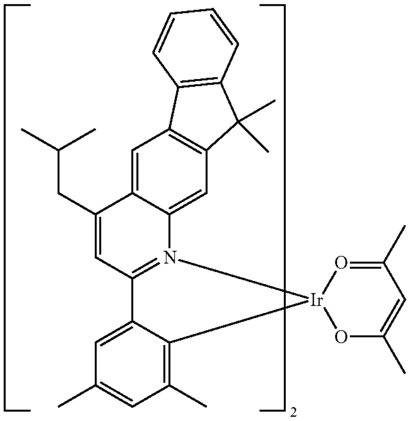
-continued
D-92
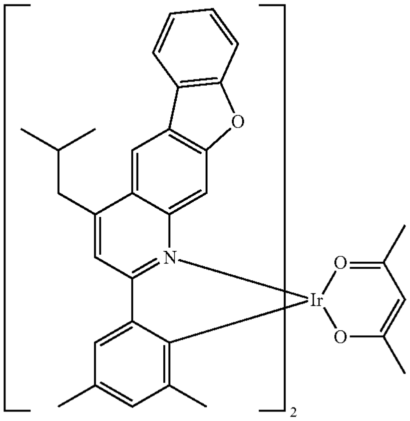
D-93
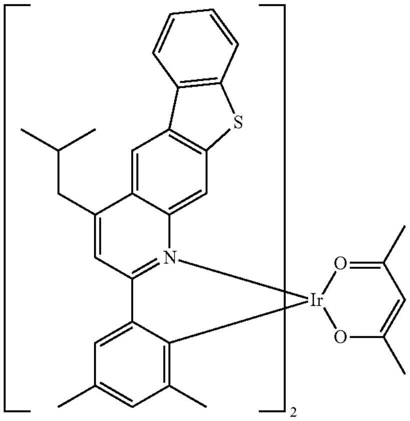
D-94
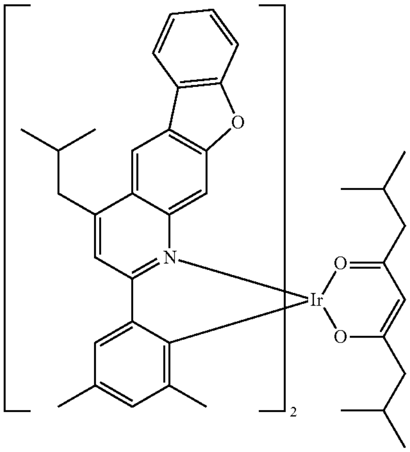

-continued
D-95
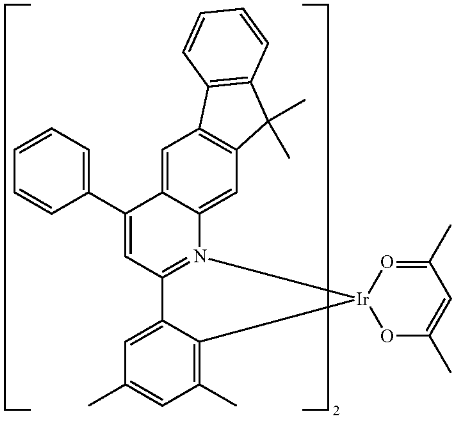
D-96
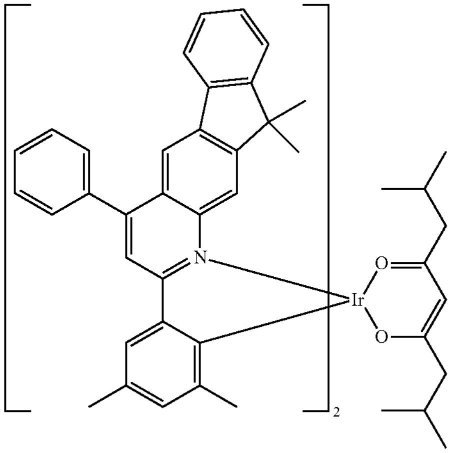
D-97
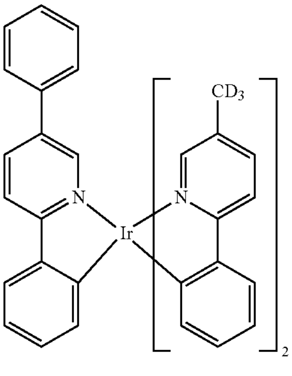
D-98
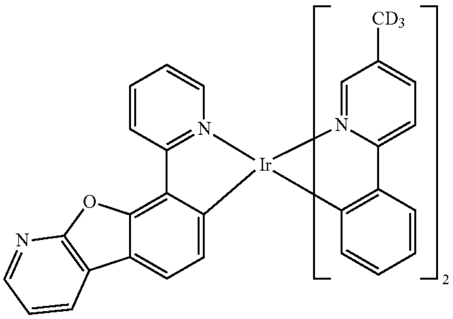
-continued
D-99
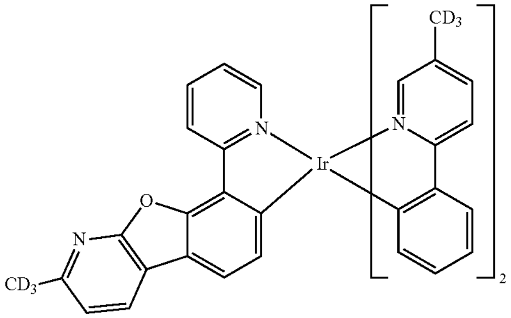
D-100
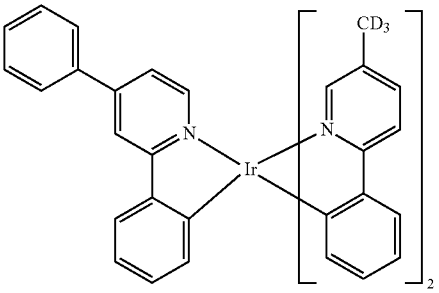
D-101
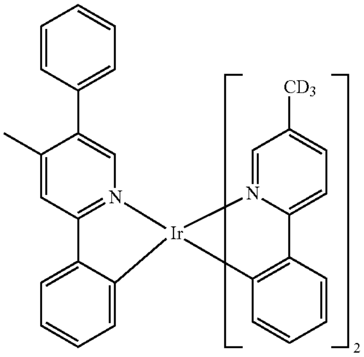
D-102
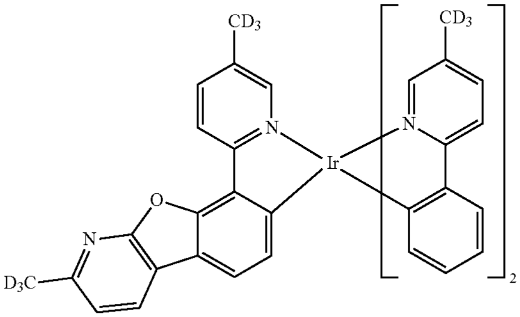

-continued
D-103
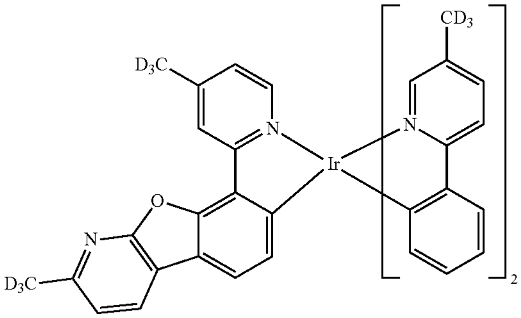
D-104
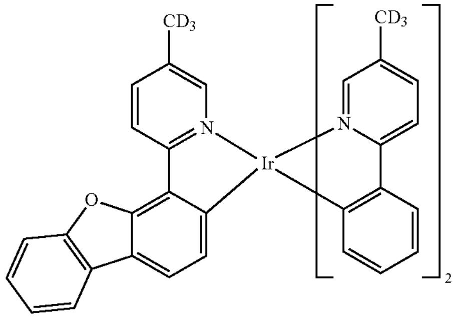
D-105
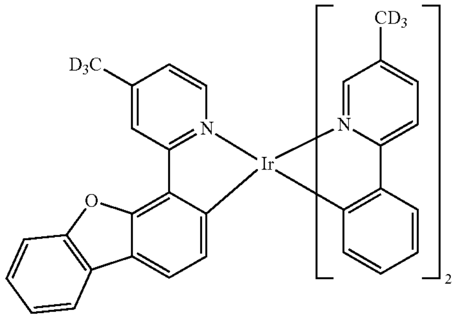
D-106
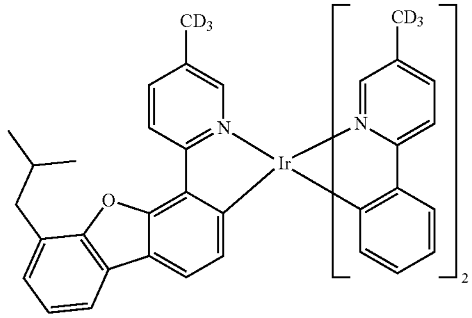
D-107
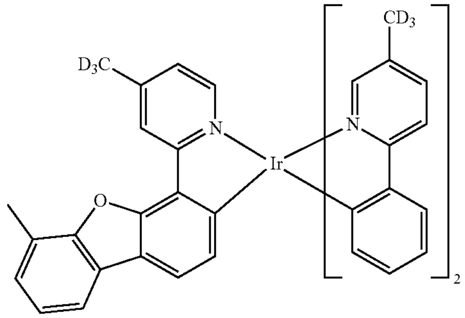
-continued
D-108
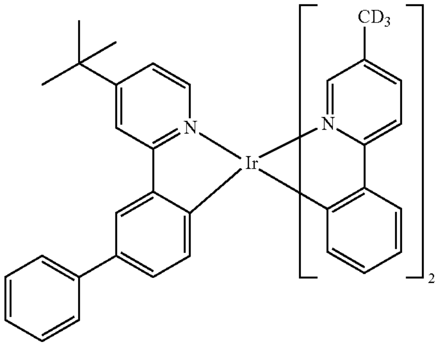
D-109
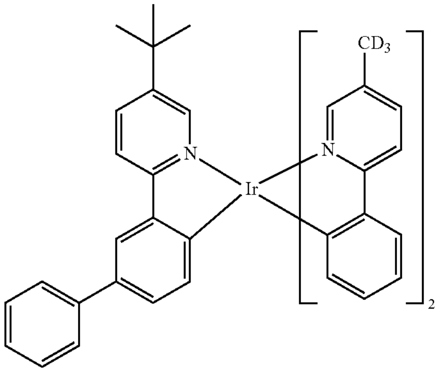
D-110
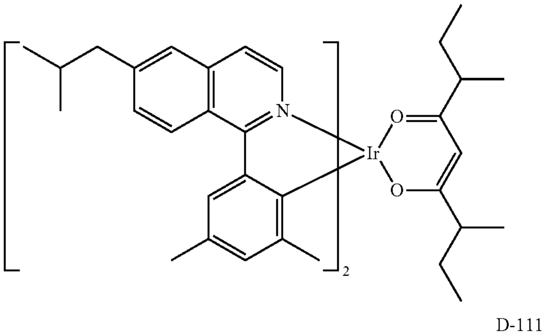
D-111
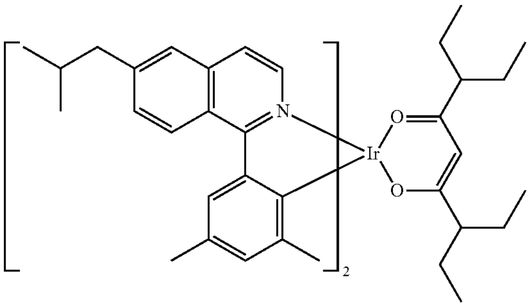

-continued
D-112
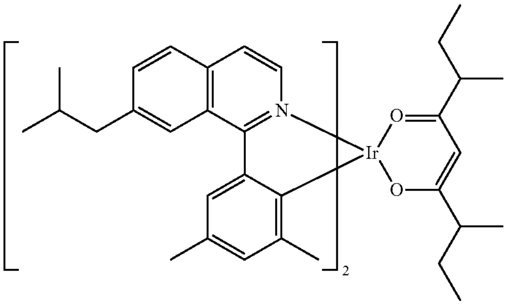
D-113
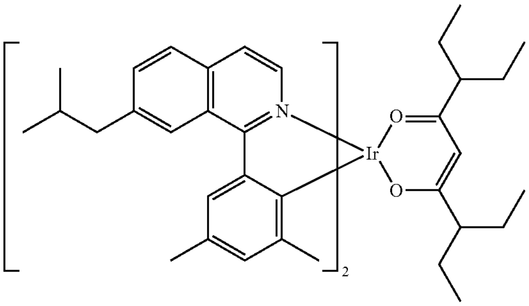
D-114
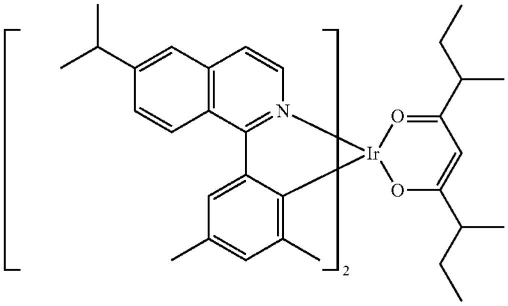
D-115
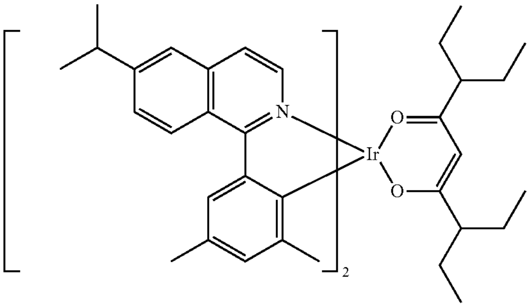
D-116
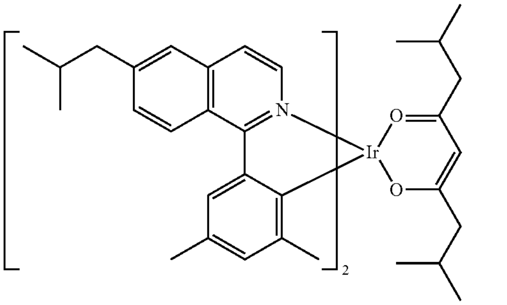
-continued
D-117
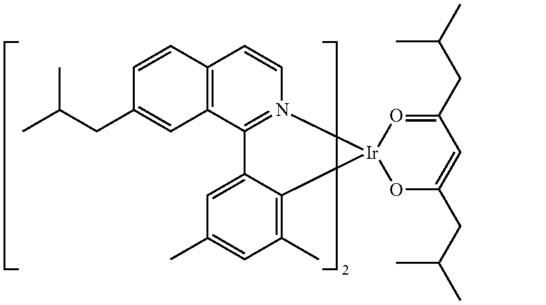
D-118
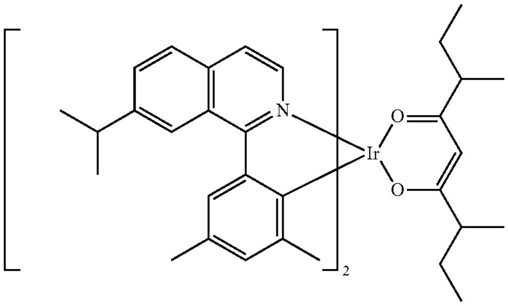
D-119
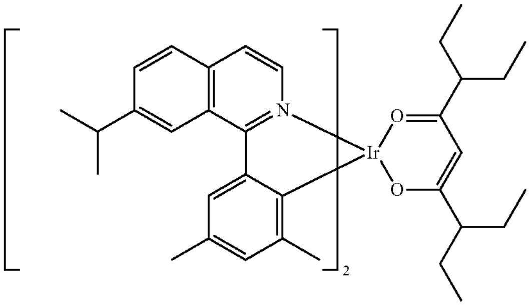
D-120
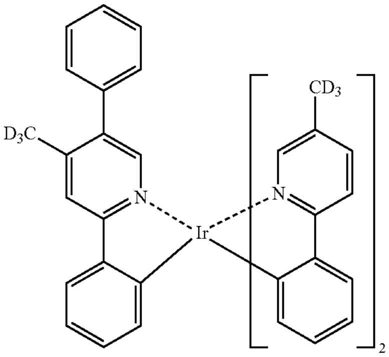

D-121
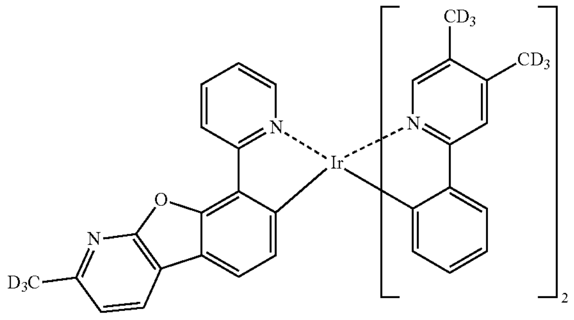
D-122
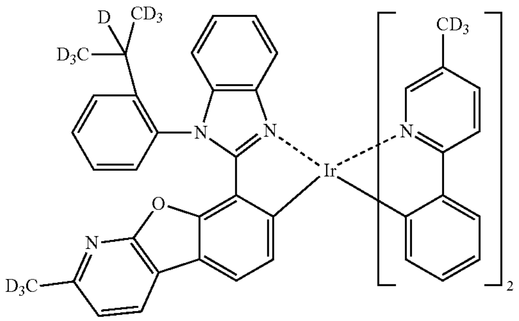
D-123
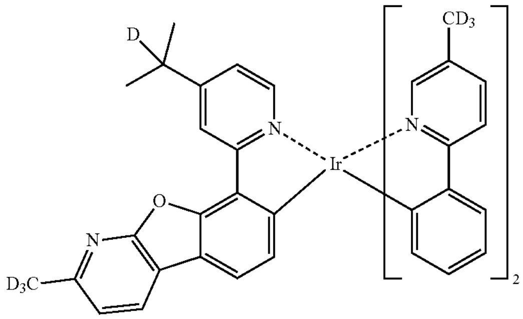
D-124
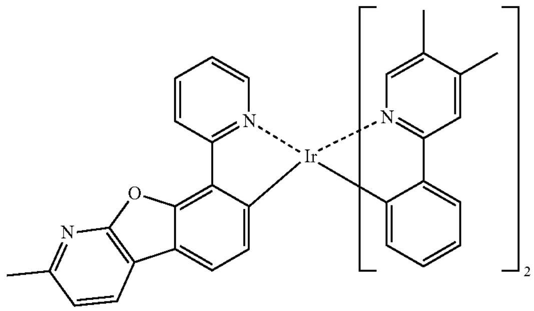
D-125
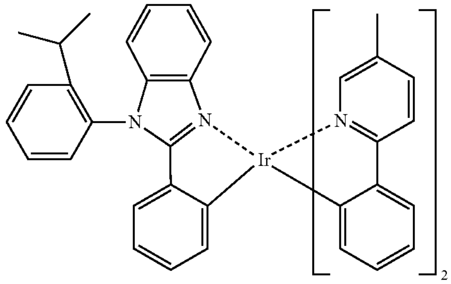
D-126
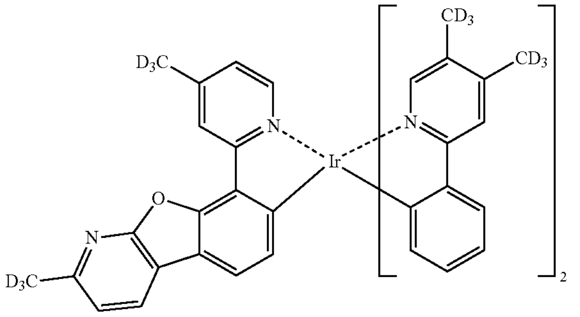
D-127
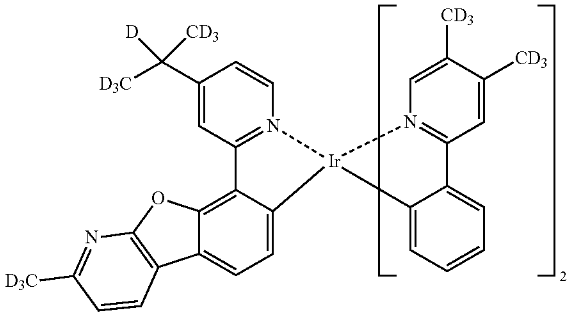
D-128
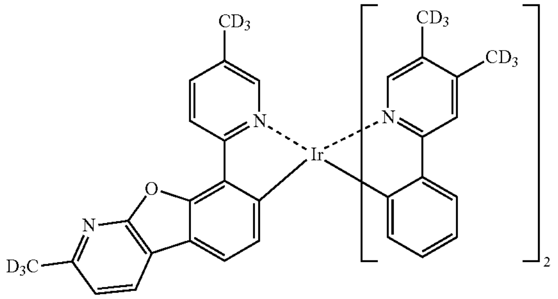
D-129
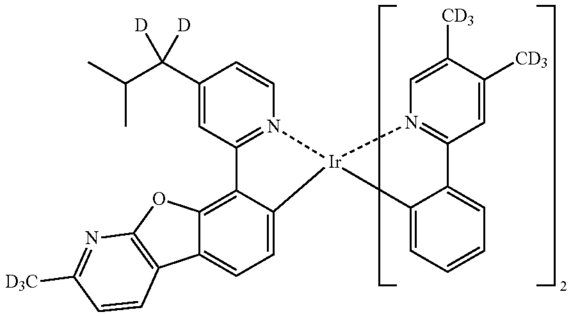

-continued
D-130
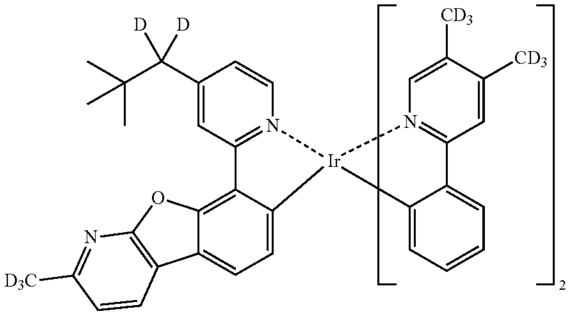
D-131
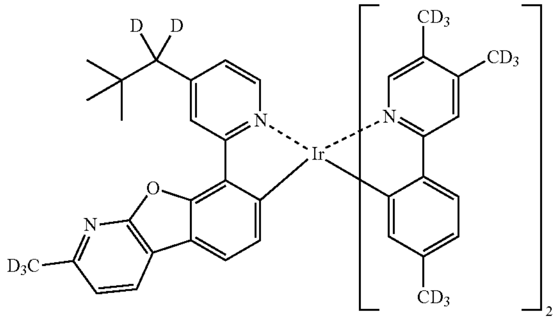
D-132
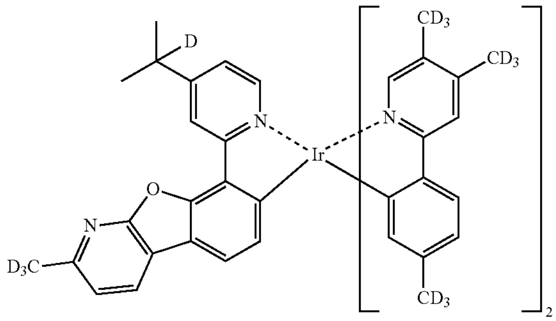
D-133
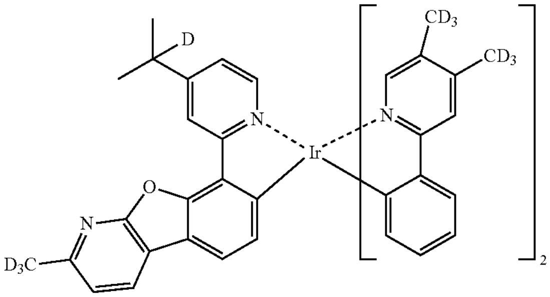
-continued
D-134
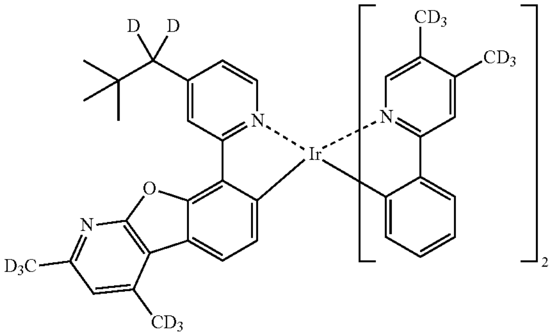
D-135
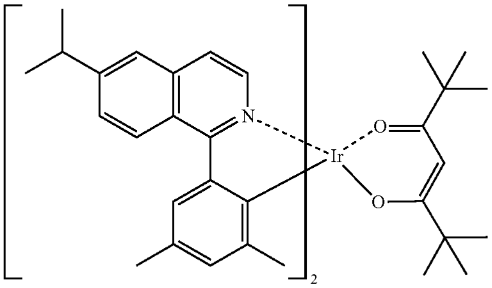
D-136
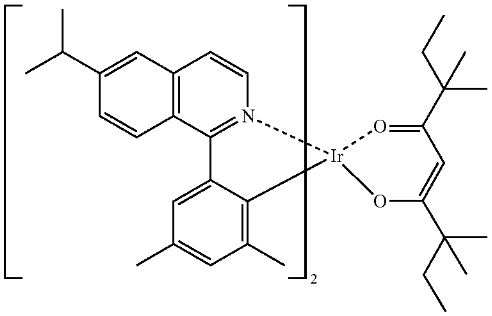
D-137
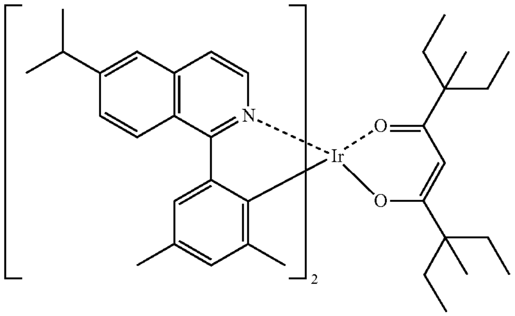

-continued
D-138
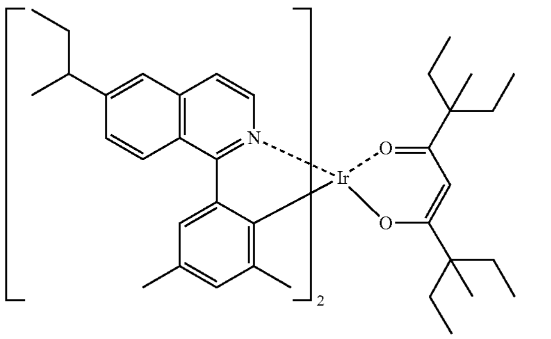
D-139
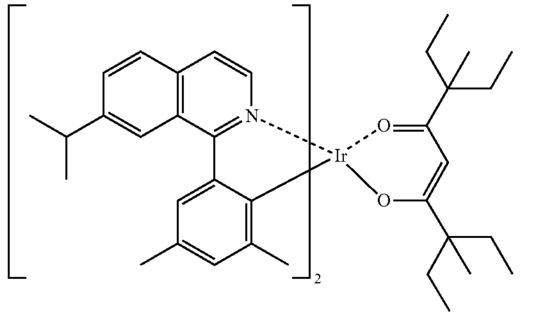
D-140
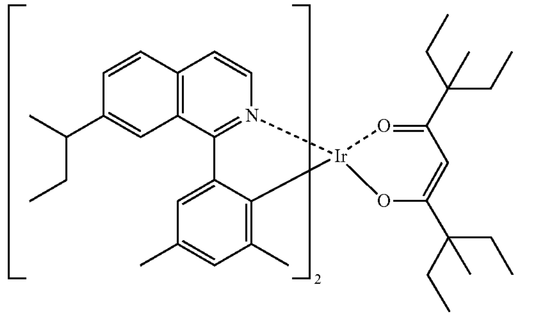
D-141
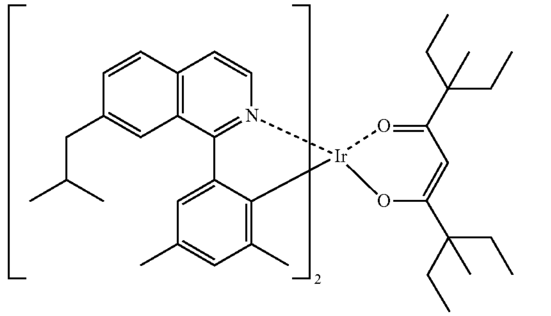
-continued
D-142
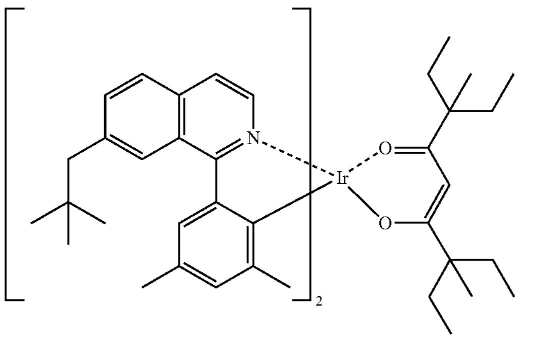
D-143
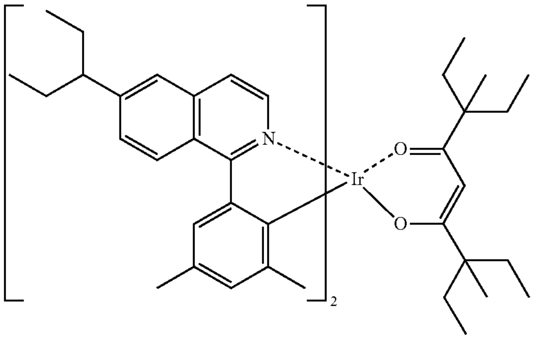
D-144
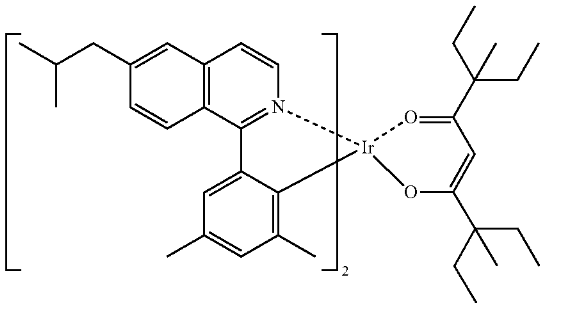
D-145
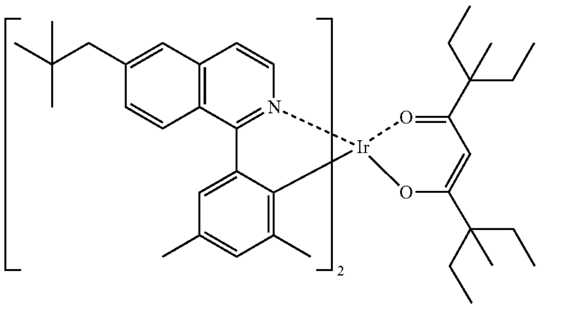

-continued

D-146

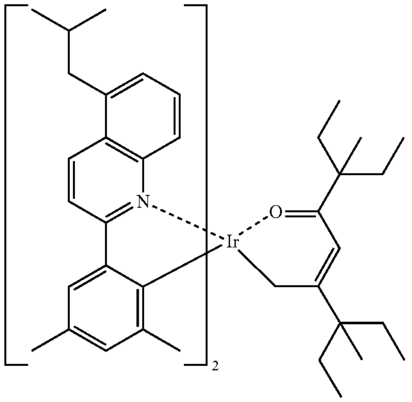

D-147

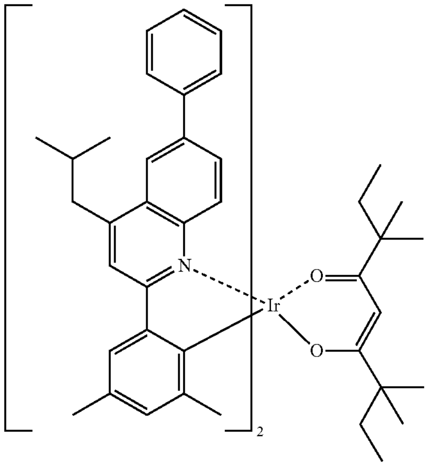

D-148

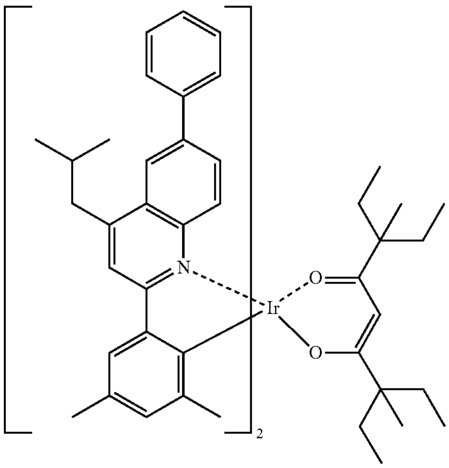

-continued

D-149

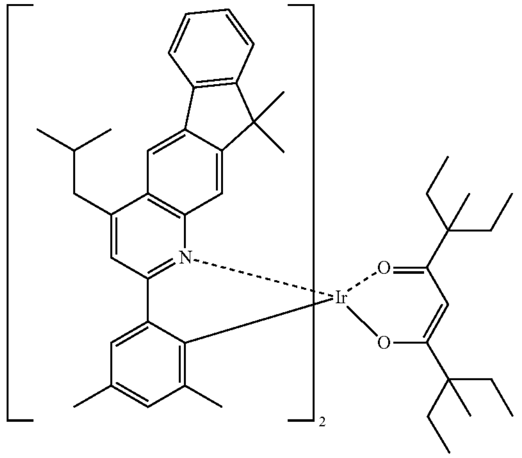

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used. When using a wet film-forming method, a thin film can be formed by dissolving or diffusing materials forming each layer into any suitable solvent such as ethanol, chloroform, tetrahydrofuran, dioxane, etc. The solvent can be any one where the materials forming each layer can be dissolved or diffused, and where there are no problems in film-formation capability.

The first and second host materials according to one embodiment of the present disclosure may be film-formed by the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to one cell to evaporate the materials.

According to one embodiment, if the first host compound and the second host compound are present in the same layer or different layers in an organic electroluminescent device, the two host compounds may individually form films. For example, the second host compound may be deposited after depositing the first host compound.

According to one embodiment, the present disclosure may provide a display system comprising a plurality of host materials comprising a first host material represented by formula 1 and a second host material represented by formula 2. In addition, it is possible to produce a display system, for example, a display system for smart phones, tablets, notebooks, PCs, TVs, or cars; or a lighting system, for example an outdoor or indoor lighting system, by using the organic electroluminescent device of the present disclosure.

Hereinafter, the preparation method of the compounds according to the present disclosure will be explained in detail with reference to the representative compounds of the present disclosure or intermediate compounds thereof. However, the present disclosure is not limited by the following examples.

Example 1: Preparation of Compound H1-1

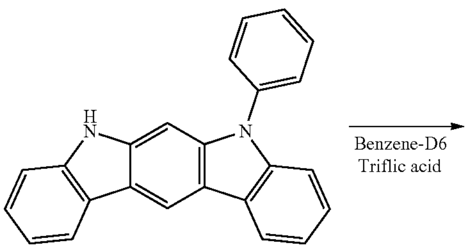

1-1

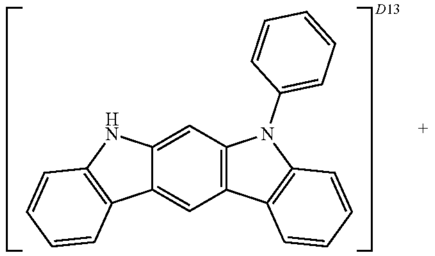

1-2

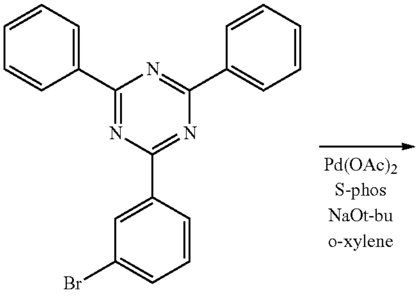

TP-1

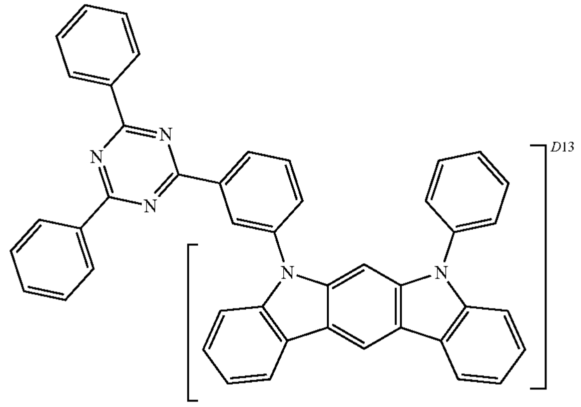

H1-1

Synthesis of Compound 1-2

In a flask, compound 1-1 (5 g, 15.04 mmol) and 100 mL of benzene-D6 were added and heated. Triflic acid (7.5 mL, 84.95 mmol) was added at 70° C., and the mixture was stirred for 3 hours and then cooled to room temperature. 5 mL of $D_2O$ was added to the mixture and stirred for 30 minutes. After completion of the reaction, the mixture was neutralized with an aqueous $K_3PO_4$ solution, and an organic layer was extracted with ethyl acetate. The residual moisture was removed using magnesium sulfate. The residue was distilled under reduced pressure and separated by column chromatography to obtain compound 1-2 (2 g, yield: 38.53%).

Synthesis of Compound H1-1

In a flask, compound 1-2 (4 g, 11.58 mmol), compound TP-1 (4.7 g, 13.67 mmol), $Pd(OAc)_2$ (0.13 g, 0.59 mmol), S-phos (0.47 g, 1.14 mmol), NaOt-bu (2.8 g, 29.13 mmol), and 58 mL of o-xylene were added and stirred under reflux. After 5 hours, the mixture was cooled to room temperature. After completion of the reaction, distilled water was added to the mixture, and an organic layer was extracted with ethyl acetate. The residual moisture was removed using magnesium sulfate. The residue was distilled under reduced pressure and separated by column chromatography to obtain compound H1-1 (2.7 g, yield: 35.76%).

Example 2: Preparation of Compound H1-37

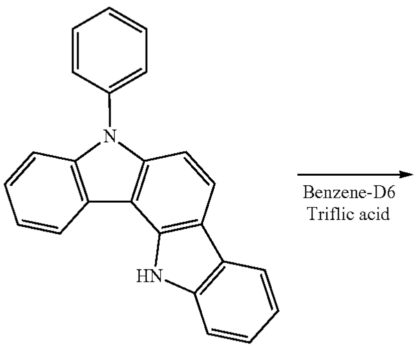

2-1

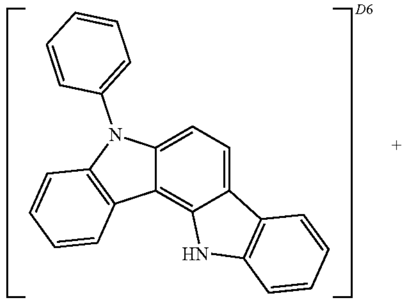

2-2

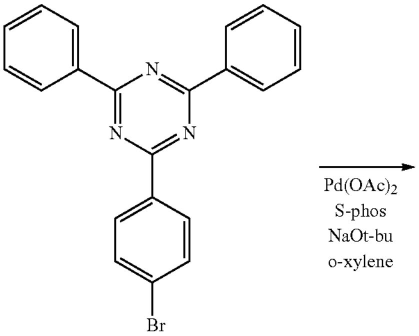

TP-2

-continued

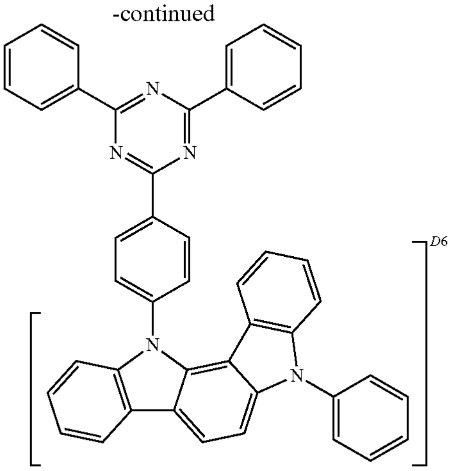

H1-37

Synthesis of Compound 2-2

In a flask, compound 2-1 (12 g, 36.09 mmol) and 300 mL of benzene-D6 were added and heated. Triflic acid (24 mL, 27.18 mmol) was added at 70° C., and the mixture was stirred for 5 hours and then cooled to room temperature. 12 mL of $D_2O$ was added to the mixture and stirred for 30 minutes. After completion of the reaction, the mixture was neutralized with an aqueous $K_3PO_4$ solution, and an organic layer was extracted with ethyl acetate. The residual moisture was removed using magnesium sulfate. The residue was distilled under reduced pressure and separated by column chromatography to obtain compound 2-2 (8 g, yield: 65.57%).

Synthesis of Compound H1-37

In a flask, compound 2-2 (4 g, 11.83 mmol), compound TP-2 (5.51 g, 14.19 mmol), $Pd(OAc)_2$ (0.13 g, 0.59 mmol), S-phos (0.48 g, 1.18 mmol), NaOt-bu (2.84 g, 29.57 mmol), and 200 mL of o-xylene were added and stirred under reflux. After 4 hours, the mixture was cooled to room temperature. After completion of the reaction, distilled water was added to the mixture, and an organic layer was extracted with ethyl acetate. The residual moisture was removed using magnesium sulfate. The residue was distilled under reduced pressure and separated by column chromatography to obtain compound H1-37 (6 g, yield: 78.63%).

Example 3: Preparation of Compound C-47

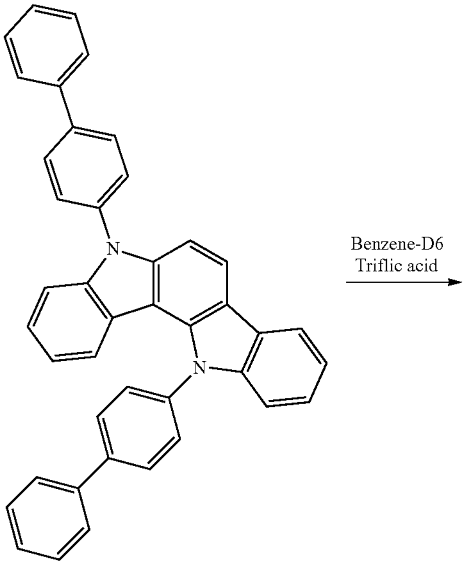

C-47-1

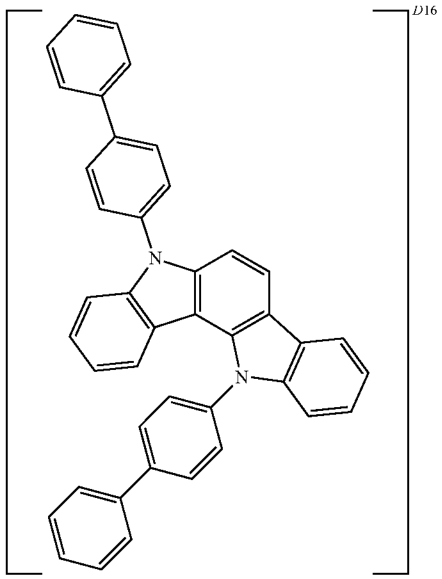

C-47

In a flask, compound C-47-1 (6 g, 10.70 mmol) and 300 mL of benzene-D6 were added and heated. Triflic acid (12 mL, 135.92 mmol) was added at 50° C., and the mixture was stirred for 5 hours and then cooled to room temperature. 6 mL of $D_2O$ was added to the mixture and stirred for 30 minutes. After completion of the reaction, the mixture was neutralized with an aqueous $K_3PO_4$ solution, and an organic layer was extracted with ethyl acetate. The residual moisture was removed using magnesium sulfate. The residue was distilled under reduced pressure and separated by column chromatography to obtain compound C-47 (6 g, yield: 97.40%).

Example 4: Preparation of Compound C-161

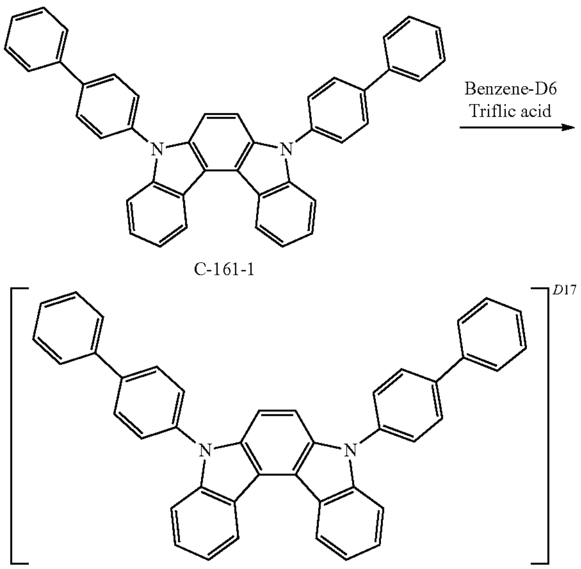

C-161-1

C-161

In a flask, compound C-161-1 (5 g, 8.91 mmol) and 250 mL of benzene-D6 were added and heated. Triflic acid (10 mL, 113.27 mmol) was added at 50° C., and the mixture was stirred for 5 hours and then cooled to room temperature. 5 mL of $D_2O$ was added to the mixture and stirred for 30 minutes. After completion of the reaction, the mixture was neutralized with an aqueous $K_3PO_4$ solution, and an organic layer was extracted with ethyl acetate. The residual moisture was removed using magnesium sulfate. The residue was distilled under reduced pressure and separated by column chromatography to obtain compound C-161 (2.8 g, yield: 54.36%).

Hereinafter, the preparation method of the OLED comprising the plurality of host materials according to the present disclosure or the organic electroluminescent compound according to the present disclosure and the properties thereof will be explained in detail. However, the present disclosure is not limited to the following examples.

Device Example 1: Producing an OLED Comprising the Host Materials According to the Present Disclosure An OLED according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm. Next, compound HT-1 was deposited on the hole injection layer to form a first hole transport layer having a thickness of 80 nm. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: the first host material (H1-37) and second host material (H2-2) shown in Table 1 below were introduced into two cells of the vacuum vapor deposition apparatus as hosts, and compound D-130 was introduced into another cell as a dopant. The two host materials were evaporated at different rates of 1:2 and the dopant material was simultaneously evaporated at a different rate, and the dopant was deposited in a doping amount of 10 wt % based on the total amount of the hosts and the dopant to form a light-emitting layer having a thickness of 40 nm on the second hole transport layer. Next, compound ETL-1 and compound EIL-1 as electron transport materials were deposited in a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Device Example 2: Producing an OLED Comprising the Host Materials According to the Present Disclosure An OLED was produced in the same manner as in Device Example 1, except that compound H1-1 was used as the first host material of the light-emitting layer.

Device Example 3: Producing an OLED Comprising the Host Materials According to the Present Disclosure An OLED was produced in the same manner as in Device Example 1, except that compound H2-48 was used as the second host material of the light-emitting layer.

Device Example 4: Producing an OLED Comprising the Host Materials According to the Present Disclosure An OLED was produced in the same manner as in Device Example 1, except that compound C-47 was used as the second host material of the light-emitting layer.

Comparative Example 1: Producing an OLED Comprising a Conventional Compound as a Host An OLED was produced in the same manner as in Device Example 1, except that compound V-1 was used as the first host material of the light-emitting layer.

Comparative Example 2: Producing an OLED Comprising a Conventional Compound as a Host An OLED was produced in the same manner as in Device Example 1, except that compound C-47-1 was used as the second host material of the light-emitting layer.

The driving voltage and light-emitting color at a luminance of 1,000 nit, and the time taken for luminance to decrease from 100% to 95% at a luminance of 20,000 nit (lifetime; T95) of the OLEDs produced in the Device Examples and the Comparative Examples are provided in Tables 1-1 and 1-2 below.

TABLE 1-1

| | First Host | Second Host | Driving Voltage (V) | Light-Emitting Color | Lifetime (T95, hr) |
|---|---|---|---|---|---|
| Device Example 1 | H1-37 | H2-2 | 3.0 | Green | 343 |
| Device Example 2 | H1-1 | H2-2 | 3.0 | Green | 222 |
| Comparative Example 1 | V-1 | H2-2 | 3.0 | Green | 195 |

TABLE 1-2

| | First Host | Second Host | Driving Voltage (V) | Light-Emitting Color | Lifetime (T95, hr) |
|---|---|---|---|---|---|
| Device Example 1 | H1-37 | H2-2 | 3.0 | Green | 343 |
| Device Example 3 | H1-37 | H2-48 | 3.0 | Green | 231 |
| Device Example 4 | H1-37 | C-47 | 3.0 | Green | 202 |
| Comparative Example 2 | H1-37 | C-47-1 | 3.0 | Green | 164 |

From Tables 1-1 and 1-2 above, it can be seen that the OLEDs comprising a specific combination of compounds according to the present disclosure as host materials exhibit significantly improved lifetime properties, compared to the OLEDs comprising a conventional host material.

Device Example 5: Producing an OLED Comprising the Host Materials According to the Present Disclosure An OLED according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm. Next, compound HT-1 was deposited on the hole injection layer to form a first hole transport layer having a thickness of 80 nm. Compound HT-3 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: compound C-47 shown in Table 2 below were introduced into two cells of the vacuum vapor deposition apparatus as a host, and compound D-50 was introduced into another cell as a dopant. The host material was evaporated and the dopant material was simultaneously evaporated at a different rate, and the dopant was deposited in a doping amount of 10 wt % based on the total amount of the host and the dopant to form a light-emitting layer having a thickness of 30 nm on the second hole transport layer. Next, compound HBL-1 was deposited to form a hole blocking layer having a thickness of 10 nm on the light-emitting layer. Compound ETL-1 and compound EIL-1 as electron transport materials were deposited in a weight ratio of 40:60 to form an electron transport layer having a thickness of 35 nm on the hole blocking layer. After depositing compound EIL-1 as an electron injection layer having a thickness of 2 nm, an $A_1$ cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Device Example 6: Producing an OLED Comprising the Host Materials According to the Present Disclosure An OLED was produced in the same manner as in Device Example 5, except that compound C-161 was used as the host material of the light-emitting layer.

Comparative Example 3: Producing an OLED Comprising a Conventional Compound as a Host An OLED was produced in the same manner as in Device Example 5, except that compound C-47-1 was used as the host material of the light-emitting layer.

Comparative Example 4: Producing an OLED Comprising a Conventional Compound as a Host An OLED was produced in the same manner as in Device Example 5, except that compound C-161-1 was used as the host material of the light-emitting layer.

The driving voltage and light-emitting color at a luminance of 1,000 nit, and the time taken for luminance to decrease from 100% to 50% at a luminance of 20,000 nit (lifetime; T50) of the OLEDs produced in the Device Examples and the Comparative Examples are provided in Tables 2 and 3 below.

TABLE 2

| | Host | Driving Voltage (V) | Light-Emitting Color | Lifetime (T50, hr) |
|---|---|---|---|---|
| Device Example 5 | C-47 | 3.7 | Green | 51 |
| Comparative Example 3 | C-47-1 | 3.7 | Green | 43 |

TABLE 3

| | Host | Driving Voltage (V) | Light-Emitting Color | Lifetime (T50, hr) |
|---|---|---|---|---|
| Device Example 6 | C-161 | 2.8 | Green | 338 |
| Comparative Example 4 | C-161-1 | 2.8 | Green | 281 |

From Tables 2 and 3 above, it can be seen that the OLED comprising the compound according to the present disclosure as a single host material exhibits significantly improved lifetime properties, compared to the OLED comprising a conventional host material.
TABLE 4
| | |
|---|---|
| Hole Injection Layer/ Hole Transport Layer | 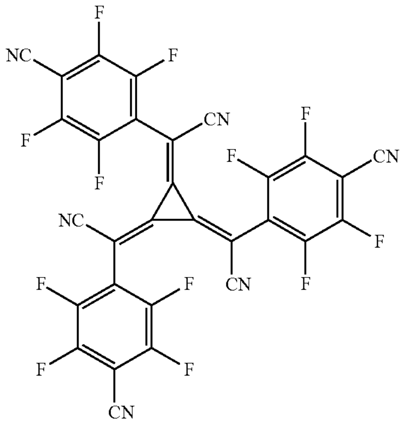 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] HI-1 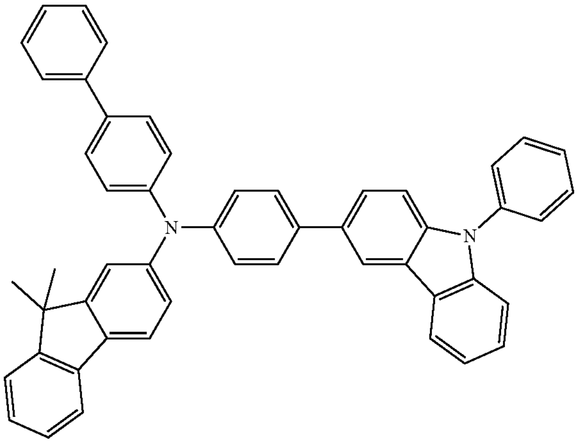 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21] HT-1 |

TABLE 4-continued
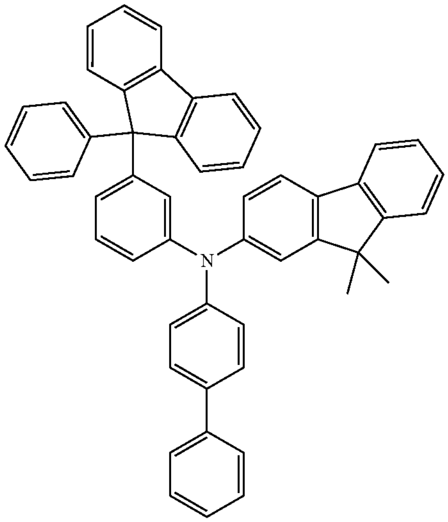 [SMILES: CC1(C)c2ccccc2-c2ccc(N(c3ccc(-c4ccccc4)cc3)c3cccc(C4(c5ccccc5)c5ccccc5-c5ccccc54)c3)cc21]
HT-2
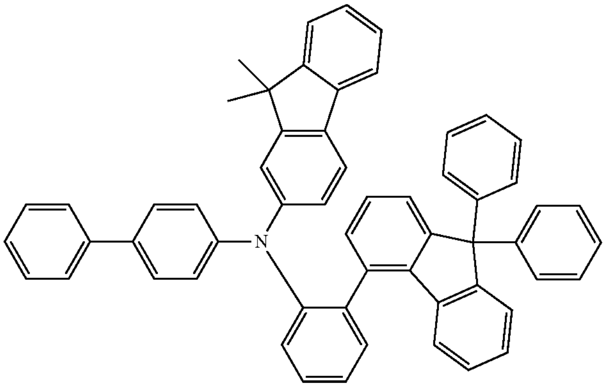 [SMILES: CC1(C)c2ccccc2-c2ccc(N(c3ccc(-c4ccccc4)cc3)c3ccccc3-c3cccc4c3-c3ccccc3C4(c3ccccc3)c3ccccc3)cc21]
HT-3
Light-Emitting Layer
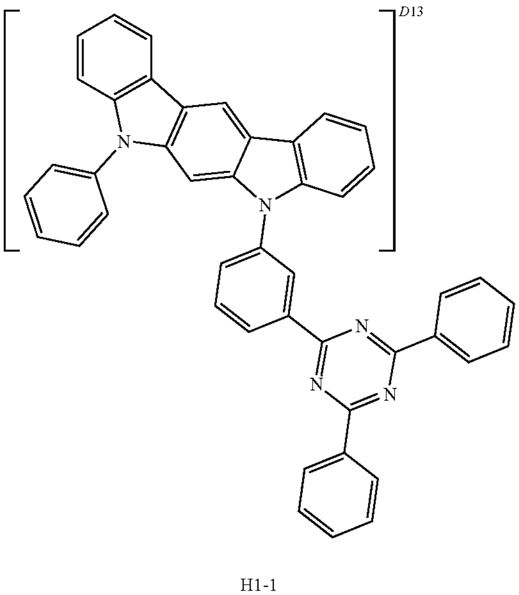
H1-1

TABLE 4-continued
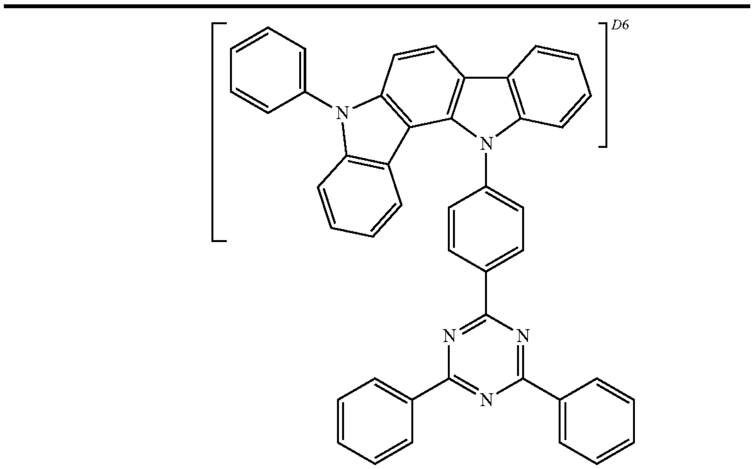
H1-37
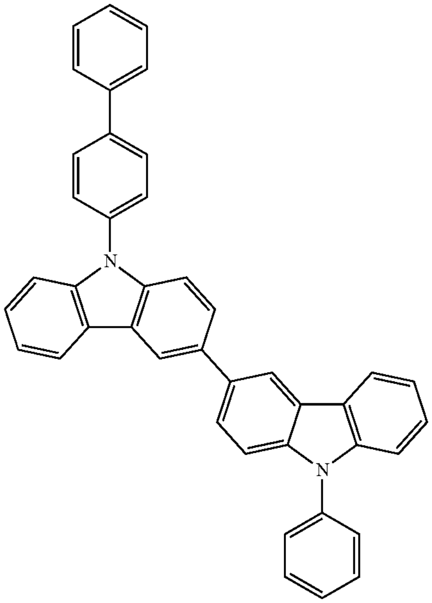 [SMILES: c1ccc(-c2ccc(-n3c4ccccc4c4cc(-c5ccc6c(c5)c5ccccc5n6-c5ccccc5)ccc43)cc2)cc1]
H2-2

TABLE 4-continued
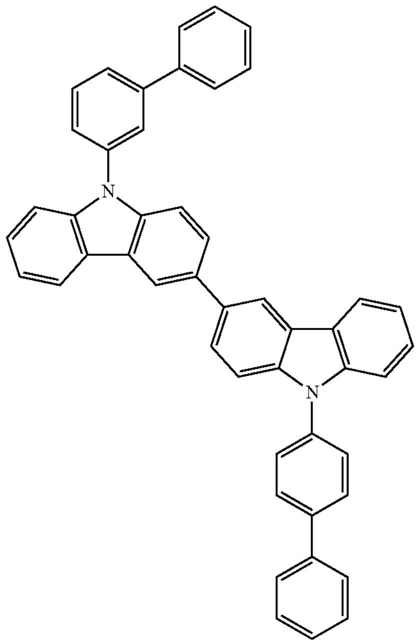 [SMILES: c1ccc(-c2ccc(-n3c4ccccc4c4cc(-c5ccc6c(c5)c5ccccc5n6-c5cccc(-c6ccccc6)c5)ccc43)cc2)cc1]
H2-48
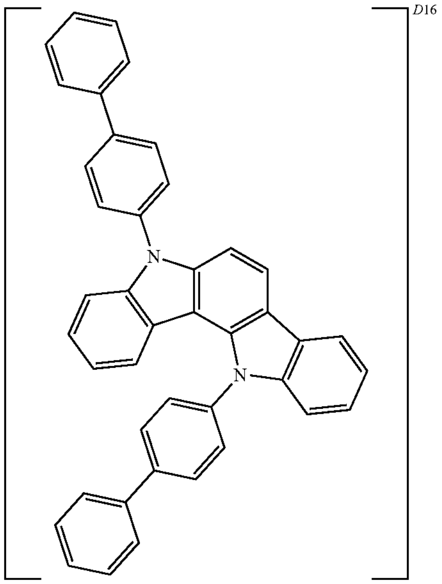
C-47

TABLE 4-continued
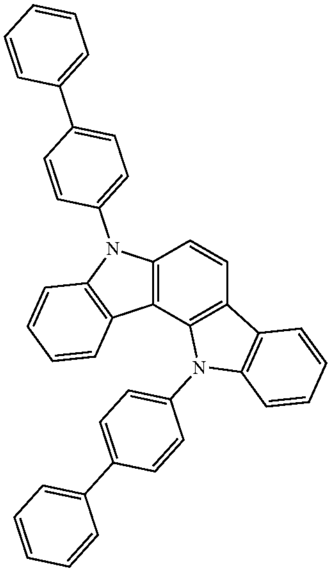 [SMILES: c1ccc(-c2ccc(-n3c4ccccc4c4c3ccc3c5ccccc5n(-c5ccc(-c6ccccc6)cc5)c34)cc2)cc1]
C-47-1
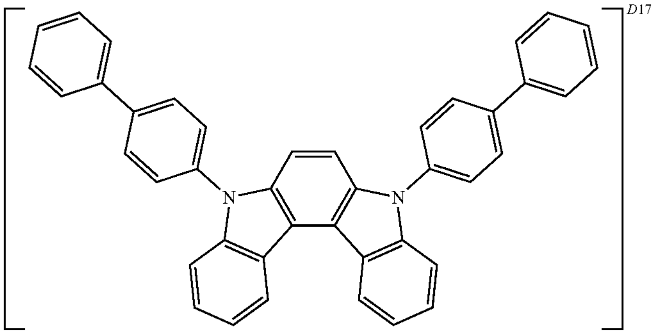
C-161
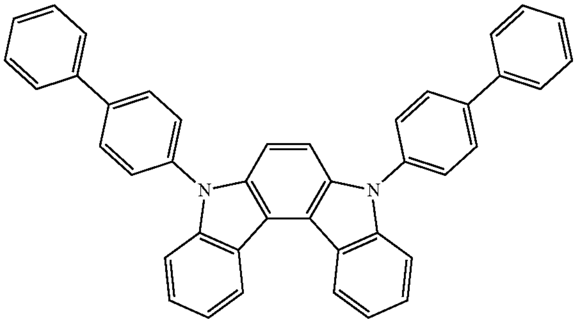 [SMILES: c1ccc(-c2ccc(-n3c4ccccc4c4c5c6ccccc6n(-c6ccc(-c7ccccc7)cc6)c5ccc43)cc2)cc1]
C-161-1

TABLE 4-continued
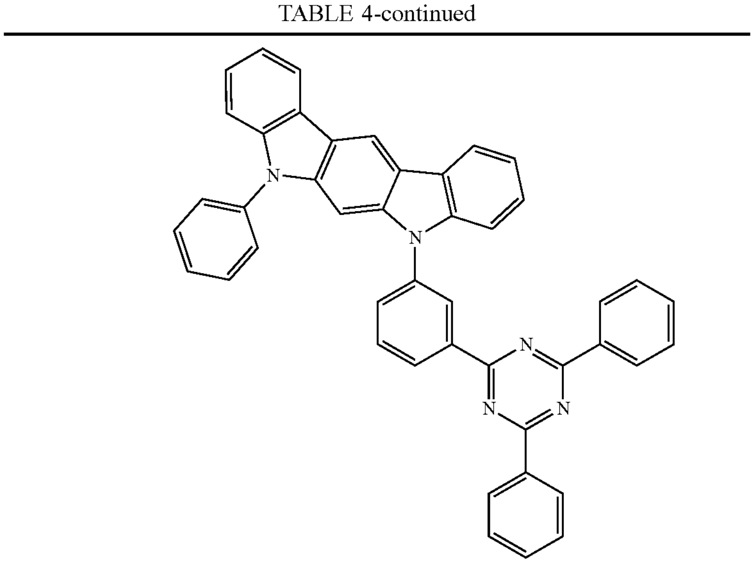
V-1
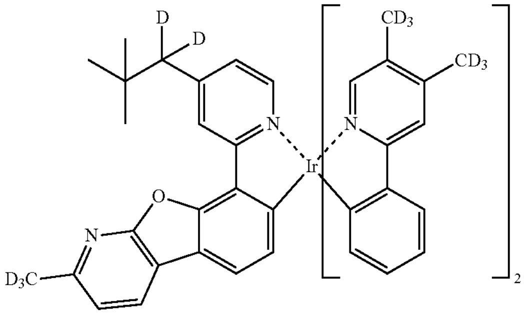
D-130
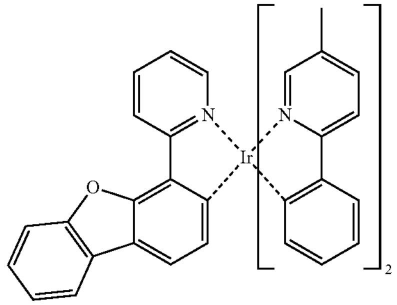
D-50
Hole Blocking Layer
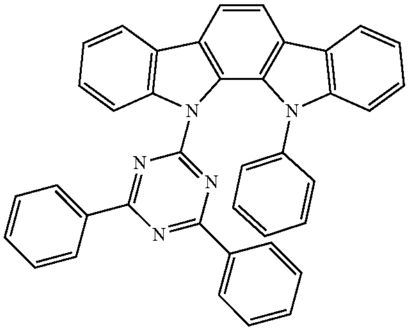 [SMILES: c1ccc(-c2nc(-c3ccccc3)nc(-n3c4ccccc4c4ccc5c6ccccc6n(-c6ccccc6)c5c43)n2)cc1]
HBL-1

TABLE 4-continued

| | |
|---|---|
| Electron Transport Layer/ Electron Injection Layer | 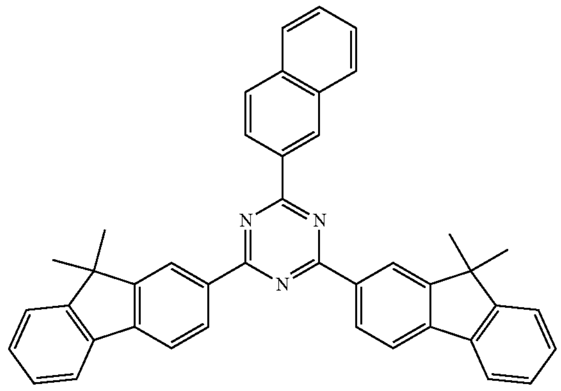 [SMILES: CC1(C)c2ccccc2-c2ccc(-c3nc(-c4ccc5c(c4)C(C)(C)c4ccccc4-5)nc(-c4ccc5ccccc5c4)n3)cc21] ETL-1 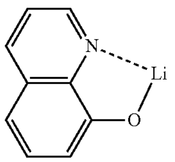 EIL-1 |

The invention claimed is:

1. A plurality of host materials comprising at least one first host compound and at least one second host compound, wherein the first host compound is represented by the following formula 1, and the second host compound is represented by the following formula 2-2:

(1)

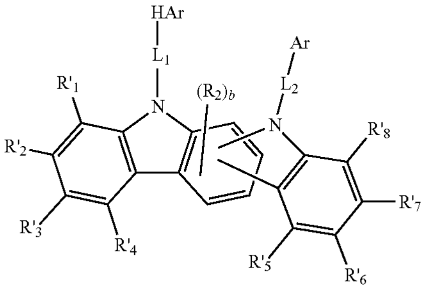

in formula 1, $L_1$ and $L_2$, each independently, represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

HAr represents a substituted or unsubstituted (3- to 30-membered)heteroaryl;

Ar represents a substituted or unsubstituted (C6-C30)aryl, or a substituted or unsubstituted (3- to 30-membered) heteroaryl;

$R'_1$ to $R'_8$, and $R_2$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_{13}R_{14}$, or $-SiR_{15}R_{16}R_{17}$; or may be linked to an adjacent substituent(s) to form a ring(s);

$R_{13}$ to $R_{17}$, each independently, represent a substituted or unsubstituted (C1-C30)alkyl, a substituted or unsubstituted (C6-C30)aryl, or a substituted or unsubstituted (3- to 30-membered)heteroaryl;

with the proviso that at least one of $R'_1$ to $R'_8$, and $R_2$ represents deuterium; and b represents an integer of 1 or 2, where if b is an integer of 2, each of $R_2$ may be the same or different from each other:

(2-2)

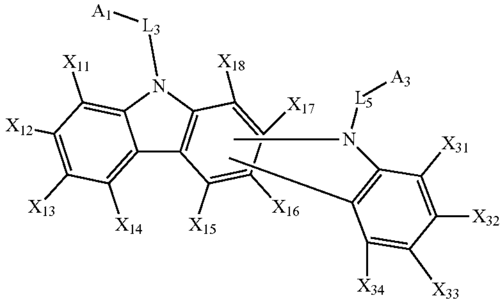

in formula 2-2, $A_1$ represents a phenyl unsubstituted or substituted with at least one selected from the group consisting of deuterium, naphthyl, carbazolyl and 9-phenylcarbazolyl, a deuterium-substituted or unsubstituted dibenzofuranyl, a deuterium-substituted or unsubstituted dibenzothiophenyl, or a carbazolyl unsubstituted or substituted with at least one selected from the group consisting of deuterium and phenyl;

$L_3$ represents a single bond;

$A_3$ represents a deuterium-substituted or unsubstituted phenyl, a deuterium-substituted or unsubstituted p-biphenyl, a deuterium-substituted or unsubstituted m-biphenyl, a deuterium-substituted or unsubstituted o-biphenyl, a deuterium-substituted or unsubstituted o-terphenyl, a deuterium-substituted or unsubstituted p-terphenyl, a substituted or unsubstituted naphthyl, a substituted or unsubstituted triphenylenyl, a substituted or unsubstituted dimethylfluorenyl, a substituted or unsubstituted dibenzofuranyl, a substituted or unsubstituted dibenzothiophenyl, or a substituted or unsubstituted carbazolyl;

$L_5$ represents a single bond, or a deuterium-substituted or unsubstituted (C6-C30)arylene; and $X_{11}$ to $X_{18}$, each independently, represent hydrogen, deuterium, a substituted or unsubstituted (C6-C30)aryl, or a substituted or unsubstituted (3- to 30-membered) heteroaryl, and two or more adjacent $X_{11}$ to $X_{18}$ may be linked to each other to form a ring(s);

at least one of $X_{11}$ to $X_{18}$, and $X_{31}$ to $X_{34}$ represents deuterium or is substituted with deuterium.

2. The plurality of host materials according to claim 1, wherein formula 1 is represented by any one of the following formulas 1-1 to 1-6:

(1-1)

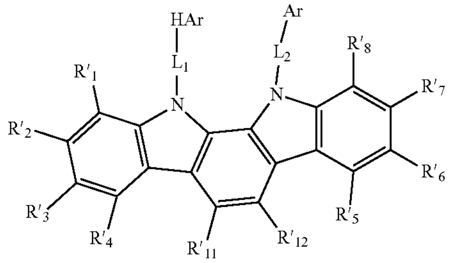

(1-2)

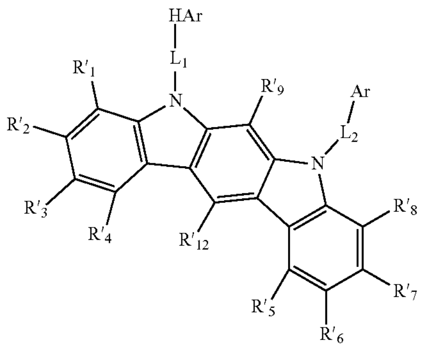

(1-3)

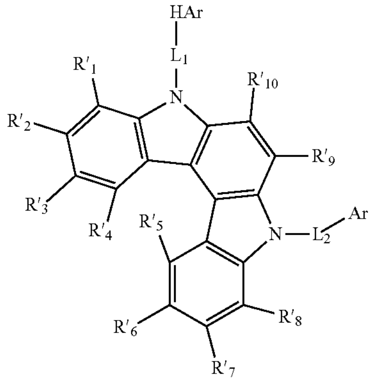

-continued (1-4)

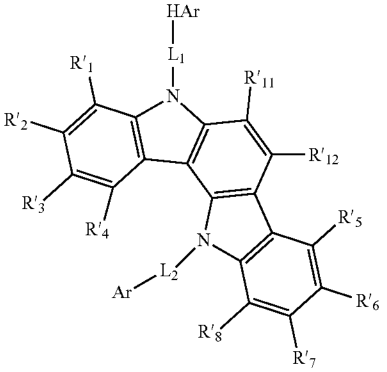

(1-5)

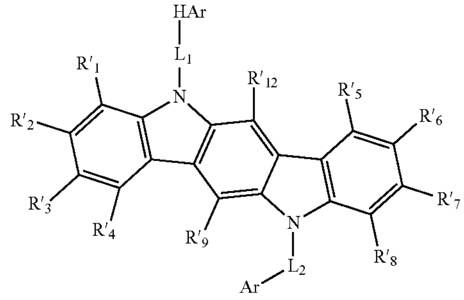

(1-6)

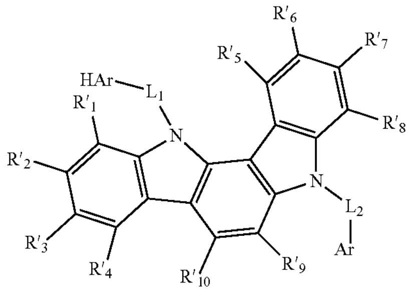

in formulas 1-1 to 1-6,

HAr, Ar, $L_1$, $L_2$, and $R'_1$ to $R'_8$ are as defined in claim 1, $R'_9$ to $R'_{12}$ are as defined for $R'_1$ to $R'_8$, with the proviso that at least one of $R'_1$ to $R'_{12}$ is deuterium.

3. The plurality of host materials according to claim 1, wherein formula 2-2 is represented by any one of the following formulas 2-11 to 2-16:

(2-11)

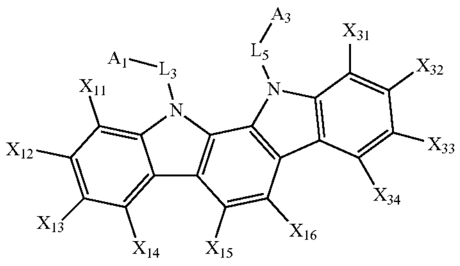

-continued (2-12)

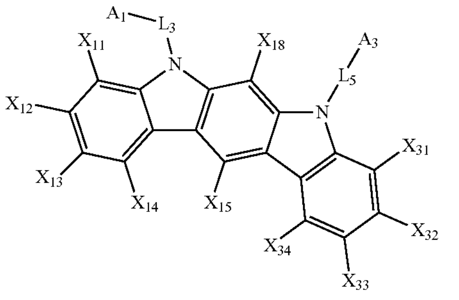

(2-13)

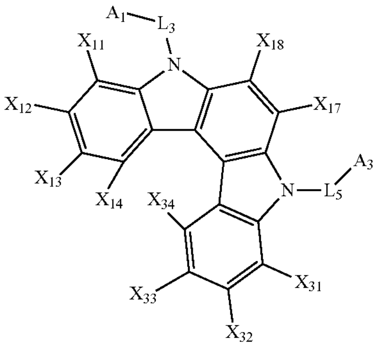

(2-14)

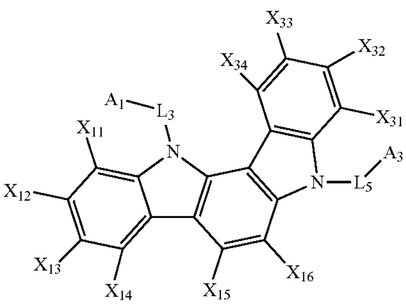

(2-15)

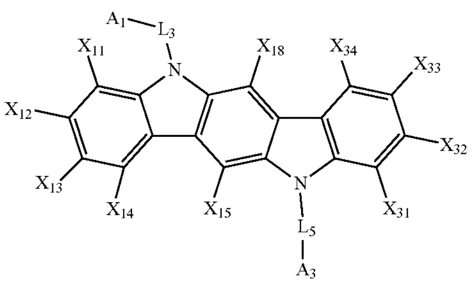

-continued (2-16)

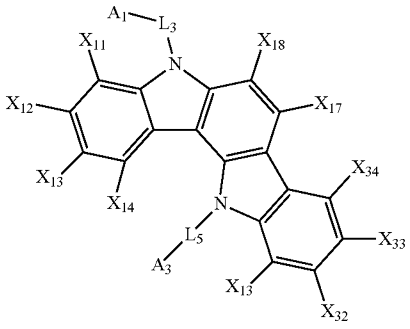

in formulas 2-11 to 2-16, $A_1$, $A_3$, $L_3$, $L_5$, $X_{11}$ to $X_{18}$, and $X_{31}$ to $X_{34}$ are as defined in claim 1.

4. The plurality of host materials according to claim 1, wherein the substituent(s) of the substituted alkyl(ene), the substituted aryl(ene), the substituted heteroaryl(ene), the substituted cycloalkyl(ene), the substituted cycloalkenyl, the substituted heterocycloalkyl, the substituted dibenzofuranyl, the substituted dibenzothiophenyl, and the substituted carbazolyl, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium, a cyano(s), a (C1-C30)alkyl(s), and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

5. The plurality of host materials according to claim 1, wherein the compound represented by formula 1 is at least one selected from the group consisting of the following compounds:

H1-1

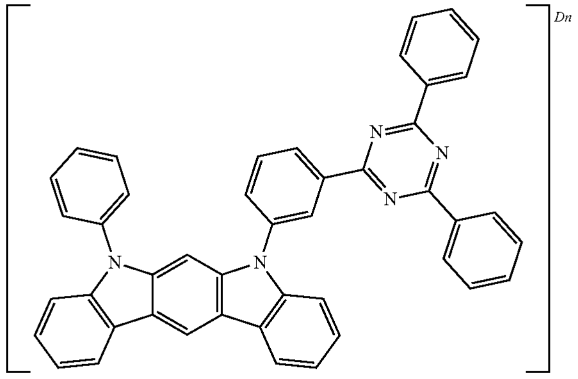

-continued
H1-2
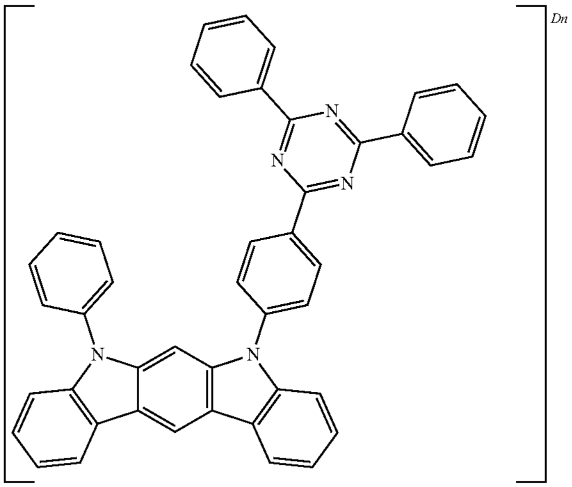
H1-3
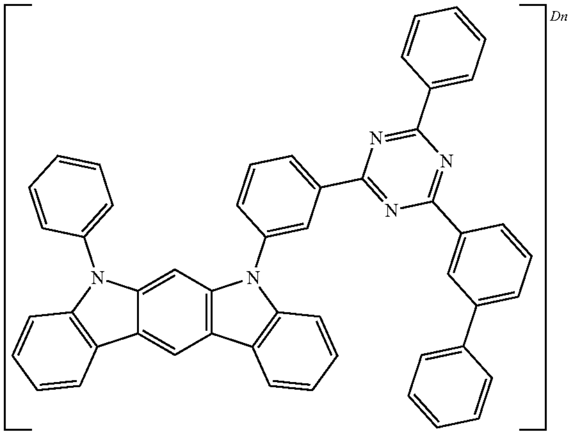
H1-4
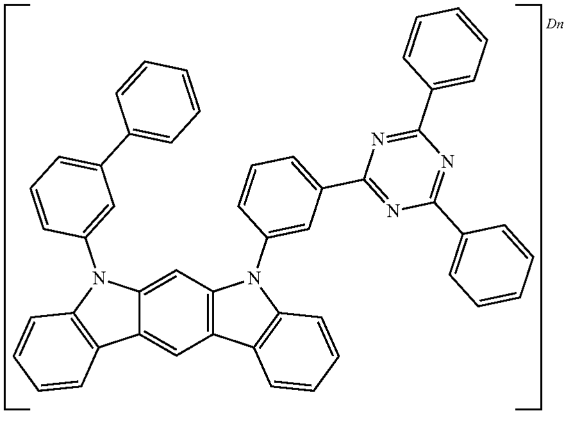
-continued
H1-5
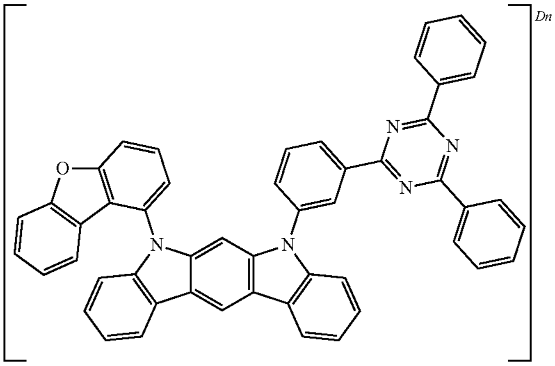
H1-6
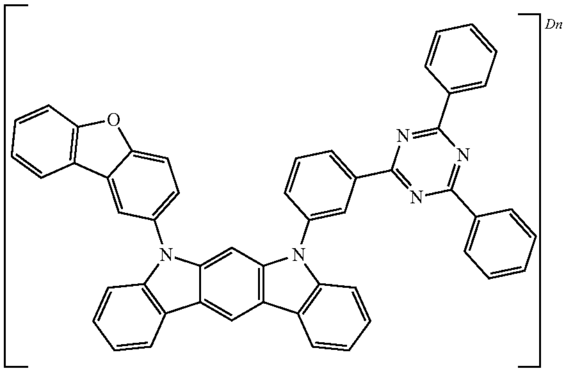
H1-7
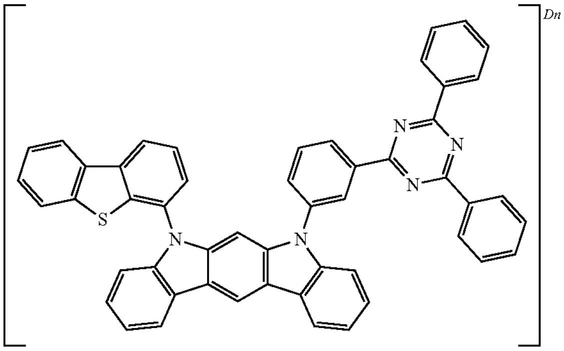
H1-8
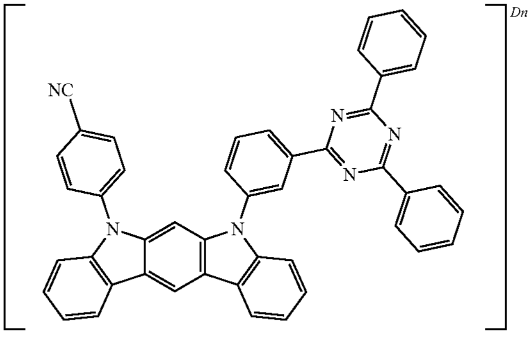

-continued
H1-9
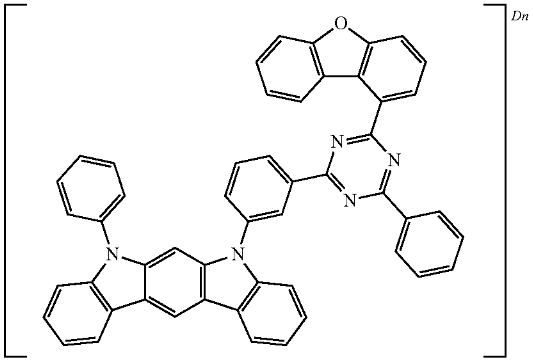
H1-10
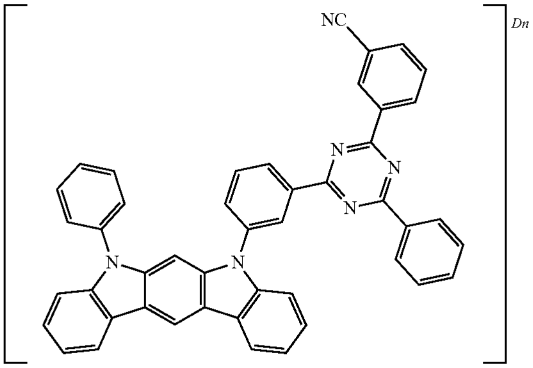
H1-11
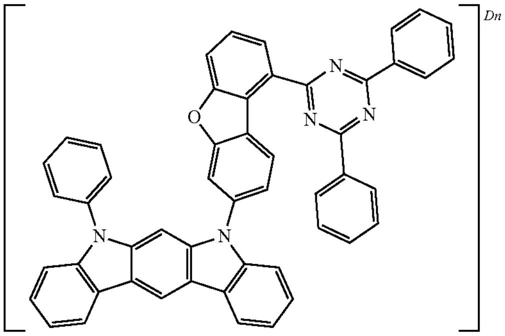
H1-12
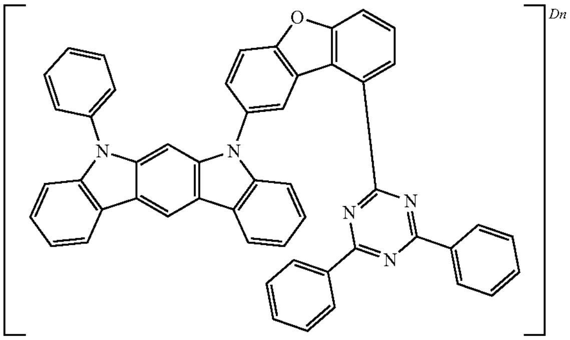
-continued
H1-13
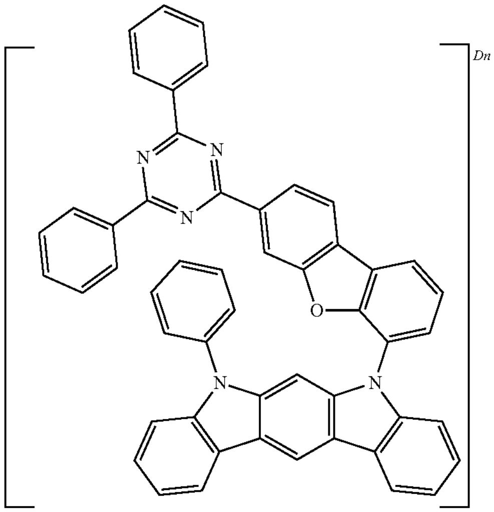
H1-14
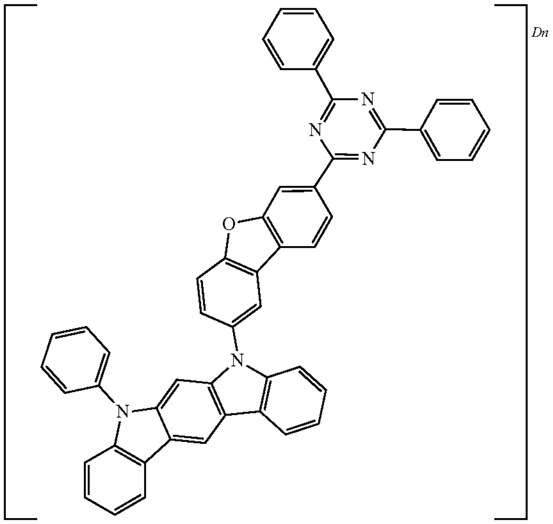
H1-15
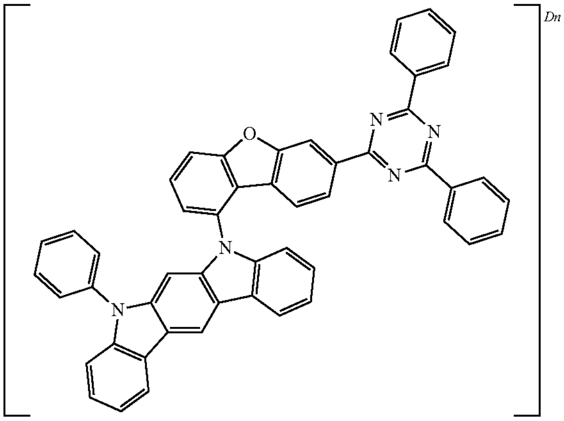

-continued
H1-16
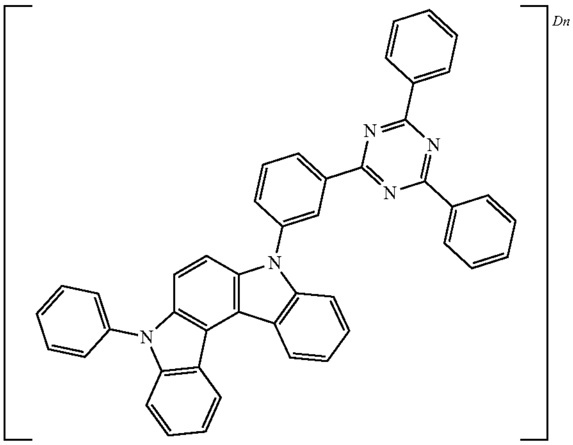
H1-17
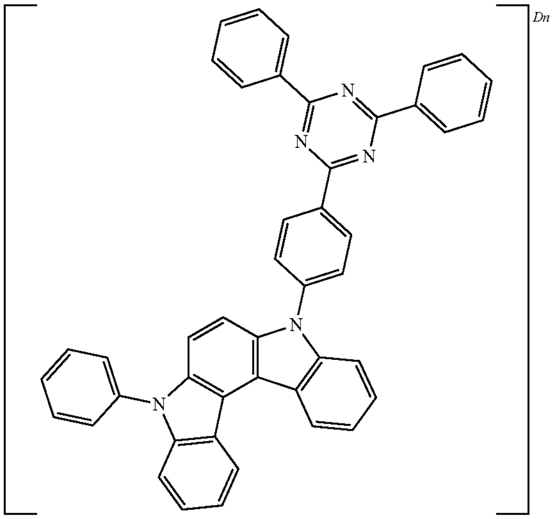
H1-18
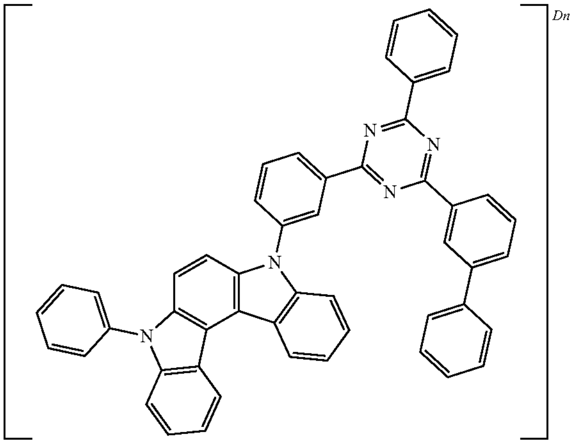
-continued
H1-19
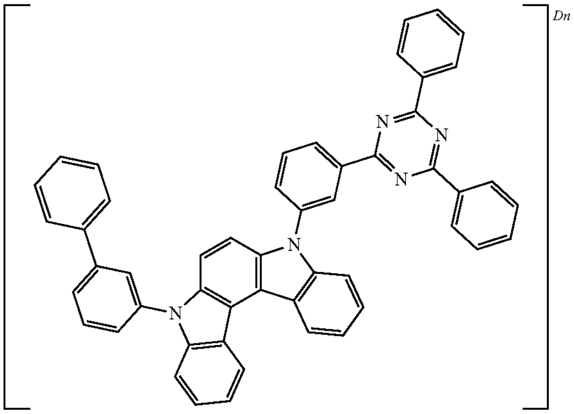
H1-20
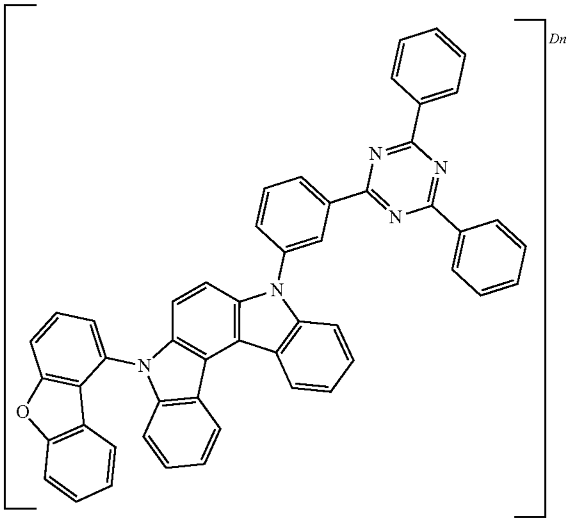
H1-21
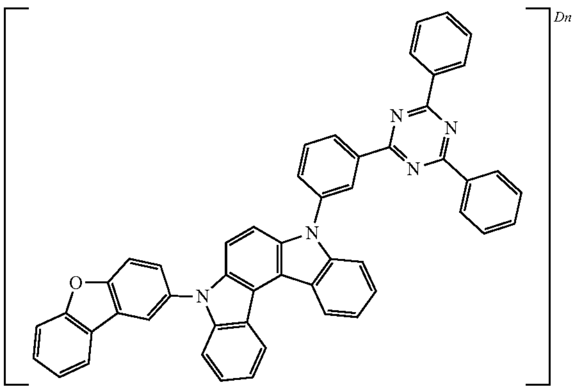

H1-22
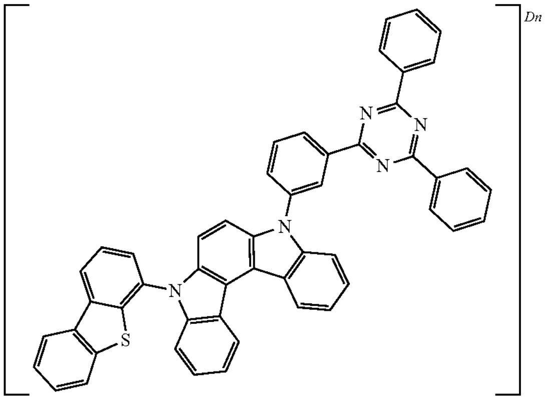
H1-23
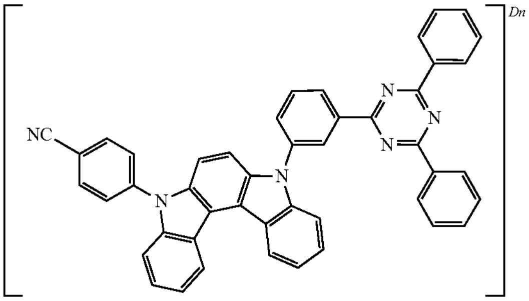
H1-24
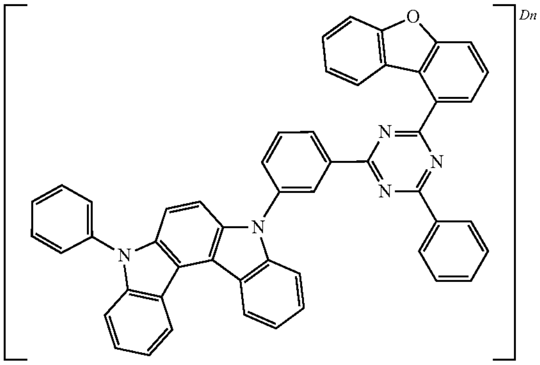
H1-25
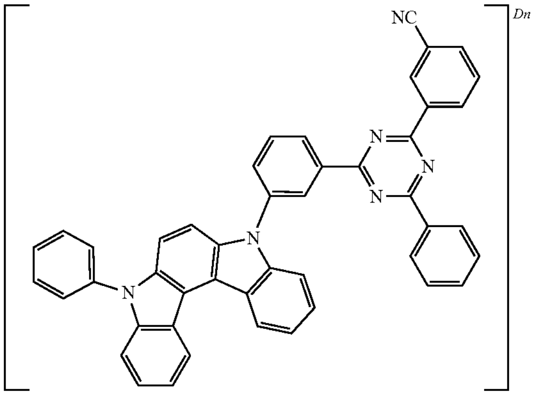
H1-26
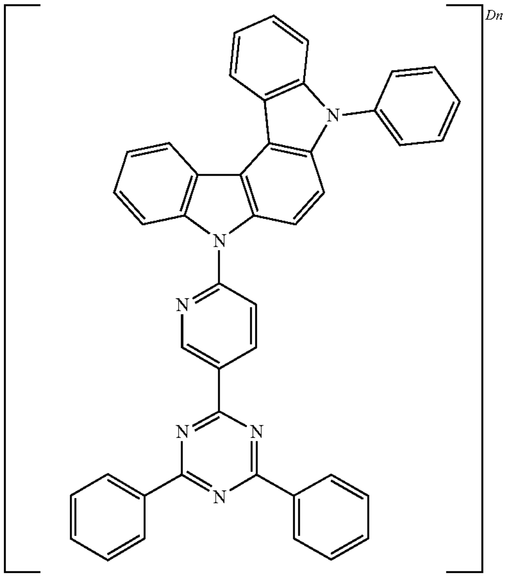
H1-27
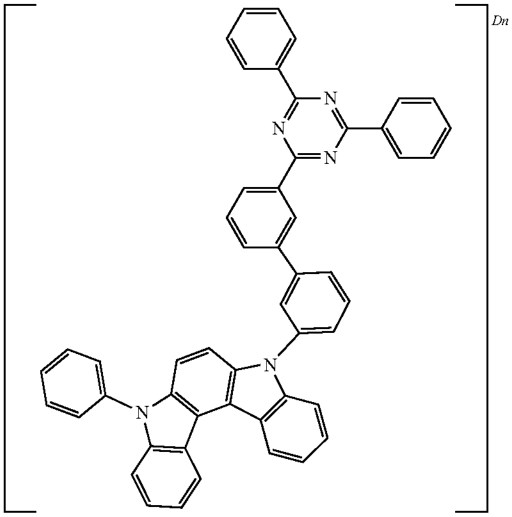
H1-28
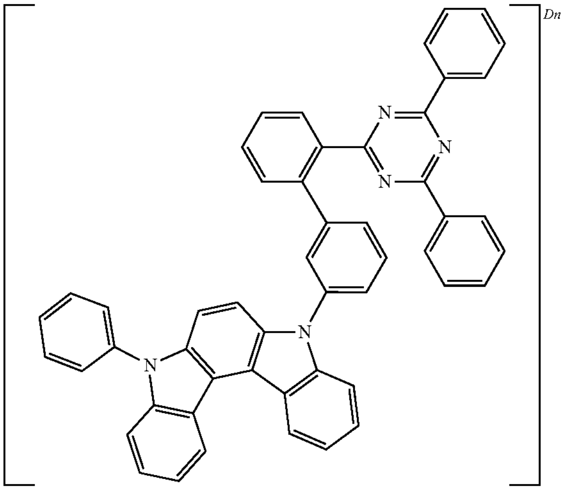

-continued
H1-29
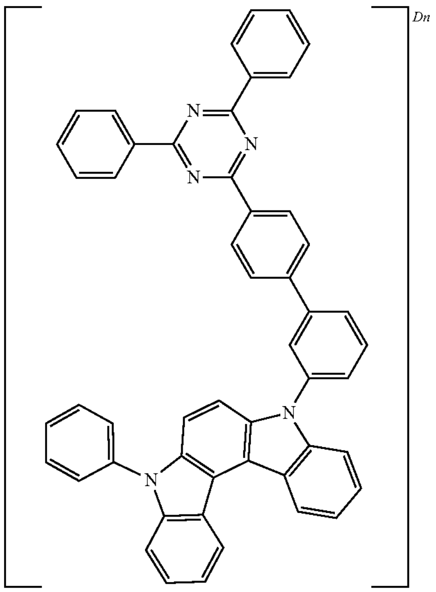
H1-30
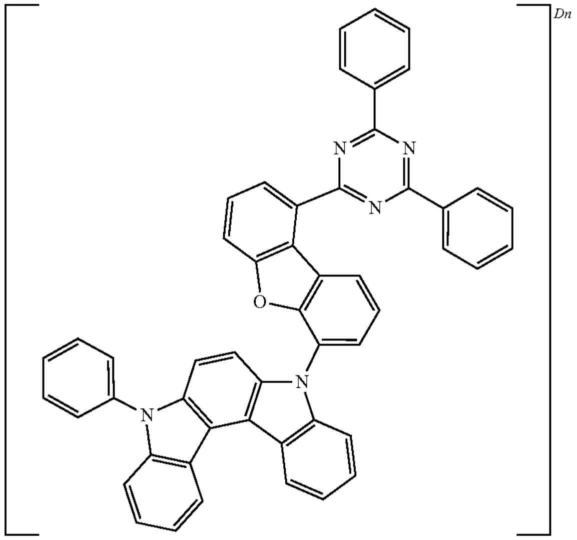
H1-31
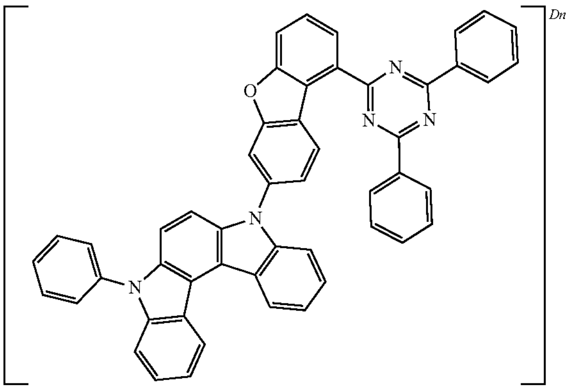
-continued
H1-32
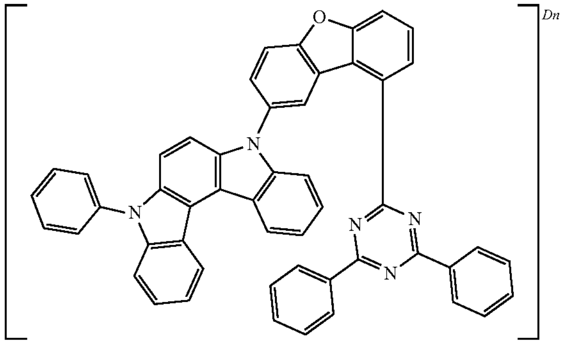
H1-33
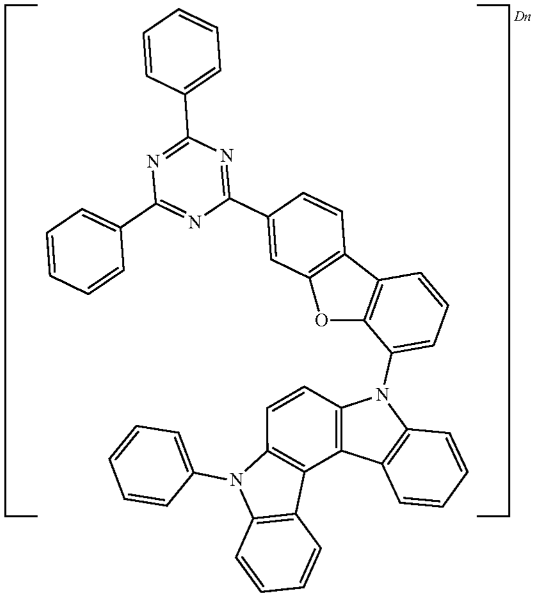
H1-34
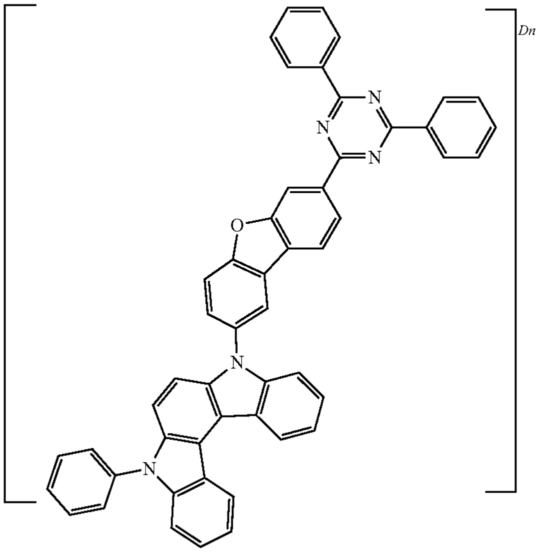

-continued
H1-35
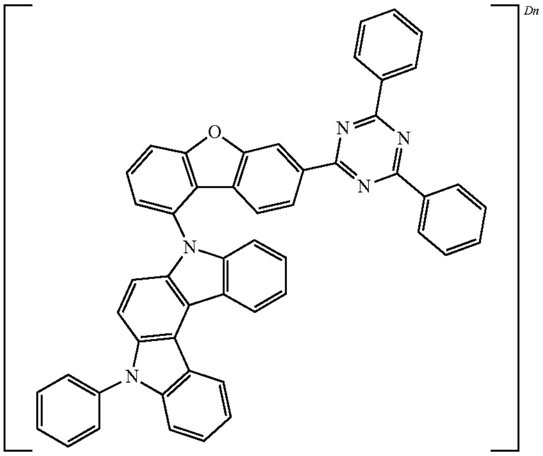
H1-36
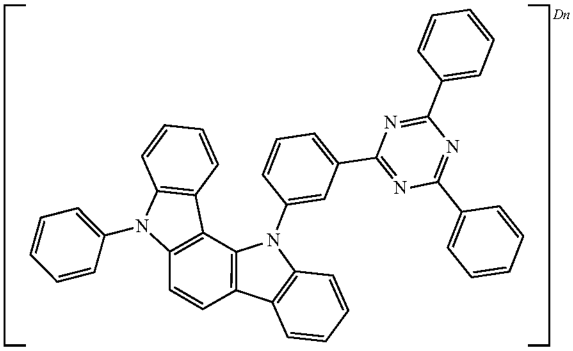
H1-37
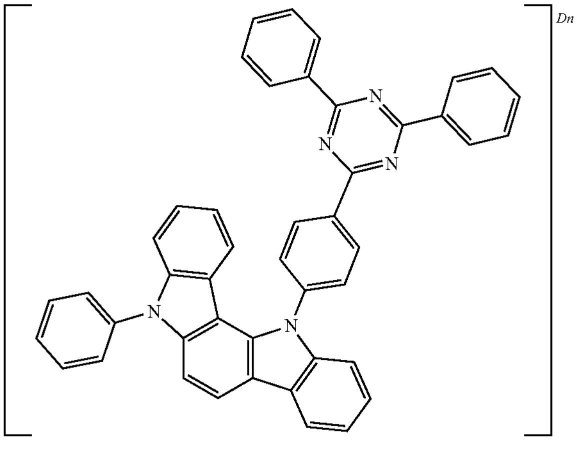
-continued
H1-38
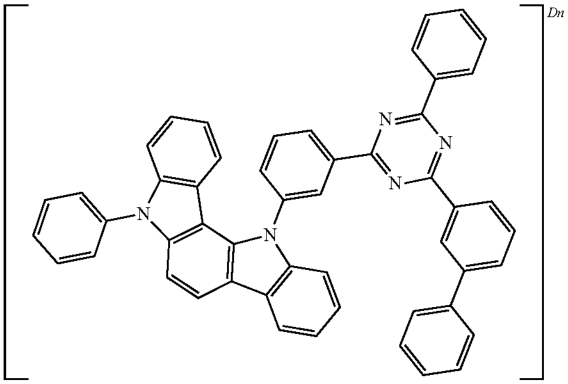
H1-39
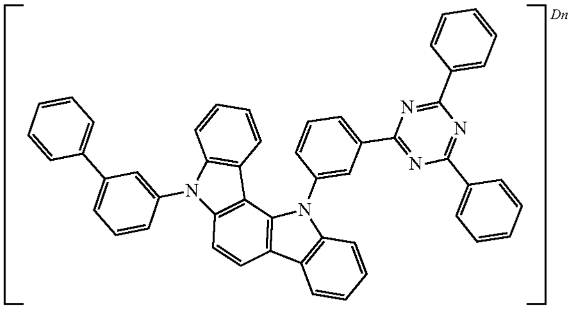
H1-40
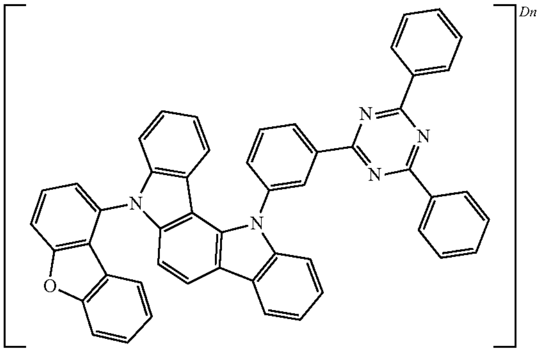
H1-41
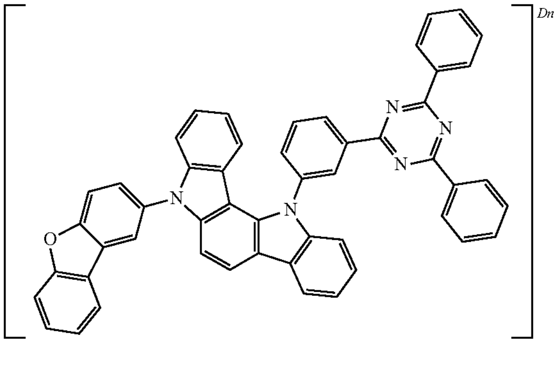

-continued
H1-42
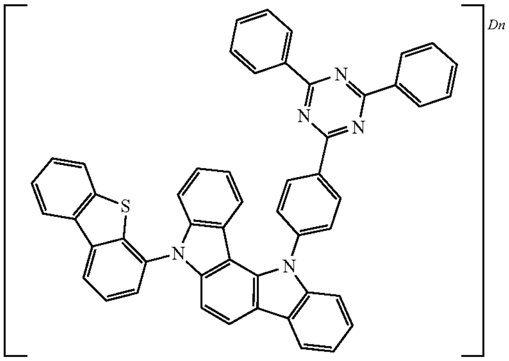
H1-43
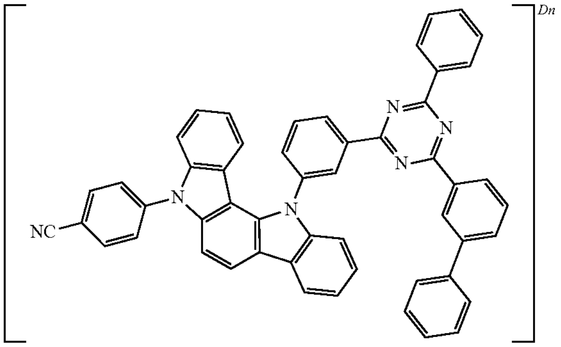
H1-44
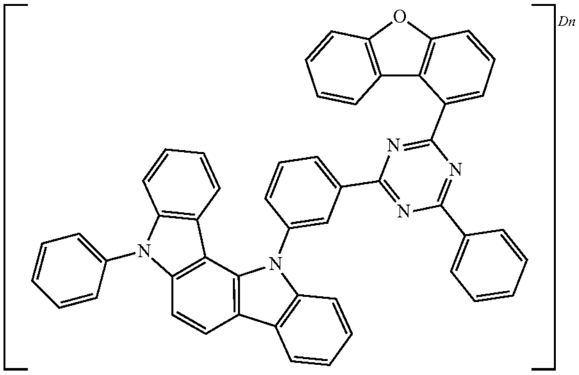
H1-45
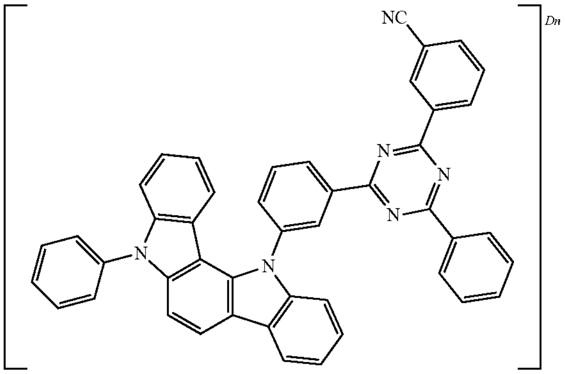
-continued
H1-46
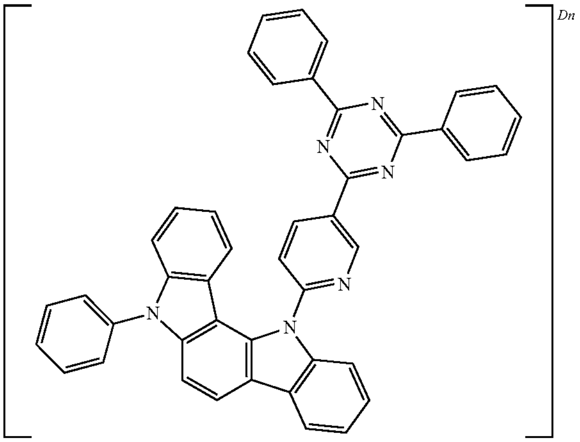
H1-47
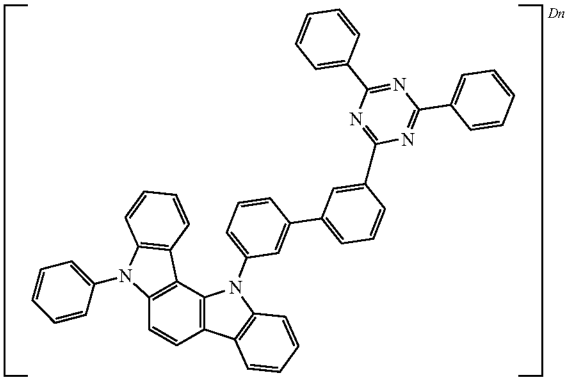
H1-48
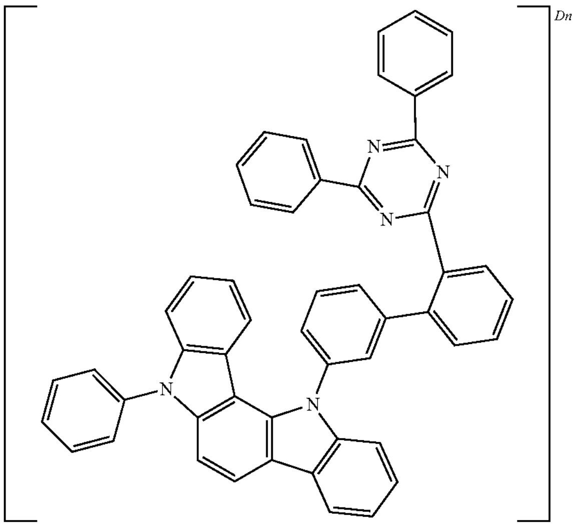

-continued
H1-49
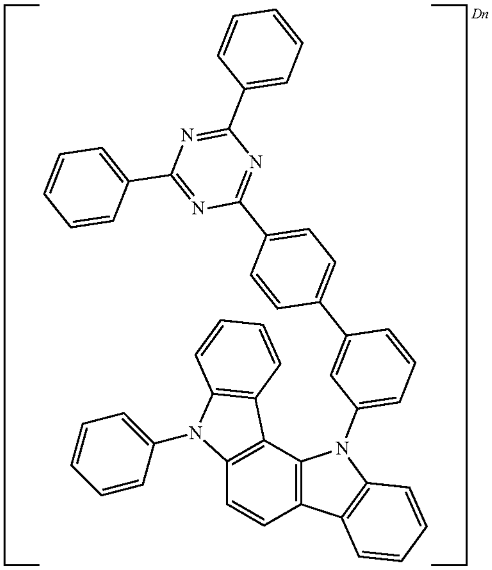
H1-50
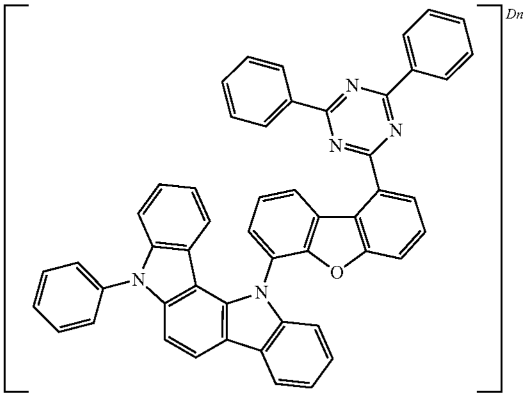
H1-51
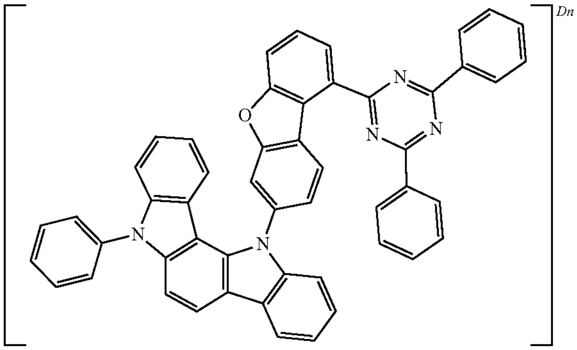
-continued
H1-52
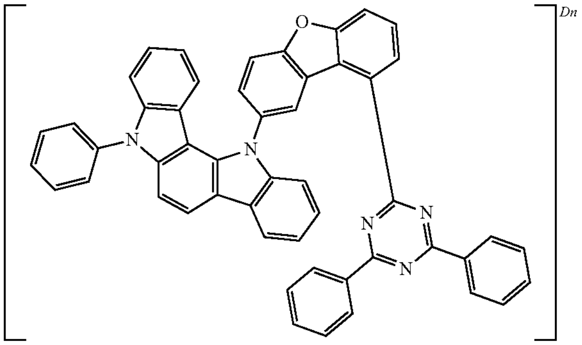
H1-53
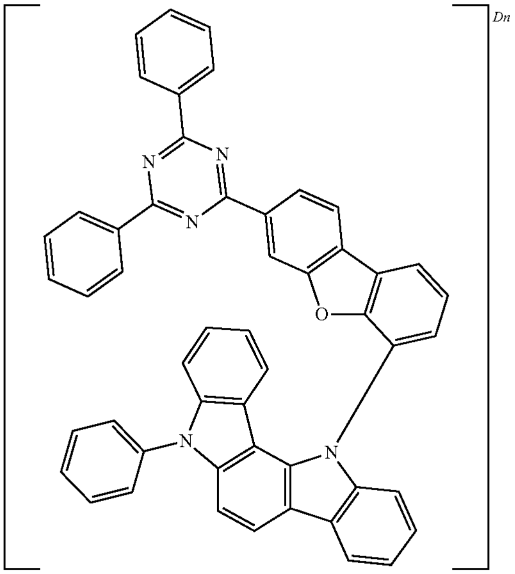
H1-54
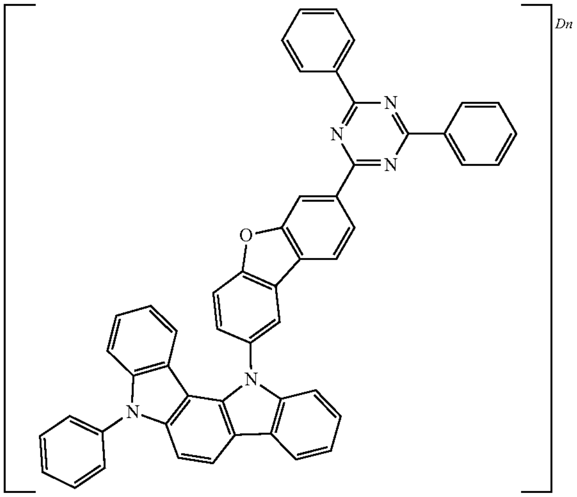

H1-55
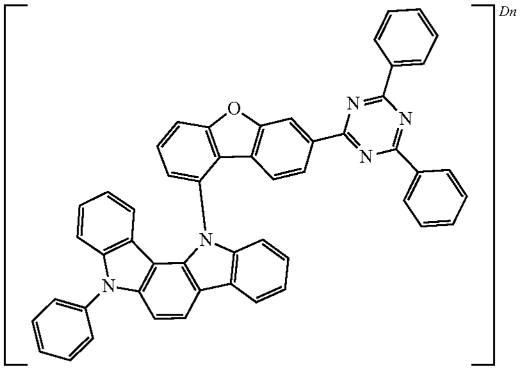
H1-56
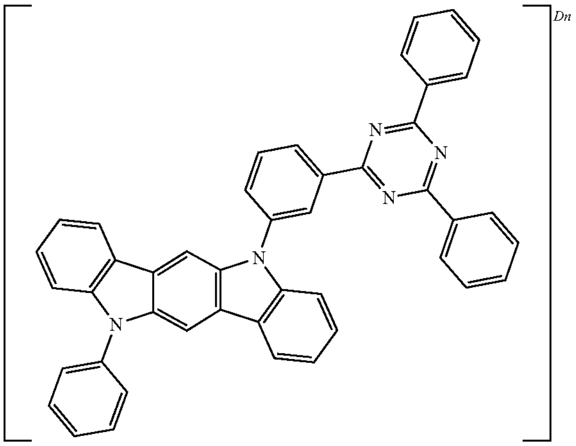
H1-57
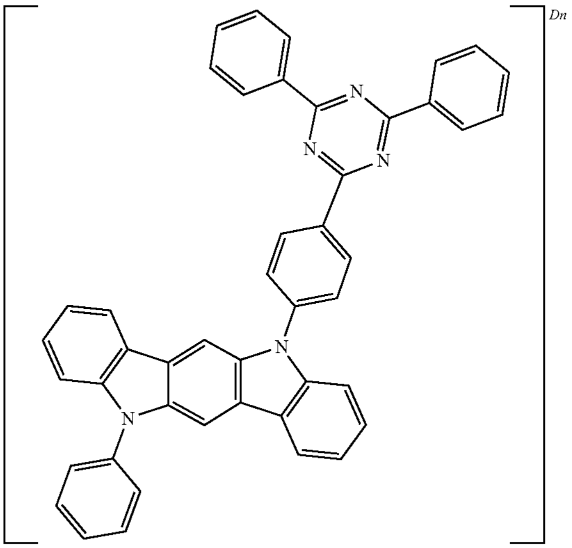
H1-58
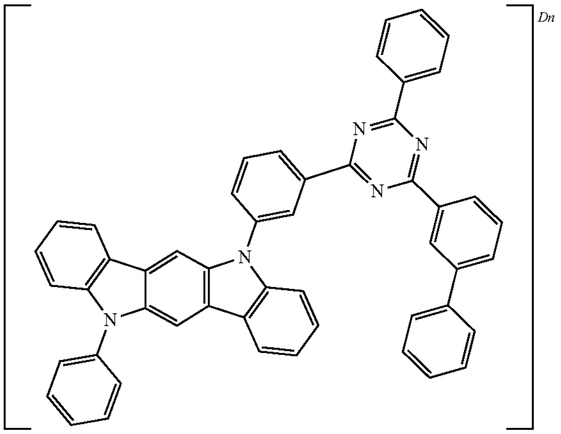
H1-59
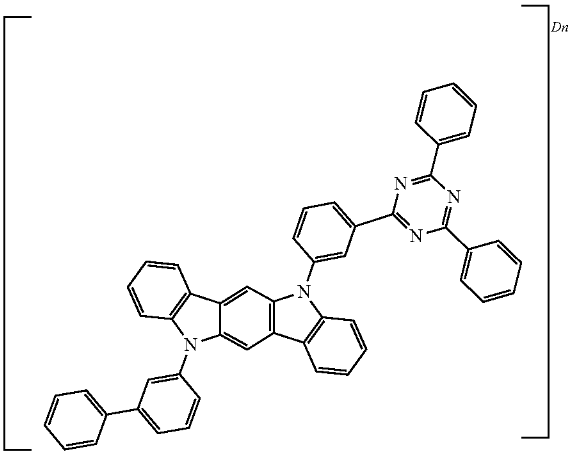
H1-60
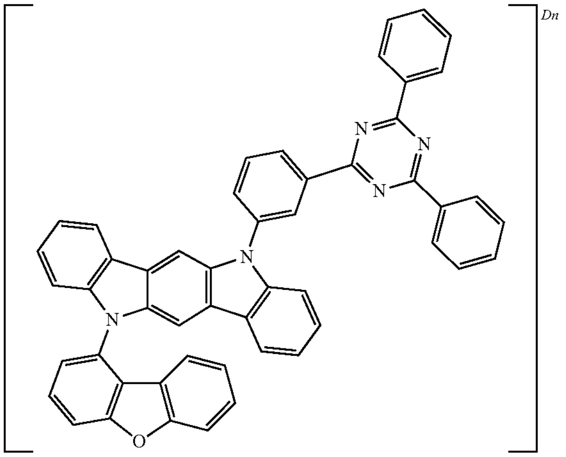

-continued
H1-61
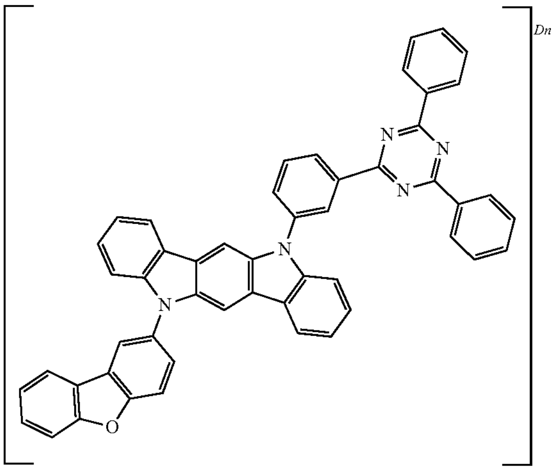
H1-62
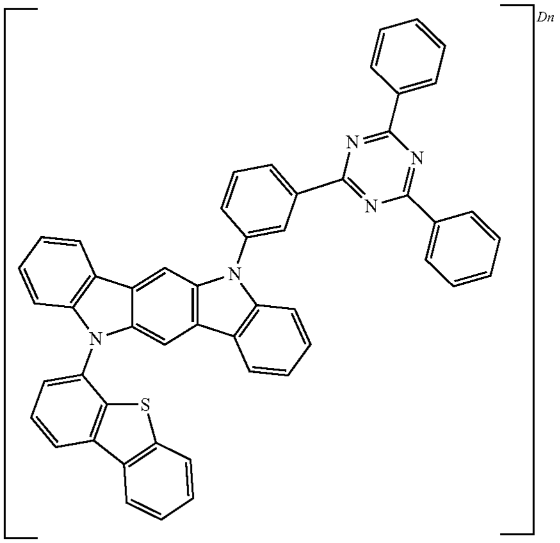
H1-63
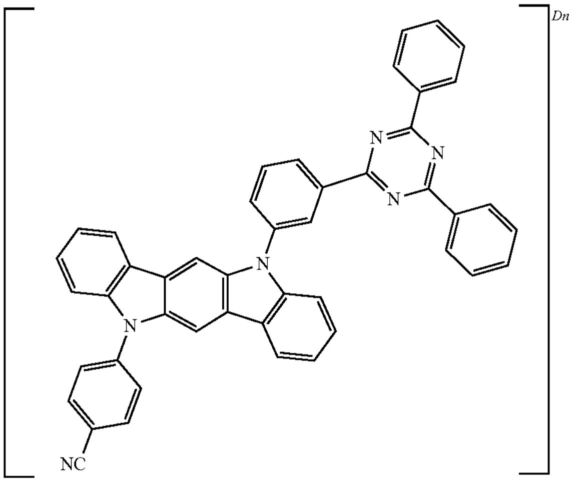
-continued
H1-64
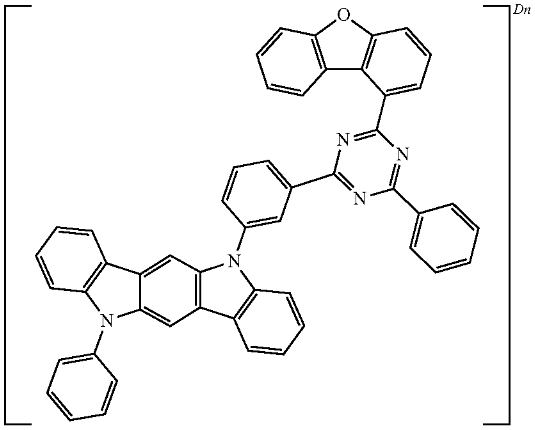
H1-65
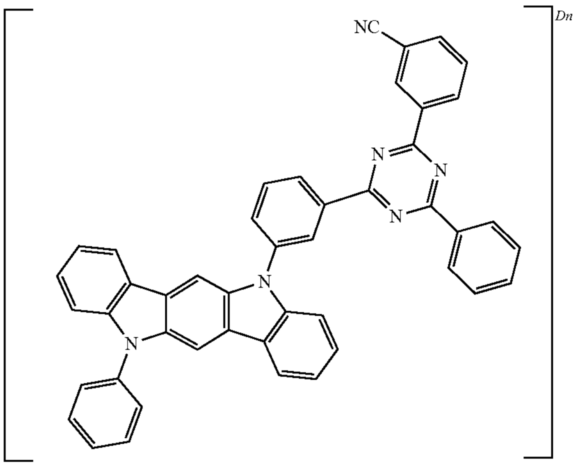
H1-66
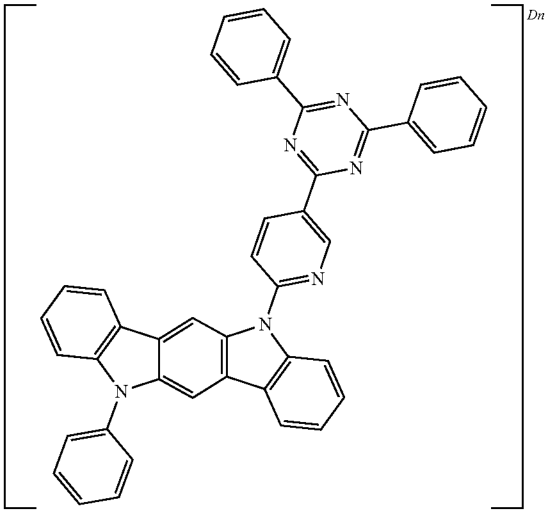

-continued
H1-67
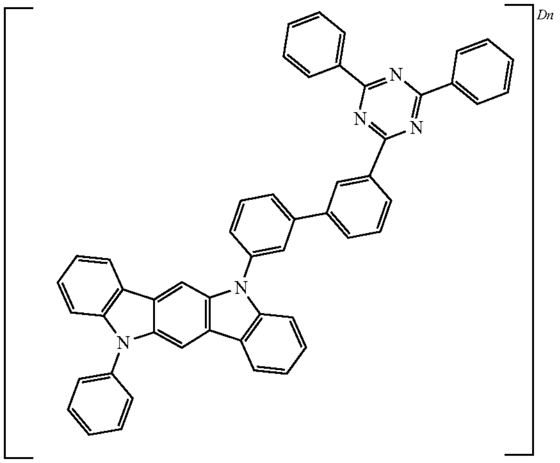
H1-68
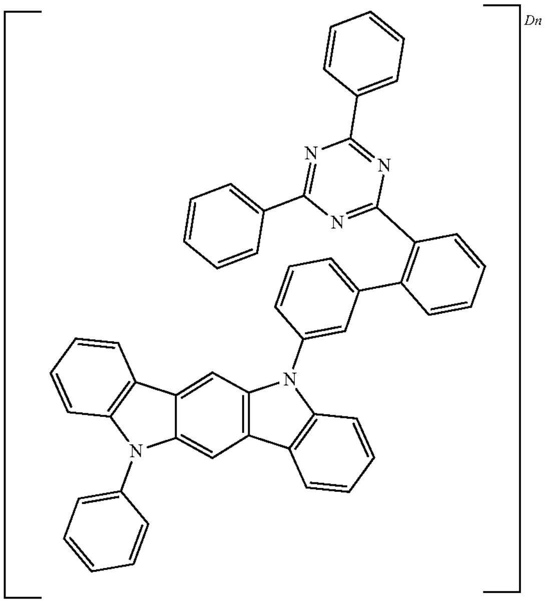
H1-69
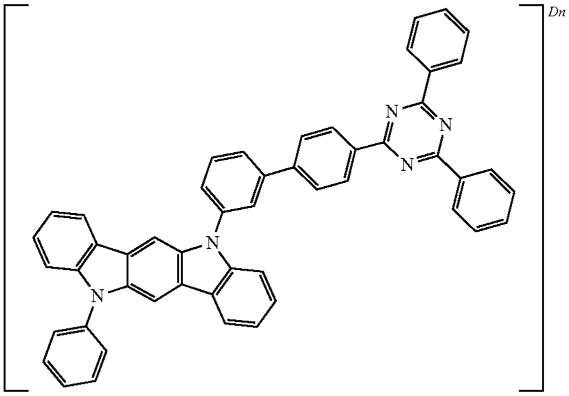
-continued
H1-70
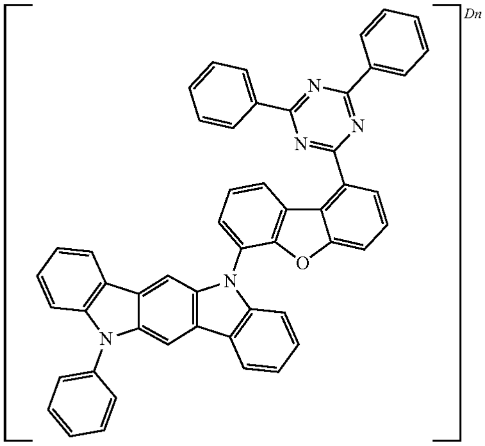
H1-71
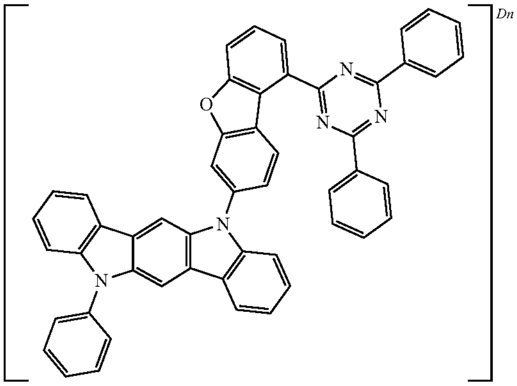
H1-72
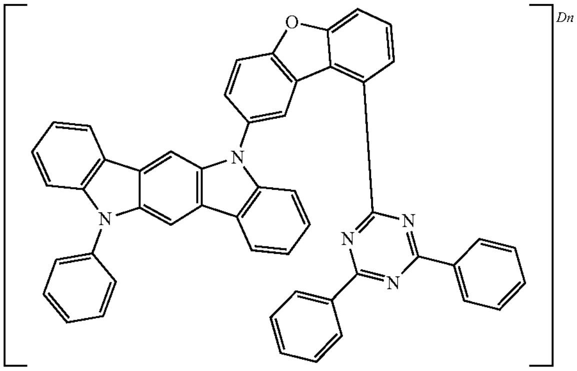
H1-73
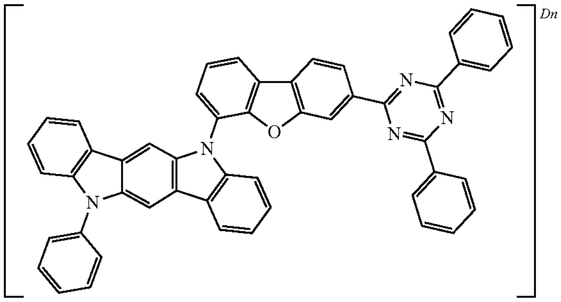

-continued
H1-74
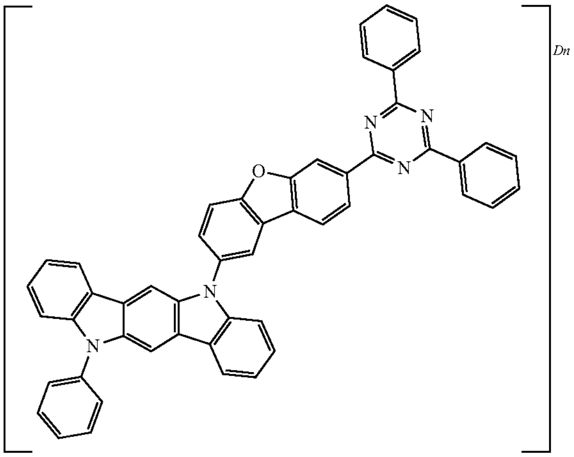
H1-75
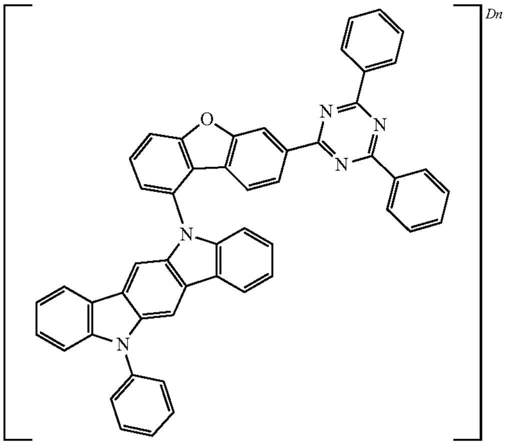
H1-76
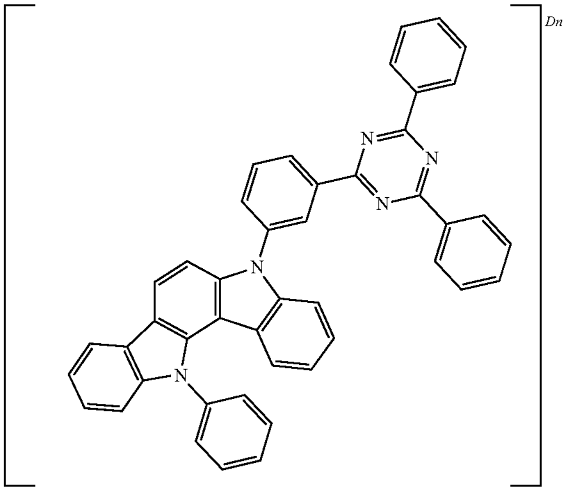
-continued
H1-77
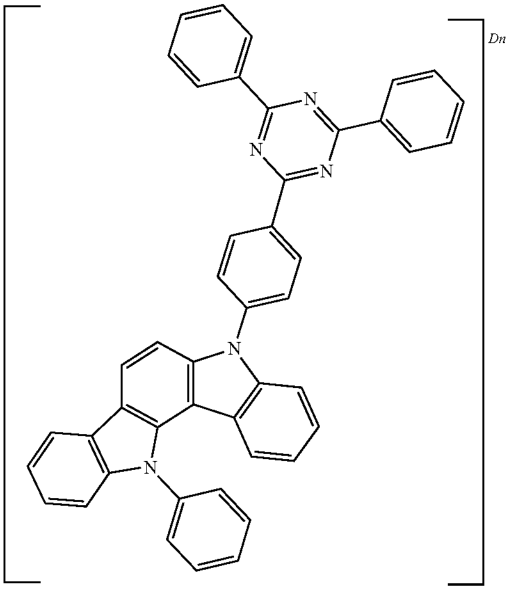
H1-78
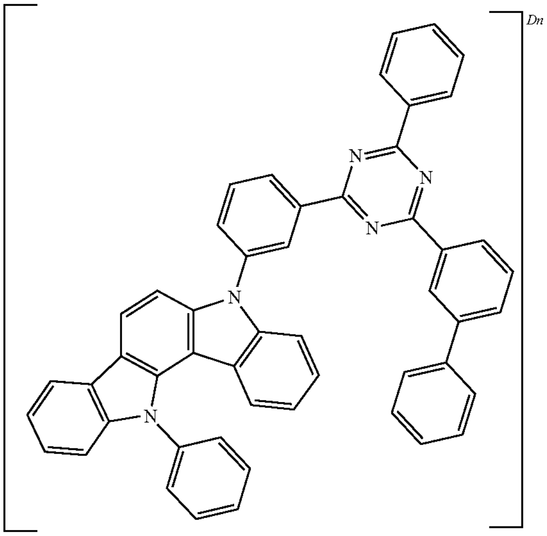

-continued
H1-79
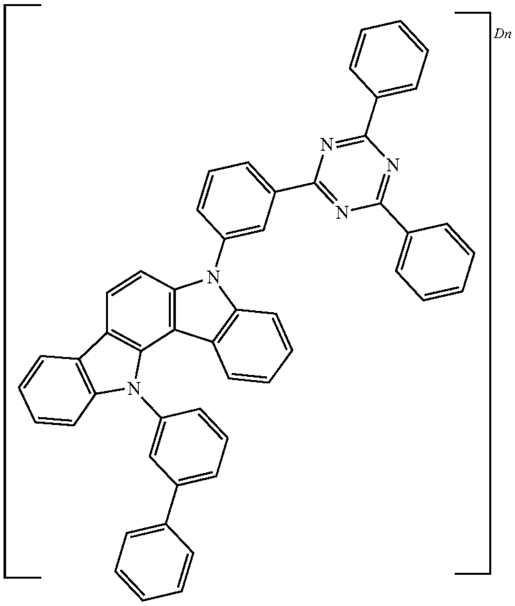
H1-80
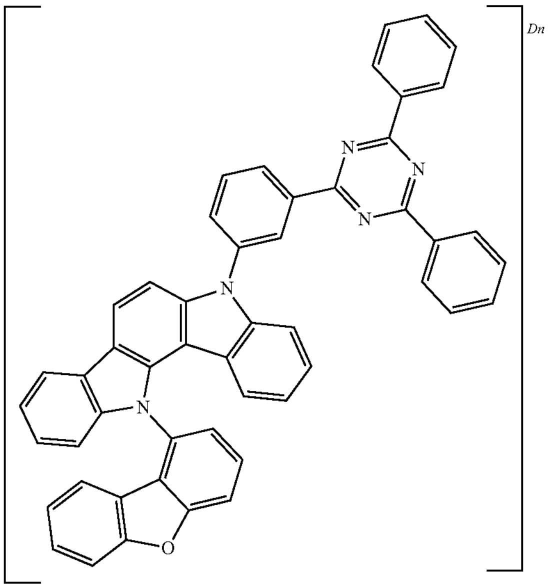
-continued
H1-81
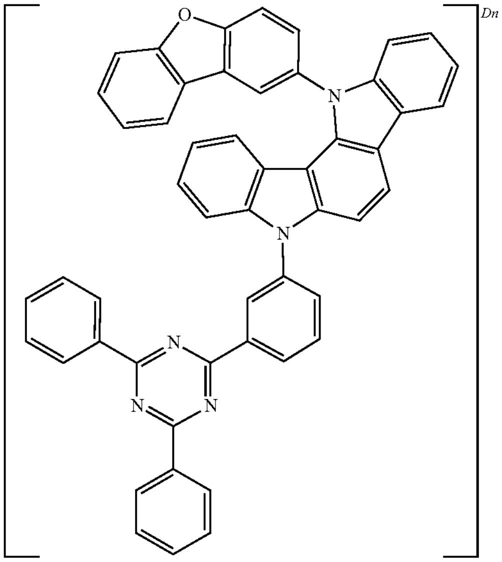
H1-82
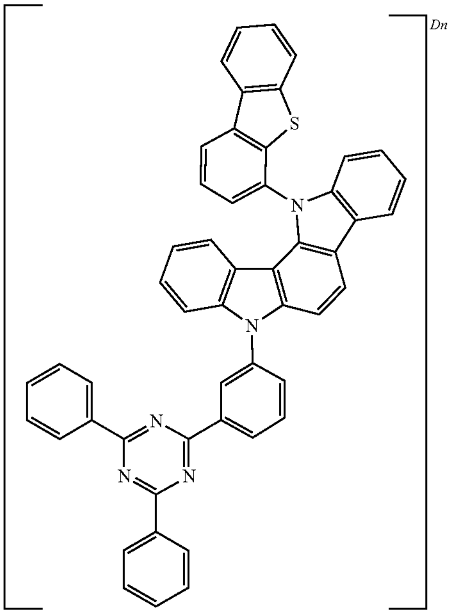

-continued
H1-83
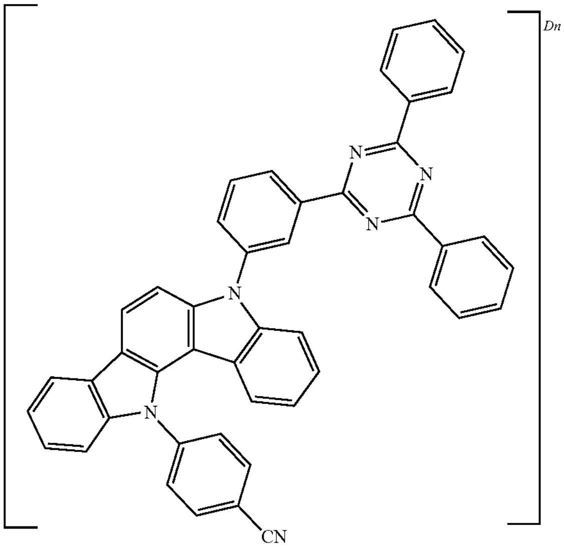
H1-84
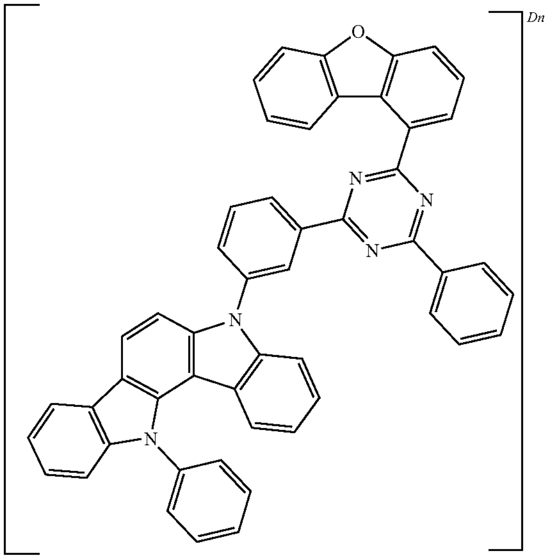
-continued
H1-85
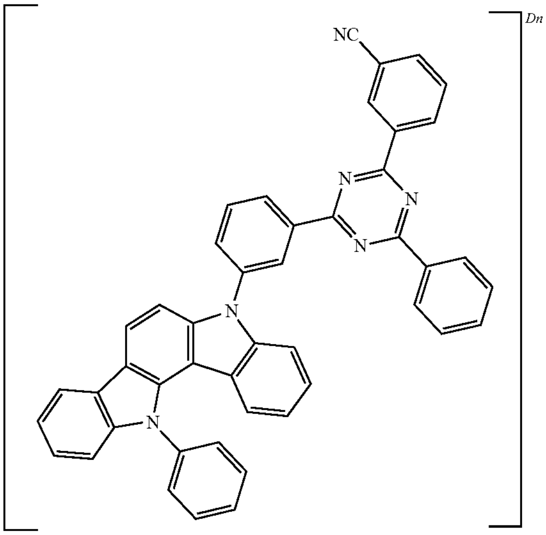
H1-86
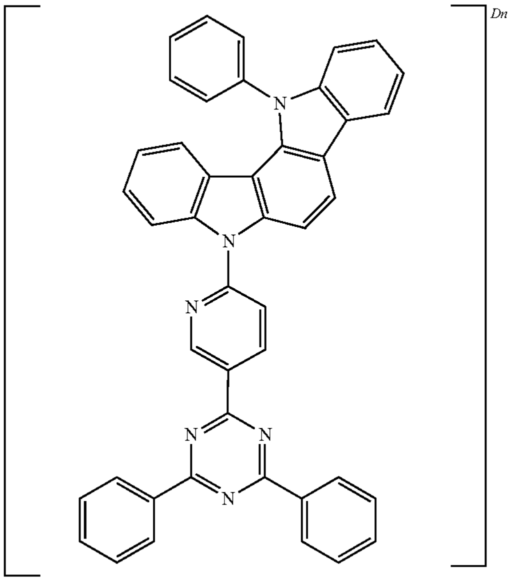
H1-87
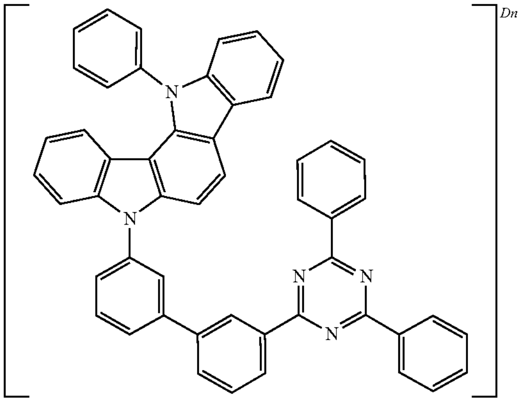

-continued
H1-88
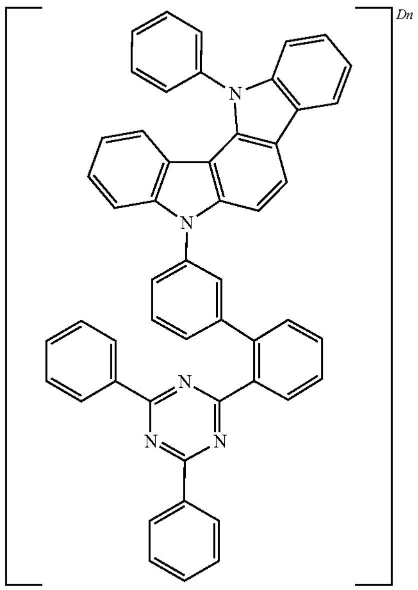
H1-89
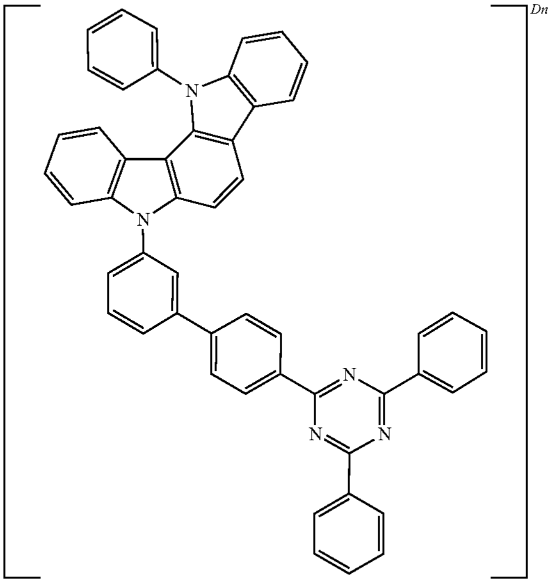
-continued
H1-90
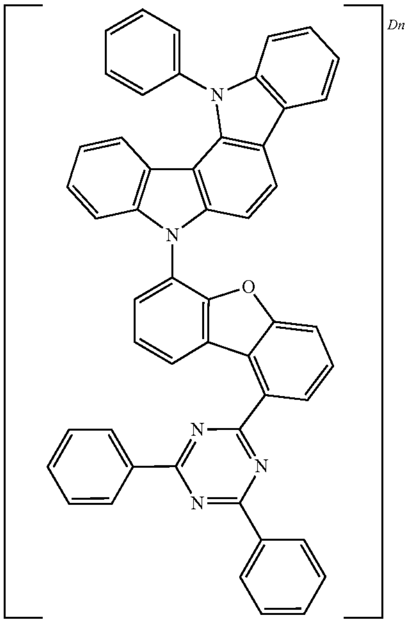
H1-91
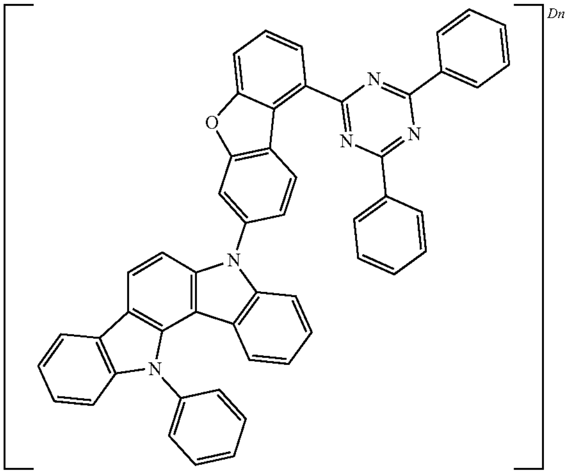
H1-92
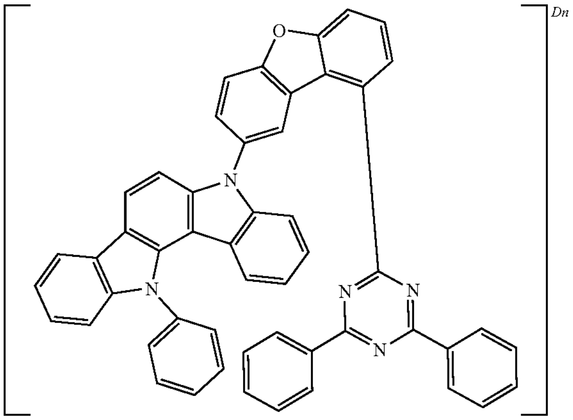

-continued
H1-93
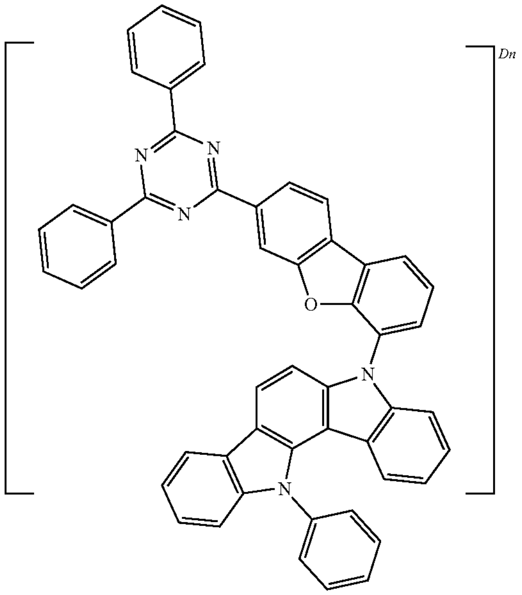
H1-94
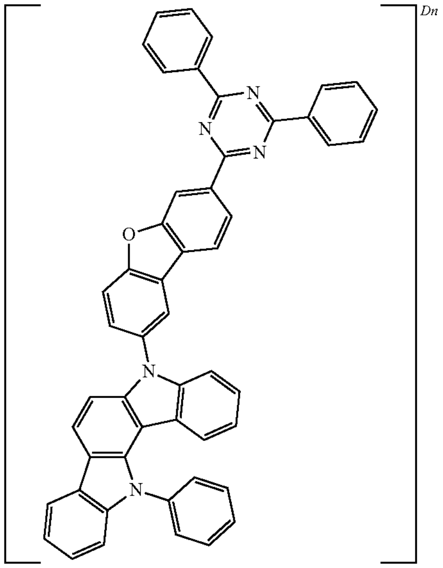
H1-95
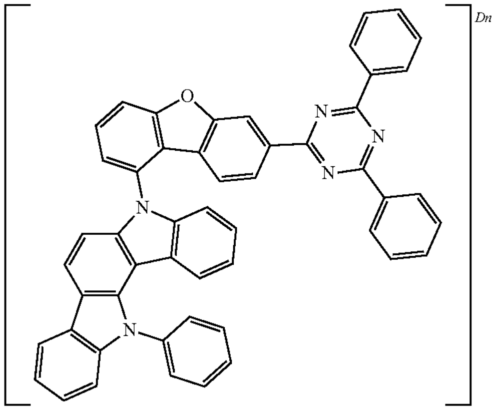
-continued
H1-96
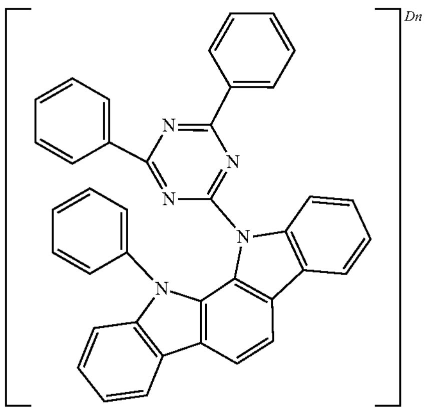
H1-97
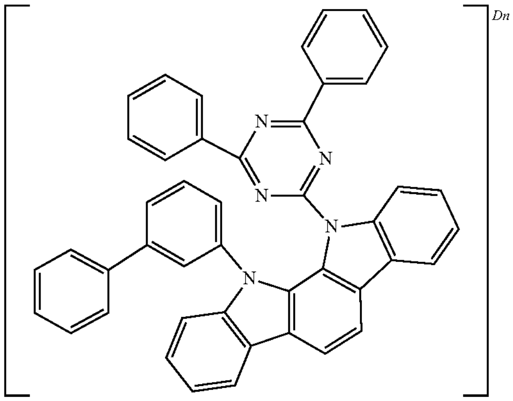
H1-99
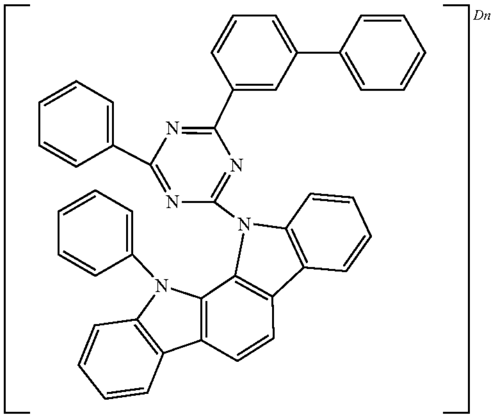

-continued
H1-100
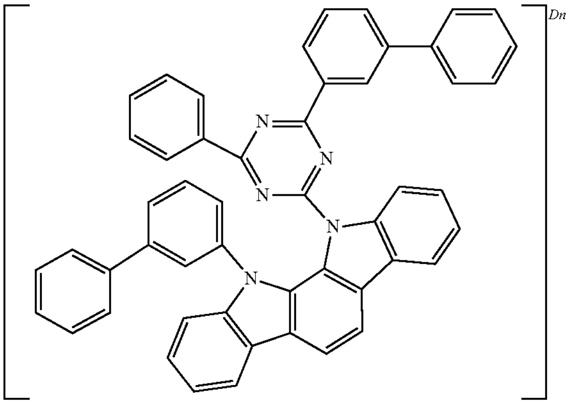
H1-101
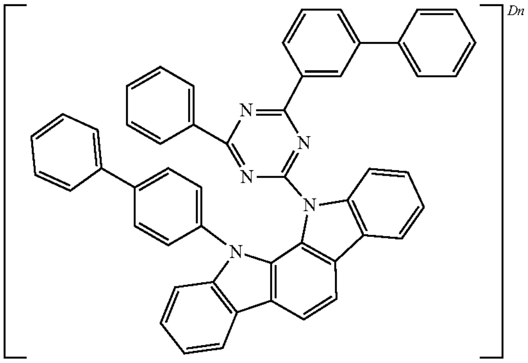
H1-102
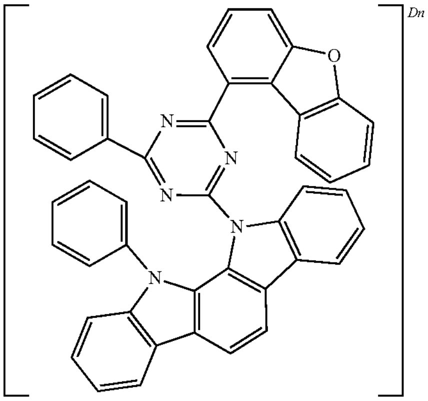
-continued
H1-103
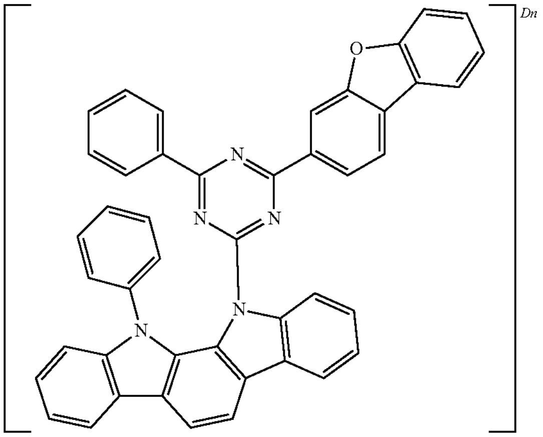
H1-104
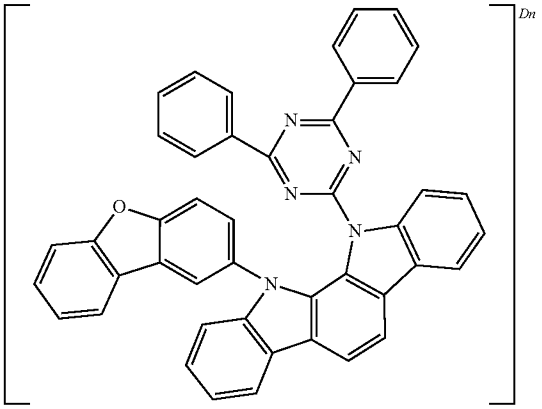
H1-105
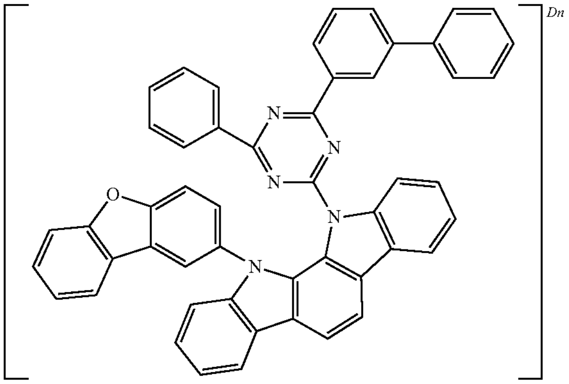

-continued
H1-106
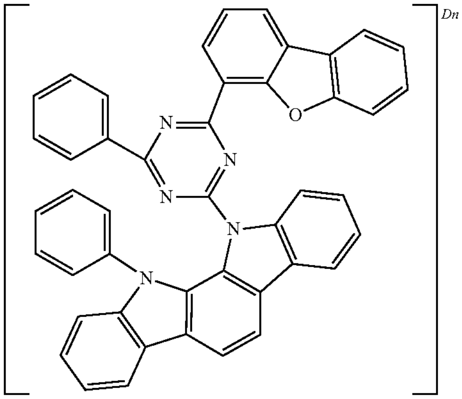
H1-107
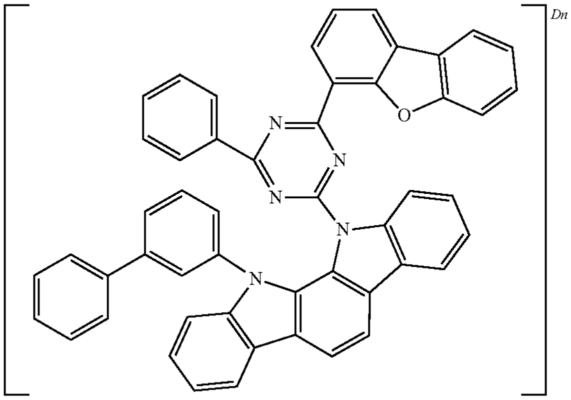
H1-108
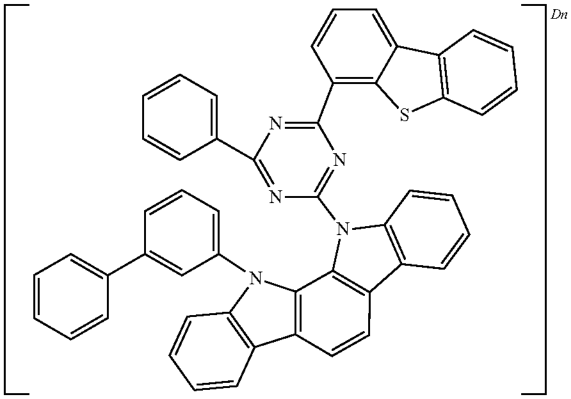
H1-109
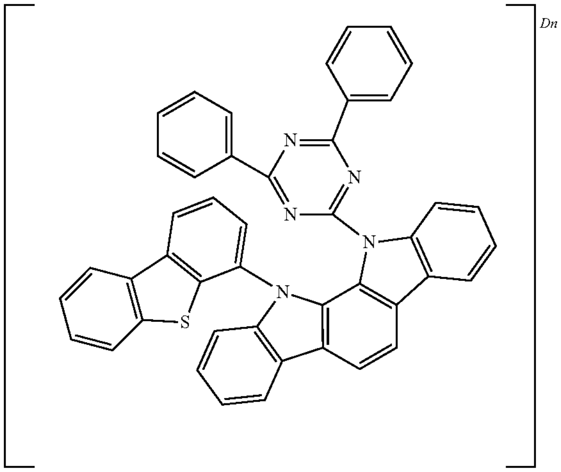
H1-110
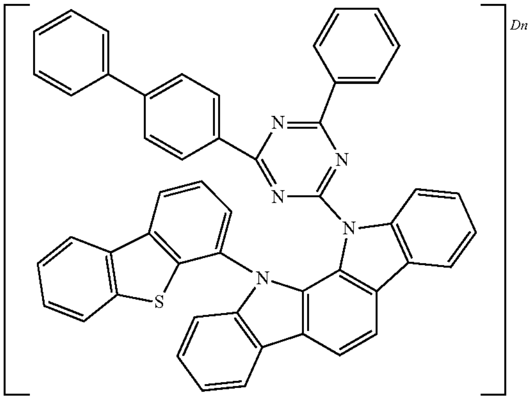
H1-111
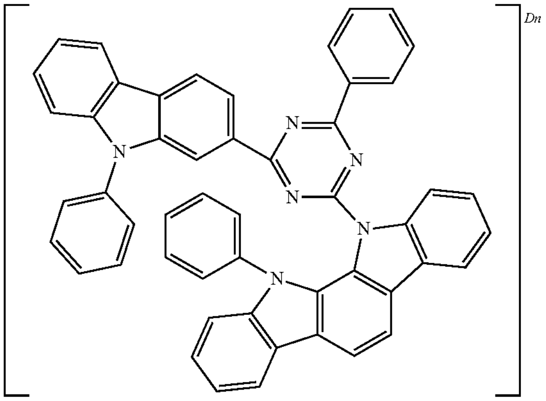

-continued
H1-112
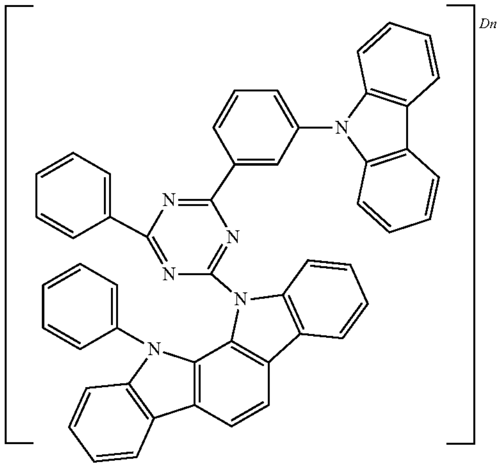
H1-113
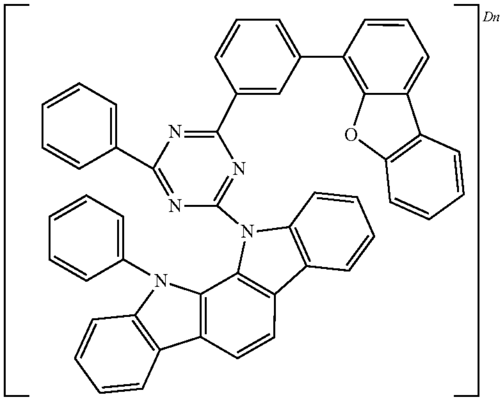
H1-114
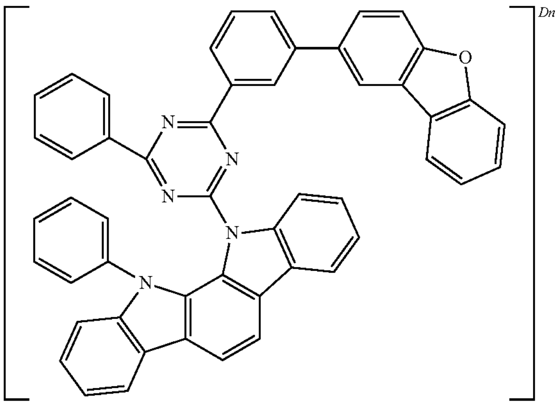
-continued
H1-115
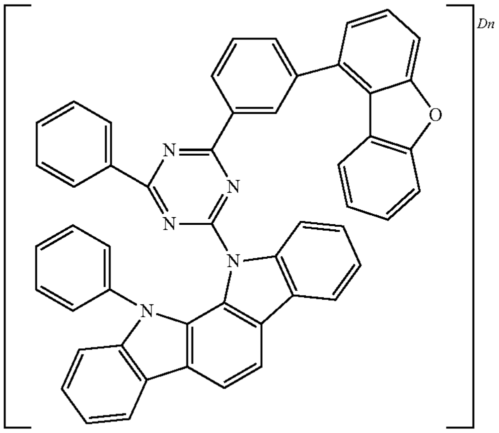
H1-116
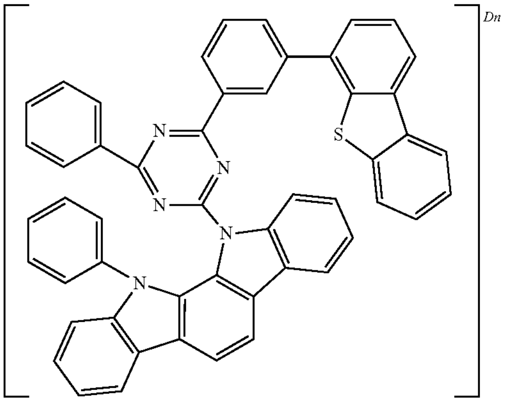
H1-117
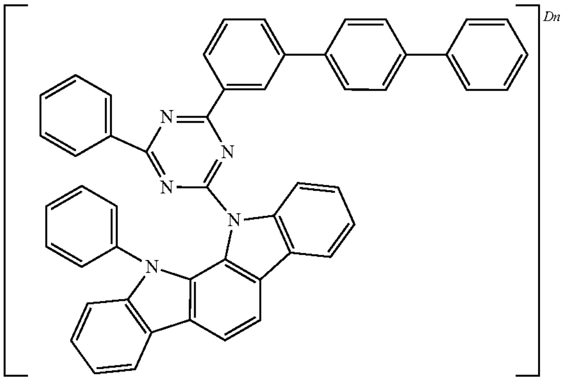

-continued
H1-118
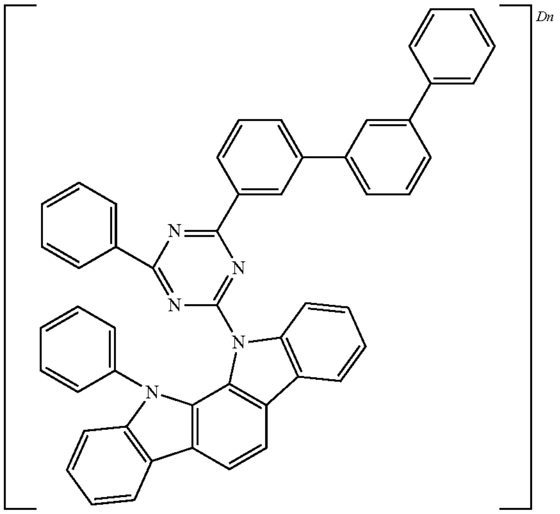
H1-119
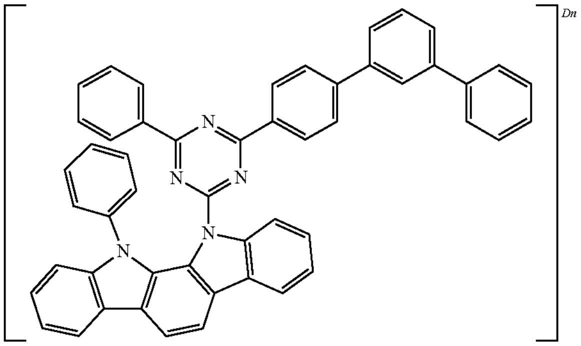
H1-120
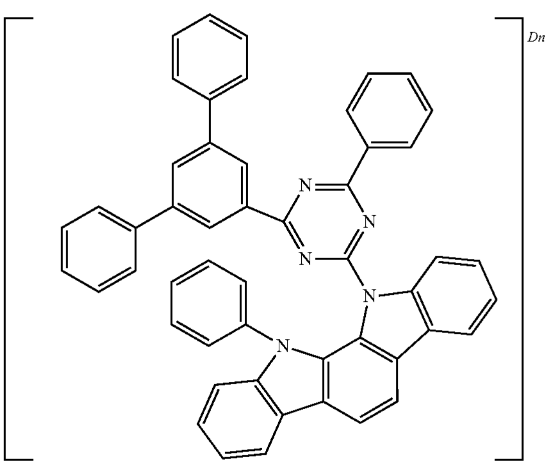
-continued
H1-121
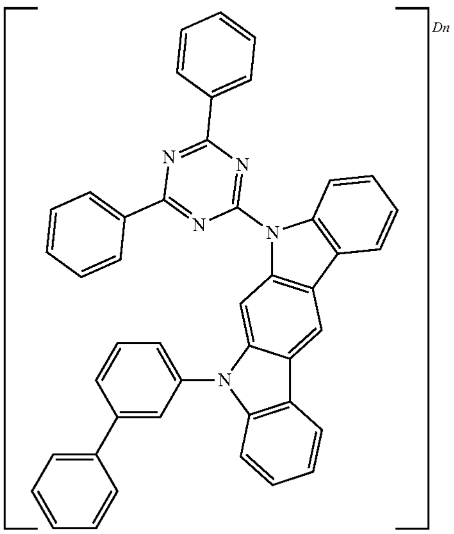
H1-122
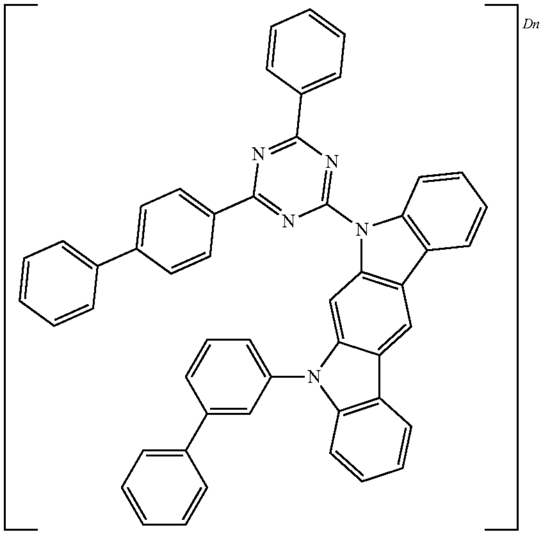

-continued
H1-123
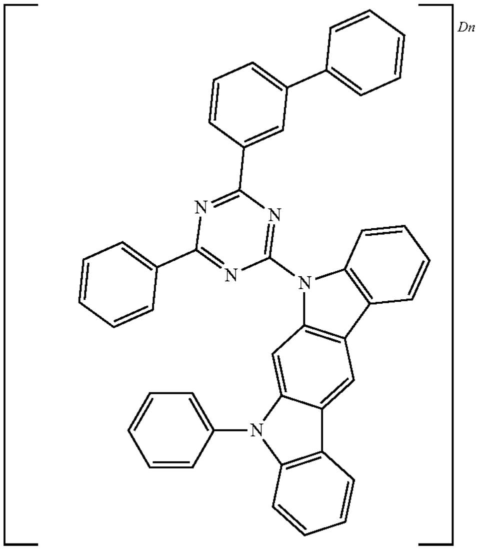
H1-124
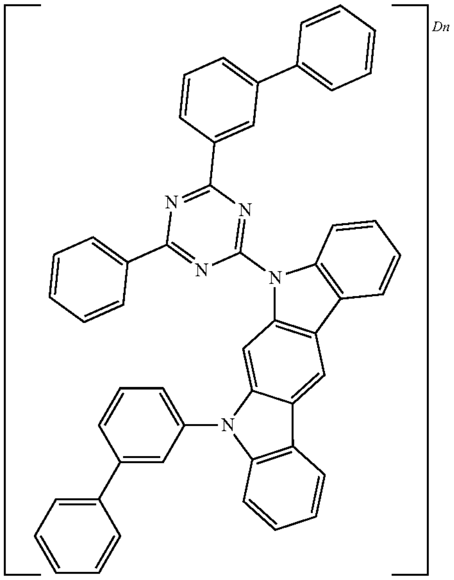
-continued
H1-125
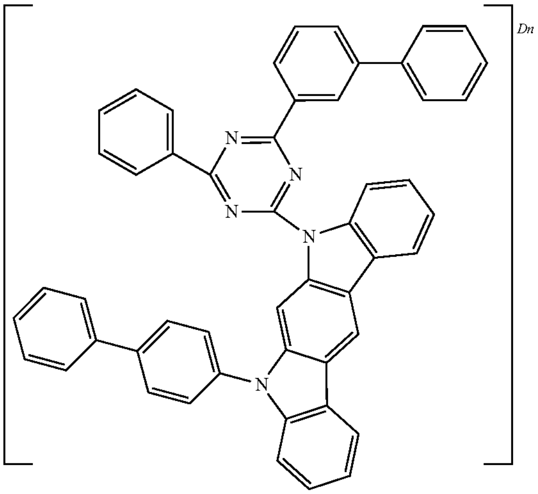
H1-126
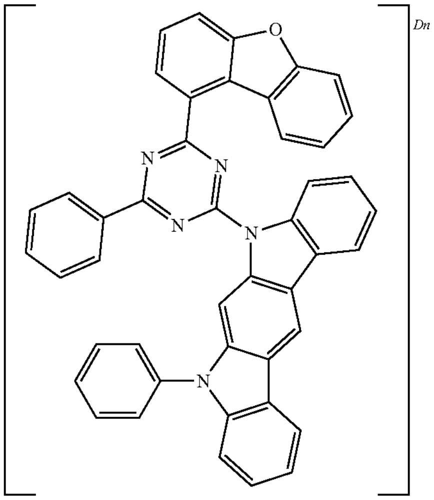
H1-127
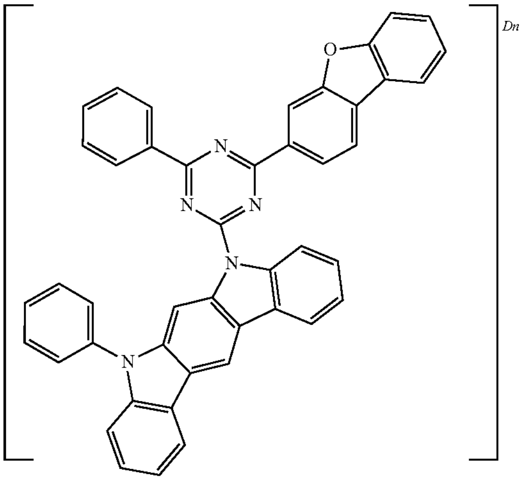

-continued
H1-128
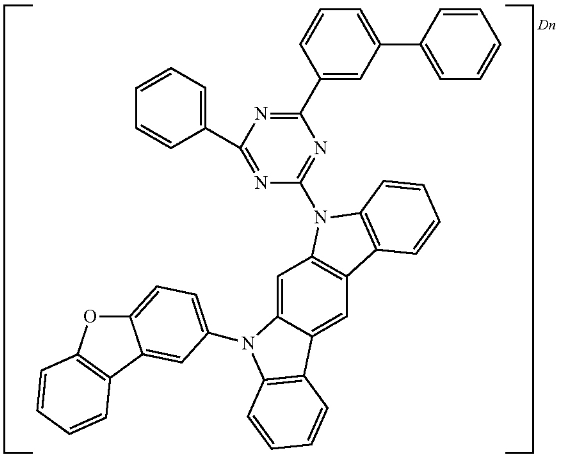
H1-129
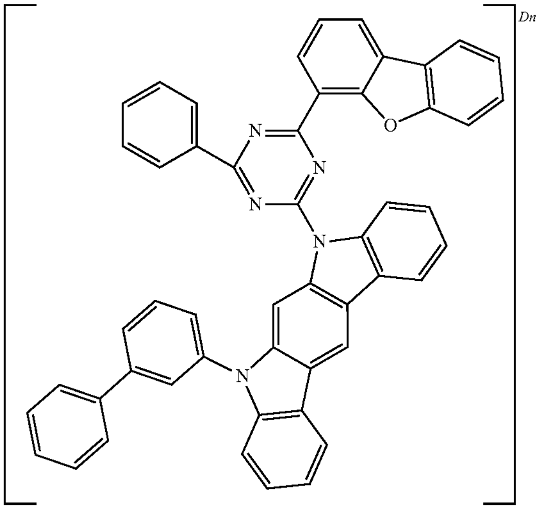
H1-130
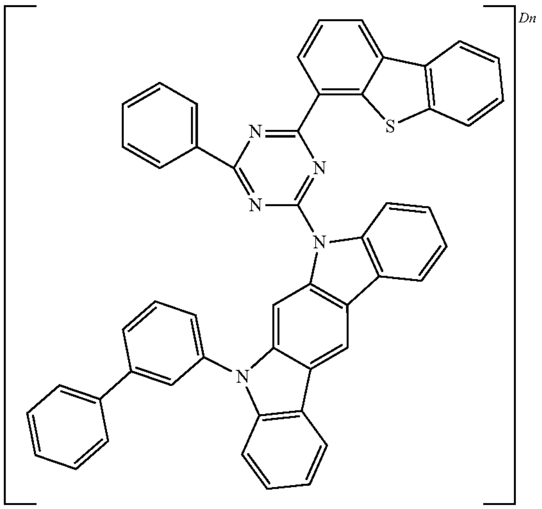
-continued
H1-131
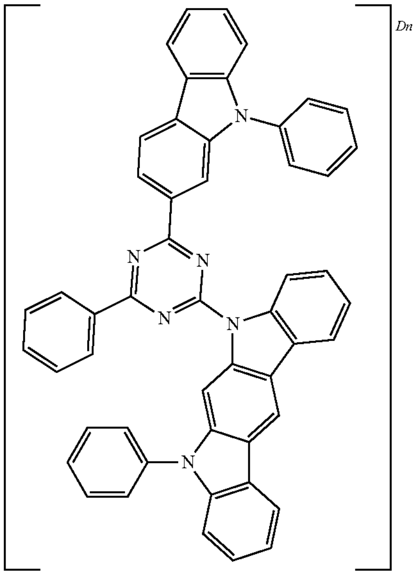
H1-132
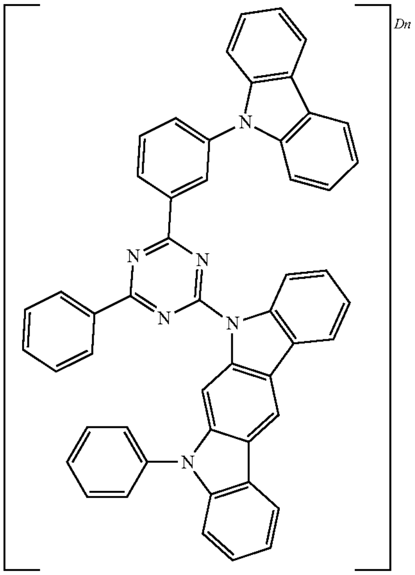

-continued
H1-133
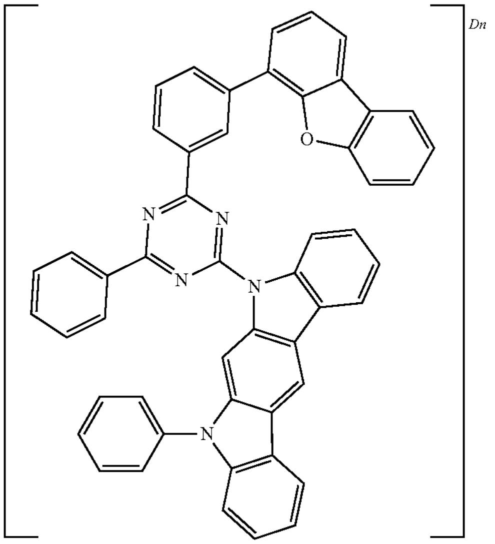
-continued
H1-135
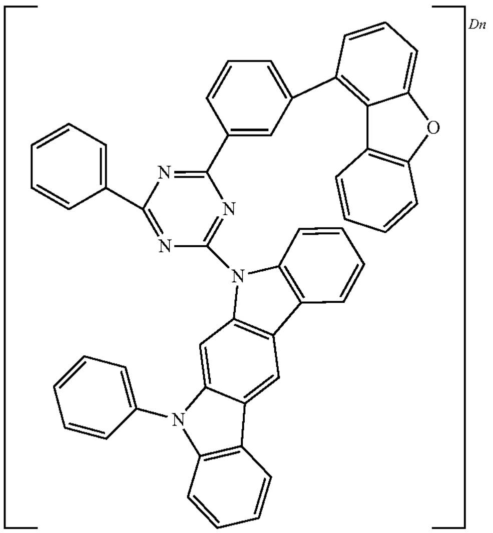
H1-134
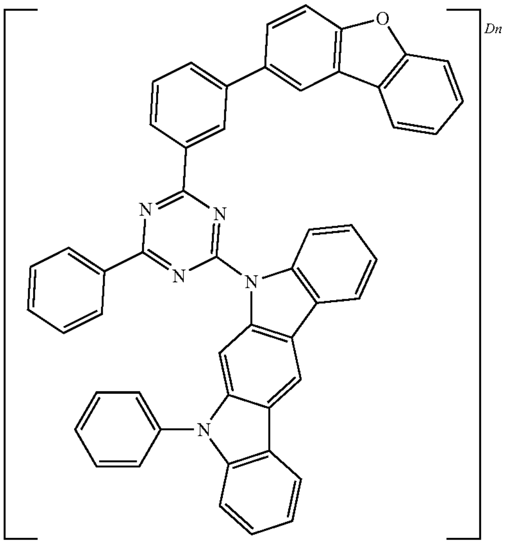
H1-136
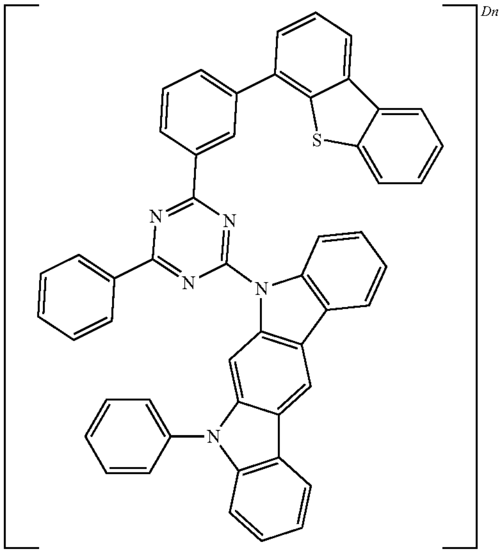

-continued
H1-137
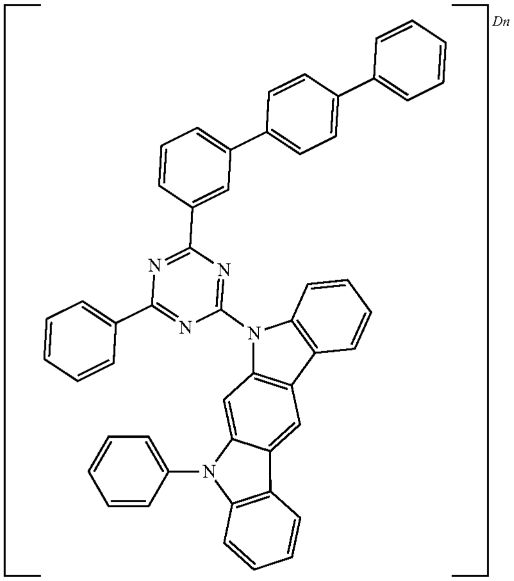
H1-138
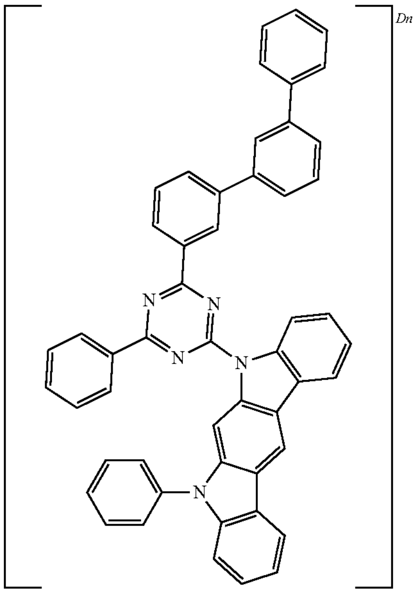
H1-139
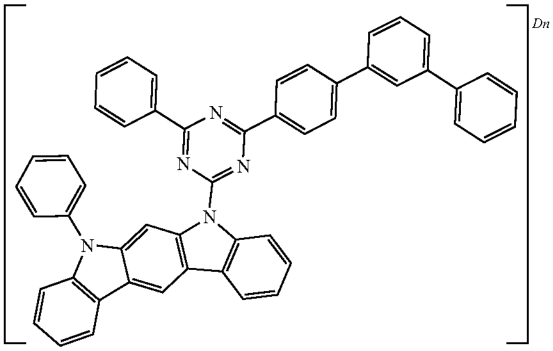
-continued
H1-140
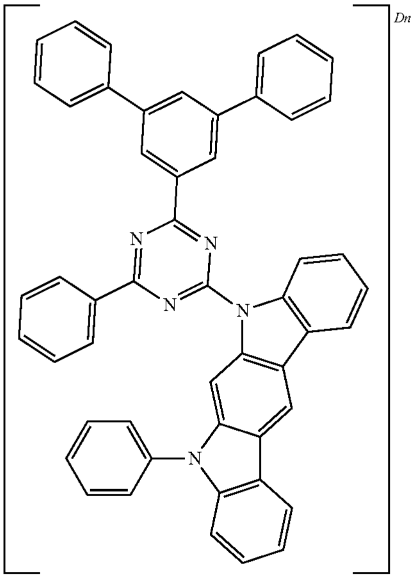
H1-141
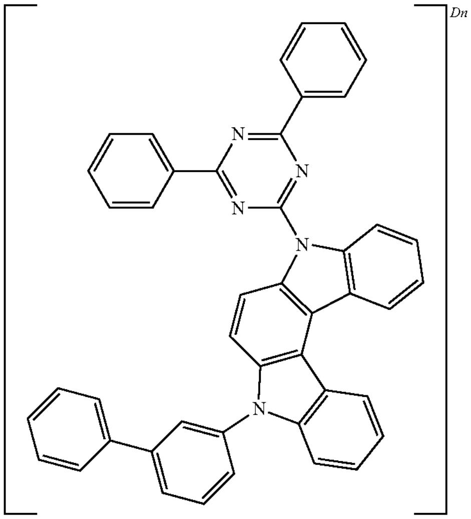
H1-142
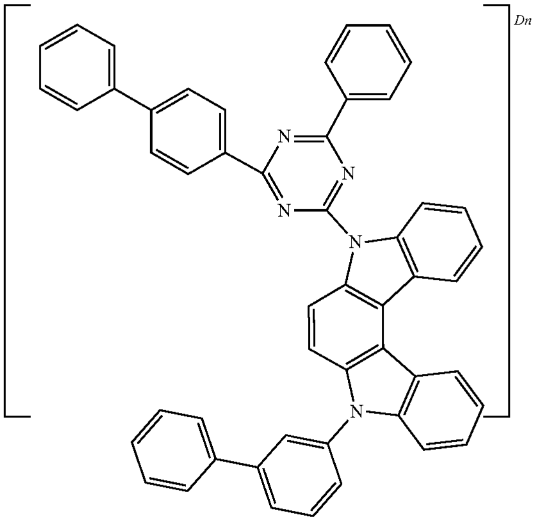

-continued
H1-143
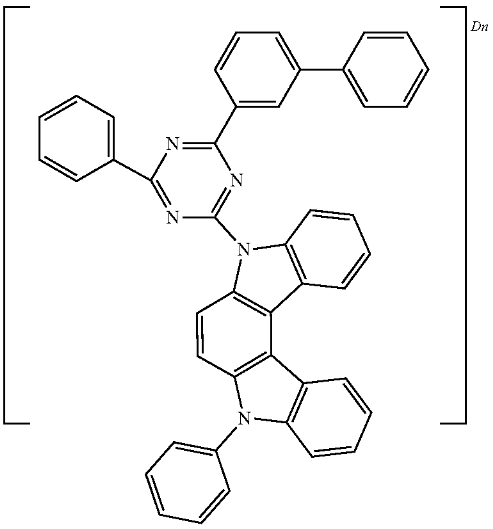
H1-144
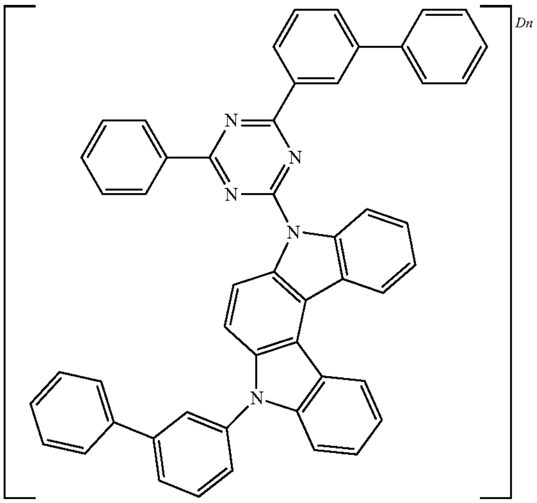
H1-145
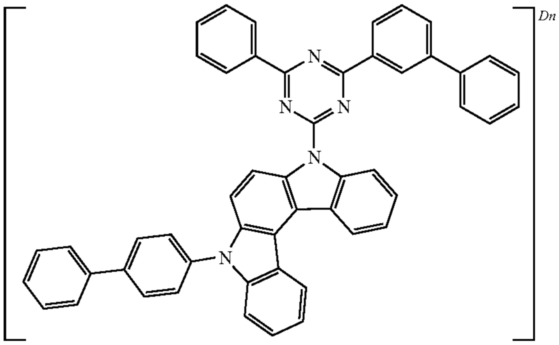
-continued
H1-146
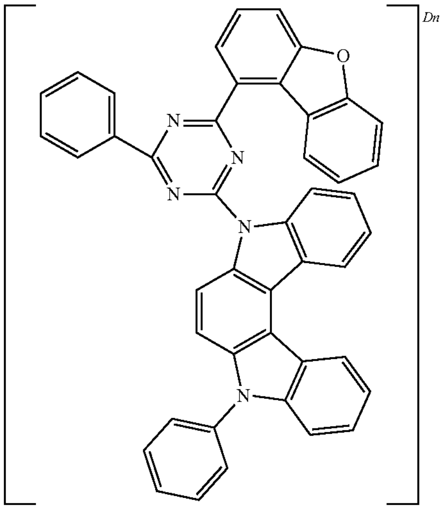
H1-147
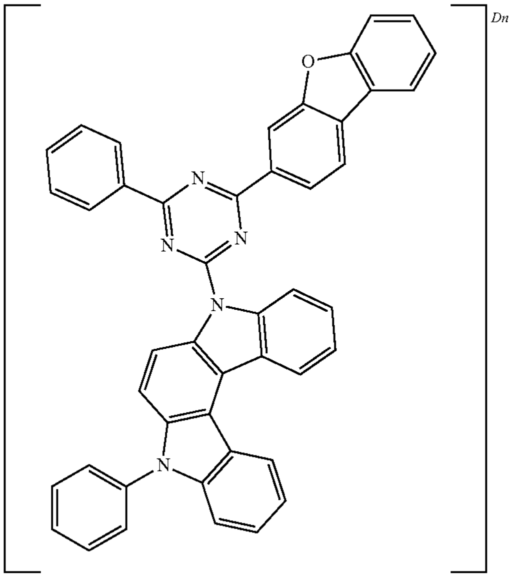

-continued
H1-148
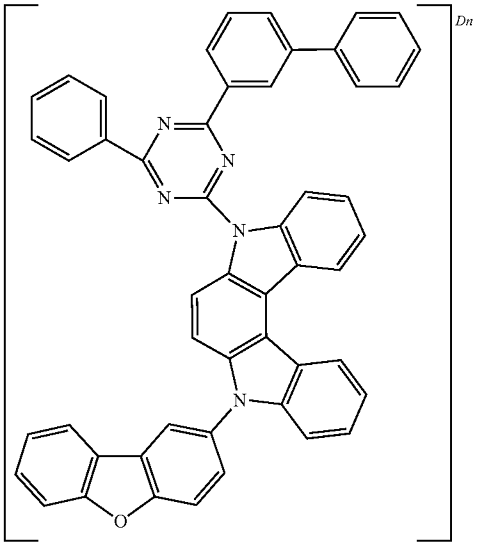
H1-149
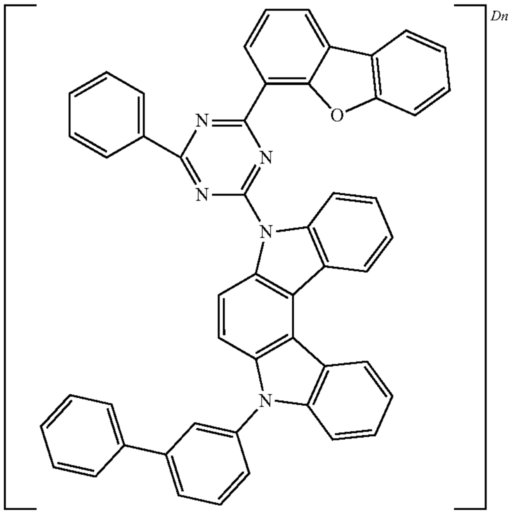
H1-150
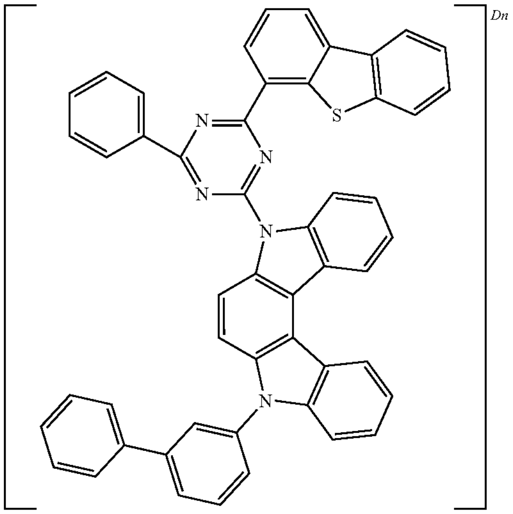
-continued
H1-151
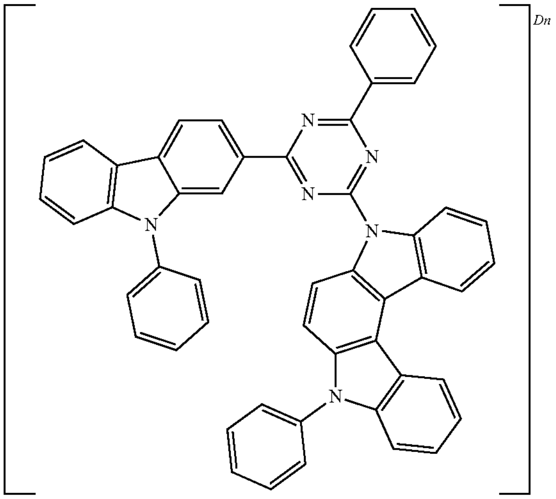
H1-152
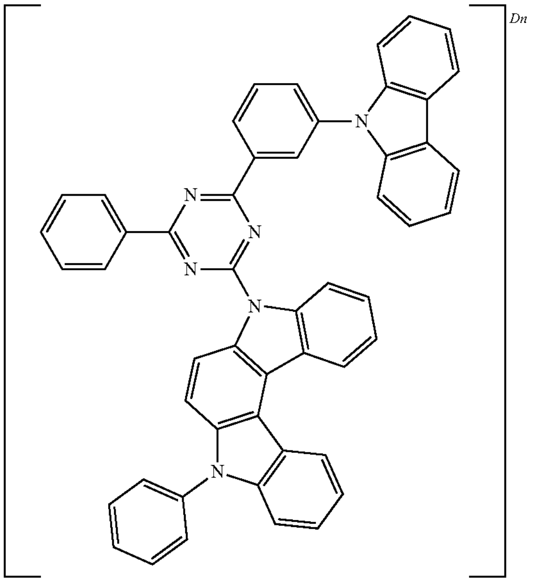
H1-153
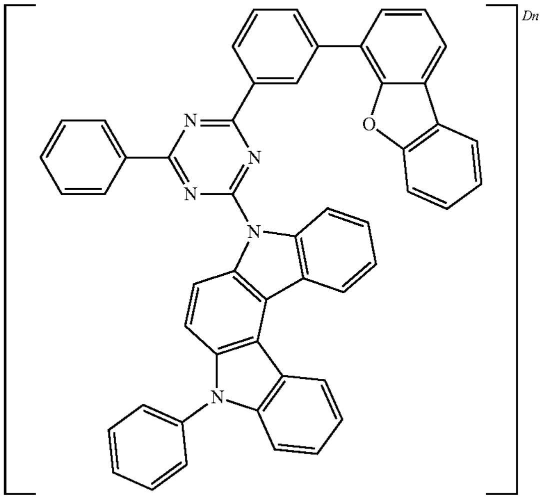

-continued
H1-154
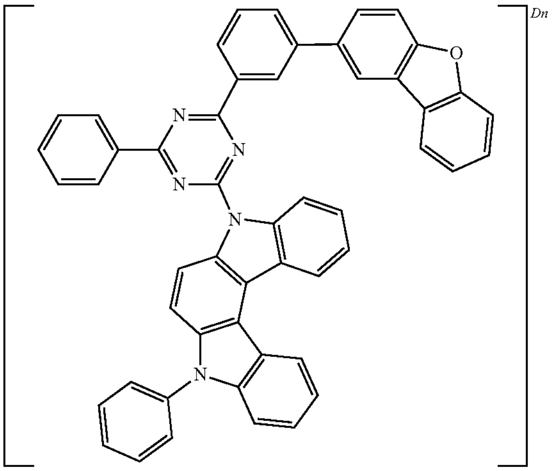
H1-155
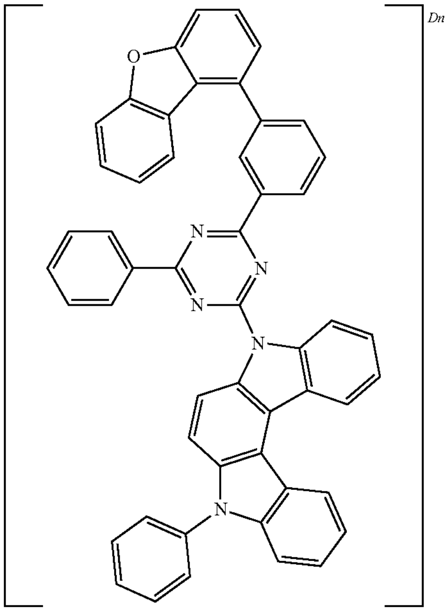
H1-156
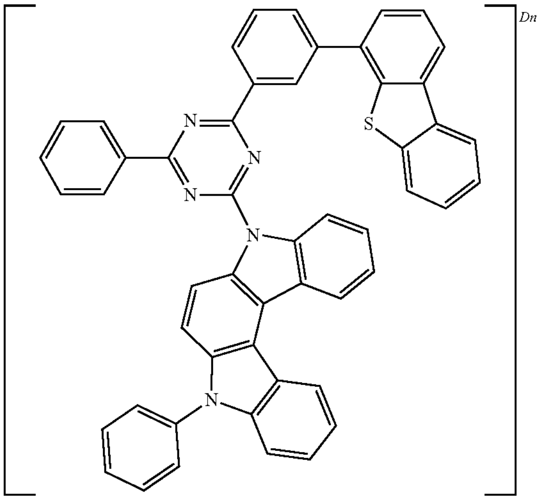
-continued
H1-157
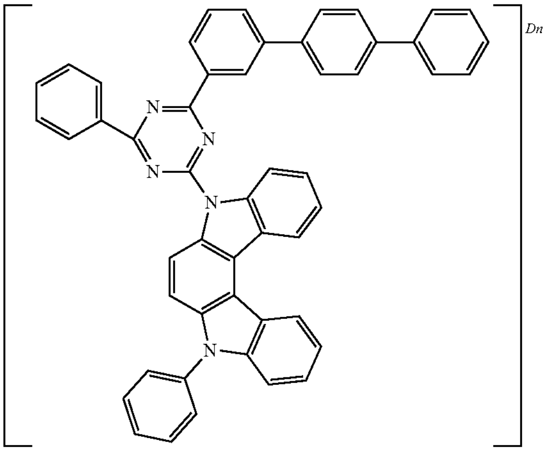
H1-158
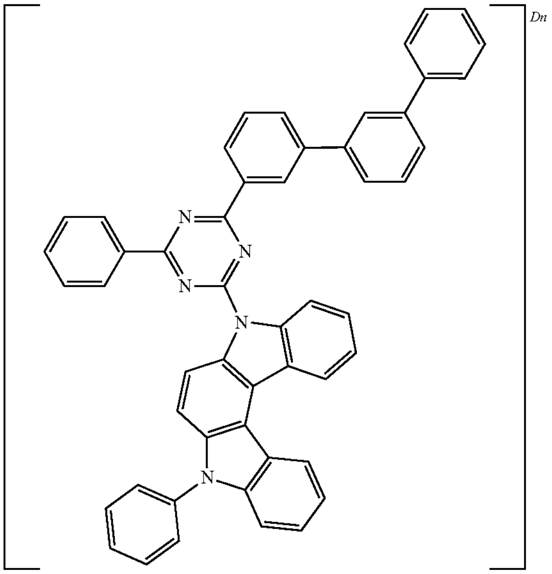
H1-159
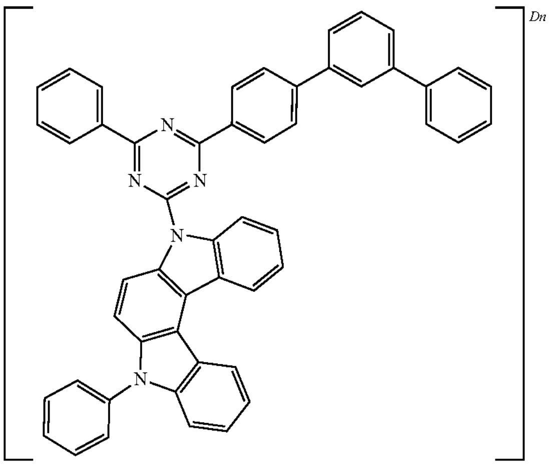

-continued
H1-160
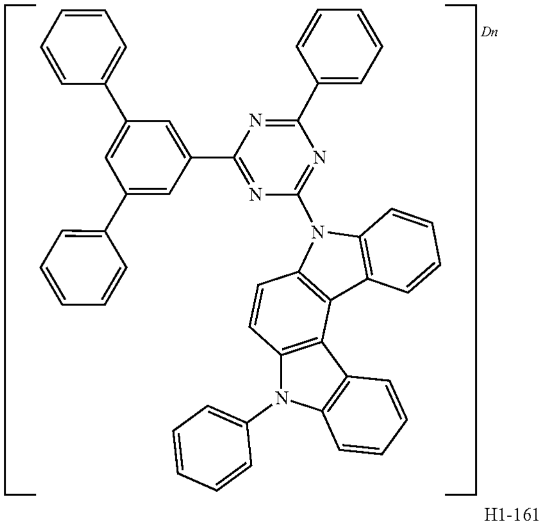
H1-161
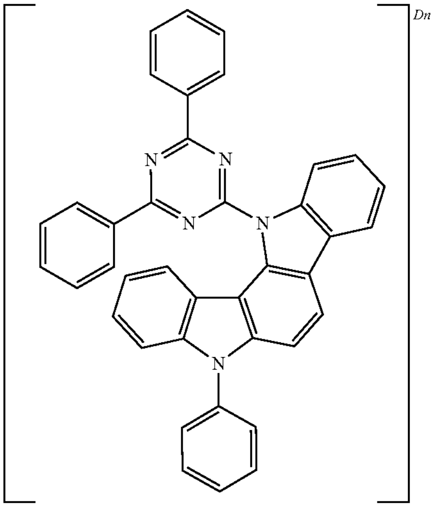
H1-162
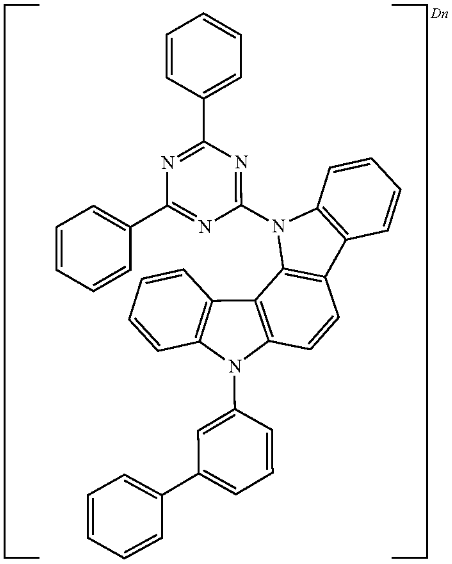
-continued
H1-163
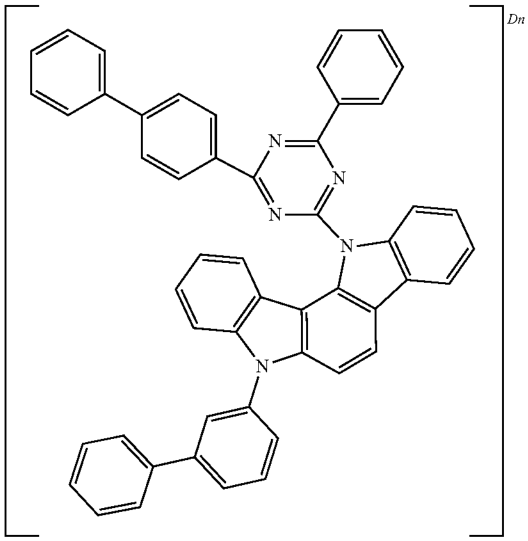
H1-164
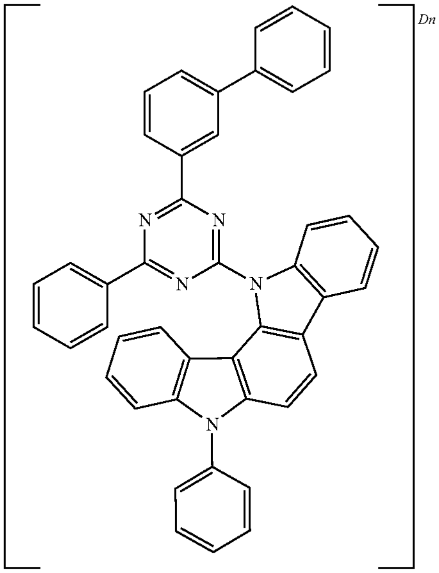

-continued
H1-165
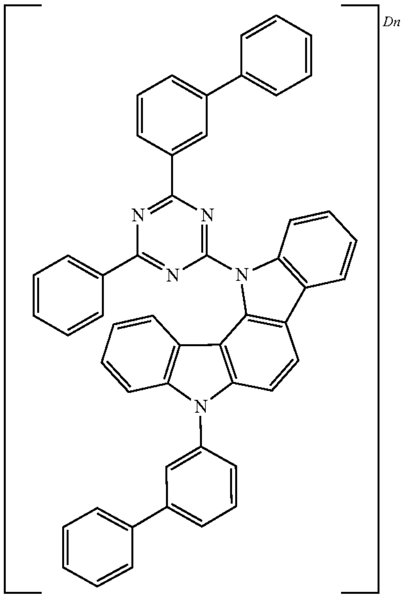
H1-166
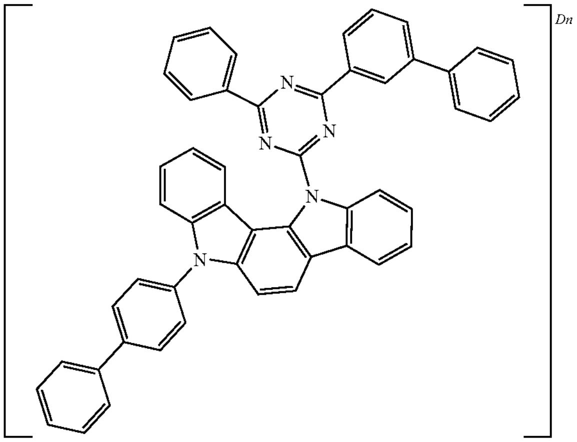
H1-167
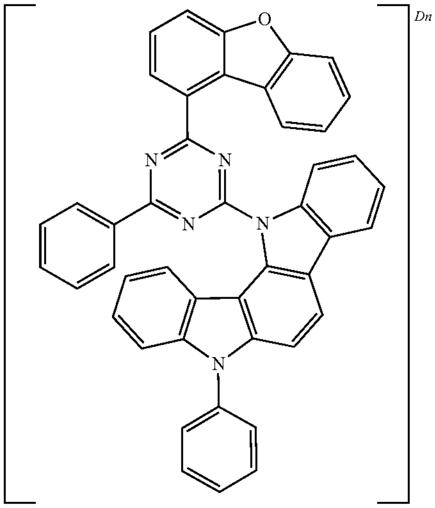
-continued
H1-168
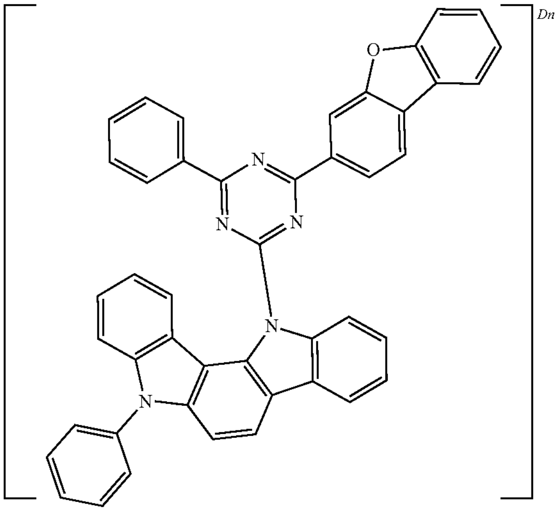
H1-169
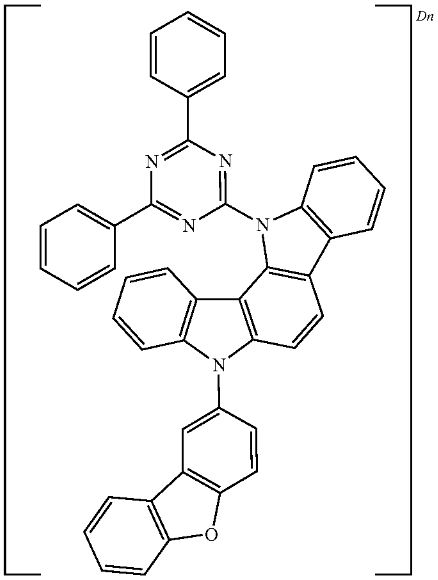

H1-170
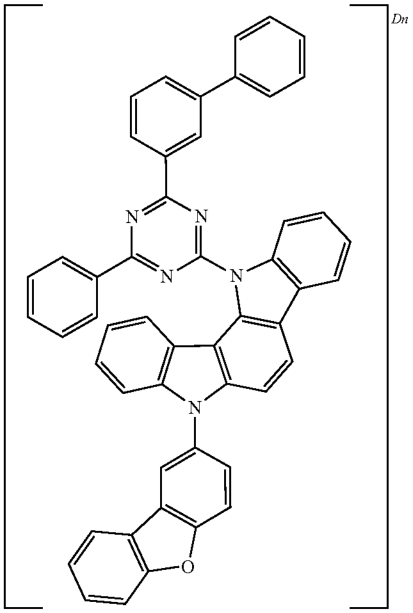
H1-171
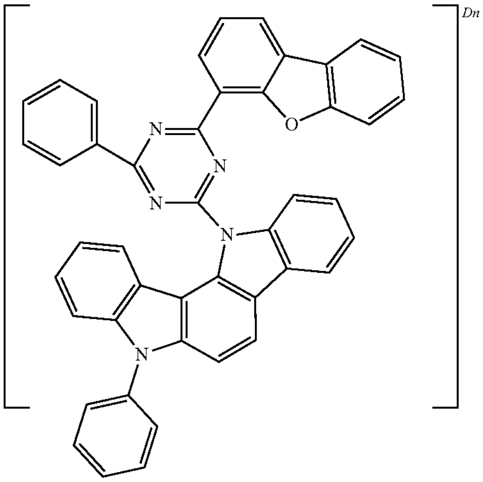
H1-172
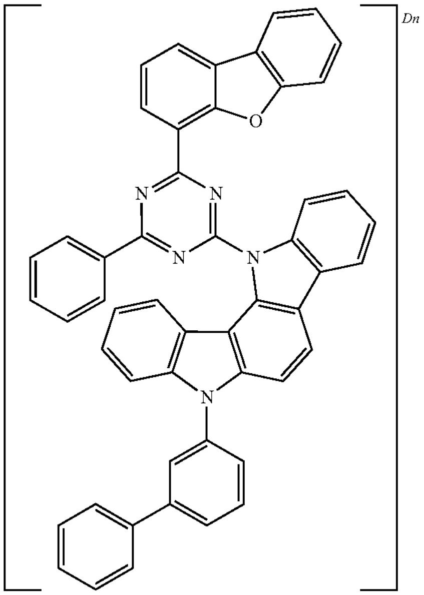
H1-173
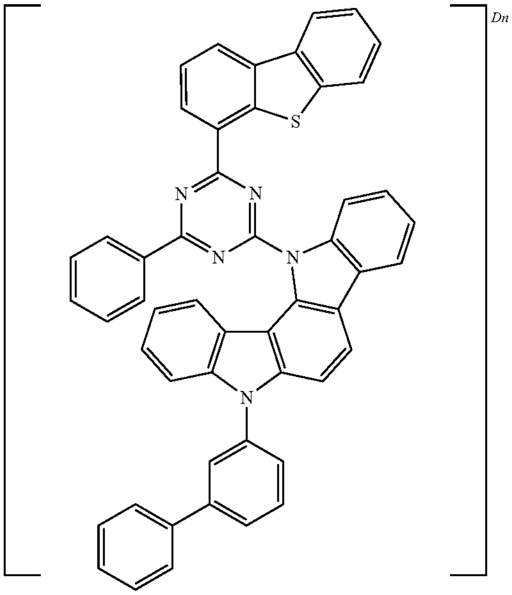

-continued
H1-174
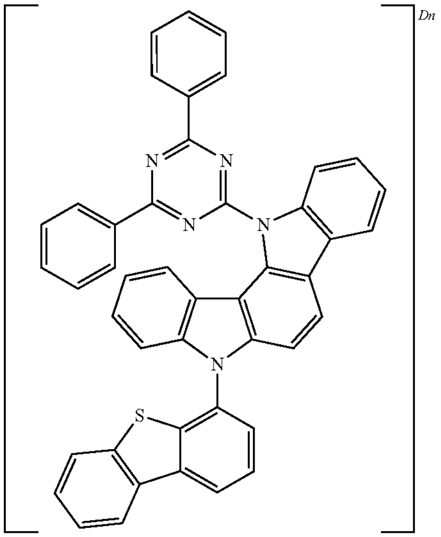
H1-175
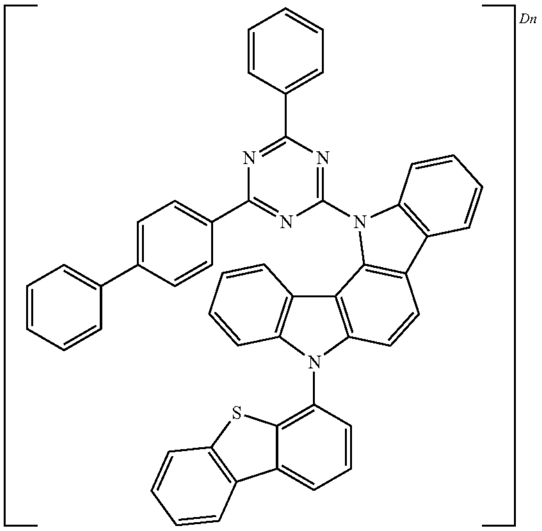
H1-176
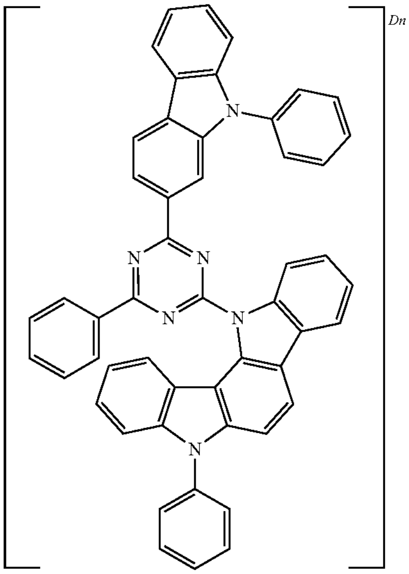
-continued
H1-177
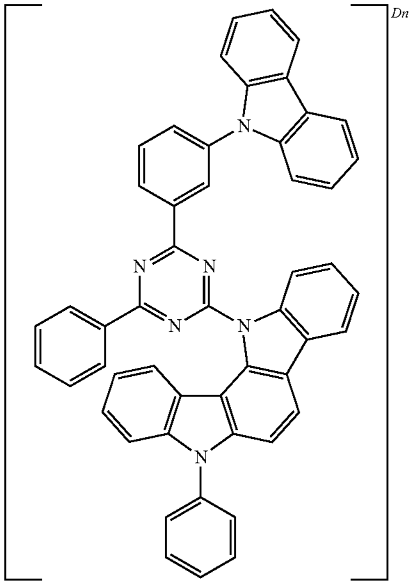
H1-178
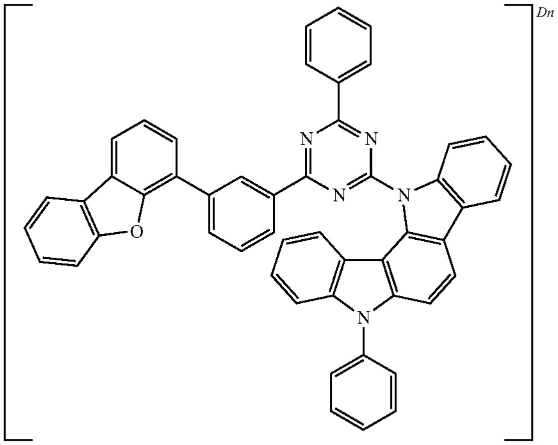
H1-179
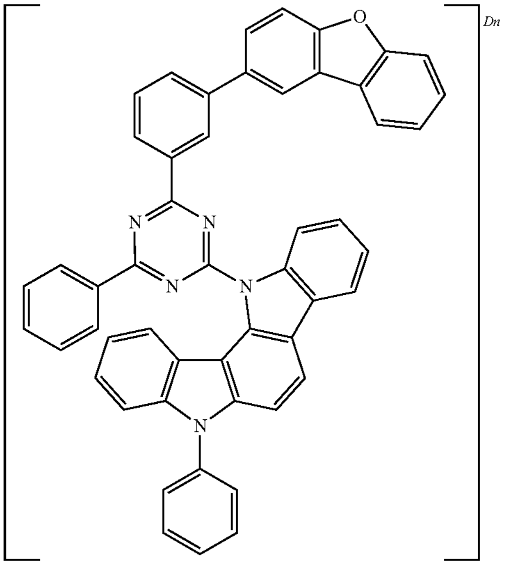

-continued
H1-180
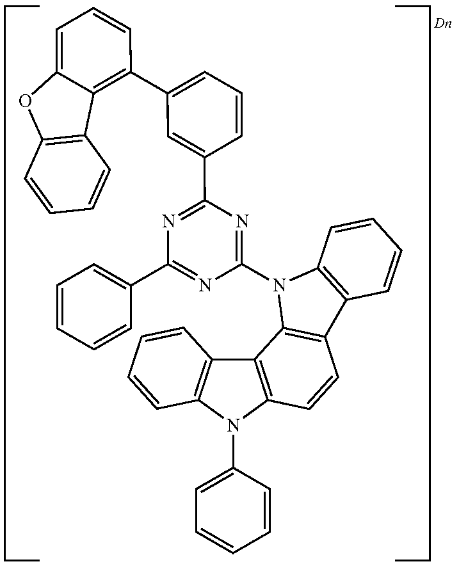
H1-181
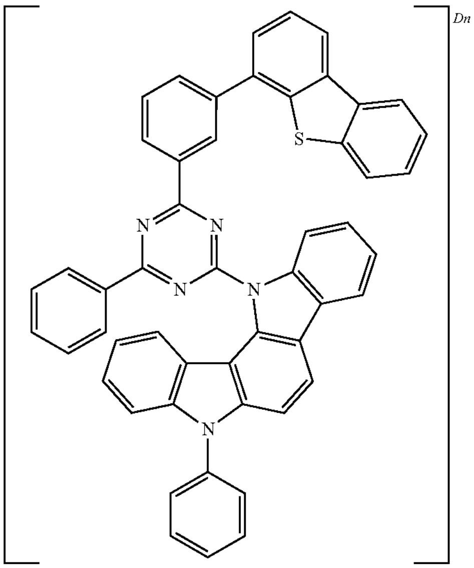
-continued
H1-182
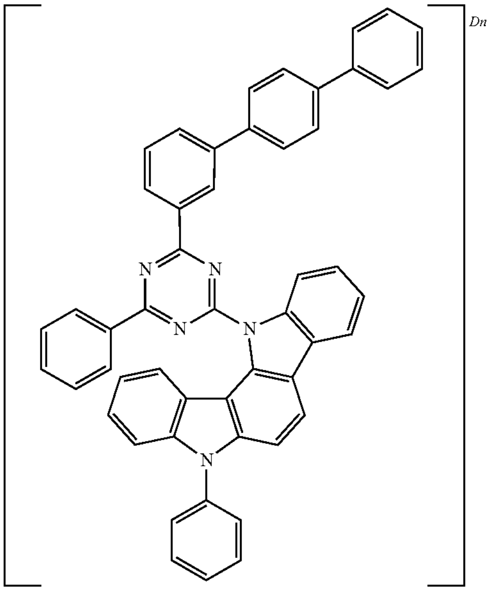
H1-183
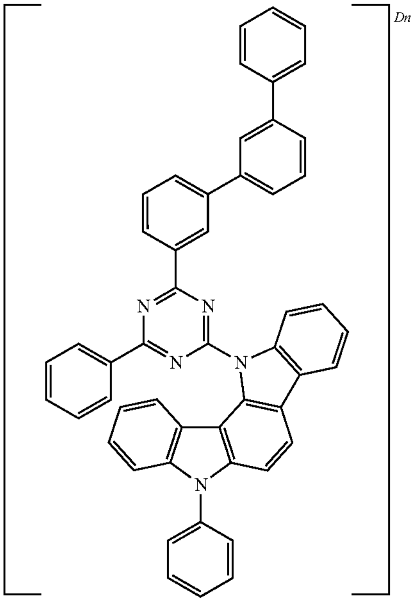
H1-184
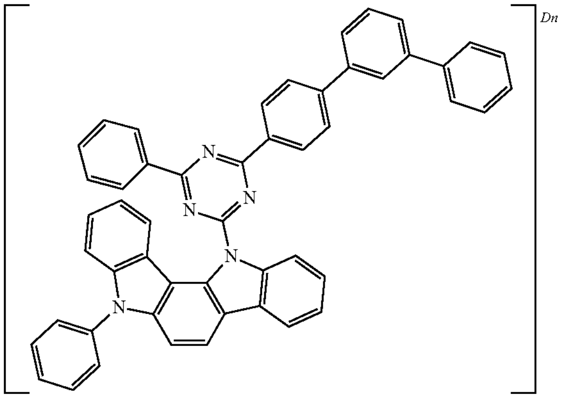

-continued
H1-185
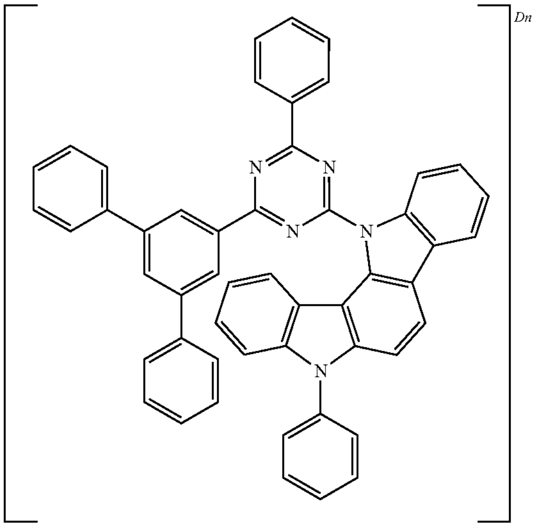
H1-186
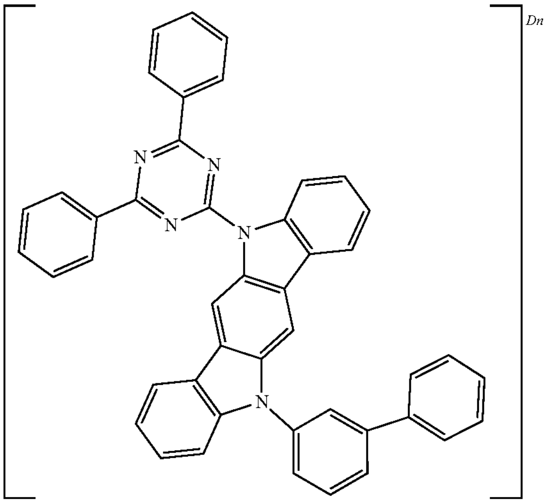
H1-187
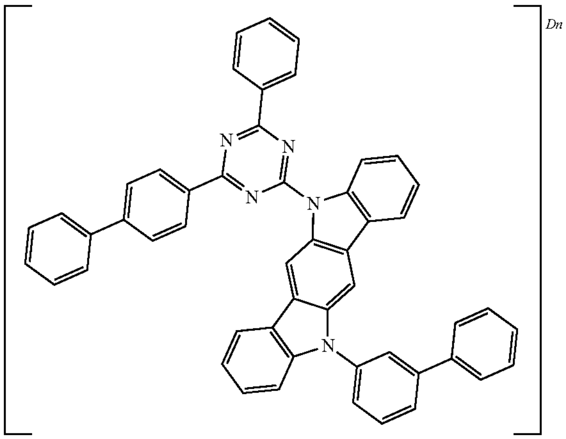
-continued
H1-188
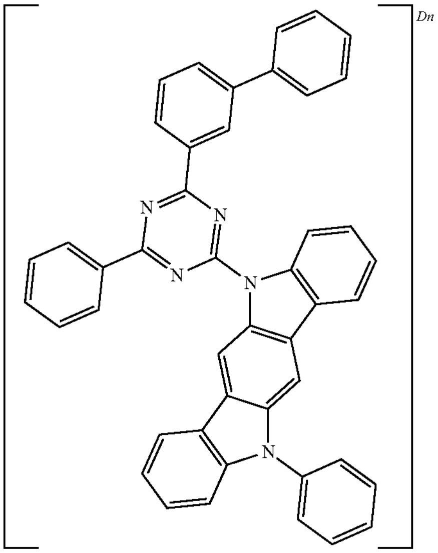
H1-189
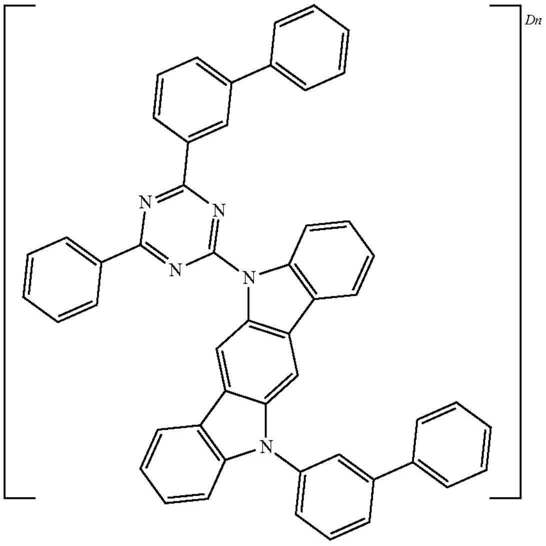

-continued
H1-190
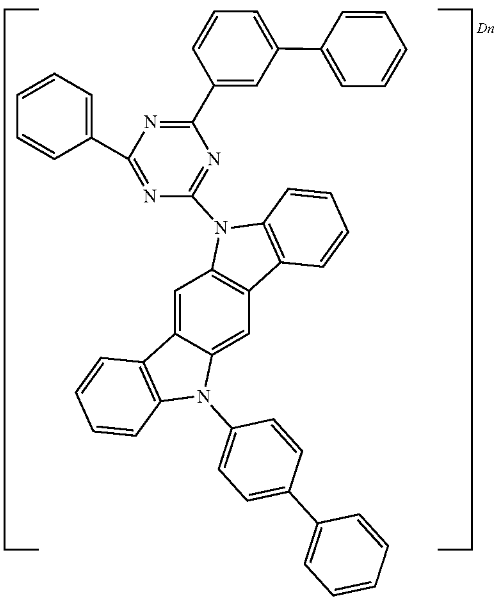
H1-191
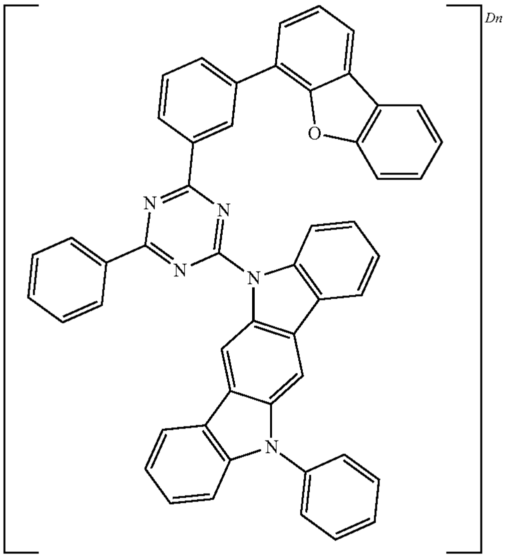
-continued
H1-192
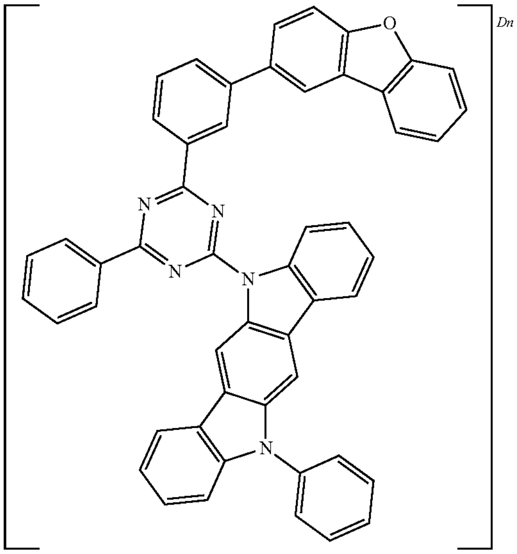
H1-193
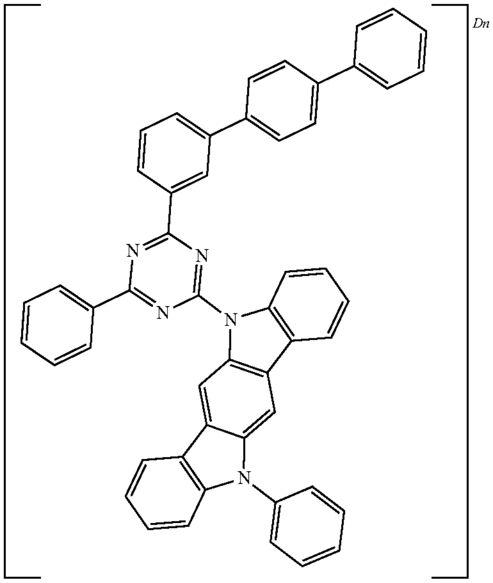

-continued
H1-194
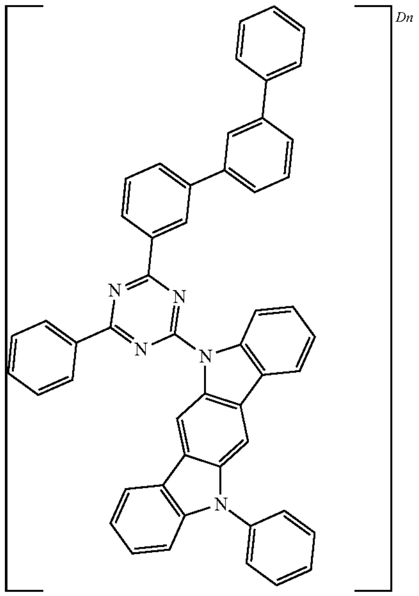
H1-195
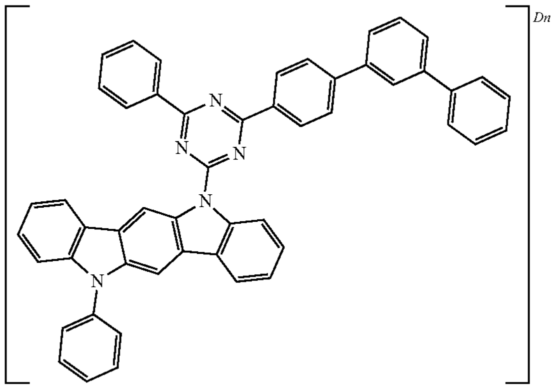
H1-196
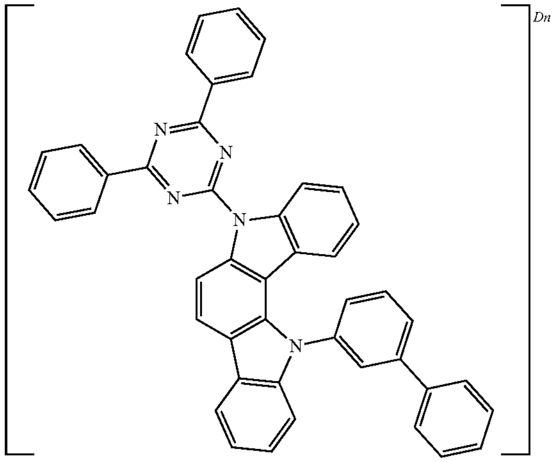
-continued
H1-197
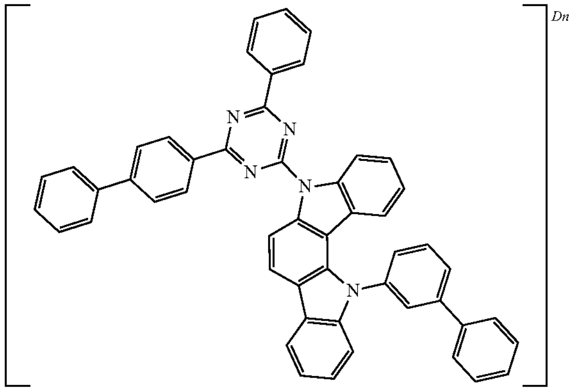
H1-198
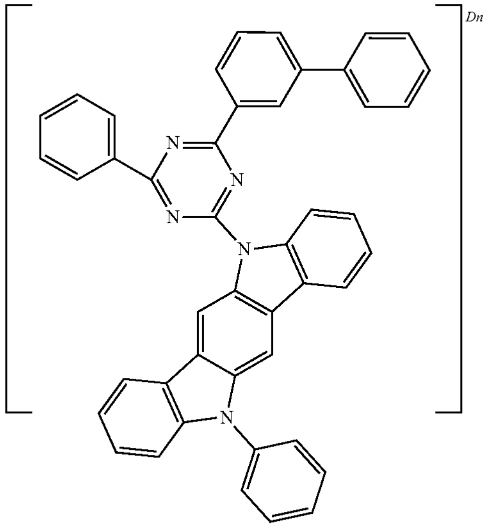
H1-199
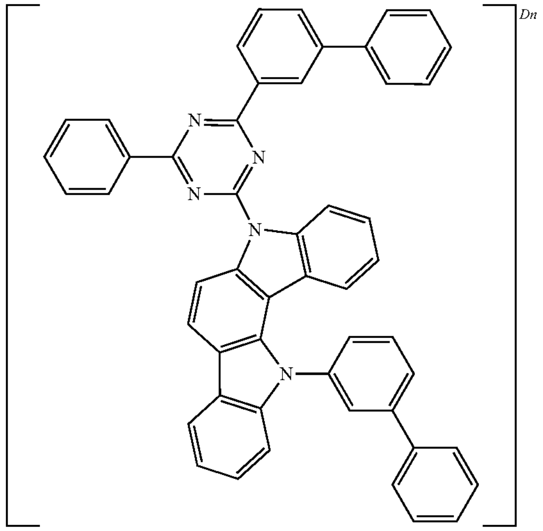

-continued
H1-200
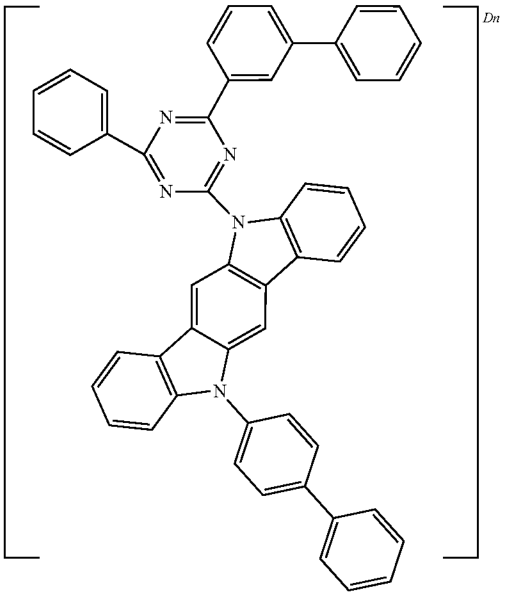
H1-201
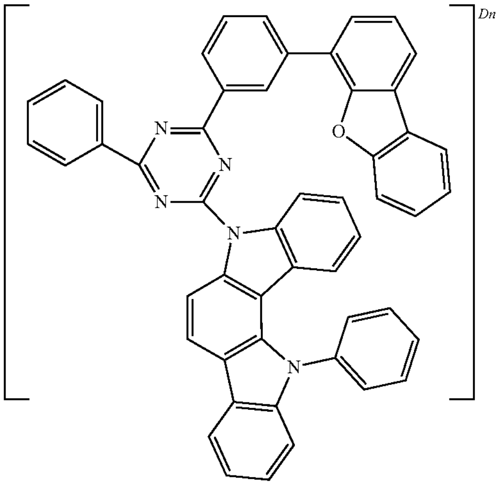
H1-202
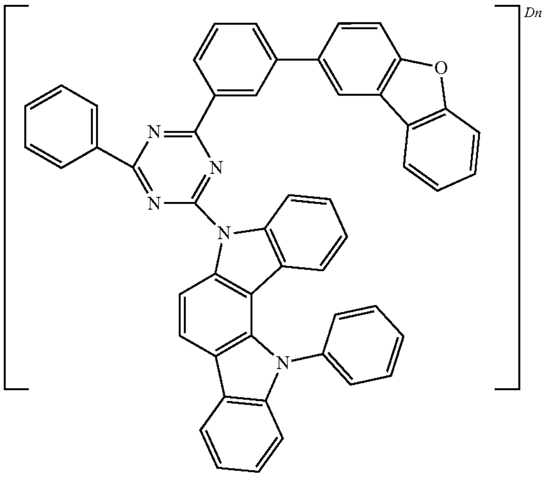
-continued
H1-203
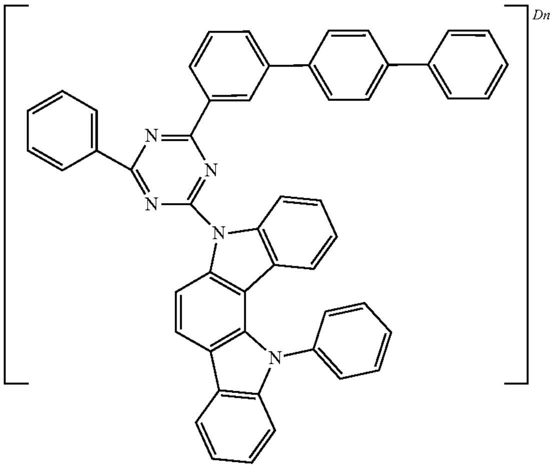
H1-204
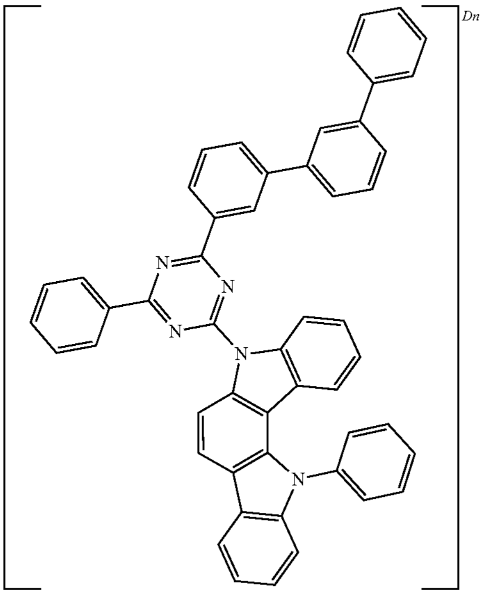
H1-205
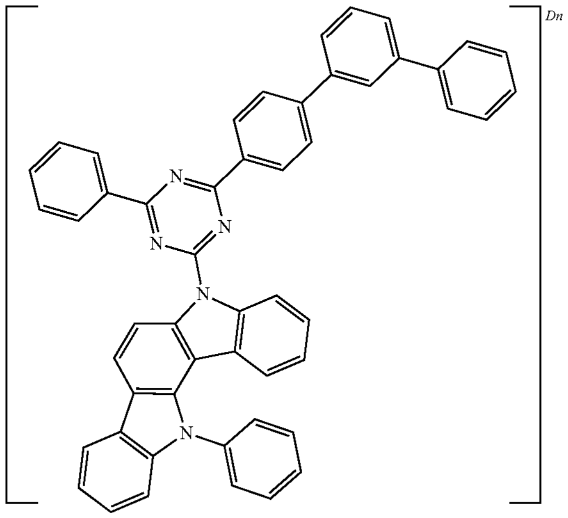

H1-206
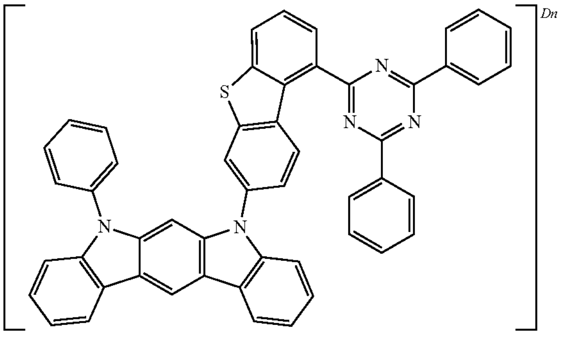
H1-207
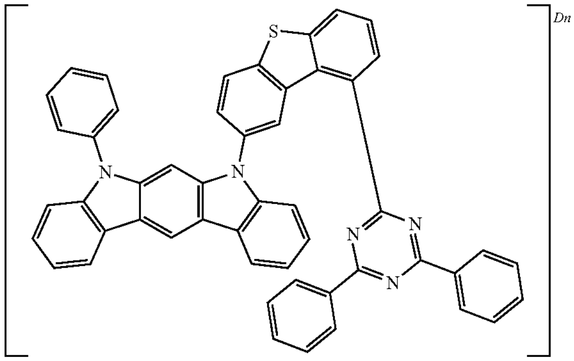
H1-208
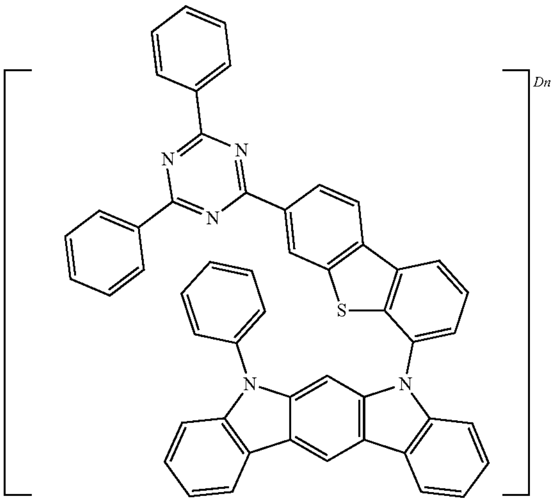
H1-209
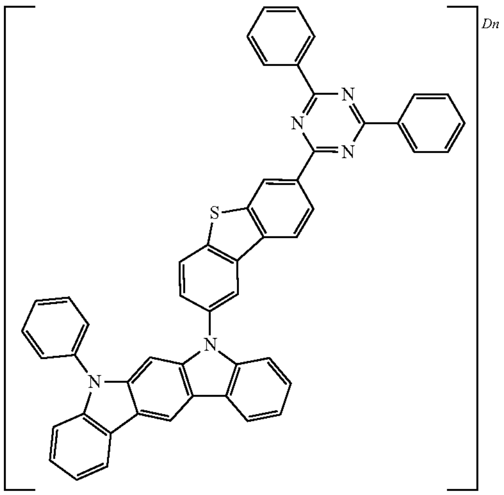
and
H1-210
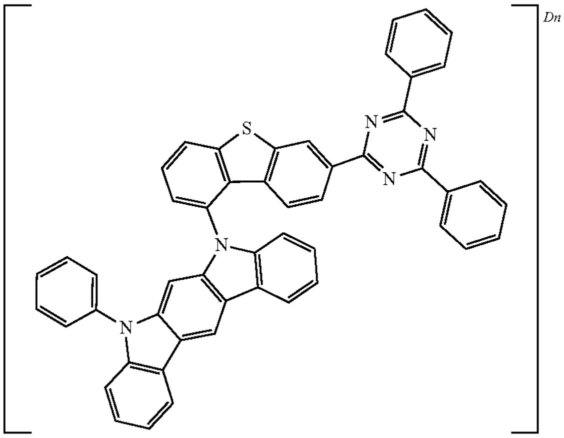
in the compounds, Dn represents that n number of hydrogens are replaced with deuterium; and n represents an integer of 1 to 50.
6. The plurality of host materials according to claim 1, wherein the compound represented by formula 2-2 is at least one selected from the group consisting of the following compounds:
C-1
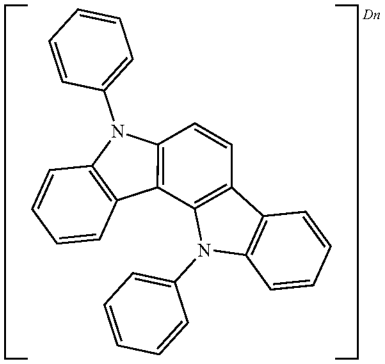

-continued
C-2
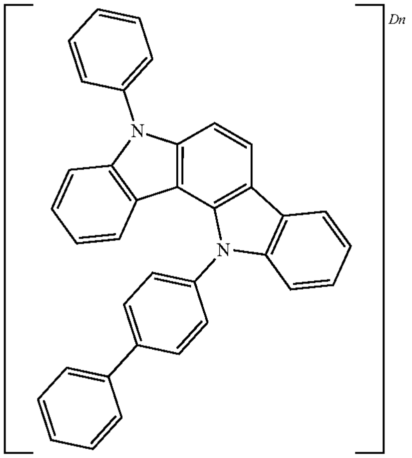
C-3
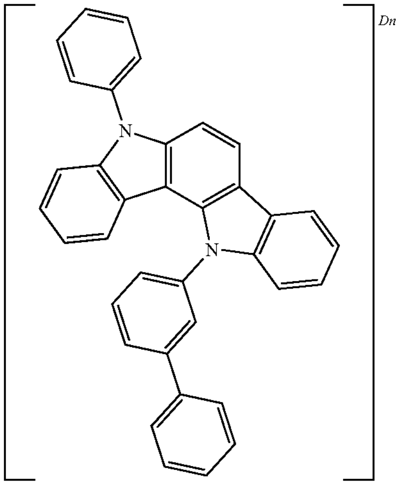
C-4
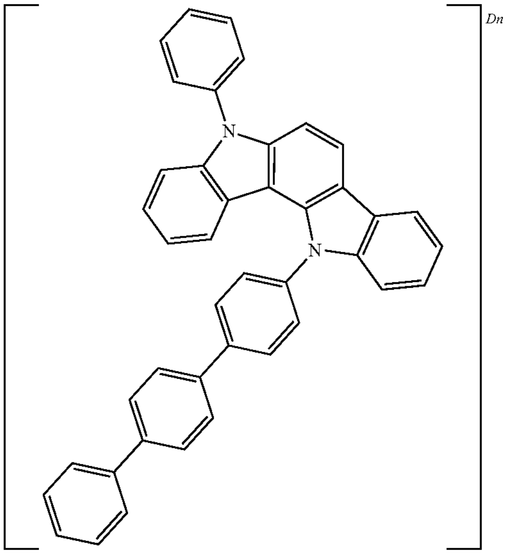
-continued
C-5
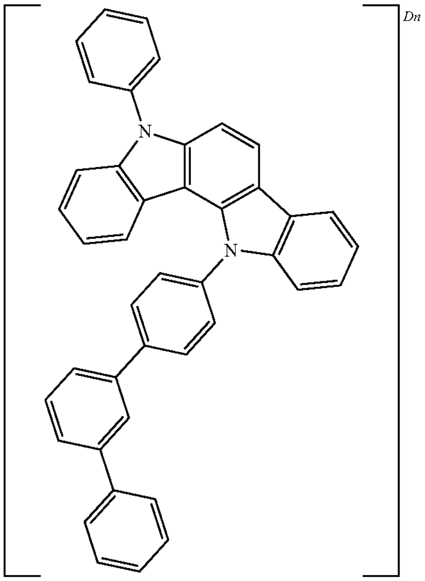
C-6
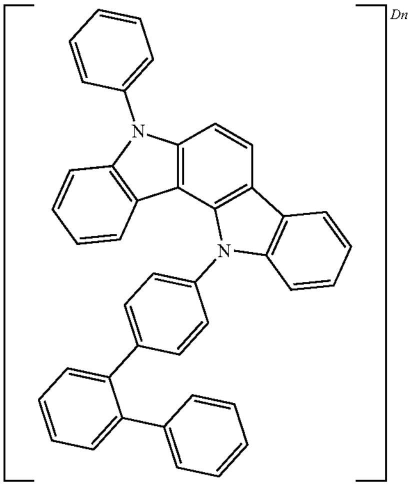

-continued
C-7
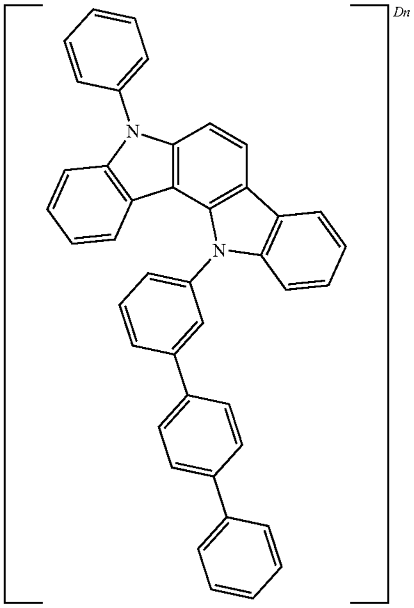
C-8
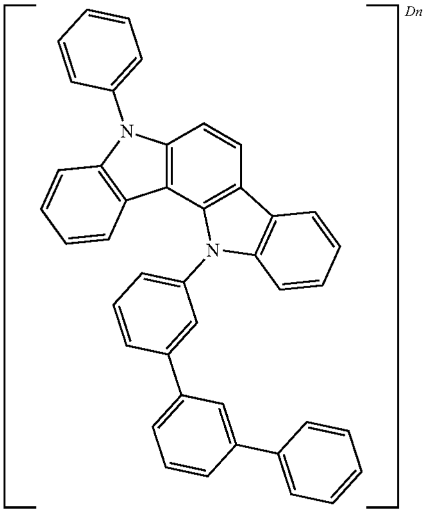
C-9
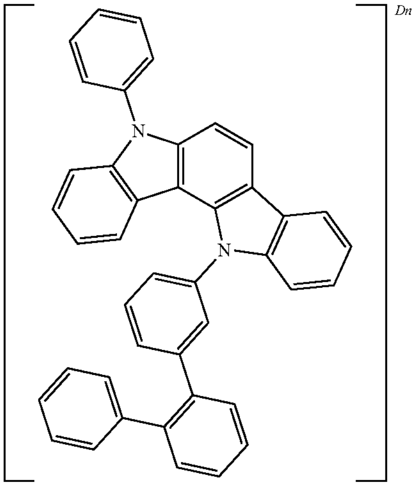
-continued
C-10
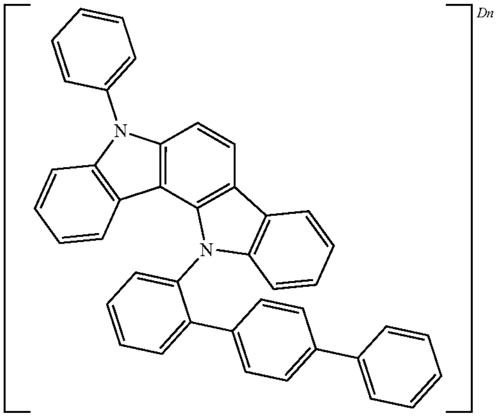
C-11
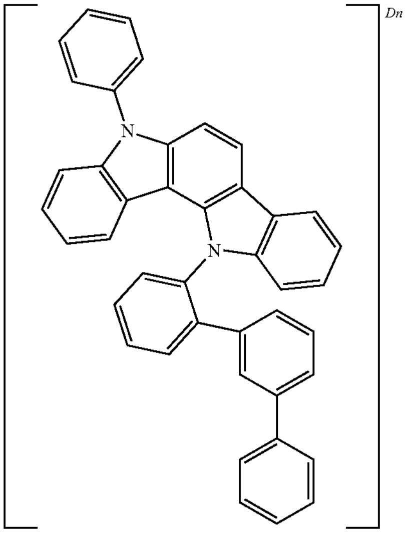
C-13
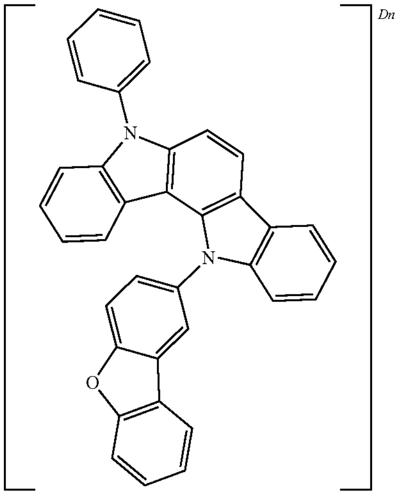

-continued
C-14
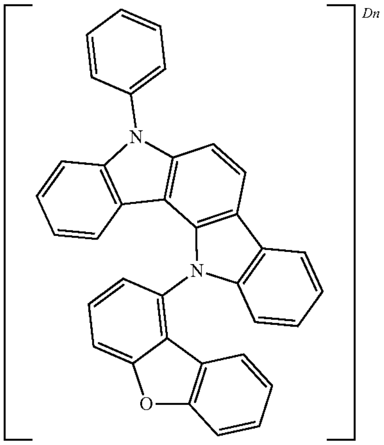
C-15
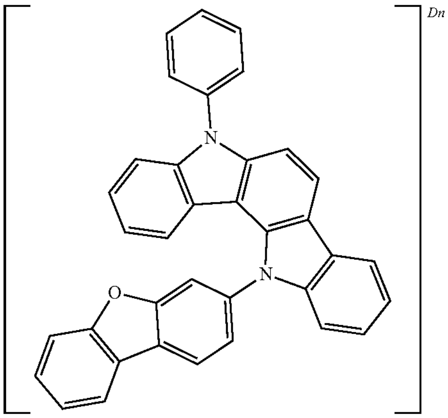
C-16
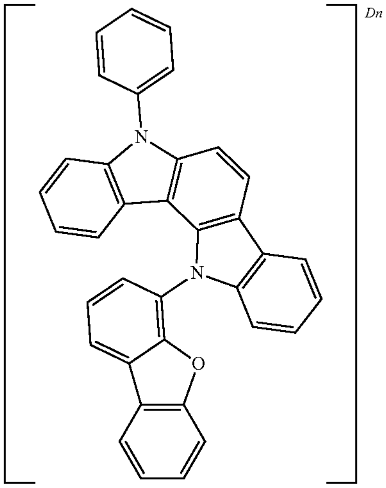
-continued
C-17
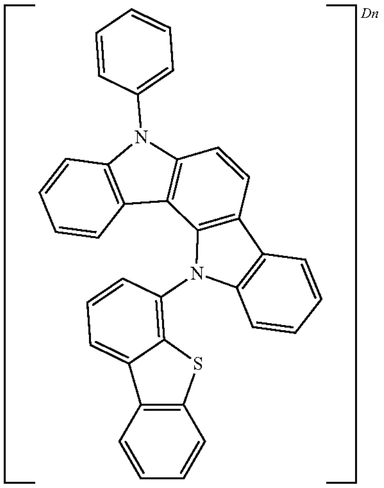
C-18
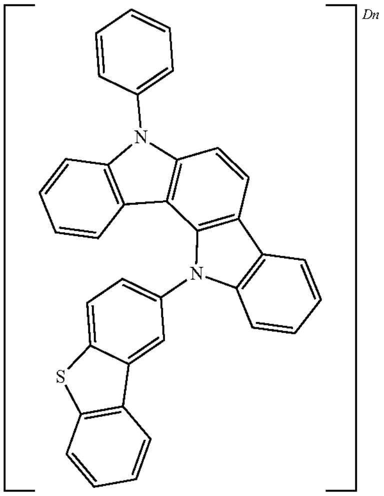
C-19
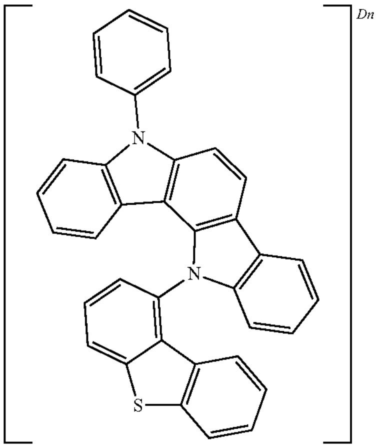

-continued
C-20
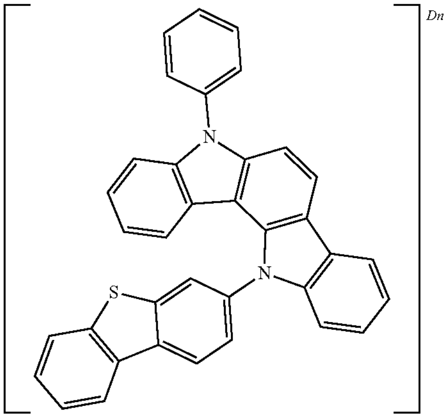
C-21
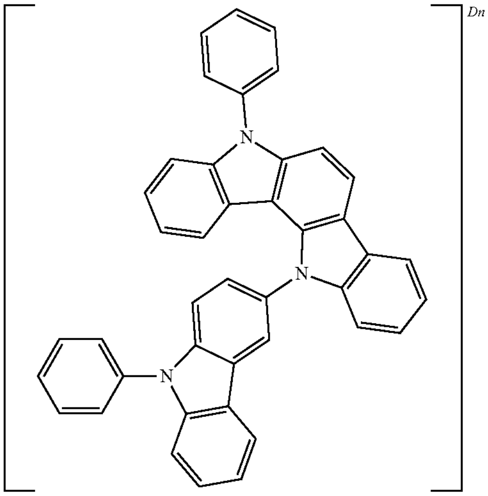
C-22
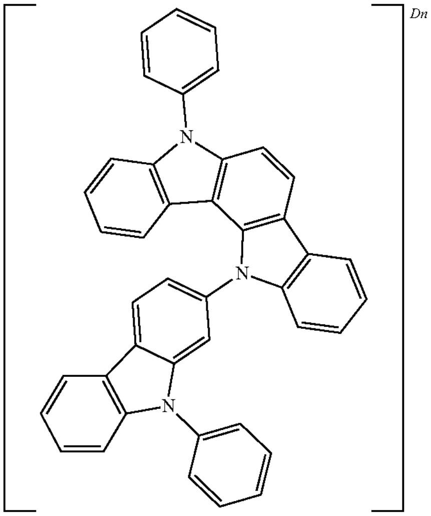
-continued
C-23
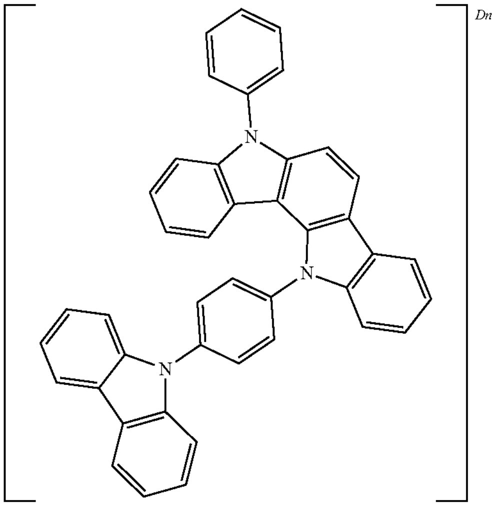
C-24
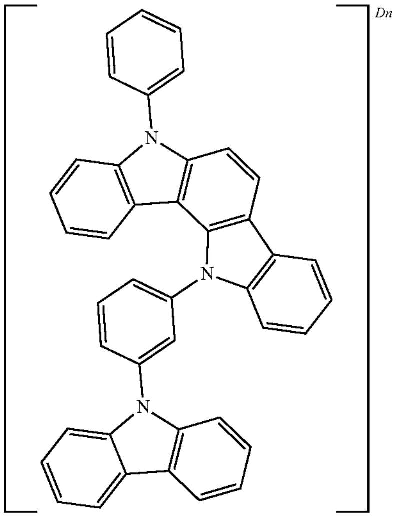
C-25
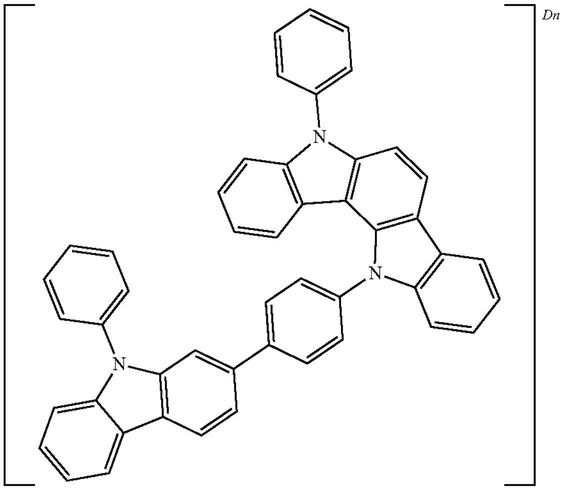

-continued
C-26
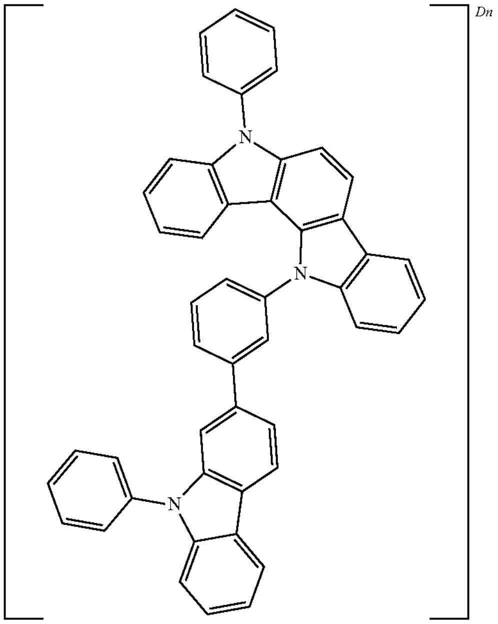
C-27
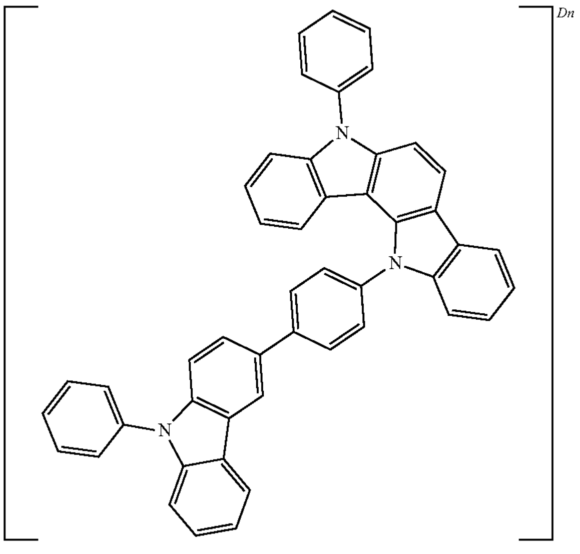
-continued
C-28
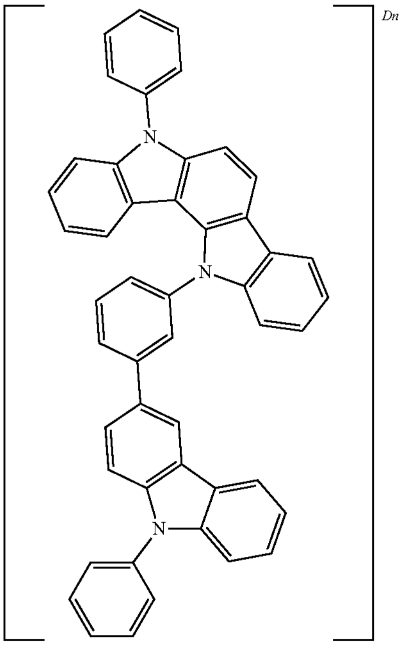
C-29
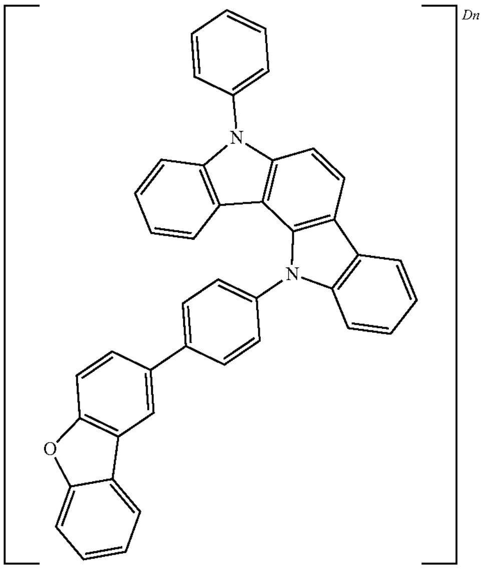

-continued
C-30
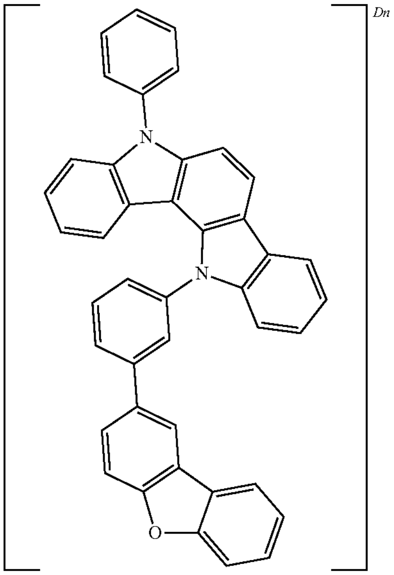
C-31
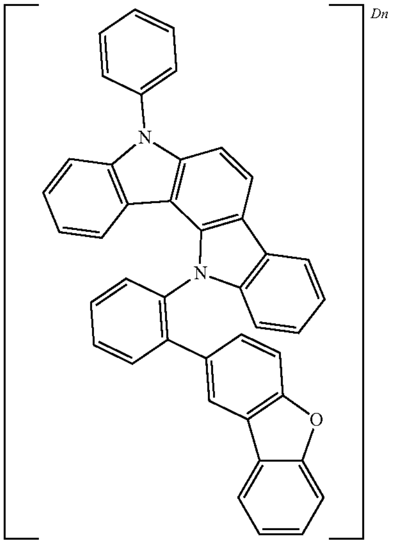
C-32
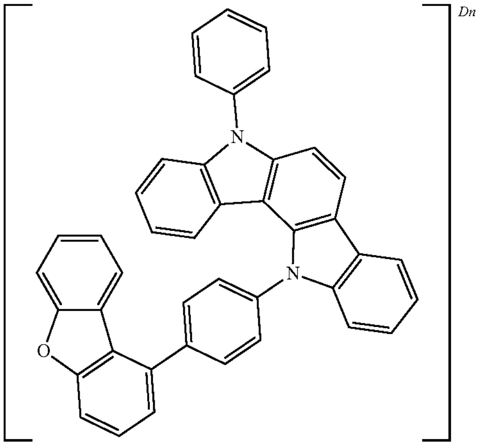
-continued
C-33
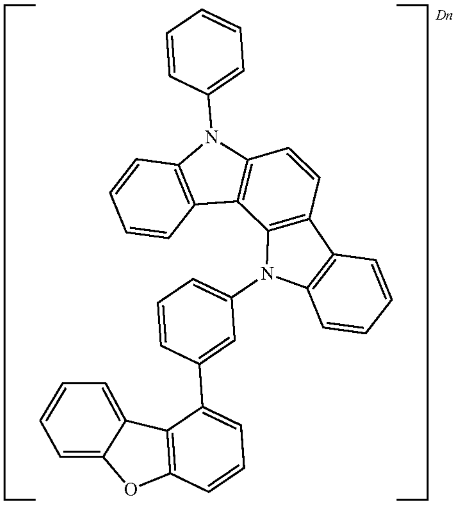
C-34
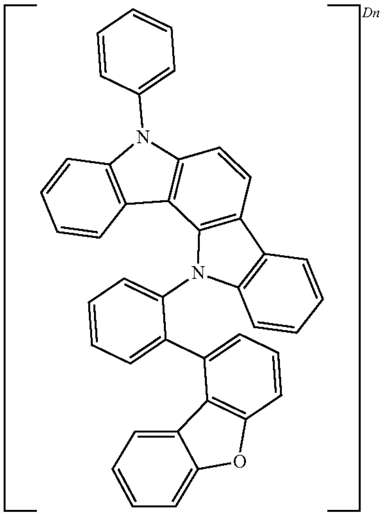
C-35
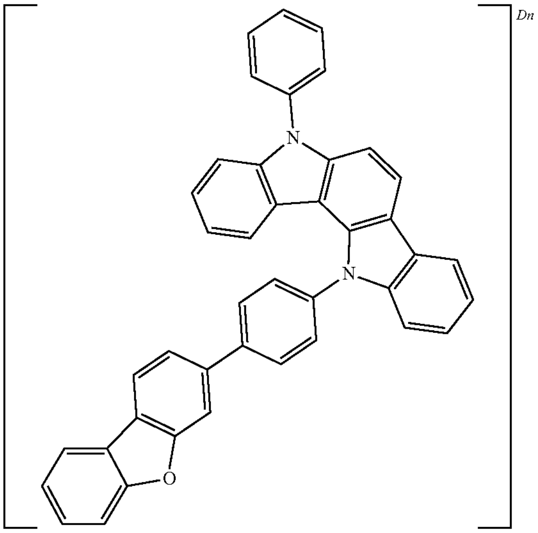

-continued
C-36
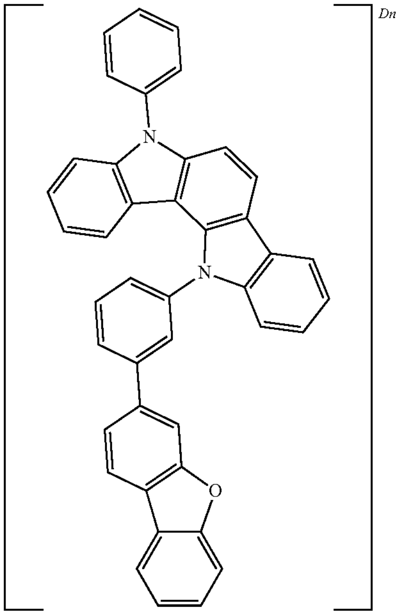
C-37
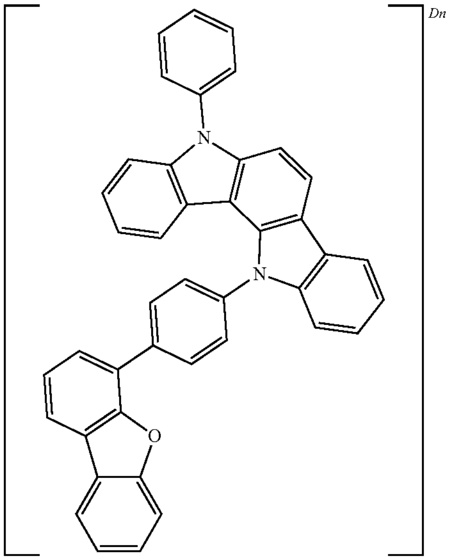
-continued
C-38
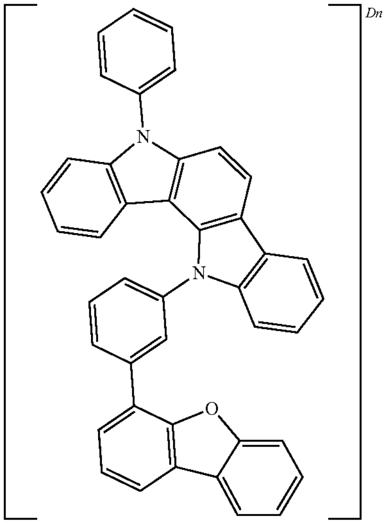
C-39
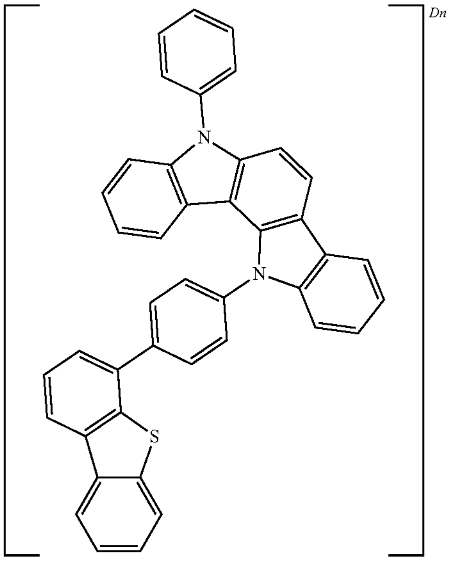
C-40
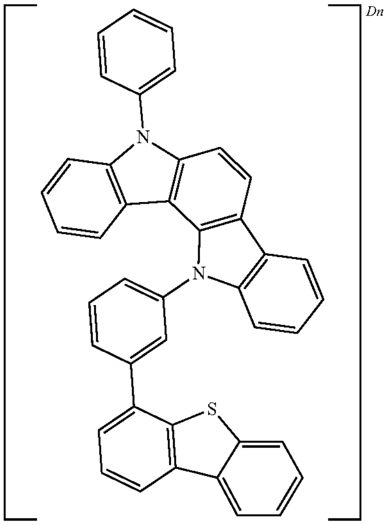

-continued
C-41
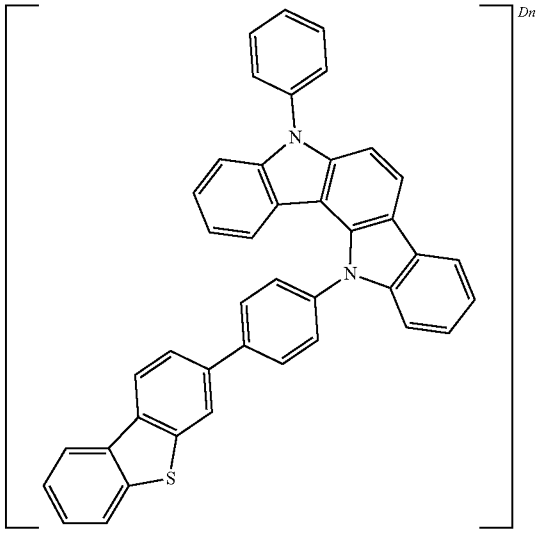
C-42
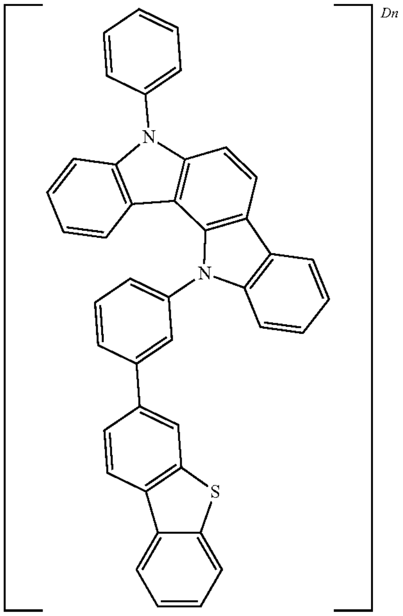
C-43
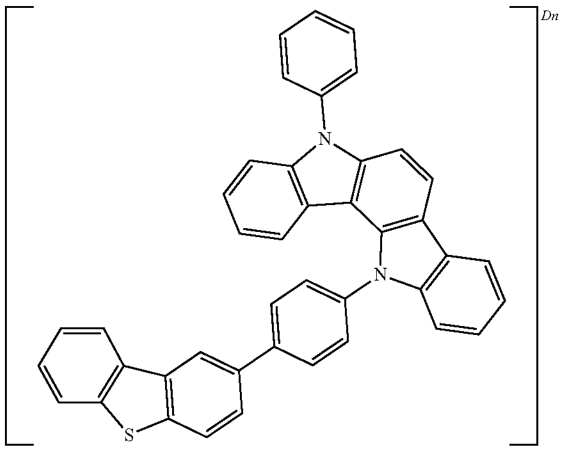
-continued
C-44
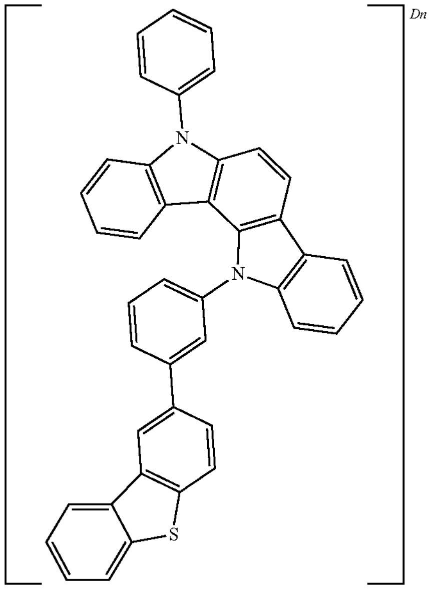
C-45
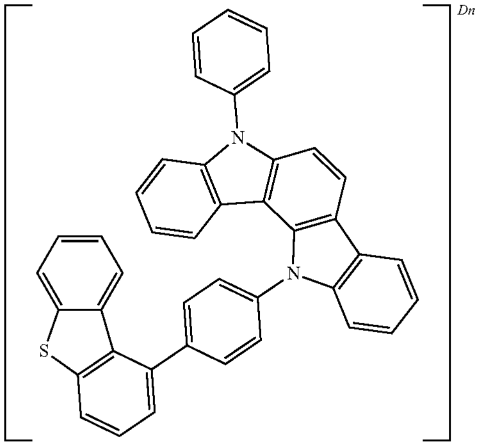
C-46
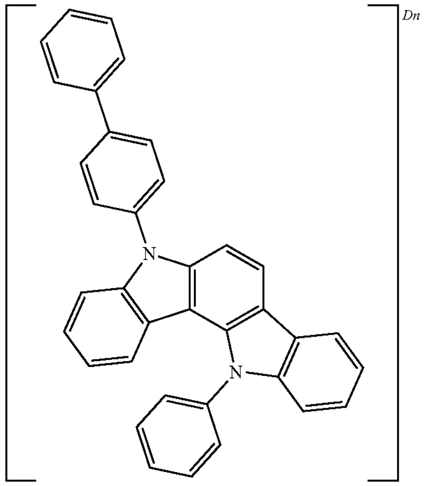

-continued
C-58
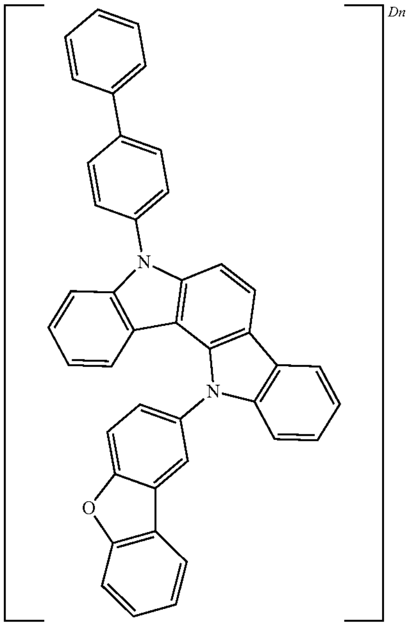
C-59
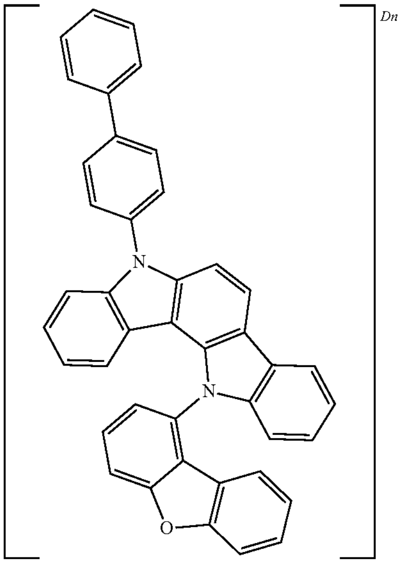
-continued
C-60
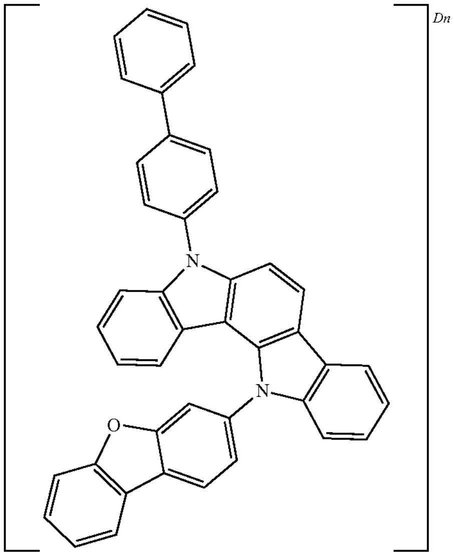
C-61
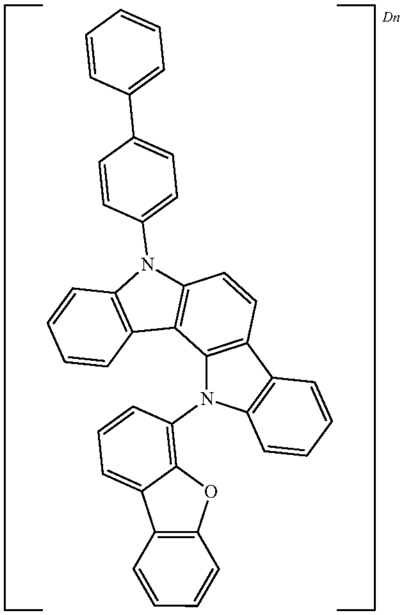

C-62
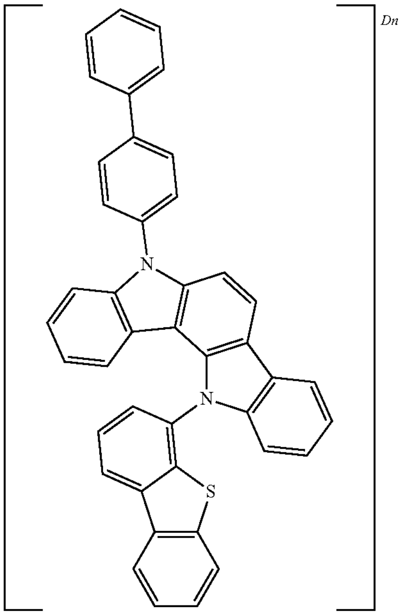
C-63
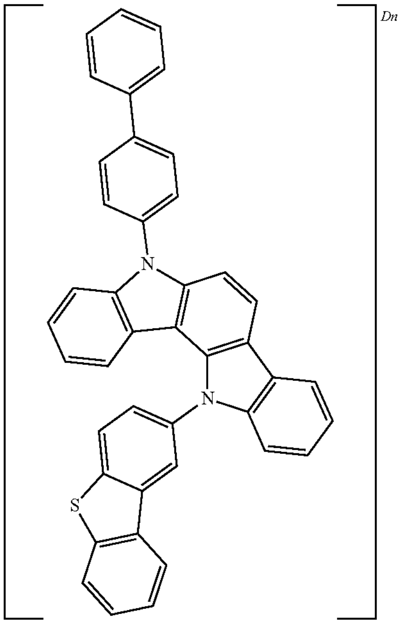
C-64
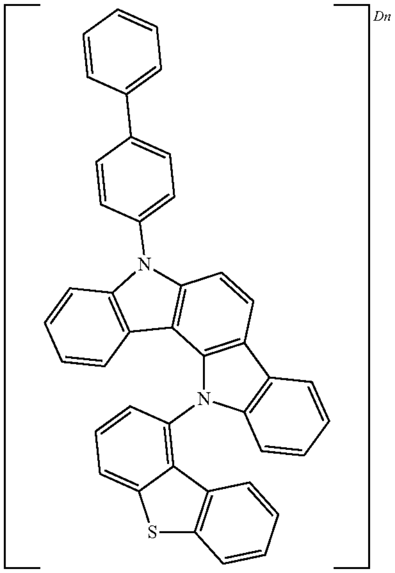
C-65
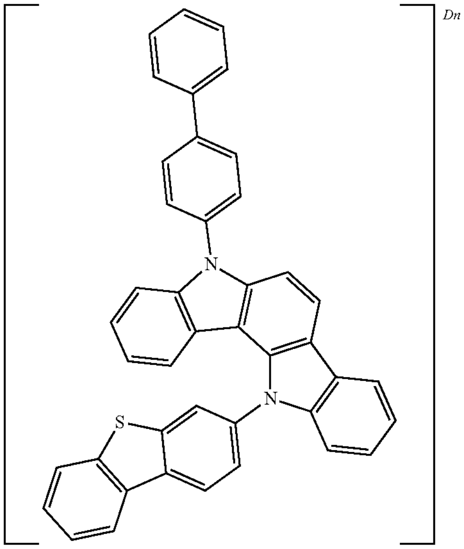

-continued
C-66
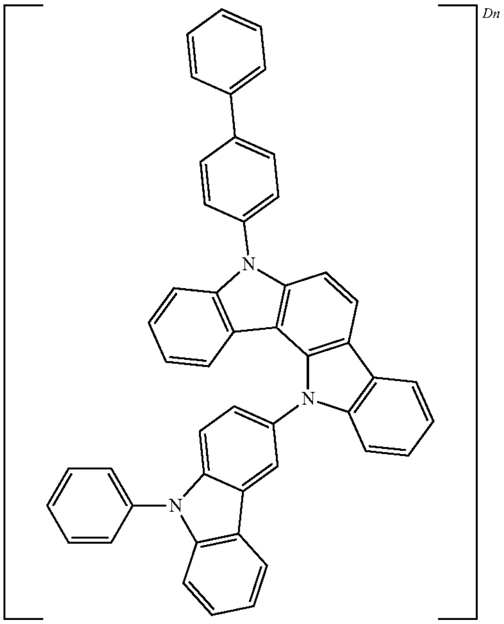
C-68
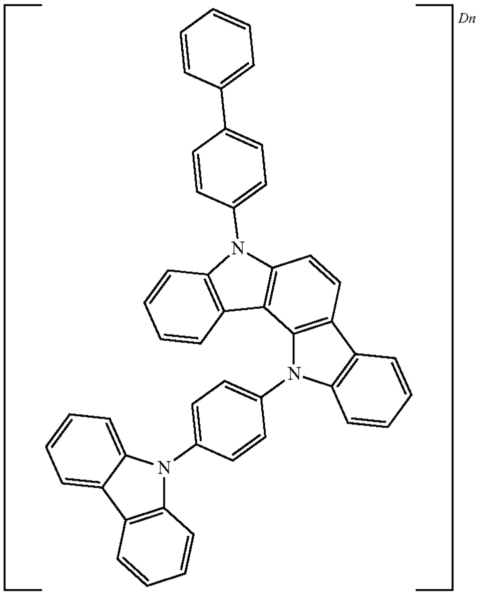
C-67
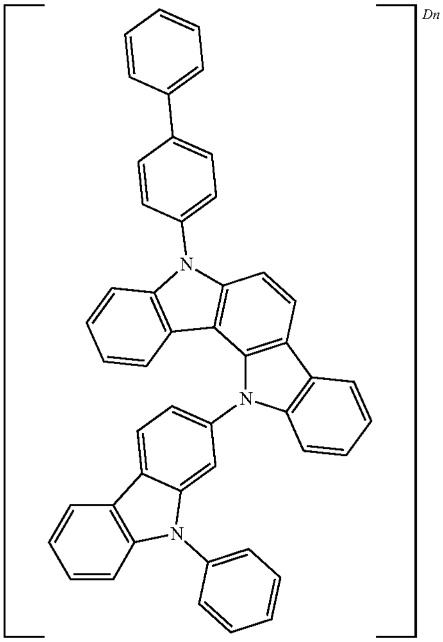
C-69
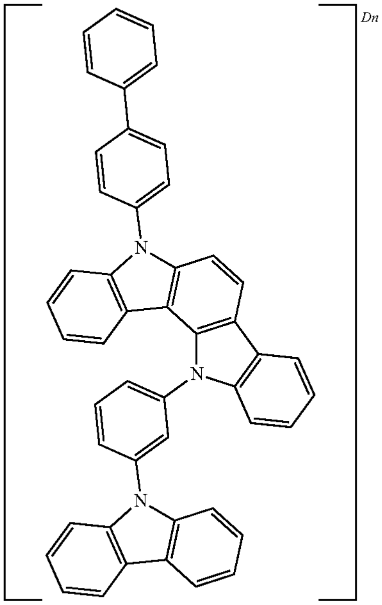

-continued
C-70
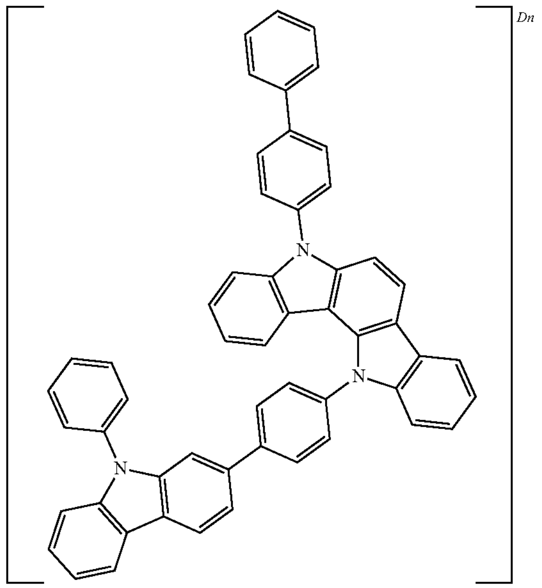
C-71
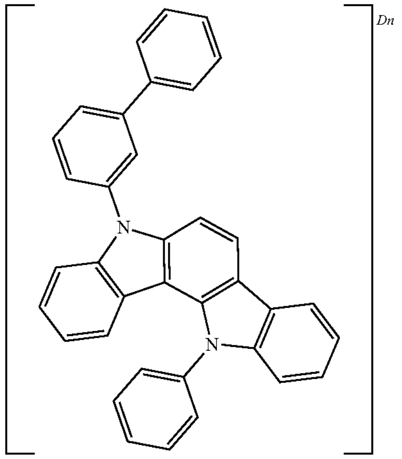
C-83
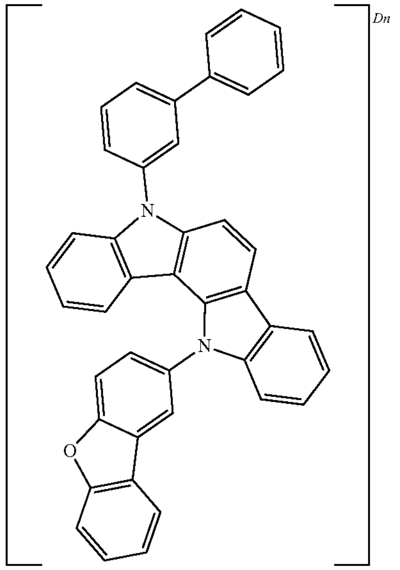
-continued
C-84
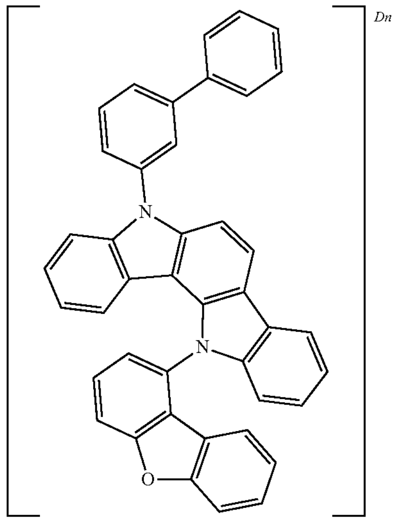
C-85
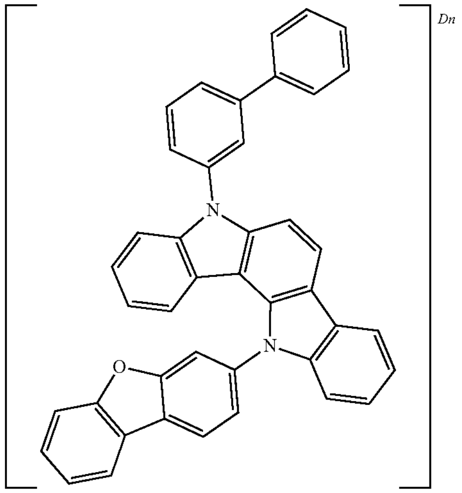
C-86
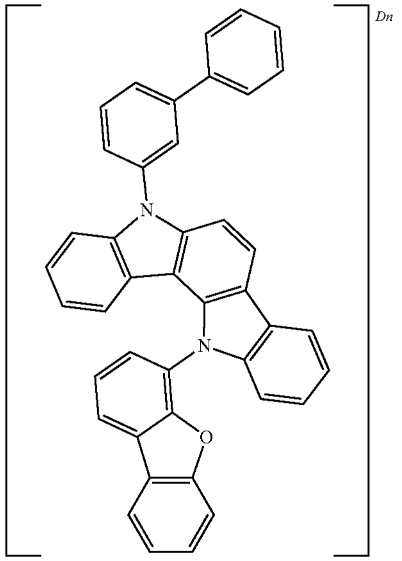

-continued
C-87
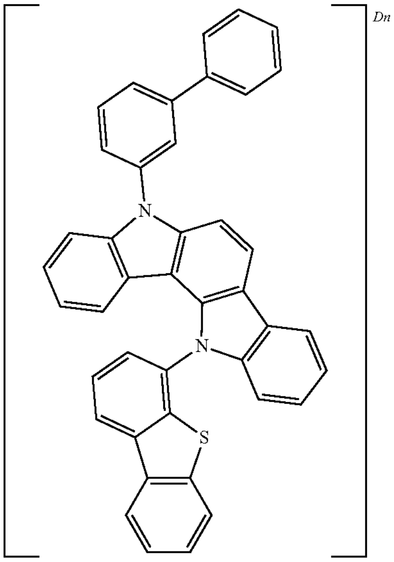
C-88
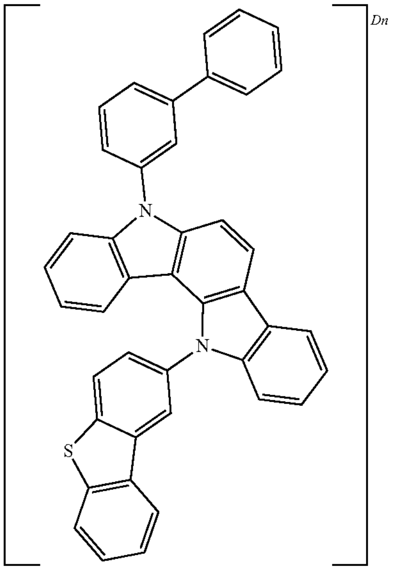
C-89
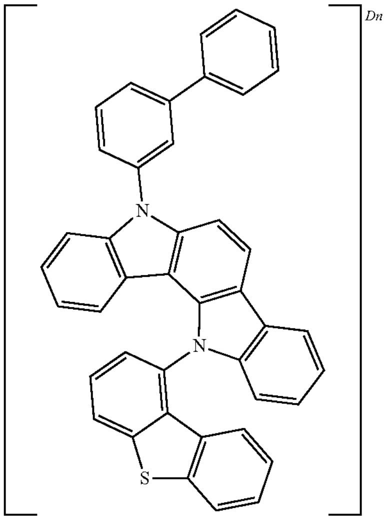
-continued
C-90
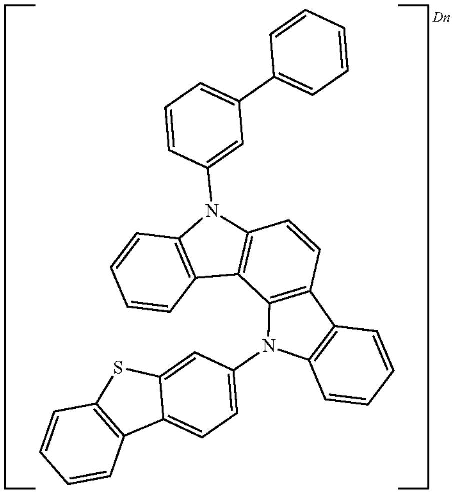
C-91
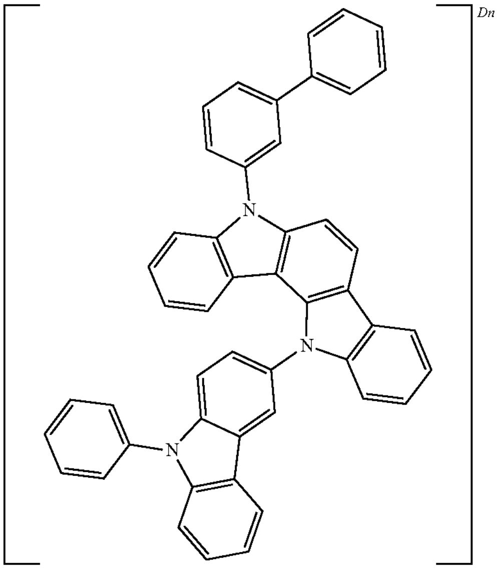
C-92
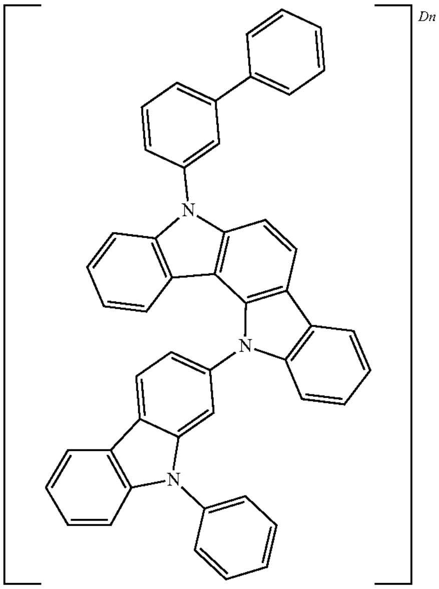

-continued
C-93
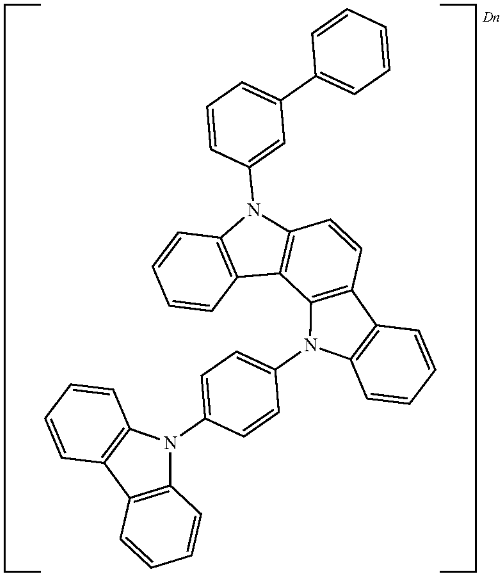
C-94
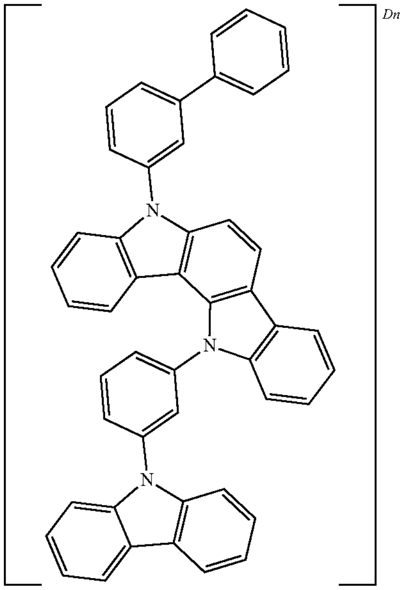
-continued
C-95
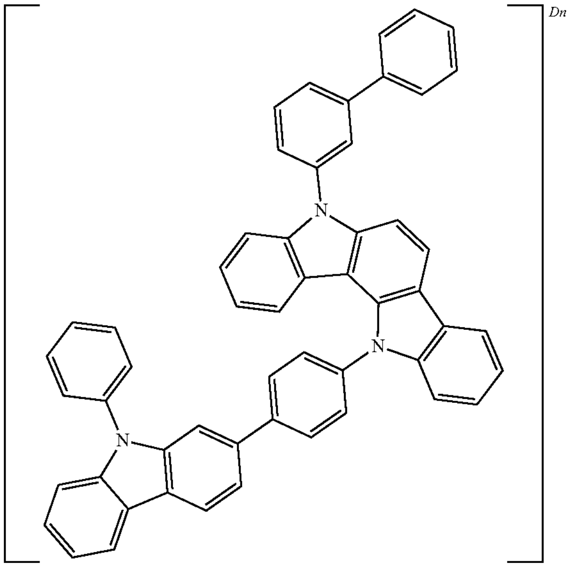
C-96
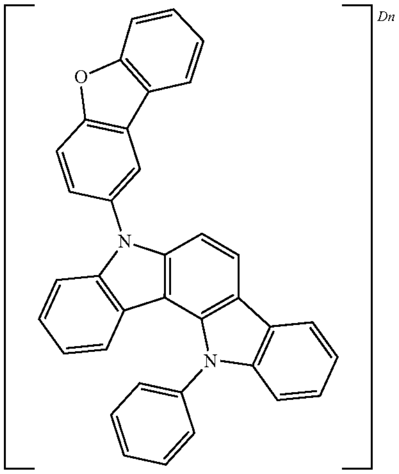
C-97
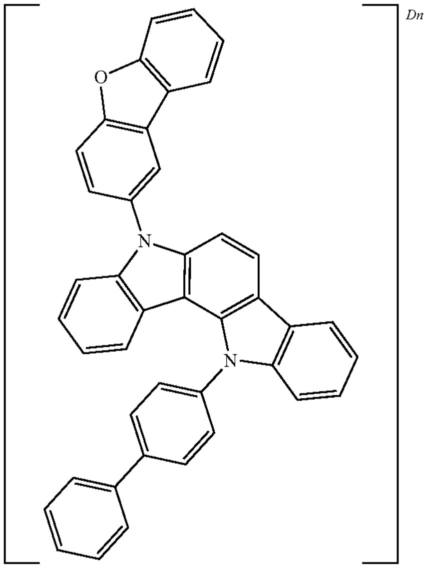

-continued
C-98
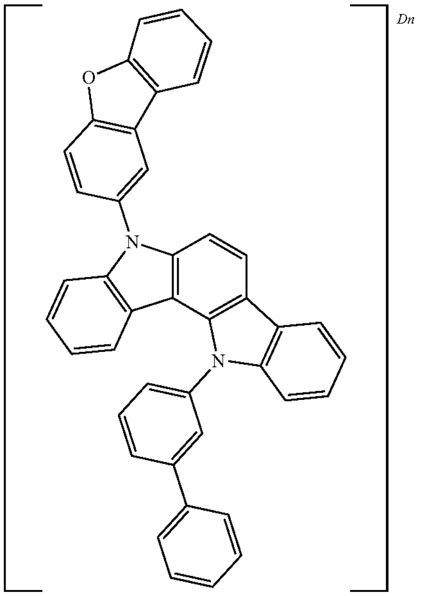
C-99
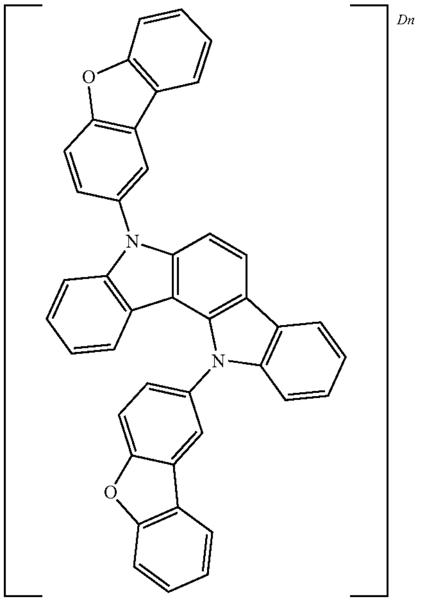
-continued
C-100
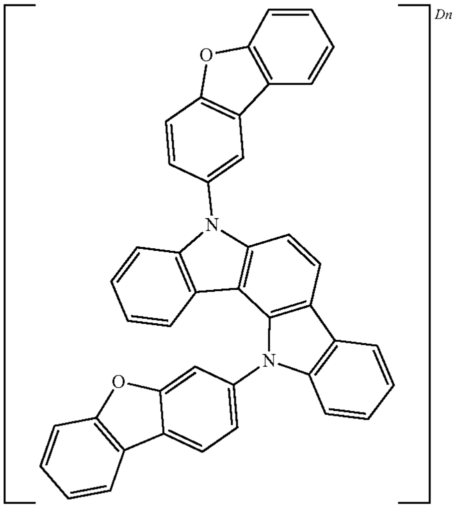
C-101
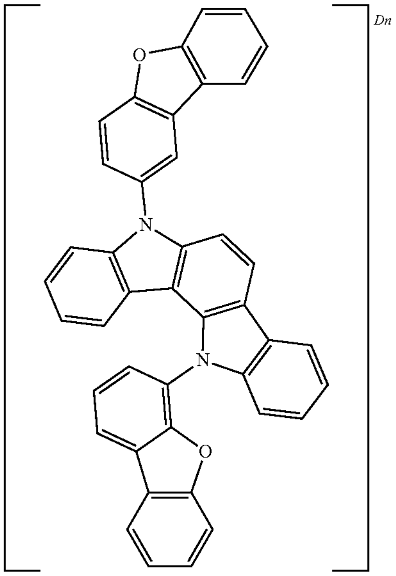
C-102
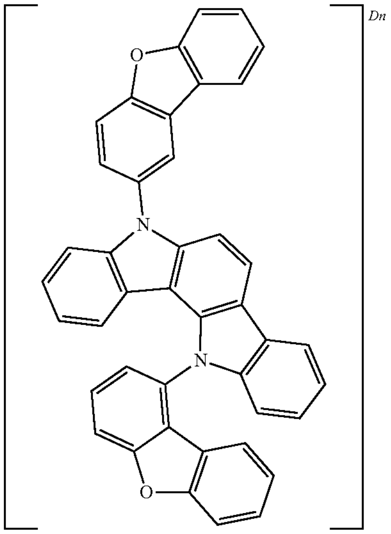

C-103
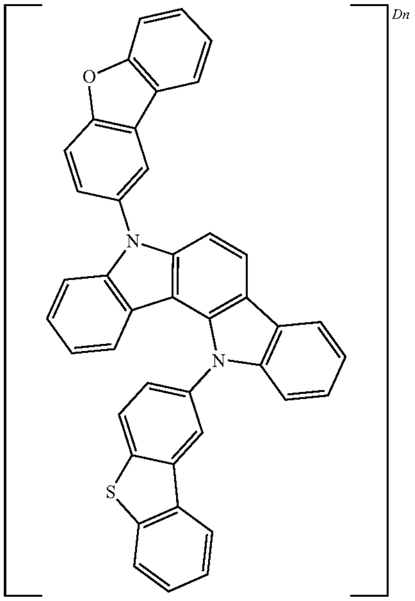
C-104
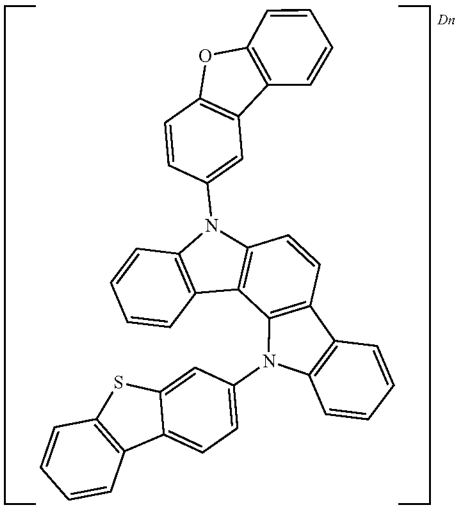
C-105
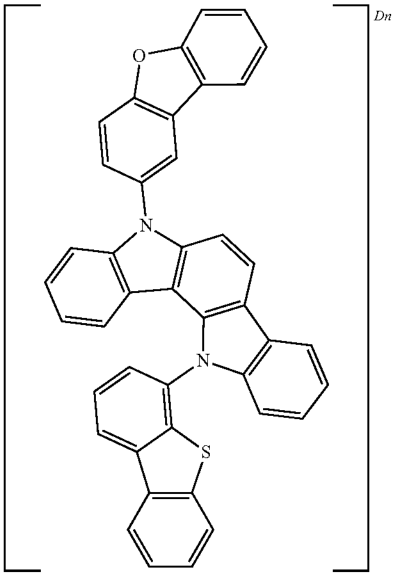
C-106
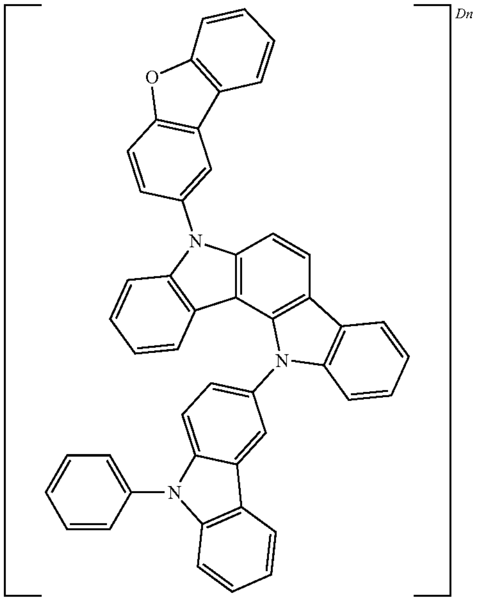

-continued
C-107
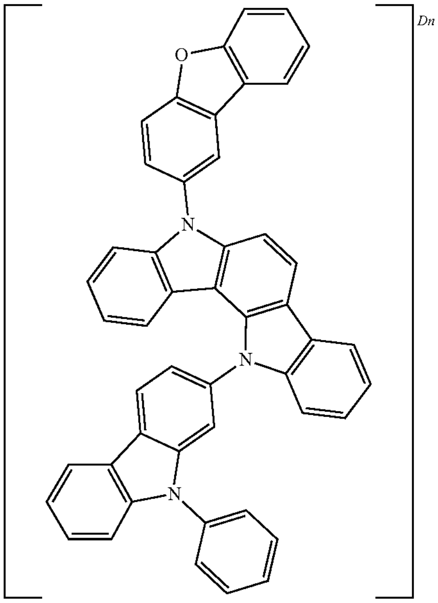
C-108
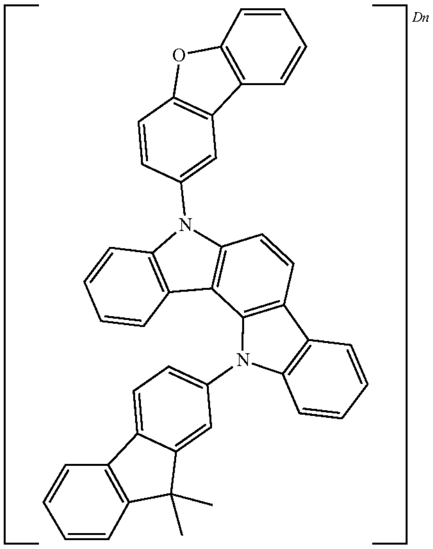
C-109
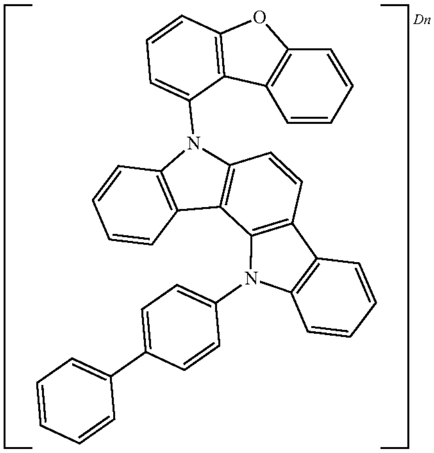
-continued
C-110
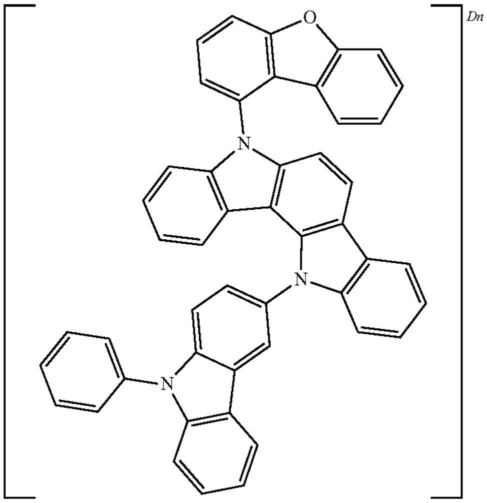
C-111
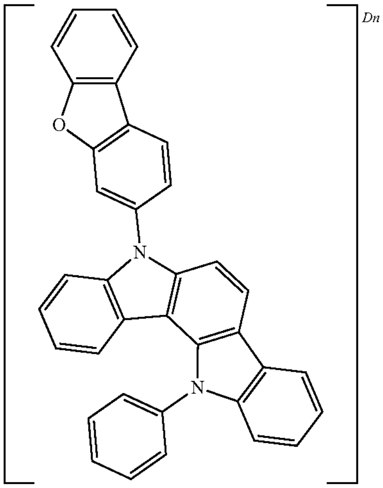
C-112
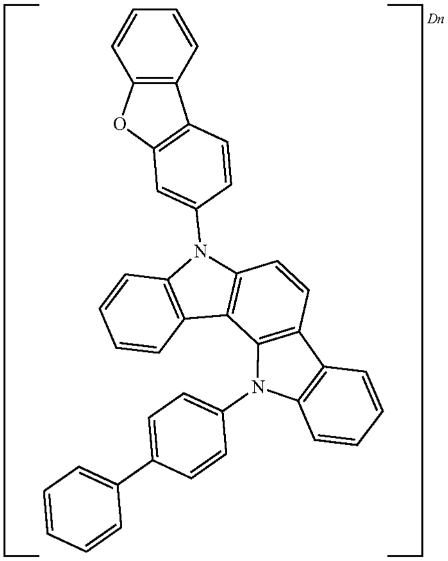

-continued
C-113
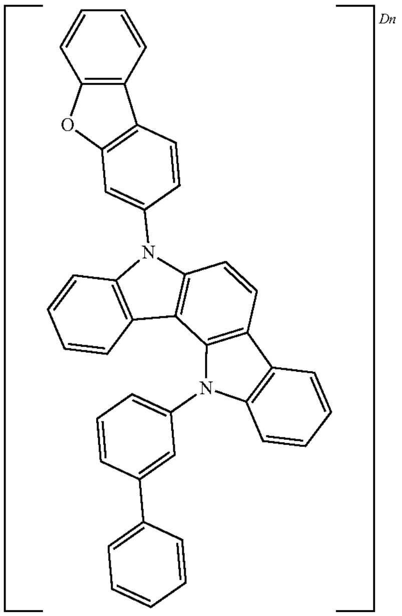
C-114
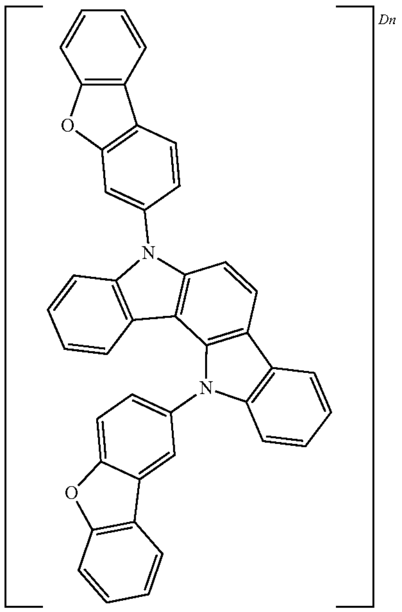
-continued
C-115
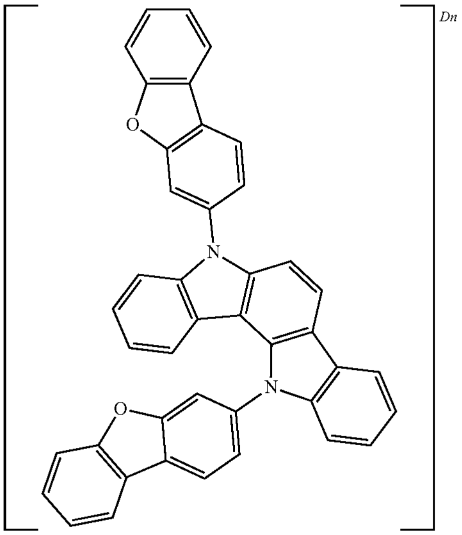
C-116
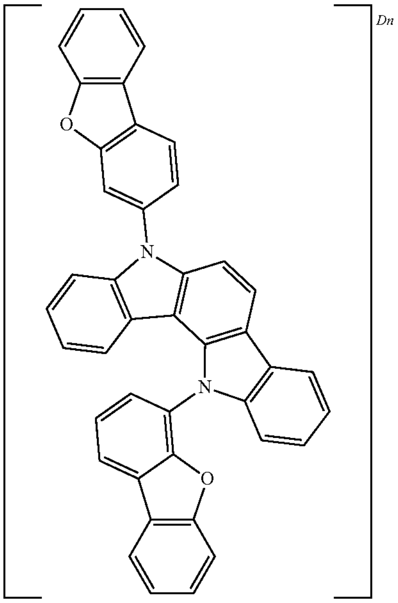

-continued
C-117
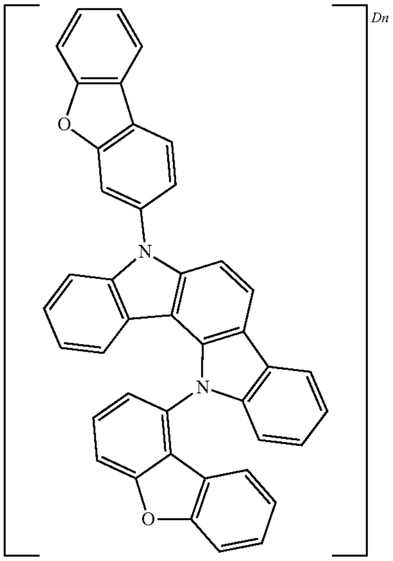
C-118
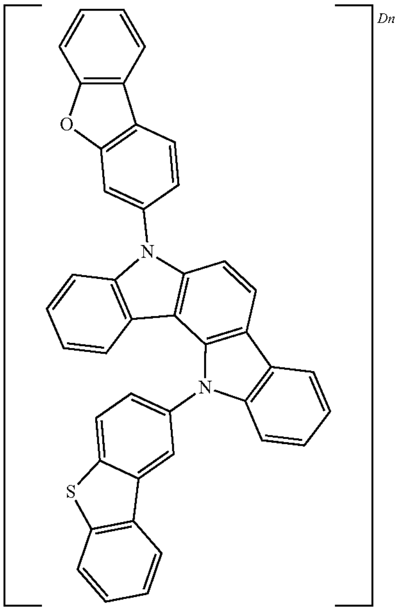
-continued
C-119
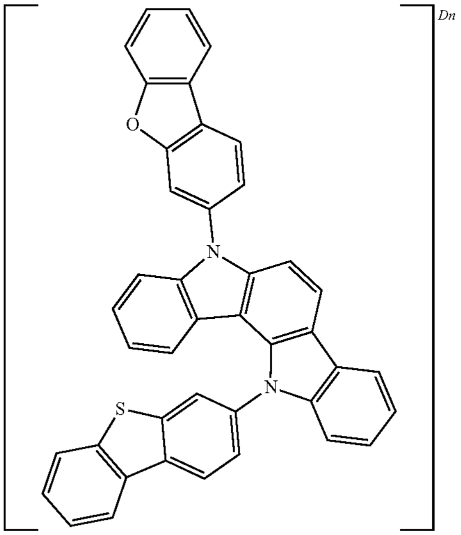
C-120
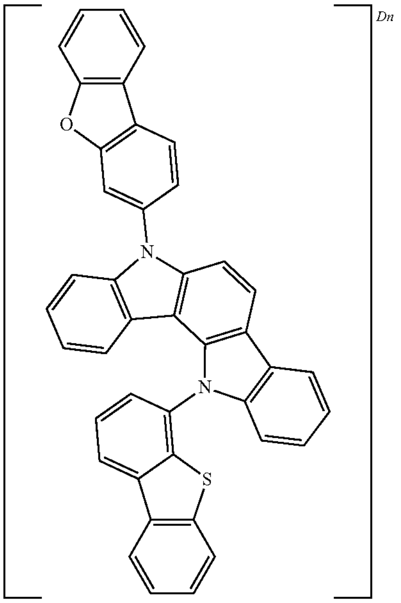
C-121
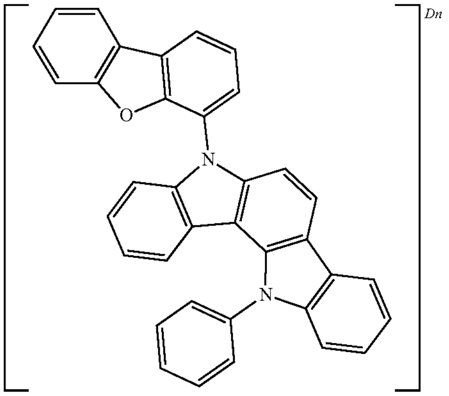

-continued
C-122
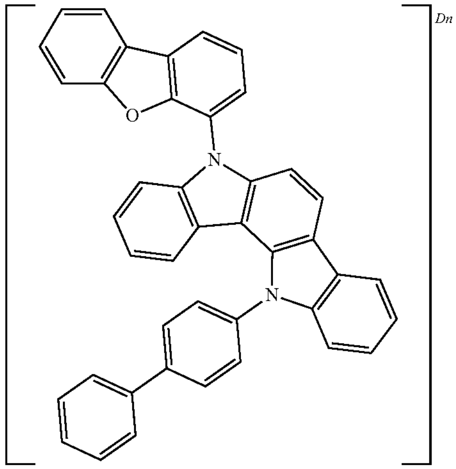
C-123
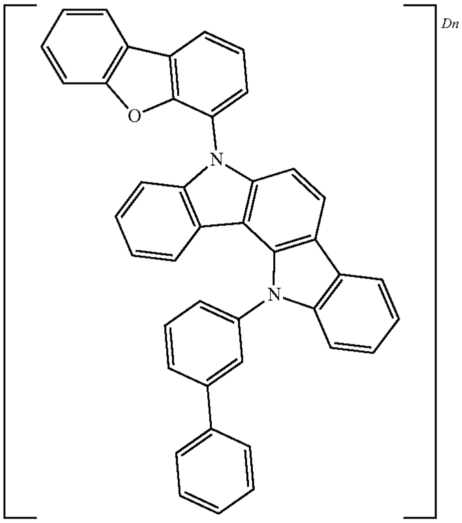
C-124
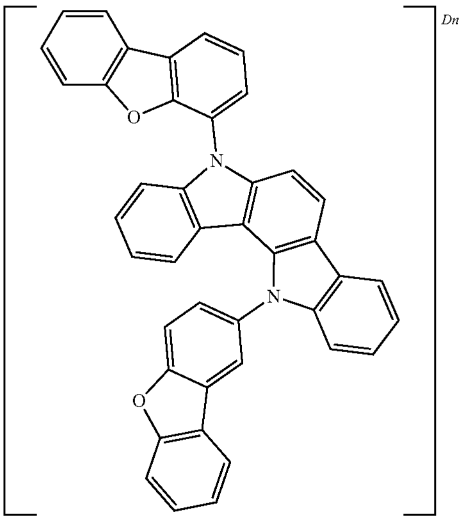
-continued
C-125
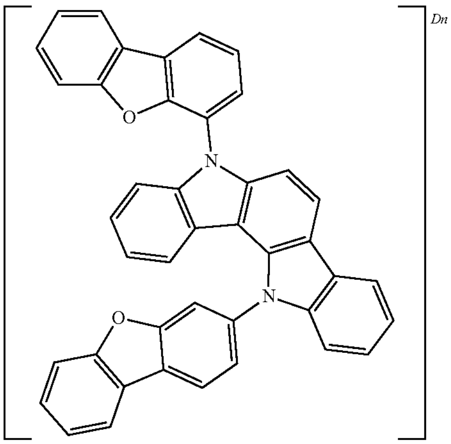
C-126
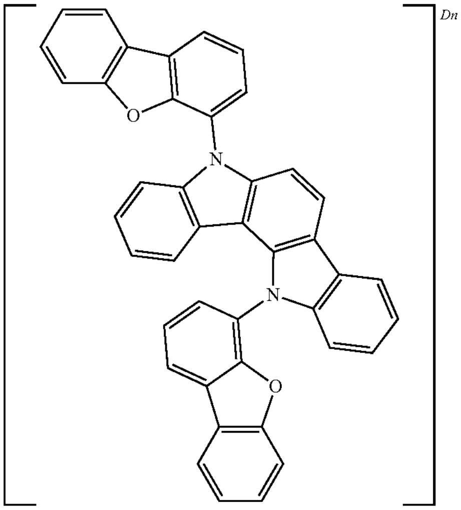
C-127
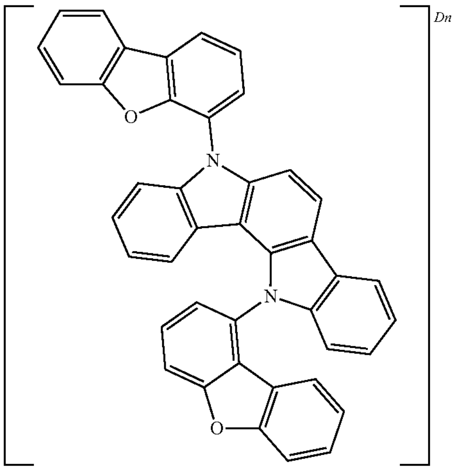

-continued
C-128
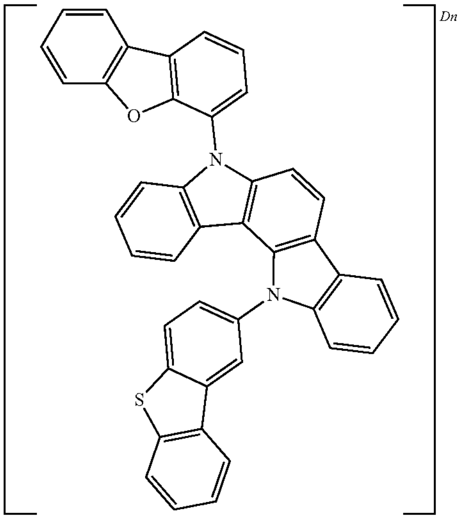
C-129
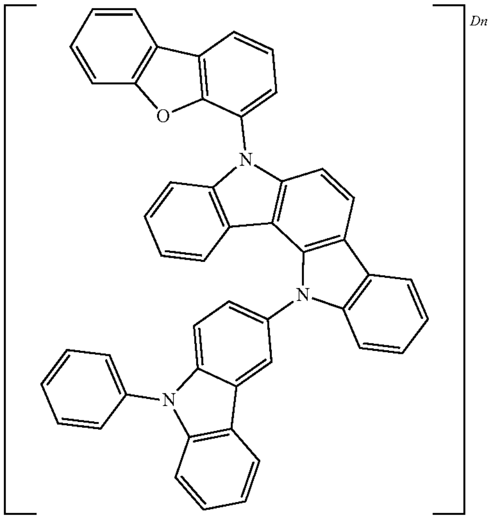
C-130
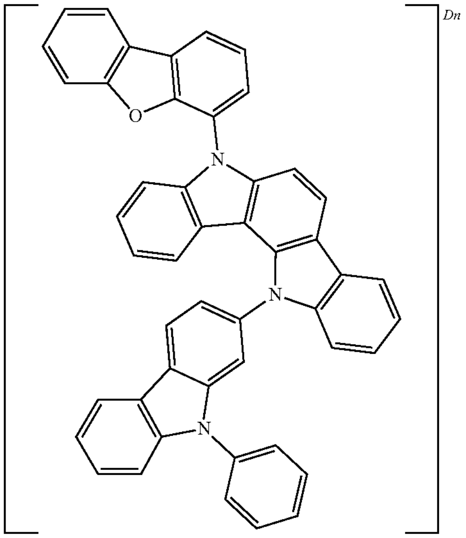
-continued
C-131
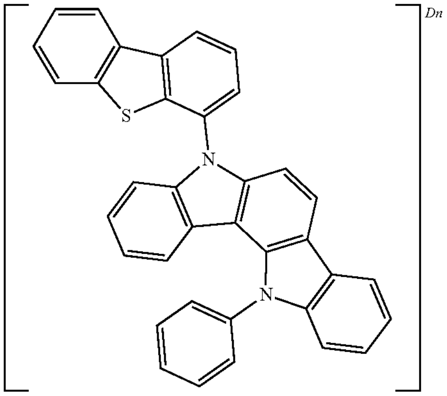
C-132
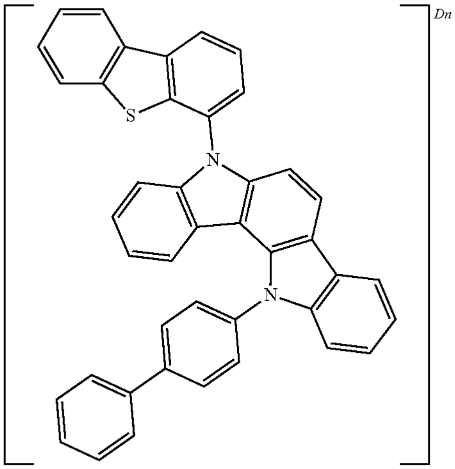
C-133
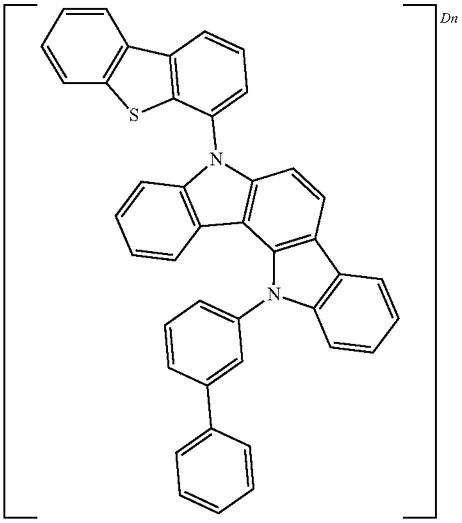

-continued
C-134
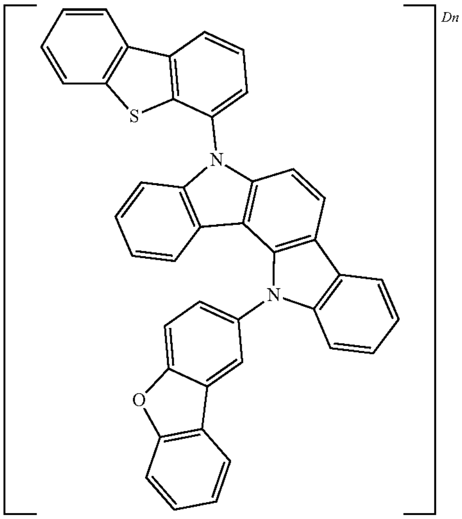
C-135
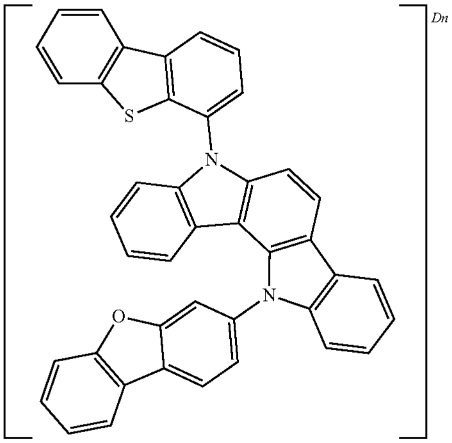
C-136
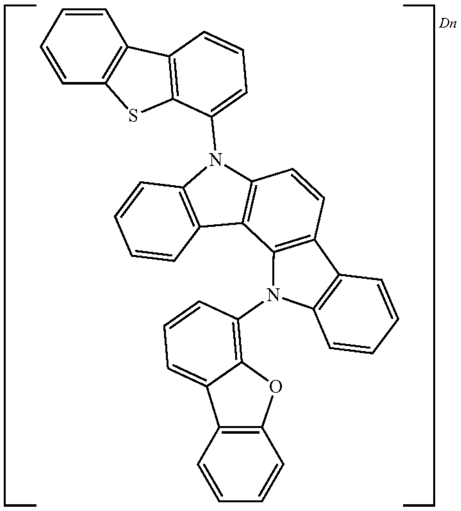
-continued
C-137
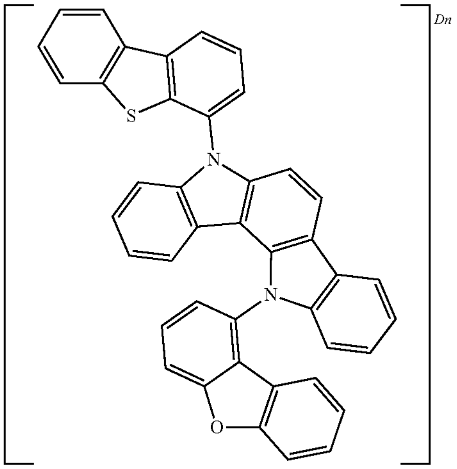
C-138
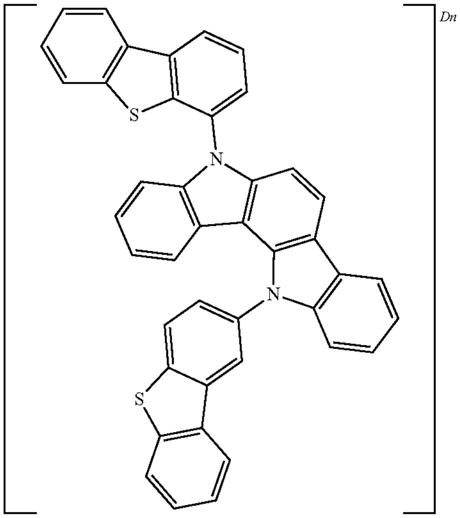
C-139
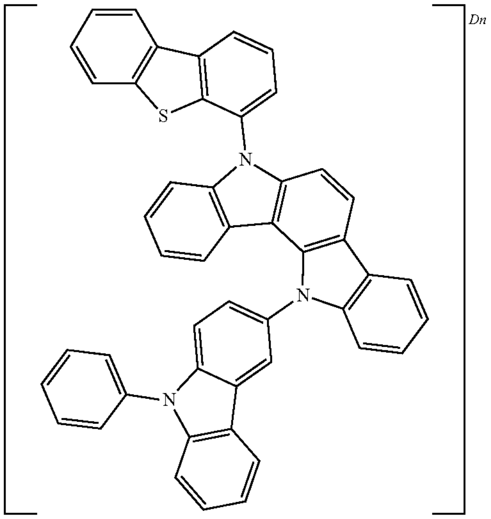

-continued
C-140
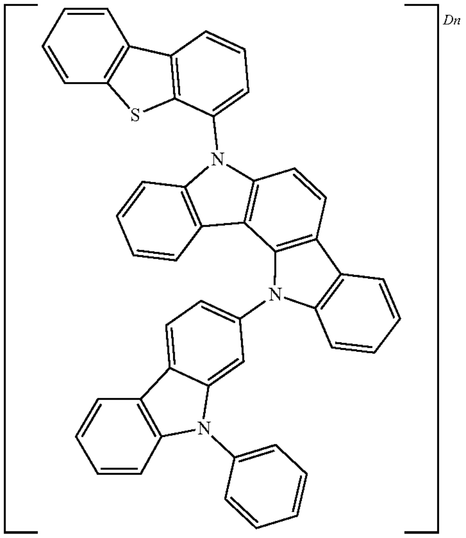
C-141
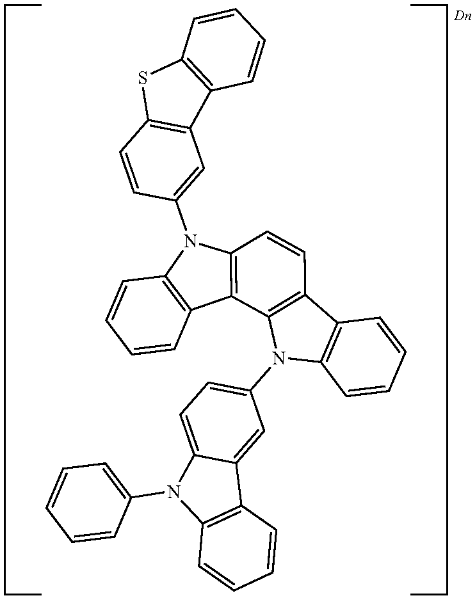
-continued
C-142
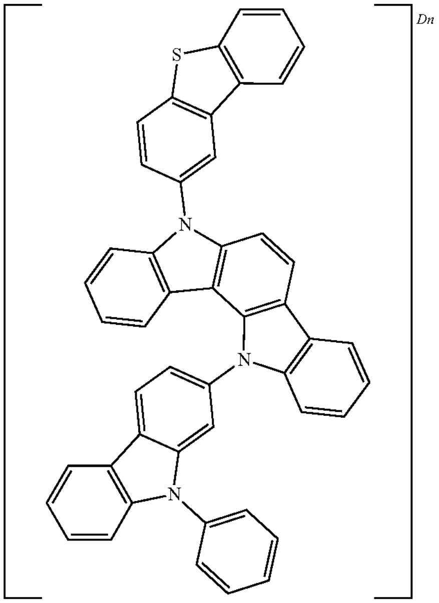
C-143
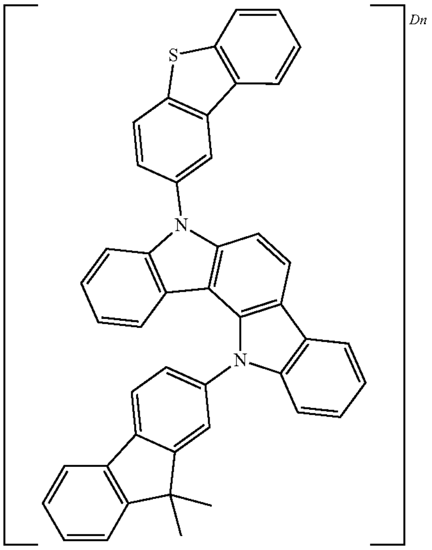
C-144
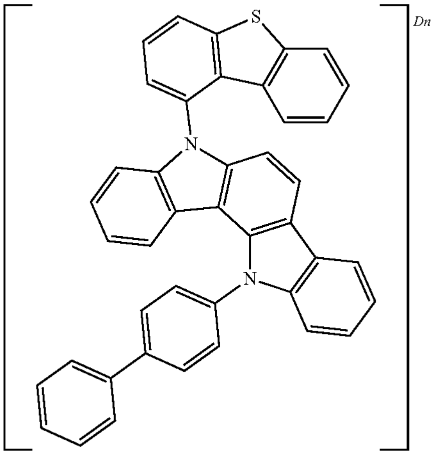

-continued
C-145
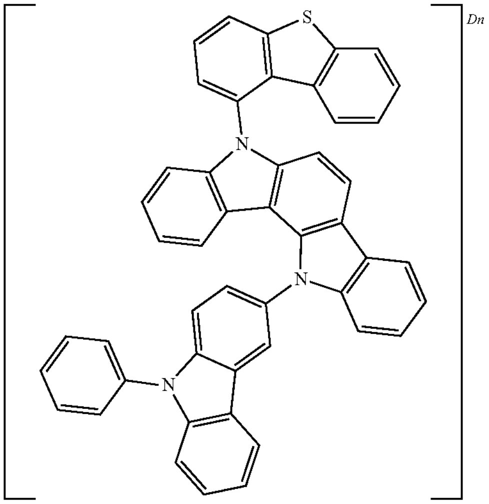
C-146
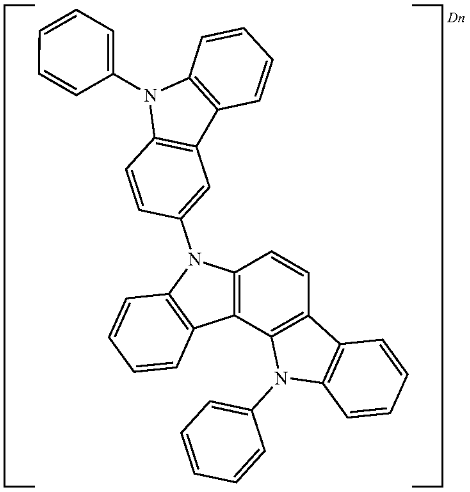
C-147
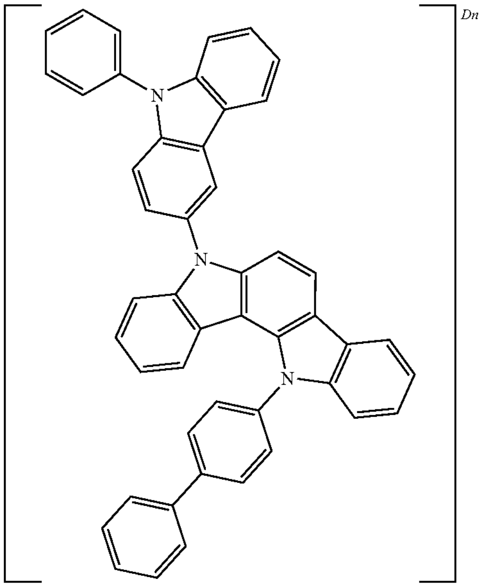
-continued
C-148
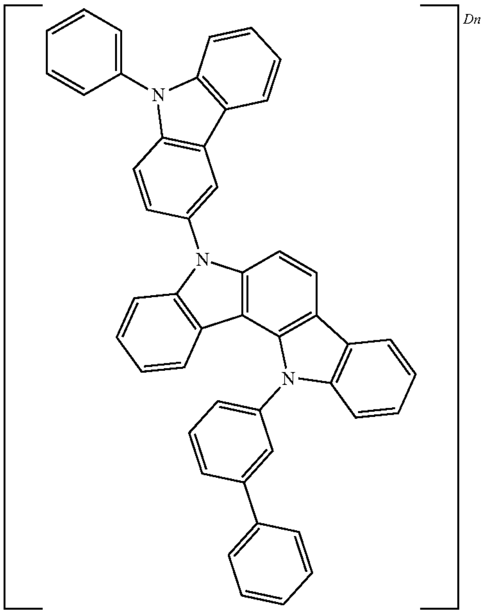
C-149
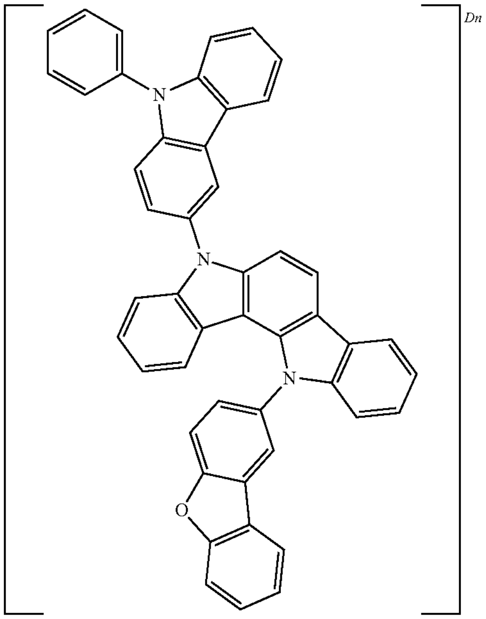

-continued
C-150
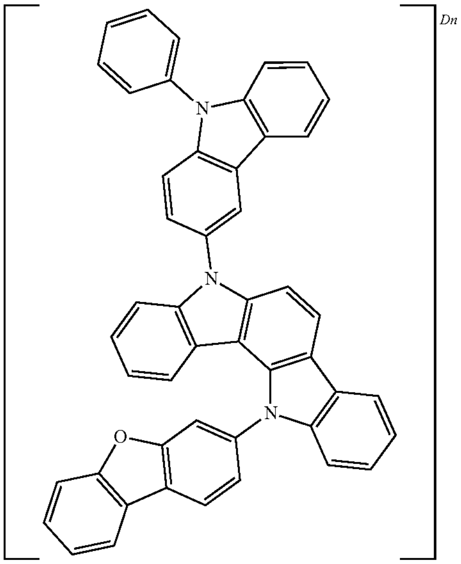
C-151
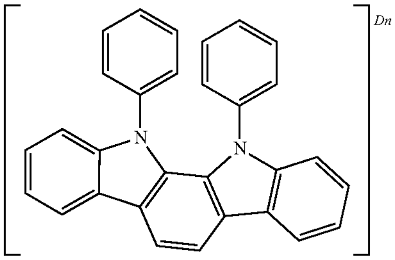
C-152
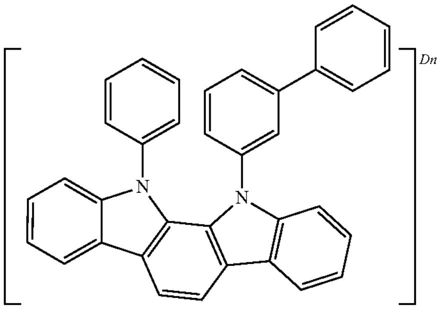
C-153
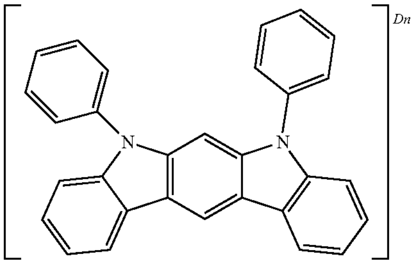
-continued
C-154
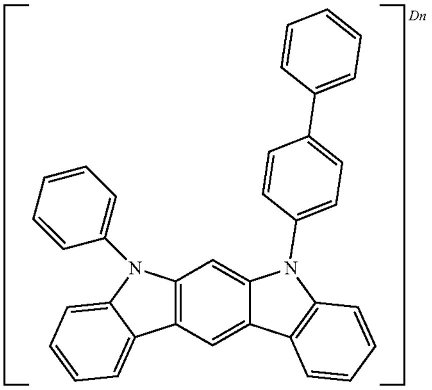
C-155
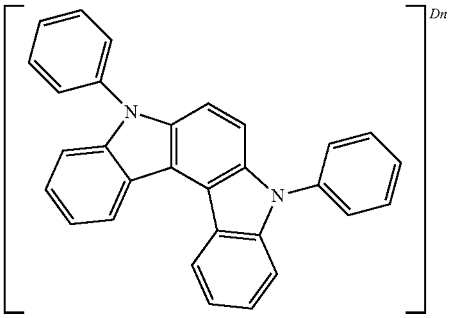
C-156
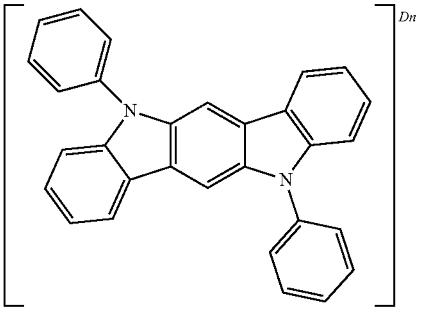
C-157
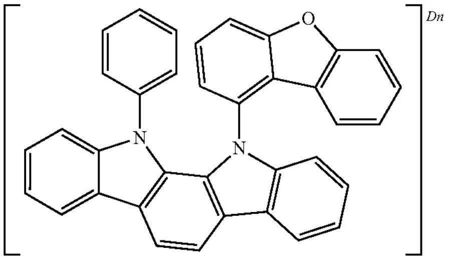

-continued

C-158

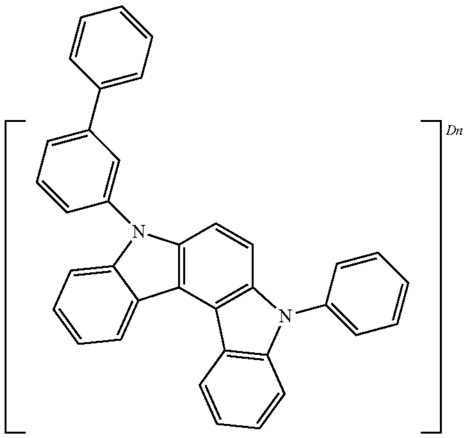

C-159

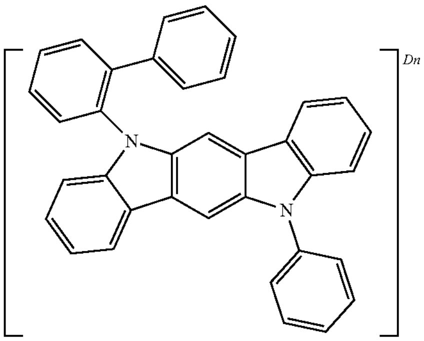

and

C-160

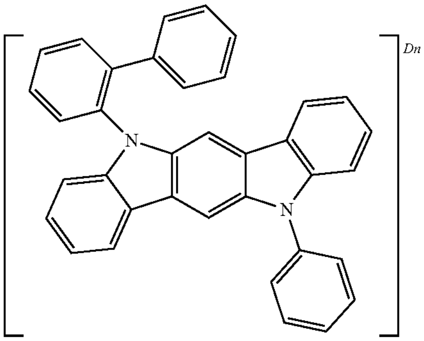

in the compounds, Dn represents that n number of hydrogens are replaced with deuterium; and n represents an integer of 1 to 50.

7. An organic electroluminescent device comprising a first electrode, a second electrode, and at least one light-emitting layer between the first electrode and the second electrode, wherein the at least one light-emitting layer comprises the plurality of host materials according to claim 1.

8. An organic electroluminescent compound represented by the following formula 2':

(2')

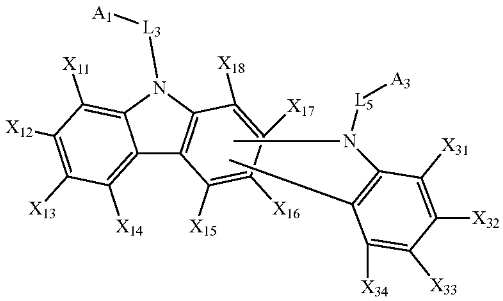

in formula 2', $A_1$ represents a Phenyl unsubstituted or substituted with at least one selected from the group consisting of deuterium, naphthyl, carbazolyl and 9-phenylcarbazolyl, a deuterium-substituted or unsubstituted dibenzofuranyl, a deuterium-substituted or unsubstituted dibenzothiophenyl, or a carbazolyl unsubstituted or substituted with at least one selected from the group consisting of deuterium and phenyl;

$L_3$ represents a single bond:

$A_3$ represents a deuterium-substituted or unsubstituted phenyl, a deuterium-substituted or unsubstituted p-biphenyl, a deuterium-substituted or unsubstituted m-biphenyl, a deuterium-substituted or unsubstituted o-biphenyl, a deuterium-substituted or unsubstituted o-terphenyl, a deuterium-substituted or unsubstituted p-terphenyl, a substituted or unsubstituted naphthyl, a substituted or unsubstituted triphenylenyl, a substituted or unsubstituted dimethylfluorenyl, a substituted or unsubstituted dibenzofuranyl, a substituted or unsubstituted dibenzothiophenyl, or a substituted or unsubstituted carbazolyl;

$L_5$ represents a single bond, or a deuterium-substituted or unsubstituted (C6-C30)arylene; and $X_{11}$ to $X_{13}$, and $X_{31}$ to $X_{34}$, each independently, represent hydrogen, deuterium, a substituted or unsubstituted (C6-C30)aryl, or a substituted or unsubstituted (3- to 30-membered)heteroaryl;

with the proviso that at least one of $X_{11}$, $X_{15}$ to $X_{13}$, and $X_{31}$ represents deuterium.

9. The organic electroluminescent compound according to claim 8, wherein the compound represented by formula 2' is represented by any one of the following formulas 2'-1 to 2'-6:

(2'-1)

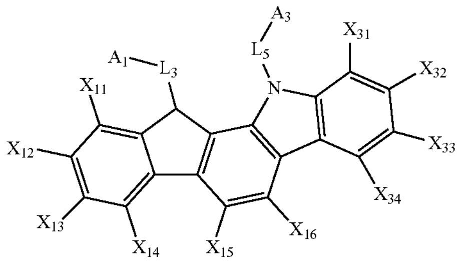

-continued
(2'-2)
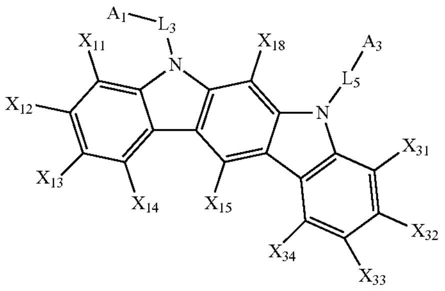
(2'-3)
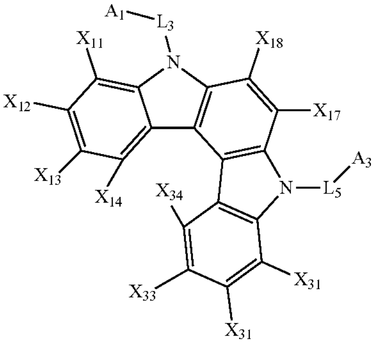
(2'-4)
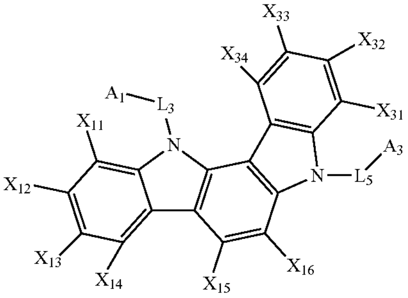
(2'-5)
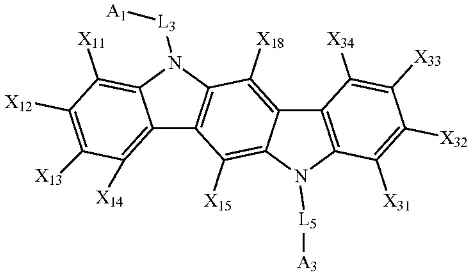
(2'-6)
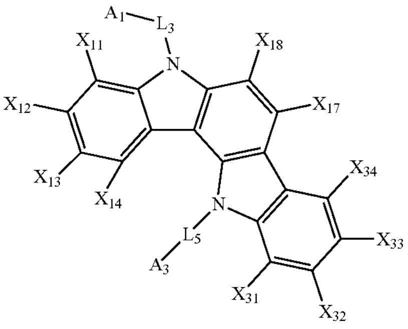
in formulas 2'-1 to 2'-6, $A_1$, $A_3$, $L_3$, $L_5$, $X_{11}$ to $X_{18}$, and $X_{31}$ to $X_{34}$ are as defined in claim 8.
10. The organic electroluminescent compound according to claim 8, wherein the organic electroluminescent compound represented by formula 2' is selected from the group consisting of the following compounds:
C-1
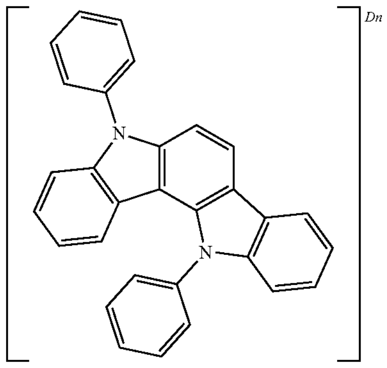
C-2
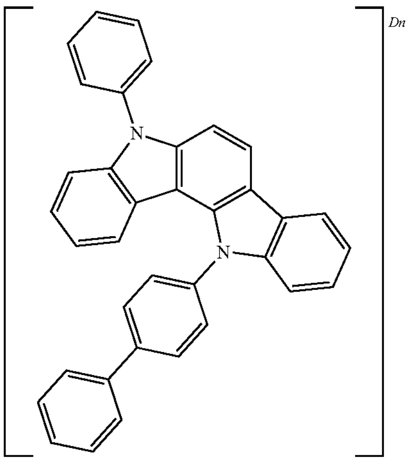
C-3
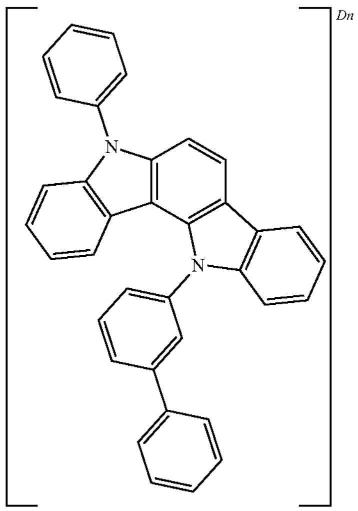

-continued
C-4
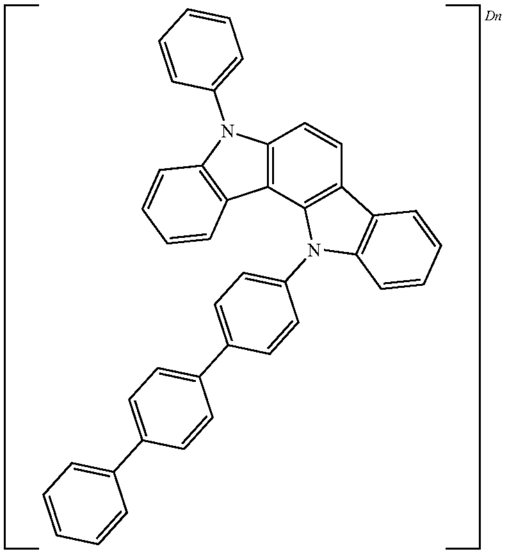
C-5
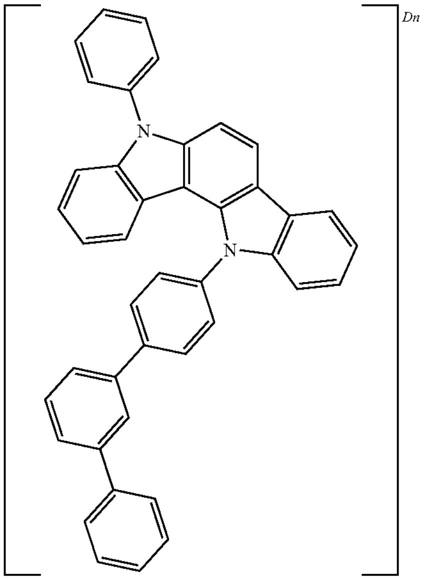
C-6
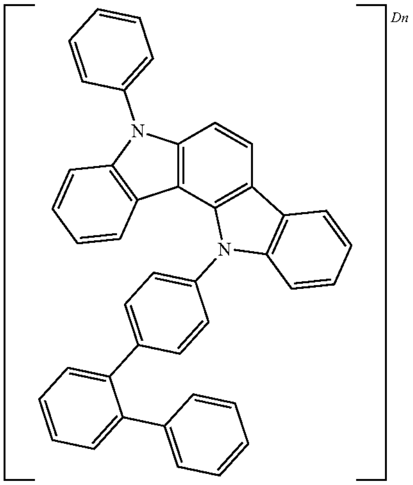
-continued
C-7
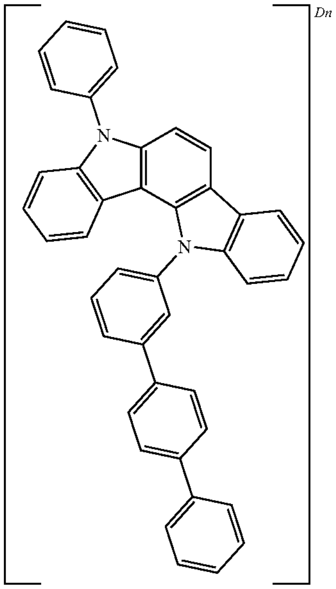
C-8
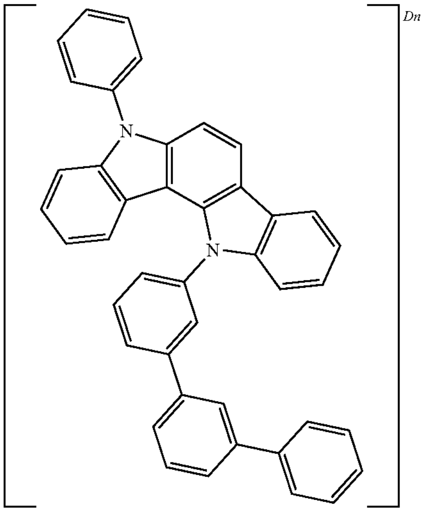
C-9
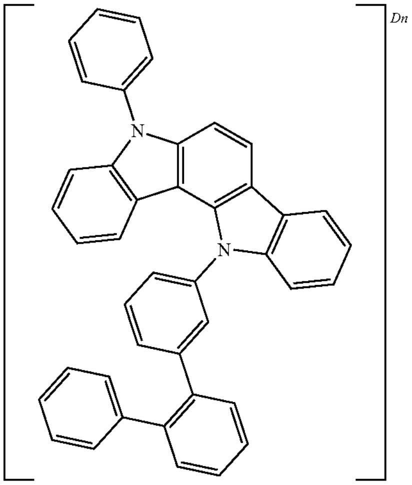

-continued
C-10
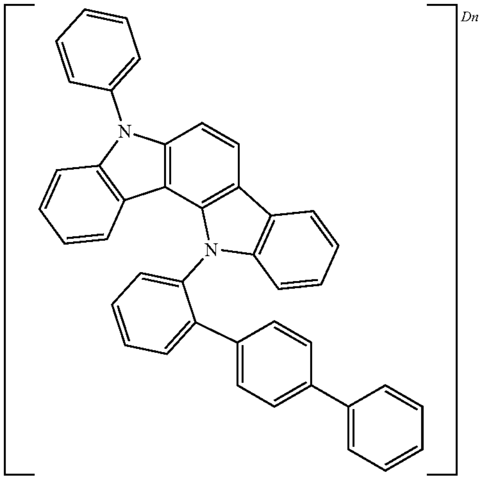
C-11
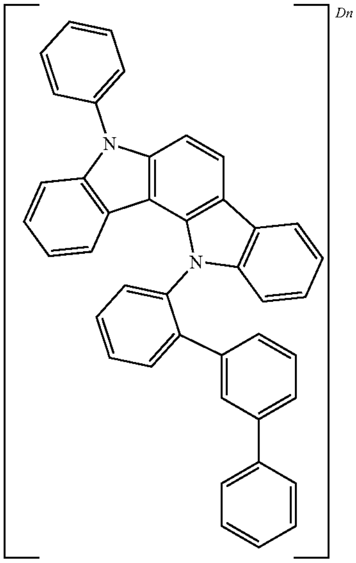
C-13
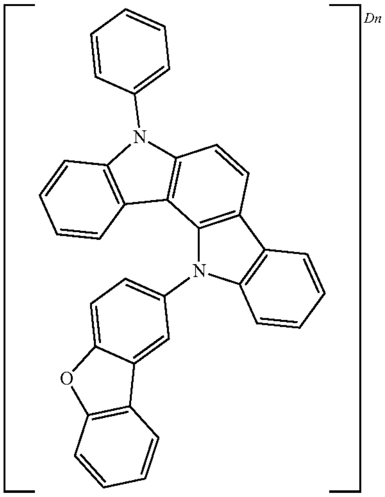
-continued
C-14
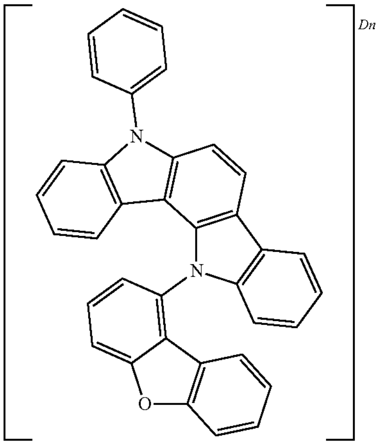
C-15
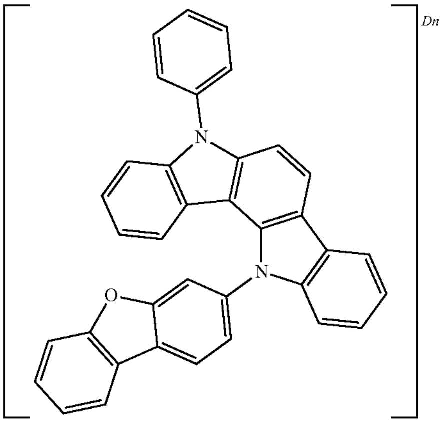
C-16
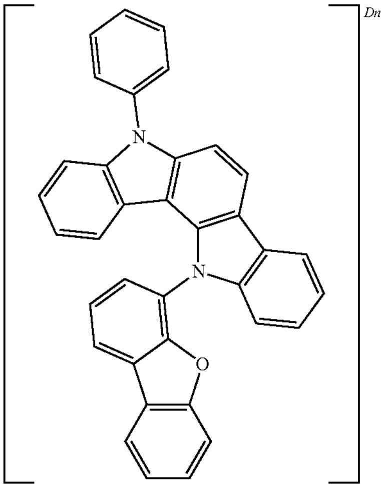

-continued
C-17
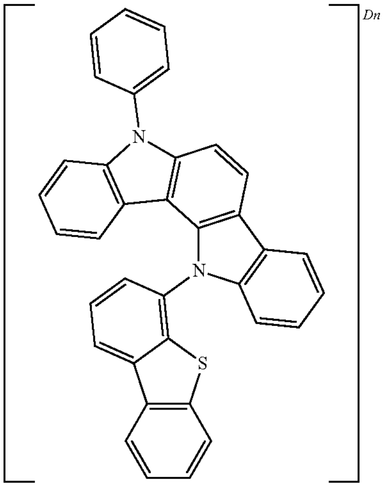
C-18
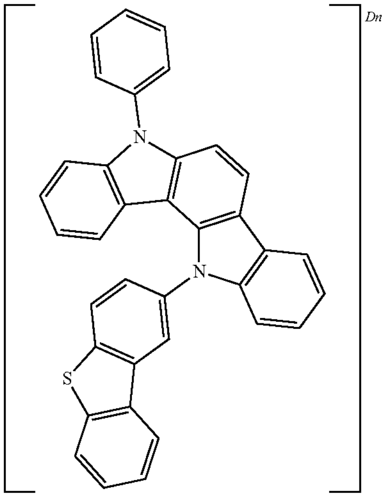
C-19
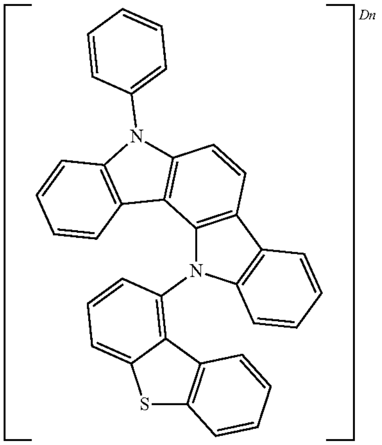
-continued
C-20
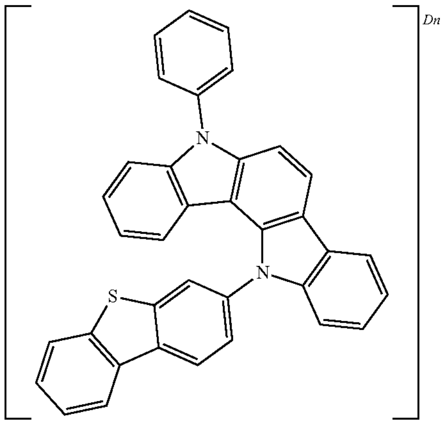
C-21
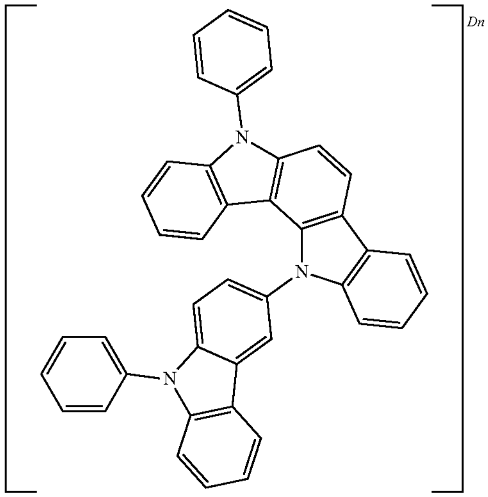
C-22
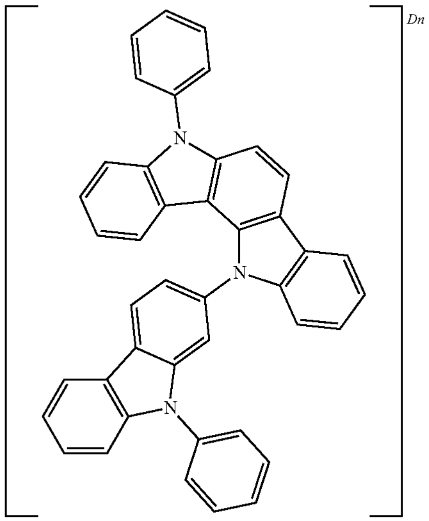

-continued
C-23
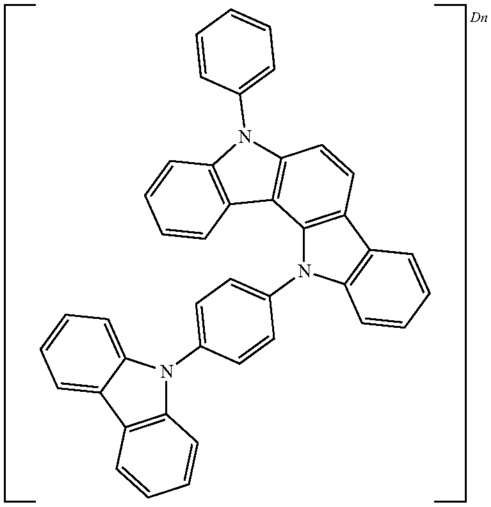
C-24
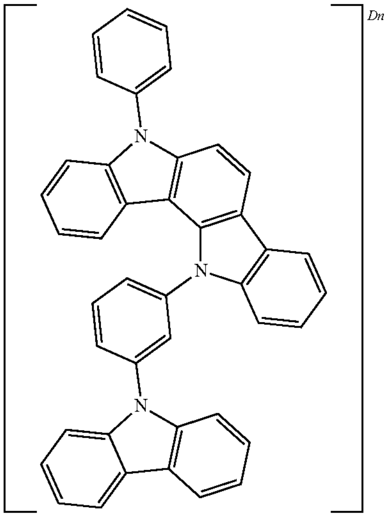
C-25
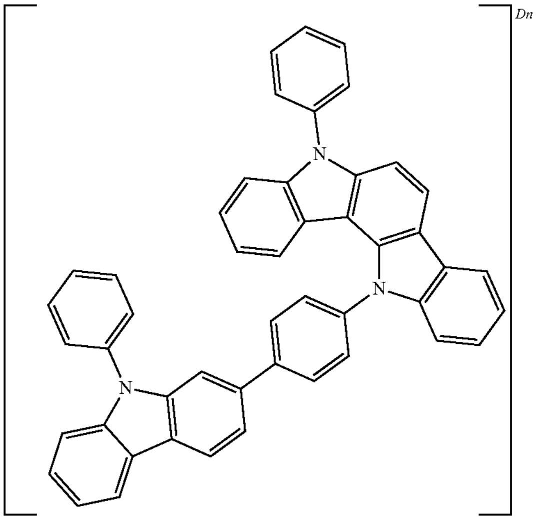
-continued
C-26
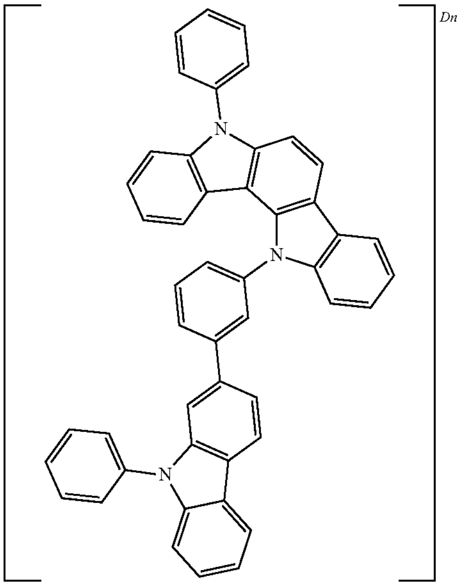
C-27
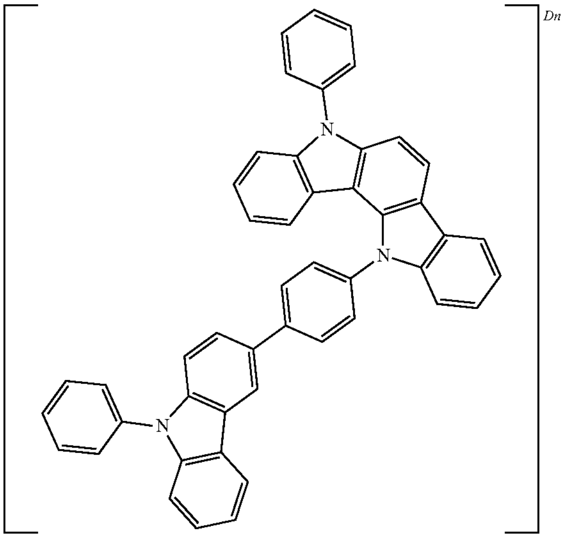

C-28
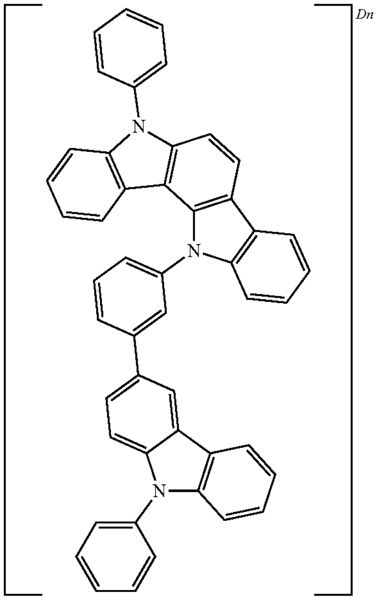
C-29
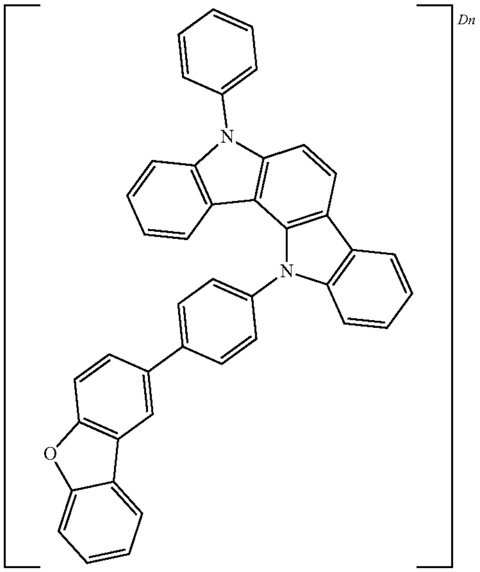
C-30
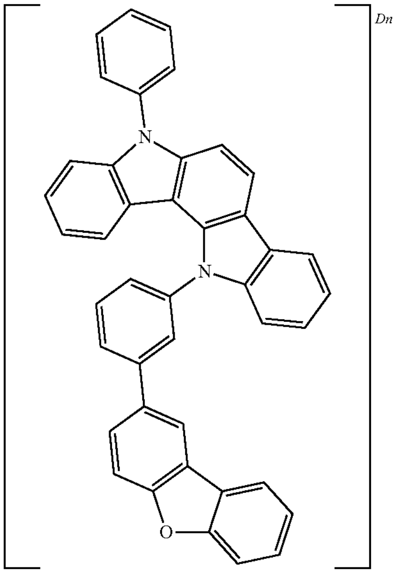
C-31
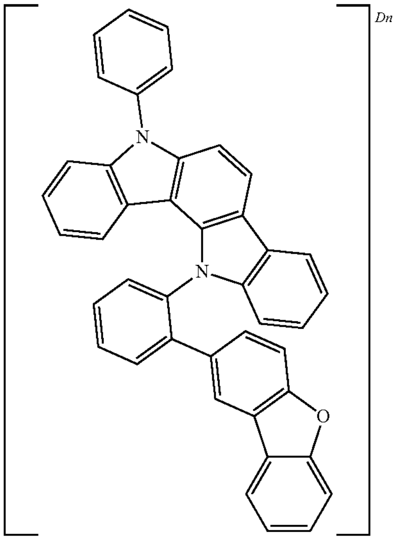
C-32
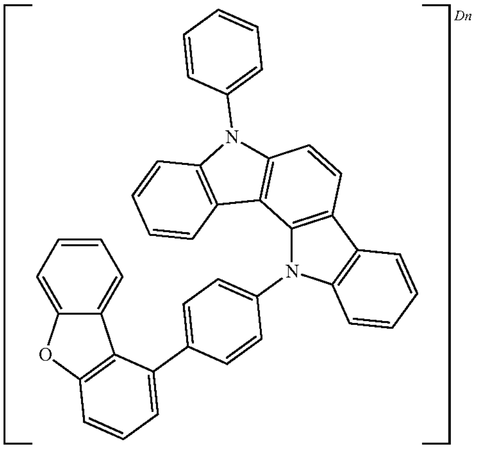

-continued
C-33
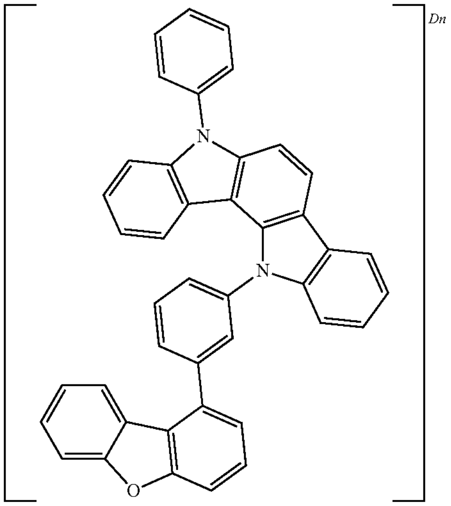
C-34
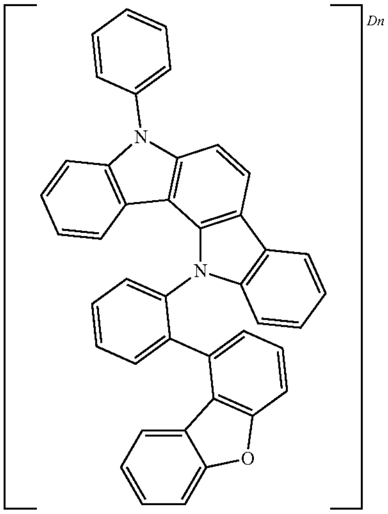
C-35
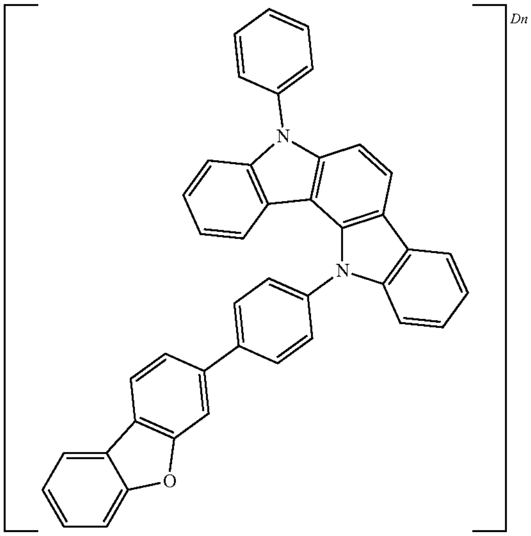
-continued
C-36
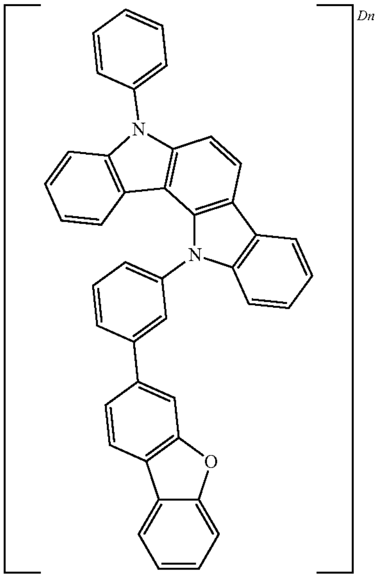
C-37
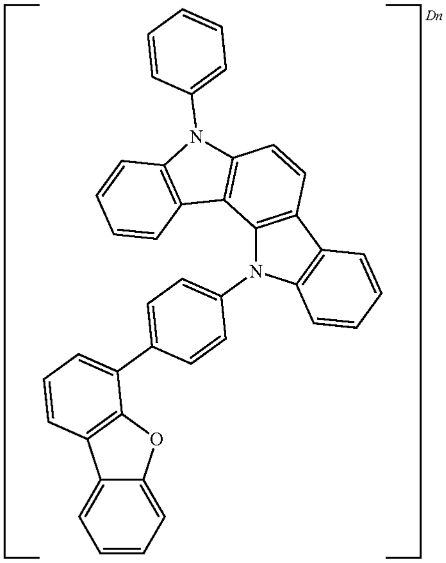

-continued
C-38
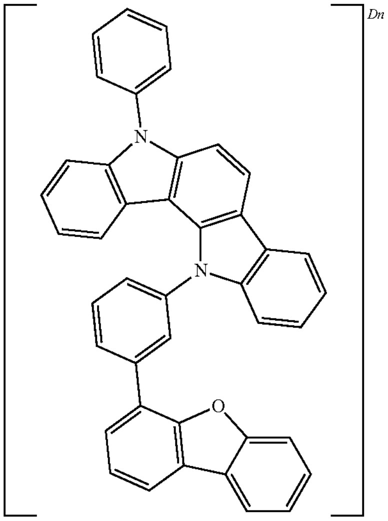
C-39
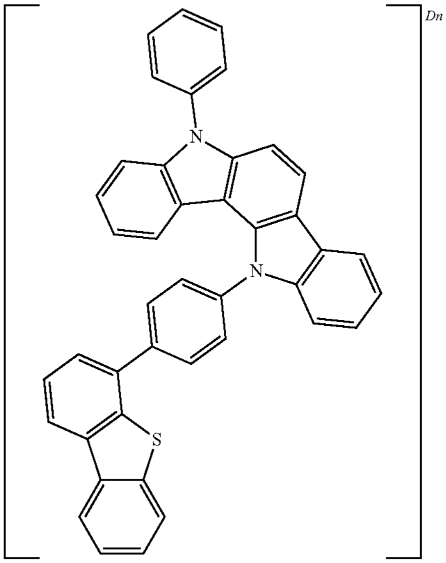
C-40
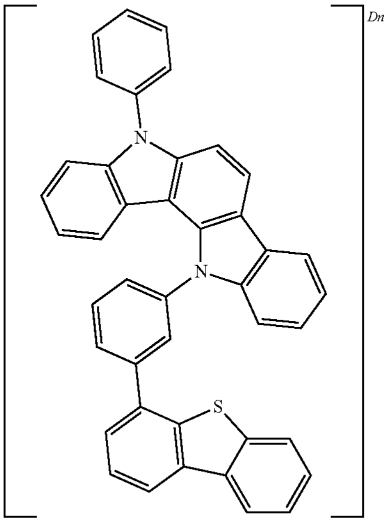
-continued
C-41
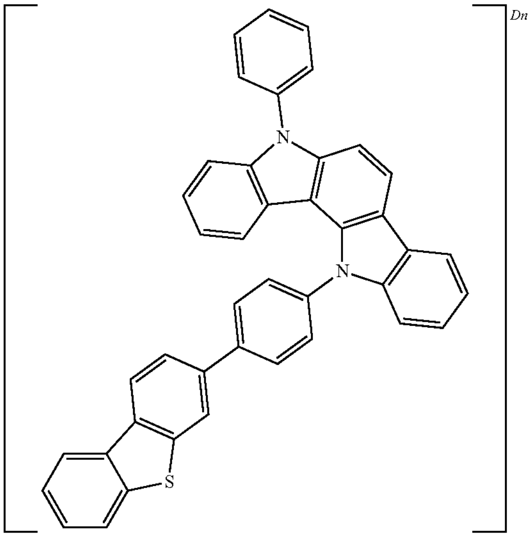
C-42
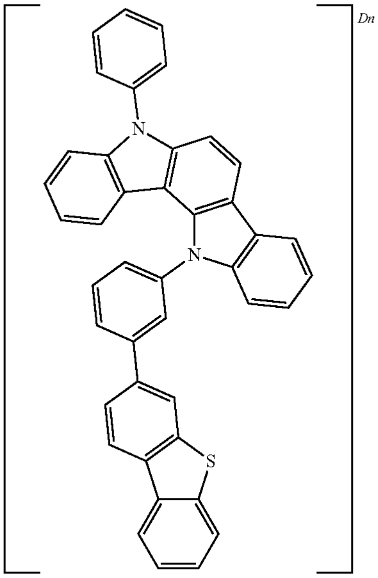
C-43
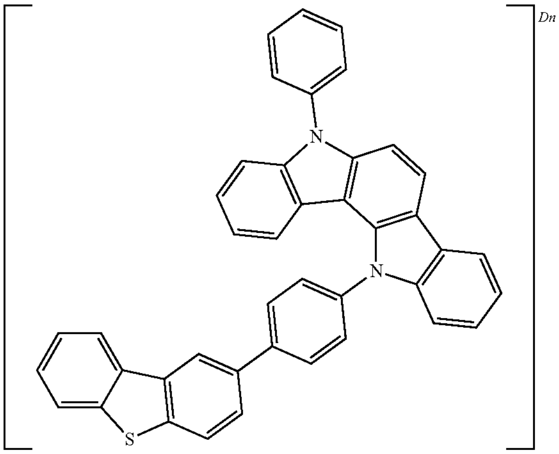

-continued
C-44
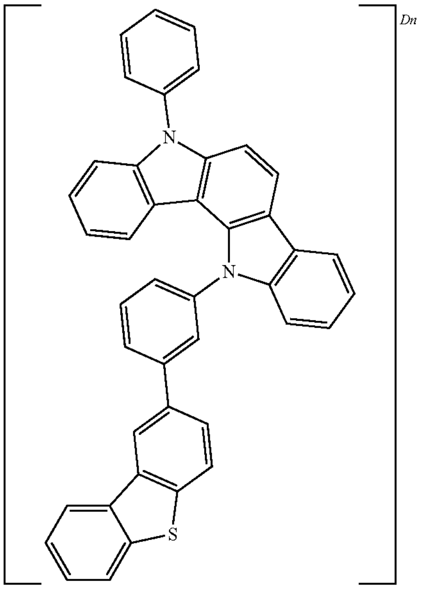
C-45
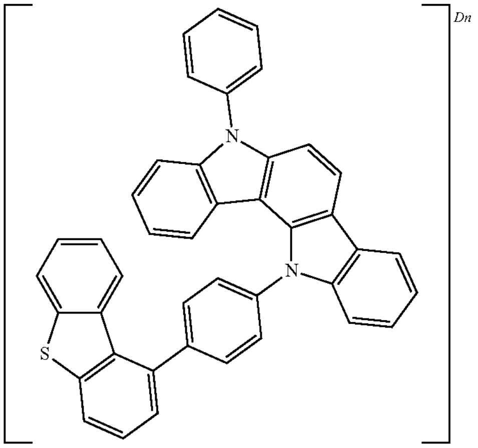
C-46
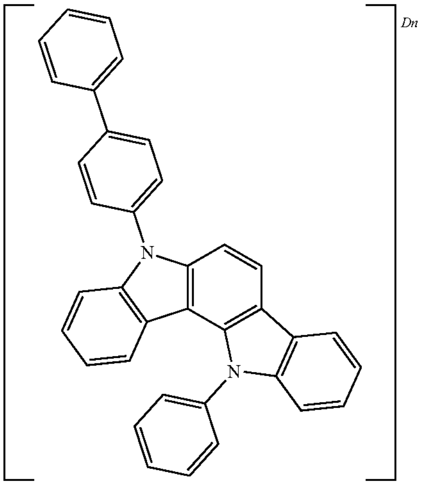
-continued
C-58
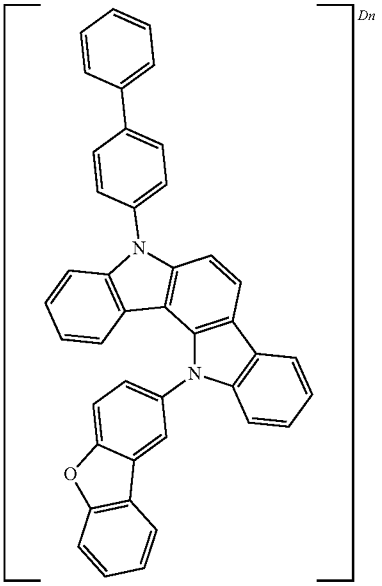
C-59
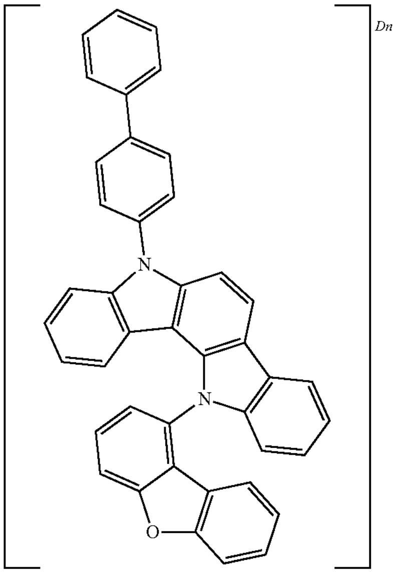

C-60
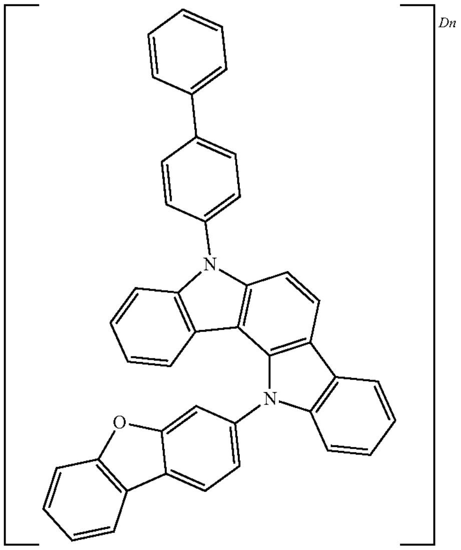
C-61
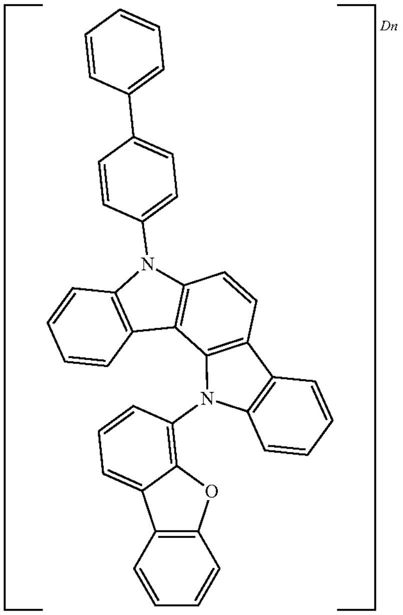
C-62
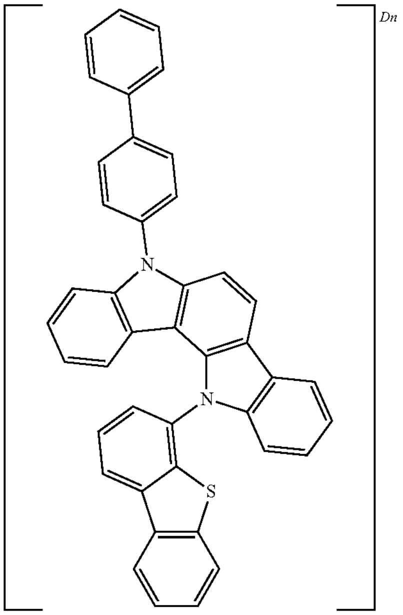
C-63
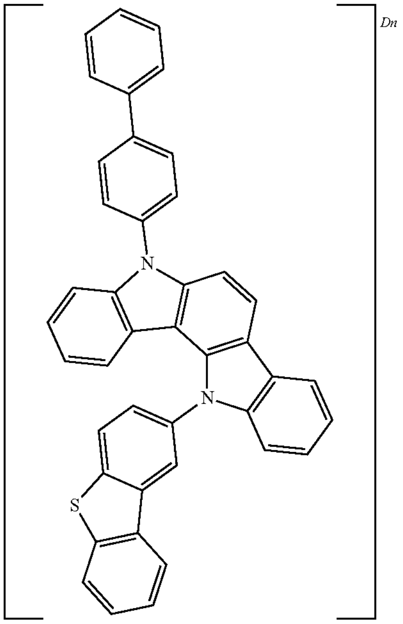

C-64
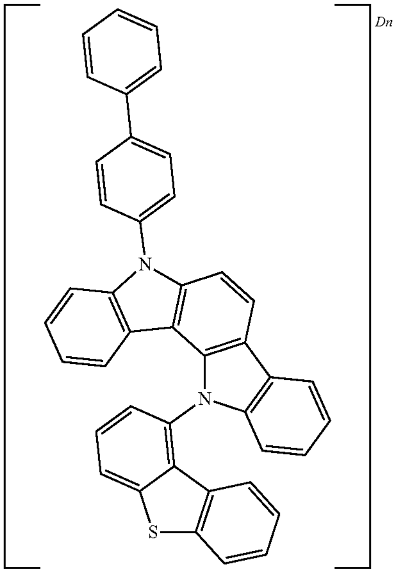
C-65
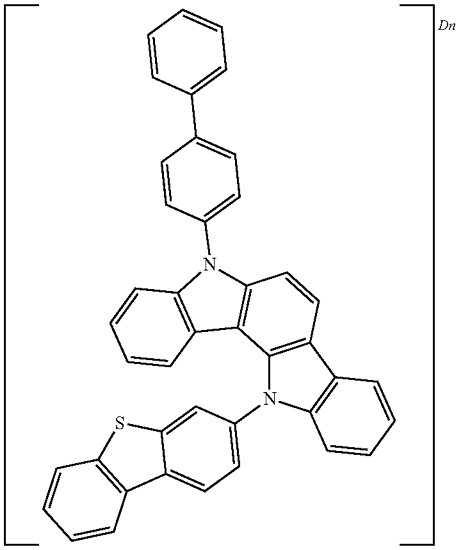
C-66
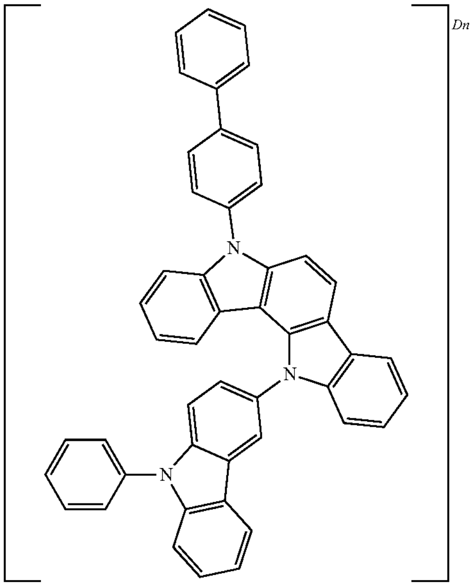
C-67
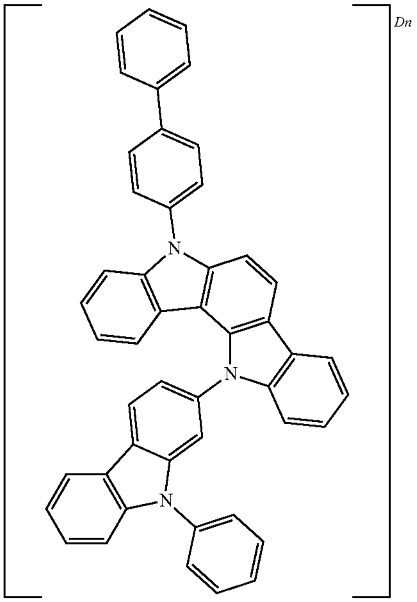

-continued
C-68
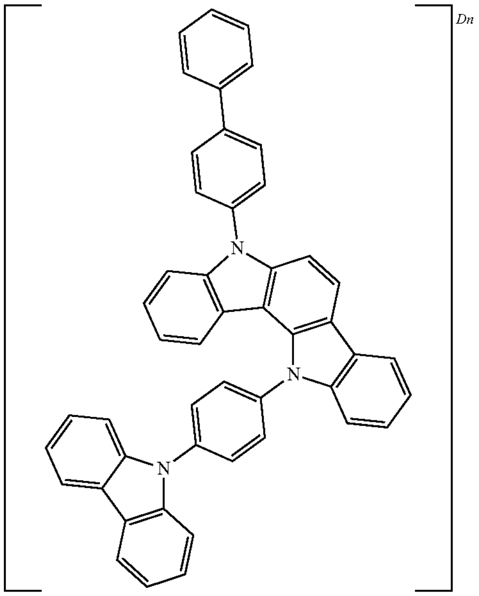
C-69
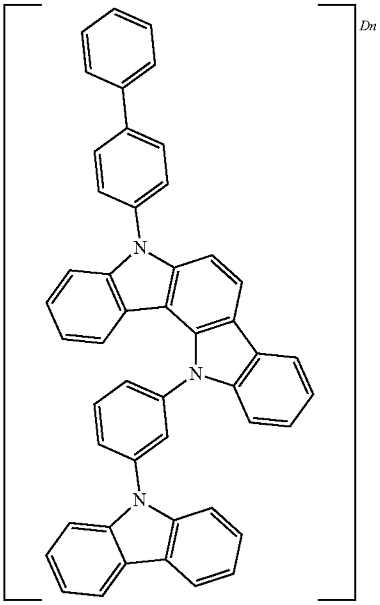
-continued
C-70
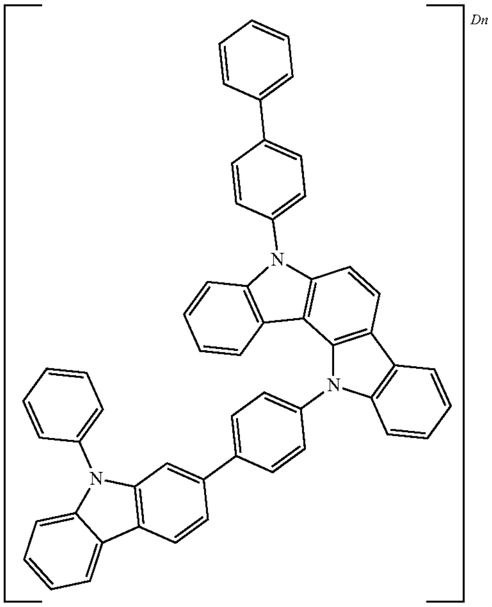
C-71
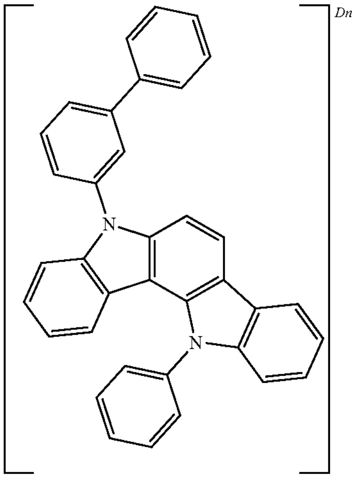
C-83
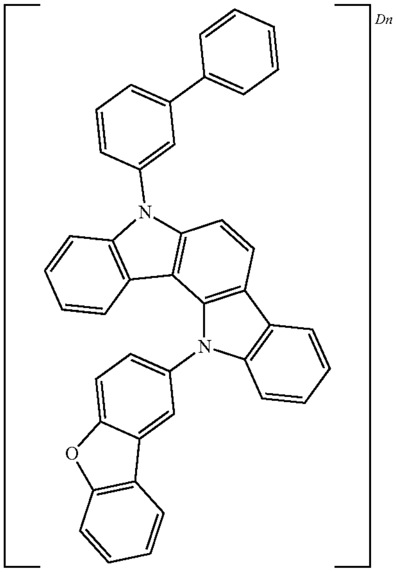

-continued
C-84
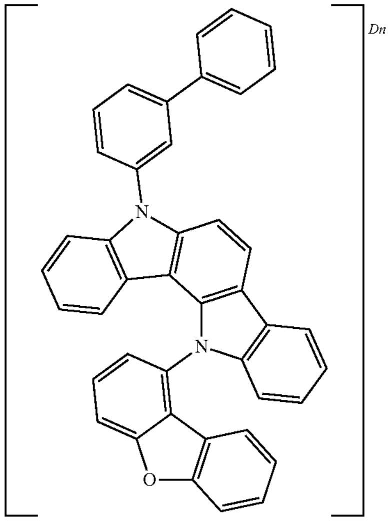
C-85
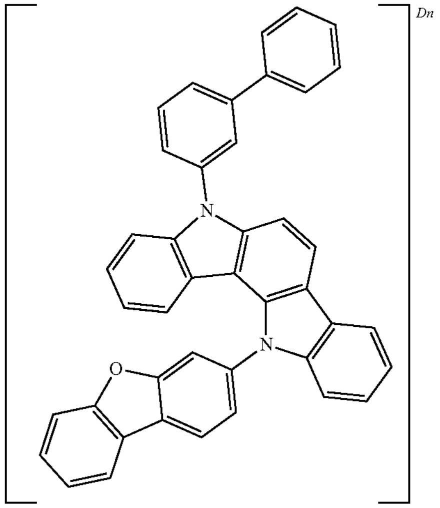
C-86
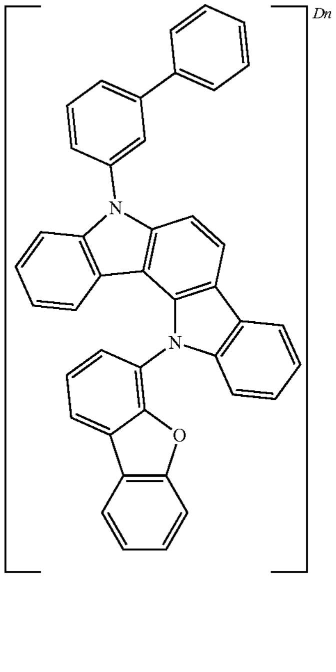
-continued
C-87
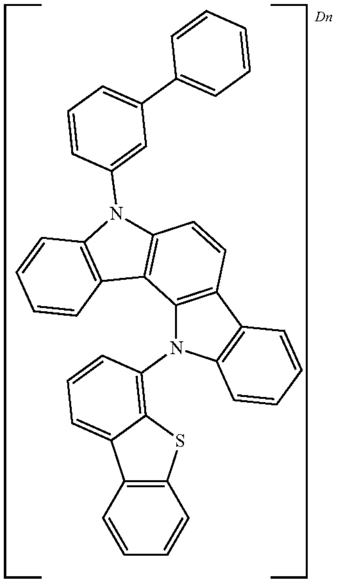
C-88
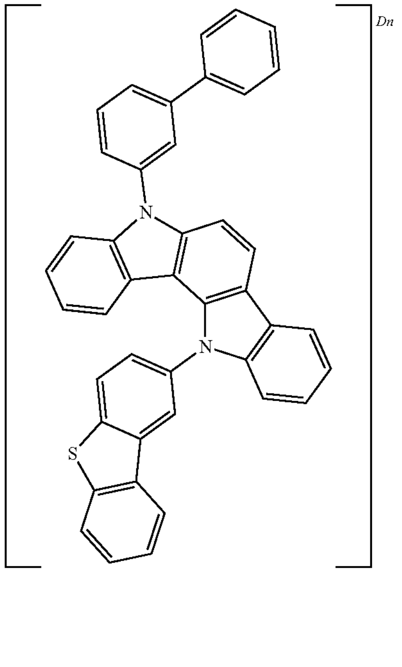

-continued
C-89
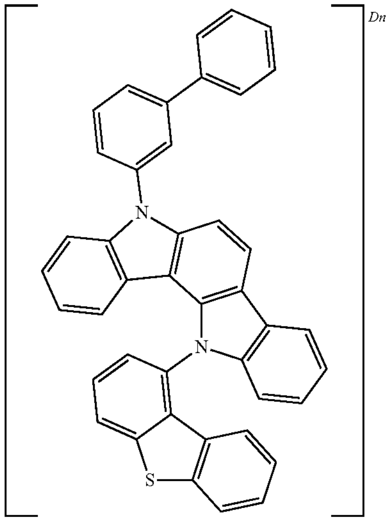
C-90
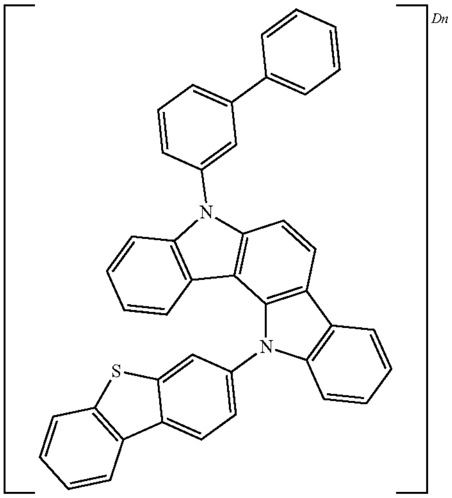
C-91
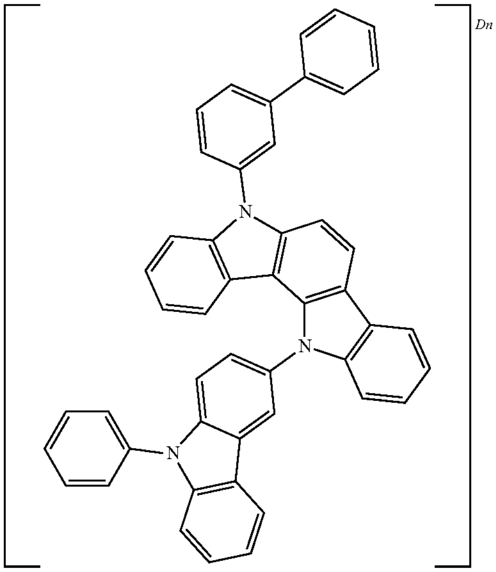
-continued
C-92
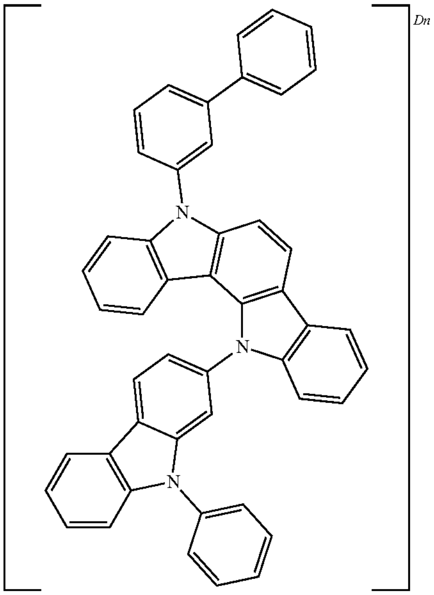
C-93
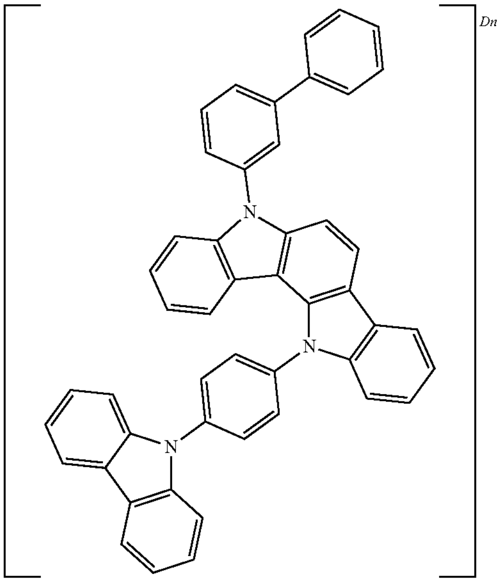

-continued
C-94
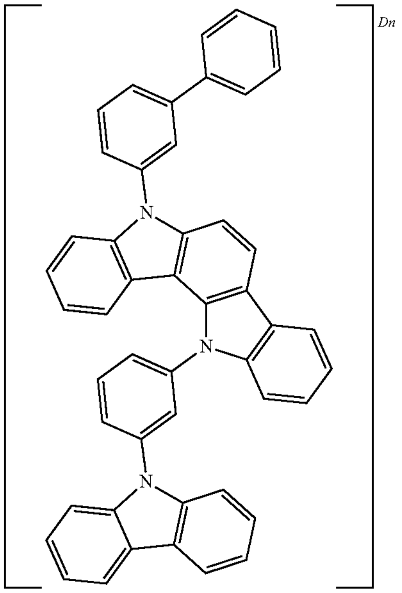
C-95
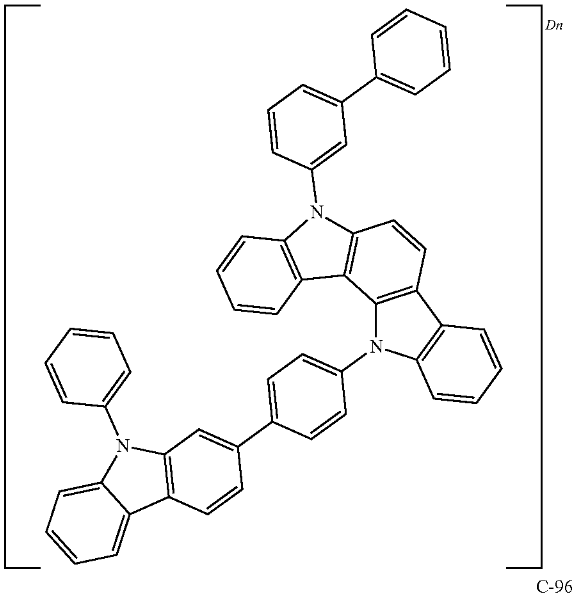
C-96
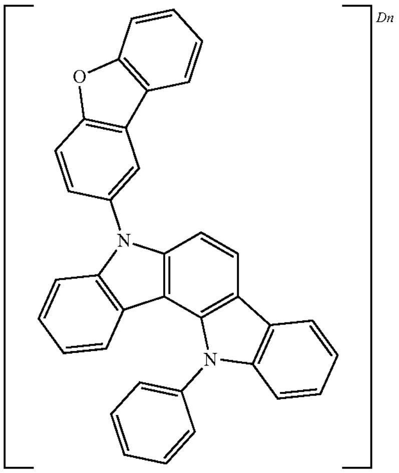
-continued
C-97
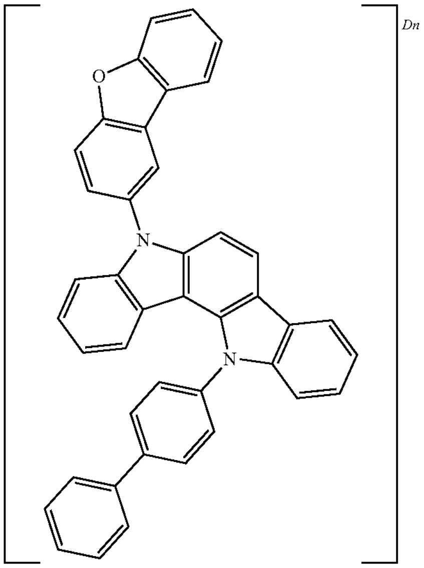
C-98
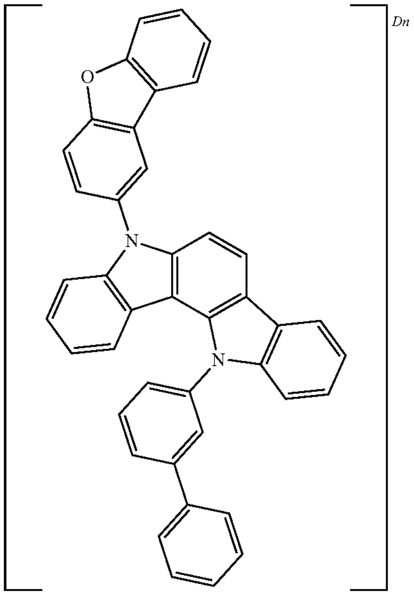

-continued
C-99
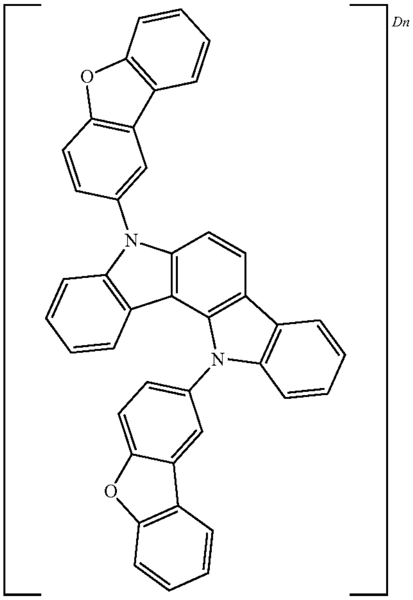
-continued
C-101
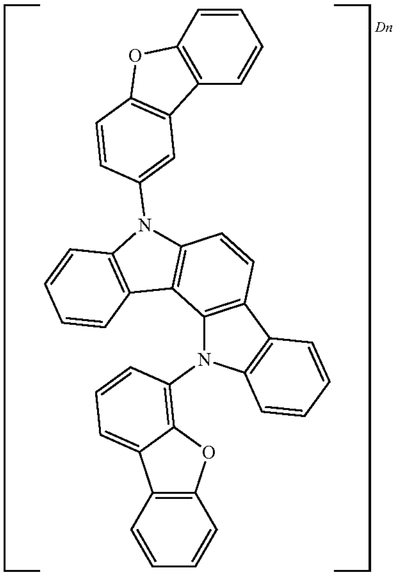
C-100
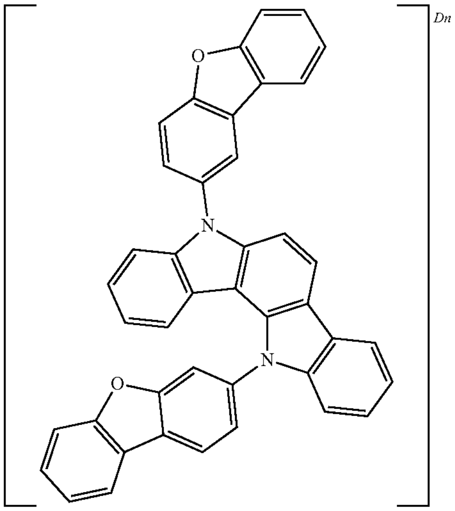
C-102
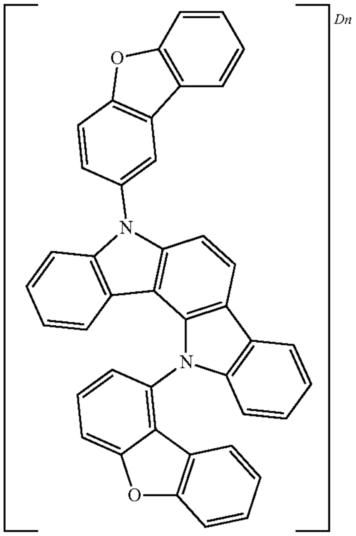

-continued
C-103
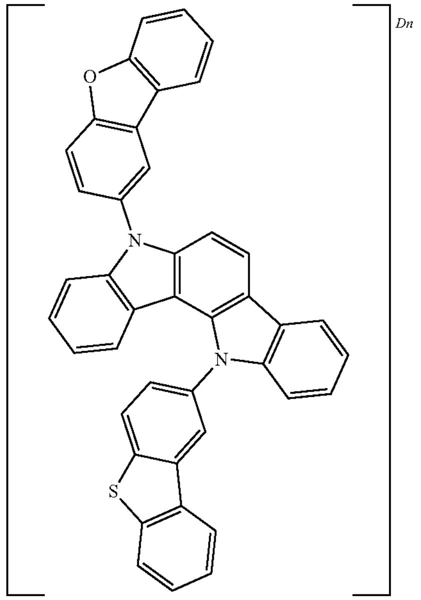
C-104
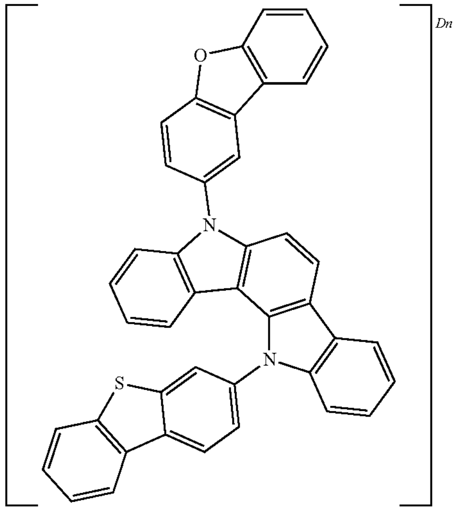
-continued
C-105
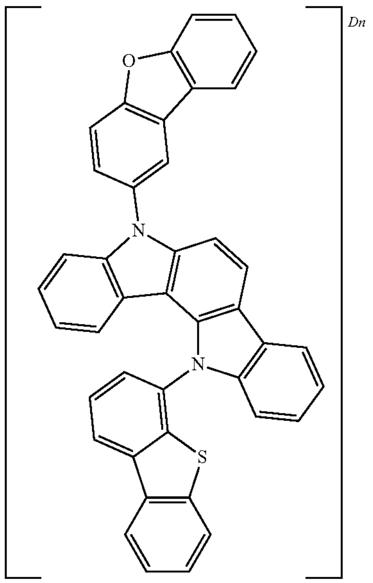
C-106
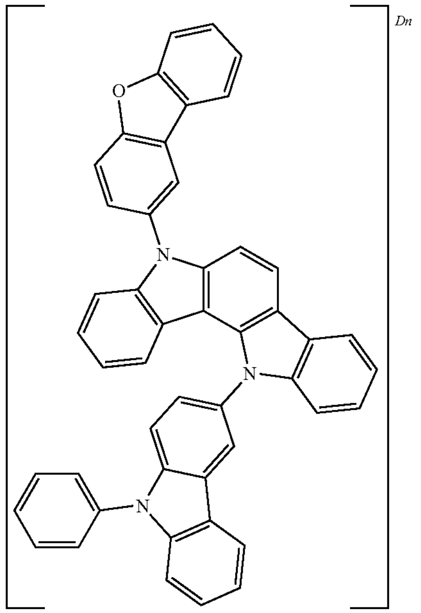

-continued
C-107
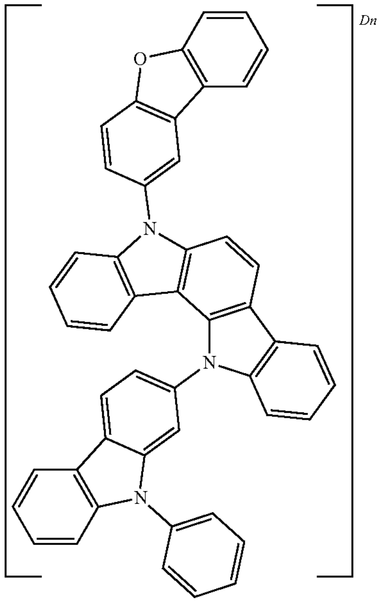
C-108
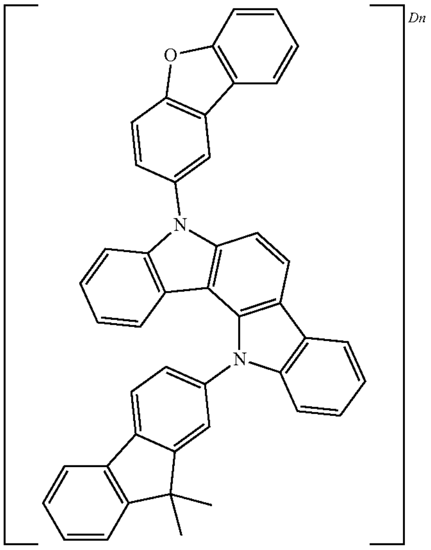
C-109
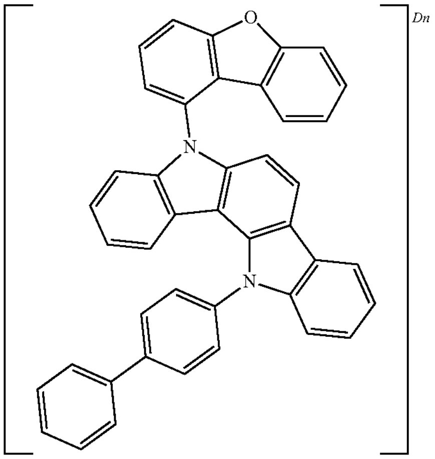
-continued
C-110
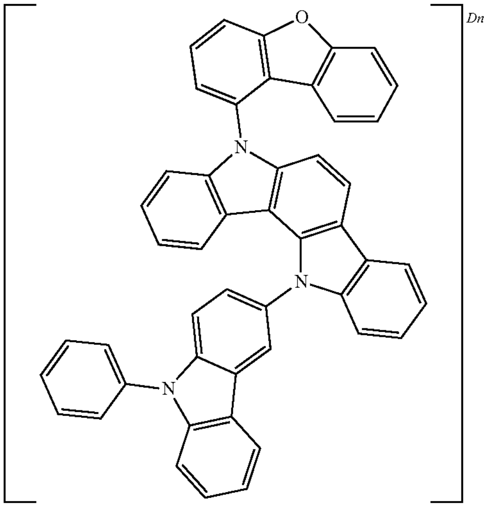
C-111
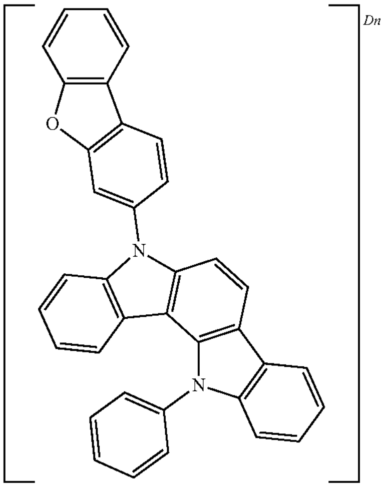
C-112
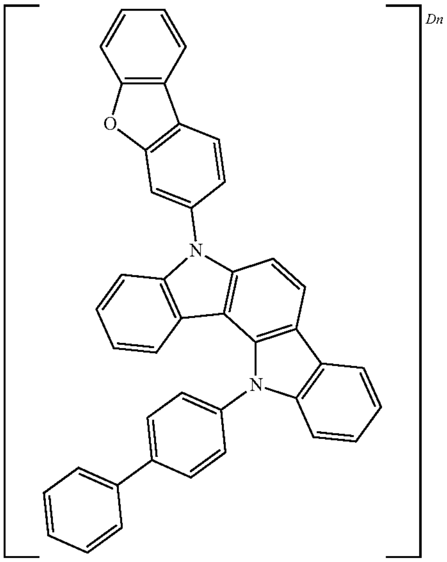

-continued
C-113
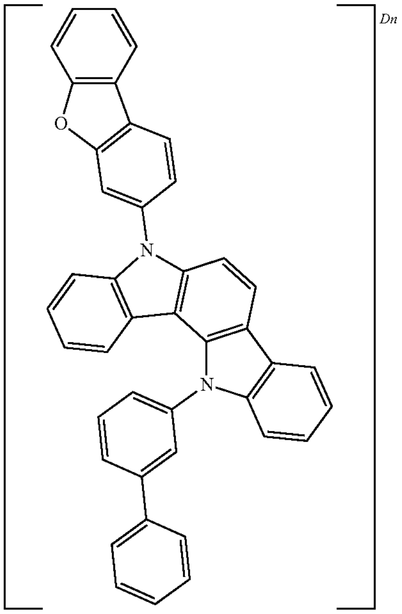
C-114
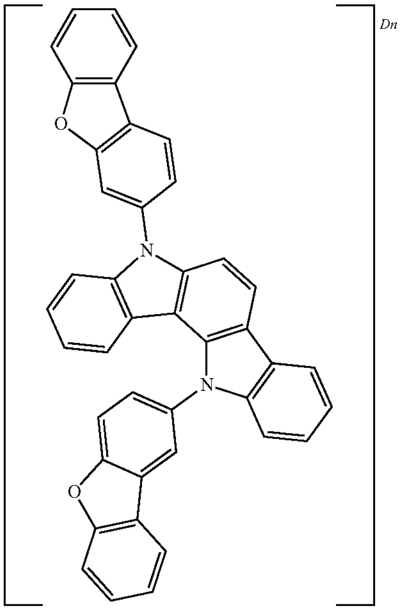
-continued
C-115
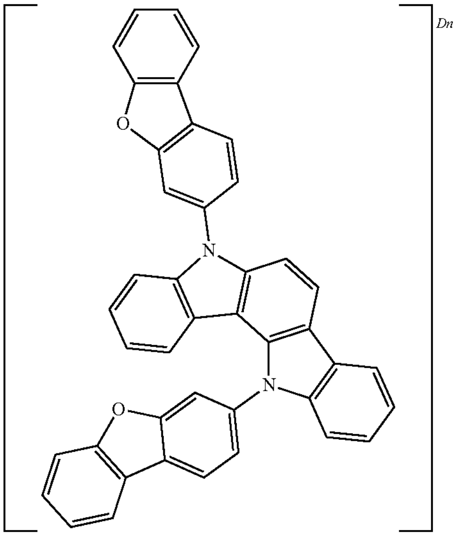
C-116
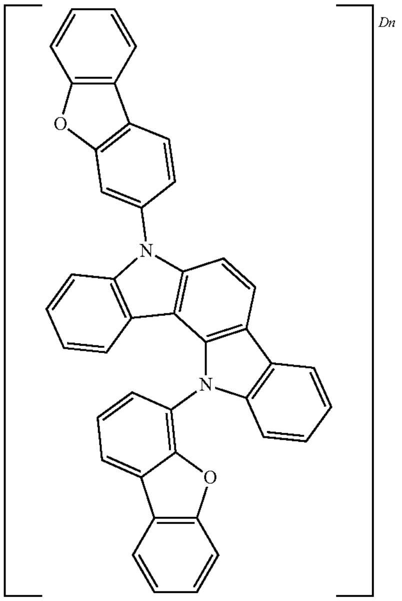

-continued
C-117
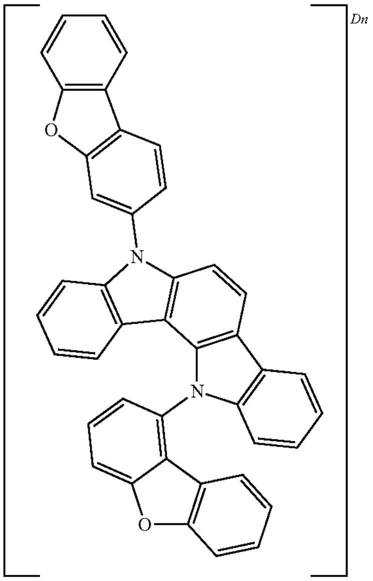
C-118
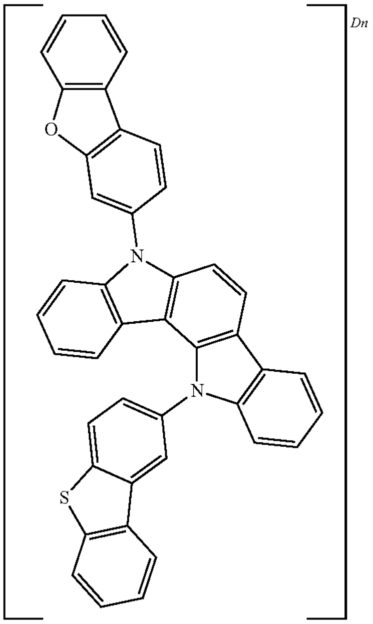
-continued
C-119
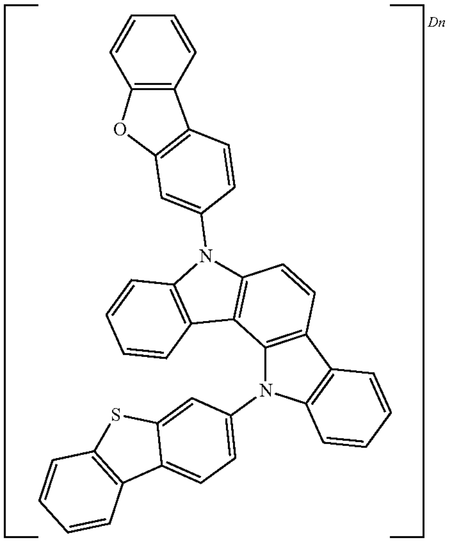
C-120
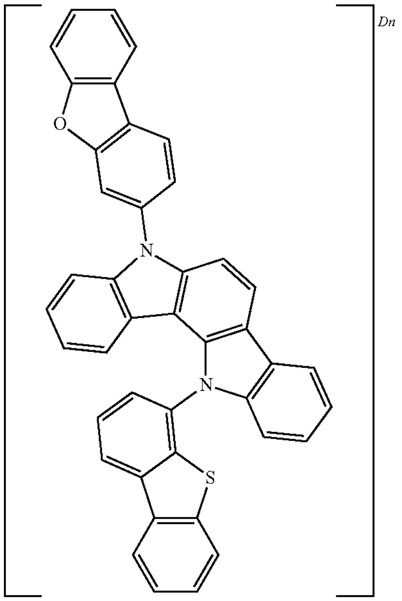
C-121
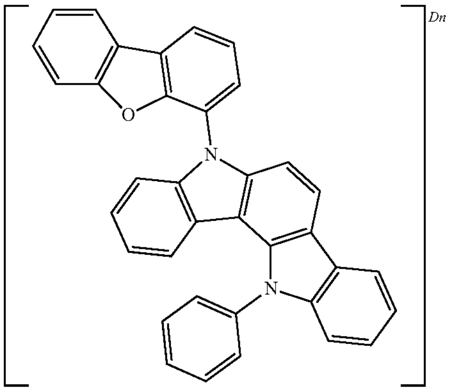

-continued
C-122
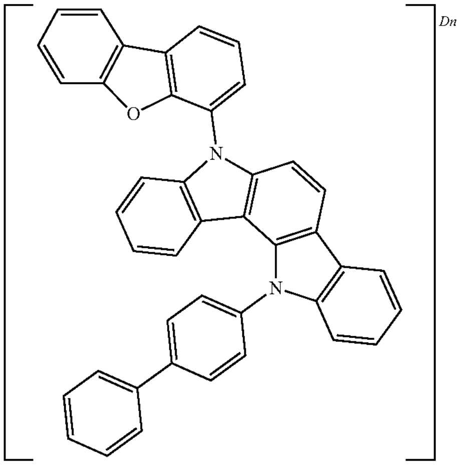
C-123
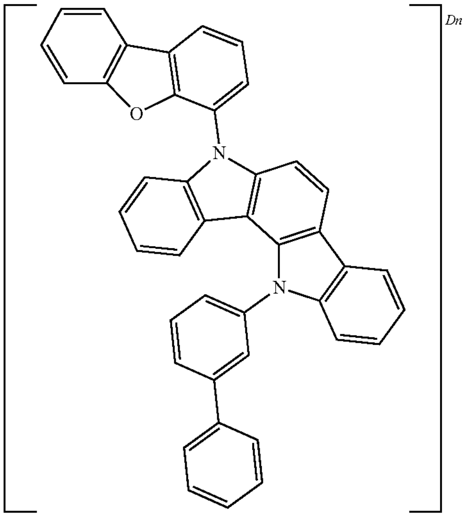
C-124
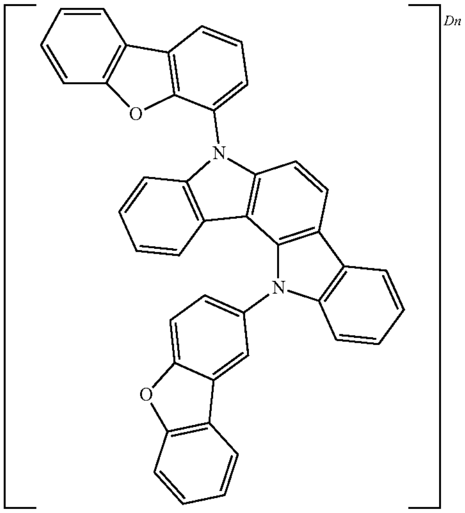
-continued
C-125
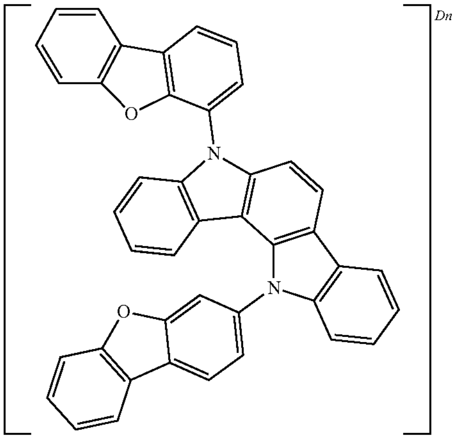
C-126
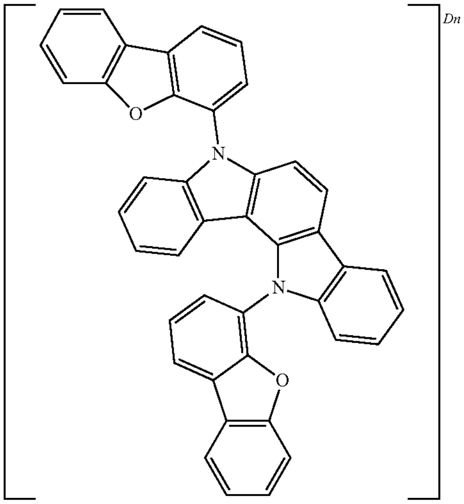
C-127
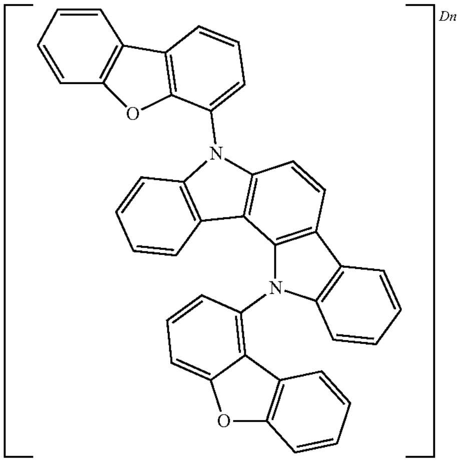

-continued
C-128
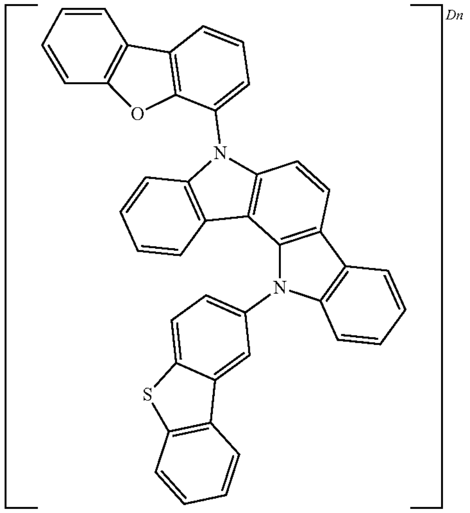
C-129
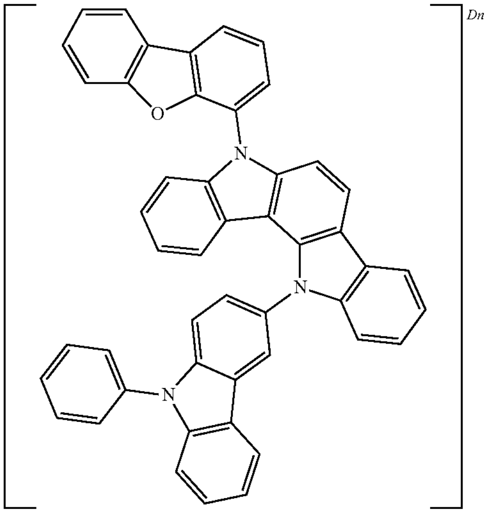
C-130
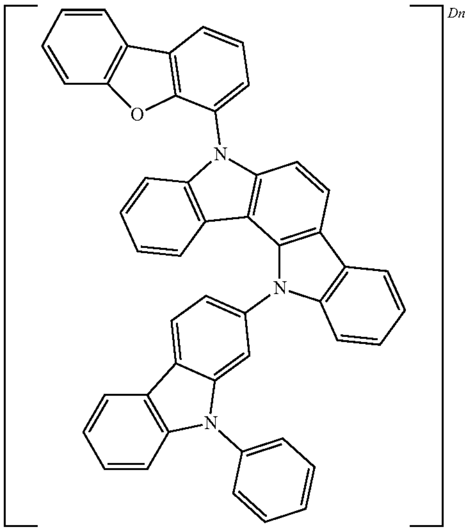
-continued
C-131
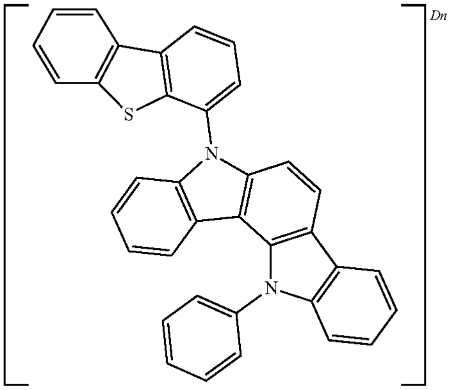
C-132
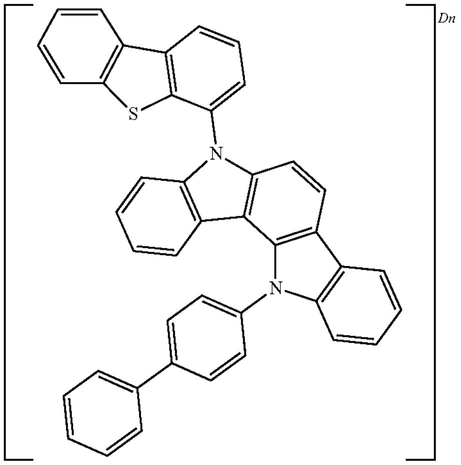
C-133
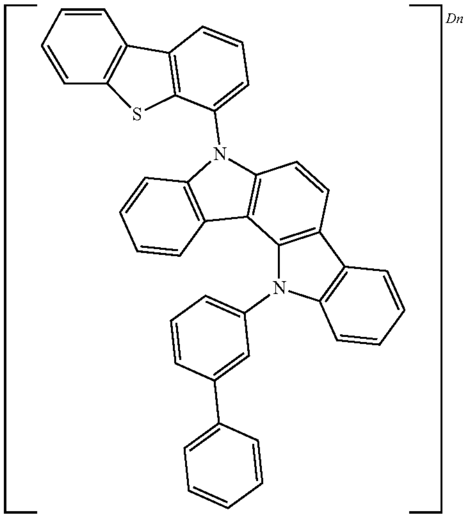

-continued
C-134
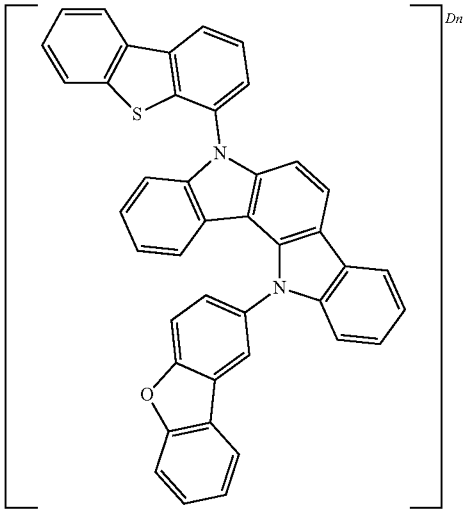
C-135
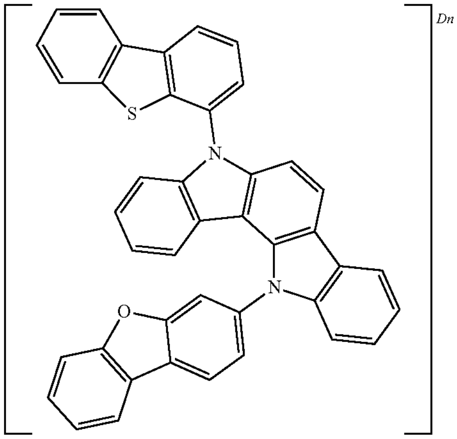
C-136
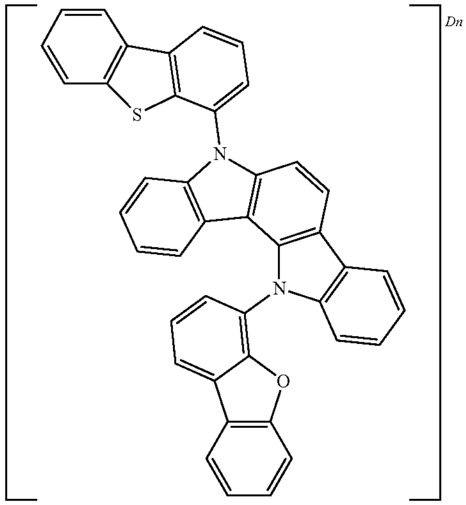
-continued
C-137
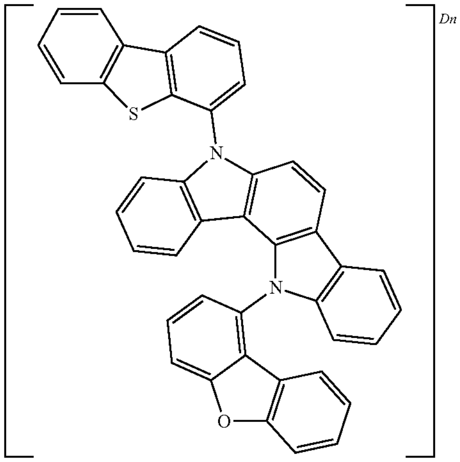
C-138
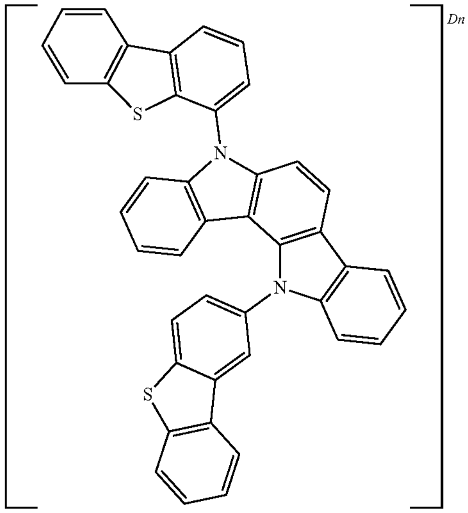
C-139
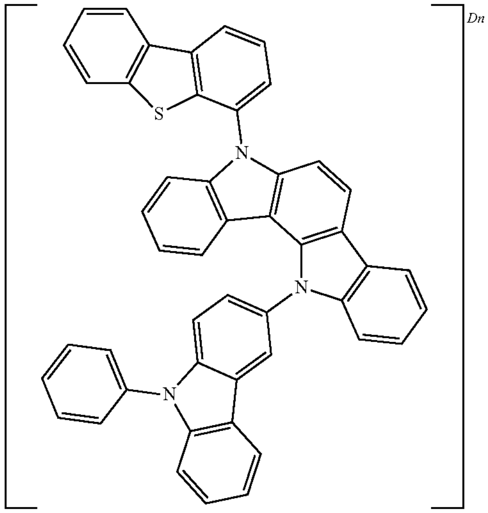

-continued
C-140
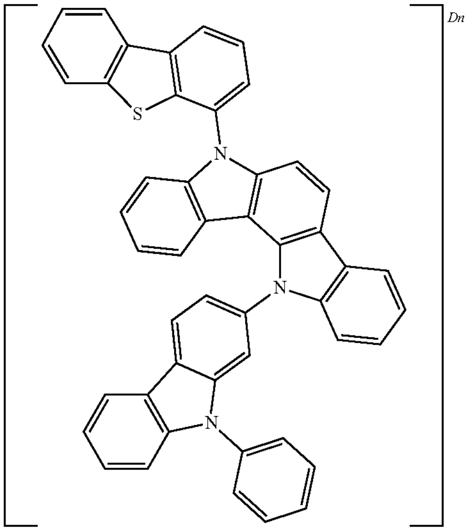
C-141
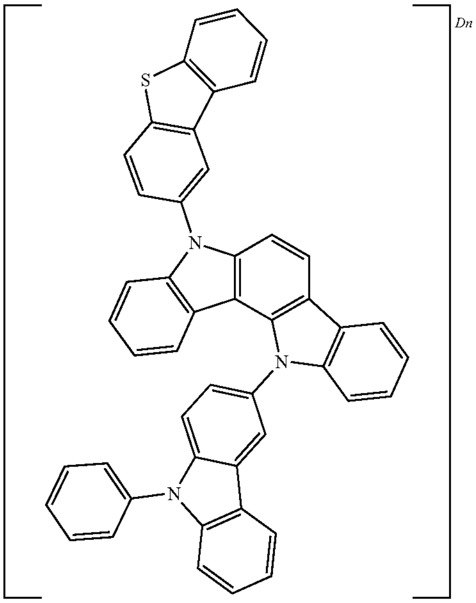
-continued
C-142
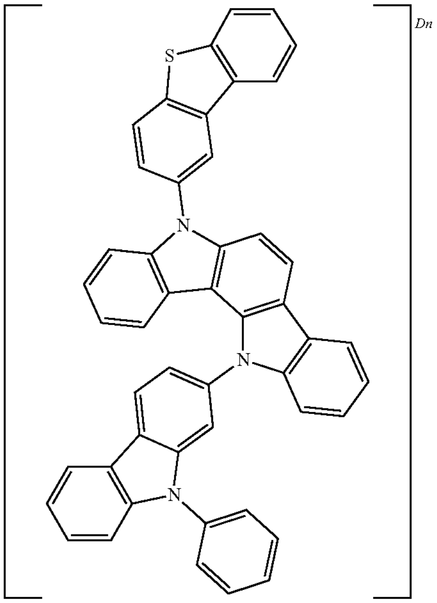
C-143
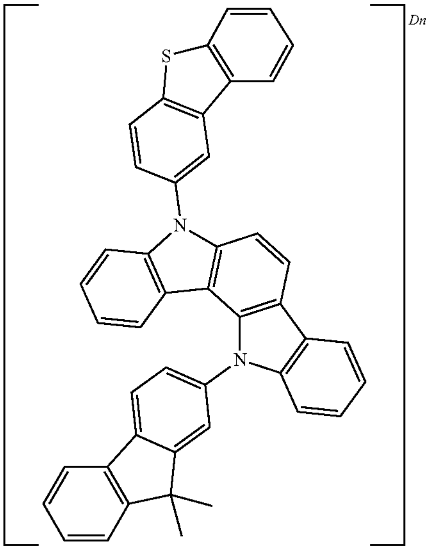
C-144
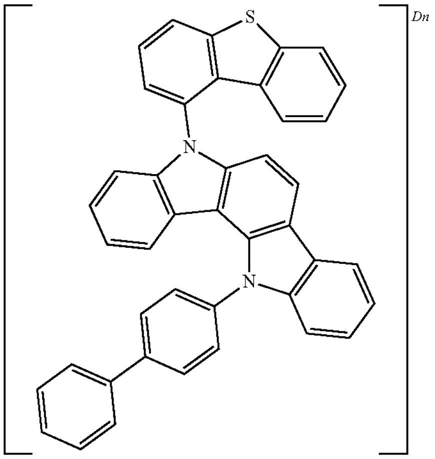

-continued
C-145
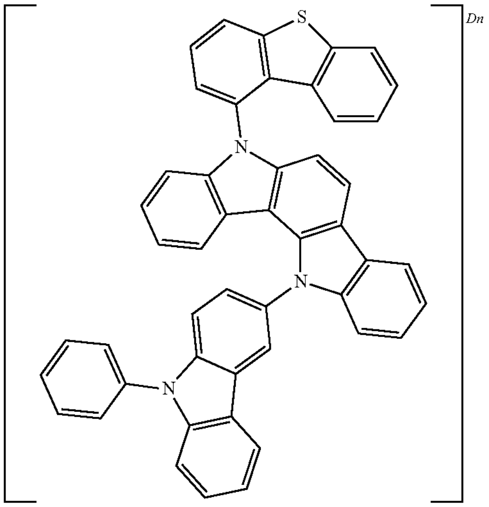
C-146
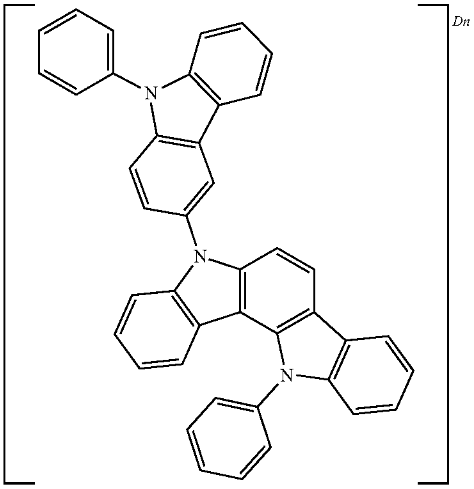
C-147
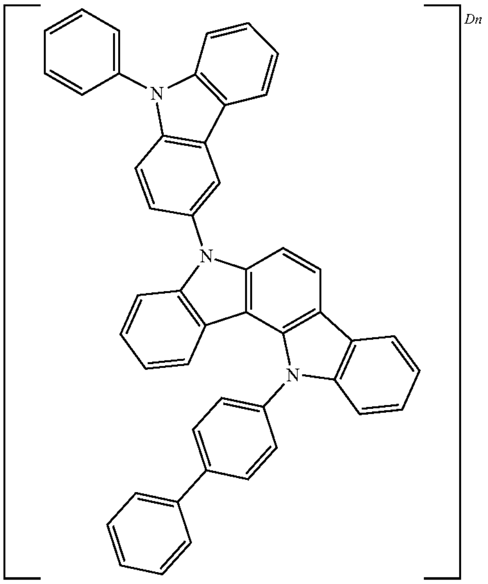
-continued
C-148
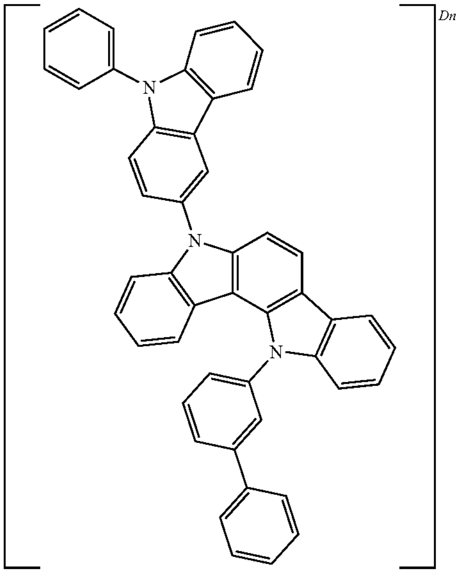
C-149
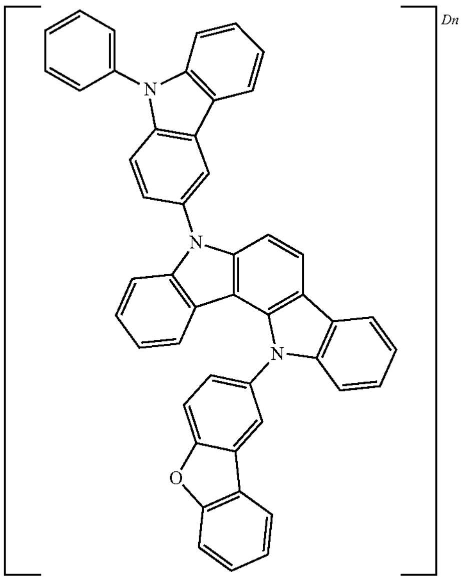

-continued
C-150
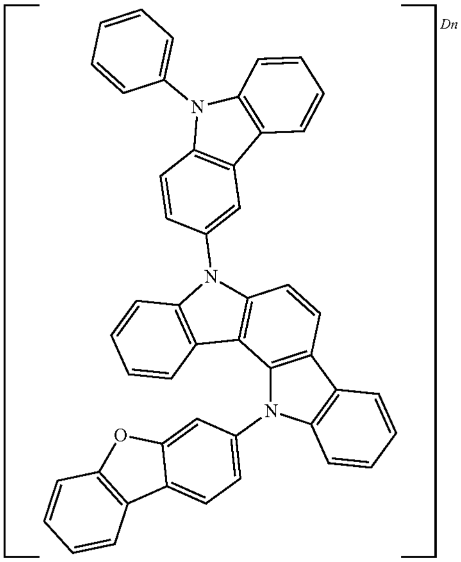
C-151
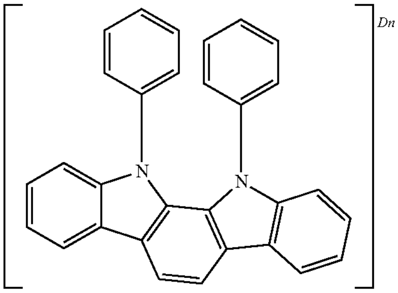
C-152
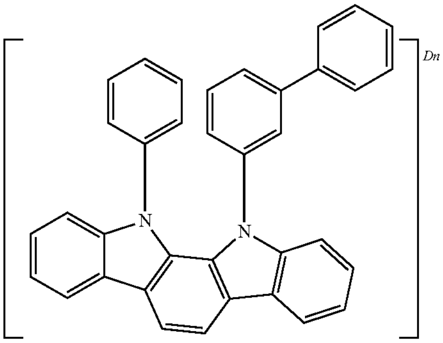
C-153
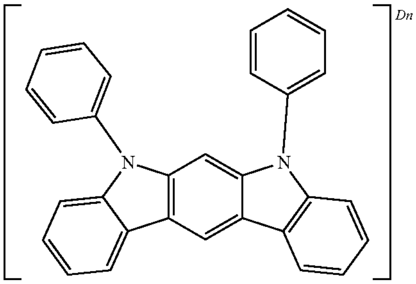
-continued
C-154
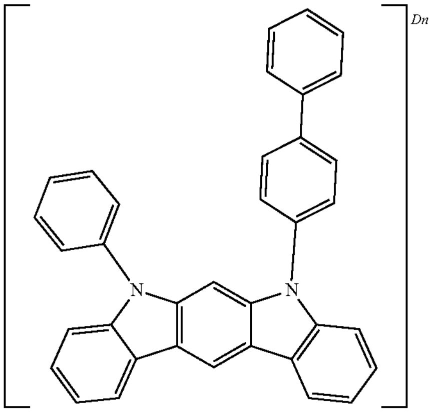
C-155
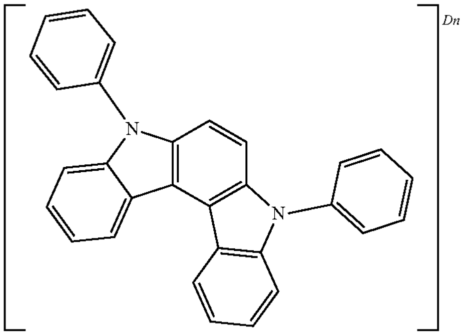
C-156
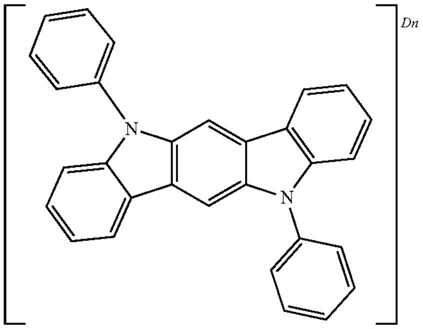
C-157
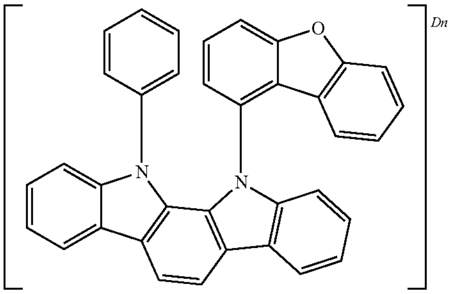

-continued
C-158
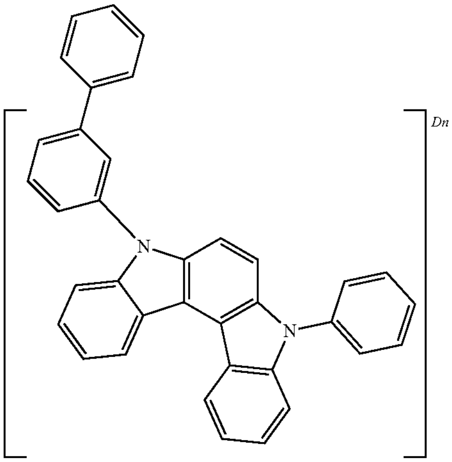
C-159
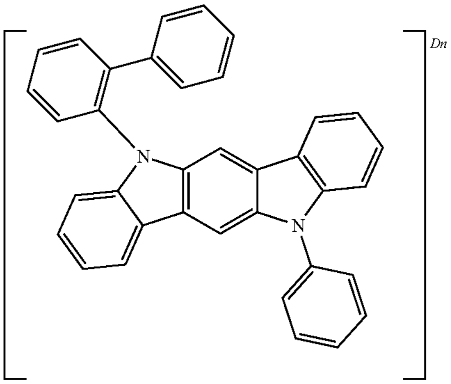
and
-continued
C-160
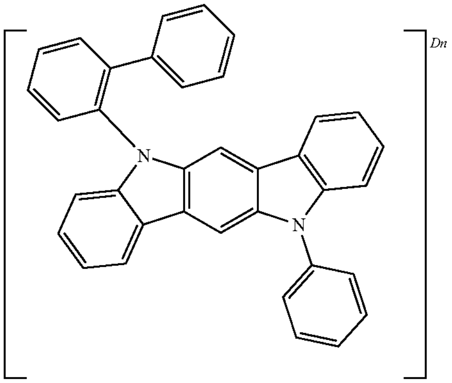
in the compounds, Dn represents that n number of hydrogens are replaced with deuterium; and n represents an integer of 1 to 50.
11. An organic electroluminescent device comprising the organic electroluminescent compound according to claim 8.
* * * * *